US008569331B2

(12) United States Patent
Ashwell et al.

(10) Patent No.: US 8,569,331 B2
(45) Date of Patent: Oct. 29, 2013

(54) SUBSTITUTED BENZO[F]LMIDAZO[1,2-D]PYRIDO[2,3-B][1,4]DIAZEPINE COMPOUNDS

(75) Inventors: Mark A. Ashwell, Carlisle, MA (US); Sudharshan Eathiraj, North Andover, MA (US); Anton Filikov, Rockville, MD (US); Steffi Koerner, Medford, MA (US); Jean-Marc Lapierre, Pelham, NH (US); Yanbin Liu, Acton, MA (US); Rocio Palma, North Andover, MA (US); David Vensel, Brookline, MA (US); Shin Iimura, Tokyo (JP); Akiko Shiina, Tokyo (JP); Kenichi Yoshida, Tokyo (JP); Takanori Yamazaki, Tokyo (JP); Akihisa Matsuda, Tokyo (JP)

(73) Assignee: ArQule, Inc., Woburn, MA (US)

( * ) Notice: Subject to any disclaimer, the term of this patent is extended or adjusted under 35 U.S.C. 154(b) by 6 days.

(21) Appl. No.: 13/286,294

(22) Filed: Nov. 1, 2011

(65) Prior Publication Data

US 2012/0108574 A1    May 3, 2012

Related U.S. Application Data

(60) Provisional application No. 61/408,910, filed on Nov. 1, 2010.

(51) Int. Cl.
*A61K 31/44*    (2006.01)
(52) U.S. Cl.
USPC ............. 514/287; 544/333; 546/77; 546/113; 546/152; 546/268.1; 548/202; 548/217; 548/235; 548/560; 549/510
(58) Field of Classification Search
USPC ............. 514/287; 544/333; 546/77, 113, 152, 546/268.1; 548/202, 217, 235, 560; 549/510
See application file for complete search history.

(56) References Cited

U.S. PATENT DOCUMENTS

| | | | |
|---|---|---|---|
| 4,522,811 | A | 6/1985 | Eppstein et al. |
| 5,747,488 | A | 5/1998 | Hargrave et al. |
| 2003/0139427 | A1 | 7/2003 | Castelhano et al. |
| 2004/0132723 | A1 | 7/2004 | Yoakim et al. |
| 2004/0229895 | A1 | 11/2004 | Jagtap et al. |
| 2009/0197869 | A1 | 8/2009 | Arvanitis et al. |
| 2010/0249108 | A1 | 9/2010 | Tandon et al. |

FOREIGN PATENT DOCUMENTS

| | | |
|---|---|---|
| DE | 102004054080 A1 | 5/2006 |
| EP | 293093 A2 | 11/1988 |
| EP | 389189 A2 | 9/1990 |
| EP | 512548 A1 | 11/1992 |
| EP | 550817 A2 | 7/1993 |
| EP | 791594 A2 | 8/1997 |
| JP | 2009013366 A | 1/1997 |
| JP | 2001160488 A | 6/2001 |
| JP | 2004059683 A | 2/2004 |
| JP | 2005340121 A | 12/2005 |
| JP | 2005340122 | 12/2005 |
| JP | 2005340123 A | 12/2005 |
| JP | 2005347160 A | 12/2005 |
| JP | 2006032599 A | 2/2006 |
| JP | 2006083353 A | 3/2006 |
| JP | 2006120689 A | 5/2006 |
| JP | 2006120762 A | 5/2006 |
| JP | 2006120763 A | 5/2006 |
| JP | 2006120821 A | 5/2006 |
| JP | 2006120905 A | 5/2006 |
| JP | 2006120906 A | 5/2006 |
| JP | 2006128257 A | 5/2006 |
| JP | 2006152101 A | 6/2006 |
| JP | 2006193546 A | 7/2006 |
| JP | 2006282965 A | 10/2006 |
| JP | 2006282966 A | 10/2006 |
| JP | 2006298999 A | 11/2006 |
| JP | 2006316162 A | 11/2006 |
| JP | 2007059310 A | 3/2007 |
| JP | 2007099961 A | 4/2007 |
| JP | 2007099962 A | 4/2007 |
| JP | 2007161886 A | 6/2007 |
| JP | 2007169541 A | 7/2007 |
| JP | 2008013616 A | 1/2008 |
| WO | WO-9409781 A1 | 5/1994 |
| WO | WO-9507918 A2 | 3/1995 |
| WO | WO-9907379 A1 | 2/1999 |
| WO | WO-9948868 | 9/1999 |
| WO | WO-02051849 | 7/2002 |
| WO | WO-2004014850 A2 | 2/2004 |
| WO | WO-2004026875 A1 | 4/2004 |
| WO | WO-2004095889 A1 | 11/2004 |
| WO | WO-2005051386 A1 | 6/2005 |

(Continued)

OTHER PUBLICATIONS

Almerico et al. "A Multivariate Analysis on Non-nucleoside HIV-1 Reverse Transcriptase Inhibitors and Resistance Induced by Mutation." *QSAR & Comb. Sci.* 22.9-10(2004):984-996.
Almerico et al. "Docking and Multivariate Methods to ExpLore HIV-1 Drug-Resistance: A Comparative Analysis." *J. Comput. Aided Mol. Des.* 22.5(2008):287-297.
Gussio et al. "All-Atom Models for the Non-Nucleoside Binding Site of HIV-1 Reverse Transcriptase Complexed with Inhibitors: A 3D QSAR Approach." *J. Med. Chem.* 39.8(1996):1645-1650.
Ishiyama et al. "Palladium(0)-Catalyzed Cross-Coupling Reaction of Alkoxydiboron with Haloarenes: A Direct Procedure for Arylboronic Esters." *J. Org. Chem.* 60.23(1995):7508-7510.

(Continued)

Primary Examiner — Douglas M Willis
(74) Attorney, Agent, or Firm — Mintz Levin Cohn Ferris Glovsky and Popeo, P.C.; Ivor R. Elrifi; Matthew Pavao

(57) ABSTRACT

The present invention relates to substituted benzo[f]imidazo [1,2-d]pyrido[2,3-b][1,4]diazepine compounds and methods of synthesizing these compounds. The present invention also relates to pharmaceutical compositions containing substituted benzo[f]imidazo[1,2-d]pyrido[2,3-b][1,4]diazepine compounds and methods of treating cell proliferative disorders, such as cancer, by administering these compounds and pharmaceutical compositions to subjects in need thereof.

19 Claims, No Drawings

(56) References Cited

FOREIGN PATENT DOCUMENTS

| WO | WO-2005072412 A2 | 8/2005 |
| --- | --- | --- |
| WO | WO-2006100888 A1 | 9/2006 |
| WO | WO-2007025090 A2 | 3/2007 |
| WO | WO-2007038215 A1 | 4/2007 |
| WO | WO-2007120752 A2 | 10/2007 |
| WO | WO-2009000412 A1 | 12/2008 |
| WO | WO-2009041635 A1 | 4/2009 |
| WO | WO-2009042711 A1 | 4/2009 |
| WO | WO-2009134658 A2 | 11/2009 |
| WO | WO-2010008454 A1 | 1/2010 |
| WO | WO-2010008459 A1 | 1/2010 |
| WO | WO-2010020432 A2 | 2/2010 |
| WO | WO-2010075561 A1 | 7/2010 |

OTHER PUBLICATIONS

Mager et al. "Evidence of a Butterfly-Like Configuration of Structurally Diverse Allosteric Inhibitors of the HIV-1 Reverse Transcriptase." *Drug Des. Disc.* 14.3(1996):241-257.

Terrett et al. "Imidazo[2',3':6,5]dipyrido[3,2-b:2',3'-e]-1,4-diazepines: Non-Nucleoside HIV-1 Transcriptase Inhibitors with Greater Enzyme Affinity Than Nevirapine." *Bioorg. Med. Chem. Lett.* 2.12(1992):1745-1750.

Wang et al. "Hierarchical Database Screenings for HIV-1 Reverse Transcriptase Using a Pharmacophore Model, Rigid Docking, Solvation Docking and MM-PB/SA." *J. Med. Chem.* 48.7(2005):2432-2444.

SUBSTITUTED BENZO[F]LMIDAZO[1,2-D]PYRIDO[2,3-B][1,4]DIAZEPINE COMPOUNDS

CROSS-REFERENCE TO RELATED APPLICATIONS

This application claims priority to, and the benefit of, U.S. Provisional Application No. 61/408,910, filed Nov. 1, 2010, the contents of which are incorporated herein by reference in their entirety.

BACKGROUND OF THE INVENTION

Cancer is the second leading cause of death in the United States, exceeded only by heart disease. (*Cancer Facts and Figures.* 2004, American Cancer Society, Inc.). Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational "mechanisms" may lead to the development of cancer. As such, heterogeneity frequently exists between cancer cells taken from tumors of the same tissue and same type that have originated in different individuals. Frequently observed mutational "mechanisms" associated with some cancers may differ between one tissue type and another (e.g., frequently observed mutational "mechanisms" leading to colon cancer may differ from frequently observed "mechanisms" leading to leukemias). It is therefore often difficult to predict whether a particular cancer will respond to a particular chemotherapeutic agent (*Cancer Medicine,* 5$^{th}$ edition, Bast et al., B. C. Decker Inc., Hamilton, Ontario).

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

AKT protein family, which members are also called protein kinases B (PKB) plays an important role in mammalian cellular signaling. In humans, there are three genes in the AKT family: Akt1, Akt2, and Akt3. These genes code for enzymes that are members of the serine/threonine-specific protein kinase family. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Akt2 is an important signaling molecule in the Insulin signaling pathway and is required to induce glucose transport. The role of Akt3 is less clear, though it appears to be predominantly expressed in brain.

The AKT family regulates cellular survival and metabolism by binding and regulating many downstream effectors, e.g. Nuclear Factor-κB, Bcl-2 family proteins and murine double minute 2 (MDM2). Akt1 is known to play a role in the cell cycle. Moreover, activated Akt1 may enable proliferation and survival of cells that have sustained a potentially mutagenic impact and, therefore, may contribute to acquisition of mutations in other genes. Akt1 has also been implicated in angiogenesis and tumor development. Studies have shown that deficiency of Akt1 enhanced pathological angiogenesis and tumor growth associated with matrix abnormalities in skin and blood vessels. Since it can block apoptosis, and thereby promote cell survival, Akt1 is a major factor in many types of cancer Accordingly, new compounds and methods for modulating AKT genes and treating proliferation disorders, including cancer, are needed. The present invention addresses these needs.

SUMMARY OF THE INVENTION

The present invention provides, in part, substituted benzo-imidazo-pyrido-diazepine compounds of formula I and methods of preparing the compounds of formula I:

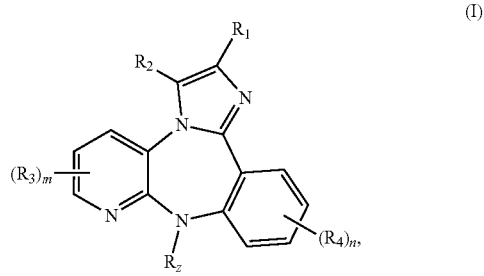

wherein:

$R_z$ is H or unsubstituted or substituted $C_1$-$C_6$ alkyl;

$R_1$ is H, halogen, cyano, unsubstituted or substituted $C_1$-$C_6$ alkyl, unsubstituted or substituted $C_2$-$C_6$ alkenyl, unsubstituted or substituted $C_2$-$C_6$ alkynyl, or $Q_1$-$T_1$;

$R_2$ is unsubstituted or substituted $C_1$-$C_6$ alkyl, unsubstituted or substituted $C_2$-$C_6$ alkenyl, unsubstituted or substituted $C_2$-$C_6$ alkynyl, or $Q_2$-$T_2$;

$Q_1$ and $Q_2$ are each independently a bond or $C_1$-$C_6$ alkyl linker;

$T_1$ is unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, unsubstituted or substituted heterocycle comprising one or two 5- or 6-membered rings and 1-4 heteroatoms selected from N, O and S, $OR_t$, $SR_t$, $C(O)NR_t'R_t$, $C(O)R_t$, $C(O)OR_t$, $NR_t'C(O)NR_t''R_t$, $NR_t'C(O)OR_t$, $NR_t'C(O)R_t$, $S(O)_2R_t$, or $NR_t'S(O)_2R_t$;

$T_2$ is unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S;

$R_t$ is H, unsubstituted or substituted $C_1$-$C_6$ alkyl, unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S;

$R_t'$ and $R_t''$ are each independently H, or unsubstituted or substituted $C_1$-$C_6$ alkyl;

m is 0, 1, 2, or 3;

n is 0, 1, 2, 3, or 4;

each $R_3$ is independently halogen, cyano, nitro, hydroxyl, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, amino, unsubstituted or substituted $C_1$-$C_6$ alkylamino, or unsubstituted or substituted di-$C_1$-$C_6$ alkylamino; and each $R_4$ is independently halogen, cyano, nitro, hydroxyl, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, amino, unsubstituted or substituted $C_1$-$C_6$ alkylamino, or unsubstituted or substituted di-$C_1$-$C_6$ alkylamino The present invention also provides pharmaceutical compositions comprising one or more compounds of each of the formulae described herein and one or more pharmaceutically acceptable carriers.

The present invention also provides enantiomers of each of the formulae described herein.

The present invention also provides methods of treating a cell proliferative disorder by administering to a subject in need thereof, a therapeutically effective amount of a compound of each of the formulae described herein, or a pharmaceutically acceptable salt, prodrug, metabolite, analog or derivative thereof, in combination with a pharmaceutically acceptable carrier, such that the disorder is treated.

The present invention also provides methods of treating cancer by administering to a subject in need thereof, a therapeutically effective amount of a compound of each of the formulae described herein, or a pharmaceutically acceptable salt, prodrug, metabolite, analog or derivative thereof, in combination with a pharmaceutically acceptable carrier, such that the cancer is treated.

The present invention also provides methods of selectively inducing cell death in precancerous or cancerous cells by contacting a cell with an effective amount of a compound of each of the formulae described herein, or a pharmaceutically acceptable salt, prodrug, metabolite, analog or derivative thereof, in combination with a pharmaceutically acceptable carrier, such that contacting the cell results in selective induction of cell death in the precancerous or cancer cells.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

1. Substituted Benzo-Imidazo-Pyrido-Diazepine Compounds

The present invention provides novel substituted benzo-imidazo-pyrido-diazepine compounds, synthetic methods for making the compounds, pharmaceutical compositions containing them and various uses of the disclosed compounds.

The present invention provides the compounds of formula I:

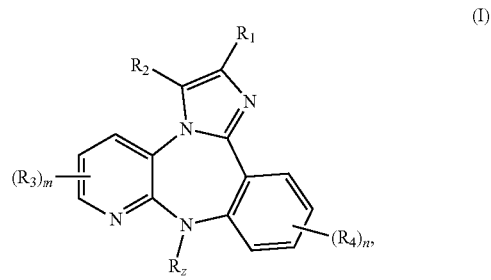

(I)

wherein:

$R_z$ is H or unsubstituted or substituted $C_1$-$C_6$ alkyl;

$R_1$ is H, halogen, cyano, unsubstituted or substituted $C_1$-$C_6$ alkyl, unsubstituted or substituted $C_2$-$C_6$ alkenyl, unsubstituted or substituted $C_2$-$C_6$ alkynyl, or $Q_1$-$T_1$;

$R_2$ is unsubstituted or substituted $C_1$-$C_6$ alkyl, unsubstituted or substituted $C_2$-$C_6$ alkenyl, unsubstituted or substituted $C_2$-$C_6$ alkynyl, or $Q_2$-$T_2$;

$Q_1$ and $Q_2$ are each independently a bond or $C_1$-$C_6$ alkyl linker;

$T_1$ is unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, unsubstituted or substituted heterocycle comprising one or two 5- or 6-membered rings and 1-4 heteroatoms selected from N, O and S, $OR_t$, $SR_t$, $C(O)NR_t'R_t$, $C(O)R_t$, $C(O)OR_t$, $NR_t'C(O)$ $NR_t''R_t$, $NR_t'C(O)OR_t$, $NR_t'C(O)R_t$, $S(O)_2R_t$, or $NR_t'S(O)_2$ $R_t$;

$T_2$ is unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S;

$R_t$ is H, unsubstituted or substituted $C_1$-$C_6$ alkyl, unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S;

$R_t'$ and $R_t''$ are each independently H, or unsubstituted or substituted $C_1$-$C_6$ alkyl;

m is 0, 1, 2, or 3;

n is 0, 1, 2, 3, or 4;

each $R_3$ is independently halogen, cyano, nitro, hydroxyl, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, amino, unsubstituted or substituted $C_1$-$C_6$ alkylamino, or unsubstituted or substituted di-$C_1$-$C_6$ alkylamino; and each $R_4$ is independently halogen, cyano, nitro, hydroxyl, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, amino, unsubstituted or substituted $C_1$-$C_6$ alkylamino, or unsubstituted or substituted di-$C_1$-$C_6$ alkylamino For example, $R_z$ is H.

For example, $R_z$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_1$ is H.

For example, $R_1$ is halogen, cyano, unsubstituted or substituted $C_1$-$C_6$ alkyl, unsubstituted or substituted $C_2$-$C_6$ alkenyl, unsubstituted or substituted $C_2$-$C_6$ alkynyl, or $Q_1$-$T_1$.

For example, $R_1$ is fluorine, chlorine, bromine, or iodine.

For example, $R_1$ is chlorine.

For example, $R_1$ is cyano.

For example, $R_1$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_1$ is unsubstituted or substituted, straight chain $C_1$-$C_6$ or branched $C_3$-$C_6$ alkyl optionally substituted with one or more groups independently selected from hydroxyl, halogen (e.g., fluorine, chlorine, bromine, and iodine), cyano, amino, and unsubstituted or substituted phenyl.

For example, $R_1$ is methyl or ethyl.

For example, $R_1$ is methyl substituted with cyano.

For example, $R_1$ is methyl or ethyl substituted with phenyl.

For example, $R_1$ is unsubstituted or substituted, straight chain $C_2$-$C_6$ or branched $C_3$-$C_6$ alkenyl, including but not limited to, ethenyl, propenyl, butenyl, pentenyl, hexenyl, and 3,3-dimethyl-1-butenyl, each of which is optionally substituted.

For example, $R_1$ is unsubstituted or substituted, straight chain $C_2$-$C_6$ or branched $C_3$-$C_6$ alkenyl optionally substituted with one or more groups independently selected from hydroxyl, halogen (e.g., fluorine, chlorine, bromine, and iodine), cyano, amino, and unsubstituted or substituted phenyl.

For example, $R_1$ is ethenyl or 3,3-dimethyl-1-butenyl.

For example, $R_1$ is ethenyl substituted with phenyl.

For example, $R_1$ is unsubstituted or substituted, straight chain $C_2$-$C_6$ or branched $C_4$-$C_6$ alkynyl, including but not limited to, ethynyl, propynyl, butynyl, pentynyl, and hexynyl, each of which is optionally substituted.

For example, $R_1$ is unsubstituted or substituted, straight chain $C_2$-$C_6$ or branched $C_4$-$C_6$ alkynyl optionally substituted with one or more groups independently selected from hydroxyl, halogen (e.g., fluorine, chlorine, bromine, and iodine), cyano, amino, and unsubstituted or substituted phenyl.

For example, $R_1$ is $Q_1$-$T_1$.

For example, $Q_1$ is a bond.

For example, $Q_1$ is an unsubstituted or substituted, straight chain $C_1$-$C_6$ or branched $C_3$-$C_6$ alkyl linker, including but not limited to, methyl, ethyl, n-propyl, i-propyl, n-butyl, s-butyl, t-butyl, n-pentyl, s-pentyl, and n-hexyl linker For example, $Q_1$ is a methyl or ethyl linker.

For example, $T_1$ is phenyl or naphthyl, each of which is optionally substituted.

For example, $T_1$ is heteroaryl selected from pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, pyrrolopyridinyl, imidazopyridinyl, and benzofuranonyl, each of which is optionally substituted.

For example, $T_1$ is pyrrolyl, pyrazolyl, pyridinyl, pyrimidinyl, quinolinyl, isoquinolinyl, or imidazopyridinyl, each of which is optionally substituted.

For example, $T_1$ is pyridinyl or pyrimidinyl, each of which is optionally substituted.

For example, $T_1$ is $C_3$-$C_{10}$ carbocycle selected from $C_3$-$C_{10}$ cycloalkyl (e.g., cyclopropyl, cyclobutyl, cyclopentyl, cyclohexyl, and cycloheptyl, each of which is optionally substituted) and $C_3$-$C_{10}$ cycloalenyl (e.g., cyclopropenyl, cyclobutenyl, cyclopentenyl, cyclohexenyl, and cycloheptenyl, each of which is optionally substituted).

For example, $T_1$ is cyclopropyl, cyclopentenyl, or cyclohexenyl, each of which is optionally substituted.

For example, $T_1$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and tetrahydropyridinyl, each of which is optionally substituted.

For example, $T_1$ is tetrahydropyridinyl, which is optionally substituted.

For example, $Q_1$ is a bond, a methyl or ethyl linker; and $T_1$ is $C_6$-$C_{10}$ aryl (e.g., phenyl and naphthyl), heteroaryl (e.g., pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, pyrrolopyridinyl, imidazopyridinyl, and benzofuranonyl), $C_3$-$C_{10}$ carbocycle (e.g., cyclopropyl, cyclobutyl, cyclopentyl, cyclohexyl, cycloheptyl, cyclopropenyl, cyclobutenyl, cyclopentenyl, cyclohexenyl, and cycloheptenyl), heterocycle (e.g., pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and tetrahydropyridinyl), each of which is optionally substituted.

For example, $T_1$ is $C_6$-$C_{10}$ aryl (e.g., phenyl and naphthyl), heteroaryl (e.g., pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, pyrrolopyridinyl, imidazopyridinyl, and benzofuranonyl), $C_3$-$C_{10}$ carbocycle (e.g., cyclopropyl, cyclobutyl, cyclopentyl, cyclohexyl, cycloheptyl, cyclopropenyl, cyclobutenyl, cyclopentenyl, cyclohexenyl, and cycloheptenyl), heterocycle (e.g., pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and tetrahydropyridinyl), each of which is optionally substituted with one or more $R_p$, wherein each $R_p$ is independently selected from:

a) hydroxyl, halogen (e.g., fluorine, chlorine, bromine, and iodine), cyano, nitro, b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted), c) unsubstituted or substituted $C_1$-$C_6$ alkoxy (e.g., methoxy, ethoxy, propyloxy, i-propyloxy, butoxy, t-butoxy, methylenedioxy, and ethylenedioxy, each of which is optionally substituted), d) amino, unsubstituted or substituted $C_1$-$C_6$ alkylamino (e.g., methylamino, ethylamino, propylamino, butylamino, and pentylamino, each of which is optionally substituted), unsubstituted or substituted di-$C_1$-$C_6$ alkylamino (e.g., dimethylamino, diethylamino, dipropylamino, dibutylamino, and dipentylamino, each of which is optionally substituted),
e) unsubstituted or substituted $C_6$-$C_{10}$ aryl (e.g., phenyl and naphthyl, each of which is optionally substituted),
f) unsubstituted or substituted heteroaryl comprising one or two 5- or 6-membered rings and 1-4 heteroatoms selected from N, O and S (e.g., pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, and purinyl, each of which is optionally substituted),
g) unsubstituted or substituted $C_3$-$C_{10}$ carbocycle (e.g., cyclopropyl, cyclobutyl, cyclopentyl, cyclohexyl, and cycloheptyl, each of which is optionally substituted),
h) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and piperidinonyl, each of which is optionally substituted),
i) $OR_5$, $NR_sR_5$, $SR_5$, $C(O)R_5$, $C(O)OR_5$, $C(O)NR_sR_5$, $NR_s'C(O)R_5$, $NR_s'C(O)OR_5$, $NR_s'C(O)NR_s'R_5$, $S(O)_2R_5$, and $NR_s'S(O)_2R_5$,
wherein $R_5$ is H, unsubstituted or substituted $C_1$-$C_6$ alkyl, unsubstituted or substituted $C_6$-$C_{10}$ aryl-$C_1$-$C_6$ alkyl, unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S; and
$R_s$ and $R_s'$ are each independently H, or unsubstituted or substituted $C_1$-$C_6$ alkyl.

For example, each $R_p$ is independently fluorine.

For example, each $R_p$ is independently $C_1$-$C_6$ alkyl optionally substituted with one or more groups independently selected from:
a) hydroxyl, halogen (e.g., fluorine, chlorine, bromine, and iodine), amino, cyano,
b) unsubstituted or substituted $C_6$-$C_{10}$ aryl (e.g., phenyl and naphthyl, each of which is optionally substituted),
c) unsubstituted or substituted heteroaryl comprising one or two 5- or 6-membered rings and 1-4 heteroatoms selected from N, O and S (e.g., pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted),
d) unsubstituted or substituted $C_3$-$C_{10}$ carbocycle (e.g., cyclopropyl, cyclobutyl, cyclopentyl, cyclohexyl, and cycloheptyl, each of which is optionally substituted),
e) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted),
f) $C(O)R_x$, and $C(O)OR_x$,
wherein $R_x$ is H or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, each $R_p$ is independently unsubstituted methyl or ethyl.

For example, each $R_p$ is independently methyl or ethyl, each of which is optionally substituted with hydroxyl, amino, cyano, phenyl, morpholinyl, C(O)OH, or $C(O)OCH_3$.

For example, each $R_p$ is independently methoxy, ethoxy, or methylenedioxy.

For example, each $R_p$ is independently dimethylamino.

For example, each $R_p$ is independently phenyl or naphthyl, each of which is optionally substituted.

For example, each $R_p$ is independently phenyl substituted with one or more groups independently selected from:
a) hydroxyl, halogen (e.g., fluorine, chlorine, bromine, and iodine), amino, cyano,
b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted),
c) $C(O)NR_x'R_x$, and $C(O)OR_x$,
wherein $R_x$ and $R_x'$ are each independently H, or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, each $R_p$ is independently phenyl substituted with methyl, ethyl, methoxy, ethoxy, $C(O)NH_2$, or $C(O)N(CH_3)_2$.

For example, each $R_p$ is independently pyridinyl.

For example, each $R_p$ is independently cyclopropyl or cyclobutyl.

For example, each $R_p$ is independently cyclobutyl substituted with amino.

For example, each $R_p$ is independently piperidinyl, piperidinonyl, or morpholinyl.

For example, each $R_p$ is independently $OR_5$, $NR_sR_5$, $SR_5$, $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$.

For example, $R_s$ is H.

For example, $R_s$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, $R_s'$ is H.

For example, $R_s'$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, $R_5$ is H.

For example, $R_5$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_5$ is unsubstituted or substituted $C_6$-$C_{10}$ aryl-$C_1$-$C_6$ alkyl, including but not limited to, benzyl, phenylethyl, naphthylmethyl, and naphthylethyl, each of which is optionally substituted.

For example, $R_5$ is phenyl or naphthyl, each of which is optionally substituted.

For example, $R_5$ is heteroaryl selected from pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted.

For example, $R_5$ is $C_3$-$C_{10}$ carbocycle selected from cyclopropyl, cyclobutyl, cyclopentyl, cyclohexyl, and cycloheptyl, each of which is optionally substituted.

For example, $R_5$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted.

For example, each $R_p$ is independently $OR_5$ or $SR_5$; and $R_5$ is unsubstituted or substituted $C_6$-$C_{10}$ aryl-$C_1$-$C_6$ alkyl (e.g., benzyl, phenylethyl, naphthylmethyl, and naphthylethyl, each of which is optionally substituted), or unsubstituted or substituted $C_6$-$C_{10}$ aryl (e.g., phenyl and naphthyl, each of which is optionally substituted).

For example, each $R_p$ is independently $OR_5$; and $R_5$ is benzyl or phenyl.

For example, each $R_p$ is independently $NR_sR_5$; $R_s$ is H, or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl); and $R_5$ is:

a) unsubstituted or substituted $C_6$-$C_{10}$ aryl (e.g., phenyl and naphthyl, each of which is optionally substituted), b) unsubstituted or substituted heteroaryl comprising one or two 5- or 6-membered rings and 1-4 heteroatoms selected from N, O and S (e.g., pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, and thiozolonyl, each of which is optionally substituted), c) unsubstituted or substituted $C_3$-$C_{10}$ carbocycle (e.g., cyclopropyl, cyclobutyl, cyclopentyl, cyclohexyl, and cycloheptyl, each of which is optionally substituted), or d) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted).

For example, each $R_p$ is independently $NR_sR_5$; $R_s$ is H or methyl; and $R_5$ is methyl, phenyl, thiazolyl, or thiozolonyl.

For example, each $R_p$ is independently $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$; $R_s$ and $R_s'$ are each independently H, or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl); and $R_5$ is:

a) H, b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted with one or more groups independently selected from:

i) hydroxyl, halogen (e.g., fluorine, chlorine, bromine, and iodine), ii) unsubstituted or substituted $C_1$-$C_6$ alkoxy (e.g., methoxy, ethoxy, propyloxy, i-propyloxy, butoxy, and t-butoxy, each of which is optionally substituted)), iii) $C(O)R_y$, and $C(O)OR_y$, wherein $R_y$ is H or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted)), c) unsubstituted or substituted $C_6$-$C_{10}$ aryl-$C_1$-$C_6$ alkyl (e.g., benzyl, phenylethyl, naphthylmethyl, and naphthylethyl, each of which is optionally substituted), d) unsubstituted or substituted $C_6$-$C_{10}$ aryl (e.g., phenyl and naphthyl, each of which is optionally substituted), e) unsubstituted or substituted heteroaryl comprising one or two 5- or 6-membered rings and 1-4 heteroatoms selected from N, O and S (e.g., pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted), f) unsubstituted or substituted $C_3$-$C_{10}$ carbocycle (e.g., cyclopropyl, cyclobutyl, cyclopentyl, cyclohexyl, and cycloheptyl, each of which is optionally substituted), or g) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted).

For example, each $R_p$ is independently $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$; $R_s$ and $R_s'$ are each independently H or methyl; and $R_5$ is H, methyl, ethyl, i-propyl, t-butyl, benzyl, phenyl, cyclopropyl, or pyrrolidinyl, each of which is optionally substituted. For example, $R_5$ is methyl, ethyl, or i-propyl, each of which is optionally substituted with hydroxyl, fluorine, or $C(O)OCH_3$.

For example, $Q_1$ is a bond, a methyl or ethyl linker; and $T_1$ is $OR_t$, $SR_t$, $C(O)NR_t'R_t$, $C(O)R_t$, $C(O)OR_t$, $NR_t'C(O)NR_t''R_t$, $NR_t'C(O)OR_t$, $NR_t'C(O)R_t$, $S(O)_2R_t$, or $NR_t'S(O)_2R_t$.

For example, $Q_1$ is a bond; and $T_1$ is $OR_t$, $SR_t$, $C(O)R_t$, or $C(O)OR_t$.

For example, $Q_1$ is a methyl or ethyl linker; and $T_1$ is $C(O)R_t$ or $C(O)NR_t'R_t$.

For example, $R_t'$ is H.

For example, $R_t'$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, $R_t''$ is H.

For example, $R_t''$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, $R_t$ is H.

For example, $R_t$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl, each of which is optionally substituted.

For example, $R_t$ is methyl.

For example, $R_t$ is phenyl and is optionally substituted.

For example, $R_t$ is heteroaryl selected from pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzofuranyl, benzoxazolyl, benzodioxazolyl, benzothiazolyl, benzothiadiazolyl, benzoimidazolyl, benzothienyl, methylenedioxyphenyl, quinolinyl, isoquinolinyl, naphthrydinyl, indolyl, purinyl, pyrrolopyridinyl, imidazopyridinyl, and benzofuranonyl, and the like, each of which is optionally substituted.

For example, $R_t$ is pyridinyl substituted with unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl).

For example, $R_t$ is carbocycle selected from cyclopropyl, cyclobutyl, cyclopentyl, cyclohexyl, cycloheptyl, cyclopropenyl, cyclobutenyl, cyclopentenyl, cyclohexenyl, and cycloheptenyl, each of which is optionally substituted.

For example, $R_t$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and tetrahydropyridinyl, and the like, each of which is optionally substituted.

For example, $R_2$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_2$ is unsubstituted or substituted, straight chain $C_2$-$C_6$ or branched $C_3$-$C_6$ alkenyl, including but not limited to, ethenyl, propenyl, butenyl, pentenyl, and hexenyl, each of which is optionally substituted.

For example, $R_2$ is unsubstituted or substituted, straight chain $C_2$-$C_6$ or branched $C_4$-$C_6$ alkynyl, including but not limited to, ethynyl, propynyl, butynyl, pentynyl, and hexynyl, each of which is optionally substituted.

For example, $R_2$ is $Q_2$-$T_2$.

For example, $Q_2$ is a bond.

For example, $Q_2$ is an unsubstituted or substituted, straight chain $C_1$-$C_6$ or branched $C_3$-$C_6$ alkyl linker, including but not limited to, methyl, ethyl, n-propyl, i-propyl, n-butyl, s-butyl, t-butyl, n-pentyl, s-pentyl, and n-hexyl linker For example, $Q_2$ is a methyl or ethyl linker.

For example, $T_2$ is unsubstituted phenyl.

For example, $T_2$ is phenyl substituted with one or more groups independently selected from:
  a) hydroxyl, halogen (e.g., fluorine, chlorine, bromine, and iodine), cyano, nitro,
  b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted),
  c) unsubstituted or substituted $C_1$-$C_6$ alkoxy (e.g., methoxy, ethoxy, propyloxy, i-propyloxy, butoxy, t-butoxy, methylenedioxy, and ethylenedioxy, each of which is optionally substituted),
  d) amino, unsubstituted or substituted $C_1$-$C_6$ alkylamino (e.g., methylamino, ethylamino, propylamino, butylamino, and pentylamino, each of which is optionally substituted), unsubstituted or substituted di-$C_1$-$C_6$ alkylamino (e.g., dimethylamino, diethylamino, dipropylamino, dibutylamino, and dipentylamino, each of which is optionally substituted),
  e) unsubstituted or substituted $C_6$-$C_{10}$ aryl (e.g., phenyl and naphthyl, each of which is optionally substituted),
  f) unsubstituted or substituted heteroaryl comprising one or two 5- or 6-membered rings and 1-4 heteroatoms selected from N, O and S (e.g., pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted),
  g) unsubstituted or substituted $C_3$-$C_{10}$ carbocycle (e.g., cyclopropyl, cyclobutyl, cyclopentyl, cyclohexyl, and cycloheptyl, each of which is optionally substituted), and
  h) unsubstituted or substituted heterocycle comprising one or two 3-, 4-, 5- or 6-membered rings and 1-4 heteroatoms selected from N, O and S (e.g., oxetanyl, oxazolidinyl, oxazolidinonyl, pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted).

For example, $T_2$ is phenyl substituted with one or more groups selected from fluorine and chlorine.

For example, $T_2$ is phenyl substituted with one or more groups selected from methyl, ethyl, cyclopropyl, cyclobutyl, oxetanyl, oxazolidinyl, and oxazolidinonyl, each of which is optionally substituted with one or more groups independently selected from hydroxyl, amino, halogen (e.g., fluorine, chlorine, bromine, and iodine), and unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, $T_2$ is phenyl substituted at least at the para-position of the phenyl ring.

For example, $T_2$ is phenyl substituted with aminomethyl, 1-methyl-1-amino-ethyl, or 1-aminoethyl.

For example, $T_2$ is phenyl substituted with 1-amino-cyclobutyl.

For example, $T_2$ is phenyl substituted with unsubstituted or substituted heterocycle comprising one 4-membered ring.

For example, $T_2$ is phenyl substituted with oxetanyl, which is substituted with amino.

For example, $T_2$ is phenyl substituted with unsubstituted or substituted heterocycle comprising one 5-membered ring.

For example, $T_2$ is phenyl substituted with oxazolidinonyl (e.g., oxazolidin-2-onyl), which is substituted with $CH_2OH$.

For example, $T_2$ is heteroaryl selected from pyrrolyl, furanyl, thiophene, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzofuranyl, benzoxazolyl, benzodioxazolyl, benzothiazolyl, benzothiadiazolyl, benzoimidazolyl, benzothiophene, methylenedioxyphenyl, quinolinyl, isoquinolinyl, naphthrydinyl, indolyl and purinyl, and the like, and is optionally substituted.

For example, $T_2$ is carbocycle selected from cyclopropyl, cyclobutyl, cyclopentyl, cyclohexyl and cycloheptyl, and is optionally substituted.

For example, $T_2$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, and the like, and is optionally substituted.

For example, m is 0.

For example, m is 1.

For example, each $R_3$ is independently fluorine, chlorine, bromine, or iodine.

For example, each $R_3$ is independently unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, each $R_3$ is independently unsubstituted or substituted, straight chain $C_2$-$C_6$ or branched $C_3$-$C_6$ alkenyl, including but not limited to, ethenyl, propenyl, butenyl, pentenyl, and hexenyl, each of which is optionally substituted.

For example, each $R_3$ is independently unsubstituted or substituted, straight chain $C_2$-$C_6$ or branched $C_4$-$C_6$ alkynyl, including but not limited to, ethynyl, propynyl, butynyl, pentynyl, and hexynyl, each of which is optionally substituted.

For example, each $R_3$ is independently unsubstituted or substituted $C_1$-$C_6$ alkoxy, including but not limited to, methoxy, ethoxy, propyloxy, i-propyloxy, butoxy, and t-butoxy, each of which is optionally substituted.

For example, each $R_3$ is independently unsubstituted or substituted $C_1$-$C_6$ alkylamino, including but not limited to, methylamino, ethylamino, propylamino, butylamino, and pentylamino, each of which is optionally substituted.

For example, each $R_3$ is independently unsubstituted or substituted di-$C_1$-$C_6$ alkylamino, including but not limited to, dimethylamino, diethylamino, dipropylamino, dibutylamino, and dipentylamino, each of which is optionally substituted.

For example, n is 0.
For example, n is 1.
For example, n is 2.

For example, each $R_4$ is independently fluorine, chlorine, bromine or iodine.

For example, each $R_4$ is independently unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, each $R_4$ is independently unsubstituted or substituted, straight chain $C_2$-$C_6$ or branched $C_3$-$C_6$ alkenyl, including but not limited to, ethenyl, propenyl, butenyl, pentenyl, and hexenyl, each of which is optionally substituted.

For example, each $R_4$ is independently unsubstituted or substituted, straight chain $C_2$-$C_6$ or branched $C_4$-$C_6$ alkynyl, including but not limited to, ethynyl, propynyl, butynyl, pentynyl, and hexynyl, each of which is optionally substituted.

For example, each $R_4$ is independently unsubstituted or substituted $C_1$-$C_6$ alkoxy, including but not limited to, methoxy, ethoxy, propyloxy, i-propyloxy, butoxy, and t-butoxy, each of which is optionally substituted.

For example, each $R_4$ is independently unsubstituted or substituted $C_1$-$C_6$ alkylamino, including but not limited to, methylamino, ethylamino, propylamino, butylamino, and pentylamino, each of which is optionally substituted.

For example, each $R_4$ is independently unsubstituted or substituted di-$C_1$-$C_6$ alkylamino, including but not limited to, dimethylamino, diethylamino, dipropylamino, dibutylamino, and dipentylamino, each of which is optionally substituted.

The present invention also provides the compounds of formula Ia or Ib:

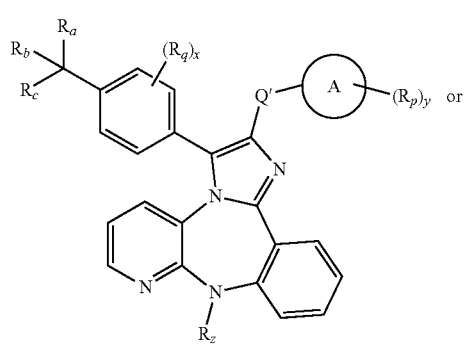

(Ia)

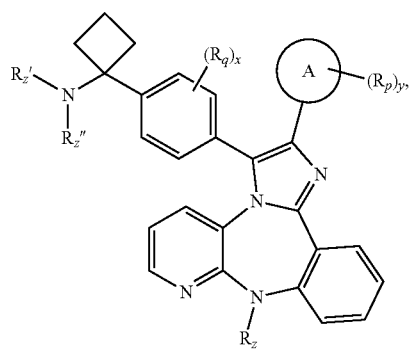

(Ib)

wherein:

$R_z$, $R_z'$ and $R_z''$ are each independently H or unsubstituted or substituted $C_1$-$C_6$ alkyl;

Q' is $(CH_2)_q$, $(CH_2)_qO$, $(CH_2)_qS$, $(CH_2)_qC(O)NR_s$, $(CH_2)_qC(O)$, $(CH_2)_qC(O)O$, $(CH_2)_qNR_s'C(O)NR_s$, $(CH_2)_qNR_s'C(O)$, or $(CH_2)_qNR_s'C(O)O$;

q is 0, 1, 2, or 3;

$R_s$ and $R_s'$ are each independently H, or unsubstituted or substituted $C_1$-$C_6$ alkyl;

comprises one or two 5- or 6-membered rings and optionally 1-4 heteroatoms selected from N, O and S;

x and y are each independently 0, 1, 2, 3, or 4;

each $R_p$ is independently hydroxyl, halogen, cyano, nitro, unsubstituted or substituted $C_1$-$C_6$ alkyl, unsubstituted or substituted $C_1$-$C_6$ alkoxy, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, unsubstituted or substituted heterocycle comprising one or two 5- or 6-membered rings and 1-4 heteroatoms selected from N, O and S, $OR_5$, $NR_sR_5$, $SR_5$, $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$;

$R_5$ is H, unsubstituted or substituted $C_1$-$C_6$ alkyl, unsubstituted or substituted $C_6$-$C_{10}$ aryl-$C_1$-$C_6$ alkyl, unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S;

each $R_q$ is independently hydroxyl, halogen, cyano, nitro, unsubstituted or substituted $C_1$-$C_6$ alkyl, unsubstituted or substituted $C_1$-$C_6$ alkoxy, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, or unsubstituted or substituted heterocycle comprising one or two 5- or 6-membered rings and 1-4 heteroatoms selected from N, O and S;

$R_a$ and $R_b$ are each independently H or unsubstituted or substituted $C_1$-$C_6$ alkyl, or $R_a$ and $R_b$, together with the carbon atom to which they are attached, form an unsubstituted or substituted $C_3$-$C_{10}$ carbocycle, or an unsubstituted or substituted heterocycle comprising one or two 3-, 4-, 5-, or 6-membered rings and 1-4 heteroatoms selected from N, O and S; and $R_c$ is H, amino, or halogen.

For example, $R_z$ is H.

For example, $R_z$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, one of $R_z'$ and $R_z''$ is H; and the other is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_z'$ and $R_z''$ are each H.

For example, $R_z'$ and $R_z''$ are each independently unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, Q' is $(CH_2)_q$; and q is 0.

For example, Q' is $(CH_2)_q$; and q is 1.

For example, Q' is $(CH_2)_q$; and q is 2.

For example, Q' is $(CH_2)_qO$, $(CH_2)_qS$, $(CH_2)_qC(O)NR_s$, $(CH_2)_qC(O)$, or $(CH_2)_qC(O)O$.

For example, q is 0 or 1.

For example, Q' is O or S.

For example, Q' is $CH_2C(O)NR_s$, $CH_2C(O)$, or $CH_2C(O)O$.

For example, $R_s$ is H.

For example, $R_s$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, Q' is $CH_2C(O)NH$.

For example, (A)

is $C_6$-$C_{10}$ aryl.

For example, (A)

is phenyl or naphthyl.

For example, (A)

is heteroaryl comprising one or two 5- or 6-membered rings and 1-4 heteroatoms selected from N, O and S.

For example, (A)

is heteroaryl selected from pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzofuranyl, benzoxazolyl, benzodioxazolyl, benzothiazolyl, benzothiadiazolyl, benzoimidazolyl, benzothienyl, methylenedioxyphenyl, quinolinyl, isoquinolinyl, naphthrydinyl, indolyl, purinyl, pyrrolopyridinyl, imidazopyridinyl, and benzofuranonyl.

For example, (A)

is heteroaryl selected from pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, pyrrolopyridinyl, imidazopyridinyl, and benzofuranonyl.

For example, (A)

is heteroaryl selected from pyrrolyl, pyrazolyl, pyridinyl, pyrimidinyl, quinolinyl, isoquinolinyl, and imidazopyridinyl.

For example, (A)

is pyridinyl or pyrimidinyl.

For example, (A)

is $C_3$-$C_{10}$ carbocycle selected from $C_3$-$C_{10}$ cycloalkyl (e.g., cyclopropyl, cyclobutyl, cyclopentyl, cyclohexyl, and cycloheptyl) and $C_3$-$C_{10}$ cycloalenyl (e.g., cyclopropenyl, cyclobutenyl, cyclopentenyl, cyclohexenyl, and cycloheptenyl).

For example, (A)

is cyclopropyl.

For example, (A)

is cyclopentenyl or cyclohexenyl.

For example,

is heterocycle comprising one or two 5- or 6-membered rings and 1-4 heteroatoms selected from N, O and S.

For example,

is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and tetrahydropyridinyl.

For example,

is tetrahydropyridinyl.

For example, y is 0.
For example, y is 1.
For example, y is 2.
For example, each $R_p$ is independently fluorine, chlorine, bromine, or iodine.

For example, each $R_p$ is independently fluorine.

For example, each $R_p$ is independently unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, each $R_p$ is independently $C_1$-$C_6$ alkyl optionally substituted with one or more groups independently selected from:

a) hydroxyl, halogen (e.g., fluorine, chlorine, bromine, and iodine), amino, cyano,
b) unsubstituted or substituted $C_6$-$C_{10}$ aryl (e.g., phenyl and naphthyl, each of which is optionally substituted),
c) unsubstituted or substituted heteroaryl comprising one or two 5- or 6-membered rings and 1-4 heteroatoms selected from N, O and S (e.g., pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted),
d) unsubstituted or substituted $C_3$-$C_{10}$ carbocycle (e.g., cyclopropyl, cyclobutyl, cyclopentyl, cyclohexyl, and cycloheptyl, each of which is optionally substituted),
e) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted),
f) $C(O)R_x$, and $C(O)OR_x$,
wherein $R_x$ is H or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, each $R_p$ is independently unsubstituted methyl or ethyl.

For example, each $R_p$ is independently methyl or ethyl, each of which is optionally substituted with hydroxyl, amino, cyano, phenyl, morpholinyl, $C(O)OH$, or $C(O)OCH_3$.

For example, each $R_p$ is independently unsubstituted or substituted $C_1$-$C_6$ alkoxy, including but not limited to, methoxy, ethoxy, propyloxy, i-propyloxy, butoxy, t-butoxy, methylenedioxy, and ethylenedioxy, each of which is optionally substituted.

For example, each $R_p$ is independently methoxy, ethoxy, or methylenedioxy.

For example, each $R_p$ is independently unsubstituted or substituted $C_1$-$C_6$ alkylamino, including but not limited to, methylamino, ethylamino, propylamino, butylamino, and pentylamino, each of which is optionally substituted.

For example, each $R_p$ is independently unsubstituted or substituted di-$C_1$-$C_6$ alkylamino, including but not limited to, dimethylamino, diethylamino, dipropylamino, dibutylamino, and dipentylamino, each of which is optionally substituted.

For example, each $R_p$ is independently dimethylamino.

For example, each $R_p$ is independently phenyl or naphthyl, each of which is optionally substituted.

For example, each $R_p$ is independently phenyl substituted with one or more groups independently selected from:

a) hydroxyl, halogen (e.g., fluorine, chlorine, bromine, and iodine), amino, cyano,
b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted),
c) $C(O)NR_x'R_x$, and $C(O)OR_x$,
wherein $R_x$ and $R_x'$ are each independently H, or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, each $R_p$ is independently phenyl substituted with methyl, ethyl, methoxy, ethoxy, $C(O)NH_2$, or $C(O)N(CH_3)_2$.

For example, each $R_p$ is independently heteroaryl selected from pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, and purinyl, each of which is optionally substituted.

For example, each $R_p$ is independently pyridinyl.

For example, each $R_p$ is independently $C_3$-$C_{10}$ carbocycle selected from cyclopropyl, cyclobutyl, cyclopentyl, cyclohexyl, and cycloheptyl, each of which is optionally substituted.

For example, each $R_p$ is independently cyclopropyl or cyclobutyl.

For example, each $R_p$ is independently cyclobutyl substituted with amino.

For example, each $R_p$ is independently heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, morpholinyl, and piperidinonyl, each of which is optionally substituted.

For example, each $R_p$ is independently piperidinyl, piperidinonyl, or morpholinyl.

For example, each $R_p$ is independently $OR_5$, $NR_sR_5$, $SR_5$, $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$.

For example, $R_s$ is H.

For example, $R_s$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, $R_s'$ is H.

For example, $R_s'$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl.

For example, $R_5$ is H.

For example, $R_5$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_5$ is unsubstituted or substituted $C_6$-$C_{10}$ aryl-$C_1$-$C_6$ alkyl, including but not limited to, benzyl, phenylethyl, naphthylmethyl, and naphthylethyl, each of which is optionally substituted.

For example, $R_5$ is phenyl or naphthyl, each of which is optionally substituted.

For example, $R_5$ is heteroaryl selected from pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted.

For example, $R_5$ is $C_3$-$C_{10}$ carbocycle selected from cyclopropyl, cyclobutyl, cyclopentyl, cyclohexyl, and cycloheptyl, each of which is optionally substituted.

For example, $R_5$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted.

For example, each $R_p$ is independently $OR_5$ or $SR_5$; and $R_5$ is unsubstituted or substituted $C_6$-$C_{10}$ aryl-$C_1$-$C_6$ alkyl (e.g., benzyl, phenylethyl, naphthylmethyl, and naphthylethyl, each of which is optionally substituted), or unsubstituted or substituted $C_6$-$C_{10}$ aryl (e.g., phenyl and naphthyl, each of which is optionally substituted).

For example, each $R_p$ is independently $OR_5$; and $R_5$ is benzyl or phenyl.

For example, each $R_p$ is independently $NR_sR_5$; $R_s$ is H, or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl); and $R_5$ is:
 a) unsubstituted or substituted $C_6$-$C_{10}$ aryl (e.g., phenyl and naphthyl, each of which is optionally substituted),
 b) unsubstituted or substituted heteroaryl comprising one or two 5- or 6-membered rings and 1-4 heteroatoms selected from N, O and S (e.g., pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, and thiozolonyl, each of which is optionally substituted),
 c) unsubstituted or substituted $C_3$-$C_{10}$ carbocycle (e.g., cyclopropyl, cyclobutyl, cyclopentyl, cyclohexyl, and cycloheptyl, each of which is optionally substituted), or
 d) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted).

For example, each $R_p$ is independently $NR_sR_5$; $R_s$ is H or methyl; and $R_5$ is methyl, phenyl, thiazolyl, or thiozolonyl.

For example, each $R_p$ is independently $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$; $R_s$ and $R_s'$ are each independently H, or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl); and $R_5$ is:
 a) H,
 b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted with one or more groups independently selected from:
   i) hydroxyl, halogen (e.g., fluorine, chlorine, bromine, and iodine),
   ii) unsubstituted or substituted $C_1$-$C_6$ alkoxy (e.g., methoxy, ethoxy, propyloxy, i-propyloxy, butoxy, and t-butoxy, each of which is optionally substituted)),
   iii) $C(O)R_y$, and $C(O)OR_y$,
   wherein $R_y$ is H or unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted)),
 c) unsubstituted or substituted $C_6$-$C_{10}$ aryl-$C_1$-$C_6$ alkyl (e.g., benzyl, phenylethyl, naphthylmethyl, and naphthylethyl, each of which is optionally substituted),
 d) unsubstituted or substituted $C_6$-$C_{10}$ aryl (e.g., phenyl and naphthyl, each of which is optionally substituted),
 e) unsubstituted or substituted heteroaryl comprising one or two 5- or 6-membered rings and 1-4 heteroatoms selected from N, O and S (e.g., pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted),
 f) unsubstituted or substituted $C_3$-$C_{10}$ carbocycle (e.g., cyclopropyl, cyclobutyl, cyclopentyl, cyclohexyl, and cycloheptyl, each of which is optionally substituted), or
 g) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted).

For example, each $R_p$ is independently $C(O)R_5$, $C(O)OR_5$, $C(O)NR_sR_5$, $NR_s'C(O)R_5$, $NR_s'C(O)OR_5$, $NR_s'C(O)NR_sR_5$, $S(O)_2R_5$, or $NR_s'S(O)_2R_5$; $R_s$ and $R_s'$ are each independently H or methyl; and $R_5$ is H, methyl, ethyl, i-propyl, t-butyl, benzyl, phenyl, cyclopropyl, or pyrrolidinyl, each of which is optionally substituted. For example, $R_5$ is methyl, ethyl, or i-propyl, each of which is optionally substituted with hydroxyl, fluorine, or $C(O)OCH_3$.

For example, x is 0.

For example, x is 1.

For example, x is 2.

For example, each $R_q$ is independently:
 a) hydroxyl, halogen (e.g., fluorine, chlorine, bromine, and iodine), cyano, nitro,
 b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted),
 c) unsubstituted or substituted $C_1$-$C_6$ alkoxy (e.g., methoxy, ethoxy, propyloxy, i-propyloxy, butoxy, t-butoxy, methylenedioxy, and ethylenedioxy, each of which is optionally substituted), d) amino, unsubstituted or substituted $C_1$-$C_6$ alkylamino (e.g., methylamino, ethylamino, propylamino, butylamino, and pentylamino, each of which is optionally substituted), unsubstituted or substituted di-$C_1$-$C_6$ alkylamino (e.g., dimethylamino, diethylamino, dipropylamino, dibutylamino, and dipentylamino, each of which is optionally substituted), e) unsubstituted or substituted $C_6$-$C_{10}$ aryl (e.g., phenyl and naphthyl, each of which is optionally substituted), f) unsubstituted or substituted heteroaryl comprising one or two 5- or 6-membered rings and 1-4 heteroatoms selected from N, O and S (e.g., pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, each of which is optionally substituted), g) unsubstituted or substituted $C_3$-$C_{10}$ carbocycle (e.g., cyclopropyl, cyclobutyl, cyclopentyl, cyclohexyl, and cycloheptyl, each of which is optionally substituted), or h) unsubstituted or substituted heterocycle comprising one or two 5- or 6-membered rings and 1-4 heteroatoms selected from N, O and S (e.g., pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted).

For example, each $R_q$ is independently hydroxyl, halogen, cyano, nitro, unsubstituted or substituted $C_1$-$C_6$ alkyl, unsubstituted or substituted $C_1$-$C_6$ alkoxy, amino, unsubstituted or substituted $C_1$-$C_6$ alkylamino, or unsubstituted or substituted di-$C_1$-$C_6$ alkylamino.

For example, each $R_q$ is independently fluorine or chlorine.

For example, $R_c$ is H, amino, fluorine, chlorine, bromine, or iodine.

For example, only one of $R_a$, $R_b$ and $R_c$ is H.

For example, $R_c$ is amino; $R_a$ and $R_b$ are each H.

For example, $R_c$ is amino; $R_b$ is H; and $R_a$ is unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_c$ is amino; $R_b$ is H; and $R_a$ is methyl.

For example, $R_c$ is amino; $R_a$ and $R_b$ are each independently unsubstituted or substituted, straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl, and n-hexyl, each of which is optionally substituted.

For example, $R_c$ is amino; $R_a$ and $R_b$ are each methyl.

For example, $R_c$ is H or amino; and $R_a$ and $R_b$, together with the carbon atom to which they are attached, form a carbocycle selected from cyclopropyl, cyclobutyl, cyclopentyl, cyclohexyl, and cycloheptyl, each of which is optionally substituted with one or more groups independently selected from:

a) hydroxyl, amino, halogen (e.g., fluorine, chlorine, bromine, and iodine), and b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, $R_c$ is H or amino; and $R_a$ and $R_b$, together with the carbon atom to which they are attached, form a heterocycle selected from oxetanyl, oxazolidinyl, oxazolidinonyl, pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, each of which is optionally substituted with one or more groups independently selected from:

a) hydroxyl, amino, halogen (e.g., fluorine, chlorine, bromine, and iodine), and b) unsubstituted or substituted $C_1$-$C_6$ alkyl (e.g., methyl, ethyl, n-propyl, i-propyl, n-butyl, s-butyl, t-butyl, n-pentyl, s-pentyl, and n-hexyl, each of which is optionally substituted).

For example, $R_c$ is H; and $R_a$ and $R_b$, together with the carbon atom to which they are attached, form oxazolidinyl or oxazolidinonyl, each of which is optionally substituted with methyl, which is optionally substituted with hydroxyl.

For example, $R_c$ is amino; and $R_a$ and $R_b$, together with the carbon atom to which they are attached, form cyclopropyl, cyclobutyl, or oxetanyl, each of which is optionally substituted.

Representative compounds of the present invention include compounds listed in Table 1.

TABLE 1

| Cmpd. No. | Structure/Chemical name |
|---|---|
| 1 | 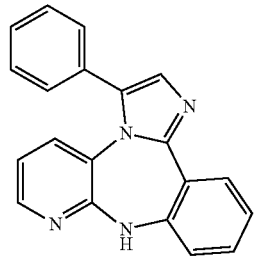<br>3-phenyl-9H-benzo[f]imidazo[1,2-d]pyrido[2,3-b][1,4]diazepine |
| 2 | 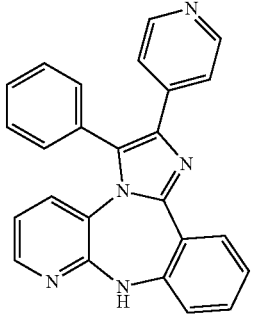<br>3-phenyl-2-(pyridin-4-yl)-9H-benzo[f]imidazo[1,2-d]pyrido[2,3-b][1,4]diazepine |
| 3 | 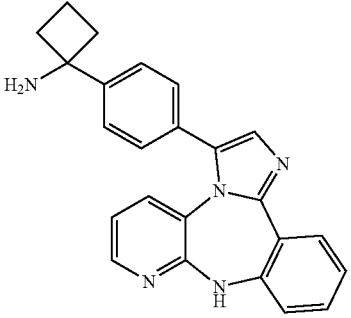<br>1-(4-(9H-benzo[f]imidazo[1,2-d]pyrido[2,3-b][1,4]diazepin-3-yl)phenyl)cyclobutanamine |

TABLE 1-continued

| Cmpd. No. | Structure/Chemical name |
|---|---|
| 4 | 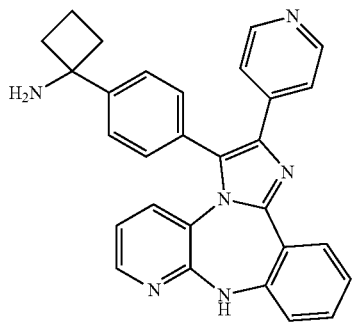

1-(4-(2-(pyridin-4-yl)-9H-benzo[f]
imidazo[1,2-d]pyrido[2,3-b][1,4]
diazepin-3-yl)phenyl)
cyclobutanamine |
| 5 | 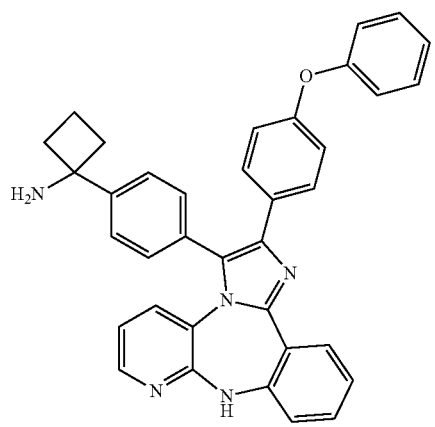

1-(4-(2-(4-phenoxyphenyl)-9H-benzo
[f]imidazo[1,2-d]pyrido[2,3-b][1,4]
diazepin-3-yl)phenyl)
cyclobutanamine |
| 6 | 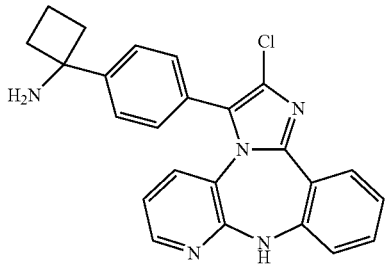

1-(4-(2-chloro-9H-benzo[f]imidazo
[1,2-d]pyrido[2,3-b][1,4]diazepin-3-
yl)phenyl)cyclobutanamine |

TABLE 1-continued

| Cmpd. No. | Structure/Chemical name |
|---|---|
| 7 | 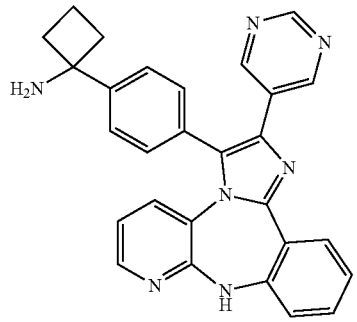

1-(4-(2-(pyrimidin-5-yl)-9H-benzo[f]
imidazo[1,2-d]pyrido[2,3-b][1,4]
diazepin-3-yl)phenyl)
cyclobutanamine |
| 8 | 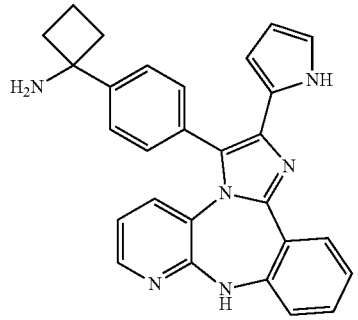

1-(4-(2-(1H-pyrrol-2-yl)-9H-benzo[f]
imidazo[1,2-d]pyrido[2,3-b][1,4]
diazepin-3-yl)phenyl)
cyclobutanamine |
| 9 | 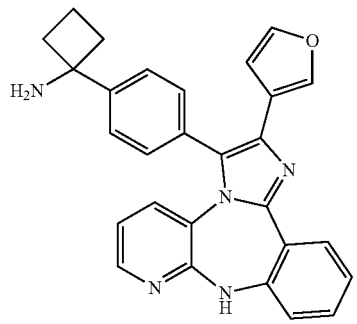

1-(4-(2-(furan-3-yl)-9H-benzo[f]
imidazo[1,2-d]pyrido[2,3-b][1,4]
diazepin-3-yl)phenyl)
cyclobutanamine |

TABLE 1-continued

| Cmpd. No. | Structure/Chemical name |
|---|---|
| 10 | 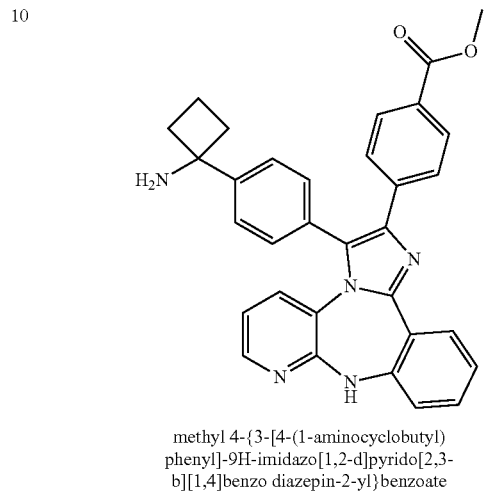<br>methyl 4-{3-[4-(1-aminocyclobutyl)phenyl]-9H-imidazo[1,2-d]pyrido[2,3-b][1,4]benzo diazepin-2-yl}benzoate |
| 11 | 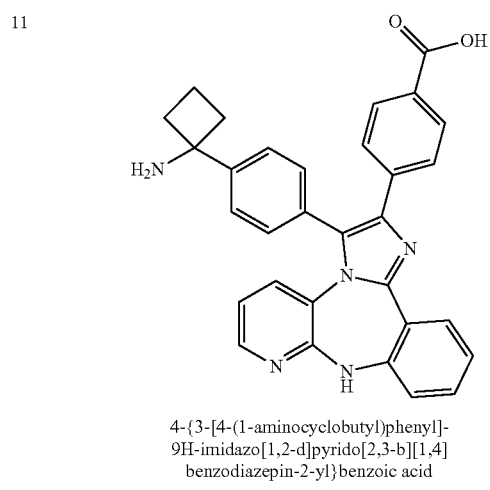<br>4-{3-[4-(1-aminocyclobutyl)phenyl]-9H-imidazo[1,2-d]pyrido[2,3-b][1,4]benzodiazepin-2-yl}benzoic acid |
| 12 | 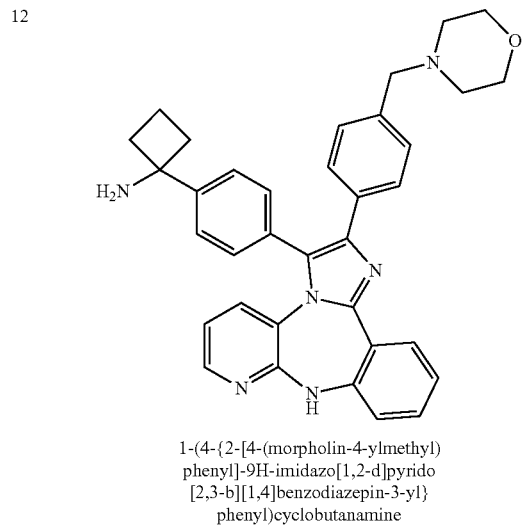<br>1-(4-{2-[4-(morpholin-4-ylmethyl)phenyl]-9H-imidazo[1,2-d]pyrido[2,3-b][1,4]benzodiazepin-3-yl}phenyl)cyclobutanamine |
| 13 | 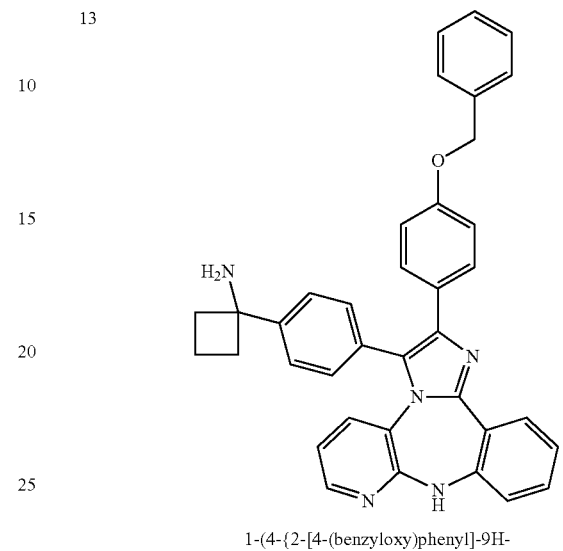<br>1-(4-{2-[4-(benzyloxy)phenyl]-9H-imidazo[1,2-d]pyrido[2,3-b][1,4]benzodiazepin-3-yl}phenyl)cyclobutanamine |
| 14 | 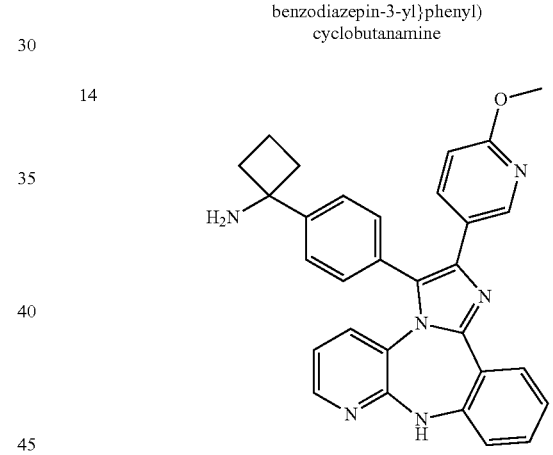<br>1-{4-[2-(6-methoxypyridin-3-yl)-9H-imidazo[1,2-d]pyrido[2,3-b][1,4]benzodiazepin-3-yl]phenyl}cyclobutanamine |
| 15 | 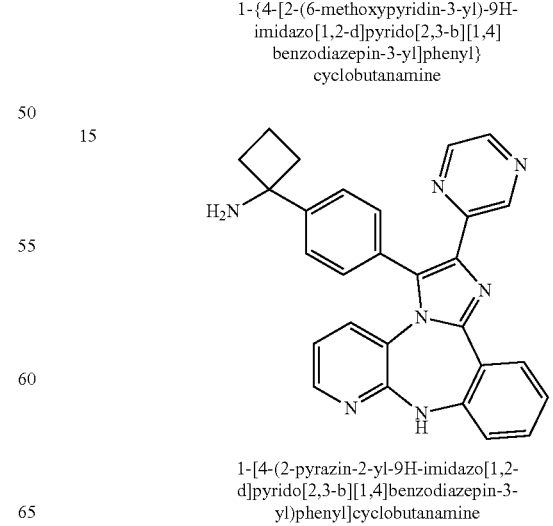<br>1-[4-(2-pyrazin-2-yl-9H-imidazo[1,2-d]pyrido[2,3-b][1,4]benzodiazepin-3-yl)phenyl]cyclobutanamine |

TABLE 1-continued

| Cmpd. No. | Structure/Chemical name |
|---|---|
| 16 | 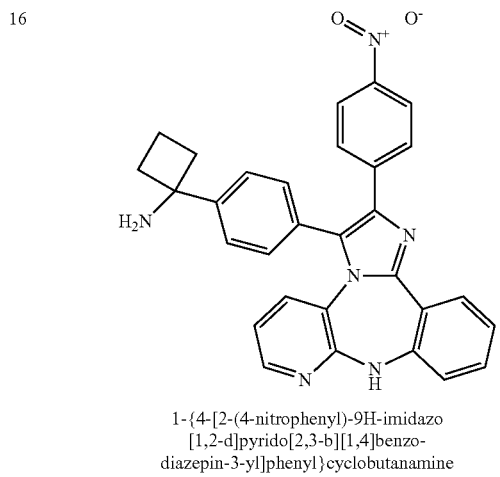<br>1-{4-[2-(4-nitrophenyl)-9H-imidazo[1,2-d]pyrido[2,3-b][1,4]benzodiazepin-3-yl]phenyl}cyclobutanamine |
| 17 | 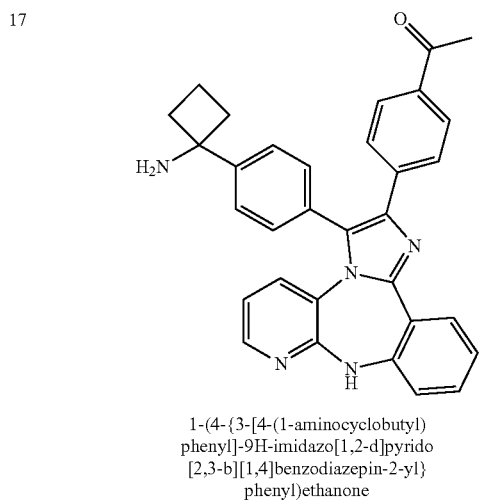<br>1-(4-{3-[4-(1-aminocyclobutyl)phenyl]-9H-imidazo[1,2-d]pyrido[2,3-b][1,4]benzodiazepin-2-yl}phenyl)ethanone |
| 18 | 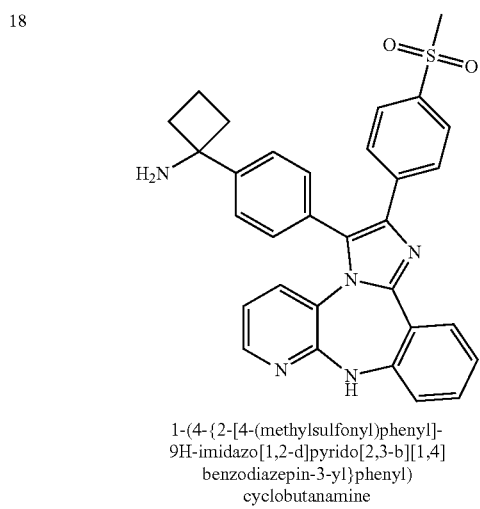<br>1-(4-{2-[4-(methylsulfonyl)phenyl]-9H-imidazo[1,2-d]pyrido[2,3-b][1,4]benzodiazepin-3-yl}phenyl)cyclobutanamine |
| 19 | 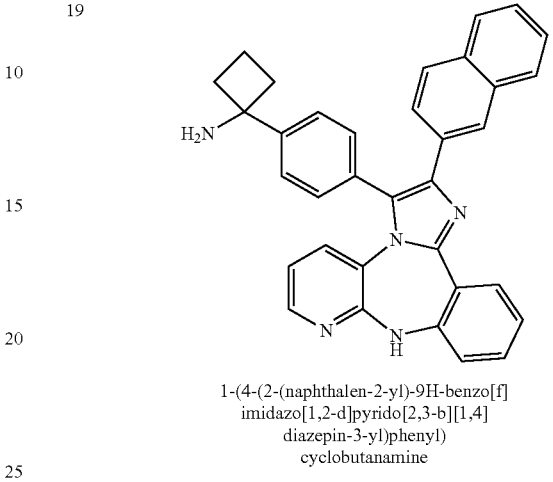<br>1-(4-(2-(naphthalen-2-yl)-9H-benzo[f]imidazo[1,2-d]pyrido[2,3-b][1,4]diazepin-3-yl)phenyl)cyclobutanamine |
| 20 | 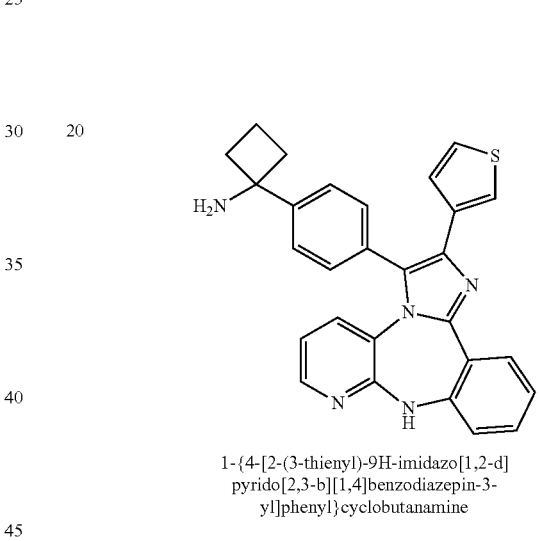<br>1-{4-[2-(3-thienyl)-9H-imidazo[1,2-d]pyrido[2,3-b][1,4]benzodiazepin-3-yl]phenyl}cyclobutanamine |
| 21 | 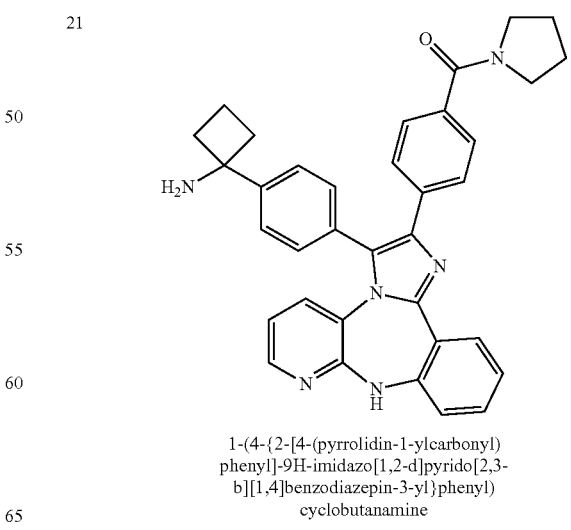<br>1-(4-{2-[4-(pyrrolidin-1-ylcarbonyl)phenyl]-9H-imidazo[1,2-d]pyrido[2,3-b][1,4]benzodiazepin-3-yl}phenyl)cyclobutanamine |

TABLE 1-continued

| Cmpd. No. | Structure/Chemical name |
|---|---|
| 22 | 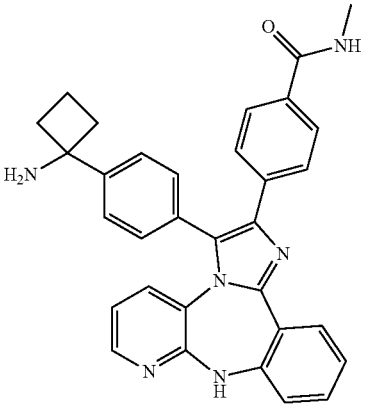<br>4-{3-[4-(1-aminocyclobutyl)phenyl]-9H-imidazo[1,2-d]pyrido[2,3-b][1,4]benzodiazepin-2-yl}-N-methylbenzamide |
| 23 | 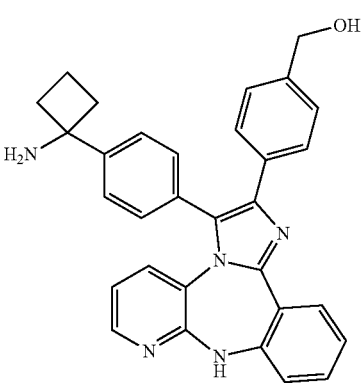<br>(4-{3-[4-(1-aminocyclobutyl)phenyl]-9H-imidazo[1,2-d]pyrido[2,3-b][1,4]benzodiazepin-2-yl}phenyl)methanol |
| 24 | 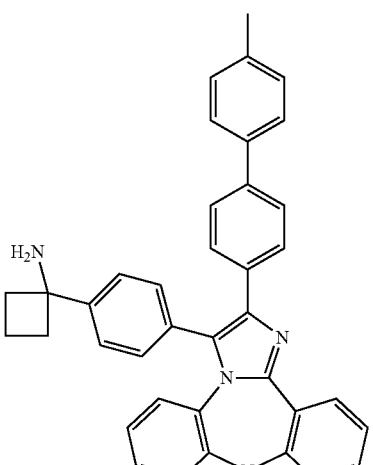<br>1-{4-[2-(4′-methylbiphenyl-4-yl)-9H-imidazo[1,2-d]pyrido[2,3-b][1,4]benzodiazepin-3-yl]phenyl}cyclobutanamine |
| 25 | 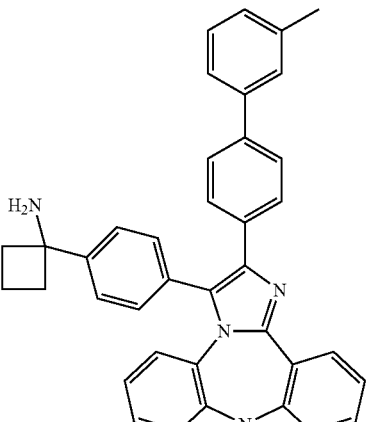<br>1-{4-[2-(3′-methylbiphenyl-4-yl)-9H-imidazo[1,2-d]pyrido[2,3-b][1,4]benzodiazepin-3-yl]phenyl}cyclobutanamine |
| 26 | 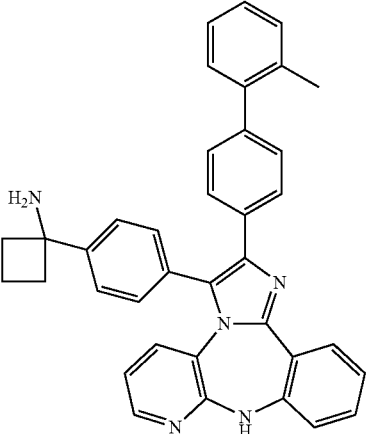<br>1-{4-[2-(2′-methylbiphenyl-4-yl)-9H-imidazo[1,2-d]pyrido[2,3-b][1,4]benzodiazepin-3-yl]phenyl}cyclobutanamine |

TABLE 1-continued

| Cmpd. No. | Structure/Chemical name |
|---|---|
| 27 | 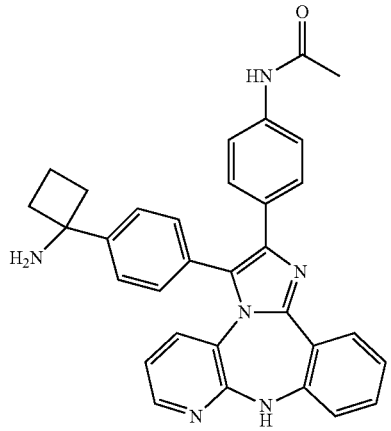<br>N-(4-{3-[4-(1-aminocyclobutyl) phenyl]-9H-imidazo[1,2-d]pyrido [2,3-b][1,4]benzodiazepin-2-yl} phenyl)acetamide |
| 28 | 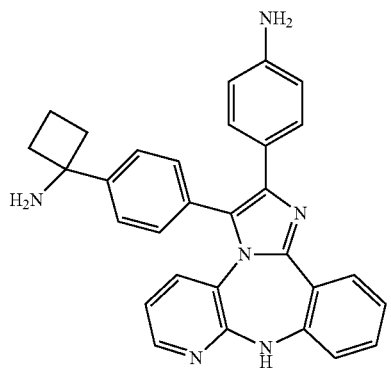<br>4-{3-[4-(1-aminocyclobutyl)phenyl]- 9H-imidazo[1,2-d]pyrido[2,3-b][1,4] benzodiazepin-2-yl}aniline |
| 29 | 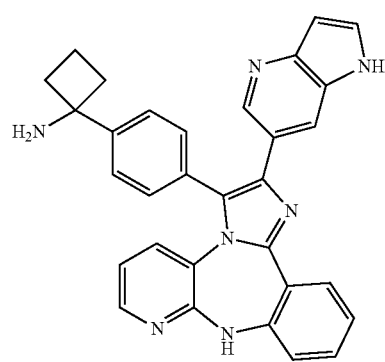<br>1-{4-[2-(1H-pyrrolo[3,2-b]pyridin-6-yl)-9H-imidazo[1,2-d]pyrido[2,3-b] [1,4]benzodiazepin-3-yl]phenyl} cyclobutanamine |

TABLE 1-continued

| Cmpd. No. | Structure/Chemical name |
|---|---|
| 30 | 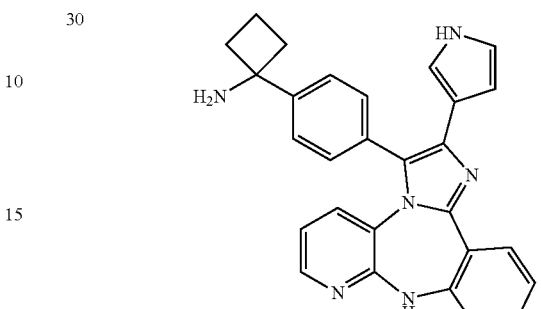<br>1-{4-[2-(1H-pyrrol-3-yl)-9H-imidazo [1,2-d]pyrido[2,3-b][1,4]benzo diazepin-3-yl]phenyl} cyclobutanamine |
| 31 | 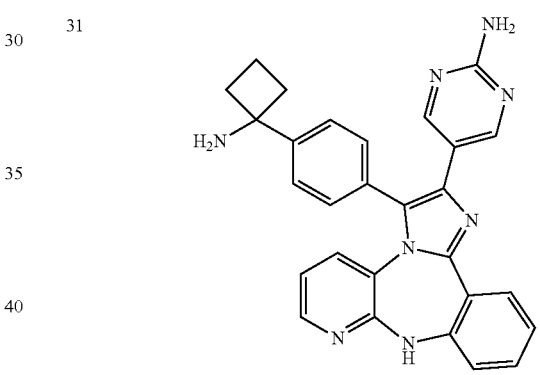<br>5-{3-[4-(1-aminocyclobutyl)phenyl]- 9H-imidazo[1,2-d]pyrido[2,3-b][1,4] benzodiazepin-2-yl}pyrimidin-2-amine |
| 32 | 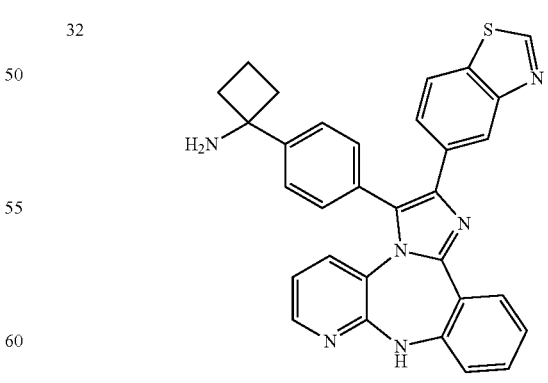<br>1-{4-[2-(1,3-benzothiazol-5-yl)-9H-imidazo[1,2-d]pyrido[2,3-b][1,4] benzodiazepin-3-yl]phenyl} cyclobutanamine |

TABLE 1-continued

| Cmpd. No. | Structure/Chemical name |
|---|---|
| 33 | 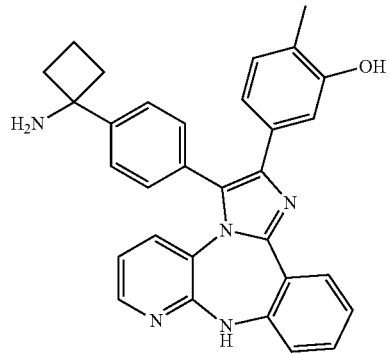<br>5-{3-[4-(1-aminocyclobutyl)phenyl]-9H-imidazo[1,2-d]pyrido[2,3-b][1,4]benzodiazepin-2-yl}-2-methylphenol |
| 34 | 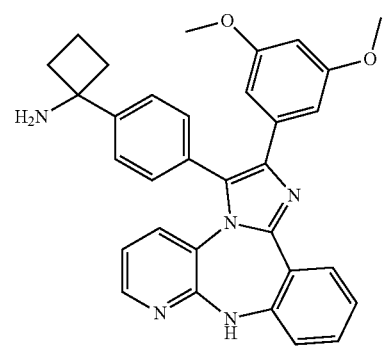<br>1-{4-[2-(3,5-dimethoxyphenyl)-9H-imidazo[1,2-d]pyrido[2,3-b][1,4]benzodiazepin-3-yl]phenyl}cyclobutanamine |
| 35 | 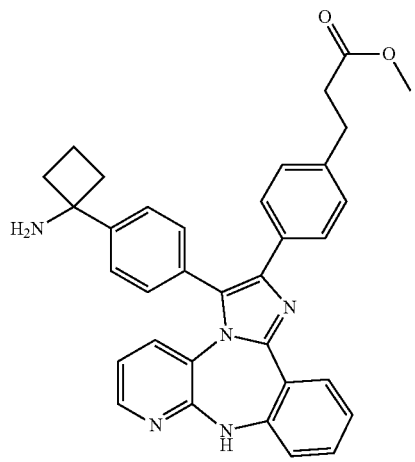<br>methyl 3-(4-{3-[4-(1-aminocyclobutyl)phenyl]-9H-imidazo[1,2-d]pyrido[2,3-b][1,4]benzodiazepin-2-yl}phenyl)propanoate |
| 36 | 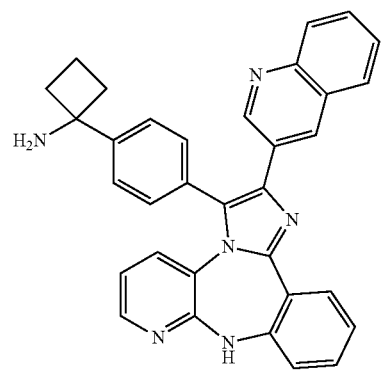<br>1-[4-(2-quinolin-3-yl-9H-imidazo[1,2-d]pyrido[2,3-b][1,4]benzodiazepin-3-yl)phenyl]cyclobutanamine |
| 37 | 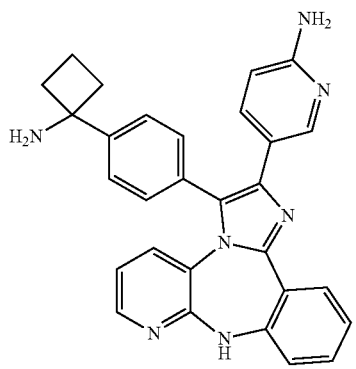<br>5-{3-[4-(1-aminocyclobutyl)phenyl]-9H-imidazo[1,2-d]pyrido[2,3-b][1,4]benzodiazepin-2-yl}pyridin-2-amine |
| 38 | 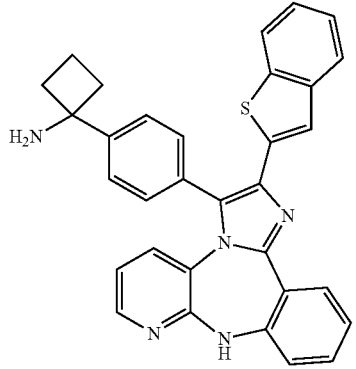<br>1-{4-[2-(1-benzothien-2-yl)-9H-imidazo[1,2-d]pyrido[2,3-b][1,4]benzodiazepin-3-yl]phenyl}cyclobutanamine |

TABLE 1-continued

| Cmpd. No. | Structure/Chemical name |
|---|---|
| 39 | 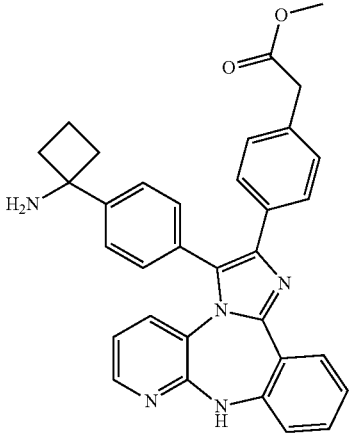<br>methyl(4-{3-[4-(1-aminocyclo-butyl)phenyl]-9H-imidazo[1,2-d]pyrido[2,3-b][1,4]benzodiazepin-2-yl}phenyl)acetate |
| 40 | 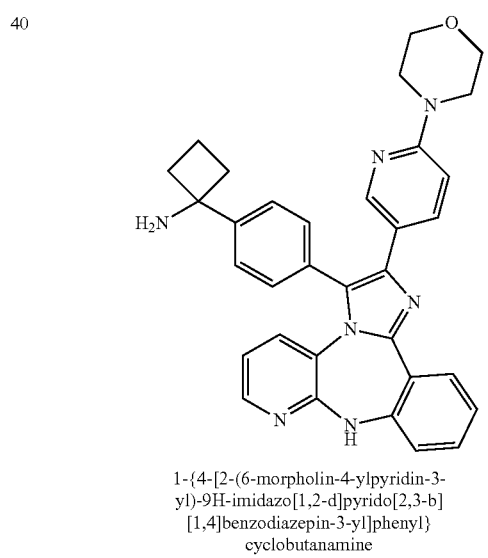<br>1-{4-[2-(6-morpholin-4-ylpyridin-3-yl)-9H-imidazo[1,2-d]pyrido[2,3-b][1,4]benzodiazepin-3-yl]phenyl}cyclobutanamine |
| 41 | 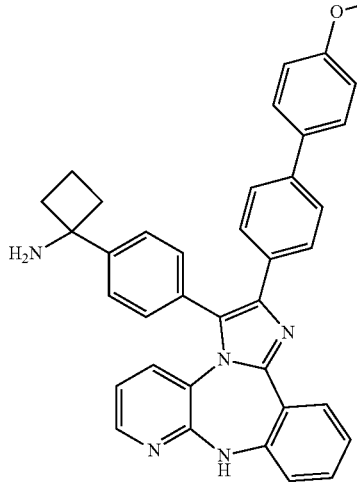<br>1-{4-[2-(4′-methoxybiphenyl-4-yl)-9H-imidazo[1,2-d]pyrido[2,3-b][1,4]benzodiazepin-3-yl]phenyl}cyclobutanamine |
| 42 | 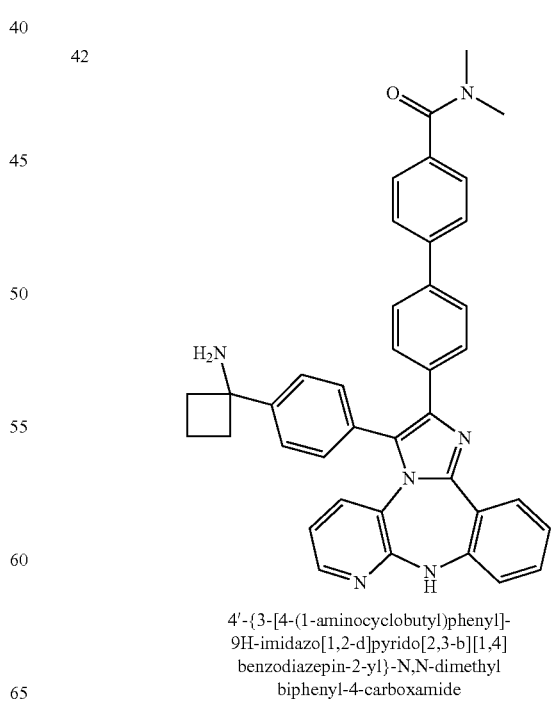<br>4′-{3-[4-(1-aminocyclobutyl)phenyl]-9H-imidazo[1,2-d]pyrido[2,3-b][1,4]benzodiazepin-2-yl}-N,N-dimethyl biphenyl-4-carboxamide |

TABLE 1-continued

| Cmpd. No. | Structure/Chemical name |
|---|---|
| 43 | 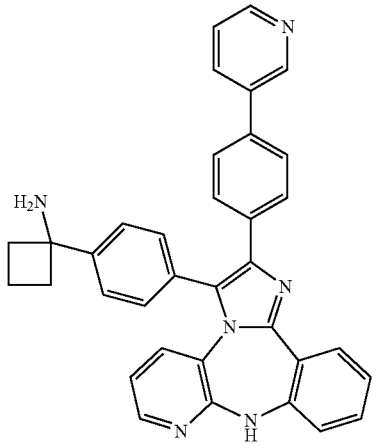<br>1-{4-[2-(4-pyridin-3-ylphenyl)-9H-imidazo[1,2-d]pyrido[2,3-b][1,4]benzodiazepin-3-yl]phenyl}cyclobutanamine |
| 44 | 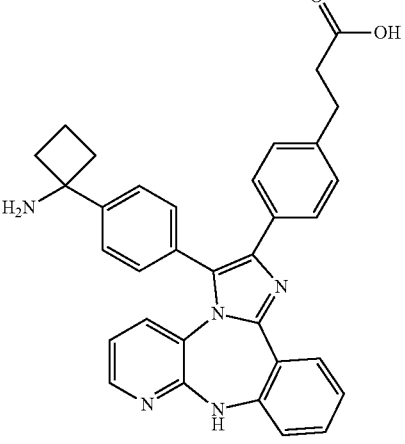<br>1-{4-[2-(4-pyridin-4-ylphenyl)-9H-imidazo[1,2-d]pyrido[2,3-b][1,4]benzodiazepin-3-yl]phenyl}cyclobutanamine |
| 45 | 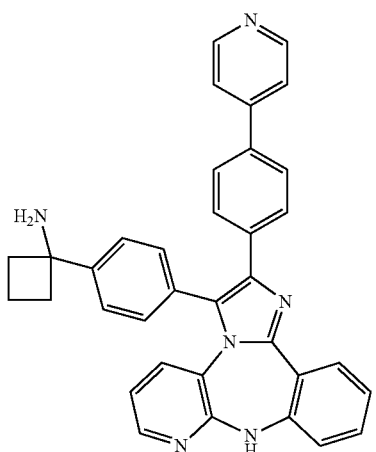<br>3-(4-{3-[4-(1-aminocyclobutyl)phenyl]-9H-imidazo[1,2-d]pyrido[2,3-b][1,4]benzodiazepin-2-yl}phenyl)propanoic acid |
| 46 | 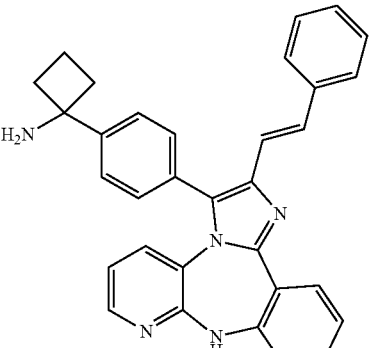<br>1-(4-{3-[4-(1-aminocyclobutyl)phenyl]-9H-imidazo[1,2-d]pyrido[2,3-b][1,4]benzodiazepin-2-yl}phenyl)ethanone |
| 47 | 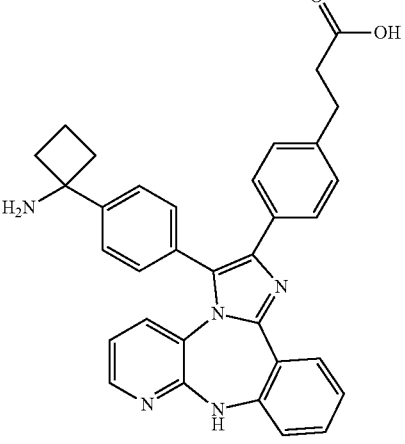<br>(E)-1-(4-(2-styryl-9H-benzo[f]imidazo[1,2-d]pyrido[2,3-b][1,4]diazepin-3-yl)phenyl)cyclobutanamine |

TABLE 1-continued

| Cmpd. No. | Structure/Chemical name |
|---|---|
| 48 | 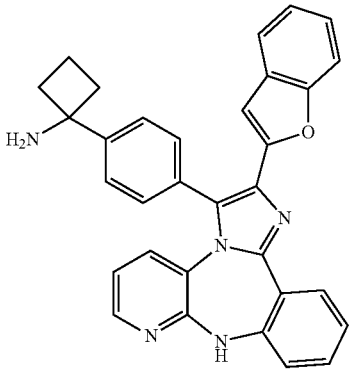
1-{4-[2-(1-benzofuran-2-yl)-9H-imidazo[1,2-d]pyrido[2,3-b][1,4]benzodiazepin-3-yl]phenyl}cyclobutanamine |
| 49 | 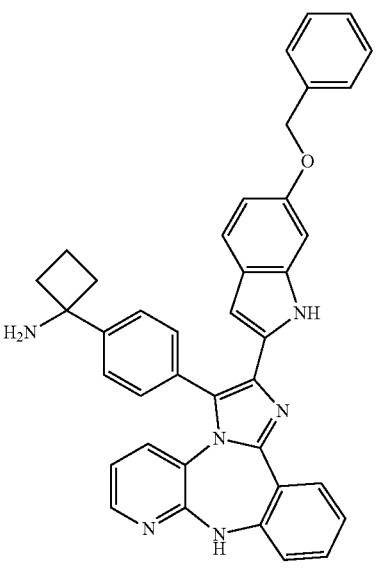
1-(4-{2-[6-(benzyloxy)-1H-indol-2-yl]-9H-imidazo[1,2-d]pyrido[2,3-b][1,4]benzodiazepin-3-yl}phenyl)cyclobutanamine |
| 50 | 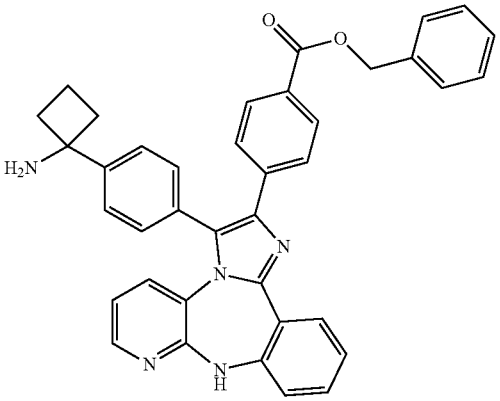
benzyl 4-{3-[4-(1-aminocyclobutyl)phenyl]-9H-imidazo[1,2-d]pyrido[2,3-b][1,4]benzodiazepin-2-yl}benzoate |
| 51 | 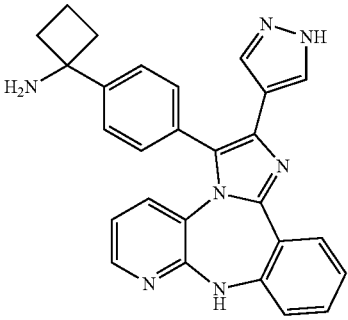
1-{4-[2-(1H-pyrazol-4-yl)-9H-imidazo[1,2-d]pyrido[2,3-b][1,4]benzodiazepin-3-yl]phenyl}cyclobutanamine |
| 52 | 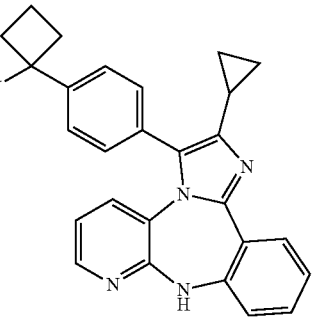
1-[4-(2-cyclopropyl-9H-imidazo[1,2-d]pyrido[2,3-b][1,4]benzodiazepin-3-yl)phenyl]cyclobutanamine |

TABLE 1-continued

| Cmpd. No. | Structure/Chemical name |
|---|---|
| 53 | 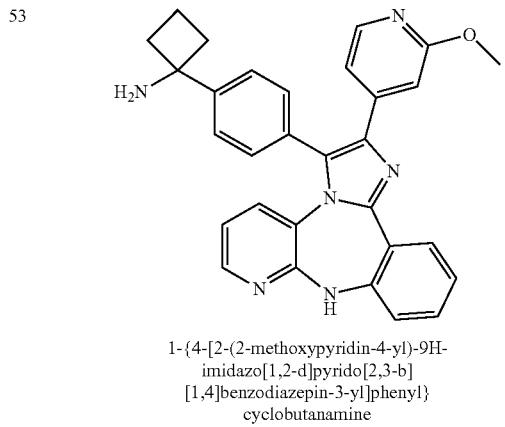
1-{4-[2-(2-methoxypyridin-4-yl)-9H-imidazo[1,2-d]pyrido[2,3-b][1,4]benzodiazepin-3-yl]phenyl}cyclobutanamine |
| 54 | 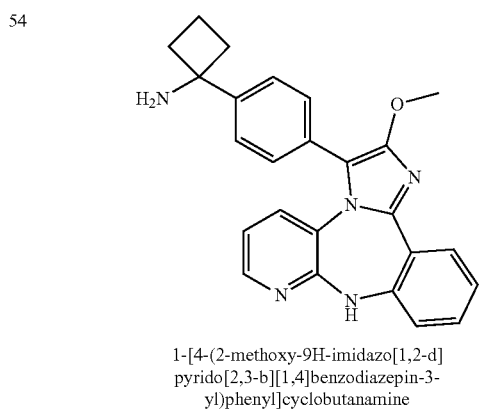
1-[4-(2-methoxy-9H-imidazo[1,2-d]pyrido[2,3-b][1,4]benzodiazepin-3-yl)phenyl]cyclobutanamine |
| 55 | 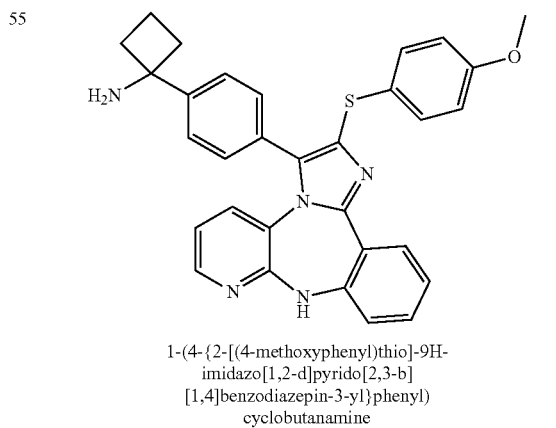
1-(4-{2-[(4-methoxyphenyl)thio]-9H-imidazo[1,2-d]pyrido[2,3-b][1,4]benzodiazepin-3-yl}phenyl)cyclobutanamine |
| 56 | 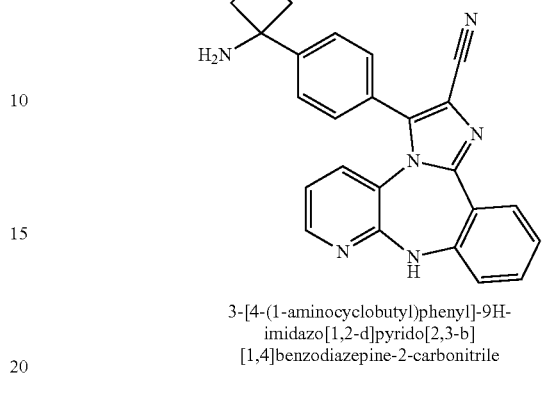
3-[4-(1-aminocyclobutyl)phenyl]-9H-imidazo[1,2-d]pyrido[2,3-b][1,4]benzodiazepine-2-carbonitrile |
| 57 | 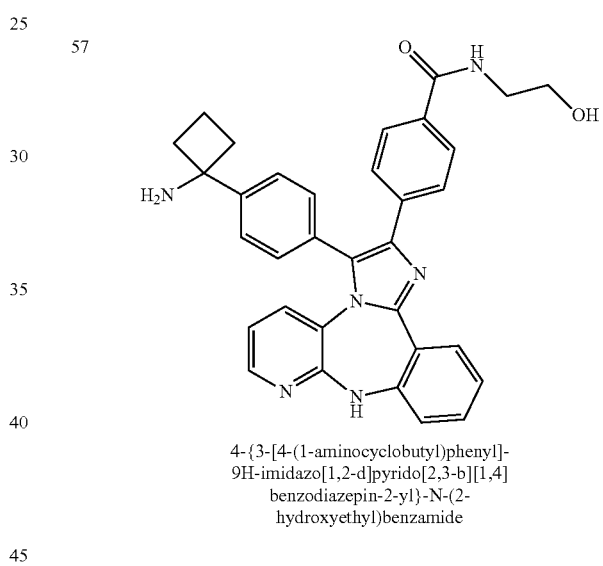
4-{3-[4-(1-aminocyclobutyl)phenyl]-9H-imidazo[1,2-d]pyrido[2,3-b][1,4]benzodiazepin-2-yl}-N-(2-hydroxyethyl)benzamide |
| 58 | 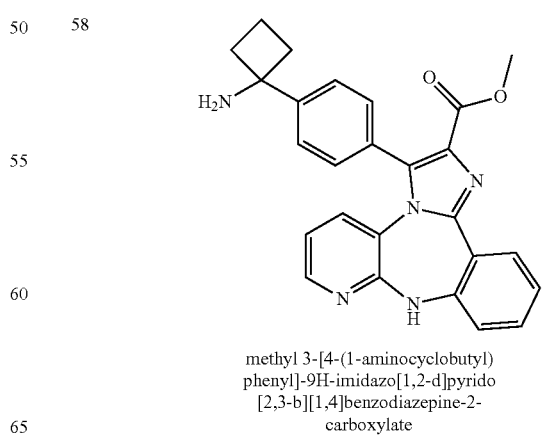
methyl 3-[4-(1-aminocyclobutyl)phenyl]-9H-imidazo[1,2-d]pyrido[2,3-b][1,4]benzodiazepine-2-carboxylate |

TABLE 1-continued

| Cmpd. No. | Structure/Chemical name |
|---|---|
| 59 | 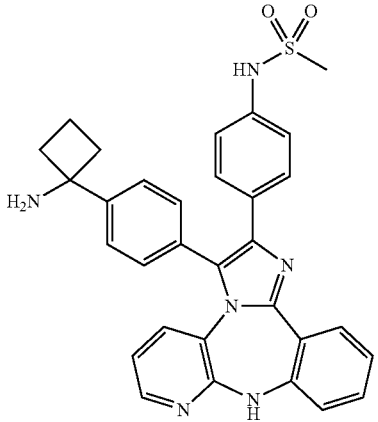<br>N-(4-{3-[4-(1-aminocyclobutyl)phenyl]-9H-imidazo[1,2-d]pyrido[2,3-b][1,4]benzodiazepin-2-yl}phenyl)methanesulfonamide |
| 60 | 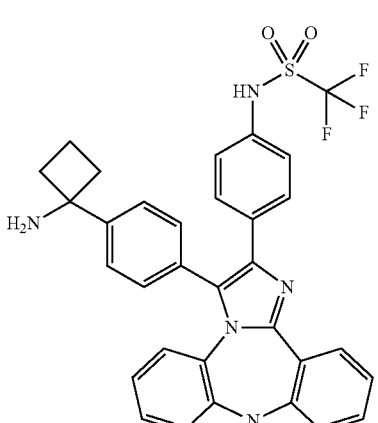<br>N-(4-{3-[4-(1-aminocyclobutyl)phenyl]-9H-imidazo[1,2-d]pyrido[2,3-b][1,4]benzodiazepin-2-yl}phenyl)-1,1,1-trifluoromethanesulfonamide |

TABLE 1-continued

| Cmpd. No. | Structure/Chemical name |
|---|---|
| 61 | 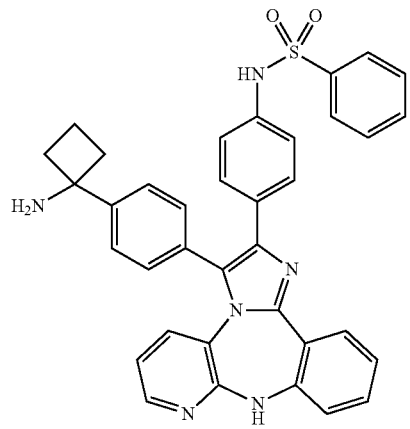<br>N-(4-{3-[4-(1-aminocyclobutyl)phenyl]-9H-imidazo[1,2-d]pyrido[2,3-b][1,4]benzodiazepin-2-yl}phenyl)benzenesulfonamide |
| 62 | 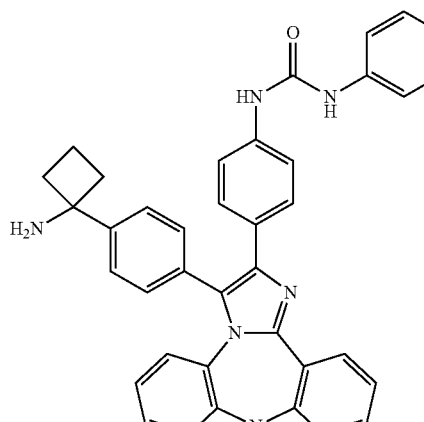<br>1-(4-{3-[4-(1-aminocyclobutyl)phenyl]-9H-imidazo[1,2-d]pyrido[2,3-b][1,4]benzodiazepin-2-yl}phenyl)-3-phenylurea |
| 63 | 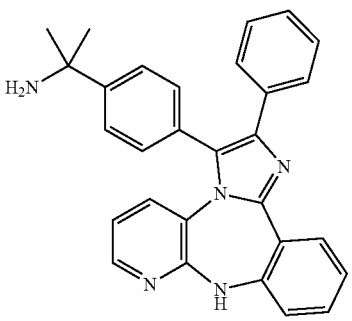<br>2-[4-(2-phenyl-9H-imidazo[1,2-d]pyrido[2,3-b][1,4]benzodiazepin-3-yl)phenyl]propan-2-amine |

TABLE 1-continued

| Cmpd. No. | Structure/Chemical name |
|---|---|
| 64 | 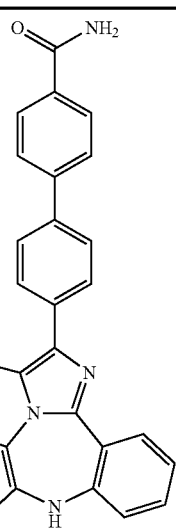<br>4'-{3-[4-(1-aminocyclobutyl)phenyl]-9H-imidazo[1,2-d]pyrido[2,3-b][1,4]benzodiazepine-2-yl}biphenyl-4-carboxamide |
| 65 | 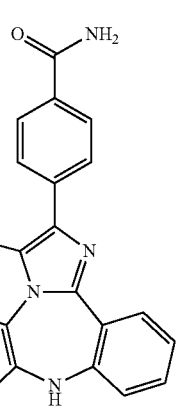<br>4-{3-[4-(1-aminocyclobutyl)phenyl]-9H-imidazo[1,2-d]pyrido[2,3-b][1,4]benzodiazepin-2-yl}benzamide |
| 66 | 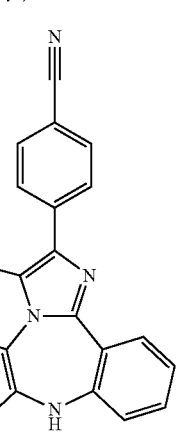<br>4-{3-[4-(1-aminocyclobutyl)phenyl]-9H-imidazo[1,2-d]pyrido[2,3-b][1,4]benzodiazepin-2-yl}benzonitrile |
| 67 | 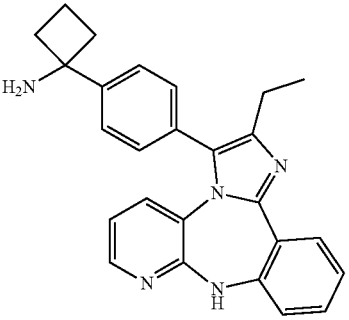<br>1-[4-(2-ethyl-9H-imidazo[1,2-d]pyrido[2,3-b][1,4]benzodiazepin-3-yl)phenyl]cyclobutanamine |
| 68 | 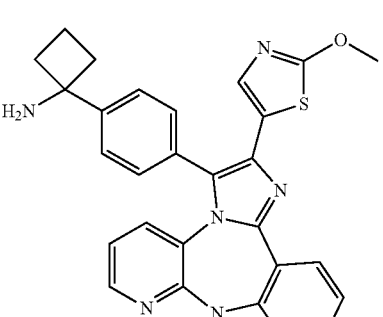<br>1-{4-[2-(2-methoxy-1,3-thiazol-5-yl)-9H-imidazo[1,2-d]pyrido[2,3-b][1,4]benzodiazepin-3-yl]phenyl}cyclobutanamine |
| 69 | 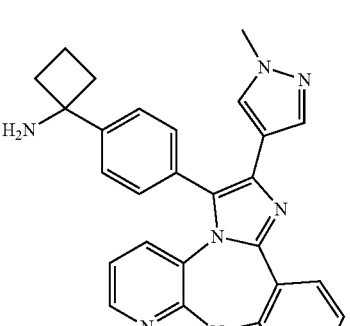<br>1-{4-[2-(1-methyl-1H-pyrazol-4-yl)-9H-imidazo[1,2-d]pyrido[2,3-b][1,4]benzodiazepin-3-yl]phenyl}cyclobutanamine |

TABLE 1-continued

| Cmpd. No. | Structure/Chemical name |
|---|---|
| 70 | 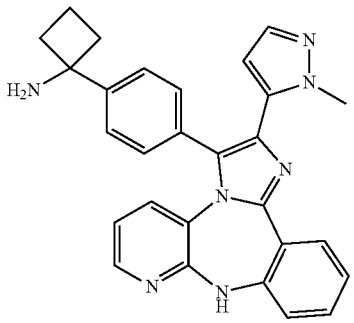<br>1-{4-[2-(1-methyl-1H-pyrazol-5-yl)-9H-imidazo[1,2-d]pyrido[2,3-b][1,4]benzodiazepin-3-yl]phenyl}cyclobutanamine |
| 71 | 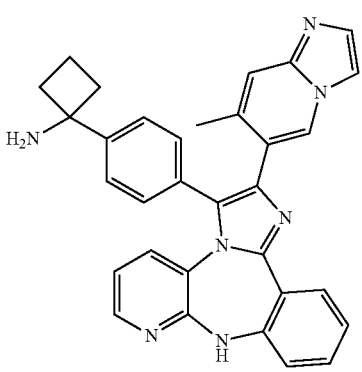<br>1-{4-[2-(7-methylimidazo[1,2-a]pyridin-6-yl)-9H-imidazo[1,2-d]pyrido[2,3-b][1,4]benzodiazepin-3-yl]phenyl}cyclobutanamine |
| 72 | 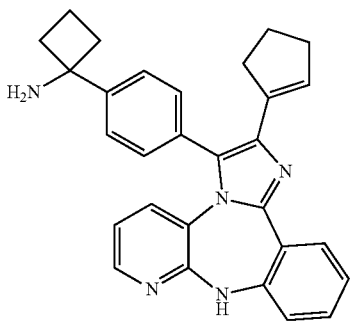<br>1-[4-(2-cyclopent-1-en-1-yl-9H-imidazo[1,2-d]pyrido[2,3-b][1,4]benzodiazepin-3-yl)phenyl]cyclobutanamine |
| 73 | 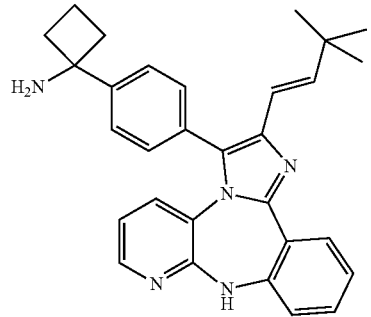<br>1-(4-{2-[(1E)-3,3-dimethylbut-1-en-1-yl]-9H-imidazo[1,2-d]pyrido[2,3-b][1,4]benzodiazepin-3-yl}phenyl)cyclobutanamine |
| 74 | 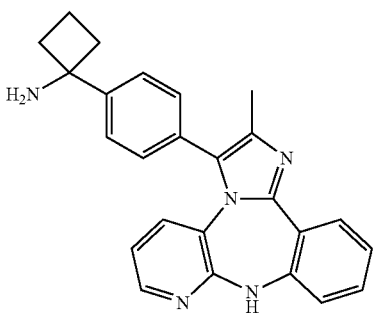<br>1-[4-(2-methyl-9H-imidazo[1,2-d]pyrido[2,3-b][1,4]benzodiazepin-3-yl)phenyl]cyclobutanamine |
| 75 | 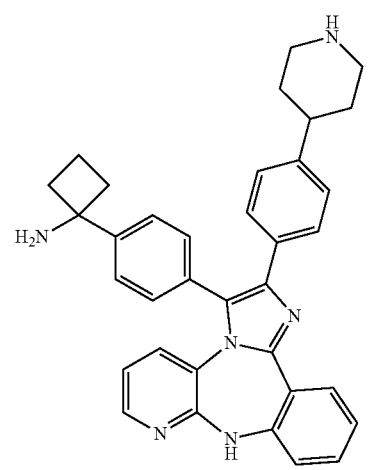<br>1-{4-[2-(4-piperidin-4-ylphenyl)-9H-imidazo[1,2-d]pyrido[2,3-b][1,4]benzodiazepin-3-yl]phenyl}cyclobutanamine |

TABLE 1-continued

| Cmpd. No. | Structure/Chemical name |
|---|---|
| 76 | 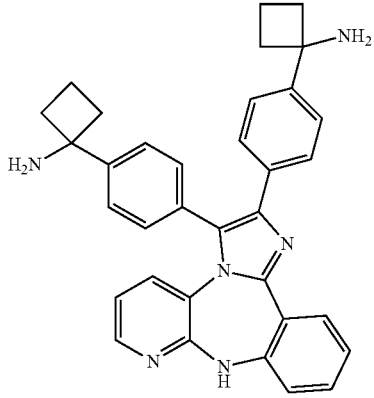<br>1,1′-(9H-imidazo[1,2-d]pyrido[2,3-b][1,4]benzodiazepine-2,3-diyldi-4,1-phenylene)dicyclobutanamine |
| 77 | 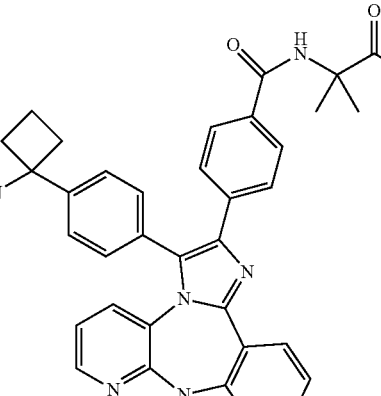<br>methyl N-(4-{3-[4-(1-amino-cyclobutyl)phenyl]-9H-imidazo[1,2-d]pyrido[2,3-b][1,4]benzodiazepin-2-yl}benzoyl)-2-methylalaninate |
| 78 | 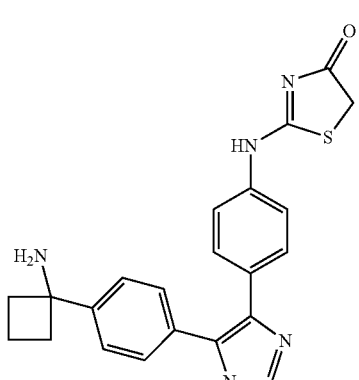<br>2-[(4-{3-[4-(1-aminocyclobutyl)phenyl]-9H-imidazo[1,2-d]pyrido[2,3-b][1,4]benzodiazepin-2-yl}phenyl)amino]-1,3-thiazol-4(5H)-one |
| 79 | 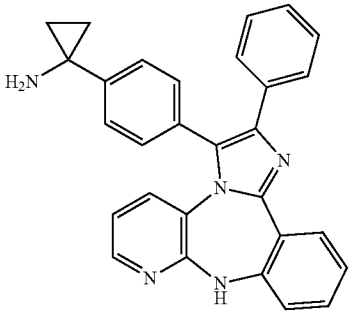<br>1-[4-(2-phenyl-9H-imidazo[1,2-d]pyrido[2,3-b][1,4]benzodiazepin-3-yl)phenyl]cyclopropanamine |
| 80 | 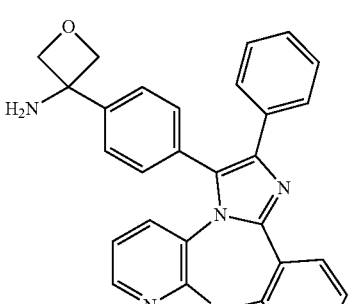<br>3-[4-(2-phenyl-9H-imidazo[1,2-d]pyrido[2,3-b][1,4]benzodiazepin-3-yl)phenyl]oxetan-3-amine |
| 81 | 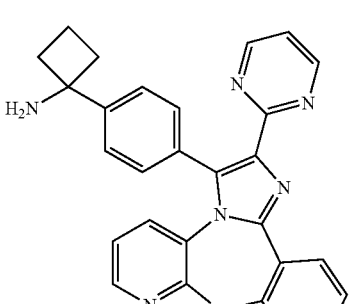<br>1-[4-(2-pyrimidin-2-yl-9H-imidazo[1,2-d]pyrido[2,3-b][1,4]benzodiazepin-3-yl)phenyl]cyclobutanamine |

TABLE 1-continued

| Cmpd. No. | Structure/Chemical name |
|---|---|
| 82 | 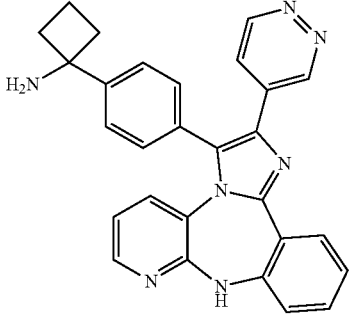

1-[4-(2-pyridazin-4-yl-9H-imidazo[1,2-d]pyrido[2,3-b][1,4]benzodiazepin-3-yl)phenyl]cyclobutanamine |
| 83 | 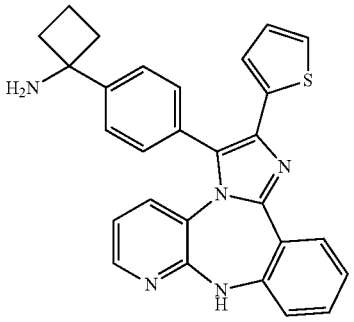

1-{4-[2-(2-thienyl)-9H-imidazo[1,2-d]pyrido[2,3-b][1,4]benzodiazepin-3-yl]phenyl}cyclobutanamine |
| 84 | 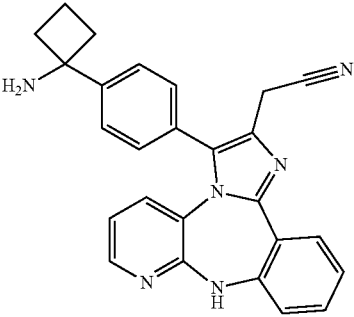

{3-[4-(1-aminocyclobutyl)phenyl]-9H-imidazo[1,2-d]pyrido[2,3-b][1,4]benzodiazepin-2-yl}acetonitrile |
| 85 | 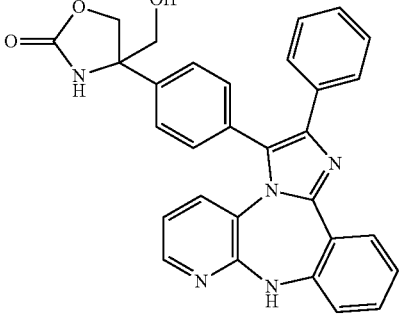

4-(hydroxymethyl)-4-[4-(2-phenyl-9H-imidazo[1,2-d]pyrido[2,3-b][1,4]benzodiazepin-3-yl)phenyl]-1,3-oxazolidin-2-one |
| 86 | 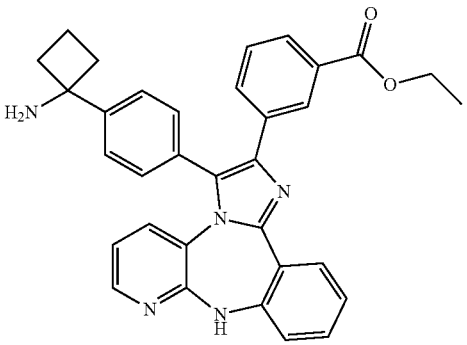

ethyl 3-{3-[4-(1-aminocyclobutyl)phenyl]-9H-imidazo[1,2-d]pyrido[2,3-b][1,4]benzodiazepin-2-yl}benzoate |
| 87 | 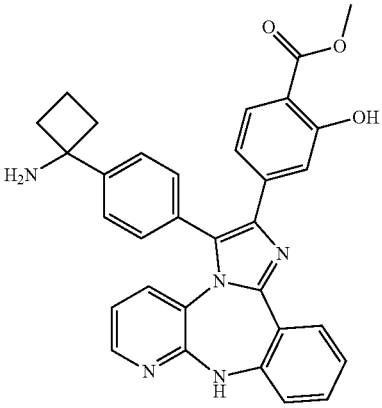

methyl 4-{3-[4-(1-aminocyclobutyl)phenyl]-9H-imidazo[1,2-d]pyrido[2,3-b][1,4]benzodiazepin-2-yl}-2-hydroxybenzoate |

TABLE 1-continued

| Cmpd. No. | Structure/Chemical name |
|---|---|
| 88 | 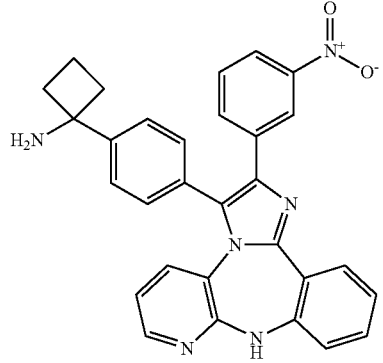 1-{4-[2-(3-nitrophenyl)-9H-imidazo [1,2-d]pyrido[2,3-b][1,4] benzodiazepin-3-yl]phenyl} cyclobutanamine |
| 89 | 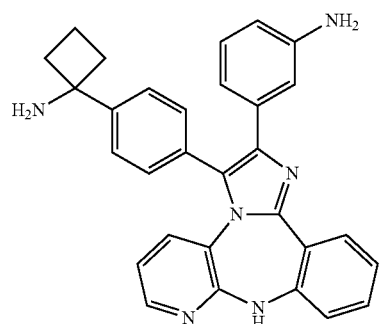 3-{3-[4-(1-aminocyclobutyl)phenyl]- 9H-imidazo[1,2-d]pyrido[2,3-b][1,4] benzodiazepin-2-yl}aniline |
| 90 | 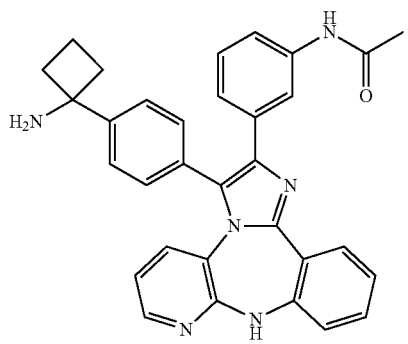 N-(3-{3-[4-(1-aminocyclobutyl) phenyl]-9H-imidazo[1,2-d]pyrido [2,3-b][1,4]benzodiazepin-2-yl} phenyl)acetamide |
| 91 | 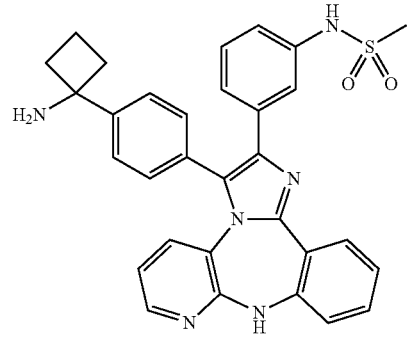 N-(3-{3-[4-(1-aminocyclobutyl) phenyl]-9H-imidazo[1,2-d]pyrido [2,3-b][1,4]benzodiazepin-2-yl} phenyl)methanesulfonamide |
| 92 | 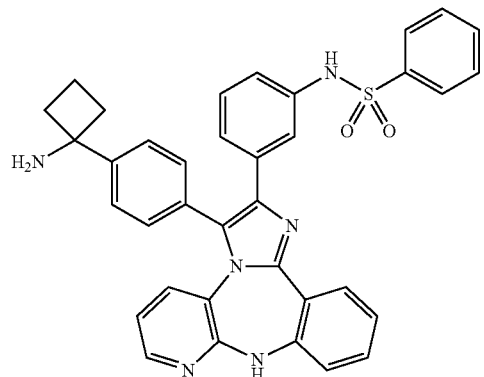 N-(3-{3-[4-(1-aminocyclobutyl) phenyl]-9H-imidazo[1,2-d]pyrido [2,3-b][1,4]benzodiazepin-2-yl} phenyl)benzenesulfonamide |
| 93 | 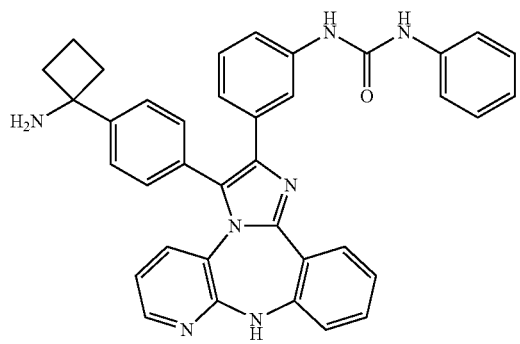 1-(3-{3-[4-(1-aminocyclobutyl) phenyl]-9H-imidazo[1,2-d]pyrido [2,3-b][1,4]benzodiazepin-2-yl} phenyl)-3-phenylurea |

TABLE 1-continued

| Cmpd. No. | Structure/Chemical name |
|---|---|
| 94 | N-(3-{3-[4-(1-aminocyclobutyl)phenyl]-9H-imidazo[1,2-d]pyrido[2,3-b][1,4]benzodiazepin-2-yl}phenyl)-1,1,1-trifluoromethane sulfonamide |
| 95 | 4-{3-[4-(1-aminocyclobutyl)phenyl]-9H-imidazo[1,2-d]pyrido[2,3-b][1,4]benzodiazepin-2-yl}phenol |
| 96 | 1-[4-(2-quinolin-6-yl-9H-imidazo[1,2-d]pyrido[2,3-b][1,4]benzodiazepin-3-yl)phenyl]cyclobutanamine |
| 97 | methyl 5-{3-[4-(1-aminocyclobutyl)phenyl]-9H-imidazo[1,2-d]pyrido[2,3-b][1,4]benzodiazepin-2-yl}pyridine-2-carboxylate |
| 98 | 5-{3-[4-(1-aminocyclobutyl)phenyl]-9H-imidazo[1,2-d]pyrido[2,3-b][1,4]benzodiazepin-2-yl}-2-benzofuran-1(3H)-one |
| 99 | 1-{4-[2-(1,2,3,6-tetrahydropyridin-4-yl)-9H-imidazo[1,2-d]pyrido[2,3-b][1,4]benzodiazepin-3-yl]phenyl}cyclobutanamine |

TABLE 1-continued

| Cmpd. No. | Structure/Chemical name |
|---|---|
| 100 | 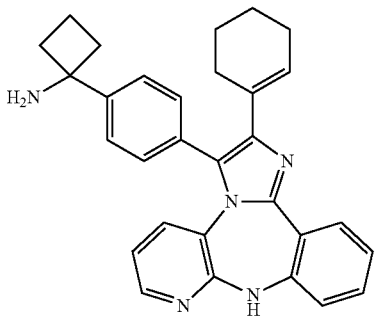  1-[4-(2-cyclohex-1-en-1-yl-9H-imidazo[1,2-d]pyrido[2,3-b][1,4]benzodiazepin-3-yl)phenyl]cyclobutanamine |
| 101 | 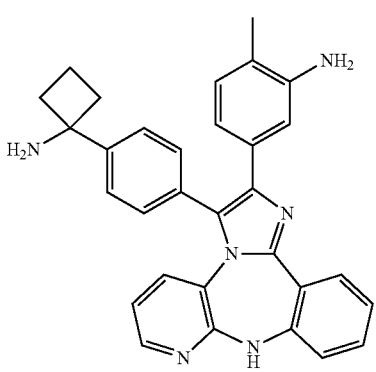  5-{3-[4-(1-aminocyclobutyl)phenyl]-9H-imidazo[1,2-d]pyrido[2,3-b][1,4]benzodiazepin-2-yl}-2-methylaniline |
| 102 | 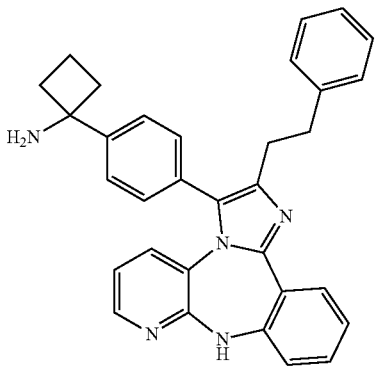 [SMILES: NC1(c2ccc(-c3c(CCc4ccccc4)nc4n3-c3cccnc3Nc3ccccc3-4)cc2)CCC1]  1-{4-[2-(2-phenylethyl)-9H-imidazo[1,2-d]pyrido[2,3-b][1,4]benzodiazepin-3-yl]phenyl}cyclobutanamine |
| 103 | 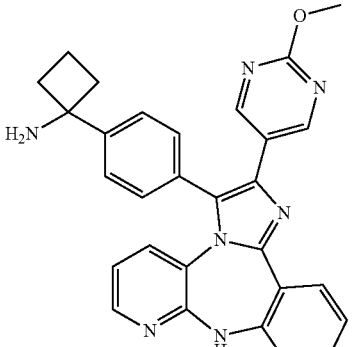  1-{4-[2-(2-methoxypyrimidin-5-yl)-9H-imidazo[1,2-d]pyrido[2,3-b][1,4]benzodiazepin-3-yl]phenyl}cyclobutanamine |
| 104 | 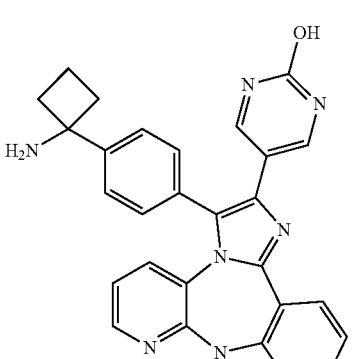  5-{3-[4-(1-aminocyclobutyl)phenyl]-9H-imidazo[1,2-d]pyrido[2,3-b][1,4]benzodiazepin-2-yl}pyrimidin-2-ol |
| 105 | 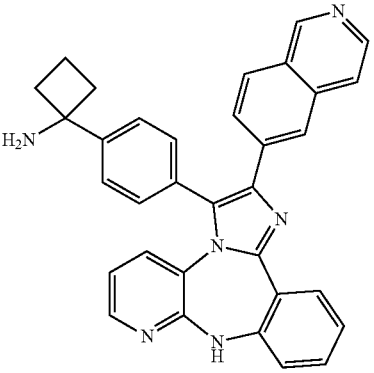  1-[4-(2-isoquinolin-6-yl-9H-imidazo[1,2-d]pyrido[2,3-b][1,4]benzodiazepin-3-yl)phenyl]cyclobutanamine |

TABLE 1-continued

| Cmpd. No. | Structure/Chemical name |
|---|---|
| 106 | 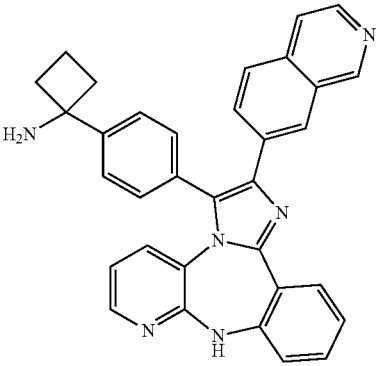<br>1-[4-(2-isoquinolin-7-yl-9H-imidazo[1,2-d]pyrido[2,3-b][1,4]benzodiazepin-3-yl)phenyl]cyclobutanamine |
| 107 | 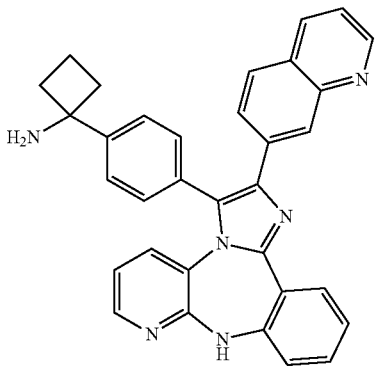<br>1-[4-(2-quinolin-7-yl-9H-imidazo[1,2-d]pyrido[2,3-b][1,4]benzodiazepin-3-yl)phenyl]cyclobutanamine |
| 108 | 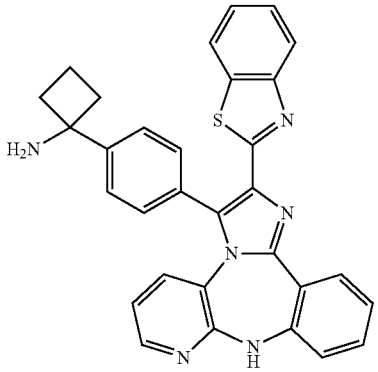<br>1-{4-[2-(1,3-benzothiazol-2-yl)-9H-imidazo[1,2-d]pyrido[2,3-b][1,4]benzodiazepin-3-yl]phenyl}cyclobutanamine |
| 109 | 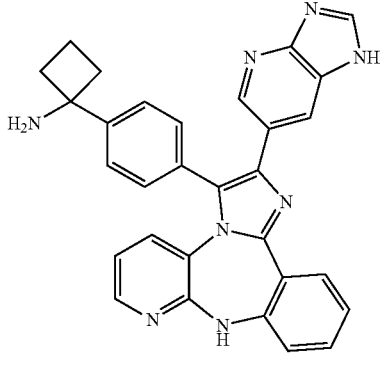<br>1-{4-[2-(1H-imidazo[4,5-b]pyridin-6-yl)-9H-imidazo[1,2-d]pyrido[2,3-b][1,4]benzodiazepin-3-yl]phenyl}cyclobutanamine |
| 110 | 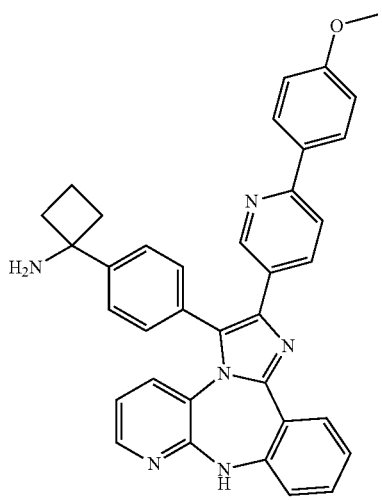<br>1-(4-{2-[6-(4-methoxyphenyl)pyridin-3-yl]-9H-imidazo[1,2-d]pyrido[2,3-b][1,4]benzodiazepin-3-yl}phenyl)cyclobutanamine |
| 111 | 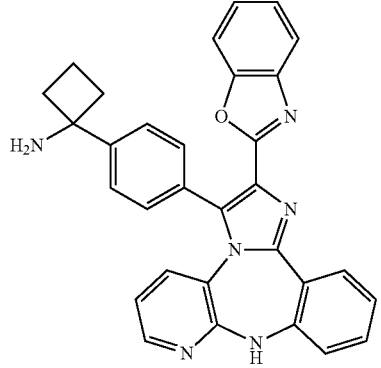<br>1-{4-[2-(1,3-benzoxazol-2-yl)-9H-imidazo[1,2-d]pyrido[2,3-b][1,4]benzodiazepin-3-yl]phenyl}cyclobutanamine |

TABLE 1-continued

| Cmpd. No. | Structure/Chemical name |
|---|---|
| 112 | 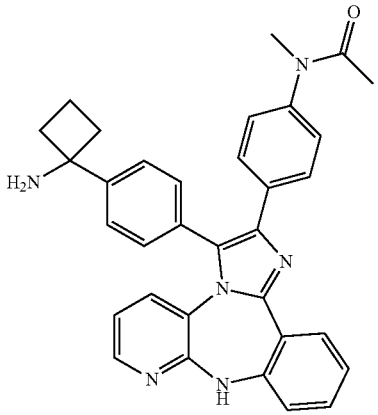<br>N-(4-{3-[4-(1-aminocyclobutyl)phenyl]-9H-imidazo[1,2-d]pyrido[2,3-b][1,4]benzodiazepin-2-yl}phenyl)-N-methylacetamide |
| 113 | 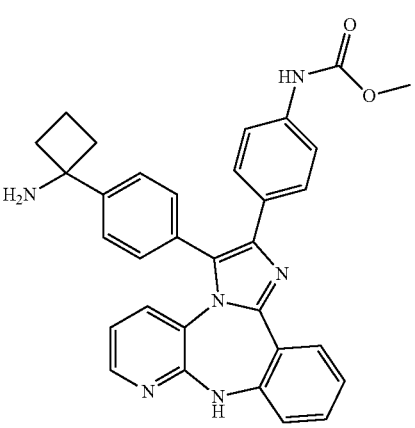<br>methyl (4-{3-[4-(1-aminocyclobutyl)phenyl]-9H-imidazo[1,2-d]pyrido[2,3-b][1,4]benzodiazepin-2-yl}phenyl)carbamate |
| 114 | 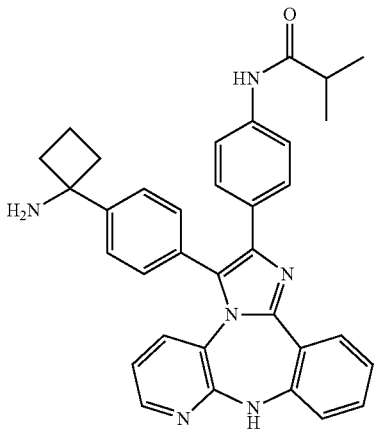<br>N-(4-{3-[4-(1-aminocyclobutyl)phenyl]-9H-imidazo[1,2-d]pyrido[2,3-b][1,4]benzodiazepin-2-yl}phenyl)-2-methylpropanamide |
| 115 | 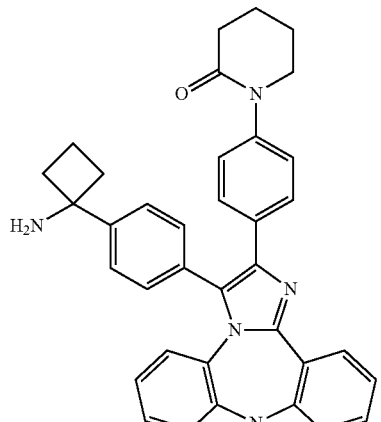<br>1-(4-{3-[4-(1-aminocyclobutyl)phenyl]-9H-imidazo[1,2-d]pyrido[2,3-b][1,4]benzodiazepin-2-yl}phenyl)piperidin-2-one |
| 116 | 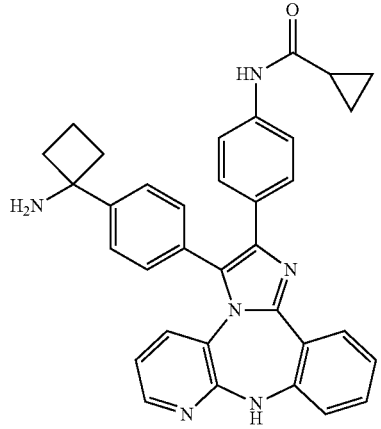<br>N-(4-{3-[4-(1-aminocyclobutyl)phenyl]-9H-imidazo[1,2-d]pyrido[2,3-b][1,4]benzodiazepin-2-yl}phenyl)cyclopropanecarboxamide |

TABLE 1-continued

| Cmpd. No. | Structure/Chemical name |
|---|---|
| 117 | 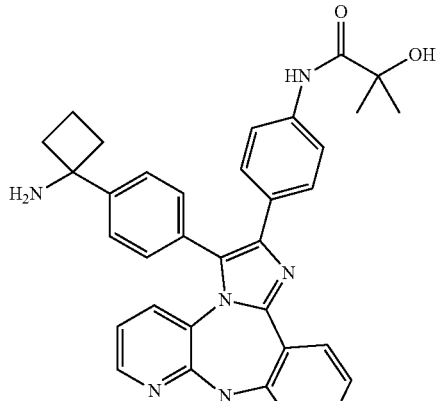<br>N-(4-{3-[4-(1-aminocyclobutyl)phenyl]-9H-imidazo[1,2-d]pyrido[2,3-b][1,4]benzodiazepin-2-yl}phenyl)-2-hydroxy-2-methylpropanamide |
| 118 | 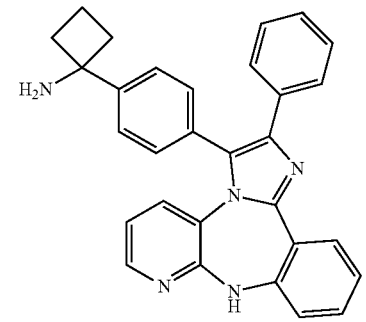<br>1-(4-(2-phenyl-9H-benzo[f]imidazo[1,2-d]pyrido[2,3-b][1,4]diazepin-3-yl)phenyl)cyclobutanamine |
| 119 | 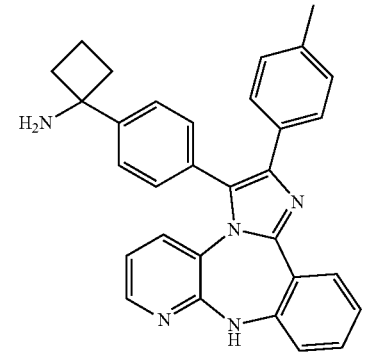<br>1-(4-(2-(p-tolyl)-9H-benzo[f]imidazo[1,2-d]pyrido[2,3-b][1,4]diazepin-3-yl)phenyl)cyclobutanamine |
| 120 | 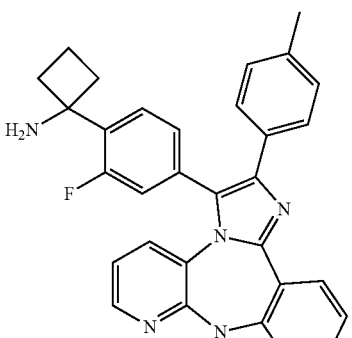<br>1-(2-fluoro-4-(2-(p-tolyl)-9H-benzo[f]imidazo[1,2-d]pyrido[2,3-b][1,4]diazepin-3-yl)phenyl)cyclobutanamine |
| 121 | 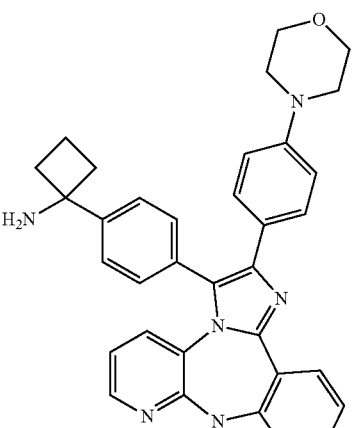<br>1-(4-(2-(4-morpholinophenyl)-9H-benzo[f]imidazo[1,2-d]pyrido[2,3-b][1,4]diazepin-3-yl)phenyl)cyclobutanamine |
| 122 | 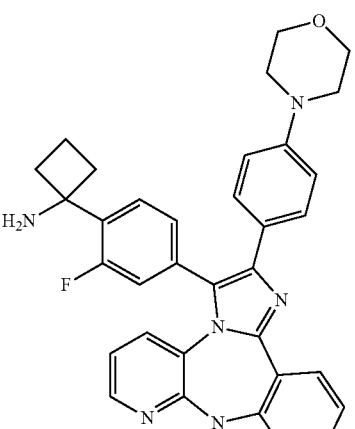<br>1-(2-fluoro-4-(2-(4-morpholinophenyl)-9H-benzo[f]imidazo[1,2-d]pyrido[2,3-b][1,4]diazepin-3-yl)phenyl)cyclobutanamine |

TABLE 1-continued

| Cmpd. No. | Structure/Chemical name |
|---|---|
| 123 | 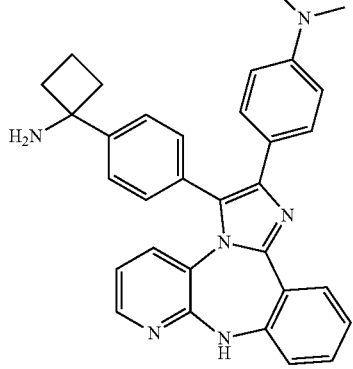<br>4-(3-(4-(1-aminocyclobutyl)phenyl)-9H-benzo[f]imidazo[1,2-d]pyrido[2,3-b][1,4]diazepin-2-yl)-N,N-dimethylaniline |
| 124 | 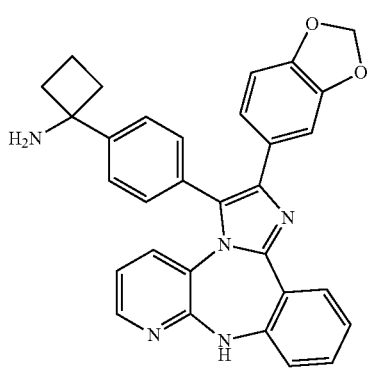<br>1-(4-(2-(benzo[d][1,3]dioxol-5-yl)-9H-benzo[f]imidazo[1,2-d]pyrido[2,3-b][1,4]diazepin-3-yl)phenyl)cyclobutanamine |
| 125 | 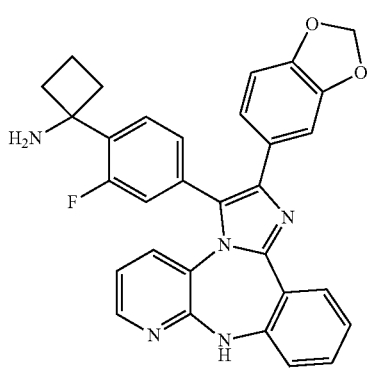<br>1-(4-(2-(benzo[d][1,3]dioxol-5-yl)-9H-benzo[f]imidazo[1,2-d]pyrido[2,3-b][1,4]diazepin-3-yl)-2-fluorophenyl)cyclobutanamine |
| 126 | 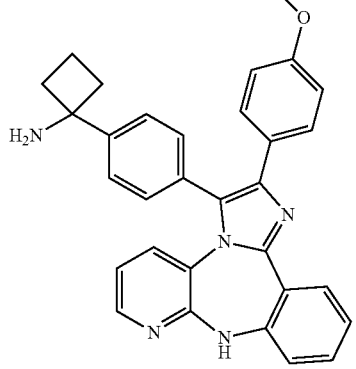<br>1-(4-(2-(4-methoxyphenyl)-9H-benzo[f]imidazo[1,2-d]pyrido[2,3-b][1,4]diazepin-3-yl)phenyl)cyclobutanamine |
| 127 | 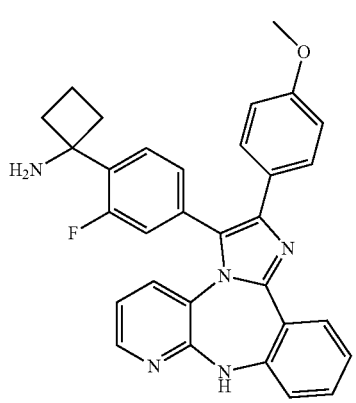<br>1-(2-fluoro-4-(2-(4-methoxyphenyl)-9H-benzo[f]imidazo[1,2-d]pyrido[2,3-b][1,4]diazepin-3-yl)phenyl)cyclobutanamine |
| 128 | 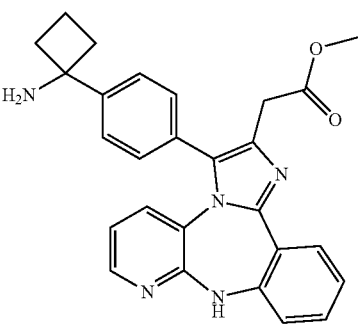<br>methyl 2-(3-(4-(1-aminocyclobutyl)phenyl)-9H-benzo[f]imidazo[1,2-d]pyrido[2,3-b][1,4]diazepin-2-yl)acetate |

TABLE 1-continued

| Cmpd. No. | Structure/Chemical name |
|---|---|
| 129 | 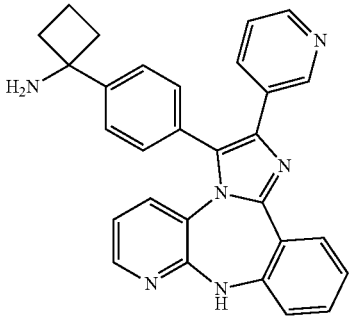<br>1-(4-(2-(pyridin-3-yl)-9H-benzo[f]imidazo[1,2-d]pyrido[2,3-b][1,4]diazepin-3-yl)phenyl)cyclobutanamine |
| 130 | 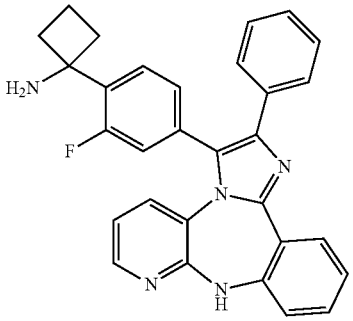<br>1-(2-fluoro-4-(2-phenyl-9H-benzo[f]imidazo[1,2-d]pyrido[2,3-b][1,4]diazepin-3-yl)phenyl)cyclobutanamine |
| 131 | 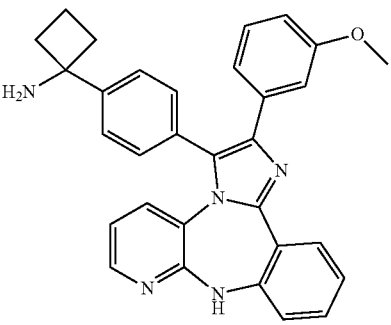<br>1-(4-(2-(3-methoxyphenyl)-9H-benzo[f]imidazo[1,2-d]pyrido[2,3-b][1,4]diazepin-3-yl)phenyl)cyclobutanamine |
| 132 | 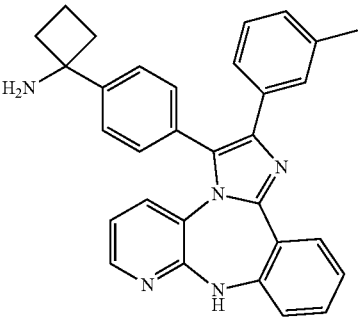<br>1-(4-(2-(m-tolyl)-9H-benzo[f]imidazo[1,2-d]pyrido[2,3-b][1,4]diazepin-3-yl)phenyl)cyclobutanamine |
| 133 | 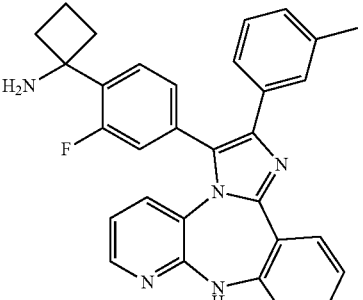<br>1-(2-fluoro-4-(2-(m-tolyl)-9H-benzo[f]imidazo[1,2-d]pyrido[2,3-b][1,4]diazepin-3-yl)phenyl)cyclobutanamine |
| 134 | 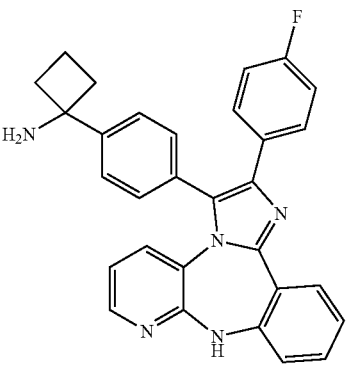<br>1-(4-(2-(4-fluorophenyl)-9H-benzo[f]imidazo[1,2-d]pyrido[2,3-b][1,4]diazepin-3-yl)phenyl)cyclobutanamine |

TABLE 1-continued

| Cmpd. No. | Structure/Chemical name |
|---|---|
| 135 | 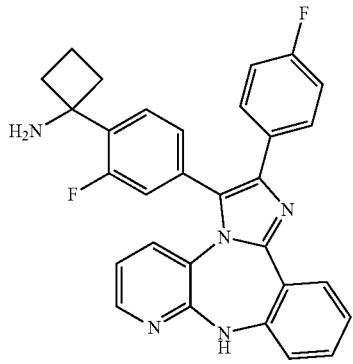<br>1-(2-fluoro-4-(2-(4-fluorophenyl)-9H-benzo[f]imidazo[1,2-d]pyrido[2,3-b][1,4]diazepin-3-yl)phenyl)cyclobutanamine |
| 136 | 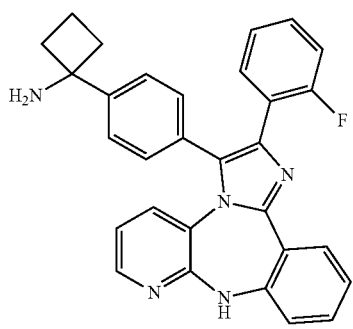<br>1-(4-(2-(2-fluorophenyl)-9H-benzo[f]imidazo[1,2-d]pyrido[2,3-b][1,4]diazepin-3-yl)phenyl)cyclobutanamine |
| 137 | 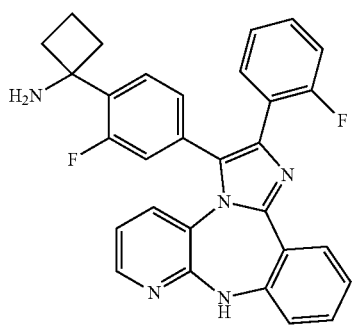<br>1-(2-fluoro-4-(2-(2-fluorophenyl)-9H-benzo[f]imidazo[1,2-d]pyrido[2,3-b][1,4]diazepin-3-yl)phenyl)cyclobutanamine |
| 138 | 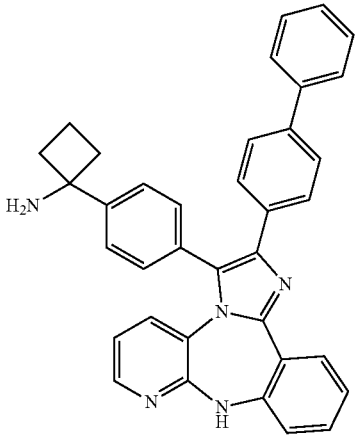<br>1-(4-(2-([1,1'-biphenyl]-4-yl)-9H-benzo[f]imidazo[1,2-d]pyrido[2,3-b][1,4]diazepin-3-yl)phenyl)cyclobutanamine |
| 139 | 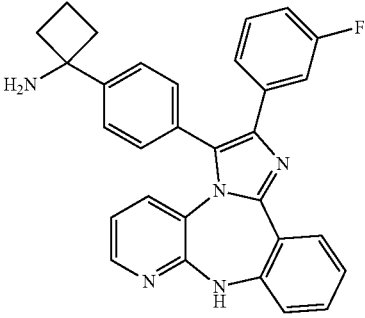<br>1-(4-(2-(3-fluorophenyl)-9H-benzo[f]imidazo[1,2-d]pyrido[2,3-b][1,4]diazepin-3-yl)phenyl)cyclobutanamine |
| 140 | 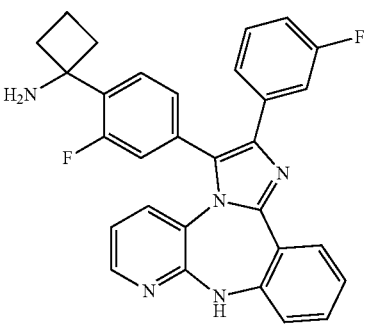<br>1-(2-fluoro-4-(2-(3-fluorophenyl)-9H-benzo[f]imidazo[1,2-d]pyrido[2,3-b][1,4]diazepin-3-yl)phenyl)cyclobutanamine |

TABLE 1-continued

| Cmpd. No. | Structure/Chemical name |
|---|---|
| 141 | 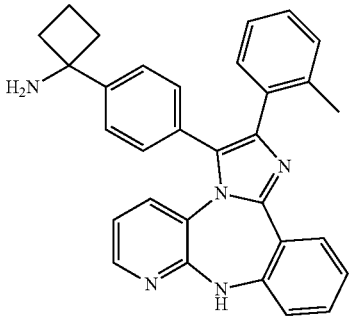<br>1-(4-(2-(o-tolyl)-9H-benzo[f]imidazo[1,2-d]pyrido[2,3-b][1,4]diazepin-3-yl)phenyl)cyclobutanamine |
| 142 | 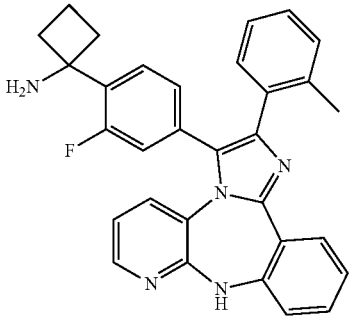<br>1-(2-fluoro-4-(2-(o-tolyl)-9H-benzo[f]imidazo[1,2-d]pyrido[2,3-b][1,4]diazepin-3-yl)phenyl)cyclobutanamine |
| 143 | 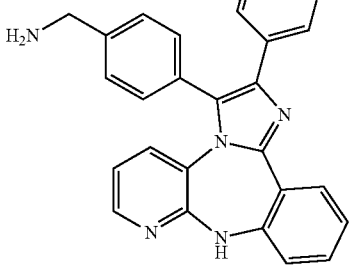<br>(4-(2-phenyl-9H-benzo[f]imidazo[1,2-d]pyrido[2,3-b][1,4]diazepin-3-yl)phenyl)methanamine |
| 144 | 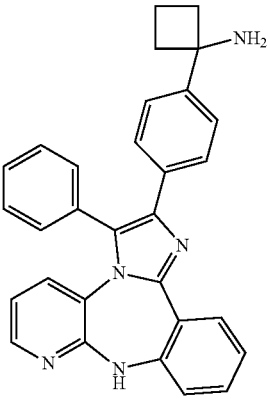<br>1-(4-(3-phenyl-9H-benzo[f]imidazo[1,2-d]pyrido[2,3-b][1,4]diazepin-2-yl)phenyl)cyclobutanamine |
| 145 | 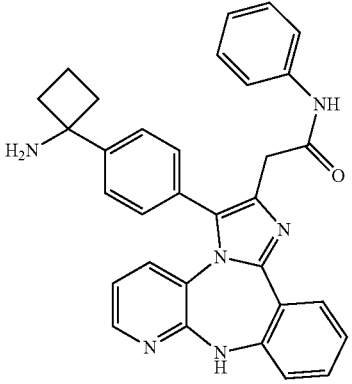<br>2-(3-(4-(1-aminocyclobutyl)phenyl)-9H-benzo[f]imidazo[1,2-d]pyrido[2,3-b][1,4]diazepin-2-yl)-N-phenylacetamide |
| 146 | 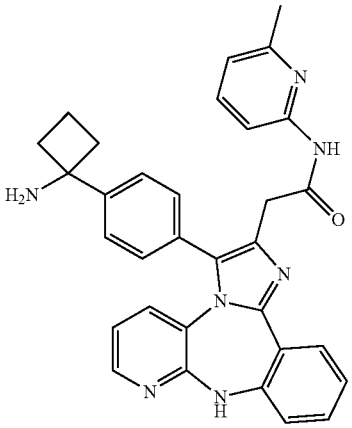<br>2-(3-(4-(1-aminocyclobutyl)phenyl)-9H-benzo[f]imidazo[1,2-d]pyrido[2,3-b][1,4]diazepin-2-yl)-N-(6-methylpyridin-2-yl)acetamide |

TABLE 1-continued

| Cmpd. No. | Structure/Chemical name |
|---|---|
| 147 | 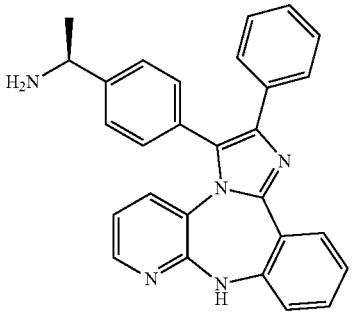<br>(S)-1-(4-(2-phenyl-9H-benzo[f]imidazo[1,2-d]pyrido[2,3-b][1,4]diazepin-3-yl)phenyl)ethanamine |
| 148 | 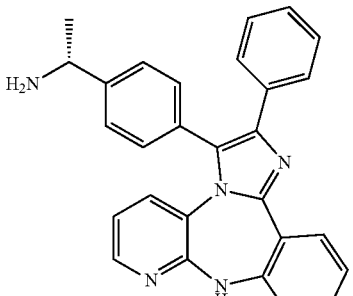<br>(R)-1-(4-(2-phenyl-9H-benzo[f]imidazo[1,2-d]pyrido[2,3-b][1,4]diazepin-3-yl)phenyl)ethanamine |
| 149 | 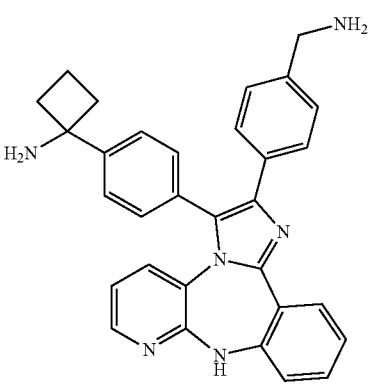<br>1-(4-(2-(4-(aminomethyl)phenyl)-9H-benzo[f]imidazo[1,2-d]pyrido[2,3-b][1,4]diazepin-3-yl)phenyl)cyclobutanamine |
| 150 | 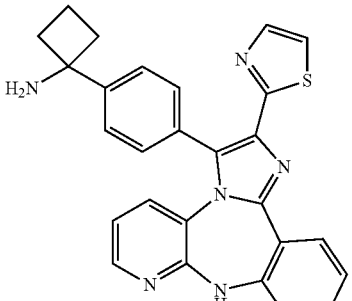<br>1-{4-[2-(1,3-thiazol-2-yl)-9H-imidazo[1,2-d]pyrido[2,3-b][1,4]benzodiazepin-3-yl]phenyl}cyclobutanamine |
| 151 | 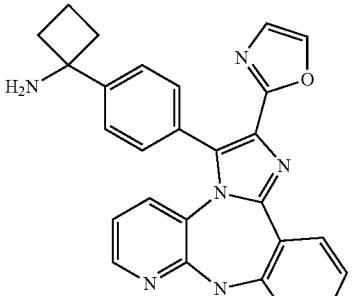<br>1-{4-[2-(1,3-oxazol-2-yl)-9H-imidazo[1,2-d]pyrido[2,3-b][1,4]benzodiazepin-3-yl]phenyl}cyclobutanamine |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or of two to four carbon atoms.

As used herein, "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Heteroalkenyl" includes alkenyl groups, as defined herein, having an oxygen, nitrogen, sulfur or phosphorous atom replacing one or more hydrocarbon backbone carbons.

The term "substituted alkenyl" refers to alkenyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, "alkenyl linker" is intended to include $C_2$, $C_3$, $C_4$, $C_5$ or $C_6$ straight chain (linear) aliphatic hydrocarbon groups and $C_3$, $C_4$, $C_5$ or $C_6$ branched aliphatic hydrocarbon groups. For example, $C_2$-$C_6$ alkenyl linker is intended to include $C_2$, $C_3$, $C_4$, $C_5$ and $C_6$ alkenyl linker groups. Examples of alkenyl linker include, moieties having from one to six carbon atoms, such as, but not limited to, ethenyl (—CH═CH—), propenyl (—CH═CHCH$_2$—, —CH$_2$CH═CH—, —C(CH$_3$)═CH—), butenyl (—CH═CHCH$_2$CH$_2$—, —CH$_2$CH═CHCH$_2$—, —CH$_2$CH$_2$CH═CH—, —C═(CH$_3$)CHCH$_2$—), pentyl (—CH═CHCH$_2$CH$_2$CH$_2$—, —CH$_2$CH═CHCH$_2$CH$_2$—, —CH$_2$CH$_2$CH═CHCH$_2$—, —CH$_2$CH$_2$CH$_2$CH═CH—, —C═(CH$_3$)CHCH$_2$CH$_2$—) or hexyl (—CH═CHCH$_2$CH$_2$CH$_2$CH$_2$—, —CH$_2$CH═CHCH$_2$CH$_2$CH$_2$—, —CH$_2$CH$_2$CH═CHCH$_2$CH$_2$—, —CH$_2$CH$_2$CH$_2$CH═CHCH$_2$—, —CH$_2$CH$_2$CH$_2$CH$_2$CH═CH—).

"Alkynyl" includes unsaturated aliphatic groups analogous in length and possible substitution to the alkyls described above, but which contain at least one triple bond.

For example, "alkynyl" includes straight chain alkynyl groups (e.g., ethynyl, propynyl, butynyl, pentynyl, hexynyl, heptynyl, octynyl, nonynyl, decynyl), branched alkynyl groups, and cycloalkyl or cycloalkenyl substituted alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

"Heteroalkynyl" includes alkynyl groups, as defined herein, having an oxygen, nitrogen, sulfur or phosphorous atom replacing one or more hydrocarbon backbone carbons.

The term "substituted alkynyl" refers to alkynyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, wherein oxygen, nitrogen or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen atom bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and "alkthioalkynyls" refers to moieties wherein an alkyl, alkenyl or alkynyl group is bonded to a sulfur atom which is covalently bonded to an alkynyl group.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by formula I are benzo-imidazo-pyrido-diazepine derivatives, and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

2. Synthesis of Substituted Benzo-Imidazo-Pyrido-Diazepine Compounds

The present invention provides methods for the synthesis of the compounds of each of the formulae described herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; and Greene, T. W., Wuts, P. G. M., *Protective Groups in Organic Synthesis,* 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of each of the formulae described herein may be prepared according to the following procedures from commercially available starting materials or starting materials which can be prepared using literature procedures. These procedures show the preparation of representative compounds of this invention.

GENERAL PROCEDURES

General Procedure A

One general procedure for the preparation of 9H-benzo[f]imidazo[1,2-d]pyrido[4,5-b][1,4]diazepines or 9H-benzo[f]imidazo[1,2-d]pyrimido[4,5-b][1,4]diazepines is illustrated below.

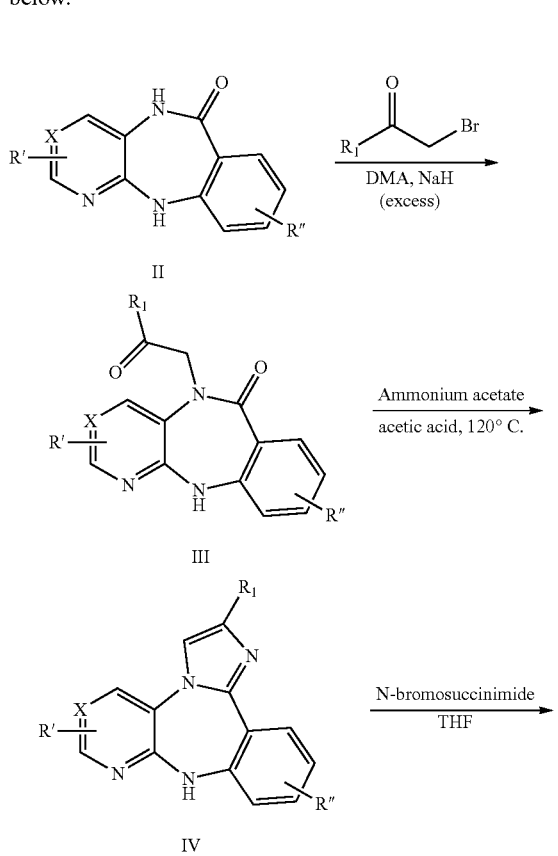

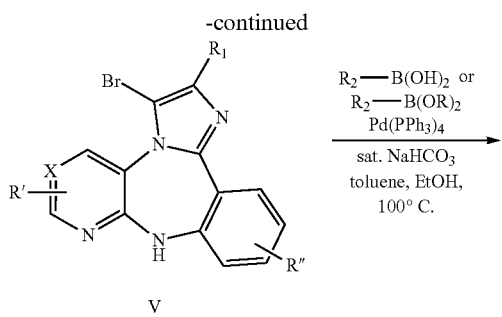

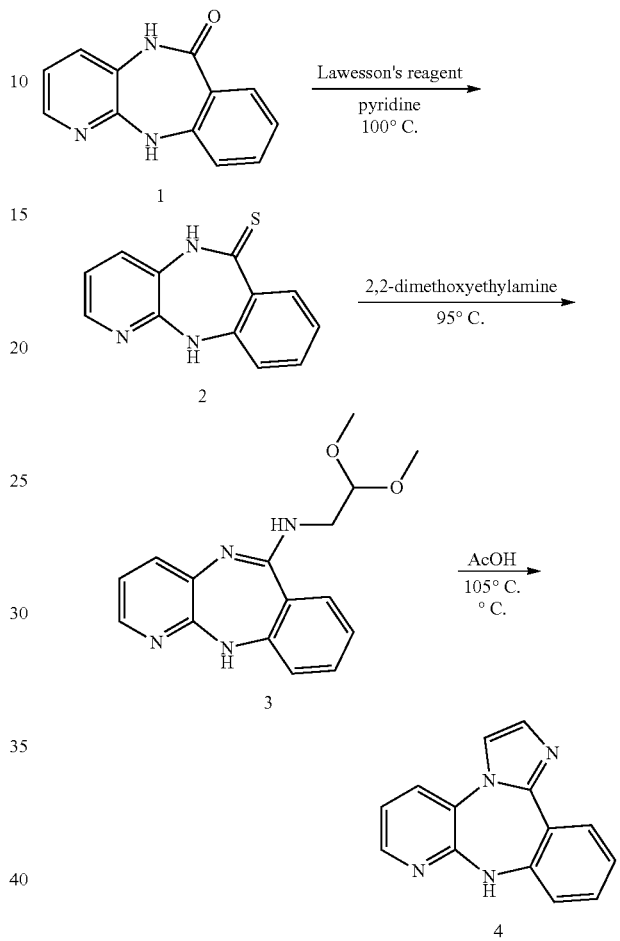

A suitably substituted 5H-benzo[e]pyrido[3,2-b][1,4]diazepin-6(11H)-one II or 5H-benzo[e]pyrimido[3,2-b][1,4]diazepin-6(11H)-one V is subjected to the action of excess sodium hydride in a polar aprotic solvent such as DMA. The resulting anion is then reacted with an appropriately substituted α-bromomethylketone, generating the intermediate III. Alternatively, the starting material II could be an amino-protected benzo-pyrido-diazepinone such as the 11-benzyl-5H-benzo[e]pyrido[3,2-b][1,4]diazepin-6(11H)-one where only a small excess of sodium hydride would be necessary to fully deprotonate the starting material. The intermediate III is then cyclized under the action of ammonium acetate in a polar protic solvent such as acetic acid at temperature sufficiently high for the reaction to proceed. The resulting intermediate IV is brominated using an appropriate reagent such as N-bromosuccinimide. Typically this reaction is conducted in an inert solvent like tetrahydrofuran (THF). The brominated material V is then used in a Suzuki type reaction using a palladium catalyst such as tetrakis(triphenylphosphine)palladium(0), a boronic acid or boronic acid ester such as a pinacolate in presence of a base such as aqueous sodium bicarbonate. Many solvent systems could be employed to conduct the reaction. A typical system is toluene/ethanol. The reaction typically requires high temperature, typically 120° C. The coupling generates the suitably substituted 9H-benzo[f]imidazo[1,2-d]pyrido[4,5-b][1,4]diazepines or 9H-benzo[f]imidazo[1,2-d]pyrimido[4,5-b][1,4]diazepines VI.

The boronic acids or boronic acid esters were typically purchased from commercial sources or prepared from the brominated precursor following the procedure found in the following article from Ishiyama, Tatsuo; Murata, Mild; Miyaura, Norio; Journal of Organic Chemistry (1995), 60(23), 7508-10.

General Procedure B

One general procedure for 9H-imidazo[1,2-d]pyrido[2,3-b][1,4]benzo diazepine is described below: imidazo pyrido benzodiazepine formation A suitably substituted 5,11-dihydro-6H-pyrido[2,3-b][1,4]benzodiazepin-6-one 1 is treated with Lawesson's reagent in an appropriate solvent such as pyridine under sufficient heating, generating the intermediate 2. A mixture of the intermediate 2 and 2,2-dimethoxyethylamine is heated under neat conditions. The resulting intermediate 3 is then cyclized under acidic conditions, typically in acetic acid under heating.

General Procedure C

One general procedure for introduction of side chain at C-3 position of 9H-imidazo[1,2-d]pyrido[2,3-b][1,4]benzodiazepine is described below: C-3 modification

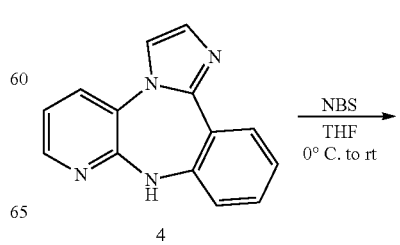

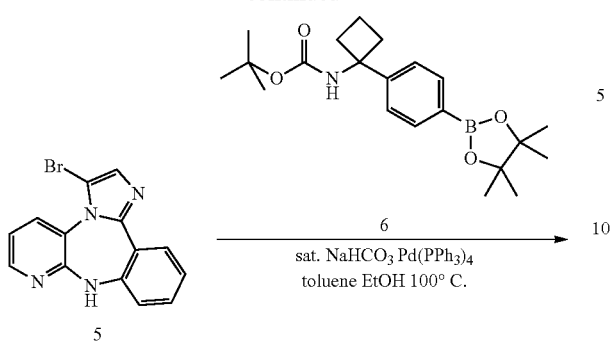

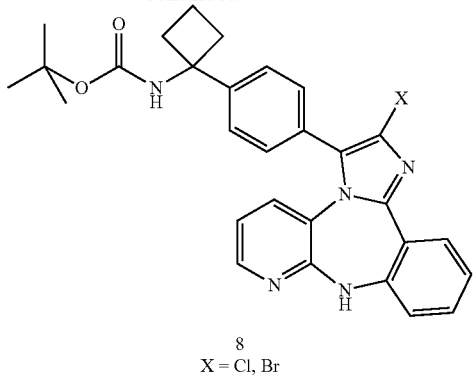

A suitably substituted 3-substituted-9H-imidazo[1,2-d]pyrido[2,3-b][1,4]benzodiazepine 7 is halogenated using an appropriate reagent such as N-chlorosuccinimide in chloroform, heated at reflux temperature.

General Procedure E

One general procedure for the preparation of 2-substituted-9H-imidazo[1,2-d]pyrido[2,3-b][1,4]benzodiazepine by Stille coupling is described below: Stille coupling A suitably substituted 9H-imidazo[1,2-d]pyrido[2,3-b][1,4]benzodiazepine 4 is brominated using an appropriate reagent such as N-bromosuccinmide in THF, 0° C. to ambient temperature to afford the 3-bromo intermediate 5. The intermediate 5 is modified at 2-position by Suzuki coupling reaction using a palladium catalyst such as tetrakis(triphenylphosphine)palladium(0), a boronic acid or boronic acid ester such as a pinacolate in presence of a base such as saturated aqueous sodium hydrogen carbonate. Many solvent systems could be employed to conduct the reaction. A typical condition is using toluene-ethanol system as solvent and heated at 100° C. The boronic acids or boronic acid esters were typically purchased from commercial sources or prepared from the appropriate bromide.

General Procedure D

One general procedure for the preparation of 2-halo-9H-imidazo[1,2-d]pyrido[2,3-b][1,4]benzodiazepine is described below: halogenation

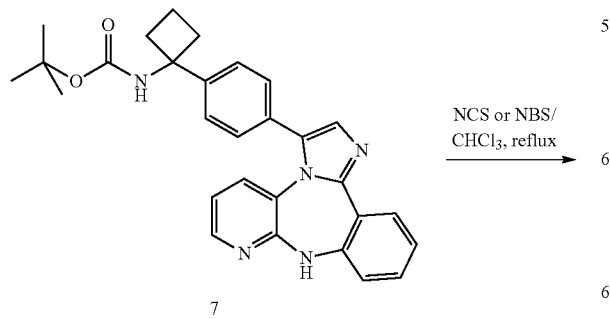

The brominated intermediate 9 is modified at 2-position by Stille coupling reaction using a palladium catalyst such as bis(triphenylphosphine)palladium(II) dichloride, organotin compound such as tributylstannyl compound 10. Many solvent systems could be employed to conduct the reaction. A typical condition is using 1,2-dimethoxyethane as solvent and heated under microwave irradiation conditions at 130° C. The organotin compounds 10 were purchased from commercial sources.

General Procedure F

One general procedure for the preparation of 2-substituted-9H-imidazo[1,2-d]pyrido[2,3-b][1,4]benzodiazepine by Suzuki coupling is described below: Suzuki coupling

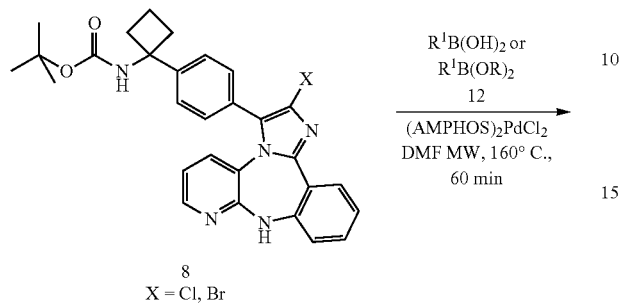

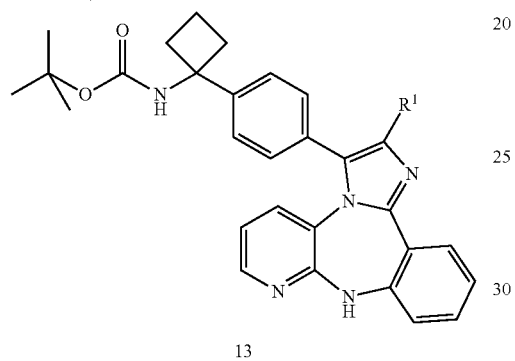

The halogenated intermediate 8 is modified at 2-position by Suzki coupling reaction using a palladium catalyst such as bis(di-tert-butyl(4-dimethylaminophenyl)phosphine)dichloropalladium(II), a boronic acid or boronic acid ester 12 such as a pinacolate in presence of a base such as aqueous sodium carbonate. Many solvent systems could be employed to conduct the reaction. A typical condition is using N,N-dimethylformamide as a solvent and heated under microwave irradiation conditions at 160° C. The boronic acids or boronic acid esters 12 were typically purchased from commercial sources or prepared from the appropriate bromide.

General Procedure G

One general procedure for reduction of nitro group is described below: Reduction of nitro group

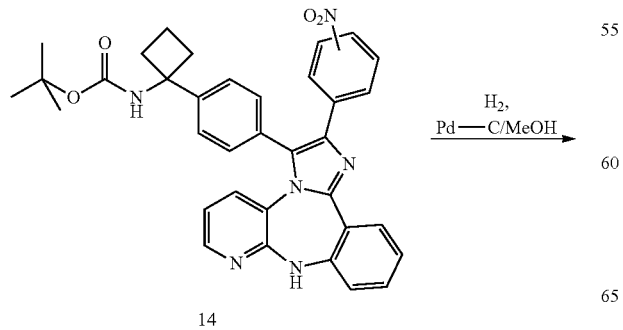

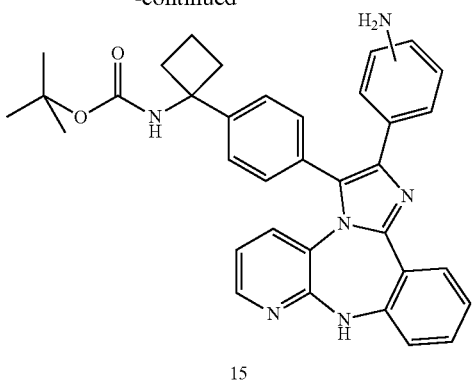

A suitably substituted aromatic nitro compound 14 is reduced by hydrogenation using palladium on charcoal to give the aniline 15.

General Procedure H

One general procedure for modification of aniline is described below: Modification of nitrogen atom

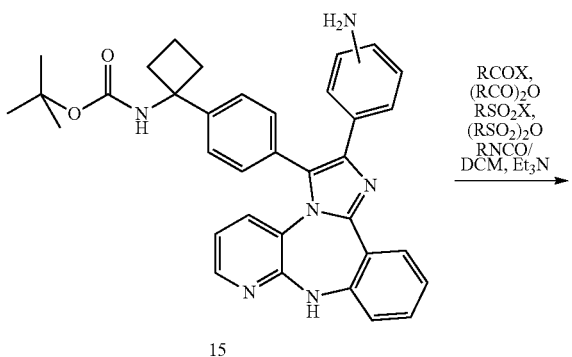

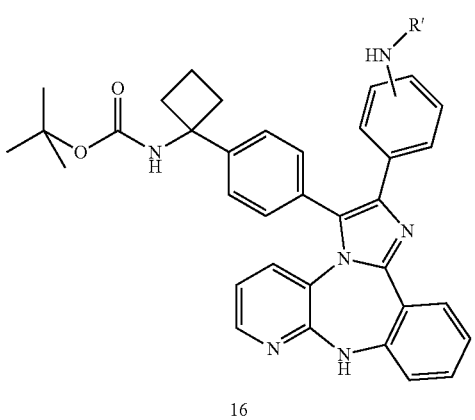

A suitably substituted aniline 15 is modified by treating with amine-modifying agent including acyl halide, acid anhydride, sulfonyl halide, sulfonic anhydride and isocyanate in presence of base such as triethylamine in an inert solvent such as dichloromethane to afford amide, sulfonamide and urea compound 16.

General Procedure I

One general procedure for hydrogenolysis of benzyl ester is described below: Hydrogenolysis of benzyl ester

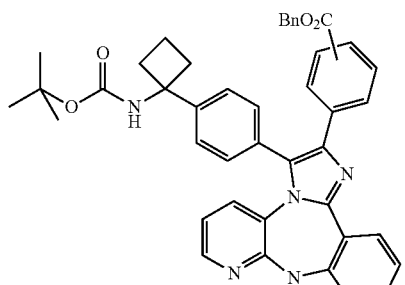

17

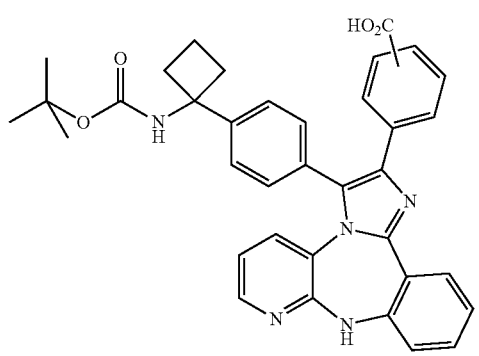

18

A suitably substituted benzyl ester 17 is hydrogenated with palladium on charcoal in THF-MeOH system at 50° C. to afford carboxylic acid 18.

General Procedure J

One general procedure for amidation of carboxylic acid is described below: Amidation

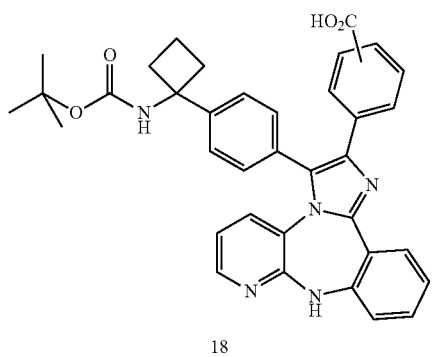

18

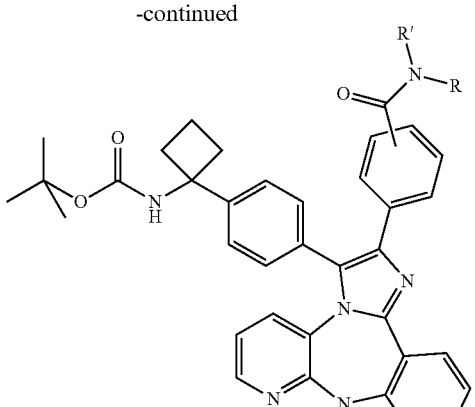

19

A suitably substituted carboxylic acid 18 is amidated by using appropriate amine by using an appropriate condensation agent such as WSC in an inert solvent such as dichloromethane to give corresponding amide 19.

General Procedure K

One general procedure for deprotection of Boc group is described below: Boc group deprotection

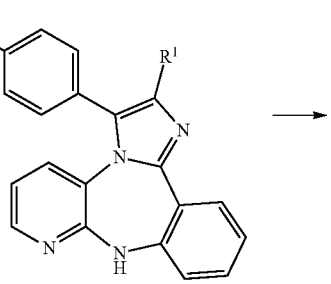

20

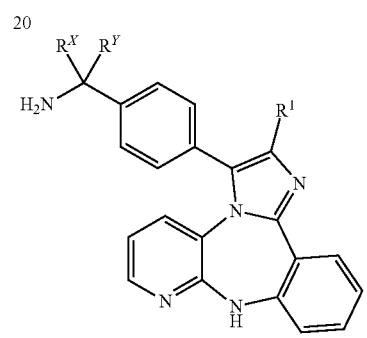

21

Deprotection of tert-butyl carbamate 20 is performed by using an appropriate acid such as 4M HCl solution in dioxane in an inert solvent like dichloromethane. After evaporation of the volatile materials, corresponding acid salt 21 is obtained.

3. Methods of Treatment

The present invention provides methods for the treatment of a cell proliferative disorder in a subject in need thereof by administering to a subject in need of such treatment, a therapeutically effective amount of a compound of the present invention, or a pharmaceutically acceptable salt, prodrug, metabolite, polymorph or solvate thereof. The cell proliferative disorder can be cancer or a precancerous condition. The present invention further provides the use of a compound of the present invention, or a pharmaceutically acceptable salt, prodrug, metabolite, polymorph or solvate thereof, for the preparation of a medicament useful for the treatment of a cell proliferative disorder.

The present invention also provides methods of protecting against a cell proliferative disorder in a subject in need thereof by administering a therapeutically effective amount of compound of the present invention, or a pharmaceutically acceptable salt, prodrug, metabolite, polymorph or solvate thereof, to a subject in need of such treatment. The cell proliferative disorder can be cancer or a precancerous condition. The present invention also provides the use of compound of the present invention, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas.

Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or T is; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www-.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target kinase) but does not significantly modulate another molecular target (e.g., a non-target kinase). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target kinase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention, or a pharmaceutically acceptable salt, prodrug, metabolite, polymorph or solvate thereof, demonstrates a minimum of a four fold differential, preferably a ten fold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a kinase of interest.

The present invention provides methods to assess biological activity of a compound of the present invention, or a pharmaceutically acceptable salt, prodrug, metabolite, polymorph or solvate thereof. In one method, an assay based on enzymatic activity can be utilized. In one specific enzymatic activity assay, the enzymatic activity is from a kinase. As used herein, "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylates particular protein/peptide substrates, they all bind the same second substrate ATP in a highly conserved pocket. About 50% of the known oncogene products are protein tyrosine kinases (PTKs), and their kinase activity has been shown to lead to cell transformation. Preferably, the kinase assayed is a tyrosine kinase.

A change in enzymatic activity caused by a compound of the present invention, or a pharmaceutically acceptable salt, prodrug, metabolite, polymorph or solvate thereof, can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci U S A*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomabhodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; AMG888; AMG-208; Axitinib; Foretinib; JNJ-38877605; MGCD-265; PF-04217903; Crizotinib; SGX-523; SU11274; MP470; PHA-665752; Tivantinib: K252a; or Cabozantinib.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur–0.4 M 5-chloro-2,4-dihydroxypyrimidine–1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Ab1), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Ab1), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

4. Pharmaceutical Compositions

The present invention also provides pharmaceutical compositions comprising a compound of each of the formulae described herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day.

In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19th edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

5. Examples

Example 1

Preparation of (4-(2-phenyl-9H-benzo[f]imidazo[1,2-d]pyrido[2,3-b][1,4]diazepin-3-yl)phenyl)methanamine hydrochloride

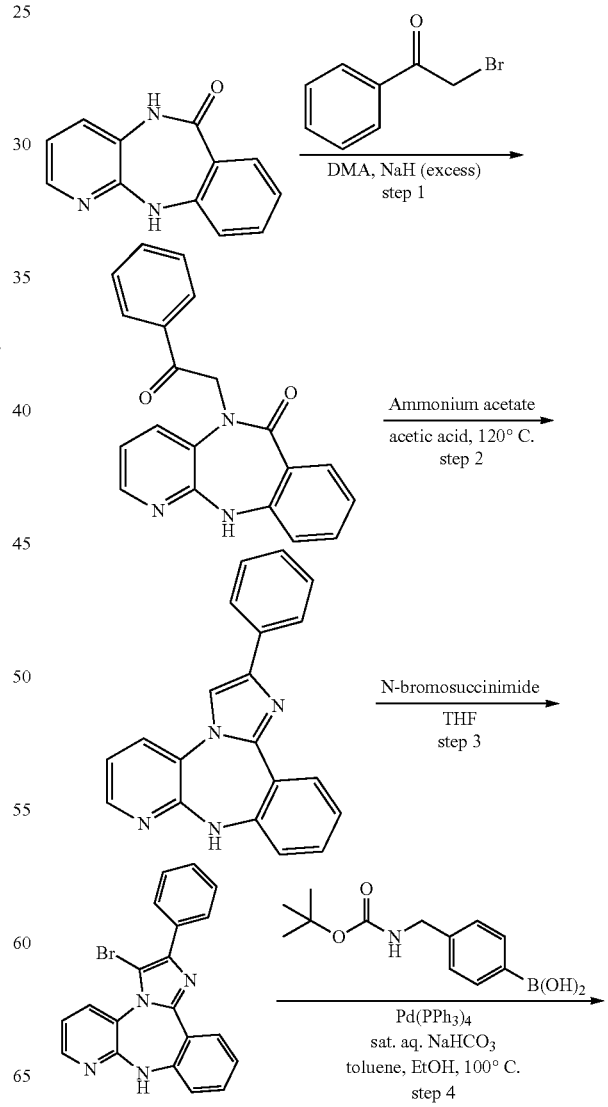

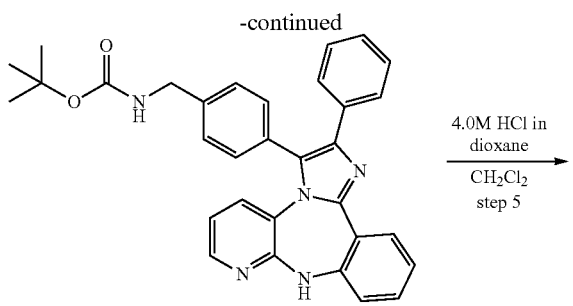

Step 1: Preparation of 5-(2-oxo-2-phenylethyl)-5H-benzo[e]pyrido[3,2-b][1,4]diazepin-6(11H)-one

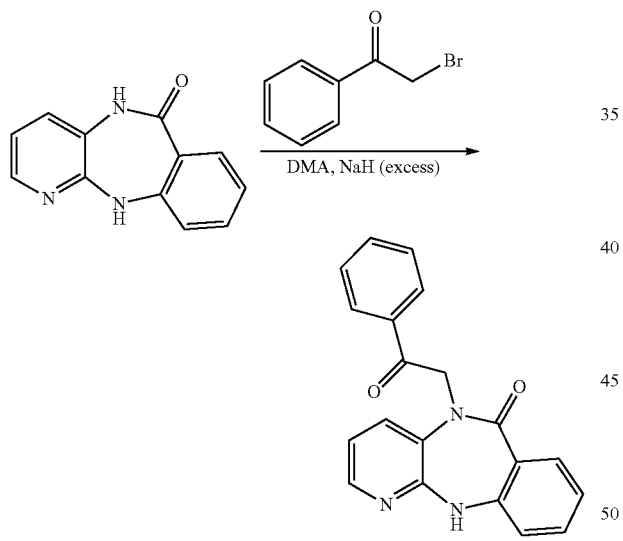

5H-benzo[e]pyrido[3,2-b][1,4]diazepin-6(11H)-one (5.0 g, 1 eq.) was suspended in dimethylacetamide (DMA) (50 mL). The reaction was cooled to 0° C. and sodium hydride (60% in mineral oil) (2.07 g, 2.2 eq.) was added. The reaction was warmed to room temperature and stirred until gas evolution ceased. The reaction was cooled to 0° C. and 2-bromo-1-phenylethanone (7.04 g, 1.5 eq.) was added. The reaction was stirred at room temperature before the addition of a further quantity of 2-bromo-1-phenylethanone (9 g, 2 eq.). The reaction was quenched after 2 hours at room temperature (the reaction did not proceed to completion). The reaction was poured onto 200 mL water and extracted with dichloromethane (3×75 mL). The organic extracts were combined, washed with water (2×100 mL), brine (2×100 mL), dried over sodium sulfate, filtered and concentrated under reduced pressure. Purification by column chromatography (0-5% methanol in dichloromethane) gave 5-(2-oxo-2-phenylethyl)-5H-benzo[e]pyrido[3,2-b][1,4]diazepin-6(11H)-one (1.9 g, 24%) as a red solid. LCMS: 330 [M+H].

Step 2: Preparation of 2-phenyl-9H-benzo[f]imidazo[1,2-d]pyrido[2,3-b][1,4]diazepine

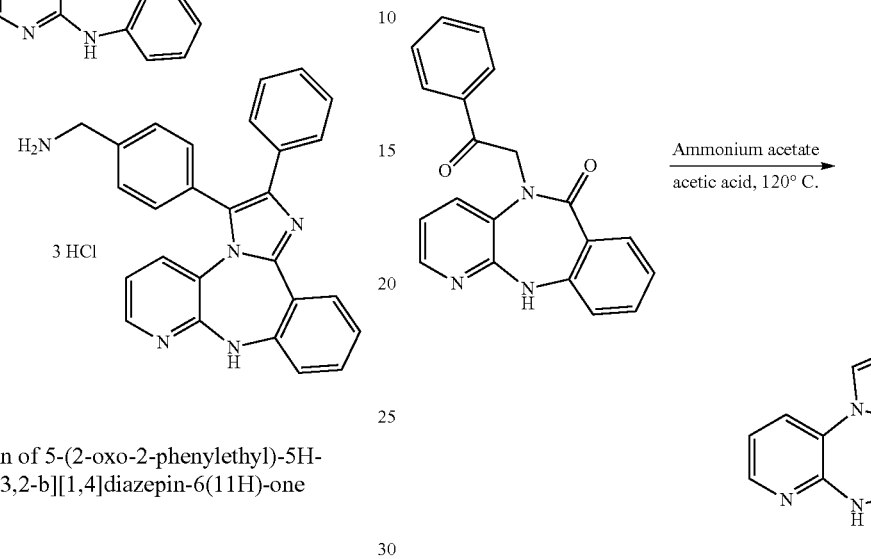

To a solution of 5-(2-oxo-2-phenylethyl)-5H-benzo[e]pyrido[3,2-b][1,4]diazepin-6(11H)-one (1.5 g, 1 eq.) in acetic acid (5 mL) was added ammonium acetate (4.6 g, 13 eq.). The reaction was stirred at 120° C. for 3 hours. The reaction was poured onto water (100 mL) and extracted with dichloromethane (2×100 mL). The organic extracts were combined, washed with sodium bicarbonate solution (3×100 mL), water (1×100 mL), brine (1×50 mL), dried over sodium sulfate, filtered and concentrated under reduced pressure. Purification by column chromatography (25-75% ethyl acetate in hexanes) gave the product which was triturated with ethyl acetate and ether to give 2-phenyl-9H-benzo[f]imidazo[1,2-d]pyrido[2,3-b][1,4]diazepine (0.9 g, 63%). $^1$H NMR (DMSO-$d_6$) 400 MHz δ 8.51 (s, 1H), 8.19 (dd, $J_A$=5.2 Hz, $J_B$=1.6 Hz, 1H), 8.14 (s, 1H), 7.96-7.87 (m, 4H), 7.45 (t, J=8 Hz, 2H), 7.36-7.28 (m, 2H), 7.22-7.15 (m, 2H), 7.12-7.07 (m, 1H); LCMS: 311 [M+H].

Step 3: Preparation of 3-bromo-2-phenyl-9H-benzo[f]imidazo[1,2-d]pyrido[2,3-b][1,4]diazepine

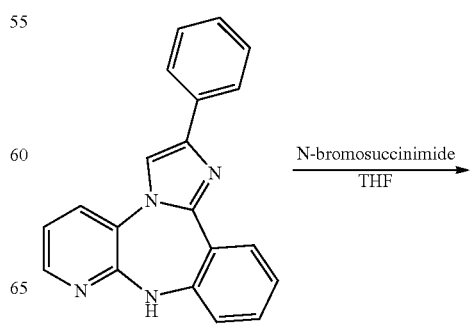

-continued

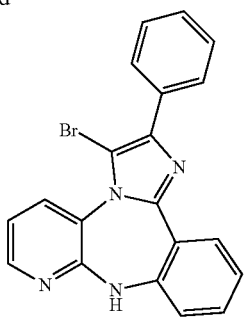

To a solution of 2-phenyl-9H-benzo[f]imidazo[1,2-d]pyrido[2,3-b][1,4]diazepine (0.7 g, 1 eq.) in THF (20 mL) was added N-bromosuccinimide (0.4 g, 1 eq.). The reaction was stirred at room temperature for 1 hour, poured onto water (100 mL) and extracted with ethyl acetate (2×100 mL). The organic extracts were combined, washed with saturated sodium bicarbonate (1×100 mL), water (1×50 mL), brine (1×50 mL) and dried over sodium sulfate. After filtration and concentration under reduced pressure 3-bromo-2-phenyl-9H-benzo[f]imidazo[1,2-d]pyrido[2,3-b][1,4]diazepine (0.85 g, 97%) was obtained which was used with no further purification. $^1$H NMR (DMSO-$d_6$) 400 MHz δ 8.64 (s, 1H), 8.28 (dd, $J_A$=4.8 Hz, $J_B$=1.6 Hz, 1H), 8.05 (dd, $J_A$=8 Hz, $J_B$=1.6 Hz, 1H), 8.02-7.98 (m, 1H), 7.85 (dd, $J_A$=8 Hz, $J_B$=1.6 Hz, 1H), 7.53-7.48 (m, J=8 Hz, 2H), 7.42-7.34 (m, 2H), 7.30-7.22 (m, 2H), 7.14-7.09 (m, 1H); LCMS: 388 [M+H].

Step 4: Preparation of tert-butyl 4-(2-phenyl-9H-benzo[f]imidazo[1,2-d]pyrido[2,3-b][1,4]diazepin-3-yl)benzylcarbamate

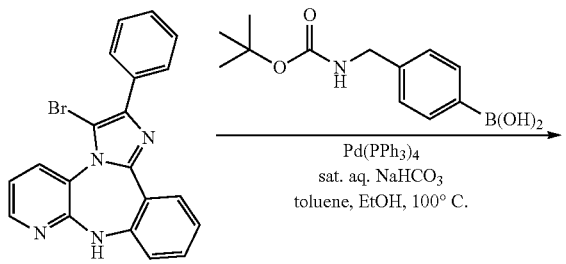

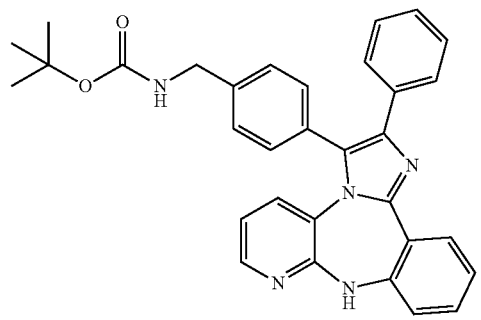

To a suspension of 3-bromo-2-phenyl-9H-benzo[f]imidazo[1,2-d]pyrido[2,3-b][1,4]diazepine (0.250 g, 1 eq.) in a mixture of toluene (5 mL), ethanol (5 mL), and saturated sodium bicarbonate (1 mL) was added (4-(((tert-butoxycarbonyl)amino)methyl)phenyl)boronic acid (0.1 g, 1.5 eq.). The reaction was degassed (nitrogen) for 5 minutes and tetrakis(triphenylphosphine)palladium(0) added (0.025 g). The reaction was again degassed for 5 minutes and stirred at 100° C. overnight. The reaction mixture was cooled to room temperature and poured onto water (50 mL). The aqueous phase was extracted with dichloromethane (2×50 mL) and the organic extracts were combined and washed with water (1×50 mL), brine (1×50 mL), dried over sodium sulfate, filtered and concentrated under reduced pressure. Purification by column chromatography (25-75% ethyl acetate in hexanes) gave the product which was triturated with ether to give tert-butyl 4-(2-phenyl-9H-benzo[f]imidazo[1,2-d]pyrido[2,3-b][1,4]diazepin-3-yl)benzylcarbamate (0.133 g, 40%). LCMS: 516 [M+H].

Step 5: Preparation of (4-(2-phenyl-9H-benzo[f]imidazo[1,2-d]pyrido[2,3-b][1,4]diazepin-3-yl)phenyl)methanamine hydrochloride

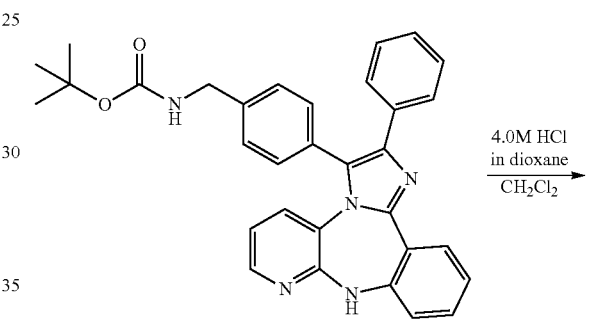

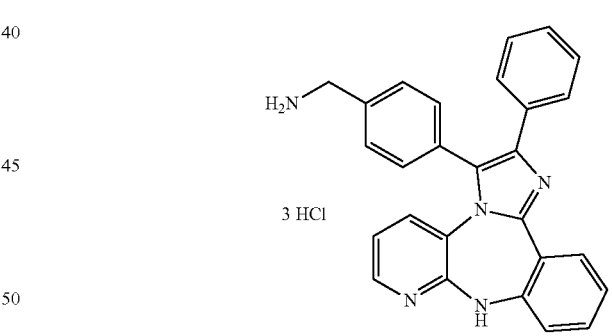

To a solution of tert-butyl 4-(2-phenyl-9H-benzo[f]imidazo[1,2-d]pyrido[2,3-b][1,4]diazepin-3-yl)benzylcarbamate (0.100 g) in dichloromethane (4 mL) was added 4.0 M HCl in dioxane (1 mL). The reaction was stirred at room temperature for 2 hours and then diluted with ether (20 mL). The product was removed by filtration under reduced pressure and dried to give (4-(2-phenyl-9H-benzo[f]imidazo[1,2-d]pyrido[2,3-b][1,4]diazepin-3-yl)phenyl)methanamine hydrochloride as a bright yellow solid (0.085 g, 83% based on tris HCl salt). $^1$H NMR (DMSO-$d_6$) 400 MHz δ 8.67 (br. s, 1 H), 8.42 (br. s, 3H), 8.13-8.10 (m, 1H), 7.98-7.95 (m, 1H), 7.51-7.42 (m, 4H), 7.39-7.38 (m, 1H), 7.35-7.26 (m, 5H), 7.15 (t, J=7.4 Hz, 1H), 6.93-6.90 (m, 1H), 6.78-6.73 (m, 1H), 4.06 (dd, $J_A$=11.3 Hz, $J_B$=5.9 Hz, 2H); LCMS: 416 [M+H];

Calc. for $C_{27}H_{21}N_5 \cdot 3.26\,HCl \cdot 0.12\,dioxane \cdot 0.16\,diethylether$: C, 60.66; H, 4.86; N, 12.58. Found C, 60.66; H, 4.99; N, 12.58.

Example 2

Preparation of (S)-1-(4-(2-phenyl-9H-benzo[f]imidazo[1,2-d]pyrido[2,3-b][1,4]diazepin-3-yl)phenyl)ethanamine hydrochloride

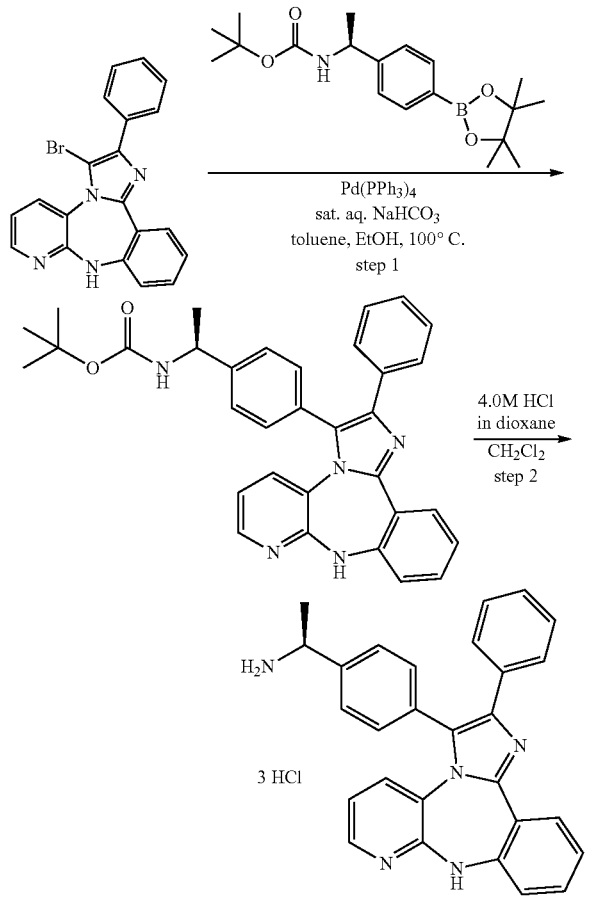

Step 1: Preparation of (S)-tert-butyl (1-(4-(2-phenyl-9H-benzo[f]imidazo[1,2-d]pyrido[2,3-b][1,4]diazepin-3-yl)phenyl)ethyl)carbamate

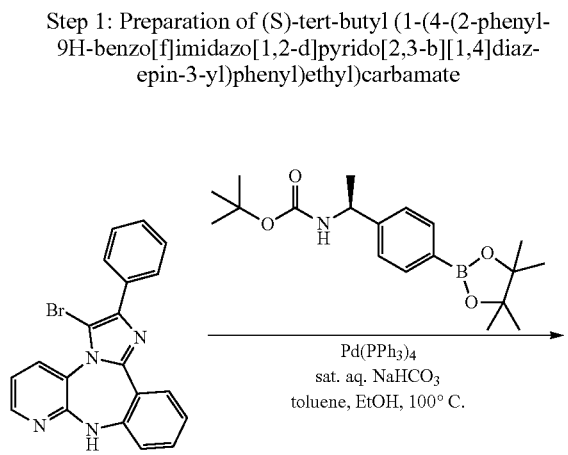

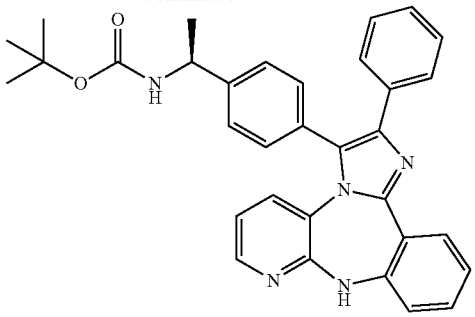

To a suspension of 3-bromo-2-phenyl-9H-benzo[f]imidazo[1,2-d]pyrido[2,3-b][1,4]diazepine (0.60 g, 1 eq.) in a mixture of toluene (10 mL), ethanol (10 mL), and saturated sodium bicarbonate (3 mL) was added (S)-tert-butyl (1-(4-(4,4,5,5-tetramethyl-1,3,2-dioxaborolan-2-yl)phenyl)ethyl)carbamate (1.31 g, 2.45 eq.). The reaction was degassed (nitrogen) for 5 minutes and tetrakis(triphenylphosphine)palladium(0) added (0.3 g). The reaction was again degassed for 5 minutes and stirred at 100° C. overnight. The reaction mixture was cooled to room temperature and poured onto water (50 mL). The aqueous phase was extracted with dichloromethane (2×50 mL) and the organic extracts were combined and washed with water (1×50 mL), brine (1×50 mL), dried over sodium sulfate, filtered and concentrated under reduced pressure. Purification by column chromatography (25-75% ethyl acetate in hexanes) gave the product which was triturated with ether to give (S)-tert-butyl (1-(4-(2-phenyl-9H-benzo[f]imidazo[1,2-d]pyrido[2,3-b][1,4]diazepin-3-yl)phenyl)ethyl)carbamate (0.251 g, 31%). LCMS: 530 [M+H].

Step 2: Preparation of (S)-1-(4-(2-phenyl-9H-benzo[f]imidazo[1,2-d]pyrido[2,3-b][1,4]diazepin-3-yl)phenyl)ethanamine hydrochloride

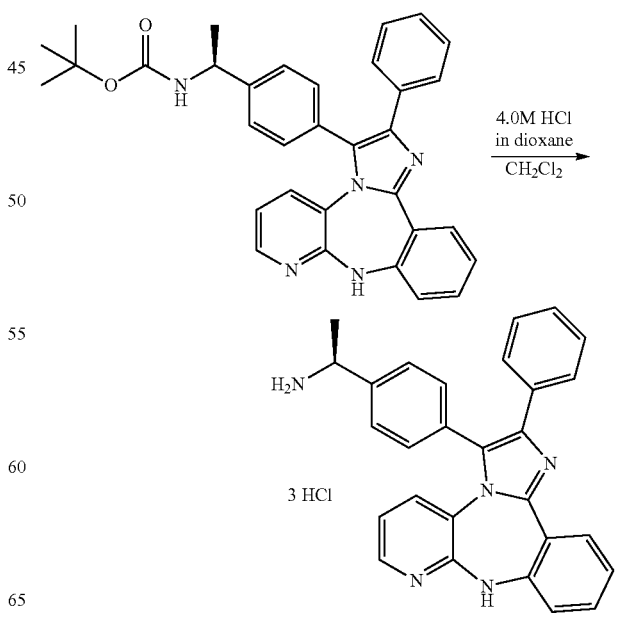

To a solution (S)-tert-butyl (1-(4-(2-phenyl-9H-benzo[f]imidazo[1,2-d]pyrido[2,3-b][1,4]diazepin-3-yl)phenyl)ethyl)carbamate (0.251 g) in dichloromethane (20 mL) was added 4.0 M HCl in dioxane (2 mL). The reaction was stirred at room temperature for 4 hours. The reaction mixture was concentrated under reduced pressure and then diluted with ether (20 mL). The product was removed by filtration under reduced pressure and dried to give (S)-1-(4-(2-phenyl-9H-benzo[f]imidazo[1,2-d]pyrido[2,3-b][1,4]diazepin-3-yl)phenyl)ethanamine hydrochloride as a yellow solid (0.215 g, 98% based on tris HCl salt). $^1$H NMR (DMSO-$d_6$) 400 MHz δ 8.83 (br. s, 1 H), 8.69 (br. s, 3H), 8.16 (dd, $J_A$=4.7 Hz, $J_B$=1.6 Hz, 1H), 8.00 (d, J=7.8 Hz, 1H), 7.56 (d, J=8.6 Hz, 2H), 7.52-7.44 (m, 3H), 7.40-7.30 (m, 3H), 7.28 (d, J=8.2 Hz, 2H), 7.19 (t, J=7.6 Hz, 1H), 6.95-6.91 (m, 1H), 6.82-6.77 (m, 1H), 4.43 (quint., J=6.1 Hz, 1H), 1.52 (d, J=6.7 Hz, 3H); LCMS: 430 [M+H]; Calc. for $C_{28}H_{23}N_5$.3.5HCl.0.05 dioxane.0.35 diethylether: C, 60.52; H, 5.22; N, 11.92. Found C, 60.57; H, 5.67; N, 12.02.

Example 3

Preparation of 1-(4-(2-phenyl-9H-benzo[f]imidazo[1,2-d]pyrido[2,3-b][1,4]diazepin-3-yl)phenyl)cyclobutanamine hydrochloride

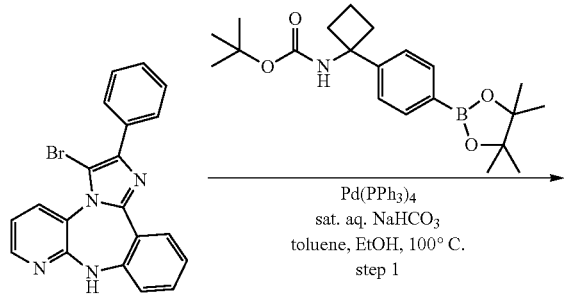

Pd(PPh₃)₄
sat. aq. NaHCO₃
toluene, EtOH, 100° C.
step 1

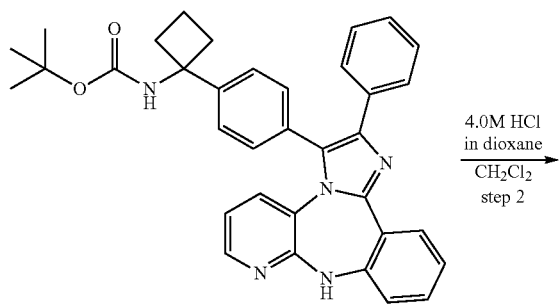

4.0M HCl in dioxane
CH₂Cl₂
step 2

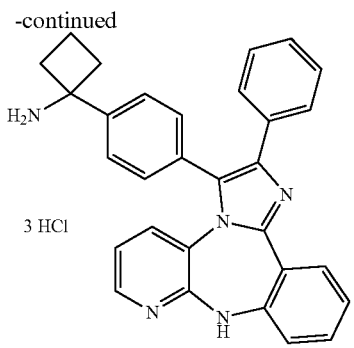

3 HCl

Step 1: Preparation of tert-butyl (1-(4-(2-phenyl-9H-benzo[f]imidazo[1,2-d]pyrido[2,3-b][1,4]diazepin-3-yl)phenyl)cyclobutyl)carbamate

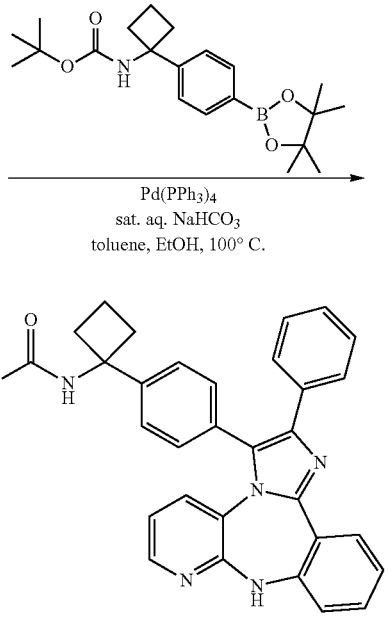

To a suspension of 3-bromo-2-phenyl-9H-benzo[f]imidazo[1,2-d]pyrido[2,3-b][1,4]diazepine (0.800 g, 1 eq.) in a mixture of toluene (10 mL), ethanol (10 mL), and saturated sodium bicarbonate (2 mL) was added tert-butyl (1-(4-(4,4,5,5-tetramethyl-1,3,2-dioxaborolan-2-yl)phenyl)cyclobutyl)carbamate (1.15 g, 1.5 eq.). The reaction was degassed (nitrogen) for 5 minutes and tetrakis(triphenylphosphine)palladium(0) added (0.08 g). The reaction was again degassed for 5 minutes and stirred at 100° C. overnight. The reaction mixture was cooled to room temperature and poured onto water (100 mL). The aqueous phase was extracted with dichloromethane (2×75 mL) and the organic extracts were combined and washed with water (1×50 mL), brine (1×50 mL), dried over sodium sulfate, filtered and concentrated under reduced pressure. Purification by column chromatography (25-75% ethyl acetate in hexanes) gave the product which was triturated with ether to give tert-butyl (1-(4-(2-phenyl-9H-benzo[f]imidazo[1,2-d]pyrido[2,3-b][1,4]diazepin-3-yl)phenyl)cyclobutyl)carbamate (0.6 g, 52%). $^1$H NMR (DMSO-$d_6$) 400 MHz δ 8.41 (s, 1H), 8.04 (dd, $J_A$=4.8 Hz, $J_B$=1.6 Hz, 1H), 7.96 (dd, $J_A$=7.6 Hz, $J_B$=1.6 Hz, 1H), 7.53-7.48 (m, 2H), 7.45-7.08 (m, 11H), 6.91-6.86 (m, 1H), 6.67-6.62 (m, 1H), 2.45-2.32 (m, 4H), 2.07-1.94 (m, 1H), 1.85-1.73 (m, 1H), 1.28 (bs, 9H); LCMS: 556 [M+H].

Step 2: Preparation of 1-(4-(2-phenyl-9H-benzo[f]imidazo[1,2-d]pyrido[2,3-b][1,4]diazepin-3-yl)phenyl)cyclobutanamine hydrochloride

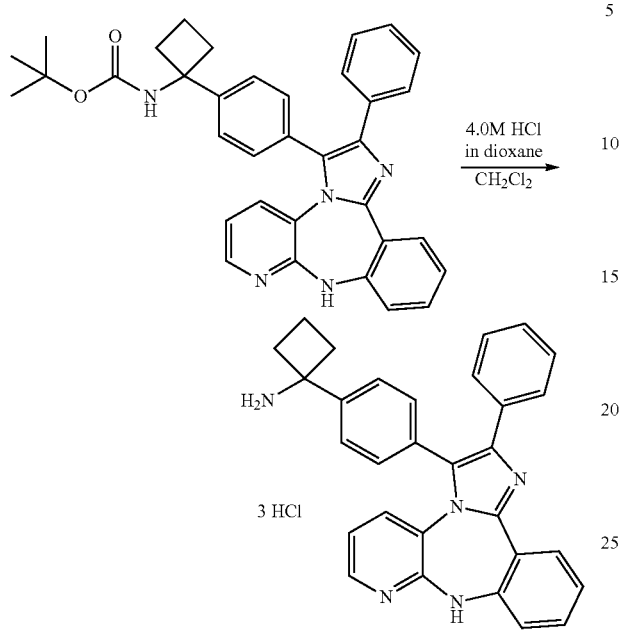

To a solution of tert-butyl (1-(4-(2-phenyl-9H-benzo[f]imidazo[1,2-d]pyrido[2,3-b][1,4]diazepin-3-yl)phenyl)cyclobutyl)carbamate (0.55 g) in dichloromethane (50 mL) was added 4.0 M HCl in dioxane (5 mL). The reaction was stirred at room temperature for 6 hours and then diluted with ether (50 mL). The product was removed by filtration under reduced pressure and dried to give 1-(4-(2-phenyl-9H-benzo[f]imidazo[1,2-d]pyrido[2,3-b][1,4]diazepin-3-yl)phenyl)cyclobutanamine hydrochloride as a pale yellow solid (0.52 g, 88% based on tris HCl salt). $^1$H NMR (DMSO-d$_6$) 400 MHz δ 8.80 (bs, 3H), 8.68 (s, 1H), 8.12 (dd, J$_A$=4.8 Hz, J$_B$=1.6 Hz, 1H), 7.98-7.95 (m, 1H), 7.57-7.48 (m, 4H), 7.43-7.27 (m, 7H), 7.15 (t, J=7.2 Hz, 1H), 6.91-6.88 (m, 1H), 6.79-6.74 (m, 1H), 2.56 (t, J=8 Hz, 4H), 2.24-2.16 (m, 1H), 1.85-1.77 (m, 1H); LCMS: 456 [M+H]. Calc. for C$_{30}$H$_{25}$N$_5$.3.07HCl.0.14 dioxane.0.28 diethylether: C, 63.36; H, 5.37; N, 11.66. Found C, 63.36; H, 5.50; N, 11.67.

Example 4

Preparation of 1-(2-fluoro-4-(2-(o-tolyl)-9H-benzo[f]imidazo[1,2-d]pyrido[2,3-b][1,4]diazepin-3-yl)phenyl)cyclobutanamine hydrochloride

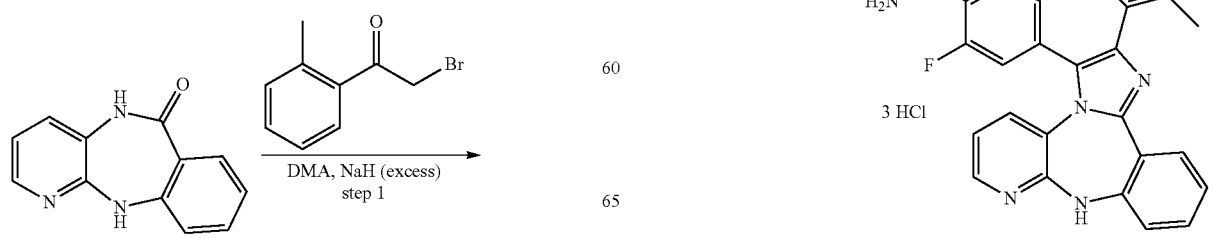

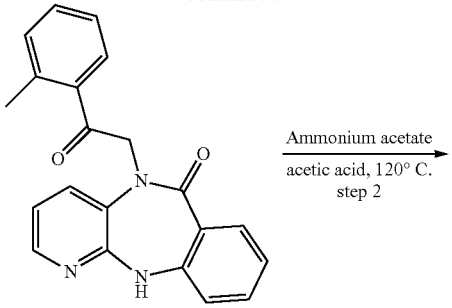

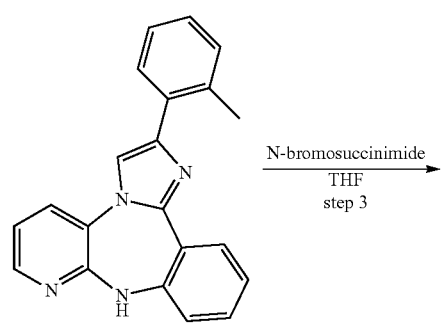

Step 1: Preparation of 5-(2-oxo-2-(o-tolyl)ethyl)-5H-benzo[e]pyrido[3,2-b][1,4]diazepin-6(11H)-one

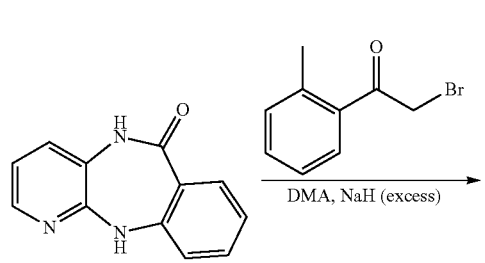

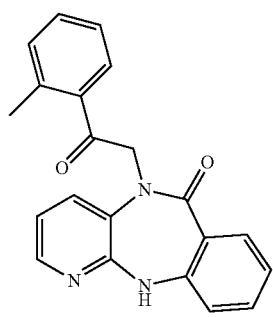

5H-benzo[e]pyrido[3,2-b][1,4]diazepin-6(11H)-one (1.0 g, 1 eq.) was suspended in dimethylacetamide (DMA) (30 mL). The reaction was cooled to 0° C. and sodium hydride (60% in mineral oil) (380 mg, 2.0 eq.) was added. The reaction was warmed to room temperature and stirred until gas evolution ceased. The reaction was cooled to 0° C. and 2-bromo-1-(o-tolyl)ethanone (1.2 g, 1.2 eq.) was added. The reaction was stirred at 50° C. overnight. The reaction was poured onto 80 mL water and extracted with dichloromethane (2×100 mL). The organic extracts were combined, washed with water (2×100 mL), brine (2×100 mL), dried over sodium sulfate, filtered and concentrated under reduced pressure. The crude product, 5-(2-oxo-2-(o-tolyl)ethyl)-5H-benzo[e]pyrido[3,2-b][1,4]diazepin-6(11H)-one (0.65 g) was used without purification. LCMS: 344 [M+H].

Step 2: Preparation of 2-(o-tolyl)-9H-benzo[f]imidazo[1,2-d]pyrido[2,3-b][1,4]diazepine

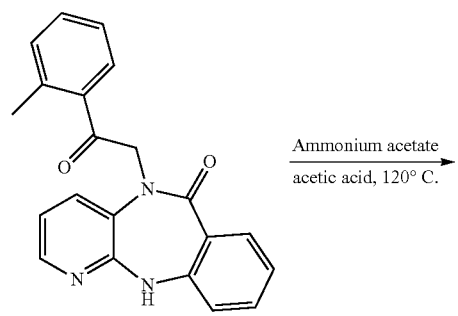

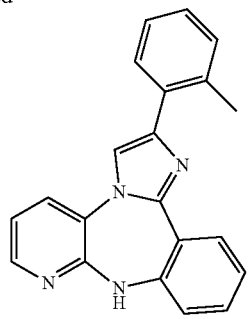

To a solution of 5-(2-oxo-2-(o-tolyl)ethyl)-5H-benzo[e]pyrido[3,2-b][1,4]diazepin-6(11H)-one (0.6 g, 1 eq.) in acetic acid (10 mL) was added ammonium acetate (2.7 g, 20 eq.). The reaction was stirred at 120° C. for 48 hours. The reaction was poured onto water (50 mL) and ethyl acetate (150 mL). The pH was adjusted to 9 by the addition of NaOH 1N. The phases were separated and washed with water (1×50 mL), brine (1×50 mL), dried over sodium sulfate, filtered and concentrated under reduced pressure. Purification by column chromatography (10% ethyl acetate in dichloromethane) gave the 2-(o-tolyl)-9H-benzo[f]imidazo[1,2-d]pyrido[2,3-b][1,4]diazepine (0.3 g, 53%). M.p.: 215-217° C.; $^1$H NMR (DMSO-$d_6$) 400 MHz δ 8.60 (s, 1H), 8.18 (dd, $J_A$=4.4 Hz, $J_B$=1.2 Hz, 1H), 7.99 (dd, $J_A$=8.0 Hz, $J_B$=1.2 Hz, 1H), 7.91-7.85 (m, 2H), 7.82 (s, 1H), 7.34-7.20 (m, 5H), 7.14 (dd, $J_A$=8.0 Hz, $J_B$=4.8 Hz, 1H), 7.05 (t, J=8.4 Hz, 1H), 2.56 (s, 3H); LCMS: 325 [M+H].

Step 3: Preparation of 3-bromo-2-(o-tolyl)-9H-benzo[f]imidazo[1,2-d]pyrido[2,3-b][1,4]diazepine

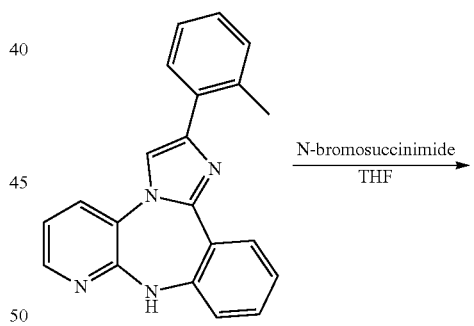

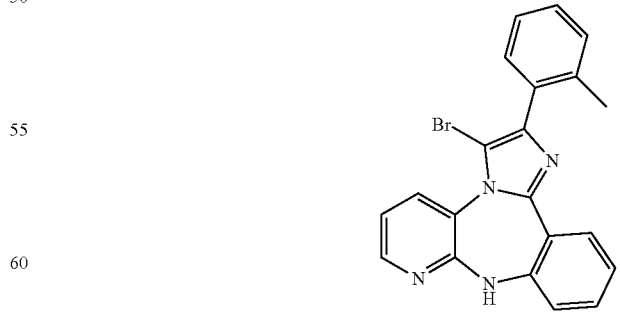

To a solution of 2-(o-tolyl)-9H-benzo[f]imidazo[1,2-d]pyrido[2,3-b][1,4]diazepine (0.2 g, 1 eq.) in THF (5 mL) was added N-bromosuccinimide (0.11 g, 1 eq.). The reaction was stirred at room temperature for 15 minutes, poured onto water (30 mL) and extracted with ethyl acetate (2×30 mL). The organic extracts were combined, washed with saturated sodium bicarbonate (1×50 mL), water (1×50 mL), brine (1×50 mL) and dried over sodium sulfate. After filtration and concentration under reduced pressure, the crude product was purified by column chromatography (20% ethyl acetate in hexanes). The 3-bromo-2-(o-tolyl)-9H-benzo[f]imidazo[1,2-d]pyrido[2,3-b][1,4]diazepine (0.19 g, 77%) was obtained as an off-white solid. M.p.: 220-222° C.; $^1$H NMR (DMSO-$d_6$) 400 MHz δ 8.64 (s, 1H), 8.27 (dd, $J_A$=3.6 Hz, $J_B$=1.6 Hz, 1H), 8.03 (dd, $J_A$=7.2 Hz, $J_B$=1.6 Hz, 1H), 7.78 (dd, $J_A$=7.6 Hz, $J_B$=1.2 Hz, 1H), 7.44 (d, J=6.8 Hz, 1H), 7.38-7.23 (m, 6H), 7.09 (t, J=7.6 Hz, 1H), 2.37 (s, 3H); LCMS: 403 [M+H].

Step 4: Preparation of tert-butyl (1-(2-fluoro-4-(2-(o-tolyl)-9H-benzo[f]imidazo[1,2-d]pyrido[2,3-b][1,4]diazepin-3-yl)phenyl)cyclobutyl)carbamate

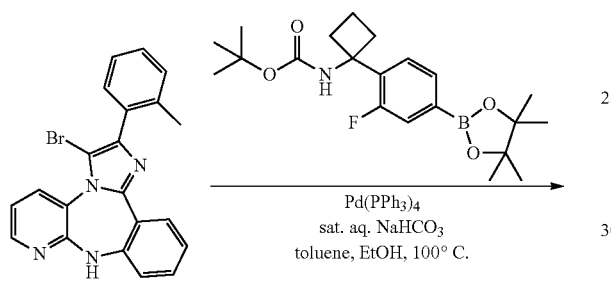

To a suspension of 3-bromo-2-(o-tolyl)-9H-benzo[f]imidazo[1,2-d]pyrido[2,3-b][1,4]diazepine (0.06 g, 1 eq.) in a mixture of toluene (0.5 mL), ethanol (0.5 mL), and saturated sodium bicarbonate (0.1 mL) was added tert-butyl (1-(2-fluoro-4-(4,4,5,5-tetramethyl-1,3,2-dioxaborolan-2-yl)phenyl)cyclobutyl)carbamate (0.088 g, 1.5 eq.). The reaction was degassed (nitrogen) for 5 minutes and tetrakis(triphenylphosphine)palladium(0) added (0.017 g). The reaction was again degassed for 5 minutes and stirred at 100° C. overnight. The reaction mixture was cooled to room temperature and poured onto water (30 mL). The aqueous phase was extracted with dichloromethane (2×30 mL) and the organic extracts were combined and washed with water (1×50 mL), brine (1×50 mL), dried over sodium sulfate, filtered and concentrated under reduced pressure. Purification by column chromatography (5% ethyl acetate in dichloromethane) gave tert-butyl (1-(2-fluoro-4-(2-(o-tolyl)-9H-benzo[f]imidazo[1,2-d]pyrido[2,3-b][1,4]diazepin-3-yl)phenyl)cyclobutyl)carbamate (0.133 g, 40%). M.p.: 138-140° C.; $^1$H NMR (DMSO-$d_6$) 400 MHz δ 8.63 (s, 1H), 8.13 (d, J=4.4 Hz, 1H), 7.91 (d, J=7.6 Hz, 1H), 7.37-7.26 (m, 2H), 7.25-7.13 (m, 5H), 7.08 (t, J=7.4 Hz, 1H), 6.95 (bs. S, 1H), 6.74 (br. S, 1H), 6.69-6.63 (m, 2H), 2.42-2.28 (m, 4H), 2.08 (s, 3H), 2.04-1.94 (m, 1H), 1.76-1.64 (m, 1H), 1.34-1.10 (m, 9H, rotamers from BOC group); LCMS: 588 [M+H].

Step 5: Preparation of 1-(2-fluoro-4-(2-(o-tolyl)-9H-benzo[f]imidazo[1,2-d]pyrido[2,3-b][1,4]diazepin-3-yl)phenyl)cyclobutanamine hydrochloride

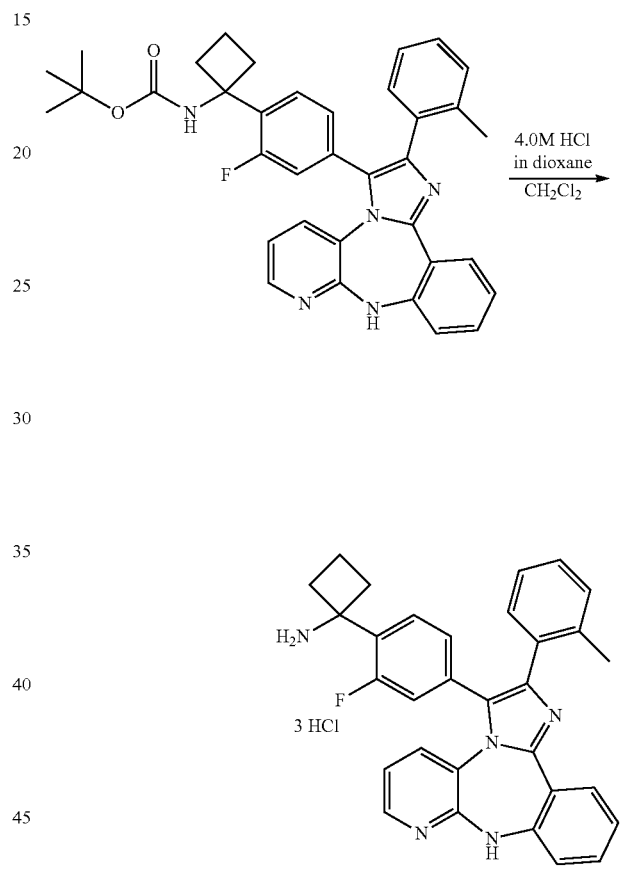

To a solution of tert-butyl (1-(2-fluoro-4-(2-(o-tolyl)-9H-benzo[f]imidazo[1,2-d]pyrido[2,3-b][1,4]diazepin-3-yl)phenyl)cyclobutyl)carbamate (0.035 g) in dichloromethane (0.5 mL) was added 4.0 M HCl in dioxane (0.05 mL). The reaction was stirred at room temperature for 3 hours. The product was removed by filtration under reduced pressure and dried to give 1-(2-fluoro-4-(2-(o-tolyl)-9H-benzo[f]imidazo[1,2-d]pyrido[2,3-b][1,4]diazepin-3-yl)phenyl)cyclobutanamine hydrochloride as a yellow solid (0.025 g, 74% based on tris HCl salt). $^1$H NMR (DMSO-$d_6$) 400 MHz δ 8.77 (br. s, 1 H), 8.73 (br. s, 3H), 8.19 (d, J=4.4 Hz, 1H), 7.91 (dd, $J_A$=7.6 Hz, $J_B$=1.2 Hz, 1H), (7.41 (t, J=6.8 Hz, 1H), 7.36-7.31 (m, 3H), 7.30-7.25 (m, 2H), 7.24-7.18 (m, 1H), 7.12 (t, J=7.6 Hz, 1H), 6.99 (d, J=7.2 Hz, 1H), 6.89-6.84 (m, 3H), 2.68-2.57 (m, 2H), 2.54-2.44 (m, 2H), 2.36-2.25 (m, 1H), 2.17 (s, 3H), 1.88-1.74 (m, 1H); LCMS: 488 [M+H]; Calc. for $C_{31}H_{26}N_5F \cdot 2.59HCl \cdot 1.05$ dioxane: C, 62.68; H, 5.53; N, 10.38. Found C, 62.69; H, 5.67; N, 10.39.

Example 5

Preparation of 1-(4-(2-phenethyl-9H-benzo[f]imidazo[1,2-d]pyrido[2,3-b][1,4]diazepin-3-yl)phenyl)cyclobutanamine (TFA salt)

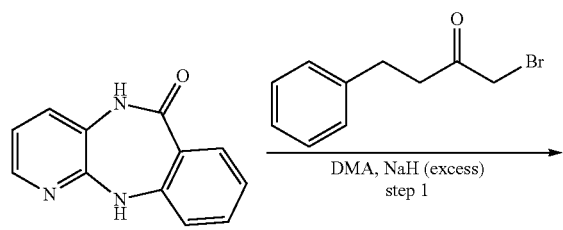

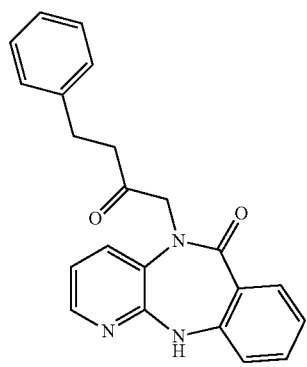

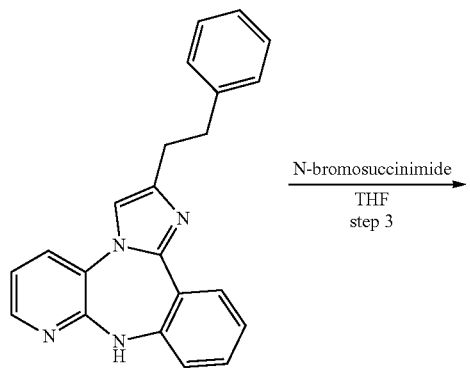

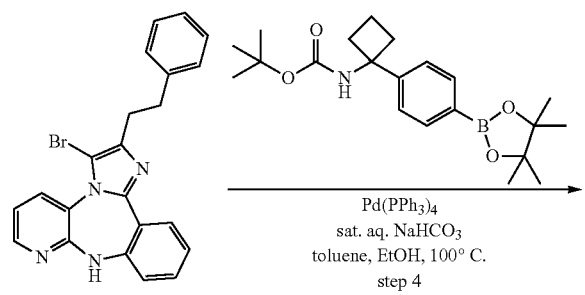

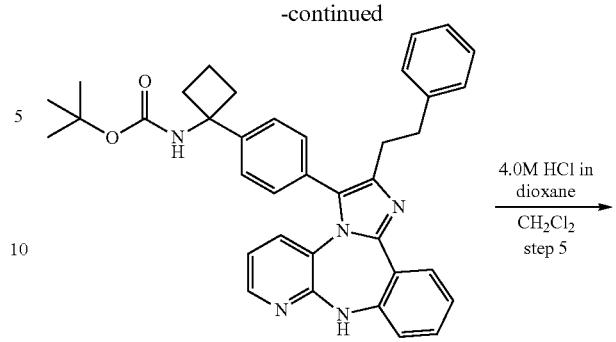

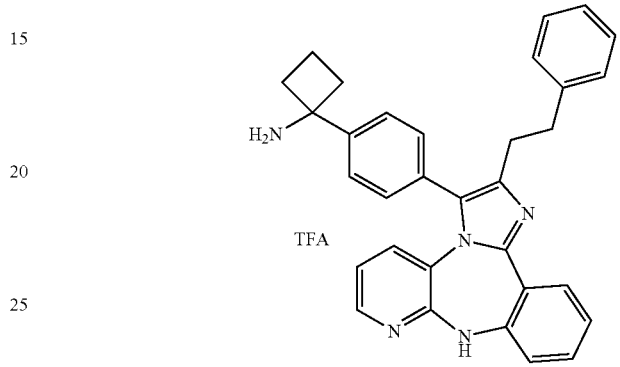

Step 1: Preparation of 5-(2-oxo-4-phenylbutyl)-5H-benzo[e]pyrido[3,2-b][1,4]diazepin-6(11H)-one

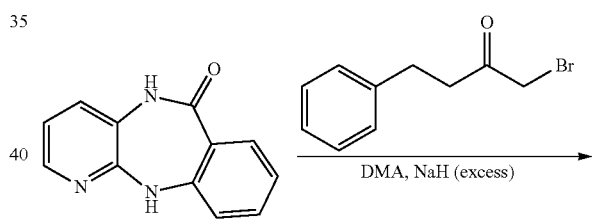

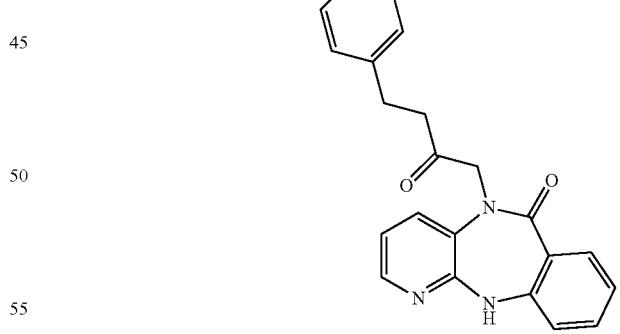

5H-benzo[e]pyrido[3,2-b][1,4]diazepin-6(11H)-one (0.863 g, 1 eq.) was suspended in dimethylacetamide (DMA) (15 mL). The reaction was cooled to 0° C. and sodium hydride (60% in mineral oil) (360 mg, 2.2 eq.) was added. The reaction was warmed to room temperature and stirred until gas evolution ceased. The reaction was cooled to 0° C. and 1-bromo-4-phenylbutan-2-one (1.1 g, 1.2 eq.) was added. The reaction was stirred at room temperature for 2 hours. The reaction was poured onto 100 mL water and extracted with dichloromethane (2×100 mL). The organic extracts were combined, washed with water (2×100 mL), brine (2×100 mL), dried over sodium sulfate, filtered and concentrated under reduced pressure. The crude product, 5-(2-oxo-4-phenylbutyl)-5H-benzo[e]pyrido[3,2-b][1,4]diazepin-6(11H)-one (1.56 g) was used without purification. LCMS: 358 [M+H].

Step 2: Preparation of 2-phenethyl-9H-benzo[f]imidazo[1,2-d]pyrido[2,3-b][1,4]diazepine

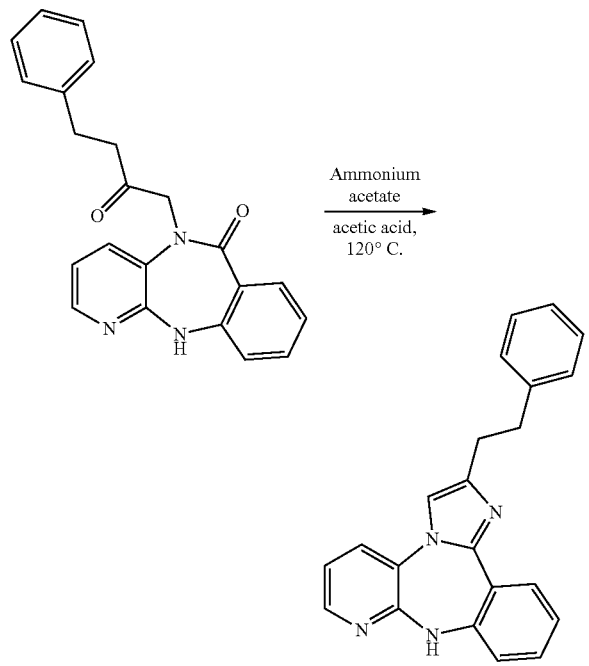

To a solution of 5-(2-oxo-4-phenylbutyl)-5H-benzo[e]pyrido[3,2-b][1,4]diazepin-6(11H)-one (1.56 g, 1 eq.) in acetic acid (10 mL) was added ammonium acetate (3.37 g, 10 eq.). The reaction was stirred at 120° C. for 8 hours. The reaction mixture was poured onto water (100 mL) and extracted with dichloromethane (3×100 mL). The combined organic extracts were dried over sodium sulfate, filtered and concentrated under reduced pressure. Purification by column chromatography (0-10% methanol in dichloromethane) gave the 2-phenethyl-9H-benzo[f]imidazo[1,2-d]pyrido[2,3-b][1,4]diazepine (0.374 g, 27%). $^1$H NMR (CDCL$_3$) 400 MHz δ 8.08 (dd, J$_A$=4.8 Hz, J$_B$=1.6 Hz, 1H), 7.97 (dd, J$_A$=8.0 Hz, J$_B$=1.2 Hz, 1H), 7.46 (dd, J$_A$=8.0 Hz, J$_B$=1.6 Hz, 1H), 7.34-7.15 (m, 6H), 7.08 (td, J$_A$=7.6 Hz, J$_B$=1.2 Hz, 1H), 6.98 (dd, J$_A$=7.6 Hz, J$_B$=4.8 Hz, 1H), 6.86 (dd, J$_A$=7.6 Hz, J$_B$=0.8 Hz, 1H), 6.81 (s, 1H), 6.27 (s, 1H), 3.07-2.90 (m, 4H); LCMS: 339 [M+H].

Step 3: Preparation of 3-bromo-2-phenethyl-9H-benzo[f]imidazo[1,2-d]pyrido[2,3-b][1,4]diazepine

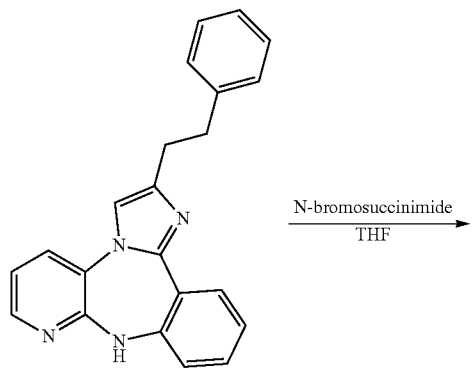

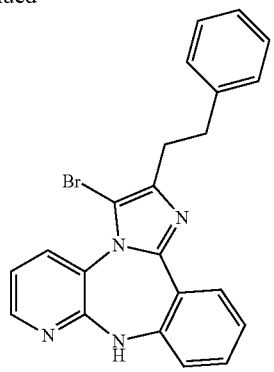

To a solution 2-phenethyl-9H-benzo[f]imidazo[1,2-d]pyrido[2,3-b][1,4]diazepine (0.374 g, 1 eq.) in THF (50 mL) was added N-bromosuccinimide (0.206 g, 1.05 eq.). The reaction was stirred at room temperature for 30 minutes, poured onto water (100 mL) and extracted with dichloromethane (2×100 mL). The organic extracts were combined, washed with brine (1×50 mL) and dried over sodium sulfate. After filtration and concentration under reduced pressure, the crude product, 3-bromo-2-phenethyl-9H-benzo[f]imidazo[1,2-d]pyrido[2,3-b][1,4]diazepine (0.197 g, 42%) was obtained as an orange solid. LCMS: 419 [M+H].

Step 4: Preparation of tert-butyl (1-(4-(2-phenethyl-9H-benzo[f]imidazo[1,2-d]pyrido[2,3-b][1,4]diazepin-3-yl)phenyl)cyclobutyl)carbamate

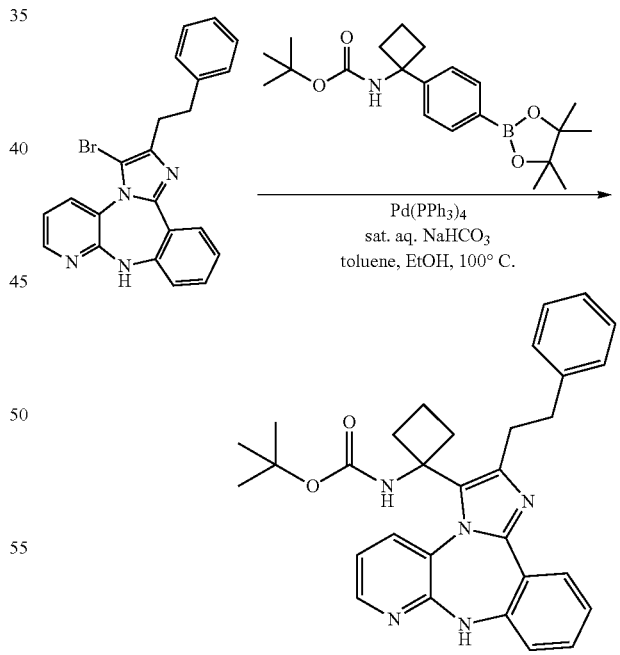

To a suspension of 3-bromo-2-phenethyl-9H-benzo[f]imidazo[1,2-d]pyrido[2,3-b][1,4]diazepine (0.197 g, 1 eq.) in a mixture of toluene (10 mL), ethanol (10 mL), and saturated sodium bicarbonate (4 mL) was added tert-butyl (1-(4-(4,4,5,5-tetramethyl-1,3,2-dioxaborolan-2-yl)phenyl)cyclobutyl)carbamate (0.353 g, 2 eq.). The reaction was degassed (nitrogen) for 5 minutes and tetrakis(triphenylphosphine)

palladium(0) added (0.054 g). The reaction was again degassed for 5 minutes and stirred at 100° C. overnight. The reaction mixture was cooled to room temperature and poured onto water (100 mL). The aqueous phase was extracted with dichloromethane (2×100 mL) and the organic extracts were combined and washed with brine (1×100 mL), dried over sodium sulfate, filtered and concentrated under reduced pressure. Purification by column chromatography (10-60% ethyl acetate in hexanes) gave tert-butyl (1-(4-(2-phenethyl-9H-benzo[f]imidazo[1,2-d]pyrido[2,3-b][1,4]diazepin-3-yl) phenyl)cyclobutyl)carbamate (0.042 g, 15%) as a yellow solid. LCMS: 584 [M+H].

Step 5: Preparation of 1-(4-(2-phenethyl-9H-benzo [f]imidazo[1,2-d]pyrido[2,3-b][1,4]diazepin-3-yl) phenyl)cyclobutanamine (TFA salt)

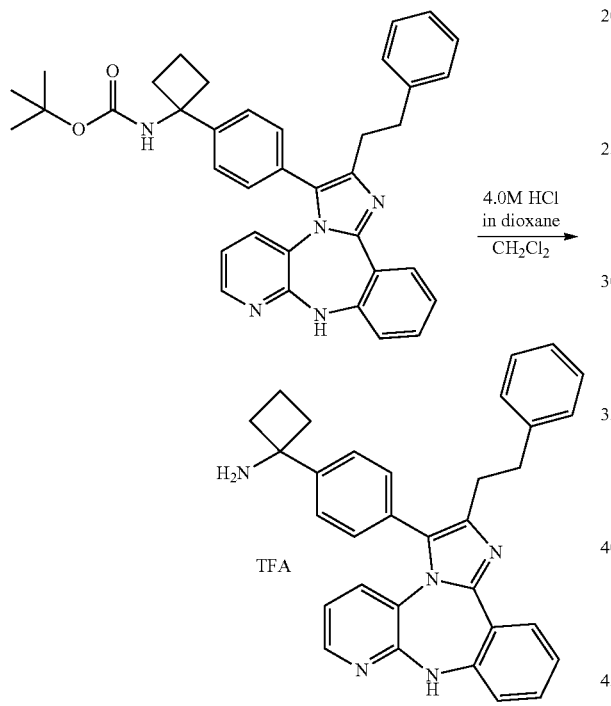

To a solution of tert-butyl (1-(4-(2-phenethyl-9H-benzo[f] imidazo[1,2-d]pyrido[2,3-b][1,4]diazepin-3-yl)phenyl)cyclobutyl)carbamate (0.042 g) in dichloromethane (2 mL) was added 4.0 M HCl in dioxane (0.18 mL). The reaction was stirred at room temperature overnight. The reaction mixture was concentrated in vacuo and the residue was treated with aq. saturated sodium bicarbonate (10 mL). The mixture was extracted with dichloromethane (2×10 mL). The combined extracts were concentrated under reduced pressure and the crude product was purified by preparative HPLC (YMC PACK ODS-AM; AM12S05-1020WT; 100×20 mm ID; CAN/0.1% TFA, 30 mL/min) The product, 1-(4-(2-phenethyl-9H-benzo[f]imidazo[1,2-d]pyrido[2,3-b][1,4]diazepin-3-yl)phenyl)cyclobutanamine was obtained as a yellow solid (0.010 g, 29%). M.p.: 158-160° C.; $^1$H NMR (DMSO-$d_6$) 400 MHz δ 8.62 (br. s, 1 H), 8.56 (br. s, 3H), 8.12 (dd, $J_A$=4.8 Hz, $J_B$=1.6 Hz, 1H), 7.91 (dd, $J_A$=7.6 Hz, $J_B$=1.6 Hz, 1H), 7.48 (d, J=8.4 Hz, 2H), 7.40-7.36 (m, 1H), 7.32-7.22 (m, 3H), 7.21-7.05 (m, 6H), 6.82 (dd, $J_A$=8.0 Hz, $J_B$=1.6 Hz, 1H), 6.76 (dd, $J_A$=7.6 Hz, $J_B$=4.0 Hz, 1H), 3.05-2.97 (m, 2H), 2.91-2.83 (m, 2H), 2.64-2.46 (m, 4H), 2.22-2.10 (m, 1H), 1.87-1.75 (m, 1H); LCMS: 484 [M+H].

Example 6

Preparation of 2-(3-(4-(1-aminocyclobutyl)phenyl)-9H-benzo[f]imidazo[1,2-d]pyrido[2,3-b][1,4]diazepin-2-yl)-N-phenylacetamide hydrochloride

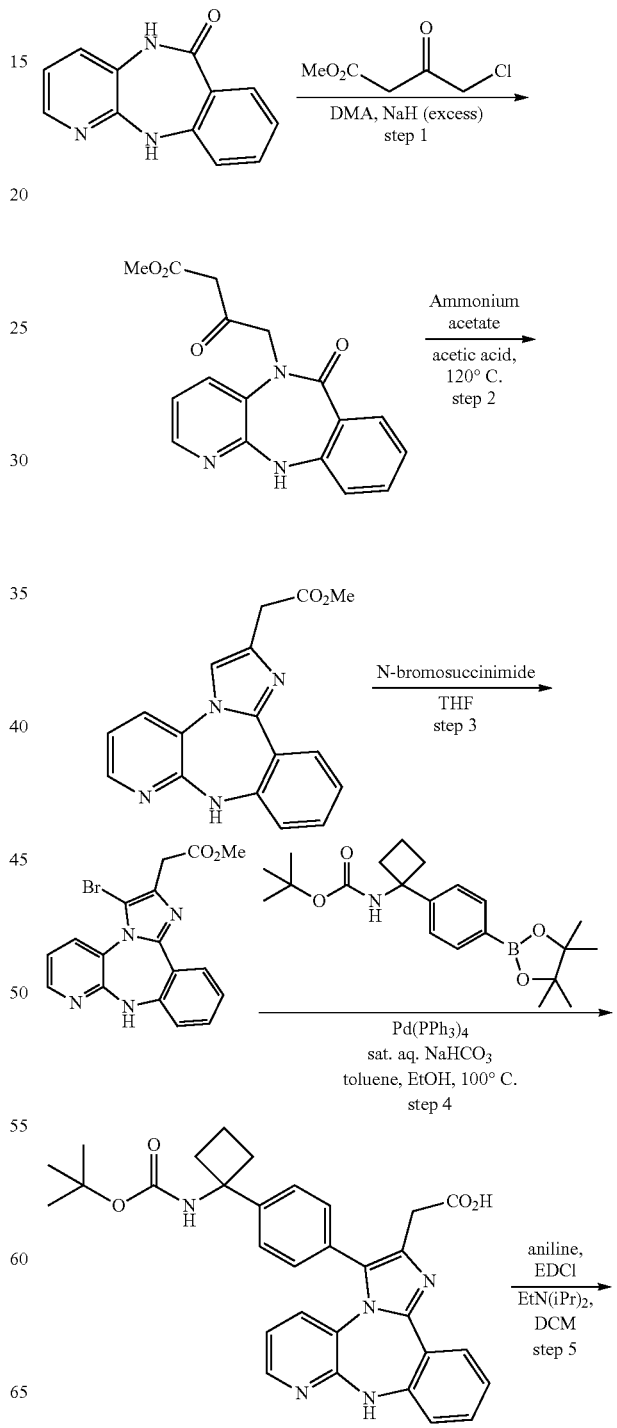

-continued

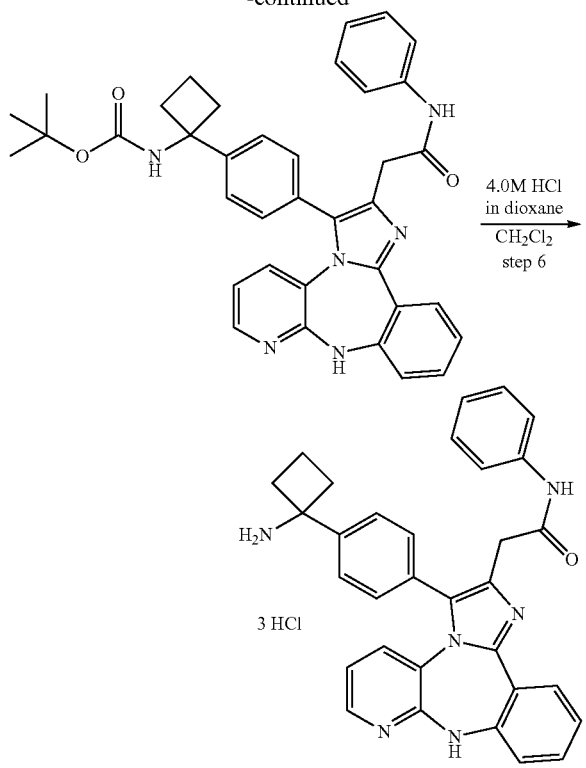

sure, giving 360 mg of crude product. Additional material was recuperated from the aqueous phase through extraction with ethyl acetate (3×50 mL). The ethyl acetate extracts were combined, washed with water (2×50 mL), brine (2×50 mL), dried over sodium sulfate, filtered and concentrated under reduced pressure, giving additional 135 mg of crude product. The crude product, 3-oxo-4-(6-oxo-6,11-dihydro-5H-benzo[e]pyrido[3,2-b][1,4]diazepin-5-yl)butanoate was used without purification. LCMS: 326 [M+H].

Step 2: Preparation of methyl 2-(9H-benzo[f]imidazo[1,2-d]pyrido[2,3-b][1,4]diazepin-2-yl)acetate

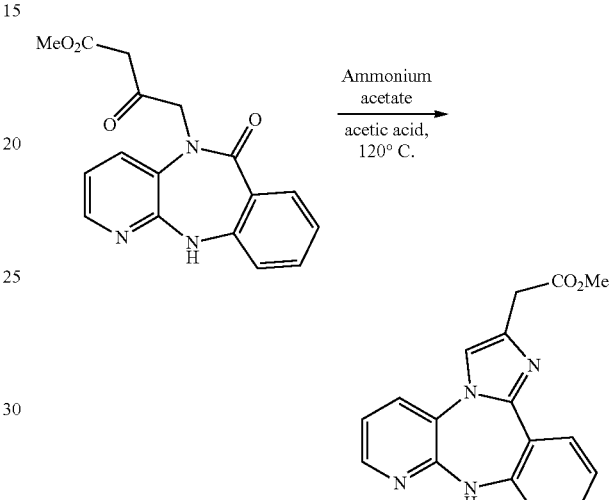

Step 1: Preparation of methyl 3-oxo-4-(6-oxo-6,11-dihydro-5H-benzo[e]pyrido[3,2-b][1,4]diazepin-5-yl)butanoate

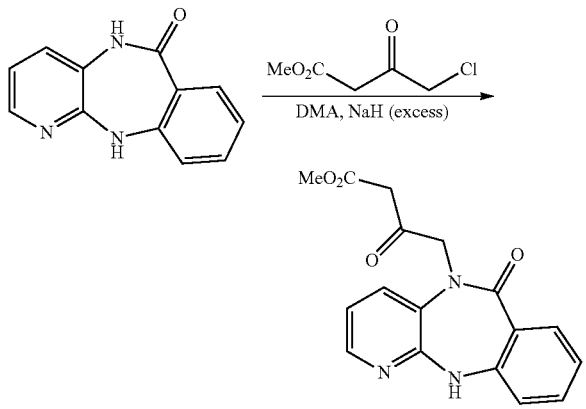

To a solution of 3-oxo-4-(6-oxo-6,11-dihydro-5H-benzo[e]pyrido[3,2-b][1,4]diazepin-5-yl)butanoate (crude product from step 1, 0.36 g, 1 eq.) in acetic acid (5 mL) was added ammonium acetate (0.385 g, 20 eq. based on the amount of starting material used in step 1). The reaction was stirred at 120° C. for 2 hours. The reaction was poured onto water (25 mL) and extracted with dichloromethane (2×25 mL). The combined extracts were washed with water (1×25 mL), saturated sodium bicarbonate (25 mL), brine (1×25 mL), dried over sodium sulfate, filtered and concentrated under reduced pressure. Purification by column chromatography (10% methanol in dichloromethane) gave the methyl 2-(9H-benzo[f]imidazo[1,2-d]pyrido[2,3-b][1,4]diazepin-2-yl)acetate (0.4 g). LCMS: 307 [M+H].

Step 3: Preparation of methyl 2-(3-bromo-9H-benzo[f]imidazo[1,2-d]pyrido[2,3-b][1,4]diazepin-2-yl)acetate

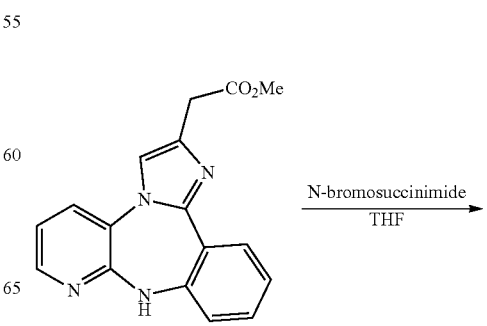

5H-benzo[e]pyrido[3,2-b][1,4]diazepin-6(11H)-one (0.5 g, 1 eq.) was suspended in dimethylformamide (DMF) (15 mL). The reaction was cooled to 0° C. and sodium hydride (60% in mineral oil) (230 mg, 2.5 eq.) was added. The reaction was warmed to room temperature and stirred until gas evolution ceased. The reaction was cooled to 0° C. and methyl 4-chloro-3-oxobutanoate (0.360 g, 1 eq.) was added. The reaction was stirred at room temperature overnight. The reaction was poured onto 50 mL water and extracted with dichloromethane (2×50 mL). The organic extracts were combined, washed with water (2×50 mL), brine (2×50 mL), dried over sodium sulfate, filtered and concentrated under reduced pres- -continued

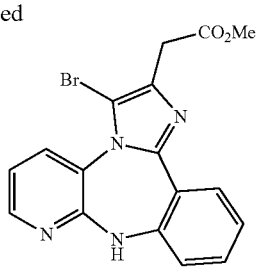

To a solution of methyl 2-(9H-benzo[f]imidazo[1,2-d]pyrido[2,3-b][1,4]diazepin-2-yl)acetate (0.14 g, 1 eq.) in THF (10 mL) was added N-bromosuccinimide (0.077 g, 1 eq.). The reaction was stirred at room temperature for 30 minutes, poured onto water (30 mL) and extracted with ethyl acetate (2×30 mL). The organic extracts were combined, washed with water (1×50 mL), brine (1×50 mL) and dried over sodium sulfate. After filtration and concentration under reduced pressure, the crude product was purified by column chromatography (2-5% methanol in dichloromethane). The methyl 2-(3-bromo-9H-benzo[f]imidazo[1,2-d]pyrido[2,3-b][1,4]diazepin-2-yl)acetate (0.162 g, 98%) was obtained. $^1$H NMR (DMSO-$d_6$) 400 MHz δ 8.23 (dd, $J_A$=4.4 Hz, $J_B$=1.6 Hz, 1H), 7.96 (dd, $J_A$=7.6 Hz, $J_B$=1.6 Hz, 1H), 7.77 (dd, $J_A$=8.0 Hz, $J_B$=1.6 Hz, 1H), 7.38-7.33 (m, 1H), 7.19 (dd, $J_A$=8.0 Hz, $J_B$=4.8 Hz, 1H), 7.14-7.05 (m, 2H), 3.75 (s, 2H), 3.74 (s, 3H); LCMS: 385, 387 [M+H].

Step 4: Preparation of 2-(3-(4-(1-((tert-butoxycarbonyl)amino)cyclobutyl)phenyl)-9H-benzo[f]imidazo[1,2-d]pyrido[2,3-b][1,4]diazepin-2-yl)acetic acid

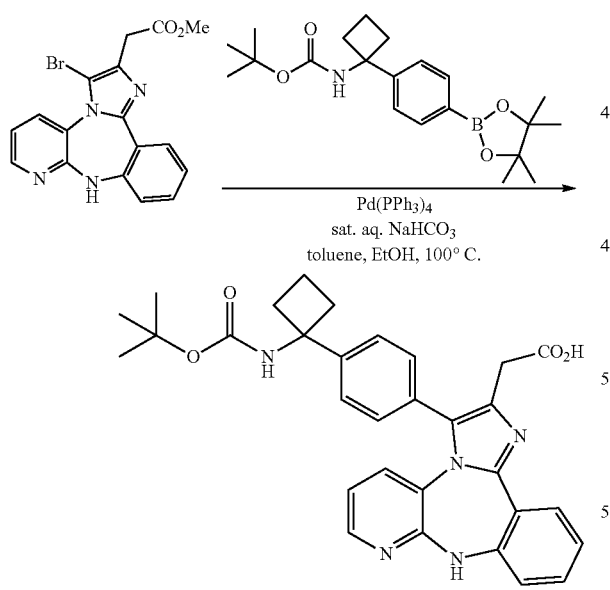

To a suspension of methyl 2-(3-bromo-9H-benzo[f]imidazo[1,2-d]pyrido[2,3-b][1,4]diazepin-2-yl)acetate (0.15 g, 1 eq.) in a mixture of toluene (8 mL), ethanol (8 mL), and saturated sodium bicarbonate (2 mL) was added tert-butyl (1-(4-(4,4,5,5-tetramethyl-1,3,2-dioxaborolan-2-yl)phenyl)cyclobutyl)carbamate (0.219 g, 1.5 eq.). The reaction was degassed (nitrogen) for 5 minutes and tetrakis(triphenylphosphine)palladium(0) added (0.045 g). The reaction was again degassed for 5 minutes and stirred at 100° C. overnight. The reaction mixture was cooled to room temperature and poured onto water (30 mL). The aqueous phase was extracted with dichloromethane (2×30 mL) and the organic extracts were combined and washed with water (1×50 mL), brine (1×50 mL), dried over sodium sulfate, filtered and concentrated under reduced pressure. Purification by column chromatography (0-100% ethyl acetate in hexanes) gave 2-(3-(4-(1-((tert-butoxycarbonyl)amino)cyclobutyl)phenyl)-9H-benzo[f]imidazo[1,2-d]pyrido[2,3-b][1,4]diazepin-2-yl)acetic acid (0.04 g, 19%). LCMS: 538 [M+H].

Step 5: Preparation of tert-butyl (1-(4-(2-(2-oxo-2-(phenylamino)ethyl)-9H-benzo[f]imidazo[1,2-d]pyrido[2,3-b][1,4]diazepin-3-yl)phenyl)cyclobutyl)carbamate

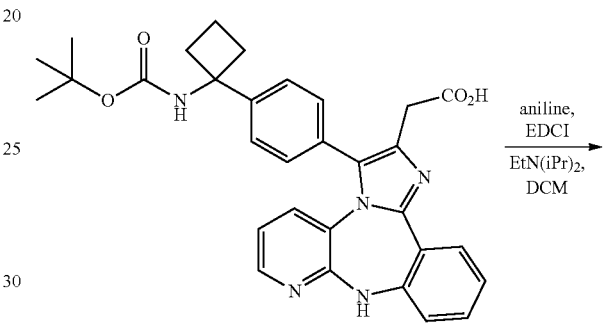

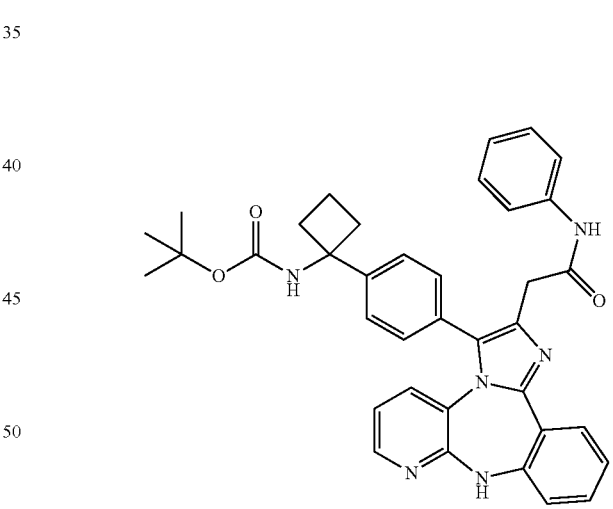

To a solution of 2-(3-(4-(1-((tert-butoxycarbonyl)amino)cyclobutyl)phenyl)-9H-benzo[f]imidazo[1,2-d]pyrido[2,3-b][1,4]diazepin-2-yl)acetic acid (0.04 g, 1 eq.) in dichloromethane (2 mL) was added successively aniline (0.027 g, 4 eq.), 1-ethyl-3-(3-dimethylaminopropyl)carbodiimide (EDCI) (0.029 g, 2 eq.) and diisopropylethylamine (70 μL, 5 eq.). The reaction was stirred at room temperature for 20 hours. The reaction mixture was diluted with dichloromethane (10 mL), washed with water (2×10 mL), dried over sodium sulfate, filtered and concentrated under reduced pressure. Purification by preparative HPLC (YMC PACK ODS-AM; AM12S05-1020WT; 100×20 mm ID; CAN/0.1% TFA, 30 mL/min) gave tert-butyl (1-(4-(2-(2-oxo-2-(phenylamino)ethyl)-9H-benzo[f]imidazo[1,2-d]pyrido[2,3-b][1,4]diazepin-3-yl)phenyl)cyclobutyl)carbamate (0.022 g, 48%). LCMS: 613 [M+H].

Step 6: Preparation of 2-(3-(4-(1-aminocyclobutyl)phenyl)-9H-benzo[f]imidazo[1,2-d]pyrido[2,3-b][1,4]diazepin-2-yl)-N-phenylacetamide hydrochloride

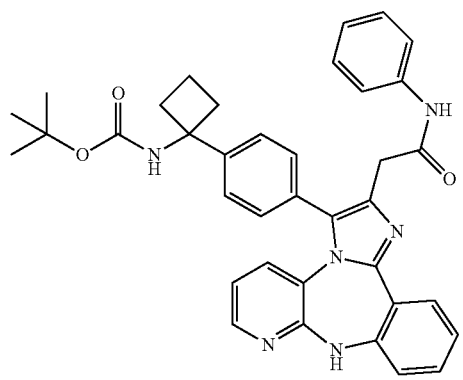

To a solution of tert-butyl (1-(4-(2-(2-oxo-2-(phenylamino)ethyl)-9H-benzo[f]imidazo[1,2-d]pyrido[2,3-b][1,4]diazepin-3-yl)phenyl)cyclobutyl)carbamate (0.020 g) in methanol (3 mL) was added 4.0 M HCl in dioxane (3 mL). The reaction was stirred at room temperature for 24 hours. The product was removed by filtration under reduced pressure and dried to give 1-(2-fluoro-4-(2-(o-tolyl)-9H-benzo[f]imidazo[1,2-d]pyrido[2,3-b][1,4]diazepin-3-yl)phenyl)cyclobutanamine hydrochloride as a yellow solid (0.007 g, 32% based on tris HCl salt). $^1$H NMR (MeOH-d$_4$) 400 MHz δ 8.16 (dd, $J_A$=5.2 Hz, $J_B$=1.6 Hz, 1H), 7.86 (dd, $J_A$=7.6 Hz, $J_B$=1.2 Hz, 1H), 7.36-7.31 (m, 3H), 7.62-7.54 (m, 4H), 7.52-7.40 (m, 3H), 7.34-7.28 (m, 2H), 7.26-7.19 (m, 2H), 7.12 (d, J=7.2 Hz, 1H), 7.08 (dd, $J_A$=8.0 Hz, $J_B$=1.6 Hz, 1H), 6.77 (dd, $J_A$=8.0 Hz, $J_B$=1.2 Hz, 1H), 3.88 (s, 2H), 2.77-2.70 (m, 2H), 2.66-2.55 (m, 2H), 2.25-2.21 (m, 1H), 2.07-1.90 (m, 1H); LCMS: 514 [M+H].

Example 7

Preparation of 1-(4-(3-phenyl-9H-benzo[f]imidazo[1,2-d]pyrido[2,3-b][1,4]diazepin-2-yl)phenyl)cyclobutanamine hydrochloride -continued

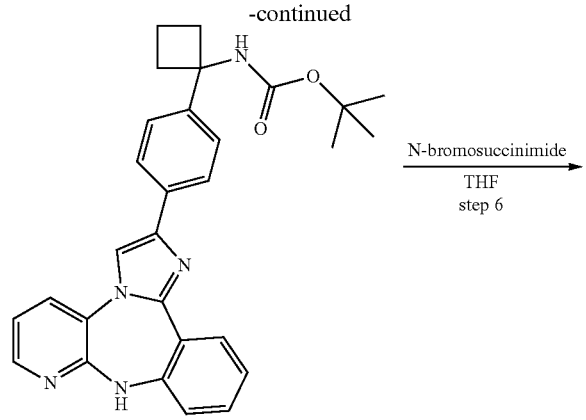

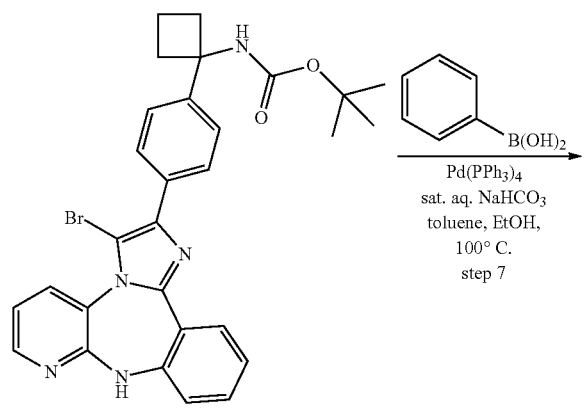

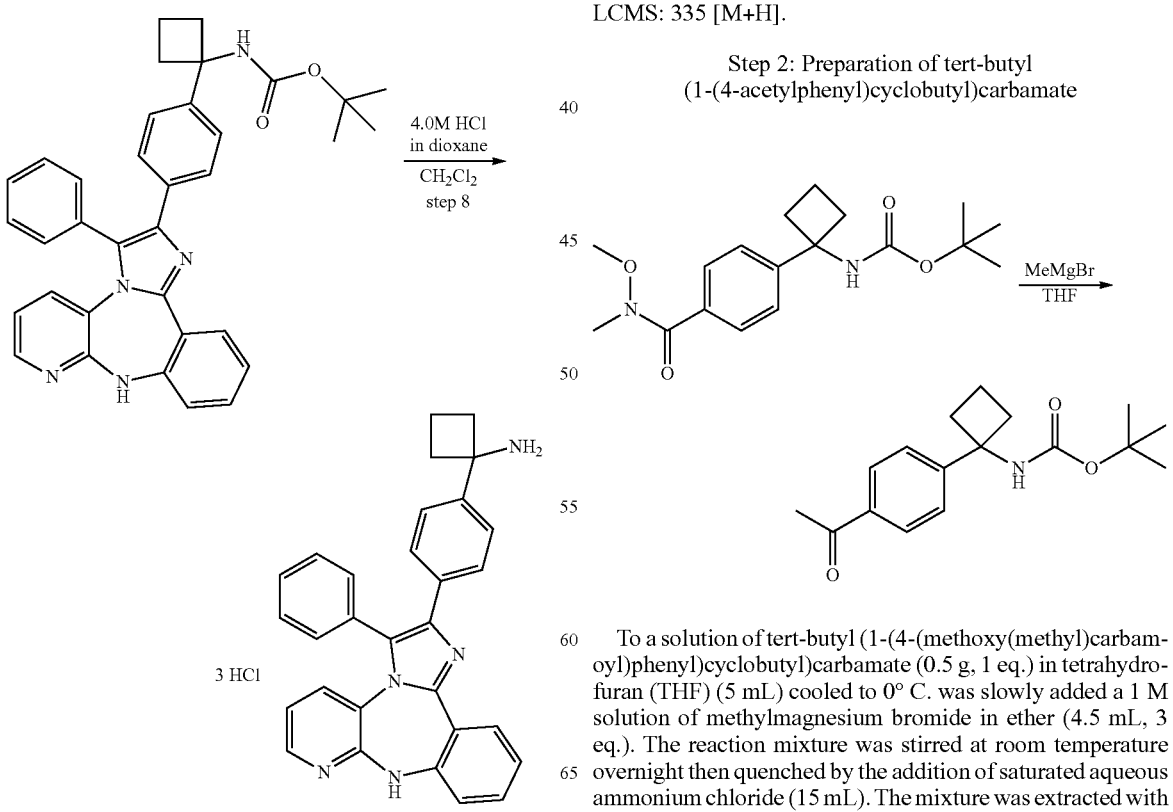

Step 1: Preparation of tert-butyl (1-(4-(methoxy(methyl)carbamoyl)phenyl)cyclobutyl)carbamate

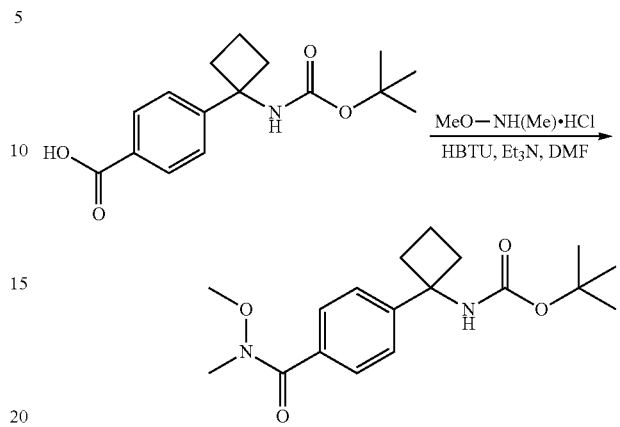

To a solution of 4-(1-((tert-butoxycarbonyl)amino)cyclobutyl)benzoic acid (2.5 g, 1 eq.) in dimethylformamide (10 mL) was added HBTU (3.41 g, 1.05 eq.) followed by triethylamine (6 mL, 5 eq.). The reaction mixture was stirred at room temperature for 10 minutes then the N,O-dimethylhydroxylamine hydrochloride was added (4.3 g, 5 eq.) and the mixture was stirred for 3 days. The reaction mixture was poured onto water (50 mL) and extracted with ethyl acetate (3×100 mL). The combined extracts were washed with water (100 mL), brine (100 mL) then dried over sodium sulfate, filtered and concentrated under reduced pressure. The crude material was purified by column chromatography (20-50% ethyl acetate in dichloromethane), giving tert-butyl (1-(4-(methoxy(methyl)carbamoyl)phenyl)cyclobutyl)carbamate (1.5 g, 52%). LCMS: 335 [M+H].

Step 2: Preparation of tert-butyl (1-(4-acetylphenyl)cyclobutyl)carbamate

To a solution of tert-butyl (1-(4-(methoxy(methyl)carbamoyl)phenyl)cyclobutyl)carbamate (0.5 g, 1 eq.) in tetrahydrofuran (THF) (5 mL) cooled to 0° C. was slowly added a 1 M solution of methylmagnesium bromide in ether (4.5 mL, 3 eq.). The reaction mixture was stirred at room temperature overnight then quenched by the addition of saturated aqueous ammonium chloride (15 mL). The mixture was extracted with dichloromethane (2×25 mL). The combined extracts were dried over sodium sulfate, filtered and concentrated under reduced pressure. The product was purified by column chromatography (15% ethyl acetate in dichloromethane), giving tert-butyl (1-(4-acetylphenyl)cyclobutyl)carbamate as a colorless oil which solidified upon standing (261 mg, 60%). $^1$H NMR (DMSO-d$_6$) 400 MHz δ 7.91 (d, J=8.0 Hz, 2H), 7.74 (br. s, 1 H), 7.50 (d, J=8.4 Hz, 2H), 2.56 (s, 3H), 2.45-2.32 (m, 4H), 2.06-1.94 (m, 1H), 1.86-1.75 (m, 1H), 1.33 (s, 9H).

Step 3: Preparation of tert-butyl (1-(4-(2-bromoacetyl)phenyl)cyclobutyl)carbamate

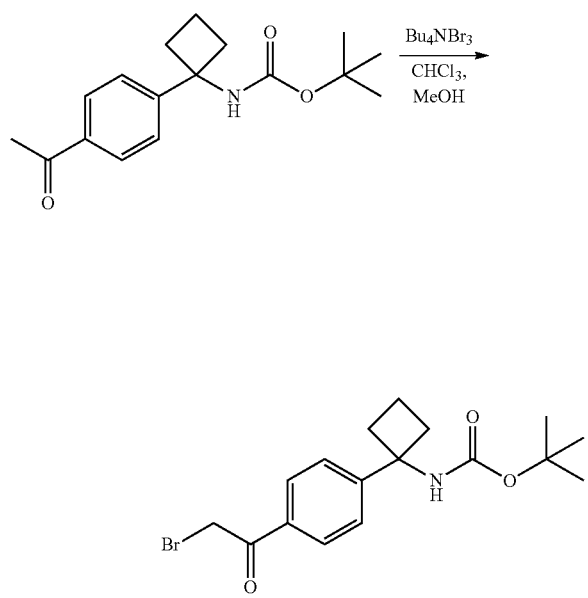

To a solution of tert-butyl (1-(4-acetylphenyl)cyclobutyl) carbamate (0.1 g, 1 eq.) in chloroform (3.5 mL) and methanol (1.5 mL) was added the tetrabutyl ammonium tribromide (0.175 g, 1.05 eq.). The mixture was stirred at 40° C. for 90 minutes. The reaction mixture was diluted with dichloromethane (10 mL), washed with water (10 mL), dried over sodium sulfate, filtered and concentrated under reduced pressure. The product was purified by column chromatography (10% ethyl acetate in dichloromethane), giving tert-butyl (1-(4-(2-bromoacetyl)phenyl)cyclobutyl)carbamate (0.1 g, 78%) as a colorless oil. LCMS: 312 [M−tBu+H], 314 [M−tBu+H].

Step 4: Preparation of tert-butyl (1-(4-(2-(6-oxo-6,11-dihydro-5H-benzo[e]pyrido[3,2-b][1,4]diazepin-5-yl)acetyl)phenyl)cyclobutyl)carbamate

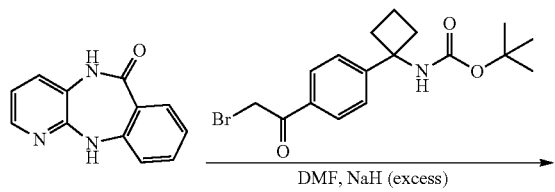

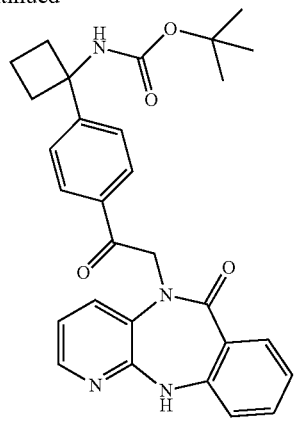

5H-benzo[e]pyrido[3,2-b][1,4]diazepin-6(11H)-one (0.362 g, 1.05 eq.) was suspended in dimethylformamide (DMF) (5 mL). The reaction was cooled to 0° C. and sodium hydride (60% in mineral oil) (0.2 g, 3.0 eq.) was added. The reaction was warmed to room temperature and stirred until gas evolution ceased. The reaction was cooled to 0° C. and tert-butyl (1-(4-(2-bromoacetyl)phenyl)cyclobutyl)carbamate (0.6 g, 1.0 eq.) in DMF (1 mL) was added. The reaction was stirred at room temperature overnight. The reaction was quenched by the addition of aqueous saturated ammonium chloride solution (1 mL). Dichloromethane was added (15 mL) and the phases were separated. The organic phase was washed with water (3×10 mL), dried over sodium sulfate, filtered and concentrated under reduced pressure. The product was purified by column chromatography (50% ethyl acetate in dichloromethane), giving tert-butyl (1-(4-(2-(6-oxo-6,11-dihydro-5H-benzo[e]pyrido[3,2-b][1,4]diazepin-5-yl)acetyl)phenyl)cyclobutyl)carbamate (0.4 g, 50%) as a yellow semi-solid. LCMS: 499 [M+H].

Step 5: Preparation of tert-butyl (1-(4-(9H-benzo[f]imidazo[1,2-d]pyrido[2,3-b][1,4]diazepin-2-yl)phenyl)cyclobutyl)carbamate

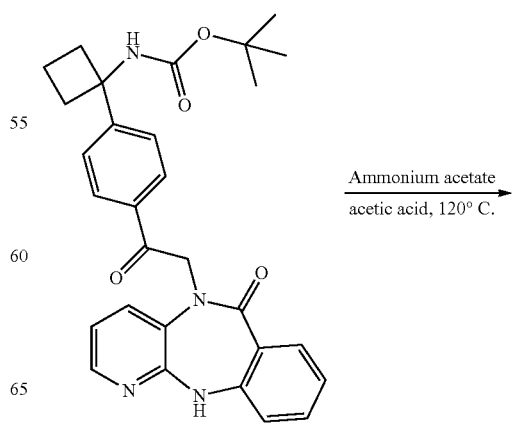

-continued

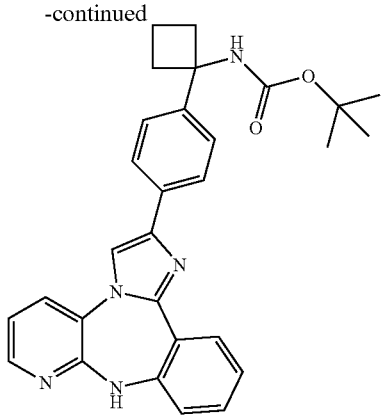

To a solution of tert-butyl (1-(4-(2-(6-oxo-6,11-dihydro-5H-benzo[e]pyrido[3,2-b][1,4]diazepin-5-yl)acetyl)phenyl)cyclobutyl)carbamate (0.3 g, 1 eq.) in acetic acid (5 mL) was added ammonium acetate (1.5 g, 20 eq.). The reaction was stirred at 120° C. for 2 hours. The reaction was carefully poured onto a saturated sodium bicarbonate solution (10 mL). The mixture was extracted with dichloromethane (3×25 mL). The combined extracts were dried over sodium sulfate, filtered and concentrated under reduced pressure. The product was purified by column chromatography (25-100% ethyl acetate in hexanes), giving tert-butyl (1-(4-(9H-benzo[f]imidazo[1,2-d]pyrido[2,3-b][1,4]diazepin-2-yl)phenyl)cyclobutyl)carbamate (0.21 g, 73%). LCMS: 480 [M+H].

Step 6: Preparation of tert-butyl (1-(4-(3-bromo-9H-benzo[f]imidazo[1,2-d]pyrido[2,3-b][1,4]diazepin-2-yl)phenyl)cyclobutyl)carbamate

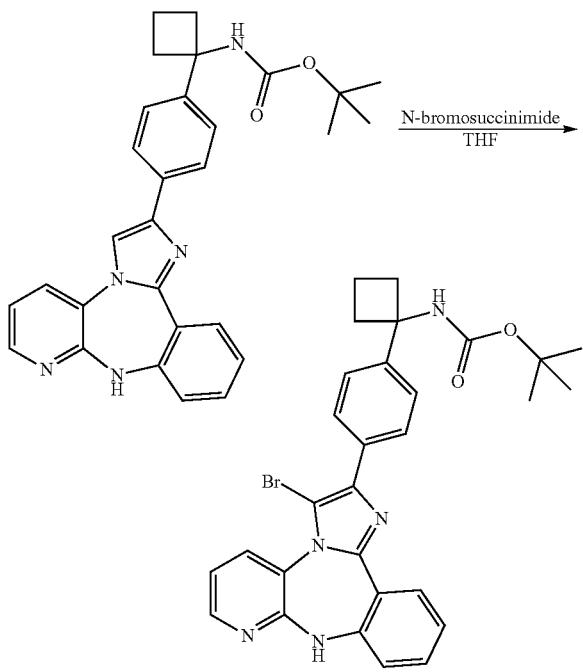

To a solution of tert-butyl (1-(4-(9H-benzo[f]imidazo[1,2-d]pyrido[2,3-b][1,4]diazepin-2-yl)phenyl)cyclobutyl)carbamate (0.19 g, 1 eq.) in THF (10 mL) was added N-bromosuccinimide (0.068 g, 1 eq.). The reaction was stirred at room temperature for 30 minutes. The mixture was diluted with ethyl acetate (50 mL) then washed with water (50 mL) and brine (50 mL). The organic phase was dried over sodium sulfate, filtered and concentrated under reduced pressure, providing, tert-butyl (1-(4-(3-bromo-9H-benzo[f]imidazo[1,2-d]pyrido[2,3-b][1,4]diazepin-2-yl)phenyl)cyclobutyl)carbamate (0.213 g) as a yellow solid. The material was used without further purification. LCMS: 558, 560 [M+H].

Step 7: Preparation of tert-butyl (1-(4-(3-phenyl-9H-benzo[f]imidazo[1,2-d]pyrido[2,3-b][1,4]diazepin-2-yl)phenyl)cyclobutyl)carbamate

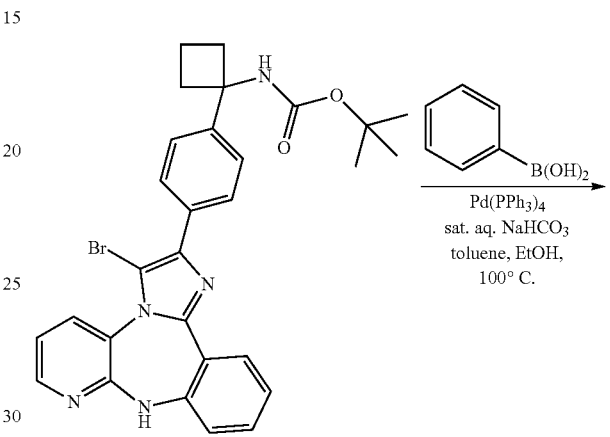

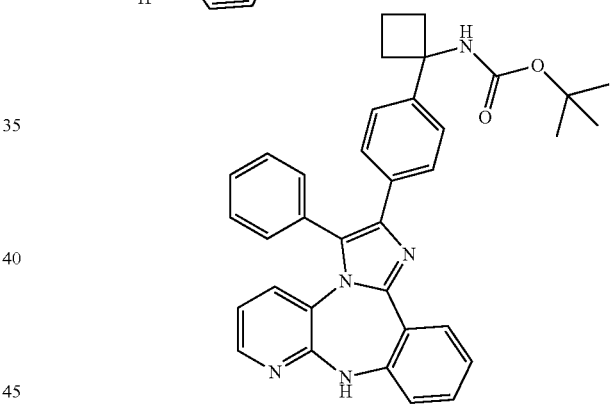

To a suspension of tert-butyl (1-(4-(3-bromo-9H-benzo[f]imidazo[1,2-d]pyrido[2,3-b][1,4]diazepin-2-yl)phenyl)cyclobutyl)carbamate (0.213 g, 1 eq.) in a mixture of toluene (5 mL), ethanol (5 mL), and saturated sodium bicarbonate (1 mL) was added phenyl boronic acid (0.07 g, 1.5 eq.). The reaction was degassed (nitrogen) for 5 minutes and tetrakis(triphenylphosphine)palladium(0) added (0.025 g). The reaction was again degassed for 5 minutes and stirred at 100° C. overnight. The reaction mixture was cooled to room temperature and poured onto water (50 mL). The aqueous phase was extracted with dichloromethane (2×50 mL) and the organic extracts were combined and washed with water (1×50 mL), brine (1×50 mL), dried over sodium sulfate, filtered and concentrated under reduced pressure. Purification by column chromatography (25-75% ethyl acetate in hexanes) gave the product which was triturated with ether to give tert-butyl (1-(4-(3-phenyl-9H-benzo[f]imidazo[1,2-d]pyrido[2,3-b][1,4]diazepin-2-yl)phenyl)cyclobutyl)carbamate (0.084 g, 40%) as a yellow solid. $^1$H NMR (DMSO-d$_6$) 400 MHz δ 8.55 (s, 1 H), 8.06 (dd, $J_A$=4.8 Hz, $J_B$=2.4 Hz, 1H), 7.95 (dd, $J_A$=7.6

Hz, $J_B$=1.2 Hz, 1H), 7.78 (dd, $J_A$=7.6 Hz, $J_B$=1.6 Hz, 1H), 7.58-7.50 (m, 1H), 7.44-7.36 (m, 4H), 7.35-7.31 (m, 2H), 7.30-7.18 (m, 4H), 7.14-7.09 (m, 1H), 6.89 (dd, $J_A$=7.6 Hz, $J_B$=1.2 Hz, 1H), 6.73 (dd, $J_A$=7.6 Hz, $J_B$=4.8 Hz, 1H), 2.45-2.28 (m, 4H), 2.04-1.92 (m, 1H), 1.83-1.70 (m, 1H), 1.33 (br. s, 9H); LCMS: 556 [M+H].

Step 8: Preparation of 1-(4-(3-phenyl-9H-benzo[f]imidazo[1,2-d]pyrido[2,3-b][1,4]diazepin-2-yl)phenyl)cyclobutanamine hydrochloride

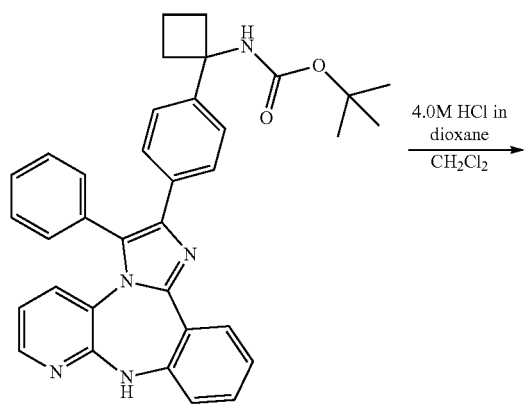

To a solution of tert-butyl (1-(4-(3-phenyl-9H-benzo[f]imidazo[1,2-d]pyrido[2,3-b][1,4]diazepin-2-yl)phenyl)cyclobutyl)carbamate (0.028 g) in dichloromethane (5 mL) was added 4.0 M HCl in dioxane (0.5 mL). The reaction was stirred at room temperature for 6 hours and then diluted with ether (20 mL). The product was removed by filtration under reduced pressure and dried to give 1-(4-(3-phenyl-9H-benzo[f]imidazo[1,2-d]pyrido[2,3-b][1,4]diazepin-2-yl)phenyl)cyclobutanamine hydrochloride as a white solid (0.022 g, 77% based on tris HCl salt). M.p.: 252-258° C.; $^1$H NMR (DMSO-d$_6$) 400 MHz δ 8.78 (br. s, 3 H), 8.73 (br. s, 1H), 8.11 (dd, $J_A$=4.8 Hz, $J_B$=1.2 Hz, 1H), 7.98 (d, J=7.6 Hz, 1H), 7.56 (d, J=8.4 Hz, 2H), 7.51 (d, J=8.8 Hz, 2H), 7.47-7.38 (m, 4H), 7.32 (d, J=8.4 Hz, 1H), 7.30-7.25 (m, 2H), 7.17 (t, J=7.6 Hz, 1H), 6.95 (d, J=7.6 Hz, 1H), 6.77 (dd, $J_A$=7.6 Hz, $J_B$=4.8 Hz, 1H), 2.60-2.52 (m, 4H), 2.24-2.13 (m, 1H), 1.85-1.72 (m, 1H); LCMS: 456 [M+H]; Calc. for $C_{30}H_{25}N_5 \cdot 3.86HCl \cdot 0.48$ diethylether: C, 60.68; H, 5.37; N, 11.08. Found C, 60.68; H, 5.52; N 11.08.

Example 8

Preparation of 5,11-dihydro-6H-pyrido[2,3-b][1,4]benzo diazepine-6-thione

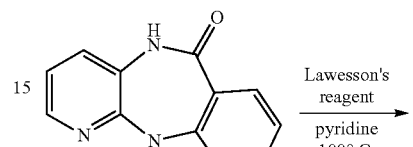

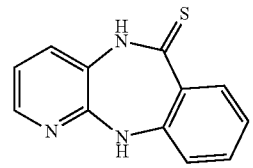

A mixture of 5,11-dihydro-6H-pyrido[2,3-b][1,4]benzodiazepin-6-one (3.00 g, 14 mmol) and Lawesson's reagent (6.51 g, 16 mmol) in pyridine (40 mL) was heated to 100° C. for 18 hours. After cooling to room temperature the mixture was poured into water and stirred. The precipitate was collected on a filter paper and dried. The crude product (yellow solid) was carried on to the next step without further purification (96%). $^1$H NMR (DMSO-d$_6$) 400 MHz δ: 11.99 (s, 1H), 8.37, (s, 1H), 7.98 (dd, J=4.6, 1.7 Hz, 1H), 7.96 (dd, J=8.0, 1.7 Hz, 1H), 7.44 (dd, J=7.7, 1.4 Hz, 1H), 7.35 (td, J=7.7, 1.7 Hz, 1H), 7.06 (dd, J=8.0, 1.2 Hz, 1H), 7.01 (dd, J=8.0, 4.6 Hz, 1H), 6.95 (td, J=8.0, 1.2 Hz, 1H); LC/MS [M+H]: 228.

Example 9

Preparation of N-(2,2-dimethoxyethyl)-11H-pyrido[2,3-b][1,4]benzodiazepin-6-amine

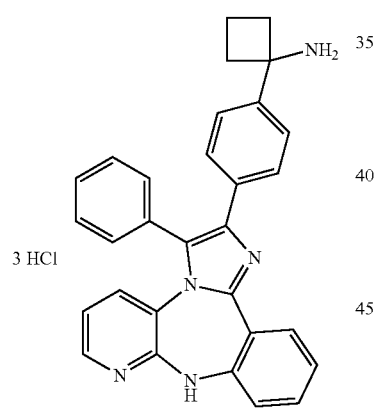

A mixture of 5,11-dihydro-6H-pyrido[2,3-b][1,4]benzodiazepine-6-thione (3.21 g, 14 mmol) and 2,2-dimethoxyethylamine (7.6 mL, 70 mmol) was heated to 95° C. for 1 hour.

After cooling to room temperature the solvent was evaporated in vacuo. The crude product was used in the next step without further purification.

Example 10

Preparation of 9H-imidazo[1,2-d]pyrido[2,3-b][1,4]benzodiazepine

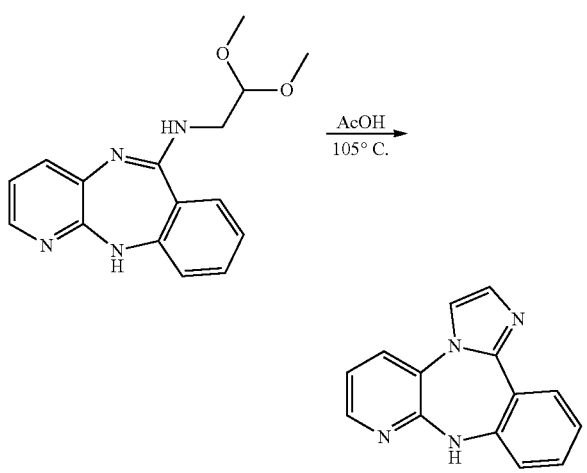

A mixture of N-(2,2-dimethoxyethyl)-11H-pyrido[2,3-b][1,4]benzodiazepin-6-amine (4.21 g, 14 mmol) and acetic acid (20 mL) was heated to 105° C. for 13 hours. After cooling to room temperature the solvent was removed under reduced pressure. The resulting crude product was diluted with acetone and filtered by suction to give a dark pink solid (74%). $^1$H NMR (DMSO-$d_6$) 400 MHz δ: 8.53 (s, 1H), 8.15 (dd, J=4.6, 1.7 Hz, 1H), 7.85 (dd, J=7.7, 1.4 Hz, 1H), 7.77 (dd, J=7.7, 1.4 Hz, 1H), 7.63 (d, J=1.2 Hz, 1H), 7.28 (td, J=8.0, 1.7 Hz, 1H), 7.24 (d, J=1.7 Hz, 1H), 7.19 (dd, J=8.0, 1.2 Hz, 1H), 7.11 (dd, J=7.7, 4.6 Hz, 1H), 7.02 (td, J=7.5, 1.2 Hz, 1H); LC/MS [M+H]: 235.

Example 11

Preparation of 3-bromo-9H-imidazo[1,2-d]pyrido[2,3-b][1,4]benzodiazepine

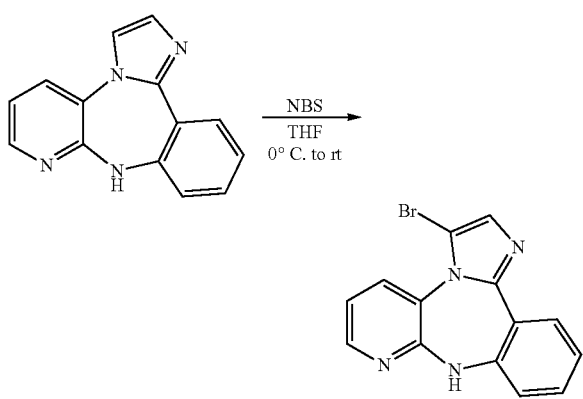

To a suspension of 9H-imidazo[1,2-d]pyrido[2,3-b][1,4]benzodiazepine (1.19 g, 5.1 mmol) in THF (60 mL) was slowly added N-bromosuccinimide (0.90 g, 4.3 mmol) at 0° C. The reaction mixture was stirred at room temperature for 2 hours, quenched with sat.NaHCO$_3$, extracted with ethyl acetate. The organic layers were washed with brine and dried over anhydrous Na$_2$SO$_4$. After filtration the solvent was removed under reduced pressure. The crude product was purified by silica gel chromatography (hexane/ethyl acetate) to give a pale yellow solid (96%). $^1$H NMR (DMSO-$d_6$) 400 MHz δ: 8.58 (s, 1H), 8.26 (dd, J=4.9, 1.4 Hz, 1H), 7.94 (dd, J=8.0, 1.7 Hz, 1H), 7.74 (dd, J=7.7, 1.4 Hz, 1H), 7.43 (s, 1H), 7.34 (td, J=7.7, 1.9 Hz, 1H), 7.25-7.21 (m, 2H), 7.08 (td, J=7.5, 1.2 Hz, 1H); LC/MS [M+H]: 314.

Example 12

Preparation of tert-butyl {1-[4-(9H-imidazo[1,2-d]pyrido[2,3-b][1,4]benzodiazepin-3-yl)phenyl]cyclobutyl}carbamate

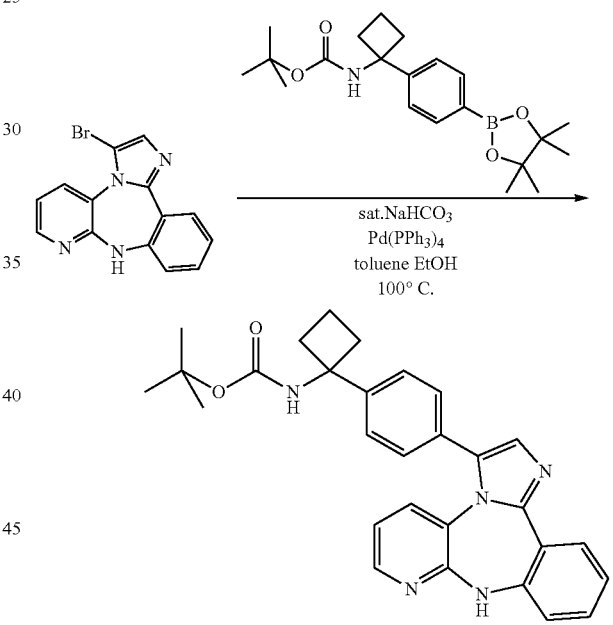

A mixture of 3-bromo-9H-imidazo[1,2-d]pyrido[2,3-b][1,4]benzodiazepine (1.48 g, 4.7 mmol), tert-butyl {1-[4-(4,4,5,5-tetramethyl-1,3,2-dioxaborolan-2-yl)phenyl]cyclobutyl}carbamate (2.12 g, 5.7 mmol), sat.NaHCO$_3$ (4 mL), and tetrakis(triphenylphosphine)palladium(0) (0.55 g, 0.47 mmol) in toluene-ethanol (1/1, 40 mL) was heated to refluxed temperature for 15 hours. After cooling to room temperature the reaction mixture was poured into water and extracted with ethyl acetate. The organic layers were washed with brine and dried over anhydrous Na$_2$SO$_4$. After filtration the solvent was evaporated in vacuo. The crude product was purified by silica gel chromatography (hexane/ethyl acetate) to give a yellow solid (quant.). $^1$HNMR (CDCl$_3$) 400 MHz δ: 8.09-8.06 (m, 2H), 7.39 (s, 1H), 7.37(d, J=8.0 Hz, 2H), 7.30 (td, J=7.6, 1.5 Hz, 1H), 7.15 (d, J=8.0 Hz, 2H), 7.16-7.10 (m, 1H), 6.98 (dd, J=8.0, 1.2 Hz, 1H), 6.95 (d, J=8.0 Hz, 1H), 6.70 (dd, J=7.7, 4.9 Hz, 1H), 6.27 (s, 1H), 5.08 (s, 1H), 2.57-2.39

(m, 4H), 2.18-2.07 (m, 1H), 1.93-1.84 (m, 1H), 1.48-1.19 (brs, 9H); LC/MS [M+H]: 480.

Example 13

Preparation of 3-phenyl-9H-imidazo[1,2-d]pyrido[2,3-b][1,4]benzodiazepine

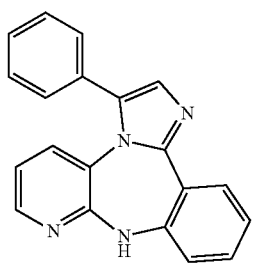 [SMILES: c1ccc(-c2cnc3n2-c2cccnc2Nc2ccccc2-3)cc1]

The title compound was synthesized according to the procedure described in the synthesis of tert-butyl {1-[4-(9H-imidazo[1,2-d]pyrido[2,3-b][1,4]benzodiazepin-3-yl)phenyl]cyclobutyl}carbamate (above) using phenylboronic acid instead of tert-butyl {1-[4-(4,4,5,5-tetramethyl-1,3,2-dioxaborolan-2-yl)phenyl]cyclobutyl}carbamate. $^1$HNMR (DMSO-$d_6$) 400 MHz δ: 8.58 (br s, 1H), 8.14 (dd, J=4.6, 1.7 Hz, 1H), 7.92-7.86 (m, 1H), 7.45 (s, 1H), 7.40-7.26 (m, 5H), 7.18-7.13 (m, 2H), 7.10-7.05 (m, 1H), 7.00-6.95 (m, 1H), 6.85 (dd, J=8.0, 4.6 Hz, 1H); LC/MS: 311 [M+H].

Example 14

Preparation of tert-butyl {1-[4-(2-chloro-9H-imidazo[1,2-d]pyrido[2,3-b][1,4]benzodiazepin-3-yl)phenyl]cyclobutyl}carbamate

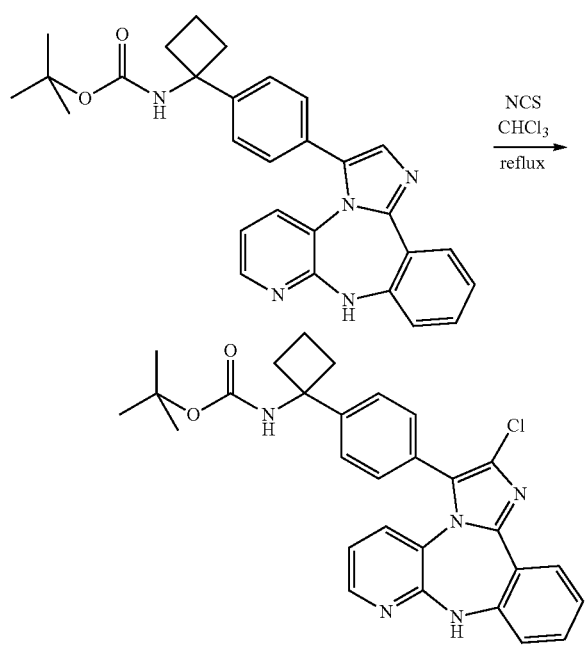

A mixture of tert-butyl {1-[4-(9H-imidazo[1,2-d]pyrido[2,3-b][1,4]benzodiazepin-3-yl)phenyl]cyclobutyl}carbamate (5.00 g, 10 mmol) and N-chlorosuccinimide (1.39 g, 10 mmol) in chloroform (100 mL) was heated to refluxed temperature for 22 hours. After cooling to room temperature the solvent was evaporated in vacuo. The crude product was purified by silica gel chromatography (hexane/ethyl acetate; 0-100% ethyl acetate over 60 min) to give a yellow solid (75%). $^1$HNMR (CDCl$_3$) 400 MHz δ: 8.06 (dd, J=5.0, 1.4 Hz, 1H), 8.03 (dd, J=7.8, 1.8 Hz, 1H), 7.40 (d, J=8.3 Hz, 2H), 7.32 (td, J=7.7, 1.5 Hz, 1H), 7.22 (d, J=8.3 Hz, 2H), 7.12 (td, J=7.6, 0.92 Hz, 1H), 6.94 (dd, J=8.3, 0.92 Hz, 1H) 6.88 (d, J=8.3 Hz, 1H), 6.66 (dd, J=7.8, 4.6 Hz, 1H), 6.30 (s, 1H), 5.10 (s, 1H), 2.59-2.38 (m, 4H), 2.19-2.07 (m, 1H), 1.95-1.83 (m, 1H), 1.48-1.21 (m, 9H); LC/MS [M+H]: 514.

Example 15

Preparation of tert-butyl {1-[4-(2-bromo-9H-imidazo[1,2-d]pyrido[2,3-b][1,4]benzodiazepin-3-yl)phenyl]cyclobutyl}carbamate

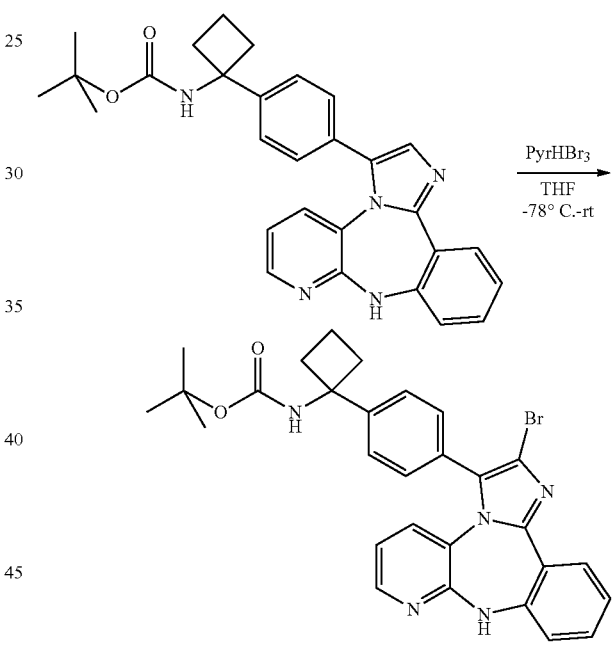

tert-Butyl {1-[4-(9H-imidazo[1,2-d]pyrido[2,3-b][1,4]benzodiazepin-3-yl)phenyl]cyclobutyl}carbamate (9.8 g, 20.4 mmol) was dissolved in THF (350 mL). A solution of pyridinium bromide perbromide (6.5 g, 20.4 mmol) in THF (50 mL) was added to the mixture at −78° C. After three hours stirring at r.t., pyridinium bromide perbromide (2.6 g, 8.2 mmol) in THF was added to the mixture and the mixture was stirred at rt overnight. The mixture was poured into ethyl acetate (1.5 L) and mixed with water and separated. The combined organic phase was washed with saturated sodium bicarbonate solution in water, then dried with anhydrous sodium sulfate and evaporated. The residue was purified with silica gel column chromatography (dichloromethane/ethyl acetate, 20:1) to give the titled compound as a white solid (6.8 g, 59%). $^1$HNMR (CDCl$_3$) 400 MHz δ: 8.04 (d, J=8.0 Hz, 2H), 7.40 (d, J=7.4 Hz, 2H), 7.31 (t, J=7.4 Hz, 1H), 7.23 (d, J=6.9 Hz, 2H), 7.12 (t, J=7.7 Hz, 1H), 6.94 (d, J=8.0 Hz, 1H), 6.88-6.80 (m, 1H), 6.66-6.62 (m, 1H), 6.29 (s, 1H), 5.10 (s, 1H), 2.58-2.37 (m, 4H), 2.18-2.08 (m, 1H), 1.94-1.84 (m, 1H), 1.39 (br s, 9H); LC/MS [M+H]: 558

Example 16

Preparation of 1-[4-(2-chloro-9H-imidazo[1,2-d]pyrido[2,3-b][1,4]benzodiazepin-3-yl)phenyl]cyclobutanamine trihydrochloride

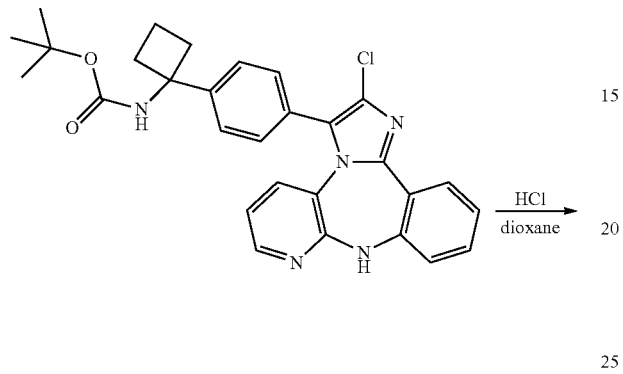

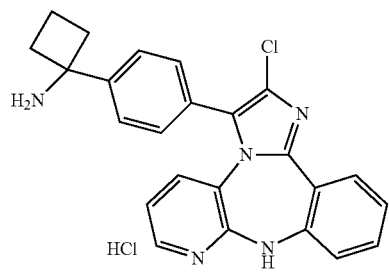

tert-Butyl {1-[4-(2-chloro-9H-imidazo[1,2-d]pyrido[2,3-b][1,4]benzodiazepin-3-yl)phenyl]cyclobutyl}carbamate (36.4 mg, 0.0708 mmol) was dissolved in DCM (1 mL). 4M HCl/dioxane (1 mL) was added to the mixture and stirred at room temperature for 15.5 hours. The mixture was concentrated and solidified with ether. The precipitated solids were collected by filtration and washed with ether to afford desired product (33.6 mg, 90.6%) as yellow solid. $^1$H NMR (DMSO-$d_6$) 400 MHz δ: 8.72 (br s, 2H), 8.68 (s, 1H), 8.16 (dd, J=4.8, 1.8 Hz, 1H), 7.82 (dd, J=7.8, 1.8 Hz, 1H), 7.61-7.55 (m, 2H), 7.42-7.27 (m, 4H), 7.13-7.07 (m, 1H), 6.98 (dd, J=7.8, 1.8 Hz, 1H), 6.81 (dd, J=7.8, 4.8 Hz, 1H), 4.27 (br s, 3H), 2.64-2.43 (m, 4H), 2.26-2.12 (m, 1H), 1.89-1.74 (m, 1H); LCMS: 414 [M+H].

Example 17

Preparation of 1-[4-(9H-imidazo[1,2-d]pyrido[2,3-b][1,4]benzodiazepin-3-yl)phenyl]cyclobutanamine

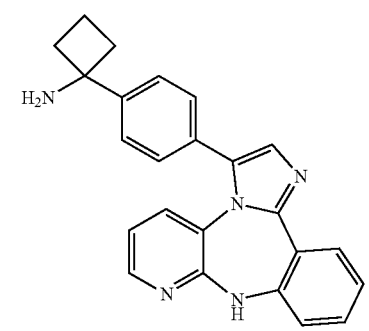 [SMILES: NC1(c2ccc(-c3cnc4n3-c3cccnc3Nc3ccccc3-4)cc2)CCC1]

The title compound was synthesized according the procedure described in example 16 using tert-butyl {1-[4-(9H-imidazo[1,2-d]pyrido[2,3-b][1,4]benzodiazepin-3-yl)phenyl]cyclobutyl}carbamate. $^1$H NMR (DMSO-$d_6$) 400 MHz δ: 8.70-8.55 (m, 3H), 8.20 (d, J=4.6 Hz, 1H), 7.89 (dd, J=7.8, 1.8 Hz, 1H), 7.61 (m, 1H), 7.52 (d, J=8.3 Hz, 2H), 7.37 (t, J=7.6 Hz, 1H), 7.31 (d, J=7.8 Hz, 1H) 7.27 (d, J=8.3 Hz, 2H), 7.11 (t, J=7.3 Hz, 1H) 7.04 (d, J=7.8 Hz, 1H), 6.87 (dd, J=8.0, 4.8 Hz, 1H), 2.62-2.44 (m, 4H), 2.21-2.11 (m, 1H), 1.86-1.74 (m, 1H); LC/MS [M+H]: 380.

Example 18

Preparation of methyl 4-{3-[4-(1-aminocyclobutyl)phenyl]-9H-imidazo[1,2-d]pyrido[2,3-b][1,4]benzodiazepin-2-yl}benzoate trihydrochloride Step 1: Preparation of methyl 4-[3-(4-{1-[(tert-butoxycarbonyl)amino]cyclobutyl}phenyl)-9H-imidazo[1,2-d]pyrido[2,3-b][1,4]benzodiazepin-2-yl]benzoate

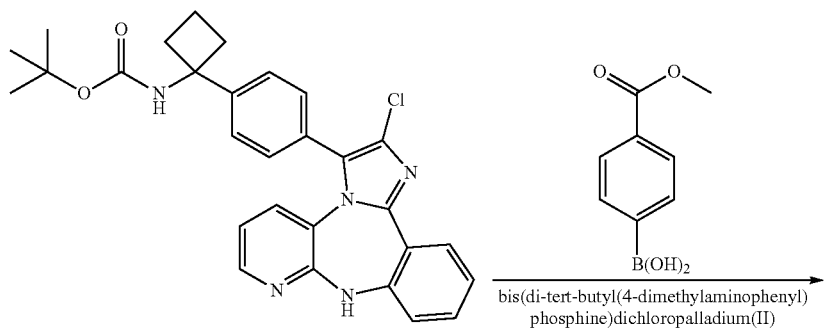

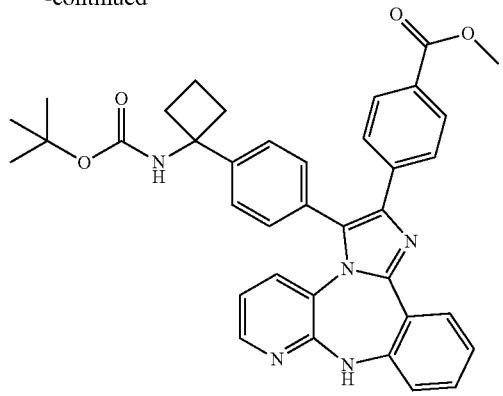

A mixture of tert-butyl {1-[4-(2-chloro-9H-imidazo[1,2-d]pyrido[2,3-b][1,4]benzodiazepin-3-yl)phenyl]cyclobutyl}carbamate (30 mg, 0.058 mmol), [4-(methoxycarbonyl)phenyl]boronic acid (21 mg, 0.12 mmol), bis(di-tert-butyl(4-dimethylaminophenyl)phosphine)dichloropalladium(II) (4 mg, 0.006 mmol), and 2M Na₂CO₃ aq. (0.058 mL, 0.12 mmol) in DMF (1 mL) was heated in microwave oven at 160° C. for 1 hour. The mixture was diluted with AcOEt, washed with water (×3), brine, dried over Na₂SO₄, then filtrated through Celite pad. The filtrate was concentrated and the residue was purified by preparative thin-layer chromatography (n-hexane/AcOEt=1:1) to afford the desired product (28 mg, 78%) as a white solid. ¹HNMR (CDCl₃) 400 MHz δ: 8.17 (dd, J=8.0 Hz and 1.7 Hz, 1H), 8.02 (d, J=4.0 Hz, 1H), 7.93 (d, J=8.6 Hz, 2H), 7.65 (d, J=8.0 Hz, 2H), 7.38 (d, J=8.0 Hz, 2H), 7.32 (td, J=7.4, 1.1 Hz, 1H), 7.18-7.15 (m, 2H), 6.95 (d, J=8.0 Hz, 1H), 6.80 (d, J=7.4 Hz, 1H), 6.60 (dd, J=8.0 Hz and 4.6 Hz, 1H), 6.25 (s, 1H), 5.13 (br s, 1H), 3.90 (s, 3H), 2.58-2.41 (m, 4H), 2.20-2.11 (m, 1H), 1.95-1.87 (m, 1H), 1.40 (br s, 9H). LCMS: 614 [M+H].

Step 2: Preparation of methyl 4-{3-[4-(1-aminocyclobutyl)phenyl]-9H-imidazo[1,2-d]pyrido[2,3-b][1,4]benzodiazepin-2-yl}benzoate trihydrochloride

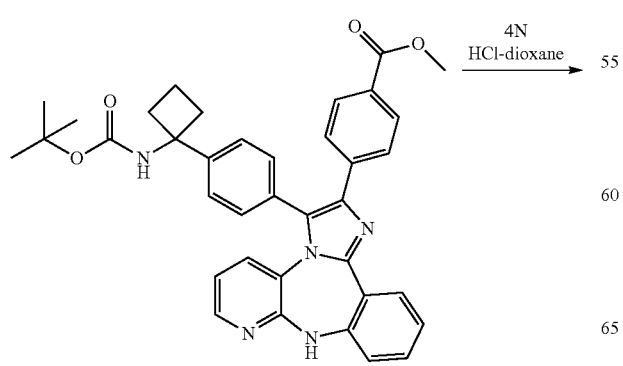

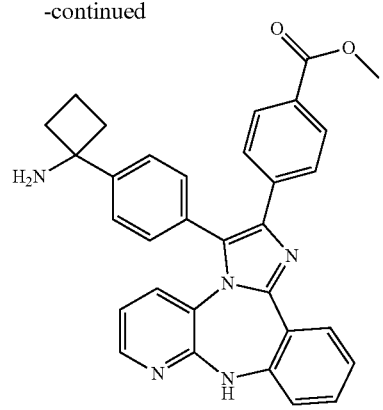

Methyl 4-[3-(4-{1-[(tert-butoxycarbonyl)amino]cyclobutyl}phenyl)-9H-imidazo[1,2-d]pyrido[2,3-b][1,4]benzodiazepin-2-yl]benzoate (28 mg, 0.046 mmol) in MeOH (0.5 mL) was added 4N HCl-dioxane (2 mL) and stirred at room temperature for 18 hours. The mixture was concentrated to afford the desired product (28 mg, 97%) as a yellow solid. ¹HNMR (DMSO-d₆) 400 MHz δ: 8.80 (s, 2H), 8.65 (s, 1H), 8.12 (dd, J=4.6 Hz and 1.7 Hz, 1H), 7.98 (dd, J=7.4 Hz and 1.7 Hz, 1H), 7.89-7.87 (m, 2H), 7.59 (dd, J=12.0 Hz and 8.6 Hz, 4H), 7.40-7.30 (m, 4H), 7.14 (t, J=7.2 Hz, 1H), 6.92 (dd, J=8.0 Hz and 1.7 Hz, 1H), 6.76 (dd, J=4.6 Hz and 4.6 Hz, 1H), 3.84 (s, 3H), 2.59 (t, J=7.4 Hz, 4H), 2.26-2.17 (m, 1H), 1.87-1.78 (m, 1H). LCMS: 514 [M+H].

Example 19

Preparation of 1-{4-[2-(1H-pyrrolo[3,2-b]pyridin-6-yl)-9H-imidazo[1,2-d]pyrido[2,3-b][1,4]benzodiazepin-3-yl]phenyl}cyclobutanamine

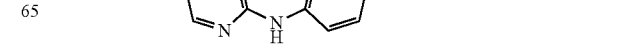

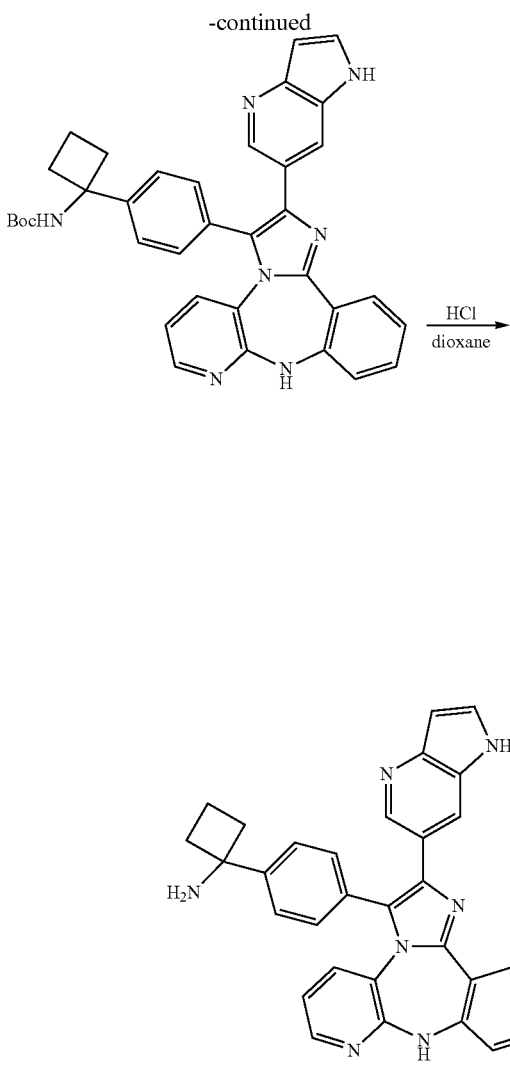

Step 1: A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), 6-(4,4,5,5-tetramethyl-1,3,2-dioxaborolan-2-yl)-1H-pyrrolo[3,2-b]pyridine (44 mg, 0.18 mmol), bis(di-tert-butyl(4-dimethylaminophenyl)phosphine)dichloropalladium(II) (6.3 mg, 0.01 mmol) and K₃PO₄ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous Na₂SO₄ and concentrated. The residue was purified by HPLC. The fraction was evaporated to dryness. Step 2: The residue was dissolved in methanol (10 mL) and 4M HCl in dioxane (10 mL) was added. After overnight reaction, the mixture was evaporated and the residue was purified by HPLC to give the titled compound as a white solid (32 mg, 60%). ¹HNMR (DMSO-d₆) 400 MHz δ: 11.39 (s, 1H), 8.58 (s, 1H), 8.38 (d, J=1.7 Hz, 1H), 8.25 (s, 1H), 8.09 (dd, J=4.6, 1.7 Hz, 1H), 7.99 (dd, J=8.0, 1.7 Hz, 1H), 7.89 (d, J=1.1 Hz, 1H), 7.63 (t, J=3.2 Hz, 1H), 7.49 (d, J=8.6 Hz, 2H), 7.36 (td, J=7.4, 1.7 Hz, 1H), 7.30 (d, J=8.0 Hz, 1H), 7.23 (d, J=8.6 Hz, 2H), 7.13 (t, J=7.4 Hz, 1H), 6.90 (dd, J=7.7, 1.4 Hz, 1H), 6.75 (dd, J=8.0, 4.6 Hz, 1H), 6.51-6.49 (m, 1H), 2.48-2.41 (m, 2H), 2.26-2.19 (m, 2H), 2.11-2.02 (m, 1H), 1.77-1.68 (m, 1H); LCMS: 496 [M+H].

Example 20

Preparation of 4-{3-[4-(1-aminocyclobutyl)phenyl]-9H-imidazo[1,2-d]pyrido[2,3-b][1,4]benzodiazepin-2-yl}benzoic acid Step 1: Preparation of benzyl 4-[3-(4-{1-[(tert-butoxycarbonyl)amino]cyclobutyl}phenyl)-9H-imidazo[1,2-d]pyrido[2,3-b][1,4]benzodiazepin-2-yl]benzoate

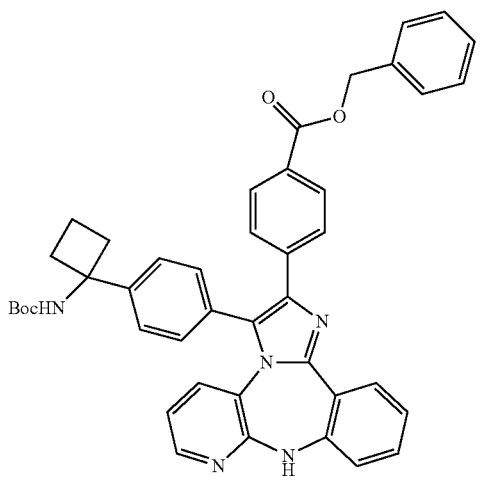 [SMILES: CC(C)(C)OC(=O)NC1(c2ccc(-c3c(-c4ccc(C(=O)OCc5ccccc5)cc4)nc4n3-c3cccnc3Nc3ccccc3-4)cc2)CCC1]

A mixture of tert-butyl {1-[4-(2-chloro-9H-imidazo[1,2-d]pyrido[2,3-b][1,4]benzodiazepin-3-yl)phenyl]cyclobutyl}carbamate (150 mg, 0.292 mmol), [4-(benzyloxycarbonyl)phenyl]boronic acid (149 mg, 0.584 mmol), bis(di-tert-butyl(4-dimethylaminophenyl)phosphine)dichloropalladium(II) (21 mg, 0.029 mmol), and 2M Na₂CO₃ aq. (0.292 mL, 0.584 mmol) in DMF (3 mL) was treated with microwave (160° C. for 1 hour). The mixture was diluted with AcOEt, washed with water (×3), brine, dried over Na₂SO₄, then filtrated through Celite pad. The filtrate was concentrated and the residue was purified by preparative thin-layer chromatography (n-hexane/AcOEt=1:2) to afford the desired product (102 mg, 51%) as a yellow solid. LCMS: 690 [M+H].

Step 2: Preparation of 4-[3-(4-{1-[(tert-butoxycarbonyl)amino]cyclobutyl}phenyl)-9H-imidazo[1,2-d]pyrido[2,3-b][1,4]benzodiazepin-2-yl]benzoic acid

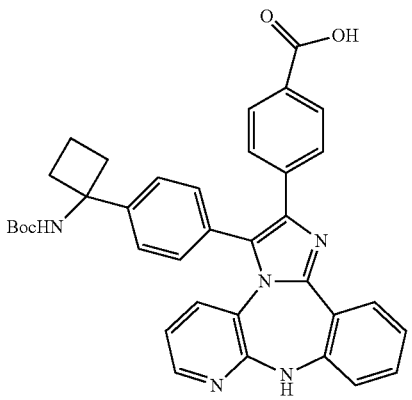 [SMILES: CC(C)(C)OC(=O)NC1(c2ccc(-c3c(-c4ccc(C(=O)O)cc4)nc4n3-c3cccnc3Nc3ccccc3-4)cc2)CCC1]

Atmosphere of starting material (102 mg, 0.148 mmol) and 10% Pd—C(dry) (10 mg) in MeOH (3 mL) was exchanged to H₂ and stirred at 50° C. for 24.5 hours. The mixture was diluted with CH₂Cl₂ and filtrated through Celite pad. The filtrate was concentrated to afford the desired product (85 mg, 96%) as a yellow solid. ¹HNMR (DMSO-d₆) 400 MHz δ: 8.07 (d, J=4.0 Hz, 1H), 7.97 (dd, J=7.4 Hz and 1.7 Hz, 1H), 7.81 (d, J=8.0 Hz, 2H), 7.58 (d, J=8.0 Hz, 2H), 7.40 (d, J=8.6 Hz, 2H), 7.36 (td, J=8.0 Hz and 1.7 Hz, 1H), 7.29 (d, J=7.4 Hz, 1H), 7.23-7.16 (m, 2H), 7.13 (td, J=7.4 Hz and 1.1 Hz, 1H), 6.96-6.87 (m, 2H), 6.69-6.65 (m, 1H), 2.44-2.35 (m, 2H), 2.05-1.96 (m, 2H), 1.82-1.76 (m, 2H), 1.35 (br s, 5H), 1.17 (br s, 3H). LCMS: 600 [M+H].

Step 3: Preparation of 4-{3-[4-(1-aminocyclobutyl) phenyl]-9H-imidazo[1,2-d]pyrido[2,3-b][1,4]benzo-diazepin-2-yl}benzoic acid

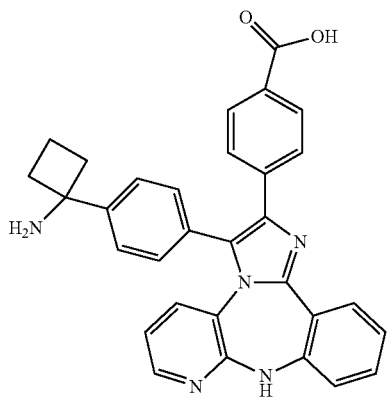 [SMILES: NC1(c2ccc(-c3c(-c4ccc(C(=O)O)cc4)nc4n3-c3cccnc3Nc3ccccc3-4)cc2)CCC1]

The title compound was synthesized according to the procedure described in step 2 of example 18. ¹HNMR (DMSO-d₆) 400 MHz δ: 8.56 (d, J=3.4 Hz, 1H), 8.06 (d, J=4.6 Hz, 1H), 7.97 (d, J=8.0 Hz, 1H), 7.76 (d, J=8.0 Hz, 2H), 7.51-7.42 (m, 2H), 7.40-7.33 (m, 2H), 7.29-7.27 (m, 2H), 7.23-7.17 (m, 2H), 7.12 (t, J=7.4 Hz, 1H), 6.94-6.88 (m, 1H), 6.70-6.67 (m, 1H), 5.76 (s, 2H), 1.87-1.85 (m, 2H), 1.45-1.34 (m, 4H). LCMS: 500 [M+H].

Example 21

Preparation of 1-(4-{2-[4-(morpholin-4-ylmethyl) phenyl]-9H-imidazo[1,2-d]pyrido[2,3-b][1,4]benzo-diazepin-3-yl}phenyl)cyclobutanamine tetrahydro-chloride Step 1: Preparation of tert-butyl[1-(4-{2-[4-(morpho-lin-4-ylmethyl)phenyl]-9H-imidazo[1,2-d]pyrido[2,3-b][1,4]benzodiazepin-3-yl}phenyl)cyclobutyl] carbamate

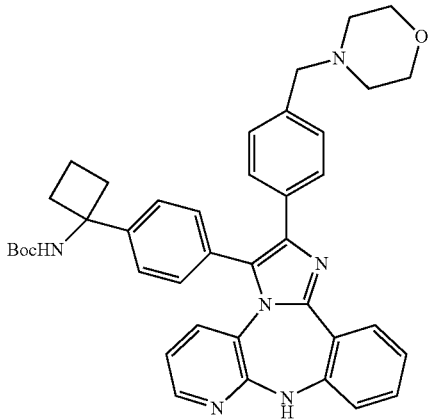 [SMILES: CC(C)(C)OC(=O)NC1(c2ccc(-c3c(-c4ccc(CN5CCOCC5)cc4)nc4n3-c3cccnc3Nc3ccccc3-4)cc2)CCC1]

A mixture of tert-butyl {1-[4-(2-chloro-9H-imidazo[1,2-d]pyrido[2,3-b][1,4]benzodiazepin-3-yl)phenyl] cyclobutyl}carbamate (50 mg, 0.097 mmol), 4-[4-(4,4,5,5-tetramethyl-1,3,2-dioxaborolan-2-yl)benzyl]morpholine (59 mg, 0.20 mmol), bis(di-tert-butyl(4-dimethylaminophenyl) phosphine)dichloropalladium(II) (7 mg, 0.1 mmol), and 2M Na₂CO₃ aq. (0.097 mL, 0.20 mmol) in DMF (1.5 mL) was treated with microwave (160° C. for 1 hour). The mixture was diluted with AcOEt, washed with water (×3), brine, dried over Na₂SO₄, then filtrated through Celite pad. The filtrate was concentrated and the residue was purified twice by preparative thin-layer chromatography (CH₂Cl₂/MeOH=10:1×2) and (AcOEt/MeOH=10:1) to afford the desired product (28 mg, 44%) as a yellow solid. ¹HNMR (CDCl₃) 400 MHz δ: 8.17 (dd, J=8.0 Hz and 1.7 Hz, 1H), 8.00 (d, J=4.6 Hz, 1H), 7.54 (d, J=8.0 Hz, 2H), 7.36 (d, J=8.0 Hz, 2H), 7.30 (td, J=8.0 Hz and 1.7 Hz, 1H), 7.22 (d, J=8.0 Hz, 1H), 7.17-7.13 (m, 3H), 6.94 (d, J=8.0 Hz, 1H), 6.80 (d, J=6.9 Hz, 1H), 6.59 (dd, J=8.0 Hz and 5.2 Hz, 1H), 6.24 (s, 1H), 5.10 (br s, 1H), 3.70 (t, J=4.6 Hz, 4H), 3.47 (s, 2H), 2.57-2.50 (m, 2H), 2.45-2.42 (m, 4H), 2.19-2.10 (m, 2H), 1.93-1.85 (m, 2H), 1.39 (br s, 9H). LCMS: 655 [M+H].

Step 2: Preparation of 1-(4-{2-[4-(morpholin-4-ylm-ethyl)phenyl]-9H-imidazo[1,2-d]pyrido[2,3-b][1,4] benzodiazepin-3-yl}phenyl)cyclobutanamine tet-rahydrochloride

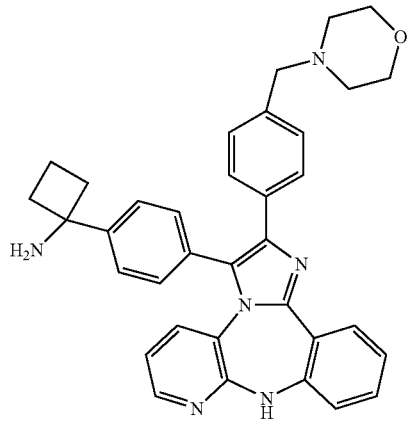 [SMILES: NC1(c2ccc(-c3c(-c4ccc(CN5CCOCC5)cc4)nc4n3-c3cccnc3Nc3ccccc3-4)cc2)CCC1]

tert-butyl[1-(4-{2-[4-(morpholin-4-ylmethyl)phenyl]-9H-imidazo[1,2-d]pyrido[2,3-b][1,4]benzodiazepin-3-yl}phenyl)cyclobutyl]carbamate (28 mg, 0.043 mmol) in MeOH (0.5 mL) was added 4N HCl-dioxane (2 mL) and stirred at r.t for 15 hours. The mixture was concentrated to afford the desired product (31 mg, quant) as a yellow solid. ¹HNMR (DMSO-d₆) 400 MHz δ: 8.74 (br s, 2H), 8.61 (s, 1H), 8.10 (dd, J=4.9 Hz and 1.4 Hz, 1H), 7.96 (dd, J=7.7 Hz and 1.4 Hz, 1H), 7.59 (dd, J=15.5 Hz and 8.6 Hz, 4H), 7.53 (d, J=8.6 Hz, 2H), 7.36 (d, J=7.4 Hz, 3H), 7.30 (dd, J=7.4 Hz and 1.1 Hz, 1H), 7.13 (td, J=7.4 Hz and 1.1 Hz, 1H), 6.88 (dd, J=8.0 Hz and 1.1 Hz, 1H), 6.73 (dd, J=7.4 Hz and 4.9 Hz, 1H), 5.76 (s, 2H), 4.30 (d, J=5.2 Hz, 2H), 3.94 (dd, J=12.0 Hz and 2.3 Hz, 2H), 3.22 (d, J=11.5 Hz, 2H), 3.11-3.04 (m, 2H), 2.59-2.55 (m, 4H), 2.24-2.16 (m, 1H), 1.87-1.78 (m, 1H). LCMS: 555 [M+H].

Example 22

Preparation of 1-(4-{2-[4-(benzyloxy)phenyl]-9H-imidazo[1,2-d]pyrido[2,3-b][1,4]benzodiazepin-3-yl}phenyl)cyclobutanamine

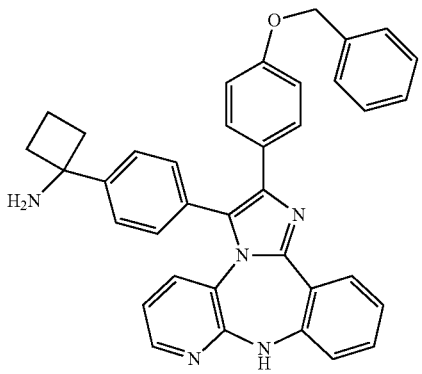 [SMILES: NC1(c2ccc(-c3c(-c4ccc(OCc5ccccc5)cc4)nc4n3-c3cccnc3Nc3ccccc3-4)cc2)CCC1]

The title compound was synthesized according to the procedure described in step 1 and 2 of example 18 using (4-(benzyloxy)phenyl)boronic acid in step 1 instead of [4-(methoxycarbonyl)phenyl]boronic acid. $^1$HNMR (DMSO-$d_6$) 400 MHz δ: 8.86 (s, 3H), 8.78 (s, 1H), 8.15 (d, J=4.58 Hz, 1H), 7.96 (d, J=8.02 Hz, 1H), 7.57 (d, J=8.59 Hz, 2H), 7.46-7.38 (m, 7H), 7.36-7.29 (m, 4H), 7.18 (t, J=7.45 Hz, 1H), 7.01 (d, J=8.59 Hz, 2H), 6.91 (d, J=8.02 Hz, 1H), 6.81-6.77 (m, 1H), 5.11 (s, 2H), 2.62-2.53 (m, 4H), 2.26-2.16 (m, 1H), 1.86-1.76 (m, 1H). LCMS: 562 [M+H].

Example 23

Preparation of 1-{4-[2-(pyridin-4-yl)-9H-imidazo[1,2-d]pyrido[2,3-b][1,4]benzodiazepin-3-yl]phenyl}cyclobutanamine Step 1: Preparation of tert-butyl (1-{4-[2-(pyridin-4-yl)-9H-imidazo[1,2-d]pyrido[2,3-b][1,4]benzodiazepin-3-yl]phenyl}cyclobutyl)carbamate

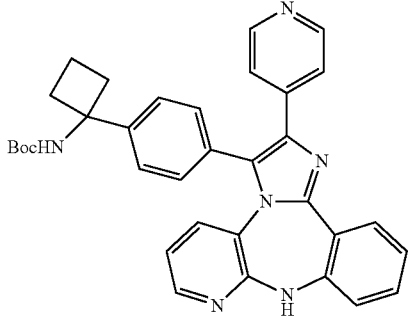 [SMILES: CC(C)(C)OC(=O)NC1(c2ccc(-c3c(-c4ccncc4)nc4n3-c3cccnc3Nc3ccccc3-4)cc2)CCC1]

The title compound was synthesized according to the procedure described in example 19 using pyridin-4-ylboronic acid in step 1 instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 8.47 (dd, J=4.6, 1.4 Hz, 2H), 8.16 (dd, J=7.8, 1.4 Hz, 1H), 8.02 (d, J=3.7 Hz, 1H), 7.50 (d, J=5.0 Hz, 2H), 7.43 (d, J=8.3 Hz, 2H), 7.33 (td, J=7.4, 1.8 Hz, 1H), 7.22-7.14 (m, 3H), 6.96 (d, J=7.3 Hz, 1H) 6.81 (d, J=7.8 Hz, 1H), 6.61 (dd, J=8.0, 4.8 Hz, 1H), 6.34 (s, 1H), 5.18 (s, 1H), 2.62-2.35 (m, 4H), 2.22-2.11 (m, 1H), 1.98-1.86 (m, 1H), 1.49-1.23 (brs, 9H); LC/MS [M+H]: 557.

Step 2: Preparation of 1-{4-[2-(pyridin-4-yl)-9H-imidazo[1,2-d]pyrido[2,3-b][1,4]benzodiazepin-3-yl]phenyl}cyclobutanamine

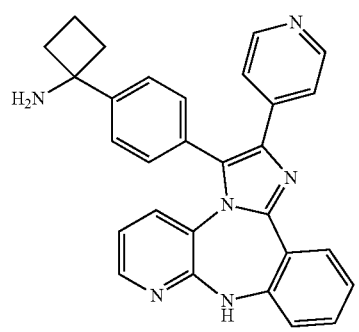 [SMILES: NC1(c2ccc(-c3c(-c4ccncc4)nc4n3-c3cccnc3Nc3ccccc3-4)cc2)CCC1]

The title compound was synthesized according to the procedure described in step 2 of example 19. $^1$HNMR (CD$_3$OD) 400 MHz δ: 8.65 (d, J=6.3 Hz, 2H), 8.13-8.07 (m, 4H), 7.68 (d, J=8.0 Hz, 2H), 7.57-7.50 (m, 2H), 7.44 (td, J=8.0, 1.7 Hz, 1H), 7.23-7.19 (m, 2H), 7.03 (dd, J=8.0, 1.7 Hz, 1H), 6.71 (dd, J=8.0, 5.2 Hz, 1H), 2.87-2.79 (m, 2H), 2.70-2.61 (m, 2H), 2.36-2.26 (m, 1H), 2.08-1.98 (m, 1H); LC/MS [M+H]: 457.

Example 24

Preparation of 1-{4-[2-(4-phenoxyphenyl)-9H-imidazo[1,2-d]pyrido[2,3-b][1,4]benzodiazepin-3-yl]phenyl}cyclobutanamine trihydrochloride

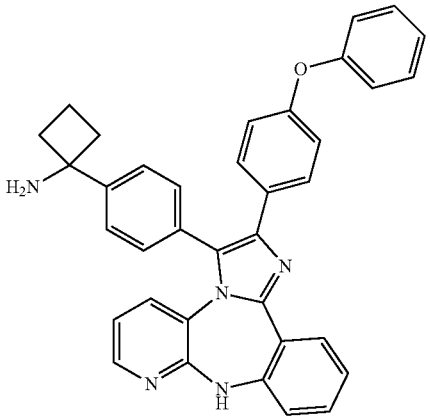 [SMILES: NC1(c2ccc(-c3c(-c4ccc(Oc5ccccc5)cc4)nc4n3-c3cccnc3Nc3ccccc3-4)cc2)CCC1]

The title compound was synthesized according to the procedure described in example 19 using (4-phenoxyphenyl)boronic acid in step 1 instead of 6-(4,4,5,5-tetramethyl-1,3,2-dioxaborolan-2-yl)-1H-pyrrolo[3,2-b]pyridine. $^1$HNMR (DMSO-$d_6$) 400 MHz δ: 8.63-8.62 (m, 3H), 8.10 (dd, J=4.6, 1.7 Hz, 1H), 7.95 (dd, J=8.0, 1.7 Hz, 1H), 7.54-7.50 (m, 3H), 7.43-7.29 (m, 5H), 7.18-7.11 (m, 2H), 7.06-7.04 (m, 2H), 6.95-6.92 (m, 2H), 6.89 (dd, J=8.0, 1.7 Hz, 1H), 6.74 (dd, J=8.0, 4.6 Hz, 1H), 2.61-2.52 (m, 4H), 2.22-2.14 (m, 1H), 1.86-1.79 (m, 1H). LCMS: 548 [M+H].

Example 25

Preparation of 1-{4-[2-(pyrimidin-5-yl)-9H-imidazo[1,2-d]pyrido[2,3-b][1,4]benzodiazepin-3-yl]phenyl}cyclobutanamine Step 1: Preparation of tert-butyl (1-{4-[2-(pyrimidin-5-yl)-9H-imidazo[1,2-d]pyrido[2,3-b][1,4]benzodiazepin-3-yl]phenyl}cyclobutyl)carbamate

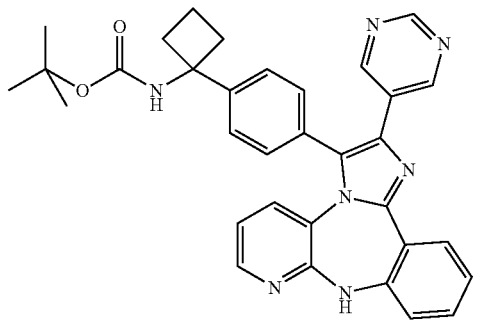 [SMILES: CC(C)(C)OC(=O)NC1(c2ccc(-c3c(-c4cncnc4)nc4n3-c3cccnc3Nc3ccccc3-4)cc2)CCC1]

The title compound was synthesized according to the procedure described in example 19 using pyrimidin-5-ylboronic acid in step 1 instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 9.07 (s, 1H), 8.94 (brs, 1H), 8.14 (dd, J=7.7, 1.4 Hz, 1H), 8.05-8.00 (m, 2H), 7.42 (d, J=8.6 Hz, 2H), 7.34 (td, J=7.5, 1.7 Hz, 1H), 7.21-7.15 (m, 3H), 6.99 (d, J=8.0 Hz, 1H) 6.85-6.78 (m, 1H), 6.63-6.58 (m, 1H), 6.43 (s, 1H), 5.20 (s, 1H), 2.61-2.34 (m, 4H), 2.20-2.10 (m, 1H), 1.95-1.87 (m, 1H), 1.48-1.23 (m, 9H); LC/MS [M+H]: 558.

Step 2: Preparation of 1-{4-[2-(pyrimidin-5-yl)-9H-imidazo[1,2-d]pyrido[2,3-b][1,4]benzodiazepin-3-yl]phenyl}cyclobutanamine

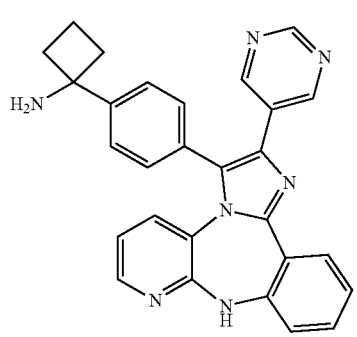 [SMILES: NC1(c2ccc(-c3c(-c4cncnc4)nc4n3-c3cccnc3Nc3ccccc3-4)cc2)CCC1]

The title compound was synthesized according to the procedure described in step 2 of example 19. $^1$HNMR (DMSO-d$_6$) 400 MHz δ: 9.08 (s, 1H), 8.83 (s, 2H), 8.66 (s, 1H), 8.65-8.59 (m, 2H), 8.13 (dd, J=5.2, 1.2 Hz, 1H), 7.98 (dd, J=8.0, 1.7 Hz, 1H), 7.58 (d, J=8.0 Hz, 2H), 7.43-7.37 (m, 3H), 7.31 (d, J=7.5 Hz, 1H), 7.15 (td, J=7.5, 1.2 Hz, 1H), 6.92 (dd, J=7.7, 1.4 Hz, 1H), 6.76 (dd, J=8.0, 4.6 Hz, 1H), 2.66-2.50 (m, 4H), 2.23-2.13 (m, 1H), 1.88-1.76 (m,k 1H); LC/MS [M+H]: 458.

Example 26

Preparation of 1-{4-[2-(1H-pyrrol-2-yl)-9H-imidazo[1,2-d]pyrido[2,3-b][1,4]benzodiazepin-3-yl]phenyl}cyclobutanamine

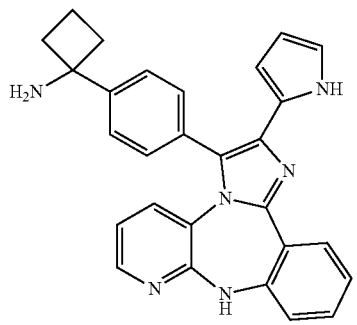 [SMILES: NC1(c2ccc(-c3c(-c4ccc[nH]4)nc4n3-c3cccnc3Nc3ccccc3-4)cc2)CCC1]

The title compound was synthesized according to the procedure described in example 19 using (1H-pyrrol-2-yl)boronic acid in step 1 instead of 6-(4,4,5,5-tetramethyl-1,3,2-dioxaborolan-2-yl)-1H-pyrrolo[3,2-b]pyridine. $^1$HNMR (DMSO-d$_6$) 400 MHz δ: 8.75-8.68 (m, 2H), 8.64 (s, 1H), 8.10 (dd, J=4.6, 1.2 Hz, 1H), 7.97 (dd, J=7.5, 1.7 Hz, 1H), 7.58 (d, J=8.6 Hz, 2H), 7.44-7.34 (m, 3H), 7.31 (d, J=8.0 Hz, 1H), 7.14 (td, J=8.0, 1.2 Hz, 1H), 6.95 (dd, J=8.0, 1.7 Hz, 1H), 6.80-6.78 (m, 1H), 6.76 (dd, J=8.0, 4.6 Hz, 1H), 5.98-5.96 (m, 2H), 2.65-2.52 (m, 4H), 2.26-2.11 (m, 1H), 1.87-1.73 (m, 1H); LC/MS [M+H]: 445.

Example 27

Preparation of 1-{4-[2-(furan-3-yl)-9H-imidazo[1,2-d]pyrido[2,3-b][1,4]benzodiazepin-3-yl]phenyl}cyclobutanamine

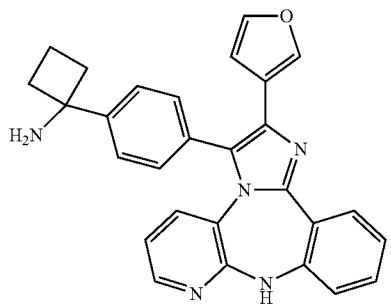 [SMILES: NC1(c2ccc(-c3c(-c4ccoc4)nc4n3-c3cccnc3Nc3ccccc3-4)cc2)CCC1]

The title compound was synthesized according to the procedure described in example 19 using furan-3-ylboronic acid in step 1 instead of 6-(4,4,5,5-tetramethyl-1,3,2-dioxaborolan-2-yl)-1H-pyrrolo[3,2-b]pyridine. $^1$HNMR (DMSO-d$_6$) 400 MHz δ: 8.68-8.58 (m, 3H), 8.09 (dd, J=4.6, 1.7 Hz, 1H), 7.90 (dd, J=7.7, 1.4 Hz, 1H), 7.76 (s, 1H), 7.66 (t, J=1.7 Hz, 1H), 7.57 (d, J=8.6 Hz, 2H), 7.38 (d, J=8.0 Hz, 2H), 7.36 (d, J=8.0 Hz, 1H), 7.29 (d, J=8.0 Hz, 1H), 7.12 (td, J=8.0, 1.2 Hz, 1H), 6.95 (dd, J=8.0, 1.7 Hz, 1H), 6.75 (dd, J=8.0, 4.6 Hz, 1H), 6.46 (d, J=1.2 Hz, 1H), 2.64-2.54 (m, 4H), 2.23-2.13 (m, 1H), 1.87-1.77 (m, 1H); LC/MS [M+H]: 446.

Example 28

Preparation of 1-{4-[2-(6-methoxypyridin-3-yl)-9H-imidazo[1,2-d]pyrido[2,3-b][1,4]benzodiazepin-3-yl]phenyl}cyclobutanamine Step 1: Preparation of tert-butyl (1-{4-[2-(6-methoxypyridin-3-yl)-9H-imidazo[1,2-d]pyrido[2,3-b][1,4]benzodiazepin-3-yl]phenyl}cyclobutyl)carbamate

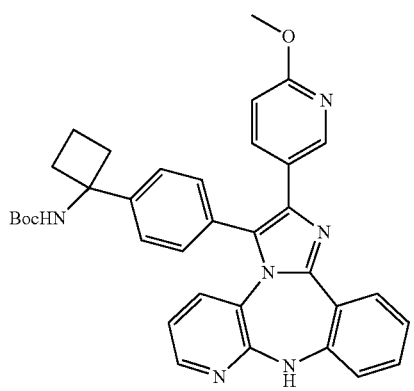 [SMILES: COc1ccc(-c2nc3n(c2-c2ccc(C4(NC(=O)OC(C)(C)C)CCC4)cc2)-c2cccnc2Nc2ccccc2-3)cn1]

The title compound was synthesized according to the procedure described in step 1 of example 18 using (6-methoxypyridin-3-yl)boronic acid instead of [4-(methoxycarbonyl)phenyl]boronic acid. ¹HNMR (CDCl₃) 400 MHz δ: 8.35 (s, 1H), 8.16 (dd, J=7.7, 1.4 Hz, 1H), 8.03 (d, J=4.0 Hz, 1H), 7.90-7.85 (brs, 1H), 7.40 (d, J=8.6 Hz, 2H), 7.33 (td, J=7.7, 1.5 Hz, 1H), 7.19-7.14 (m, 3H), 6.98 (d, J=7.5 Hz, 1H), 6.84-6.78 (m, 1H), 6.72 (d, J=8.6 Hz, 1H), 6.62 (dd, J=8.0, 5.2 Hz, 1H), 6.30 (s, 1H), 5.13 (s, 1H), 3.95 (s, 3H), 2.62-2.38 (m, 4H), 2.21-2.12 (m, 1H), 1.96-1.88 (m, 1H), 1.50-1.24 (m, 9H); LC/MS [M+H]: 587.

Step 2: Preparation of 1-{4-[2-(6-methoxypyridin-3-yl)-9H-imidazo[1,2-d]pyrido[2,3-b][1,4]benzodiazepin-3-yl]phenyl}cyclobutanamine

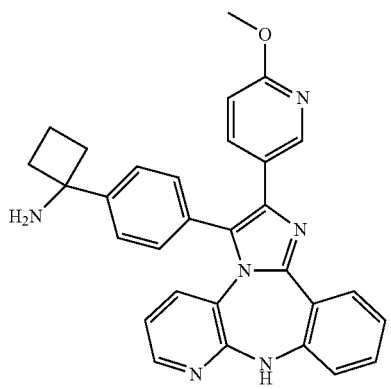 [SMILES: COc1ccc(-c2nc3n(c2-c2ccc(C4(N)CCC4)cc2)-c2cccnc2Nc2ccccc2-3)cn1]

The title compound was synthesized according to the procedure described in step 2 of example 18. LC/MS [M+H]: 487.

Example 29

Preparation of 1-{4-[2-(pyrazin-2-yl)-9H-imidazo[1,2-d]pyrido[2,3-b][1,4]benzodiazepin-3-yl]phenyl}cyclobutanamine Step 1: Preparation of tert-butyl (1-{4-[2-(pyrazin-2-yl)-9H-imidazo[1,2-d]pyrido[2,3-b][1,4]benzodiazepin-3-yl]phenyl}cyclobutyl)carbamate

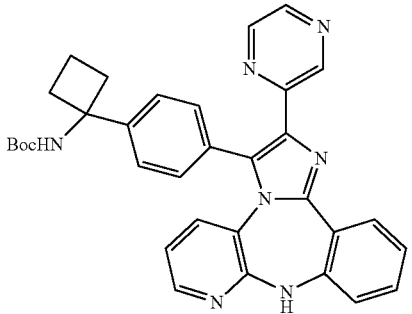 [SMILES: CC(C)(C)OC(=O)NC1(c2ccc(-c3c(-c4cnccn4)nc4n3-c3cccnc3Nc3ccccc3-4)cc2)CCC1]

The title compound was synthesized according to the procedure described in step 1 of example 18 using (pyrazin-2-yl)boronic acid instead of [4-(methoxycarbonyl)phenyl]boronic acid. ¹HNMR (CDCl₃) 400 MHz δ: 8.89 (d, J=1.7 Hz, 1H), 8.51 (s, 1H), 8.39 (d, J=2.3 Hz, 1H), 8.22 (dd, J=7.7, 1.4 Hz, 1H), 8.03 (d, J=4.0 Hz, 1H), 7.38 (d, J=8.0 Hz, 2H), 7.33 (td, J=7.4, 1.2 Hz, 1H), 7.25 (d, J=8.6 Hz, 2H), 7.16 (t, J=7.5 Hz, 1H), 6.97 (d, J=7.5 Hz, 1H), 6.85-6.78 (m, 1H), 6.61 (dd, J=8.0, 4.6 Hz, 1H), 6.33 (s, 1H), 5.12 (s, 1H), 2.58-2.38 (m, 4H), 2.18-2.08 (m, 1H), 1.93-1.85 (m, 1H), 1.48-1.18 (m, 9H); LC/MS [M+H]: 558.

Step 2: Preparation of 1-{4-[2-(pyrazin-2-yl)-9H-imidazo[1,2-d]pyrido[2,3-b][1,4]benzodiazepin-3-yl]phenyl}cyclobutanamine

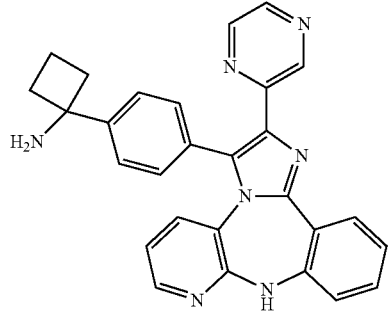 [SMILES: NC1(c2ccc(-c3c(-c4cnccn4)nc4n3-c3cccnc3Nc3ccccc3-4)cc2)CCC1]

The title compound was synthesized according to the procedure described in step 2 of example 18. LC/MS [M+H]: 458.

Example 30

Preparation of 1-{4-[2-(4-nitrophenyl)-9H-imidazo[1,2-d]pyrido[2,3-b][1,4]benzodiazepin-3-yl]phenyl}cyclobutanamine trihydrochloride Step 1: Preparation of tert-butyl (1-{4-[2-(4-nitrophenyl)-9H-imidazo[1,2-d]pyrido[2,3-b][1,4]benzodiazepin-3-yl]phenyl}cyclobutyl)carbamate

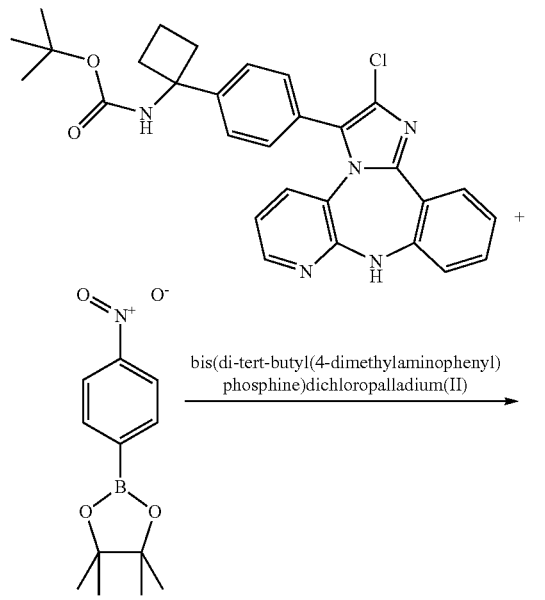

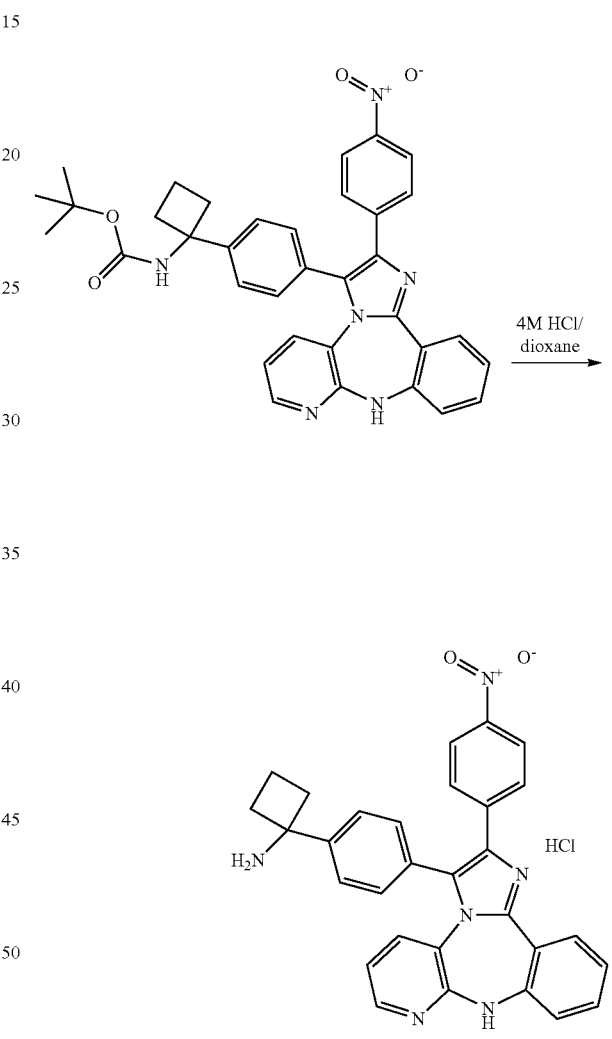

A mixture of tert-butyl {1-[4-(2-chloro-9H-imidazo[1,2-d]pyrido[2,3-b][1,4]benzodiazepin-3-yl)phenyl]cyclobutyl}carbamate (250 mg, 0.486 mmol), 4-nitrophenylboronic acid pinacol ester (152 mg, 0.730 mmol), bis(di-tert-butyl(4-dimethylaminophenyl)phosphine)dichloropalladium(II) (34.4 mg, 0.0486 mmol) and 2M $Na_2CO_3$ aq. (0.485 mL, 0.970 mmol) in DMF (1.00 mL) was heated at 160° C. under microwave irradiation for 1 hour under nitrogen. After cooling to room temperature, the mixture was diluted with EtOAc and washed with water (×3). The organic layer was dried over anhydrous $Na_2SO_4$ and concentrated. The residue was purified by silica gel column chromatography (EtOAc/hexane=1:4→1:2) and TLC (EtOAc/hexane=1:1, DCM/EtOAc=1:1) to afford desired product (51.4 mg, 17.6%) as yellow solid. $^1$HNMR (CDCl$_3$) 400 MHz δ: 8.19-8.08 (m, 3H), 8.06-8.01 (m, 1H), 7.80-7.70 (m, 2H), 7.47-7.40 (m, 2H), 7.36-7.30 (m, 1H), 7.22-7.14 (m, 3H), 7.00-6.93 (m, 1H), 6.85-6.78 (m, 1H), 6.65-6.58 (m, 1H), 6.38 (s, 1H), 5.19 (s, 1H), 2.67-2.30 (m, 4H), 2.25-2.09 (m, 1H), 1.98-1.84 (m, 1H), 1.39 (br s, 9H).

Step 2: Preparation of 1-{4-[2-(4-nitrophenyl)-9H-imidazo[1,2-d]pyrido[2,3-b][1,4]benzodiazepin-3-yl]phenyl}cyclobutanamine trihydrochloride tert-Butyl (1-{4-[2-(4-nitrophenyl)-9H-imidazo[1,2-d]pyrido[2,3-b][1,4]benzodiazepin-3-yl]phenyl}cyclobutyl)carbamate (7.70 mg, 0.0128 mmol) was dissolved in DCM (0.5 mL). 4M HCl/dioxane (0.5 mL) was added to the mixture and stirred at room temperature for 4 hours. The mixture was concentrated and solidified with ether. The precipitated solids were collected by filtration and washed with ether to afford desired product (8.04 mg, quant.) as an orange solid. $^1$HNMR (DMSO-d$_6$) 400 MHz δ: 8.72 (br s, 2H), 8.65 (s, 1H), 8.19-8.14 (m, 2H), 8.13-8.10 (m, 1H), 8.00-7.96 (m, 1H), 7.73-7.68 (m, 2H), 7.62-7.56 (m, 2H), 7.42-7.36 (m, 3H), 7.33-7.29 (m, 1H), 7.18-7.12 (m, 1H), 6.96-6.92 (m, 1H), 6.75 (dd, J=8.0, 4.8 Hz, 1H), 2.69-2.44 (m, 4H), 2.28-2.15 (m, 1H), 1.93-1.78 (m, 1H); LCMS: 501 [M+H].

Example 31

Preparation of 1-(4-{3-[4-(1-aminocyclobutyl)phenyl]-9H-imidazo[1,2-d]pyrido[2,3-b][1,4]benzodiazepin-2-yl}phenyl)ethanone trihydrochloride Step 1: Preparation of tert-butyl (1-{4-[2-(4-acetylphenyl)-9H-imidazo[1,2-d]pyrido[2,3-b][1,4]benzodiazepin-3-yl]phenyl}cyclobutyl)carbamate

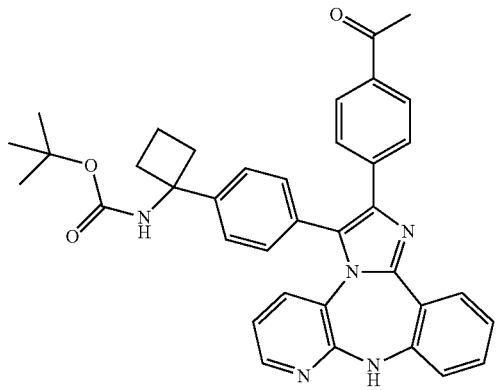 [SMILES: CC(=O)c1ccc(-c2nc3n(c2-c2ccc(C4(NC(=O)OC(C)(C)C)CCC4)cc2)-c2cccnc2Nc2ccccc2-3)cc1]

A mixture of tert-butyl {1-[4-(2-chloro-9H-imidazo[1,2-d]pyrido[2,3-b][1,4]benzodiazepin-3-yl)phenyl]cyclobutyl}carbamate (30 mg, 0.058 mmol), m-acetylphenyl boronic acid (19 mg, 0.12 mmol), bis(di-tert-butyl(4-dimethylaminophenyl)phosphine)dichloropalladium(II) (4 mg, 0.006 mmol), and 2M Na$_2$CO$_3$ aq. (0.058 mL, 0.12 mmol) in DMF (1 mL) was treated with microwave (160° C. for 1 hour). The mixture was diluted with AcOEt, washed with water (×3), brine, dried over Na$_2$SO$_4$, then filtrated through Celite pad. The filtrate was concentrated and the residue was purified by preparative thin-layer chromatography (n-hexane/AcOEt=1:1×2) to afford the desired product (27 mg, 77%) as a yellow solid. $^1$HNMR (CDCl$_3$) 400 MHz δ: 8.17 (dd, J=7.7, 1.4 Hz, 1H), 8.02 (d, J=4.6 Hz, 1H), 7.86 (d, J=8.6 Hz, 2H), 7.68 (d, J=8.6 Hz, 2H), 7.40 (d, J=8.0 Hz, 2H), 7.32 (td, J=8.0, 1.7 Hz, 1H), 7.18-7.15 (m, 2H), 6.96 (d, J=8.0 Hz, 1H), 6.80 (d, J=7.4 Hz, 1H), 6.60 (dd, J=8.0, 5.2 Hz, 1H), 6.25 (s, 1H), 5.13 (br s, 2H), 2.59-2.53 (m, 5H), 2.50-2.42 (m, 2H), 2.21-2.12 (m, 1H), 1.95-1.87 (m, 1H), 1.40 (br s, 9H). LCMS: 598 [M+H].

Step 2: Preparation of 1-(4-{3-[4-(1-aminocyclobutyl)phenyl]-9H-imidazo[1,2-d]pyrido[2,3-b][1,4]benzodiazepin-2-yl}phenyl)ethanone trihydrochloride

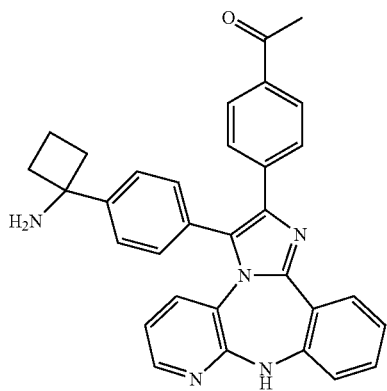 [SMILES: CC(=O)c1ccc(-c2nc3n(c2-c2ccc(C4(N)CCC4)cc2)-c2cccnc2Nc2ccccc2-3)cc1]

tert-Butyl (1-{4-[2-(4-acetylphenyl)-9H-imidazo[1,2-d]pyrido[2,3-b][1,4]benzodiazepin-3-yl]phenyl}cyclobutyl)carbamate (27 mg, 0.045 mmol) in MeOH (0.5 mL) was added 4N HCl-dioxane (2 mL) and stirred at room temperature for 22.5 hours. The mixture was concentrated to afford the desired product (27 mg, 98%) as a pale yellow solid. $^1$HNMR (DMSO-d$_6$) 400 MHz δ: 8.66-8.63 (m, 3H), 8.11 (dd, J=4.6 Hz and 1.7 Hz, 1H), 7.98 (dd, J=8.0 Hz and 1.7 Hz, 1H), 7.88 (d, J=8.6 Hz, 2H), 7.61 (d, J=8.6 Hz, 2H), 7.56 (d, J=8.6 Hz, 2H), 7.35-7.35 (m, 2H), 7.31 (d, J=7.4 Hz, 1H), 7.14 (t, J=7.2 Hz, 1H), 6.91 (dd, J=8.0 Hz and 1.7 Hz, 1H), 6.74 (dd, J=8.0 Hz and 4.6 Hz, 1H), 3.73-3.70 (m, 1H), 3.68-3.65 (m, 1H), 2.64-2.53 (m, 5H), 2.24-2.15 (m, 1H), 1.89-1.80 (m, 1H). LCMS: 498 [M+H].

Example 32

Preparation of 1-(4-{2-[4-(methylsulfonyl)phenyl]-9H-imidazo[1,2-d]pyrido[2,3-b][1,4]benzodiazepin-3-yl}phenyl)cyclobutanamine Step 1: Preparation of tert-butyl[1-(4-{2-[4-(methylsulfonyl)phenyl]-9H-imidazo[1,2-d]pyrido[2,3-b][1,4]benzodiazepin-3-yl}phenyl)cyclobutyl]carbamate

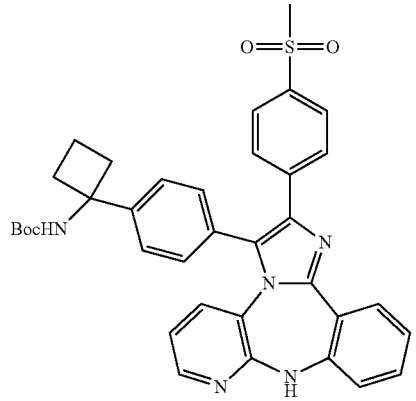 [SMILES: CC(C)(C)OC(=O)NC1(c2ccc(-c3c(-c4ccc(S(C)(=O)=O)cc4)nc4n3-c3cccnc3Nc3ccccc3-4)cc2)CCC1]

A mixture of tert-butyl {1-[4-(2-chloro-9H-imidazo[1,2-d]pyrido[2,3-b][1,4]benzodiazepin-3-yl)phenyl]cyclobutyl}carbamate (50 mg, 0.097 mmol), [4-(methyl sulfonyl)phenyl]boronic acid (39 mg, 0.20 mmol), bis(di-tert-butyl(4-dimethylaminophenyl)phosphine)dichloropalladium(II) (7 mg, 0.1 mmol), and 2M Na$_2$CO$_3$ aq. (0.097 mL, 0.20 mmol) in DMF (1.5 mL) was treated with microwave (160° C. for 1 hour). The mixture was diluted with AcOEt, washed with water (×3), brine, dried over Na$_2$SO$_4$, and then filtrated through Celite pad. The filtrate was concentrated and the residue was purified by preparative thin-layer chromatography (n-hexane/AcOEt=1:1×2) to afford the mixture of the desired product and tert-butyl {1-[4-(2-chloro-9H-imidazo[1,2-d]pyrido[2,3-b][1,4]benzodiazepin-3-yl]phenyl)cyclobutyl}carbamate (51 mg) as a yellow solid. LCMS: 634 [M+H].

Step 2: Preparation of 1-(4-{2-[4-(methylsulfonyl)phenyl]-9H-imidazo[1,2-d]pyrido[2,3-b][1,4]benzodiazepin-3-yl}phenyl)cyclobutanamine

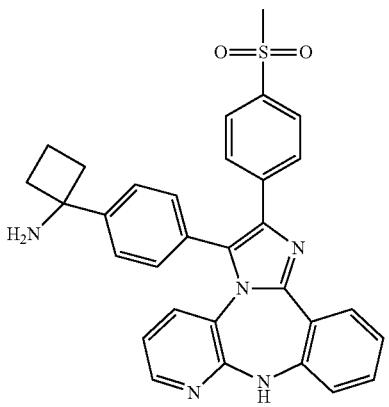 [SMILES: CS(=O)(=O)c1ccc(-c2nc3n(c2-c2ccc(C4(N)CCC4)cc2)-c2cccnc2Nc2ccccc2-3)cc1]

tert-Butyl[1-(4-{2-[4-(methylsulfonyl)phenyl]-9H-imidazo[1,2-d]pyrido[2,3-b][1,4]benzodiazepin-3-yl}phenyl)cyclobutyl]carbamate (51 mg) in MeOH (0.5 mL) was added 4N HCl-dioxane (2 mL) and stirred at room temperature for 23 hours. The mixture was concentrated, then sat.NaHCO₃ aq. was added. The mixture was extracted with AcOEt+MeOH, dried over Na₂SO₄, then filtrated through Celite pad. The filtrate was concentrated to afford the desired product (37 mg, 72%, 2 steps) as a pale yellow solid. ¹HNMR (DMSO-d₆) 400 MHz δ: 8.60 (s, 1H), 8.09 (dd, J=4.6 Hz and 1.7 Hz, 1H), 7.98 (dd, J=8.0 Hz and 1.7 Hz, 1H), 7.84 (d, J=8.6 Hz, 2H), 7.73 (d, J=8.0 Hz, 2H), 7.52 (d, J=8.0 Hz, 2H), 7.37 (td, J=7.4 Hz and 1.7 Hz, 1H), 7.30 (d, J=7.4 Hz, 1H), 7.24 (d, J=8.6 Hz, 2H), 7.14 (td, J=7.4 Hz and 1.7 Hz, 2H), 6.92 (dd, J=8.0 Hz and 1.7 Hz, 1H), 6.74 (dd, J=8.0 Hz and 5.2 Hz, 1H), 3.21 (s, 3H), 2.45-2.39 (m, 2H), 2.18-2.13 (m, 2H), 2.08-2.00 (m, 1H), 1.75-1.67 (m, 1H). LCMS: 534 [M+H].

Example 33

Preparation of 1-{4-[2-(naphthalen-2-yl)-9H-imidazo[1,2-d]pyrido[2,3-b][1,4]benzodiazepin-3-yl]phenyl}cyclobutanamine

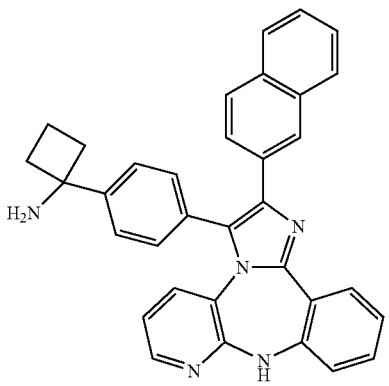 [SMILES: NC1(c2ccc(-c3c(-c4ccc5ccccc5c4)nc4n3-c3cccnc3Nc3ccccc3-4)cc2)CCC1]

The title compound was synthesized according to the procedure described in step 1 and 2 of example 18 using naphthalen-2-ylboronic acid in step 1 instead of [4-(methoxycarbonyl)phenyl]boronic acid. ¹HNMR (DMSO-d₆) 400 MHz δ: 8.58 (s, 1H), 8.09 (dd, J=4.6, 1.7 Hz, 1H), 8.06 (s, 1H), 8.02 (d, J=6.9 Hz, 1H), 7.88-7.84 (m, 1H), 7.80 (d, J=9.2 Hz, 1H), 7.78-7.74 (m, 1H), 7.58 (dd, J=8.6, 1.7 Hz, 1H), 7.52-7.45 (m, 4H), 7.37 (td, J=7.5, 1.2 Hz, 1H), 7.30 (d, J=7.5 Hz, 1H), 7.23 (d, J=8.0 Hz, 2H), 7.14 (t, J=7.2 Hz, 1H), 6.94 (d, J=7.5 Hz, 1H), 6.76 (dd, J=8.0, 4.6 Hz, 1H), 2.44-2.35 (m, 2H), 2.18-2.10 (m, 2H), 2.07-1.99 (m, 1H), 1.74-1.66 (m, 1H); LC/MS [M+H]: 506.

Example 34

Preparation of 1-{4-[2-(thiophen-3-yl)-9H-imidazo[1,2-d]pyrido[2,3-b][1,4]benzodiazepin-3-yl]phenyl}cyclobutanamine Step 1: Preparation of tert-butyl (1-{4-[2-(thiophen-3-yl)-9H-imidazo[1,2-d]pyrido[2,3-b][1,4]benzodiazepin-3-yl]phenyl}cyclobutyl)carbamate

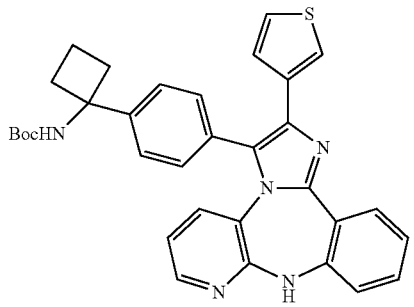 [SMILES: CC(C)(C)OC(=O)NC1(c2ccc(-c3c(-c4ccsc4)nc4n3-c3cccnc3Nc3ccccc3-4)cc2)CCC1]

The title compound was synthesized according to the procedure described in step 1 of example 18 using thiophen-3-ylboronic acid in step 1 instead of [4-(methoxycarbonyl)phenyl]boronic acid. ¹HNMR (CDCl₃) 400 MHz δ: 8.14 (dd, J=7.7, 1.4 Hz, 1H), 8.00 (d, J=3.4 Hz, 1H), 7.46-7.44 (m, 1H), 7.39 (d, J=8.6 Hz, 2H), 7.29 (td, J=7.7, 1.5 Hz, 1H), 7.23 (d, J=8.0 Hz, 2H), 7.22-7.18 (m, 2H), 7.14 (td, J=7.5, 1.2 Hz, 1H), 6.94 (d, J=7.5 Hz, 1H), 6.84 (d, J=6.9 Hz, 1H), 6.59 (dd, J=8.0, 4.6 Hz, 1H), 6.46 (s, 1H), 5.22 (s, 1H), 2.60-2.30 (m, 4H), 2.20-2.09 (m, 1H), 1.94-1.86 (m, 1H), 1.49-1.16 (m, 9H); LC/MS [M+H]: 562.

Step 2: Preparation of 1-{4-[2-(thiophen-3-yl)-9H-imidazo[1,2-d]pyrido[2,3-b][1,4]benzodiazepin-3-yl]phenyl}cyclobutanamine

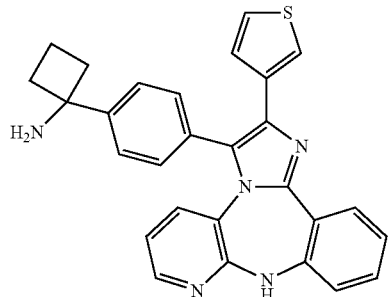

The title compound was synthesized according to the procedure described in step 2 of example 18. ¹HNMR (DMSO-d₆) 400 MHz δ: 8.78-8.59 (m, 4H), 8.10 (d, J=4.6 Hz, 1H), 7.93 (d, J=7.5 Hz, 1H), 7.60-7.50 (m, 4H), 7.39 (d, J=8.0 Hz, 2H), 7.30 (d, J=8.0 Hz, 1H), 7.16-7.11 (m, 2H), 6.94 (d, J=8.0 Hz, 1H), 6.76-6.72 (m, 1H), 2.65-2.52 (m, 4H), 2.25-2.15 (m, 1H), 1.87-1.78 (m, 1H); LC/MS [M+H]: 462.

Example 35

Preparation of 1-(4-{2-[4-(pyrrolidin-1-ylcarbonyl)phenyl]-9H-imidazo[1,2-d]pyrido[2,3-b][1,4]benzo-diazepin-3-yl}phenyl)cyclobutanamine trihydrochloride Step 1: Preparation of tert-butyl[1-(4-{2-[4-(pyrrolidin-1-ylcarbonyl)phenyl]-9H-imidazo[1,2-d]pyrido[2,3-b][1,4]benzodiazepin-3-yl}phenyl)cyclobutyl]carbamate

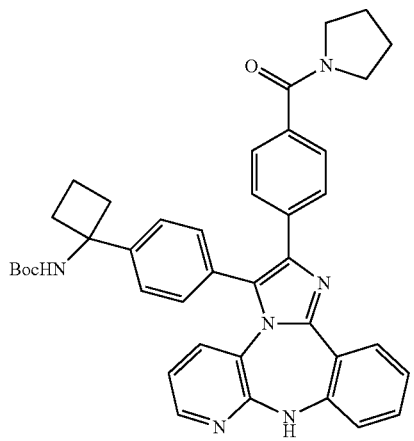 [SMILES: CC(C)(C)OC(=O)NC1(c2ccc(-c3c(-c4ccc(C(=O)N5CCCC5)cc4)nc4n3-c3cccnc3Nc3ccccc3-4)cc2)CCC1]

A mixture of 4-[3-(4-{1-[tert-butoxycarbonyl)amino]cyclobutyl}phenyl)-9H-imidazo[1,2-d]pyrido[2,3-b][1,4]benzodiazepin-2-yl]benzoic acid (40 mg, 0.067 mmol) in $CH_2Cl_2$ (1.5 mL) was added pyrrolidine (0.008 mL, 0.1 mmol), 1-ethyl-3-(3-dimethylaminopropyl)carbodiimide (19 mg, 0.10 mmol) and stirred at r.t for 24 hours. The mixture was diluted with AcOEt, washed with water, brine, dried over $Na_2SO_4$, then filtrated through Celite pad. The filtrate was concentrated and the residue was purified by preparative thin-layer chromatography (n-hexane/AcOEt=1:3) to afford the desired product (12 mg, 28%) as a pale yellow solid. $^1$HNMR (CDCl$_3$) 400 MHz δ: 8.17 (dd, J=8.0 Hz and 1.7 Hz, 1H), 8.02 (d, J=4.0 Hz, 1H), 7.60 (d, J=8.0 Hz, 2H), 7.43 (d, J=8.0 Hz, 2H), 7.36 (d, J=8.0 Hz, 2H), 7.31 (td, J=7.4 Hz and 1.7 Hz, 1H), 7.17-7.14 (m, 2H), 6.95 (d, J=8.0 Hz, 1H), 6.79 (d, J=7.4 Hz, 1H), 6.61 (dd, J=8.0 Hz and 4.9 Hz, 1H), 6.25 (s, 1H), 5.11 (br s, 1H), 3.64 (t, J=6.9 Hz, 2H), 3.42 (t, J=6.3 Hz, 2H), 2.57-2.38 (m, 4H), 2.19-2.10 (m, 2H), 1.98-1.91 (m, 2H), 1.90-1.83 (m, 2H), 1.40 (br s, 9H); LCMS: 653 [M+H].

Step 2: Preparation of 1-(4-{2-[4-(pyrrolidin-1-ylcarbonyl)phenyl]-9H-imidazo[1,2-d]pyrido[2,3-b][1,4]benzodiazepin-3-yl}phenyl)cyclobutanamine trihydrochloride

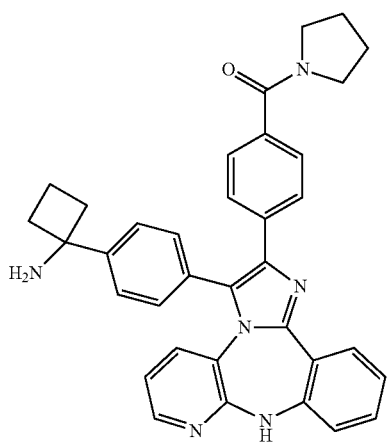 [SMILES: NC1(c2ccc(-c3c(-c4ccc(C(=O)N5CCCC5)cc4)nc4n3-c3cccnc3Nc3ccccc3-4)cc2)CCC1]

tert-Butyl[1-(4-{2-[4-(pyrrolidin-1-ylcarbonyl)phenyl]-9H-imidazo[1,2-d]pyrido[2,3-b][1,4]benzodiazepin-3-yl}phenyl)cyclobutyl]carbamate (12 mg, 0.018 mmol) in MeOH (0.5 mL) was added 4N HCl-dioxane (2 mL) and stirred at r.t for 12 hours. The mixture was concentrated to afford the desired product (12 mg, quant) as a yellow solid. $^1$HNMR (DMSO-d$_6$) 400 MHz δ: 8.62 (s, 1H), 8.60 (br s, 2H), 8.11 (dd, J=4.6 Hz and 1.7 Hz, 1H), 7.97 (dd, J=8.0 Hz and 1.7 Hz, 1H), 7.53 (t, J=8.0 Hz, 4H), 7.45 (d, J=8.6 Hz, 2H), 7.39-7.34 (m, 3H), 7.30 (d, J=7.4 Hz, 1H), 7.13 (td, J=8.6 Hz and 1.1 Hz, 1H), 6.90 (dd, J=8.0 Hz and 1.7 Hz, 1H), 6.74 (dd, J=8.0 Hz and 4.6 Hz, 1H), 3.73-3.65 (m, 1H), 2.61-2.53 (m, 6H), 2.23-2.14 (m, 1H), 1.89-1.78 (m, 6H). LCMS: 553 [M+H].

Example 36

Preparation of 4-{3-[4-(1-aminocyclobutyl)phenyl]-9H-imidazo[1,2-d]pyrido[2,3-b][1,4]benzodiazepin-2-yl}-N-methylbenzamide trihydrochloride

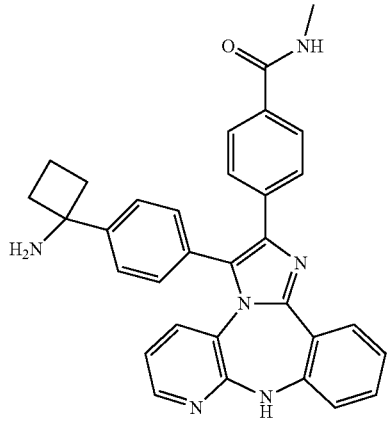 [SMILES: CNC(=O)c1ccc(-c2nc3n(c2-c2ccc(C4(N)CCC4)cc2)-c2cccnc2Nc2ccccc2-3)cc1]

The title compound was synthesized according to the procedure described in step 1 and 2 of example 35 using methylamine in step 1 instead of pyrrolidine. $^1$HNMR (DMSO-d$_6$) 400 MHz δ: 8.65 (s, 2H), 8.62 (s, 1H), 8.45-8.42 (m, 1H), 8.11 (dd, J=4.6 Hz and 1.7 Hz, 1H), 7.98 (dd, J=8.0 Hz and 1.7 Hz, 1H), 7.75 (d, J=8.6 Hz, 2H), 7.54 (t, J=8.6 Hz, 3H), 7.40-7.29 (m, 4H), 7.14 (td, J=8.6 Hz and 1.1 Hz, 1H), 6.90 (dd, J=8.0 Hz and 1.7 Hz, 1H), 6.74 (dd, J=8.0 Hz and 4.6 Hz, 1H), 3.73-3.65 (m, 1H), 3.51-3.43 (m, 1H), 2.77 (d, J=4.6 Hz, 3H), 2.61-2.52 (m, 2H), 2.23-2.15 (m, 1H), 1.88-1.79 (m, 1H). LCMS: 513 [M+H].

Example 37

Preparation of (4-{3-[4-(1-aminocyclobutyl)phenyl]-9H-imidazo[1,2-d]pyrido[2,3-b][1,4]benzodiazepin-2-yl}phenyl)methanol Step 1: Preparation of tert-butyl[1-(4-{2-[4-(hydroxymethyl)phenyl]-9H-imidazo[1,2-d]pyrido[2,3-b][1,4]benzodiazepin-3-yl}phenyl)cyclobutyl]carbamate

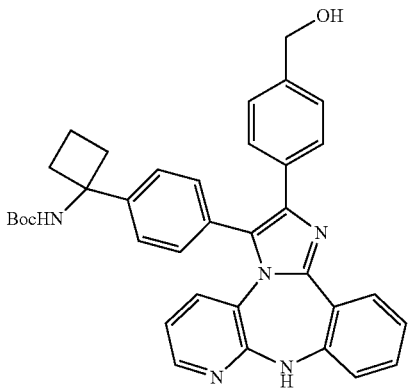 [SMILES: CC(C)(C)OC(=O)NC1(c2ccc(-c3c(-c4ccc(CO)cc4)nc4n3-c3cccnc3Nc3ccccc3-4)cc2)CCC1]

A mixture of tert-butyl {1-[4-(2-chloro-9H-imidazo[1,2-d]pyrido[2,3-b][1,4]benzodiazepin-3-yl)phenyl]cyclobutyl}carbamate (50 mg, 0.097 mmol), [4-(hydroxymethyl)phenyl]boronic acid (30 mg, 0.20 mmol), bis(di-tert-butyl(4-dimethylaminophenyl)phosphine)dichloropalladium(II) (7 mg, 0.01 mmol), and 2M Na₂CO₃ aq. (0.097 mL, 0.20 mmol) in DMF (1.5 mL) was treated with microwave (160° C. for 1 hour). The mixture was diluted with AcOEt, washed with water (×3), brine, dried over Na₂SO₄, then filtrated through Celite pad. The filtrate was concentrated and the residue was purified by preparative thin-layer chromatography (n-hexane/AcOEt=1:2) to afford the desired product (15 mg, 26%) as a pale yellow solid. ¹HNMR (CDCl₃) 400 MHz δ: 8.17 (dd, J=8.0 Hz and 1.1 Hz, 1H), 8.01 (d, J=4.0 Hz, 1H), 7.58 (d, J=8.0 Hz, 2H), 7.36 (d, J=8.0 Hz, 2H), 7.31 (td, J=7.4 Hz and 1.7 Hz, 1H), 7.28-7.24 (m, 2H), 7.16-7.13 (m, 3H), 6.95 (d, J=7.4 Hz, 1H), 6.80 (d, J=7.4 Hz, 1H), 6.60 (dd, J=8.0 Hz and 5.2 Hz, 1H), 6.24 (s, 1H), 5.11 (br s, 1H), 4.68 (d, J=5.7 Hz, 2H), 3.49 (d, J=5.7 Hz, 1H), 2.57-2.51 (m, 4H), 2.19-2.10 (m, 1H), 1.94-1.85 (m, 1H), 1.39 (br s, 9H). LCMS: 586 [M+H].

Step 2: Preparation of (4-{3-[4-(1-aminocyclobutyl)phenyl]-9H-imidazo[1,2-d]pyrido[2,3-b][1,4]benzodiazepin-2-yl}phenyl)methanol

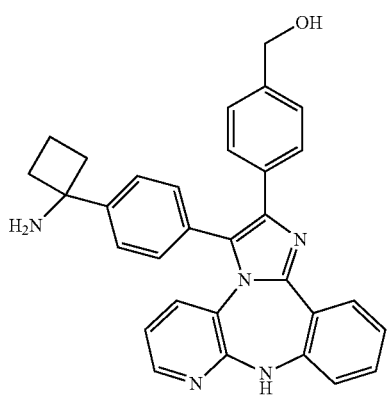 [SMILES: NC1(c2ccc(-c3c(-c4ccc(CO)cc4)nc4n3-c3cccnc3Nc3ccccc3-4)cc2)CCC1]

Starting material (15 mg, 0.026 mmol) in MeOH (0.5 mL) was added 4N HCl-dioxane (2 mL) and stirred at room temperature for 22.5 hours. The mixture was concentrated, then sat.NaHCO₃ aq. was added. The mixture was extracted with CH₂Cl₂(×2), and the organic phase was dried over Na₂SO₄, then filtrated through Celite pad. The filtrate was concentrated and the residue was purified by preparative thin-layer chromatography (AcOEt/MeOH=5:1) to afford the desired product (5 mg, 39%) as a pale yellow solid. ¹HNMR (CDCl₃) 400 MHz δ: 8.16 (dd, J=7.7 Hz and 1.4 Hz, 1H), 8.03 (dd, J=4.9 Hz and 1.4 Hz, 1H), 7.56 (d, J=8.6 Hz, 2H), 7.36 (d, J=8.6 Hz, 2H), 7.32-7.28 (m, 3H), 7.17-7.15 (m, 2H), 6.98 (d, J=8.0 Hz, 1H), 6.80 (dd, J=7.7 Hz and 1.4 Hz, 1H), 6.63 (dd, J=7.7 Hz and 4.6 Hz, 1H), 6.39 (s, 1H), 4.67 (s, 2H), 2.59-2.53 (m, 3H), 2.22-2.16 (m, 2H), 1.84-1.76 (m, 2H). LCMS: 486 [M+H].

Example 38

Preparation of 1-{4-[2-(3'-methylbiphenyl-4-yl)-9H-imidazo[1,2-d]pyrido[2,3-b][1,4]benzodiazepin-3-yl]phenyl}cyclobutanamine

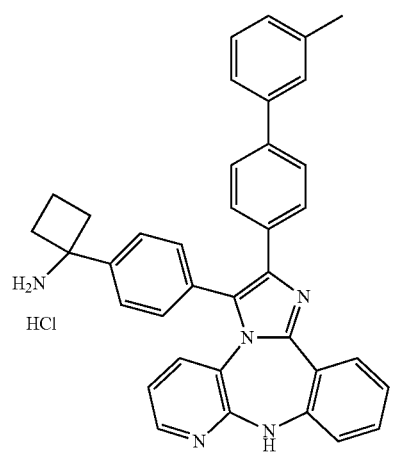 [SMILES: Cc1cccc(-c2ccc(-c3nc4n(c3-c3ccc(C5(N)CCC5)cc3)-c3cccnc3Nc3ccccc3-4)cc2)c1 ; Cl]

The title compound was synthesized according to the procedure described in step 1 and 2 of example 18 using (3'-methyl-[1,1'-biphenyl]-4-yl)boronic acid in step 1 instead of [4-(methoxycarbonyl)phenyl]boronic acid. ¹HNMR (DMSO-d₆) 400 MHz δ: 8.81 (br s, 2H), 8.69 (br s, 1H), 8.14-8.10 (m, 1H), 7.99 (d, J=7.79 Hz, 1H), 7.64-7.55 (m, 5H), 7.50-7.44 (m, 2H), 7.41-7.30 (m, 4H), 7.21-7.12 (m, 2H), 6.93-6.88 (m, 1H), 6.78-6.73 (m, 1H), 2.60-2.54 (m, 4H), 2.37 (s, 3H), 2.26-2.15 (m, 1H), 1.89-1.77 (m, 1H). LCMS: 546 [M+H].

Example 39

Preparation of 1-{4-[2-(2'-methylbiphenyl-4-yl)-9H-imidazo[1,2-d]pyrido[2,3-b][1,4]benzodiazepin-3-yl]phenyl}cyclobutanamine

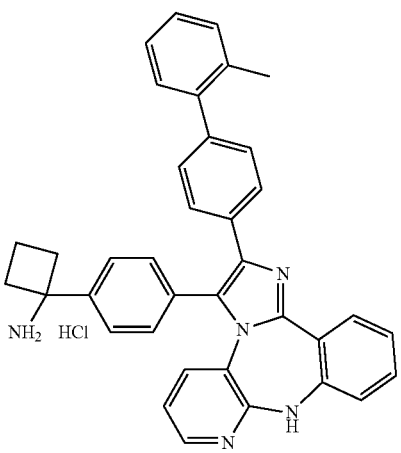 [SMILES: Cc1ccccc1-c1ccc(-c2nc3n(c2-c2ccc(C4(N)CCC4)cc2)-c2cccnc2Nc2ccccc2-3)cc1 ; Cl]

The title compound was synthesized according to the procedure described in step 1 and 2 of example 18 using (2'-methyl-[1,1'-biphenyl]-4-yl)boronic acid in step 1 instead of [4-(methoxycarbonyl)phenyl]boronic acid. $^1$HNMR (DMSO-d$_6$) 400 MHz δ: 8.74 (br s, 2H), 8.67 (br s, 1H), 8.12 (d, J=4.58 Hz, 1H), 7.98 (dd, J=7.79, 1.83 Hz, 1H), 7.61-7.55 (m, 4H), 7.39 (d, J=8.25 Hz, 2H), 7.33-7.25 (m, 6H), 7.15 (t, J=7.57 Hz, 1H), 6.91 (d, J=7.79 Hz, 1H), 6.76 (dd, J=8.02, 4.81 Hz, 1H), 2.61-2.53 (m, 4H), 2.25-2.14 (m, 1H), 2.25 (s, 3H), 1.88-1.75 (m, 1H). LCMS: 546 [M+H].

Example 40

Preparation of N-(4-{3-[4-(1-Aminocyclobutyl)phenyl]-9H-imidazo[1,2-d]pyrido[2,3-b][1,4]benzodiazepin-2-yl}phenyl)acetamide trihydrochloride Step 1: Preparation of tert-butyl (1-{4-[2-(4-acetamidophenyl)-9H-imidazo[1,2-d]pyrido[2,3-b][1,4]benzodiazepin-3-yl]phenyl}cyclobutyl)carbamate

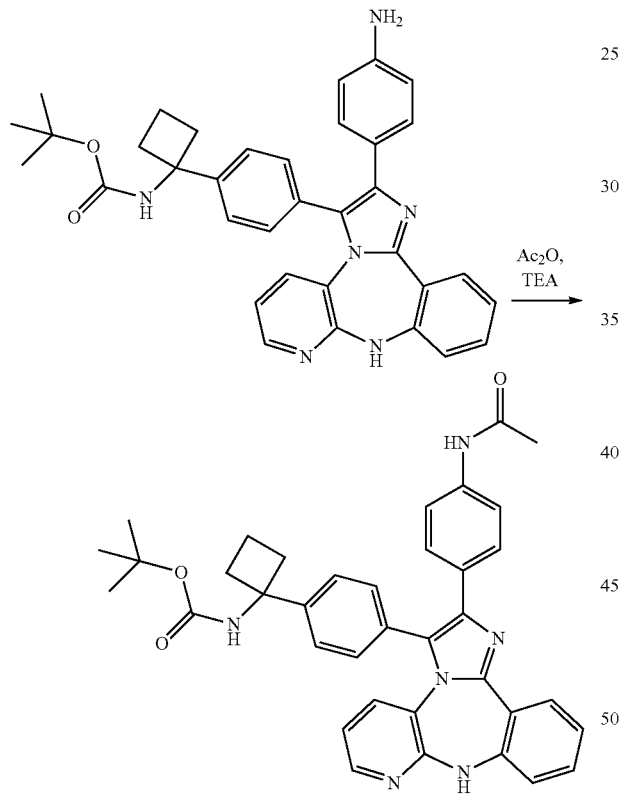

Et$_3$N (25.9 μL, 0.186 mmol) and Ac$_2$O (6.45 μL, 0.0682 mmol) were added to a solution of tert-butyl (1-{4-[2-(4-aminophenyl)-9H-imidazo[1,2-d]pyrido[2,3-b][1,4]benzodiazepin-3-yl]phenyl}cyclobutyl)carbamate (35.4 mg, 0.0620 mmol) in DCM (1 mL) at 0° C. After stiffing the mixture for 17.5 hours at room temperature, the mixture was concentrated. The residue was diluted with sat. NaHCO$_3$ aq. and extracted with CHCl$_3$ (3×). The combined organic layers were dried over anhydrous Na$_2$SO$_4$, and concentrated. The residue was purified by PTLC (CHCl$_3$/MeOH=9:1) to afford desired product (22.6 mg, 59.5%) as a white solid. $^1$HNMR (CDCl$_3$) 400 MHz δ: 8.18-8.13 (m, 1H), 8.03-7.97 (m, 1H), 7.60-7.49 (m, 2H), 7.45-7.25 (m, 8H), 7.19-7.10 (m, 3H), 6.95 (d, J=7.8 Hz, 1H), 6.85-6.73 (m, 1H), 6.59 (dd, J=8.0, 4.8 Hz, 1H), 6.46-6.37 (m, 1H), 5.27-5.17 (m, 1H), 2.64-2.25 (m, 4H), 2.20-2.01 (m, 1H), 2.14 (s, 3H), 1.98-1.83 (m, 1H), 1.38 (br s, 9H); LCMS: 613 [M+H].

Step 2: Preparation of N-(4-{3-[4-(1-aminocyclobutyl)phenyl]-9H-imidazo[1,2-d]pyrido[2,3-b][1,4]benzodiazepin-2-yl}phenyl)acetamide trihydrochloride tert-Butyl (1-{4-[2-(4-acetamidophenyl)-9H-imidazo[1,2-d]pyrido[2,3-b][1,4]benzodiazepin-3-yl]phenyl}cyclobutyl)carbamate (22.6 mg, 0.0369 mmol) was dissolved in DCM (1 mL). 4M HCl/dioxane (1 mL) was added to the mixture and stirred at room temperature for 6 hours. The mixture was concentrated and solidified with ether. The precipitated solids were collected by filtration and washed with ether to afford desired product (21.5 mg, 93.5%) as pale yellow solid. $^1$HNMR (DMSO-d$_6$) 400 MHz δ: 10.08 (s, 1H), 8.70 (br s, 2H), 8.64 (s, 1H), 8.11 (dd, J=4.8, 1.6 Hz, 1H), 7.95 (dd, J=7.8, 1.8 Hz, 1H), 7.58-7.49 (m, 4H), 7.44-7.36 (m, 3H), 7.34-7.28 (m, 3H), 7.17-7.10 (m, 1H), 6.89 (dd, J=8.0, 1.6 Hz, 1H), 6.75 (dd, J=7.8, 4.6 Hz, 1H), 2.65-2.39 (m, 4H), 2.26-2.13 (m, 1H), 2.04 (s, 3H), 1.89-1.75 (m, 1H); LCMS: 513 [M+H].

Example 41

Preparation of 4-{3-[4-(1-aminocyclobutyl)phenyl]-9H-imidazo[1,2-d]pyrido[2,3-b][1,4]benzodiazepin-2-yl}aniline tetrahydrochloride

Step 1: Preparation of tert-butyl (1-{4-[2-(4-aminophenyl)-9H-imidazo[1,2-d]pyrido[2,3-b][1,4]benzodiazepin-3-yl]phenyl}cyclobutyl)carbamate

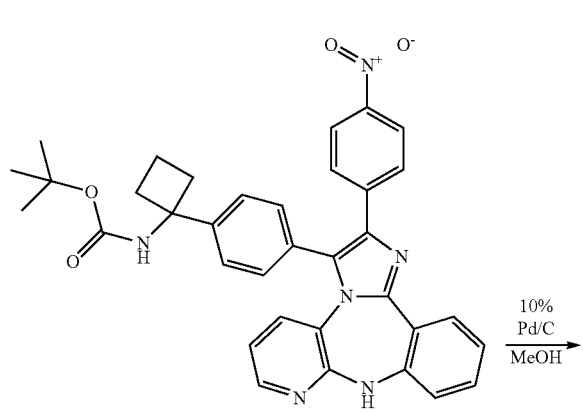

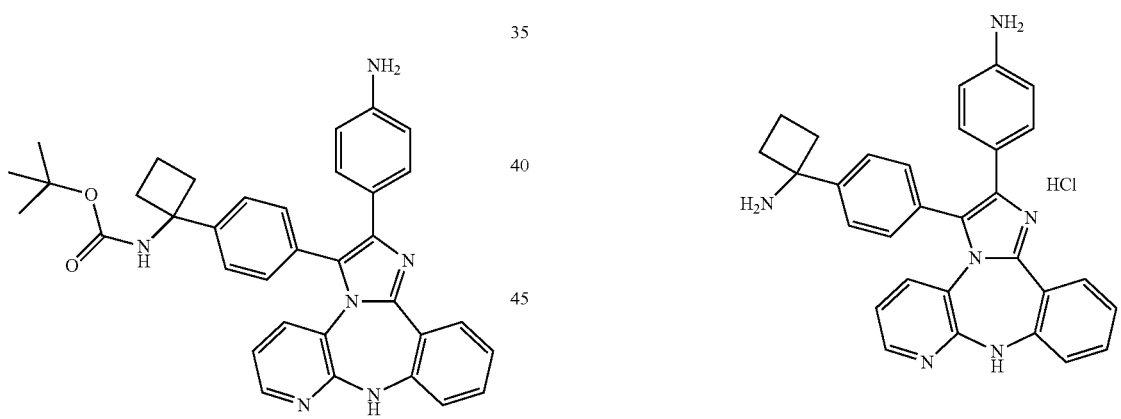

10% Pd/C (51.4 mg) was added to a solution of tert-butyl (1-{4-[2-(4-nitrophenyl)-9H-imidazo[1,2-d]pyrido[2,3-b][1,4]benzodiazepin-3-yl]phenyl}cyclobutyl)carbamate (51.4 mg, 0.0856 mmol) in MeOH (5 mL), and the mixture was stirred for 4 hours under hydrogen atmosphere. The catalyst was filtered off and washed with MeOH. The combined filtrate and washings were concentrated, and the residue was purified by PTLC (CHCl$_3$/MeOH=9:1) to afford desired product (32.0 mg, 65.5%) as an orange solid. $^1$HNMR (CDCl$_3$) 400 MHz δ: 8.16 (dd, J=7.8, 1.4 Hz, 1H), 8.02-7.97 (m, 1H), 7.46-7.24 (m, 5H), 7.18-7.09 (m, 3H), 6.97-6.91 (m, 1H), 6.83-6.73 (m, 1H), 6.64-6.55 (m, 3H), 6.45 (s, 1H), 5.21 (br s, 1H), 3.70 (br s, 2H), 2.65-2.25 (m, 4H), 2.19-2.05 (m, 1H), 1.94-1.81 (m, 1H), 1.38 (br s, 9H).

Step 2: Preparation of 4-{3-[4-(1-aminocyclobutyl)phenyl]-9H-imidazo[1,2-d]pyrido[2,3-b][1,4]benzodiazepin-2-yl}aniline tetrahydrochloride

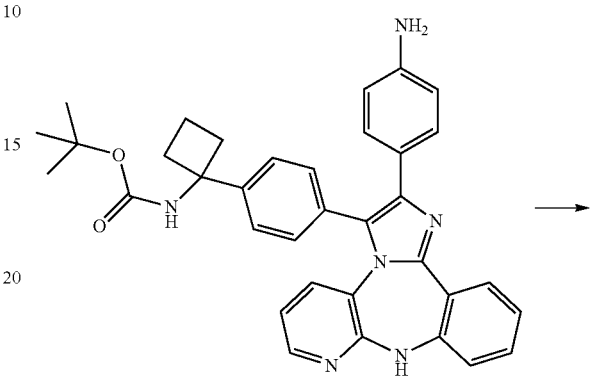

tert-Butyl (1-{4-[2-(4-aminophenyl)-9H-imidazo[1,2-d]pyrido[2,3-b][1,4]benzodiazepin-3-yl]phenyl}cyclobutyl)carbamate (32.0 mg, 0.0561 mmol) was dissolved in DCM (1 mL). 4M HCl/dioxane (1 mL) was added to the mixture and stirred at room temperature for 6 hours. The mixture was concentrated and solidified with ether. The precipitated solids were collected by filtration and washed with ether to afford desired product (28.4 mg, 82.3%) as a pale red solid. $^1$HNMR (DMSO-d$_6$) 400 MHz δ: 8.78 (br s, 3H), 8.66 (br s, 1H), 8.12 (dd, J=4.8, 1.6 Hz, 1H), 7.95 (dd, J=7.8, 1.4 Hz, 1H), 7.59-7.53 (m, 2H), 7.52-7.46 (m, 2H), 7.43-7.36 (m, 1H), 7.35-7.28 (m, 3H), 7.22-7.09 (m, 3H), 6.90 (dd, J=8.0, 1.6 Hz, 1H), 6.76 (dd, J=8.0, 4.8 Hz, 1H), 2.61-2.53 (m, 4H), 2.27-2.13 (m, 1H), 1.89-1.75 (m, 1H); LCMS: 471 [M+H].

Example 42

Preparation of 1-{4-[2-(1H-pyrrol-3-yl)-9H-imidazo[1,2-d]pyrido[2,3-b][1,4]benzodiazepin-3-yl]phenyl}cyclobutanamine

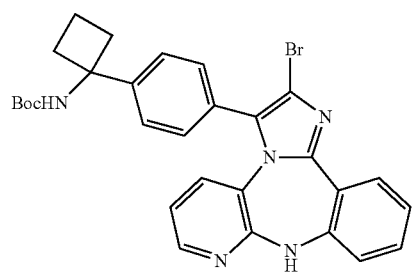

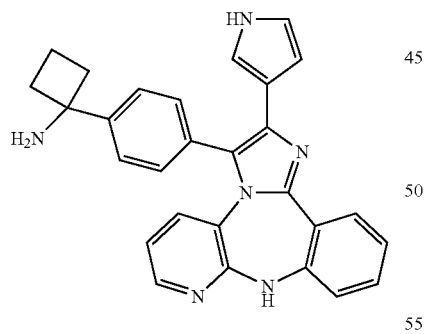

The title compound was synthesized according to the procedure described in step 1 and 2 of example of 19 using (1H-pyrrol-3-yl)boronic acid in step 1 instead of 6-(4,4,5,5-tetramethyl-1,2,3-dioxaborolan-2-yl)-1H-pyrrolo[3,2-b]pyridine. $^1$HNMR (DMS O-$d_6$) 400 MHz δ: 10.76 (s, 1H), 8.47 (s, 1H), 8.24 (s, 1H), 8.03 (dd, J=4.6, 1.7 Hz, 1H), 7.89 (dd, J=7.7, 1.4 Hz, 1H), 7.48 (d, J=8.6 Hz, 2H), 7.32 (td, J=7.6, 1.5 Hz, 1H), 7.27-7.24 (m, 3H), 7.09 (t, J=7.4 Hz, 1H), 6.90-6.87 (m, 2H), 6.71 (dd, J=8.0, 4.6 Hz, 1H), 6.66 (q, J=2.5 Hz, 1H), 6.12 (dd, J=4.0, 2.3 Hz, 1H), 2.46-2.40 (m, 2H), 2.23-2.16 (m, 2H), 2.09-2.00 (m, 1H), 1.76-1.67 (m, 1H); LCMS: 445 [M+H].

Example 43

Preparation of 5-{3-[4-(1-aminocyclobutyl)phenyl]-9H-imidazo[1,2-d]pyrido[2,3-b][1,4]benzodiazepin-2-yl}pyrimidin-2-amine

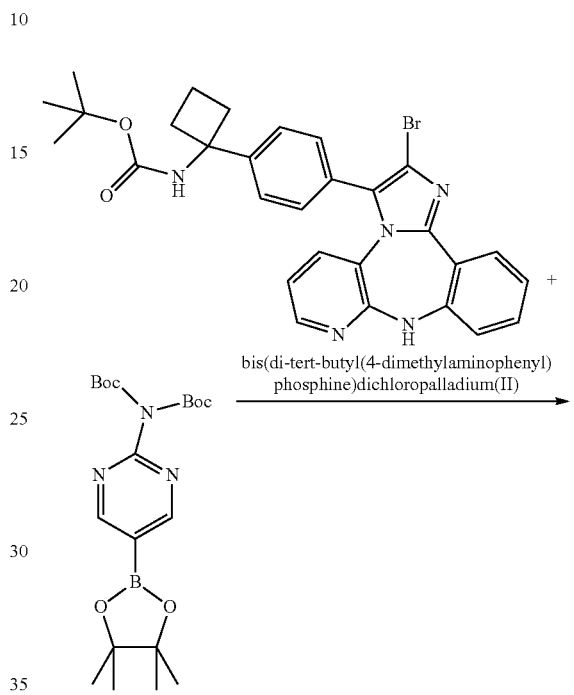

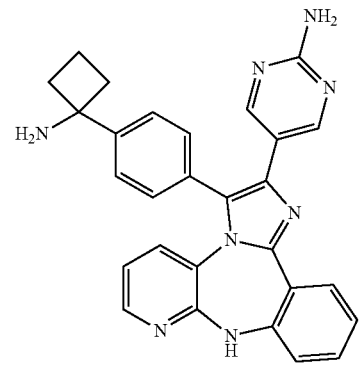

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), di-tert-butyl[5-

(4,4,5,5-tetramethyl-1,3,2-dioxaborolan-2-yl)pyrimidin-2-yl]imidodicarbonate (75 mg, 0.18 mmol), bis(di-tert-butyl(4-dimethylaminophenyl)phosphine)dichloropalladium(II) (6.3 mg, 0.01 mmol) and $K_3PO_4$ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous$Na_2SO_4$ and concentrated. The residue was purified by HPLC. The fraction was evaporated and the residue was dissolved in methanol (10 mL) and 4M HCl in dioxane (10 mL). After overnight reaction, the mixture was evaporated and the residue was purified by HPLC to give the titled compound as a white solid (24 mg, 43%). $^1$HNMR (DMSO-$d_6$) 400 MHz δ: 8.56 (s, 1H), 8.26 (d, J=15.5 Hz, 2H), 8.08 (dd, J=4.6, 1.7 Hz, 1H), 7.93 (dd, J=8.0, 1.7 Hz, 1H), 7.50 (d, J=8.6 Hz, 2H), 7.35 (td, J=7.6, 1.5 Hz, 1H), 7.28 (d, J=7.4 Hz, 1H), 7.21 (d, J=8.6 Hz, 2H), 7.10 (t, J=7.4 Hz, 1H), 6.89 (dd, J=8.0, 1.7 Hz, 1H), 6.75 (dd, J=8.0, 4.6 Hz, 1H), 6.72 (s, 2H), 2.45-2.38 (m, 2H), 2.23-2.16 (m, 2H), 2.10-2.00 (m, 1H), 1.75-1.66 (m, 1H); LCMS: 473 [M+H].

Example 44

Preparation of 5-{3-[4-(1-aminocyclobutyl)phenyl]-9H-imidazo[1,2-d]pyrido[2,3-b][1,4]benzodiazepin-2-yl}-2-methylphenol

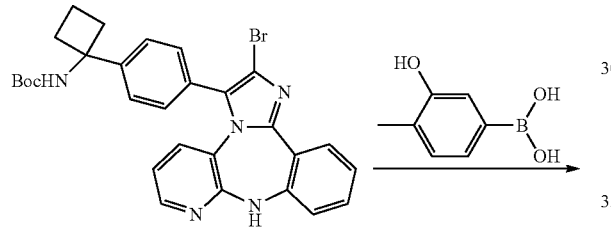

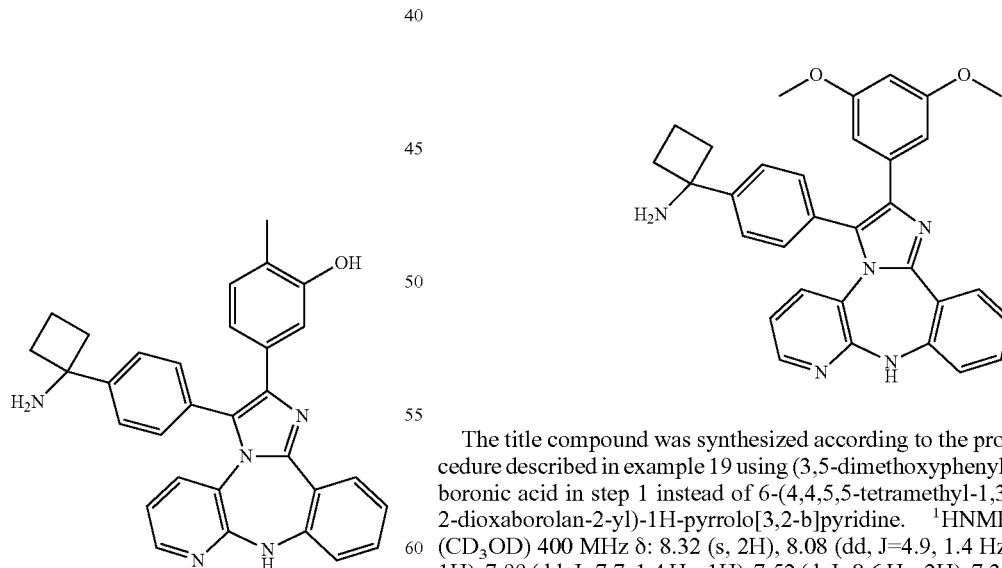

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), (3-hydroxy-4-methylphenyl)boronic acid (27 mg, 0.18 mmol), bis(di-tert-butyl(4-dimethylaminophenyl)phosphine)dichloropalladium(II) (6.3 mg, 0.01 mmol) and $K_3PO_4$ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous $Na_2SO_4$ and concentrated. The residue was purified by HPLC. The fraction was evaporated and the residue was dissolved in methanol (10 mL) and 4M HCl in dioxane (10 mL). After overnight reaction, the mixture was evaporated and the residue was purified by HPLC to give the titled compound as a white solid (1 mg, 2%). LCMS: 486 [M+H].

Example 45

Preparation of 1-{4-[2-(3,5-dimethoxyphenyl)-9H-imidazo[1,2-d]pyrido[2,3-b][1,4]benzodiazepin-3-yl]phenyl}cyclobutanamine

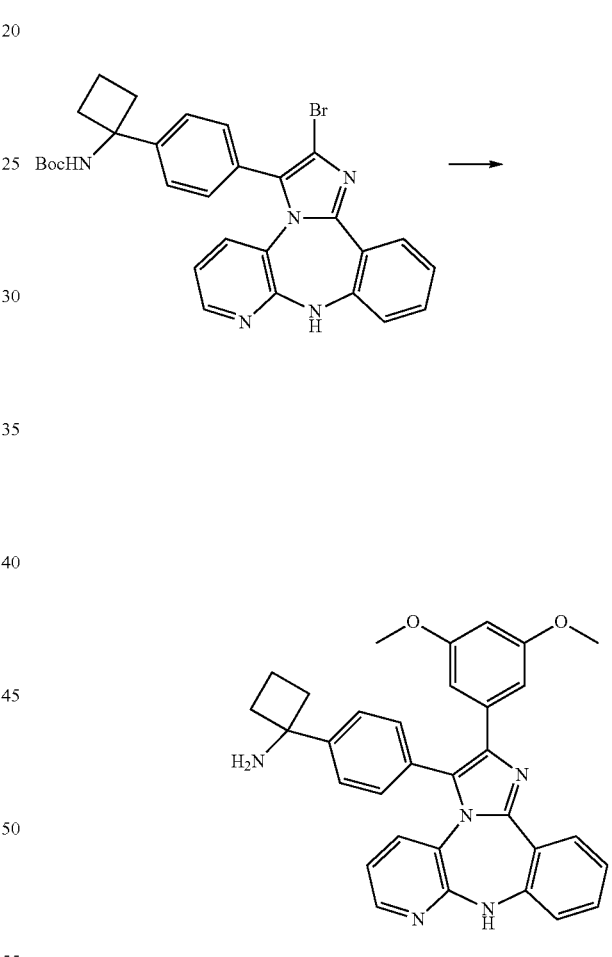

The title compound was synthesized according to the procedure described in example 19 using (3,5-dimethoxyphenyl)boronic acid in step 1 instead of 6-(4,4,5,5-tetramethyl-1,3,2-dioxaborolan-2-yl)-1H-pyrrolo[3,2-b]pyridine. $^1$HNMR ($CD_3OD$) 400 MHz δ: 8.32 (s, 2H), 8.08 (dd, J=4.9, 1.4 Hz, 1H), 7.99 (dd, J=7.7, 1.4 Hz, 1H), 7.52 (d, J=8.6 Hz, 2H), 7.39 (td, J=7.7, 1.7 Hz, 1H), 7.33 (d, J=8.6 Hz, 2H), 7.18 (d, J=8.6 Hz, 1H), 7.17 (dt, J=1.1, 7.4 Hz, 1H), 6.97 (dd, J=8.0, 1.7 Hz, 1H), 6.70 (dd, J=8.0, 5.2 Hz, 1H), 6.61 (d, J=2.3 Hz, 2H), 6.40 (t, J=2.3 Hz, 1H), 3.68 (s, 6H), 2.80-2.73 (m, 2H), 2.63-2.56 (m, 2H), 2.29-2.20 (m, 1H), 2.01-1.91 (m, 1H); LCMS: 516 [M+H].

Example 46

Preparation of methyl 3-(4-{3-[4-(1-aminocyclobutyl)phenyl]-9H-imidazo[1,2-d]pyrido[2,3-b][1,4]benzodiazepin-2-yl}phenyl)propanoate

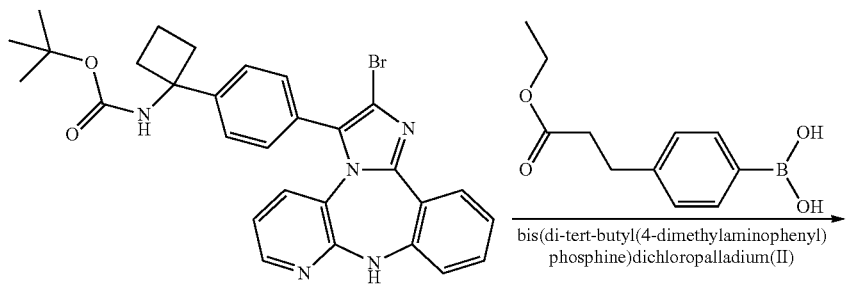

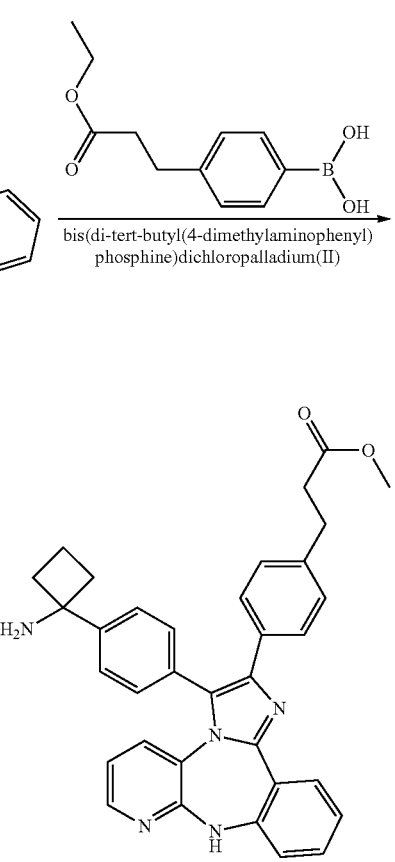

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), [4-(3-ethoxy-3-oxopropyl)phenyl]boronic acid (40 mg, 0.18 mmol), bis(di-tert-butyl(4-dimethylamino phenyl)phosphine)dichloropalladium(II) (6.3 mg, 0.01 mmol) and $K_3PO_4$ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous $Na_2SO_4$ and concentrated. The residue was purified by HPLC. To the fraction, conc. HCl (3 ml) and methanol (3 ml) were added and the residue was evaporated after 24 h. The residue was purified by HPLC to give the titled compound as a white solid (24 mg, 42%). $^1$HNMR (DMSO-$d_6$) 400 MHz δ: 8.54 (s, 1H), 8.22 (s, 1H), 8.07 (dd, J=4.6, 1.7 Hz, 1H), 7.94 (dd, J=7.7, 1.4 Hz, 1H), 7.47 (d, J=8.6 Hz, 2H), 7.42 (d, J=8.6 Hz, 2H), 7.34 (td, J=7.7, 1.5 Hz, 1H), 7.28 (dd, J=8.0, 1.1 Hz, 1H), 7.19 (d, J=8.0 Hz, 2H), 7.14 (d, J=8.6 Hz, 2H), 7.11 (t, J=8.0 Hz, 1H), 6.86 (dd, J=8.0, 1.1 Hz, 1H), 6.72 (dd, J=7.7, 4.9 Hz, 1H), 3.58 (s, 3H), 2.83 (t, J=7.4 Hz, 2H), 2.63 (t, J=8.0 Hz, 2H), 2.43-2.36 (m, 2H), 2.20-2.13 (m, 2H), 2.09-2.00 (m, 1H), 1.75-1.66 (m, 1H); LCMS: 542 [M+H].

Example 47

Preparation of 1-(4-{2-[6-(benzyloxy)-1H-indol-2-yl]-9H-imidazo[1,2-d]pyrido[2,3-b][1,4]benzodiazepin-3-yl}phenyl)cyclobutanamine

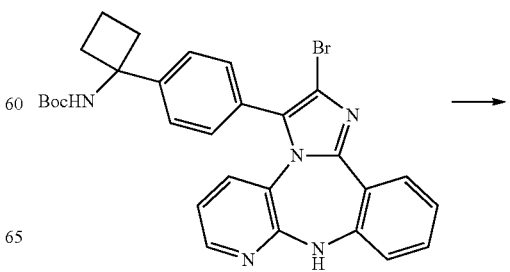

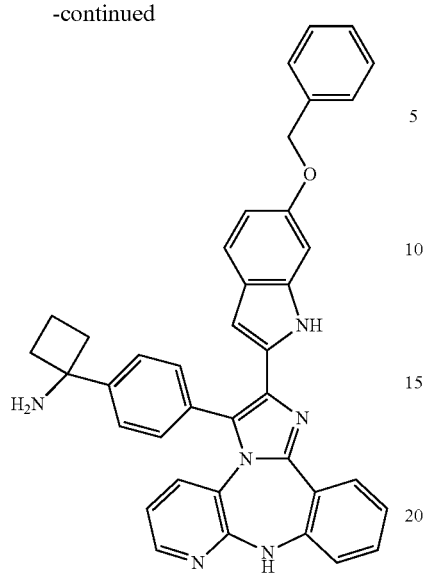

The title compound was synthesized according to the procedure described in example 46 using (6-(phenoxymethyl)-1H-indol-2-yl)boronic acid instead of [4-(3-ethoxy-3-oxopropyl)phenyl]boronic acid. $^1$HNMR (CD$_3$OD) 400 MHz δ: 8.54 (s, 1H), 8.06 (dd, J=5.2, 1.7 Hz, 1H), 8.05-8.04 (m, 1H), 7.52 (d, J=8.6 Hz, 2H), 7.44 (d, J=7.4 Hz, 2H), 7.41-7.34 (m, 6H), 7.30 (d, J=7.4 Hz, 1H), 7.20 (d, J=8.6 Hz, 1H), 7.18-7.14 (m, 2H), 7.00 (d, J=2.3 Hz, 1H), 6.94 (dd, J=8.0, 1.1 Hz, 1H), 6.70 (dd, J=8.6, 2.3 Hz, 1H), 6.67 (dd, J=8.0, 5.2 Hz, 1H), 6.16 (s, 1H), 5.06 (s, 2H), 2.76-2.69 (m, 2H), 2.53-2.46 (m, 2H), 2.26-2.17 (m, 1H), 1.98-1.89 (m, 1H); LCMS: 601 [M+H].

Example 48

Preparation of 1-[4-(2-quinolin-3-yl-9H-imidazo[1,2-d]pyrido[2,3-b][1,4]benzodiazepin-3-yl)phenyl]cyclobutanamine

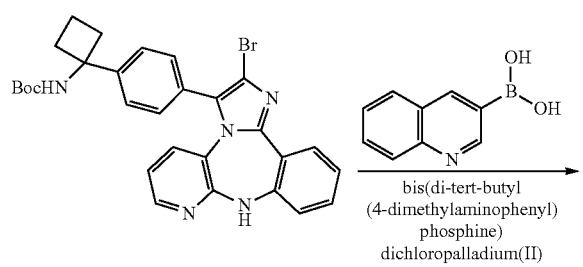

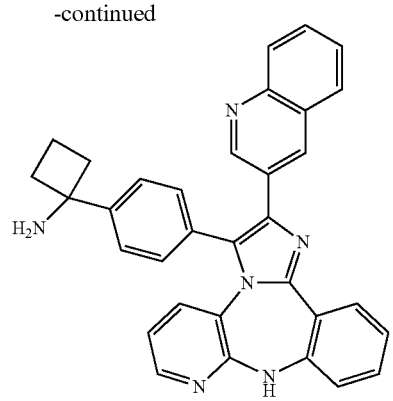

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), quinolin-3-ylboronic acid (31 mg, 0.18 mmol), bis(di-tert-butyl(4-dimethylaminophenyl)phosphine)dichloropalladium(II) (6.3 mg, 0.01 mmol) and K$_3$PO$_4$ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous Na$_2$SO$_4$ and concentrated. The residue was purified by HPLC. To the fraction, conc. HCl (3 ml) and methanol (3 ml) were added and the residue was evaporated after 24 h. The residue was purified by HPLC to give the titled compound as a white solid (30 mg, 55%). $^1$HNMR (DMSO-d$_6$) 400 MHz δ: 8.85 (d, J=2.3 Hz, 1H), 8.63 (s, 1H), 8.48 (d, J=2.3 Hz, 1H), 8.24 (s, 1H), 8.11 (dd, J=4.6, 1.7 Hz, 1H), 8.03 (dd, J=8.0, 1.7 Hz, 1H), 7.96 (d, J=8.6 Hz, 1H), 7.93 (d, J=7.4 Hz, 1H), 7.73 (t, J=7.4 Hz, 1H), 7.60 (t, J=7.4 Hz, 1H), 7.53 (d, J=8.6 Hz, 2H), 7.38 (t, J=8.6 Hz), 7.31 (d, J=7.4 Hz, 1H), 7.29 (d, J=8.0 Hz, 2H), 7.15 (t, J=8.0 Hz, 1H), 6.96 (dd, J=8.0, 1.7 Hz, 1H), 6.77 (dd, J=8.0, 4.6 Hz, 1H), 2.47-2.41 (m, 2H), 2.24-2.17 (m, 2H), 2.10-2.02 (m, 1H), 1.77-1.68 (m, 1H); LCMS: 507 [M+H].

Example 49

Preparation of 5-{3-[4-(1-aminocyclobutyl)phenyl]-9H-imidazo[1,2-d]pyrido[2,3-b][1,4]benzodiazepin-2-yl}pyridin-2-amine

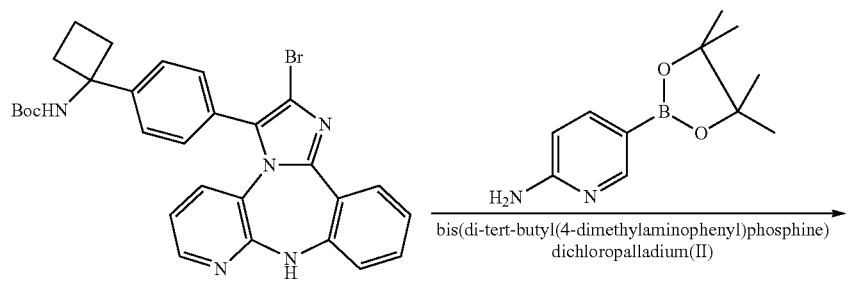

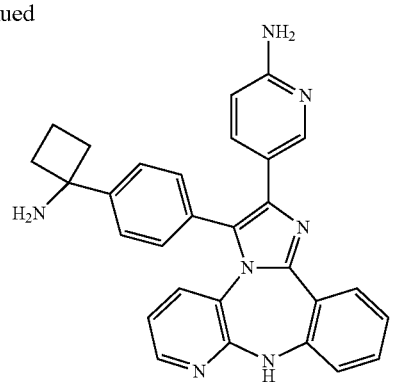

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), 5-(4,4,5,5-tetramethyl-1,3,2-dioxaborolan-2-yl)pyridin-2-amine (39 mg, 0.18 mmol), bis(di-tert-butyl(4-dimethylaminophenyl)phosphine)dichloropalladium(II) (6.3 mg, 0.01 mmol) and K$_3$PO$_4$ (72 mg, 0.27 mmol) in DMF/water (0.9 mL, 6:1, v/v) was heated at 160° C. under microwave irradiation for 1 hour.

After cooling to room temperature, the mixture was diluted with EtOAc and washed with water (×3). The organic layer was dried over anhydrous Na$_2$SO$_4$ and concentrated. The residue was purified by HPLC. To the fraction, conc. HCl (3 ml) and methanol (3 ml) were added and the residue was evaporated after 24 h. The residue was purified by HPLC to give the titled compound as a white solid (24 mg, 43%). $^1$HNMR (DMSO-d$_6$) 400 MHz δ: 8.53 (s, 1H), 8.25 (s, 1H), 8.07 (dd, J=4.9, 1.4 Hz, 1H), 7.96 (d, J=2.3 Hz, 1H), 7.92 (dd, J=7.7, 1.4 Hz, 1H), 7.51 (dd, J=8.6, 2.3 Hz, 1H), 7.47 (d, J=8.6 Hz, 2H), 7.33 (td, J=7.7, 1.7 Hz, 1H), 7.27 (d, J=7.4 Hz, 1H), 7.18 (d, J=8.6 Hz, 2H), 7.10 (t, J=8.0 Hz), 6.86 (dd, J=8.0, 1.7 Hz, 1H), 6.73 (dd, J=8.0, 4.6 Hz, 1H), 6.39 (d, J=8.6 Hz, 1H), 5.97 (s, 2H), 2.45-2.38 (m, 2H), 2.23-2.15 (m, 2H), 2.09-2.00 (m, 1H), 1.75-1.66 (m, 1H); LCMS: 472 [M+H].

Example 50

Preparation of 1-{4-[2-(1-benzothien-2-yl)-9H-imidazo[1,2-d]pyrido[2,3-b][1,4]benzodiazepin-3-yl]phenyl}cyclobutanamine

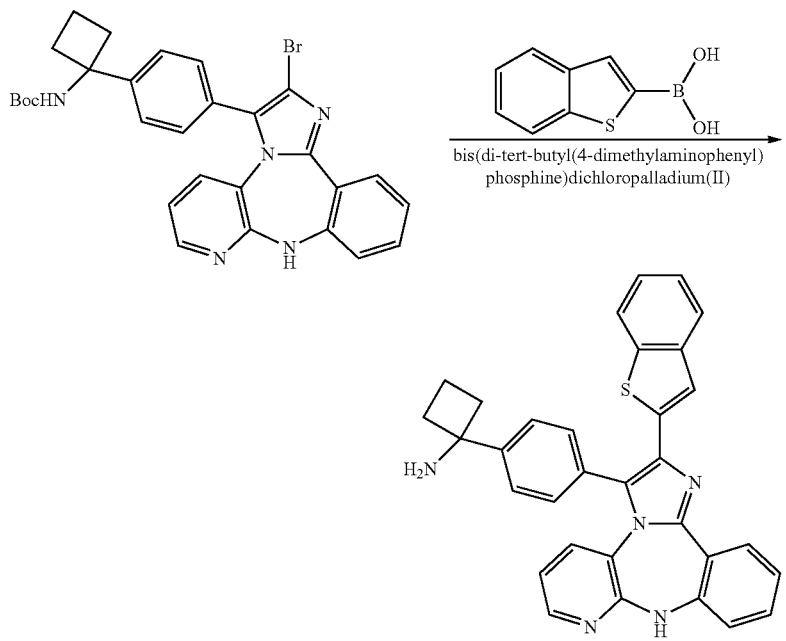

The title compound was synthesized according to the procedure described in example 49 using benzo[b]thiophen-2-ylboronic acid instead of 5-(4,4,5,5-tetramethyl-1,3,2-dioxaborolan-2-yl)pyridin-2-amine. $^1$HNMR (DMSO-d$_6$) 400 MHz δ: 8.61 (s, 1H), 8.20 (s, 1H), 8.09 (dd, J=4.6, 1.7 Hz, 1H), 7.93 (dd, J=7.7, 1.4 Hz, 1H), 7.88 (d, J=7.4 Hz, 1H), 7.70 (dd, J=6.9, 1.7 Hz, 1H), 7.58 (d, J=8.6 Hz, 2H), 7.41 (d, J=7.4 Hz, 1H), 7.38 (t, J=7.4 Hz, 1H), 7.35 (s, 1H), 7.33-7.27 (m, 3H), 7.15 (t, J=7.4 Hz, 1H), 6.98 (dd, J=8.0, 1.1 Hz, 1H), 6.75 (dd, J=8.0, 4.6 Hz, 1H), 2.49-2.45 (m, 2H), 2.29-2.21 (m, 2H), 2.13-2.04 (m, 1H), 1.80-1.71 (m, 1H); LCMS: 512 [M+H].

Example 51

Preparation of methyl (4-{3-[4-(1-aminocyclobutyl)phenyl]-9H-imidazo[1,2-d]pyrido[2,3-b][1,4]benzo-diazepin-2-yl}phenyl)acetate

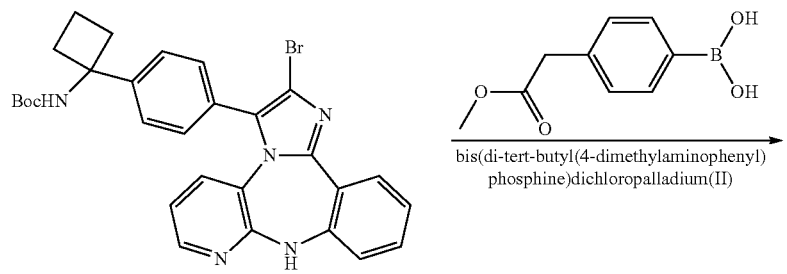

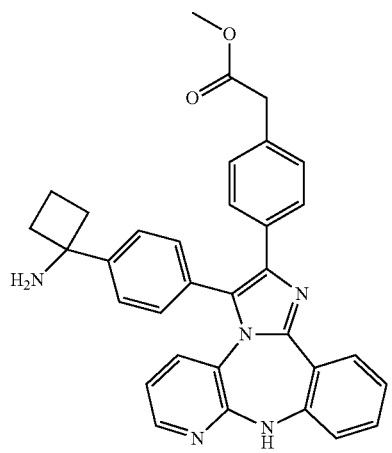

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), [4-(dihydroxyboryl)phenyl]acetic acid (32 mg, 0.18 mmol), bis(di-tert-butyl(4-dimethylaminophenyl)phosphine)dichloropalladium(II) (6.3 mg, 0.01 mmol) and $K_3PO_4$ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous $Na_2SO_4$ and concentrated. The residue was purified by HPLC. To the fraction, conc. HCl (3 ml) and methanol (3 ml) were added and the residue was evaporated after 24 h. The residue was purified by HPLC to give the titled compound as a white solid (23 mg, 41%). $^1$HNMR (DMSO-$d_6$) 400 MHz δ: 8.55 (s, 1H), 8.25 (s, 1H), 8.07 (dd, J=4.6, 1.7 Hz, 1H), 7.95 (dd, J=7.7, 1.4 Hz, 1H), 7.48 (d, J=10.0 Hz, 2H), 7.46 (d, J=8.6 Hz, 2H), 7.35 (td, J=7.7, 1.7 Hz, 1H), 7.28 (dd, J=8.0, 1.1 Hz, 1H), 7.19 (dd, J=8.3, 6.0 Hz, 4H), 7.11 (t, J=7.4 Hz, 1H), 6.88 (dd, J=8.0, 1.7 Hz, 1H), 6.73 (dd, J=7.7, 4.9 Hz, 1H), 3.66 (s, 2H), 3.61 (s, 3H), 2.44-2.37 (m, 2H), 2.17-2.14 (m, 2H), 2.08-1.99 (m, 1H), 1.74-1.66 (m, 1H); LCMS: 514 [M+H].

Example 52
Preparation of 1-{4-[2(6-morpholin-4-ylpyridin-3-yl)-9H-imidazo[1,2-d]pyrido[2,3-b][1,4]benzodiazepin-3-yl]phenyl}cyclobutanamine
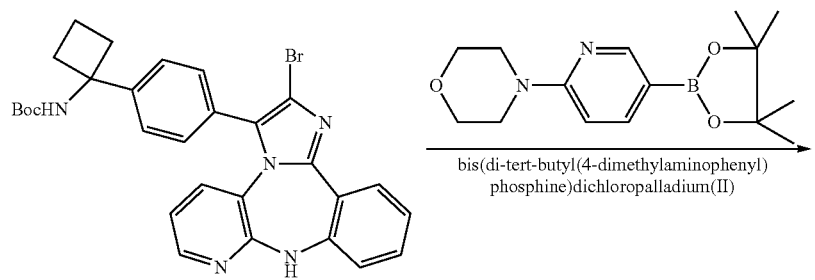
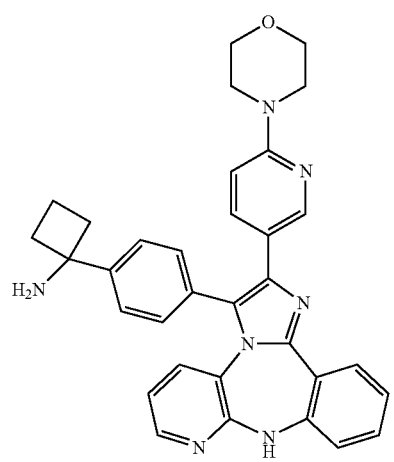

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), 4-[5-(4,4,5,5-tetramethyl-1,3,2-dioxaborolan-2-yl)pyridin-2-yl]morpholine (52 mg, 0.18 mmol), bis(di-tert-butyl(4-dimethylaminophenyl)phosphine)dichloropalladium(II) (6.3 mg, 0.01 mmol) and $K_3PO_4$ (72 mg, 0.27 mmol) in DMF/water (0.9 mL, 6:1, v/v) was heated at 160° C. under microwave irradiation for 1 hour. After cooling to room temperature, the mixture was diluted with EtOAc and washed with water (×3). The organic layer was dried over anhydrous $Na_2SO_4$ and concentrated. The residue was purified by HPLC. To the fraction, conc. HCl (3 ml) and methanol (3 ml) were added and the residue was evaporated after 24 h. The residue was purified by HPLC to give the titled compound as a white solid (24 mg, 39%). $^1$HNMR (DMSO-$d_6$) 400 MHz δ: 8.54 (s, 1H), 8.26 (s, 1H), 8.21 (d, J=2.3 Hz, 1H), 8.07 (dd, J=4.9, 1.4 Hz, 1H), 7.93 (dd, J=7.7, 1.4 Hz, 1H), 7.70 (dd, J=8.9, 2.6 Hz, 1H), 7.49 (d, J=8.6 Hz, 2H), 7.34 (t, J=7.4 Hz, 1H), 7.28 (d, J=7.4 Hz, 1H), 7.21 (d, J=8.6 Hz, 2H), 7.11 (t, J=7.4 Hz, 1H), 6.86 (dd, J=8.0, 1.1 Hz, 1H), 6.81 (d, J=9.2 Hz, 1H), 6.73 (dd, J=7.7, 4.9 Hz, 1H), 3.68 (t, J=4.9 Hz, 4H), 3.43 (t, J=5.2 Hz, 4H), 2.45-2.38 (m, 2H), 2.22-2.15 (m, 2H), 2.10-2.01 (m, 1H), 1.75-1.67 (m, 1H); LCMS: 542 [M+H].

Example 53

Preparation of 1-{4-[2-(4'-methoxybiphenyl-4-yl)-9H-imidazo[1,2-d]pyrido[2,3-b][1,4]benzodiazepin-3-yl]phenyl}cyclobutanamine trihydrochloride

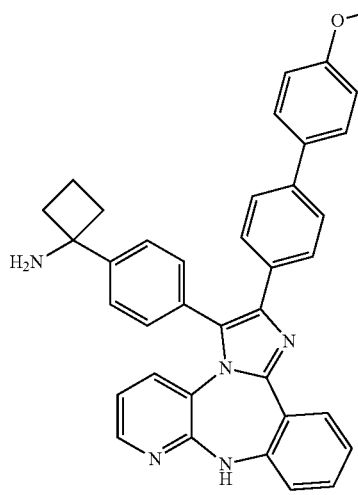

The title compound was synthesized according to the procedure described in example 19 using (4'-methoxy-[1,1'-biphenyl]-4-yl)boronic acid in step 1 instead of 6-(4,4,5,5-tetramethyl-1,3,2-dioxaborolan-2-yl)-1H-pyrrolo[3,2-b]pyridine. $^1$HNMR (DMSO-$d_6$) 400 MHz δ: 8.65-8.62 (m, 3H), 8.11 (dd, J=4.9, 1.7 Hz, 1H), 7.98 (dd, J=8.0, 1.7 Hz, 1H), 7.62 (d, J=8.6 Hz, 2H), 7.56 (d, J=8.6 Hz, 4H), 7.36-7.36 (m, 2H), 7.31 (d, J=7.4 Hz, 1H), 7.14 (td, J=7.4, 1.7 Hz, 1H), 7.02 (d, J=9.2 Hz, 2H), 6.90 (dd, J=8.0, 1.7 Hz, 1H), 6.74 (dd, J=8.0, 4.6 Hz, 1H), 3.80 (s, 3H), 2.64-2.54 (m, 4H), 2.23-2.15 (m, 1H), 1.88-1.80 (m, 1H). LCMS: 562 [M+H].

Example 54

Preparation of 4'-{3-[4-(1-aminocyclobutyl)phenyl]-9H-imidazo[1,2-d]pyrido[2,3-b][1,4]benzodiazepin-2-yl}-N,N-dimethylbiphenyl-4-carboxamide

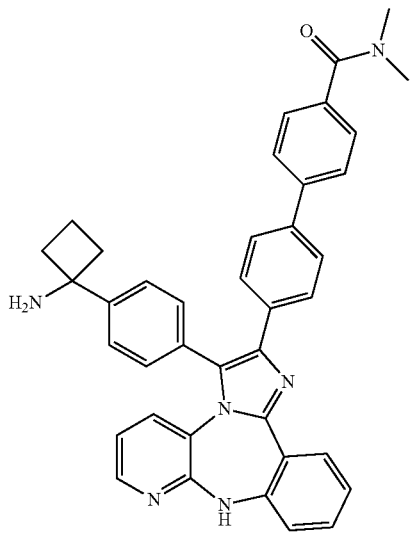 [SMILES: CN(C)C(=O)c1ccc(-c2ccc(-c3nc4n(c3-c3ccc(C5(N)CCC5)cc3)-c3cccnc3Nc3ccccc3-4)cc2)cc1]

The title compound was synthesized according to the procedure described in example 19 using (4'-(dimethylcarbamoyl)[1,1'-biphenyl]-4-yl)boronic acid in step 1 instead of 6-(4,4,5,5-tetramethyl-1,3,2-dioxaborolan-2-yl)-1H-pyrrolo[3,2-b]pyridine. $^1$HNMR (DMSO-$d_6$) 400 MHz δ: 8.70 (br s, 2H), 8.63 (br s, 1H), 8.12 (d, J=4.58 Hz, 1H), 7.99 (dd, J=8.02, 1.15 Hz, 1H), 7.74 (d, J=8.02 Hz, 2H), 7.67 (d, J=8.59 Hz, 2H), 7.61 (d, J=6.87 Hz, 2H), 7.59-7.55 (m, 1H), 7.49 (d, J=8.59 Hz, 2H), 7.38 (d, J=7.45 Hz, 2H), 7.31 (d, J=8.02 Hz, 1H), 7.15 (t, J=7.16 Hz, 1H), 6.91 (d, J=8.02 Hz, 1H), 6.78-

6.71 (m, 1H), 3.02-2.93 (m, 6H), 2.62-2.53 (m, 4H), 2.25-2.15 (m, 1H), 1.88-1.80 (m, 1H). LCMS: 603 [M+H].

Example 55

Preparation of 1-{4-[2-(4-pyridin-3-ylphenyl)-9H-imidazo[1,2-d]pyrido[2,3-b][1,4]benzodiazepin-3-yl]phenyl}cyclobutanamine

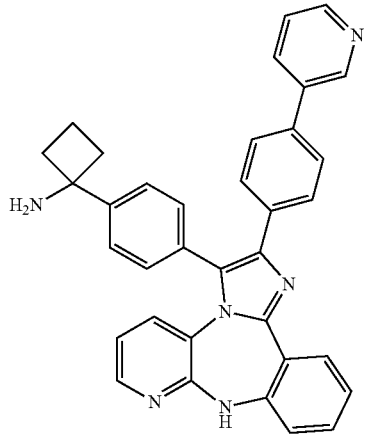 [SMILES: NC1(c2ccc(-c3c(-c4ccc(-c5cccnc5)cc4)nc4n3-c3cccnc3Nc3ccccc3-4)cc2)CCC1]

The title compound was synthesized according to the procedure described in example 19 using (4-(pyridin-3-yl)phenyl)boronic acid in step 1 instead of 6-(4,4,5,5-tetramethyl-1,3,2-dioxaborolan-2-yl)-1H-pyrrolo[3,2-b]pyridine.
$^1$HNMR (DMSO-d$_6$) 400 MHz δ: 9.19 (br s, 1H), 8.80 (br s, 2H), 8.64 (br s, 1H), 8.11 (d, J=4.58 Hz, 1H), 7.99 (d, J=7.45 Hz, 2H), 7.85-7.79 (m, 2H), 7.70-7.66 (m, 2H), 7.62-7.57 (m, 2H), 7.41-7.36 (m, 3H), 7.32 (d, J=8.02 Hz, 1H), 7.15 (t, J=7.45 Hz, 1H), 6.90 (d, J=8.02 Hz, 1H), 6.78-6.72 (m, 1H), 2.61-2.56 (m, 4H), 2.27-2.16 (m, 1H), 1.88-1.80 (m, 1H). LCMS: 533 [M+H].

Example 56

Preparation of 1-{4-[2-(4-pyridin-4-ylphenyl)-9H-imidazo[1,2-d]pyrido[2,3-b][1,4]benzodiazepin-3-yl]phenyl}cyclobutanamine

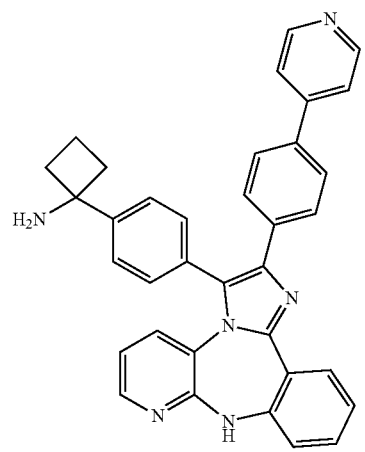 [SMILES: NC1(c2ccc(-c3c(-c4ccc(-c5ccncc5)cc4)nc4n3-c3cccnc3Nc3ccccc3-4)cc2)CCC1]

The title compound was synthesized according to the procedure described in example 19 using (4-(pyridin-4-yl)phenyl)boronic acid in step 1 instead of 6-(4,4,5,5-tetramethyl-1,3,2-dioxaborolan-2-yl)-1H-pyrrolo[3,2-b]pyridine.
$^1$HNMR (DMSO-d$_6$) 400 MHz δ: 8.89 (d, J=5.73 Hz, 1H), 8.79 (br s, 2H), 8.64 (s, 1H), 8.29 (br s, 2H), 8.12 (dd, J=4.58, 1.72 Hz, 1H), 8.01-7.97 (m, 3H), 7.72 (d, J=8.59 Hz, 2H), 7.60 (d, J=8.59 Hz, 2H), 7.40 (d, J=8.02 Hz, 2H), 7.31 (d, J=6.87 Hz, 1H), 7.16-7.13 (m, 1H), 6.91 (dd, J=7.73, 1.43 Hz, 1H), 6.75 (dd, J=8.02, 4.58 Hz, 1H), 2.62-2.55 (m, 4H), 2.26-2.17 (m, 1H), 1.89-1.81 (m, 1H). LCMS: 533 [M+H].

Example 57

Preparation of benzyl 4-{3-[4-(1-aminocyclobutyl)phenyl]-9H-imidazo[1,2-d]pyrido[2,3-b][1,4]benzodiazepin-2-yl}benzoate trihydrochloride

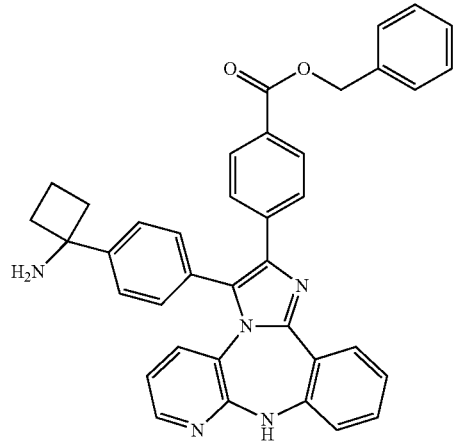 [SMILES: NC1(c2ccc(-c3c(-c4ccc(C(=O)OCc5ccccc5)cc4)nc4n3-c3cccnc3Nc3ccccc3-4)cc2)CCC1]

The title compound was synthesized from benzyl 4-[3-(4-{1-[(tert-butoxycarbonyl)amino]cyclobutyl}phenyl)-9H-imidazo[1,2-d]pyrido[2,3-b][1,4]benzodiazepin-2-yl]benzoate according to the procedure described in example 18 step 2. $^1$HNMR (DMSO-d$_6$) 400 MHz δ: 8.66-8.63 (m, 3H), 8.11 (dd, J=4.6, 1.7 Hz, 1H), 7.97 (dd, J=8.0, 1.7 Hz, 1H), 7.90 (d, J=8.6 Hz, 2H), 7.55 (d, J=8.6 Hz, 2H), 7.47-7.46 (m, 2H), 7.42-7.30 (m, 6H), 7.14 (td, J=7.4, 1.1 Hz, 1H), 6.92 (dd, J=8.0, 1.7 Hz, 1H), 6.74 (dd, J=8.0, 4.6 Hz, 1H), 5.34 (s, 2H), 3.73-3.65 (m, 1H), 3.51-3.45 (m, 1H), 2.62-2.52 (m, 2H), 2.24-2.15 (m, 1H), 1.87-1.79 (m, 1H). LCMS: 590 [M+H].

Example 58

Preparation of 1-{4-[2-(1H-pyrazol-4-yl)-9H-imidazo[1,2-d]pyrido[2,3-b][1,4]benzodiazepin-3-yl]phenyl}cyclobutanamine

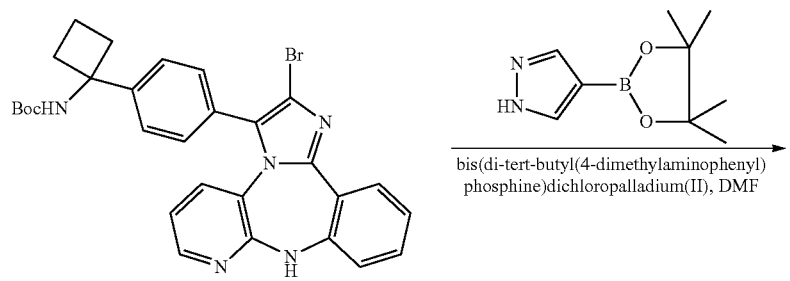

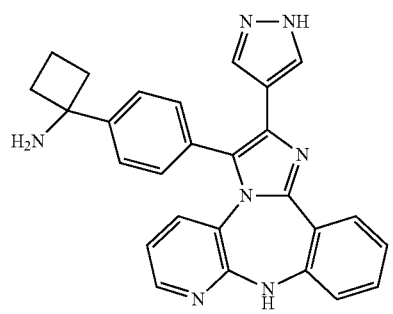

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), 4-(4,4,5,5-tetramethyl-1,3,2-dioxaborolan-2-yl)-1H-pyrazole (35 mg, 0.18 mmol), bis(di-tert-butyl(4-dimethylaminophenyl)phosphine)dichloropalladium(II) (6.3 mg, 0.01 mmol) and $K_3PO_4$ (72 mg, 0.27 mmol) in DMF/water (0.9 mL, 6:1, v/v) was heated at 160° C. under microwave irradiation for 2 hour in total. After cooling to room temperature, the mixture was diluted with EtOAc and washed with water (×3). The organic layer was dried over anhydrous $Na_2SO_4$ and concentrated. The residue was purified by HPLC. To the fraction, conc. HCl (3 mL) and methanol (3 mL) were added and the residue was evaporated after 24 h. The residue was purified by HPLC to give the titled compound as a white solid (7 mg, 15%). $^1$HNMR (CD$_3$OD) 400 MHz δ: 8.23 (s, 1H), 8.07 (dd, J=4.9, 1.4 Hz, 1H), 7.95 (dd, J=7.7, 1.4 Hz, 1H), 7.65 (s, 2H), 7.56 (d, J=8.6 Hz, 2H), 7.41 (d, J=8.0 Hz, 2H), 7.39 (t, J=7.4 Hz, 1H), 7.18 (d, J=8.0 Hz, 1H), 7.16 (t, J=7.4 Hz, 1H), 7.01 (dd, J=8.0, 1.7 Hz, 1H), 6.70 (dd, J=8.0, 5.2 Hz, 1H), 2.84-2.76 (m, 2H), 2.65-2.57 (m, 2H), 2.31-2.22 (m, 1H), 2.05-1.95 (m, 1H); LCMS: 446 [M+H].

Example 59

Preparation of 1-[4-(2-methoxy-9H-imidazo[1,2-d]pyrido[2,3-b][1,4]benzodiazepin-3-yl)phenyl]cyclobutanamine

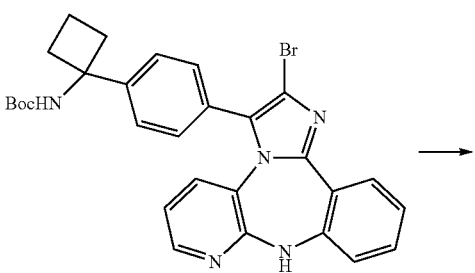

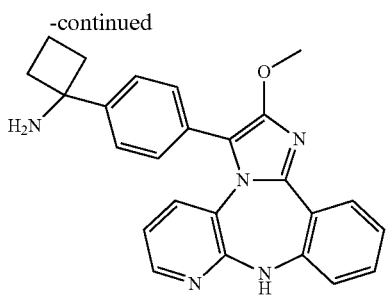

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol) and copper iodide (1.7 mg, 0.01 mmol) in sodium methoxide solution (1 M, 5 mL) was heated at 100° C. for 24 hour. After cooling to room temperature, the precipitate was collected and purified by HPLC to give the title compound as a white solid (5 mg, 11%).

$^1$HNMR (CD$_3$OD) 400 MHz δ: 8.10 (d, J=4.0 Hz, 1H), 7.91 (dd, J=8.0, 1.1 Hz, 1H), 7.42 (d, J=8.0 Hz, 2H), 7.33 (t, J=7.4 Hz, 1H), 7.21 (d, J=8.0 Hz, 2H), 7.14 (d, J=7.4 Hz, 1H), 7.10 (t, J=7.4 Hz, 1H), 7.03 (dd, J=8.0, 1.7 Hz, 1H), 6.79 (dd, J=8.0, 4.6 Hz, 1H), 4.02 (s, 3H), 2.75-2.62 (m, 2H), 2.51-2.41 (m, 2H), 2.22-2.12 (m, 1H), 1.94-1.83 (m, 1H); LCMS: 410 [M+H].

Example 60

Preparation of 1-(4-{2-[(4-methoxyphenyl)thio]-9H-imidazo[1,2-d]pyrido[2,3-b][1,4]benzodiazepin-3-yl}phenyl)cyclobutanamine

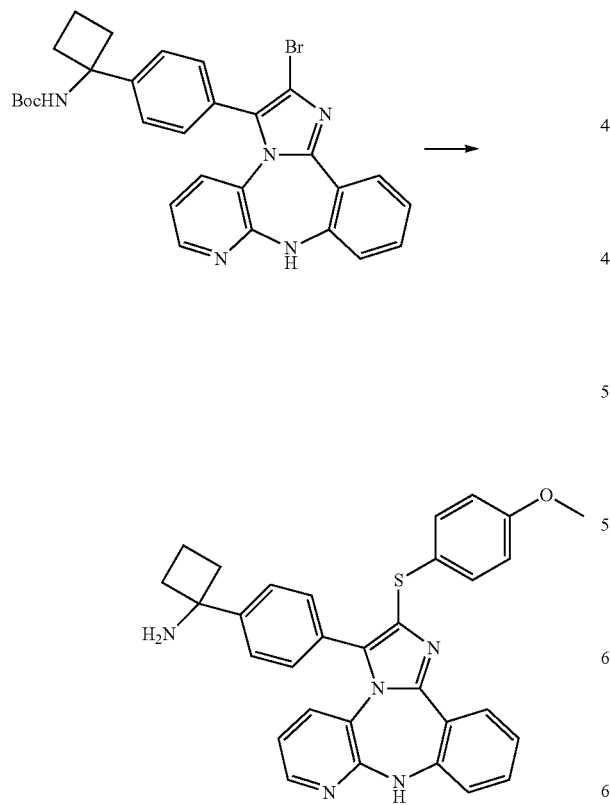

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), 4-methoxythiophenol (0.022 mL, 0.18 mmol), Pd$_2$(dba)$_3$ (8 mg, 0.01 mmol), xantphos (10 mg, 0.02 mmol), and K$_2$CO$_3$ (25 mg, 0.18 mmol) in DMF (0.9 mL) was heated at 160° C. for 1 hour. After cooling to room temperature, the mixture was purified by HPLC to give the titled compound as a white solid (9 mg, 15%). $^1$HNMR (CD$_3$OD) 400 MHz δ: 8.33 (s, 2H), 8.11 (dd, J=4.6, 1.7 Hz, 1H), 7.90 (dd, J=7.7, 1.4 Hz, 1H), 7.50 (d, J=8.6 Hz, 2H), 7.40-7.33 (m, 3H), 7.19-7.11 (m, 4H), 7.02 (dd, J=8.0, 1.7 Hz, 1H), 6.81 (td, J=6.0, 3.4 Hz, 2H), 6.73 (dd, J=8.0, 4.6 Hz, 1H), 3.73 (s, 3H), 2.81-2.73 (m, 2H), 2.62-2.55 (m, 2H), 2.28-2.19 (m, 1H), 2.02-1.92 (m, 1H); LCMS: 518 [M+H].

Example 61

Preparation of 3-[4-(1-aminocyclobutyl)phenyl]-9H-imidazo[1,2-d]pyrido[2,3-b][1,4]benzodiazepine-2-carbonitrile

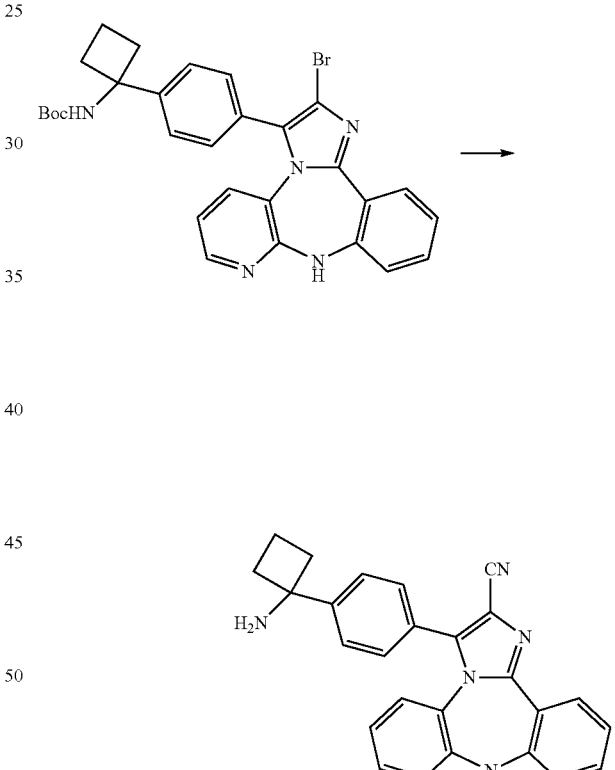

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.09 mmol), Pd(PPh$_3$)$_4$ (20 mg, 0.02 mmol), and zinc cyanide (33 mg, 0.27 mmol) in DMF (0.9 mL) was heated at 160° C. for 2 hour. After cooling to room temperature, the mixture was purified by HPLC to give the titled compound as a white solid (4 mg, 8%). $^1$HNMR (CD$_3$OD) 400 MHz δ: 8.45 (s, 1H), 8.18 (dd, J=4.9, 1.4 Hz, 1H), 7.92 (dd, J=7.4, 1.1 Hz, 1H), 7.61 (d, J=8.6 Hz, 2H), 7.47 (d, J=8.6 Hz, 2H), 7.43 (t, J=7.4 Hz, 1H), 7.20 (d, J=8.0 Hz, 1H), 7.16 (t, J=8.0 Hz, 1H), 7.08 (dd, J=8.0, 1.7 Hz, 1H), 6.78

(dd, J=8.0, 4.6 Hz, 1H), 2.83-2.75 (m, 2H), 2.63-2.56 (m, 2H), 2.30-2.20 (m, 1H), 2.04-1.94 (m, 1H); LCMS: 405 [M+H].

Example 62

Preparation of methyl 3-[4-(1-aminocyclobutyl)phenyl]-9H-imidazo[1,2-d]pyrido[2,3-b][1,4]benzodiazepine-2-carboxylate trihydrochloride Step 1: Preparation of methyl 3-(4-{1-[(tert-butoxycarbonyl)amino]cyclobutyl}phenyl)-9H-imidazo[1,2-d]pyrido[2,3-b][1,4]benzodiazepine-2-carboxylate

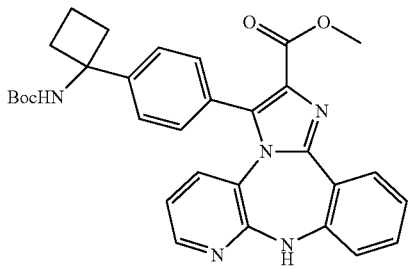 [SMILES: COC(=O)c1nc2n(c1-c1ccc(C3(NC(=O)OC(C)(C)C)CCC3)cc1)-c1cccnc1Nc1ccccc1-2]

tert-butyl {1-[4-(2-bromo-9H-imidazo[1,2-d]pyrido[2,3-b][1,4]benzodiazepin-3-yl)phenyl]cyclobutyl}carbamate (100 mg, 0.179 mmol), triethylamine (0.5 mL), bis(triphenylphosphine)dichloropalladium(II) (38 mg, 0.054 mmol) were dissolved in DMF (3 mL) and MeOH (3 mL). Atmosphere of the mixture was exchanged to CO gas, then heated to 100° C. for 88 hours. The mixture was diluted with AcOEt, washed with water(×3), brine, dried over Na$_2$SO$_4$, then filtrated through Celite pad. The filtrate was concentrated and the residue was purified by preparative thin-layer chromatography (n-hexane/AcOEt=1:2×3) to afford the desired product (36 mg, 37%) as a colorless oil. $^1$HNMR (CDCl$_3$) 400 MHz δ: 8.13 (dd, J=8.0 Hz and 1.7 Hz, 1H), 8.02 (d, J=4.0 Hz, 1H), 7.40 (d, J=8.0 Hz, 2H), 7.33 (td, J=7.4 Hz and 1.7 Hz, 2H), 7.30-7.24 (m, 4H), 7.14 (td, J=7.4 Hz and 1.1 Hz, 1H), 6.95 (d, J=7.4 Hz, 1H), 6.82-6.78 (m, 1H), 6.59 (dd, J=8.0 Hz and 4.6 Hz, 1H), 6.24 (s, 1H), 5.11 (br s, 1H), 3.88 (s, 3H), 2.57-2.42 (m, 4H), 2.17-2.08 (m, 1H), 1.91-1.83 (m, 1H), 1.39 (br s, 9H). LCMS: 538 [M+H].

Step 2: Preparation of methyl 3-[4-(1-aminocyclobutyl)phenyl]-9H-imidazo[1,2-d]pyrido[2,3-b][1,4]benzodiazepine-2-carboxylate trihydrochloride

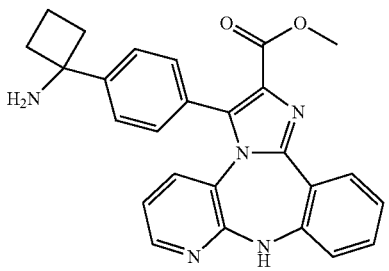 [SMILES: COC(=O)c1nc2n(c1-c1ccc(C3(N)CCC3)cc1)-c1cccnc1Nc1ccccc1-2]

Starting material (36 mg, 0.067 mmol) in MeOH (0.5 mL) was added 4N HCl-dioxane (2 mL) and stirred at room temperature for 15.5 hours. The mixture was concentrated to afford the desired product (29 mg, 79%) as a pale yellow solid. $^1$HNMR (DMSO-d$_6$) 400 MHz δ: 8.67 (s, 1H), 8.61 (br s, 2H), 8.13 (dd, J=5.2 Hz and 1.7 Hz, 1H), 7.89 (dd, J=7.4 Hz and 1.7 Hz, 1H), 7.52 (d, J=8.6 Hz, 2H), 7.40-7.38 (m, 2H), 7.30 (d, J=7.4 Hz, 1H), 7.13 (td, J=7.4 Hz and 1.1 Hz, 1H), 6.89 (dd, J=8.0 Hz and 1.7 Hz, 1H), 6.73 (dd, J=8.0 Hz and 4.6 Hz, 1H), 3.72 (s, 3H), 2.62-2.54 (m, 2H), 2.22-2.13 (m, 2H), 1.87-1.78 (m, 2H). LCMS: 438 [M+H].

Example 63

Preparation of N-(4-{3-[4-(1-Aminocyclobutyl)phenyl]-9H-imidazo[1,2-d]pyrido[2,3-b][1,4]benzodiazepin-2-yl}phenyl)methanesulfonamide trihydrochloride Step 1: Preparation of tert-butyl {1-[4-(2-{4-[(methylsulfonyl)amino]phenyl}-9H-imidazo[1,2-d]pyrido[2,3-b][1,4]benzodiazepin-3-yl)phenyl]cyclobutyl}carbamate

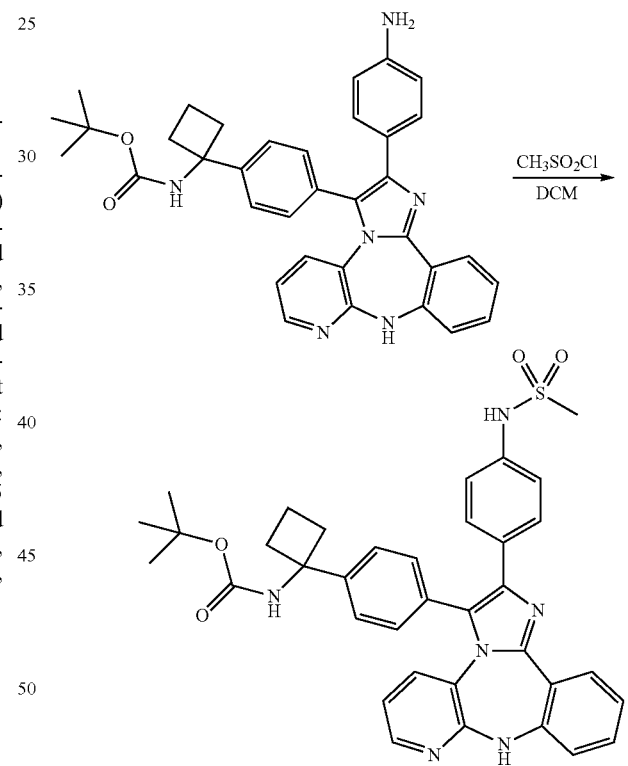

Et$_3$N (36.6 μL, 0.263 mmol) and methanesulfonyl chloride (7.46 μL, 0.0964 mmol) were added to a solution of tert-butyl (1-{4-[2-(4-aminophenyl)-9H-imidazo[1,2-d]pyrido[2,3-b][1,4]benzodiazepin-3-yl]phenyl}cyclobutyl)carbamate (50.0 mg, 0.0876 mmol) in DCM (1 mL) at 0° C., and stirred at room temperature. After reaction was completed, the mixture was diluted with sat. NaHCO$_3$ and extracted with CHCl$_3$ (3×). The combined organic layers were dried over anhydrous Na$_2$SO$_4$, and concentrated. The residue was purified by PTLC (CHCl$_3$/MeOH=9:1, CHCl$_3$/EtOAc=1:1) to afford desired product (30.9 mg, 54.4%) as pale yellow solid. $^1$HNMR (CDCl$_3$) 400 MHz δ: 8.18-8.12 (m, 1H), 8.04-7.97 (m, 1H), 7.63-7.50 (m, 2H), 7.41-7.33 (m, 2H), 7.33-7.23 (m, 2H), 7.19-7.08 (m, 5H), 6.96 (d, J=7.8 Hz, 1H), 6.80 (d, J=7.8 Hz, 1H), 6.60 (dd, J=7.8, 4.6 Hz, 1H), 6.44 (br s, 1H), 5.69-4.98 (m, 1H), 2.98 (s, 3H), 2.63-2.27 (m, 4H), 2.21-2.06 (m, 1H), 1.96-1.82 (m, 1H), 1.38 (br s, 9H).

Step 2: Preparation of N-(4-{3-[4-(1-aminocyclobutyl)phenyl]-9H-imidazo[1,2-d]pyrido[2,3-b][1,4]benzodiazepin-2-yl}phenyl)methanesulfonamide trihydrochloride

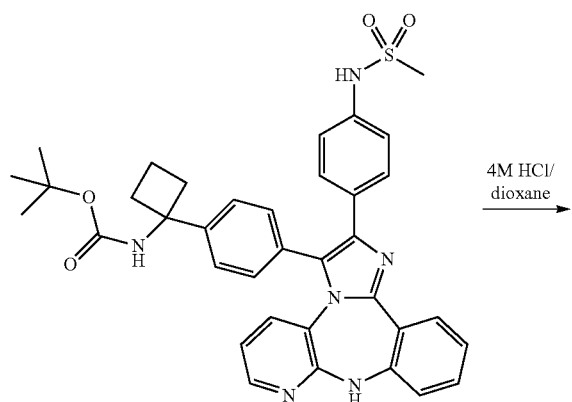

tert-Butyl {1-[4-(2-{4-[(methylsulfonyl)amino]phenyl}-9H-imidazo[1,2-d]pyrido[2,3-b][1,4]benzodiazepin-3-yl)phenyl]cyclobutyl}carbamate (30.9 mg, 0.0476 mmol) was dissolved in DCM (1 mL). 4M HCl/dioxane (1 mL) was added to the mixture and stirred at room temperature for 13.5 hours. The mixture was concentrated and solidified with ether. The precipitated solids were collected by filtration and washed with ether to afford desired product (24.4 mg, 77.9%) as pale yellow solid. ¹HNMR (DMSO-$d_6$) 400 MHz δ: 9.90 (s, 1H), 8.76 (br s, 2H), 8.67 (s, 1H), 8.12 (dd, J=4.8, 1.6 Hz, 1H), 7.95 (dd, J=8.0, 1.6 Hz, 1H), 7.59-7.53 (m, 2H), 7.49-7.45 (m, 2H), 7.43-7.37 (m, 1H), 7.36-7.29 (m, 3H), 7.18-7.11 (m, 3H), 6.90 (dd, J=8.0, 1.6 Hz, 1H), 6.76 (dd, J=8.0, 4.8 Hz, 1H), 3.02 (s, 3H), 2.62-2.53 (m, 4H), 2.27-2.13 (m, 1H), 1.88-1.75 (m, 1H); LCMS: 549 [M+H].

Example 64

Preparation of N-(4-{3-[4-(1-aminocyclobutyl)phenyl]-9H-imidazo[1,2-d]pyrido[2,3-b][1,4]benzodiazepin-2-yl}phenyl)-1,1,1-trifluoromethane sulfonamide trihydrochloride Step 1: Preparation of tert-butyl (1-{4-[2-(4-{[(trifluoromethyl)sulfonyl]amino}phenyl)-9H-imidazo[1,2-d]pyrido[2,3-b][1,4]benzodiazepin-3-yl]phenyl}cyclobutyl)carbamate

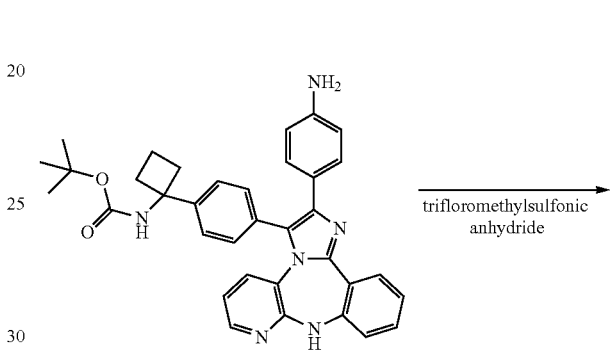

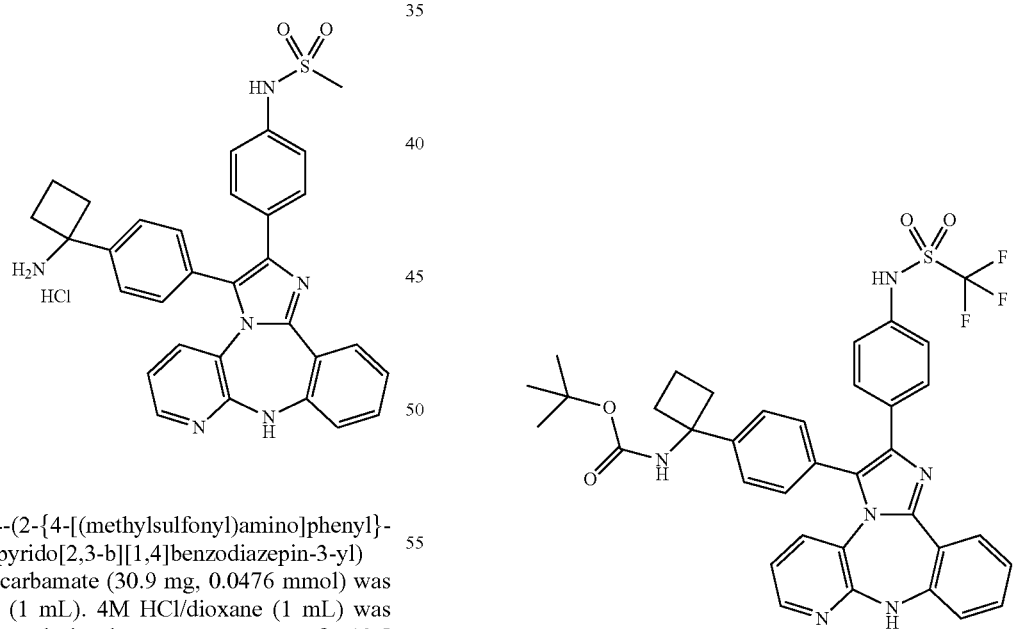

The title compound was synthesized according to the procedure described in example 63 step 1 using trifloromethylsulfonic anhydride instead of methanesulfonyl chloride. ¹HNMR (DMSO-$d_6$) 400 MHz δ: 8.16-8.11 (m, 1H), 8.04-7.98 (m, 1H), 7.49-7.40 (m, 2H), 7.37-7.29 (m, 3H), 7.19-7.13 (m, 1H), 7.12-7.07 (m, 2H), 7.06-7.01 (m, 2H), 6.96 (d, J=7.3 Hz, 1H), 6.80 (d, J=7.3 Hz, 1H), 6.60 (dd, J=8.0, 4.8 Hz, 1H), 6.43-6.36 (m, 1H), 5.65-4.99 (m, 1H), 2.65-2.27 (m, 4H), 2.21-2.07 (m, 1H), 1.98-1.81 (m, 1H), 1.56-1.05 (m, 9H).

Step 2: Preparation of N-(4-{3-[4-(1-aminocyclobutyl)phenyl]-9H-imidazo[1,2-d]pyrido[2,3-b][1,4]benzodiazepin-2-yl}phenyl)-1,1,1-trifluoromethanesulfonamide trihydrochloride

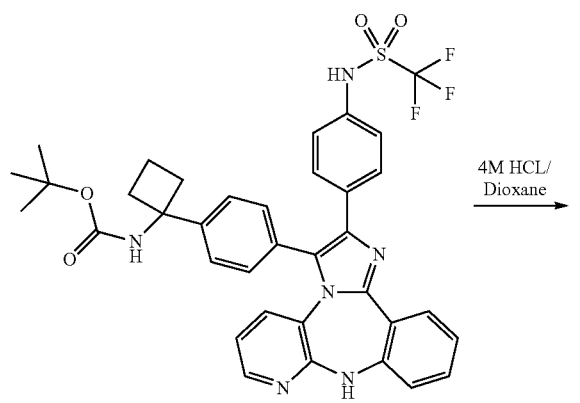

The title compound was synthesized according to the procedure described in example 63 step 2. ¹HNMR (DMSO-d₆) 400 MHz δ: 8.70 (br s, 2H), 8.62 (s, 1H), 8.10 (dd, J=4.8, 1.6 Hz, 1H), 7.95 (dd, J=8.0, 1.6 Hz, 1H), 7.58-7.50 (m, 4H), 7.41-7.28 (m, 4H), 7.23-7.17 (m, 2H), 7.16-7.10 (m, 1H), 6.89 (dd, J=8.0, 1.6 Hz, 1H), 6.74 (dd, J=8.0, 4.8 Hz, 1H), 2.64-2.52 (m, 4H), 2.26-2.13 (m, 1H), 1.89-1.75 (m, 1H); LCMS: 603 [M+H].

Example 65

Preparation of N-(4-{3-[4-(1-aminocyclobutyl)phenyl]-9H-imidazo[1,2-d]pyrido[2,3-b][1,4]benzodiazepin-2-yl}phenyl)benzenesulfonamide trihydrochloride Step 1: Preparation of tert-butyl {1-[4-(2-{4-[(phenylsulfonyl)amino]phenyl}-9H-imidazo[1,2-d]pyrido[2,3-b][1,4]benzodiazepin-3-yl) phenyl] cyclobutyl}carbamate

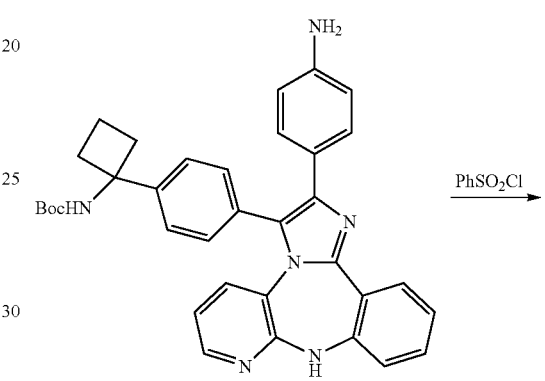

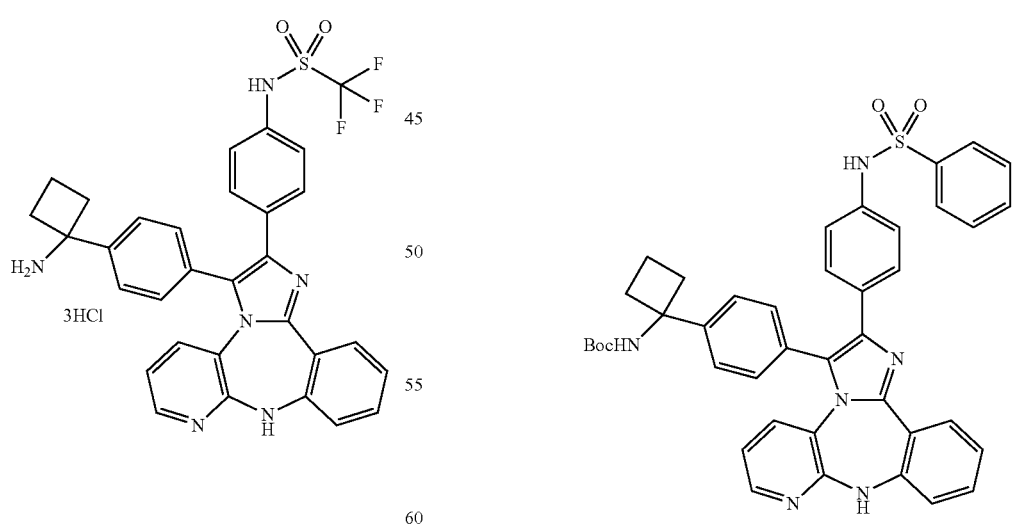

The title compound was synthesized according to the procedure described in example 63 step 1 using benzenesulfonyl chloride instead of methanesulfonyl chloride. ¹HNMR (DMSO-d₆) 400 MHz δ: 8.15-8.09 (m, 1H), 8.03-7.97 (m, 1H), 7.77-7.70 (m, 2H), 7.55-7.24 (m, 9H), 7.16-7.06 (m, 3H), 7.01-6.92 (m, 3H), 6.77 (d, J=7.8 Hz, 1H), 6.58 (dd, J=7.8, 4.8 Hz, 1H), 6.46-6.37 (m, 1H), 5.75-4.98 (m, 1H), 2.64-2.27 (m, 4H), 2.21-2.07 (m, 1H), 1.97-1.81 (m, 1H), 1.53-1.09 (m, 9H).

Step 2: Preparation of N-(4-{3-[4-(1-aminocyclobutyl)phenyl]-9H-imidazo[1,2-d]pyrido[2,3-b][1,4]benzodiazepin-2-yl}phenyl)benzenesulfonamide trihydrochloride

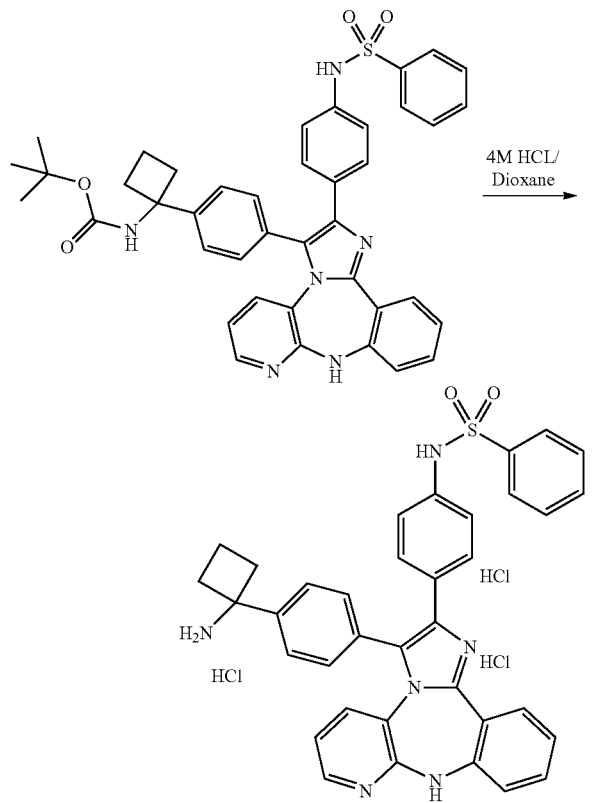

The title compound was synthesized according to the procedure described in example 63 step 2. ¹HNMR (DMSO-d₆) 400 MHz δ: 10.41 (s, 1H), 8.69 (br s, 3H), 8.61 (s, 1H), 8.10 (dd, J=4.8, 1.6 Hz, 1H), 7.91 (dd, J=7.8, 1.6 Hz, 1H), 7.79-7.74 (m, 2H), 7.65-7.49 (m, 5H), 7.40-7.33 (m, 3H), 7.31-7.24 (m, 3H), 7.15-7.08 (m, 1H), 7.06-7.00 (m, 2H), 6.86 (dd, J=8.0, 1.6 Hz, 1H), 6.73 (dd, J=8.0, 4.8 Hz, 1H), 2.61-2.52 (m, 4H), 2.27-2.12 (m, 1H); LCMS: 611 [M+H].

Example 66

Preparation of 2-[4-(2-phenyl-9H-imidazo[1,2-d]pyrido[2,3-b][1,4]benzodiazepin-3-yl)phenyl]propan-2-amine hydrochloride Step 1: Preparation of 2-(4-bromophenyl)-2-methylpropanenitrile

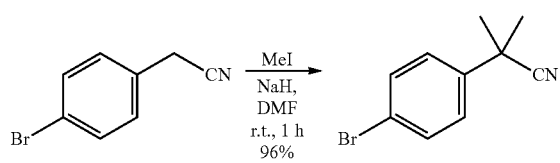

To a solution of (4-bromophenyl)acetonitrile (3 g) in N,N-dimethylformamide (45 ml) chilled to 0° C. was added sodium hydride (55 wt %, 1.47 g) portionwise. The reaction mixture was stirred at the same temperature for 15 min Iodomethane (2.86 mL) was added to the mixture at 0° C. dropwise. After being stirred at 0° C. for 10 min then at room temperature for 1 h, the reaction mixture was poured into ammonium chloride aqueous solution and extracted with diisopropyl ether (3 times) and washed with saturated sodium bicarbonate aqueous solution then brine. The organics were dried over anhydrous sodium sulfate and concentrated under reduced pressure. Purification by column chromatography (0-10% ethyl acetate in hexanes) gave the product (3.29 g, 96%). ¹HNMR (CDCl₃) 400 MHz δ: 7.52 (d, J=8.6 Hz, 2H), 7.35 (d, J=8.6 Hz, 2H), 1.71 (s, 6H).

Step 2: Preparation of 2-(4-bromophenyl)-2-methylpropanamide

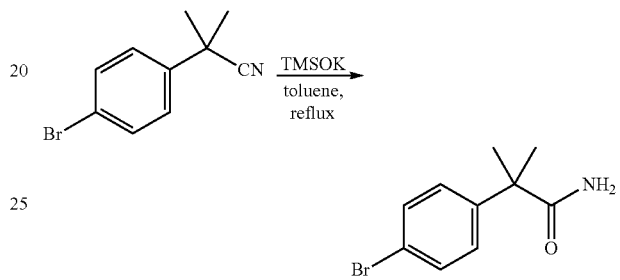

To a solution of 2-(4-bromophenyl)-2-methylpropanenitrile (3.29 g) in toluene (33 mL) was added potassium trimethylsilanolate (8.37 g) portionwise. After being stirred at reflux temperature for 5 h, the reaction mixture was cooled to room temperature. Water(17 mL) was added to the mixture dropwise. Filtration gave the product (3.28 g, 92%). ¹HNMR (CDCl₃) 400 MHz δ: 7.49 (d, J=8.7 Hz, 2H), 7.28 (d, J=8.7 Hz, 2H), 5.52-4.93 (m, 2H), 1.57 (s, 6H).

Step 3: Preparation of tert-butyl[1-(4-bromophenyl)-1-methylethyl]carbamate

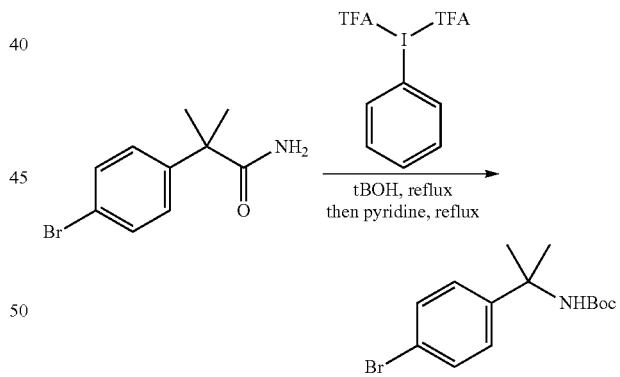

To a suspension of 2-(4-bromophenyl)-2-methylpropanamide (3 g) in tert-butanol (31 mL) was added [bis(trifluoroacetoxy)iodo]benzene (8 g) portionwise at room temperature. The reaction mixture was stirred at reflux temperature for 30 min Pyridine (3 mL) was added to the mixture. After being stirred at reflux temperature for 1 h, the reaction mixture was concentrated to dryness. The residue was dissolved in benzene and washed with 1 M citric acid aqueous solution (2 times), sodium bicarbonate aqueous solution (5 times) then brine. The organics were dried over anhydrous sodium sulfate and concentrated under reduced pressure. Purification by column chromatography (0-20% ethyl acetate in hexanes) gave the product (3.29 g, 84%). ¹HNMR (CDCl₃) 400 MHz δ: 7.43 (d, J=8.6 Hz, 2H), 7.27 (d, J=8.6 Hz, 2H), 1.59 (br s, 6H), 1.48-1.05 (m, 9H).

Step 4: Preparation of tert-butyl {1-methyl-1-[4-(4,5,5-tetramethyl-1,3,2-dioxaborolan-2-yl)phenyl]ethyl}carbamate

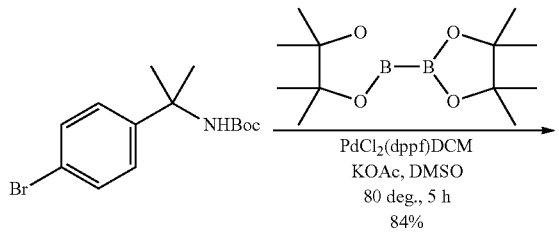

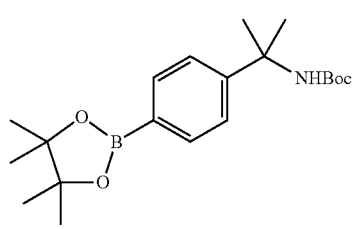

A suspension of tert-butyl[1-(4-bromophenyl)-1-methylethyl]carbamate (500 mg) and 4,4,4',4',5,5,5',5'-octamethyl-2,2'-bi-1,3,2-dioxaborolane (485 mg) and potassium acetate (468 mg) and PdCl₂(dppf)CH₂Cl₂ (39 mg) in dimethylsulfoxide (8 mL) was degassed for 5 min. then stirred at 80° C. for 5 h. The reaction mixture was diluted with benzene and filtered. The filtrate was washed with brine (5 times). The organics were dried over anhydrous sodium sulfate and concentrated under reduced pressure. Purification by column chromatography (0-15% ethyl acetate in hexanes) gave the product (481 mg, 84%). $^1$HNMR (CDCl$_3$) 400 MHz δ: 7.77 (d, J=8.3 Hz, 2H), 7.40 (d, J=8.3 Hz, 2H), 4.95 (br s, 1H), 1.61 (br s, 6H), 1.46-1.07 (m, 9H), 1.33 (s, 12H).

Step 5: Preparation of tert-butyl {1-methyl-1-[4-(2-phenyl-9H-imidazo[1,2-d]pyrido[2,3-b][1,4]benzodiazepin-3-yl)phenyl]ethyl}carbamate

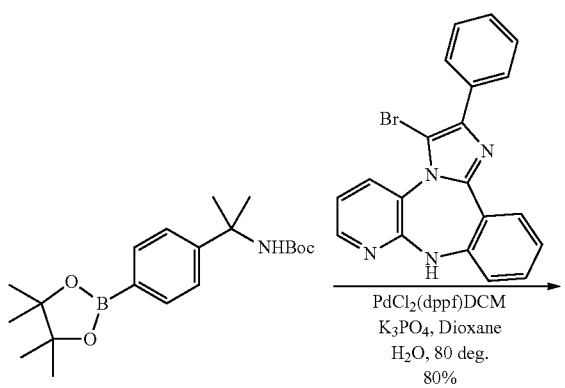

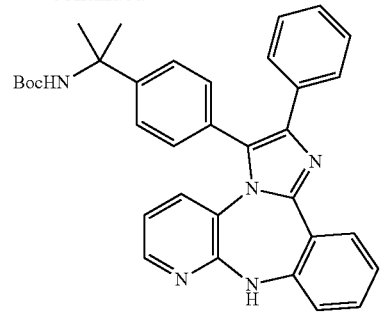

A suspension of 3-bromo-2-phenyl-9H-imidazo[1,2-d]pyrido[2,3-b][1,4]benzodiazepine (50 mg) and tert-butyl {1-methyl-1-[4-(4,4,5,5-tetramethyl-1,3,2-dioxaborolan-2-yl)phenyl]ethyl}carbamate (93 mg) and potassium phosphate (82 mg) and PdCl₂(dppf)CH₂Cl₂ (11 mg) in dioxane (2.5 mL) and H₂O (0.25 mL) was degassed for 5 min then stirred at 80° C. for 18 h. The reaction mixture was concentrated under reduced pressure. Purification by column chromatography (0-50% ethyl acetate in hexanes) gave the product (56 mg, 80%). $^1$HNMR (DMSO-d$_6$) 400 MHz δ: 8.54 (s, 1H), 8.09-8.00 (m, 1H), 7.95 (dd, 1H, J=7.8, 1.4 Hz), 7.55-7.48 (m, 2H), 7.38-7.32 (m, 3H), 7.31-7.19 (m, 5H), 7.17-7.07 (m, 3H), 6.91-6.77 (m, 1H), 6.70-6.59 (m, 1H), 1.50 (br s, 6H), 1.41-1.05 (m, 9H). LCMS: 544 [M+H].

Step 6: Preparation of 2-[4-(2-phenyl-9H-imidazo[1,2-d]pyrido[2,3-b][1,4]benzodiazepin-3-yl)phenyl]propan-2-amine hydrochloride

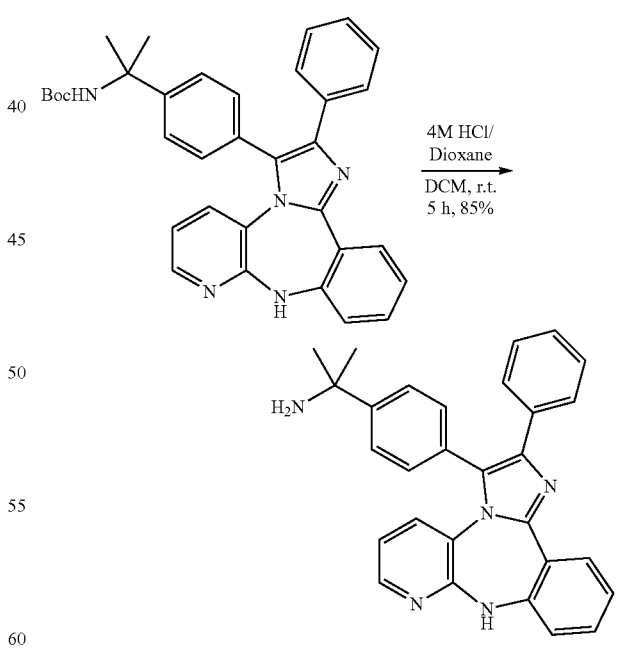

To a solution of tert-butyl {1-methyl-1-[4-(2-phenyl-9H-imidazo[1,2-d]pyrido[2,3-b][1,4]benzodiazepin-3-yl)phenyl]ethyl}carbamate (41 mg) in dichloromethane (4 mL) was added hydrogen chloride in 1,4-dioxane (2.5 mL) dropwise at room temperature. After being stirred at the same temperature for 5 h, the reaction mixture was concentrated under reduced pressure. The residue was suspended with ethyl acetate and filtered to give the product (37 mg, 85%). ¹HNMR (DMSO-d₆) 400 MHz δ: 8.72-8.62 (m, 3H), 8.11 (dd, J=4.6, 1.8 Hz, 1H), 7.96 (dd, J=7.8, 1.4 Hz, 1H), 7.57 (d, J=8.7 Hz, 2H), 7.52-7.47 (m, 2H), 7.42-7.25 (m, 7H), 7.17-7.11 (m, 1H), 6.88 (dd, J=8.0, 1.8 Hz, 1H), 6.74 (dd, J=8.0, 4.6 Hz, 1H), 1.63 (s, 6H). LCMS: 444 [M+H].

Example 67

Preparation of 1-[4-(2-Methyl-9H-imidazo[1,2-d]pyrido[2,3-b][1,4]benzodiazepin-3-yl)phenyl]cyclobutanamine trihydrochloride Step 1: Preparation of tert-butyl {1-[4-(2-methyl-9H-imidazo[1,2-d]pyrido[2,3-b][1,4]benzodiazepin-3-yl)phenyl]cyclobutyl}carbamate

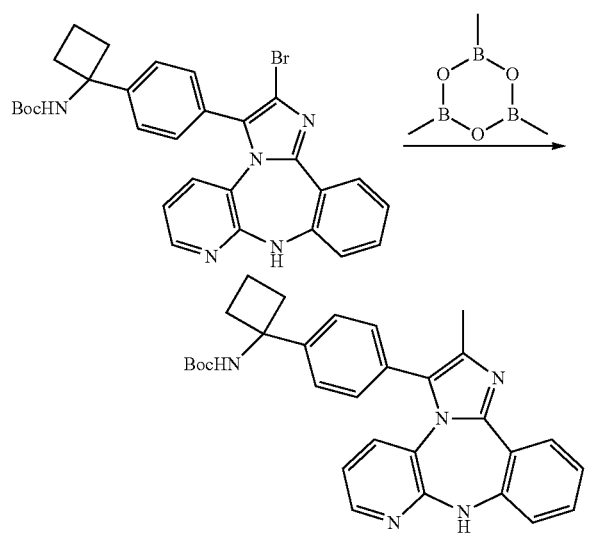

The title compound was synthesized according to the procedure described in example 19 using 2,4,6-trimethyl-1,3,5,2,4,6-trioxatriborinane in step 1 instead of 6-(4,4,5,5-tetramethyl-1,3,2-dioxaborolan-2-yl)-1H-pyrrolo[3,2-b]pyridine. ¹HNMR (DMSO-d₆) 400 MHz δ: 8.08-7.98 (m, 2H), 7.43-7.34 (m, 2H), 7.31-7.23 (m, 1H), 7.14-7.06 (m, 3H), 6.94 (d, J=7.8 Hz, 1H), 6.84 (d, J=7.8 Hz, 1H), 6.62 (dd, J=7.8, 4.8 Hz, 1H), 6.55-6.45 (m, 1H), 5.18 (br s, 1H), 2.62-2.34 (m, 4H), 2.40 (s, 3H), 2.20-2.06 (m, 1H), 1.97-1.81 (m, 1H), 1.67-1.05 (m, 9H).

Step 2: Preparation of 1-[4-(2-methyl-9H-imidazo[1,2-d]pyrido[2,3-b][1,4]benzodiazepin-3-yl)phenyl]cyclobutanamine trihydrochloride

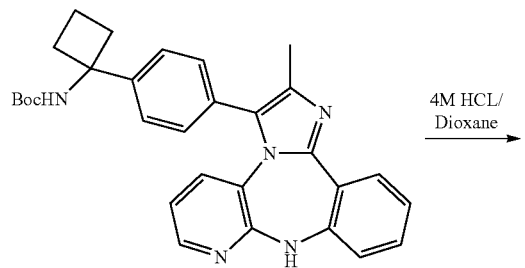

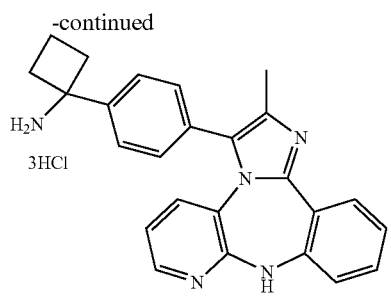

The title compound was synthesized according to the procedure described in step 2 of example 19. ¹HNMR (DMSO-d₆) 400 MHz δ: 8.88-8.65 (m, 3H), 8.19 (dd, J=4.8, 1.6 Hz, 1H), 7.86 (dd, J=8.0, 1.6 Hz, 1H), 7.59 (d, J=8.2 Hz, 2H), 7.46 (t, J=7.8 Hz, 1H), 7.34 (d, J=7.8 Hz, 1H), 7.28 (d, J=7.8 Hz, 2H), 7.17 (t, J=7.8 Hz, 1H), 6.95 (dd, J=7.8, 1.6 Hz, 1H), 6.83 (dd, J=8.2, 4.8 Hz, 1H), 2.63-2.53 (m, 4H), 2.35 (s, 3H), 2.26-2.12 (m, 1H), 1.88-1.74 (m, 1H); LCMS: 394 [M+H].

Example 68

Preparation of 1-[4-(2-phenyl-9H-imidazo[1,2-d]pyrido[2,3-b][1,4]benzodiazepin-3-yl)phenyl]cyclopropanamine Step 1: Preparation of tert-butyl[1-(4-bromophenyl)cyclopropyl]carbamate

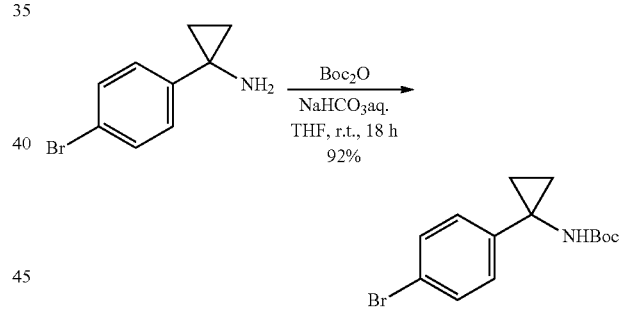

To a solution of 1-(4-bromophenyl)cyclopropanamine (1 g) in THF (30 mL) and saturated sodium bicarbonate solution (30 mL) was added a solution of di-tert-butyl dicarbonate (3.1 g) in THF (30 mL) at 0° C. dropwise. After being stirred at room temperature for 18 h, the reaction mixture was extracted with diisopropyl ether. The organic layer was washed with saturated sodium bicarbonate solution then brine. The organics were dried over anhydrous sodium sulfate and concentrated under reduced pressure. Purification by column chromatography (0-20% ethyl acetate in hexanes) gave the product (1.4 g, 92%). ¹HNMR (CDCl₃) 400 MHz δ: 7.40 (d, J=8.3 Hz, 2H), 7.10 (d, J=8.3 Hz, 2H), 5.23 (br s, 1H), 1.48-1.15 (m, 13H).

Step 2: Preparation of tert-butyl {1-[4-(4,4,5,5-tetramethyl-1,3,2-dioxaborolan-2-yl)phenyl]cyclopropyl}carbamate

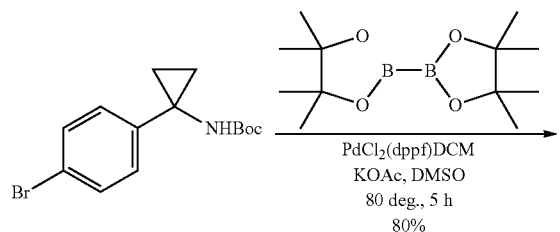

A suspension of tert-butyl[1(4-bromophenyl)cyclopropyl]carbamate (400 mg) and 4,4,4',4',5,5,5',5¹-octamethyl-2,2'-bi-1,3,2-dioxaborolane (390 mg) and potassium acetate (377 mg) and PdCl₂(dppf)CH₂Cl₂ (31 mg) in dimethylsulfoxide (6.5 mL) was degassed for 5 min then stirred at 80° C. for 5 h. The reaction mixture was diluted with benzene and filtered. The filtrate was washed with brine (5 times). The organics were dried over anhydrous sodium sulfate and concentrated under reduced pressure. Purification by column chromatography (0-20% ethyl acetate in hexanes) gave the product (367 mg, 80%). ¹HNMR (CDCl₃) 400 MHz δ: 7.73 (d, J=8.3 Hz, 2H), 7.19 (d, J=8.3 Hz, 2H), 5.25 (br s, 1H), 1.47-1.18 (m, 25H).

Step 3: Preparation of tert-butyl {1-[4-(2-phenyl-9H-imidazo[1,2-d]pyrido[2,3-b][1,4]benzodiazepin-3-yl)phenyl]cyclopropyl}carbamate

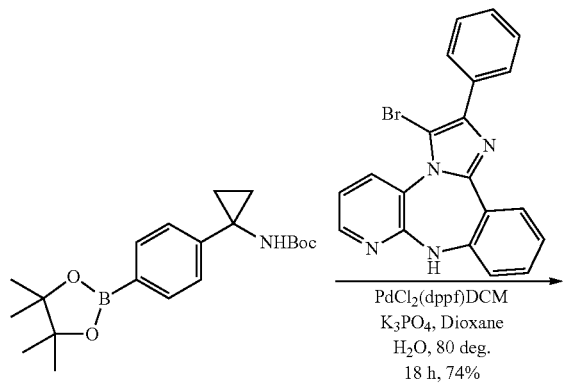

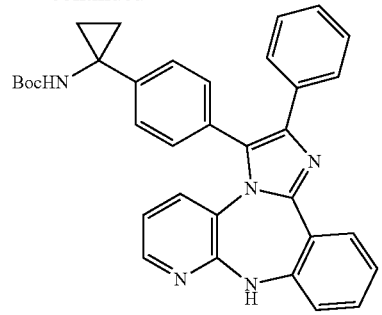

A suspension of 3-bromo-2-phenyl-9H-imidazo[1,2-d]pyrido[2,3-b][1,4]benzodiazepine (50 mg) and tert-butyl {1-[4-(4,4,5,5-tetramethyl-1,3,2-dioxaborolan-2-yl)phenyl]cyclopropyl}carbamate (92 mg) and potassium phosphate (82 mg) and PdCl₂(dppf)CH₂Cl₂ (11 mg) in dioxane (2.5 mL) and H₂O (0.25 mL) was degassed for 5 min then stirred at 80° C. for 18 h. The reaction mixture was concentrated under reduced pressure. Purification by column chromatography (0-50% ethyl acetate in hexanes) gave the product (51 mg, 74%). ¹HNMR (DMSO-d₆) 400 MHz δ: 8.55 (s, 1H), 8.09-8.04 (m, 1H), 7.98-7.93 (m, 1H), 7.70 (br s, 1H), 7.48 (d, J=6.9 Hz, 2H), 7.39-7.06 (m, 10H), 6.94-6.87 (m, 1H), 6.78-6.65 (m, 1H), 1.44-1.08 (m, 13H). LCMS: 542 [M+H].

Step 4: Preparation of 1-[4-(2-phenyl-9H-imidazo[1,2-d]pyrido[2,3-b][1,4]benzodiazepin-3-yl)phenyl]cyclopropanamine

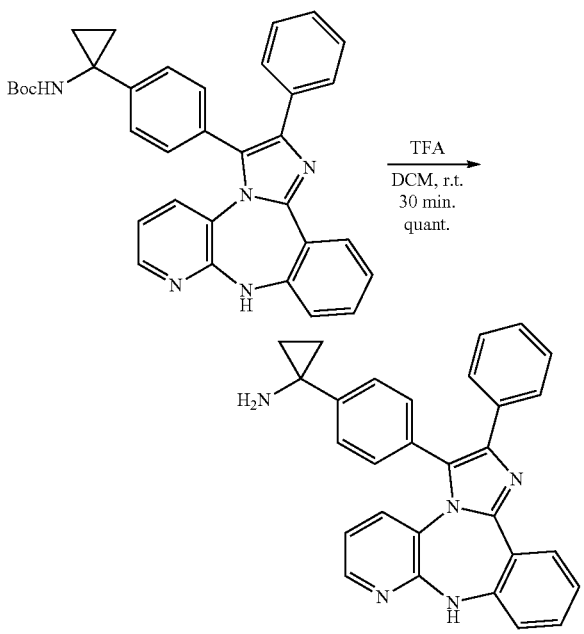

To a suspension of tert-butyl {1-[4-(2-phenyl-9H-imidazo[1,2-d]pyrido[2,3-b][1,4]benzodiazepin-3-yl)phenyl]cyclopropyl}carbamate (27 mg) in dichloromethane (4 mL) was added trifluoroacetic acid (2 mL) at 0° C. dropwise. After being stirred at room temperature for 30 min, the reaction mixture was concentrated under reduced pressure. Purification by column chromatography (NH-silica gel: 10-100% chloroform in hexanes then 10% methanol in chloroform) gave the product (25 mg, quant.). ¹HNMR (DMSO-d₆) 400 MHz δ: 8.54 (s, 1H), 8.07 (dd, J=4.8, 1.6 Hz, 1H), 7.95 (dd, J=7.8, 1.4 Hz, 1H), 7.49 (d, J=6.9 Hz, 2H), 7.38-7.20 (m, 7H), 7.14-7.07 (m, 3H), 6.90 (dd, J=8.0, 1.6 Hz, 1H), 6.75 (dd, J=8.0, 4.8 Hz, 1H), 1.06-1.00 (m, 2H), 0.99-0.93 (m, 2H). LCMS: 442 [M+H].

Example 69

Preparation of 3-[4-(2-phenyl-9H-imidazo[1,2-d]pyrido[2,3-b][1,4]benzodiazepin-3-yl)phenyl]oxetan-3-amine Step 1: Preparation of 2-methyl-N-oxetan-3-ylidenepropane-2-sulfinamide

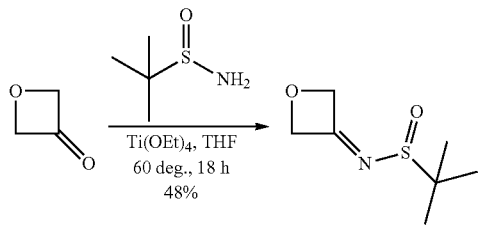

To a solution of 2-methyl-2-propanesulfinamide (1.47 g) and 3-oxetanone (0.85 mL) in THF (24 mL) was added Ti(OEt)₄ (5.34 mL) dropwise over the course of 15 minutes at room temperature. After being stirred at 60° C. for 18 h, the reaction mixture was quenched by the rapid addition into ice cooled saturated sodium bicarbonate aqueous solution. The suspension was filtered through glass fiber filter paper and the cake was washed with ethyl acetate. The filtrate was washed with saturated sodium bicarbonate solution then brine. The organics were dried over anhydrous sodium sulfate and concentrated under reduced pressure. Purification by column chromatography (10-100% ethyl acetate in hexanes) gave the product (1.02 g, 48%). ¹HNMR (CDCl₃) 400 MHz δ: 5.80 (ddd, J=15.6, 4.1, 2.3 Hz, 1H), 5.66 (ddd, J=15.6, 4.1, 2.3 Hz, 1H), 5.52-5.41 (m, 2H), 1.27 (s, 9H).

Step 2: Preparation of N-[3-(4-bromophenyl)oxetan-3-yl]-2-methylpropane-2-sulfinamide

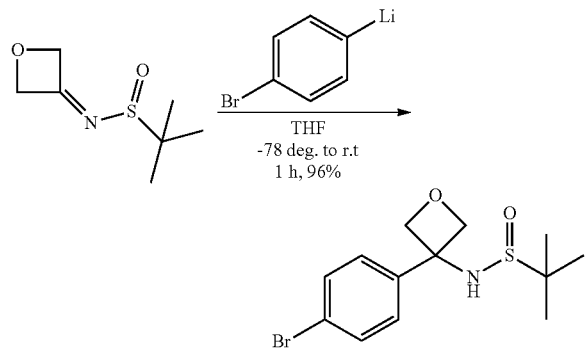

A solution of n-butyllithium in hexanes (1.65M, 4.92 mL) was added dropwise to a solution of 1,4-dibromobenzene (2.05 g) in THF (25 mL) dropwise over the course of 30 min at −78° C. The resulting mixture was stirred at the same temperature for 1 h. To the mixture was added a solution of 2-methyl-N-oxetan-3-ylidenepropane-2-sulfinamide (1.02 g) in THF (5 mL) dropwise over the course of 30 min at −78° C. The reaction mixture was stirred for an additional 30 min. at −78° C. then allowed to warm to room temperature. After being stirred for 1 h at room temperature, the reaction mixture was quenched by addition of saturated ammonium chloride aqueous solution. The aqueous layer was extracted with ethyl acetate. The combined organic layer was washed with saturated sodium bicarbonate solution then brine. The organics were dried over anhydrous sodium sulfate and concentrated under reduced pressure. Purification by column chromatography (50-100% ethyl acetate in hexanes then 5% methanol in ethyl acetate) gave the product (1.85 g, 96%). ¹HNMR (CDCl₃) 400 MHz δ: 7.55 (d, J=8.7 Hz, 2H), 7.27 (d, J=8.7 Hz, 2H), 5.16 (d, J=6.9 Hz, 1H), 5.06 (d, J=6.9 Hz, 1H), 5.02 (d, J=6.9 Hz, 1H), 4.94 (d, J=6.9 Hz, 1H), 4.05 (br s, 1H), 1.22 (s, 9H). LCMS: 332, 334 [M+H].

Step 3: Preparation of tert-butyl[3-(4-bromophenyl)oxetan-3-yl]carbamate

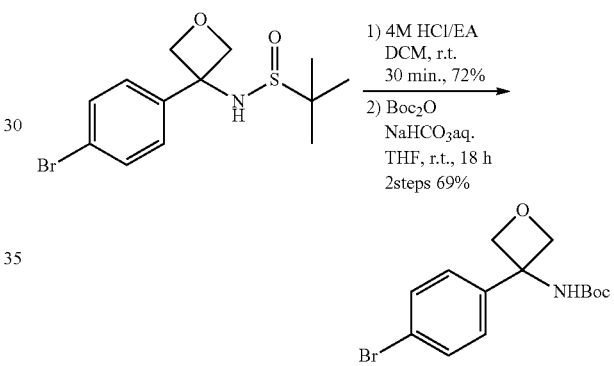

To a solution of N-[3-(4-bromophenyl)oxetan-3-yl]-2-methylpropane-2-sulfinamide (284 mg) in dichloromethane (17 mL) was added a solution of hydrogen chloride in ethyl acetate (4 M, 427 μl) dropwise at room temperature. After being stirred at the same temperature for 30 min, the reaction mixture was diluted with hexane. Filtration gave 3-(4-bromophenyl)oxetan-3-amine hydrochloride. To a solution of 3-(4-bromophenyl)oxetan-3-amine hydrochloride in THF (10 mL) and saturated sodium bicarbonate aqueous solution (10 mL) was added a solution of di-tert-butyl dicarbonate (403 mg) in THF (10 mL) dropwise. After being stirred at room temperature for 48 h, the reaction mixture was extracted with ethyl acetate. The organic layer was washed with saturated sodium bicarbonate aqueous solution then brine. The organics were dried over anhydrous sodium sulfate and concentrated under reduced pressure. Purification by column chromatography (5-30% ethyl acetate in hexanes) gave the product (194 mg, 2 steps 69%). ¹HNMR (CDCl₃) 400 MHz δ: 7.53 (d, J=8.7 Hz, 2H), 7.42 (d, J=8.7 Hz, 2H), 5.29 (br s, 1H), 5.01-4.90 (m, 2H), 4.85-4.73 (m, 2H), 1.50-1.26 (m, 9H). LCMS: 328, 330 [M+H].

Step 4: Preparation of tert-butyl {3-[4-(4,4,5,5-tetramethyl-1,3,2-dioxaborolan-2-yl)phenyl]oxetan-3-yl}carbamate

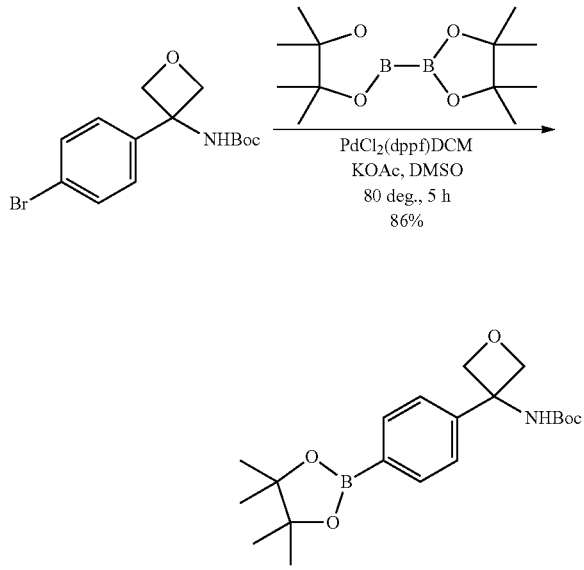

A suspension of tert-butyl[3-(4-bromophenyl)oxetan-3-yl]carbamate (193 mg) and 4,4,4',4',5,5,5',5'-octamethyl-2,2'-bi-1,3,2-dioxaborolane (179 mg) and potassium acetate (173 mg) and PdCl$_2$(dppf)CH$_2$Cl$_2$ (14 mg) in dimethylsulfoxide (3 mL) was degassed for 5 min. then stirred at 80° C. for 5 h. The reaction mixture was diluted with ethyl acetate and filtered. The filtrate was washed with brine (5 times). The organics were dried over anhydrous sodium sulfate and concentrated under reduced pressure. Purification by column chromatography (0-20% ethyl acetate in hexanes) gave the product (189 mg, 86%). $^1$HNMR (CDCl$_3$) 400 MHz δ: 7.85 (d, J=8.3 Hz, 2H), 7.55 (d, J=8.3 Hz, 2H), 5.29 (br s, 1H), 5.08-4.74 (m, 4H), 1.49-1.18 (m, 9H), 1.35 (s, 12H). LCMS: 376 [M+H].

Step 5: Preparation of tert-butyl {3-[4-(2-phenyl-9H-imidazo[1,2-d]pyrido[2,3-b][1,4]benzodiazepin-3-yl)phenyl]oxetan-3-yl}carbamate

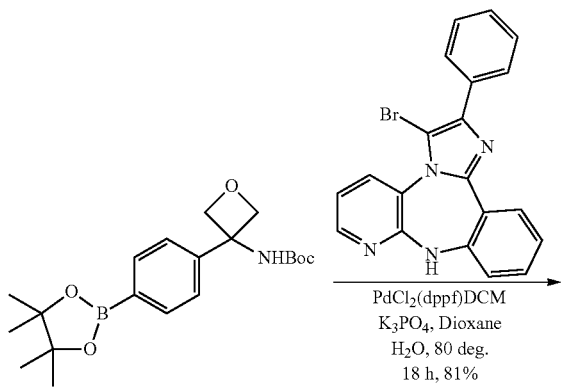

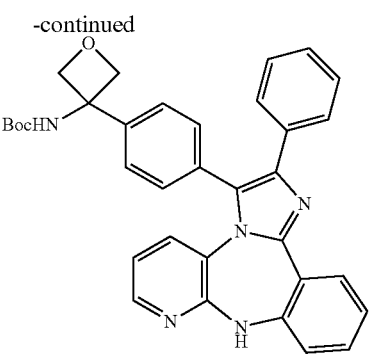

A suspension of 3-bromo-2-phenyl-9H-imidazo[1,2-d]pyrido[2,3-b][1,4]benzodiazepine (50 mg) and tert-butyl {3-[4-(4,4,5,5-tetramethyl-1,3,2-dioxaborolan-2-yl)phenyl]oxetan-3-yl}carbamate (96 mg) and potassium phosphate (82 mg) and PdCl$_2$(dppf)CH$_2$Cl$_2$ (11 mg) in dioxane (2.5 mL) and H$_2$O (0.25 mL) was degassed for 5 min then stirred at 80° C. for 18 h. The reaction mixture was concentrated under reduced pressure. Purification by column chromatography (5-100% ethyl acetate in hexanes) gave the product (58 mg, 81%). $^1$HNMR (DMSO-d$_6$) 400 MHz δ: 8.57 (s, 1H), 8.16-7.83 (m, 3H), 7.55-7.44 (m, 4H), 7.39-7.21 (m, 7H), 7.15-7.09 (m, 1H), 6.98-6.84 (m, 1H), 6.68 (dd, J=7.8, 4.6 Hz, 1H), 4.87-4.75 (m, 2H), 4.73-4.60 (m, 2H), 1.57-1.03 (m, 9H). LCMS: 558 [M+H].

Step 6: Preparation of 3-[4-(2-phenyl-9H-imidazo[1,2-d]pyrido[2,3-b][1,4]benzodiazepin-3-yl)phenyl]oxetan-3-amine

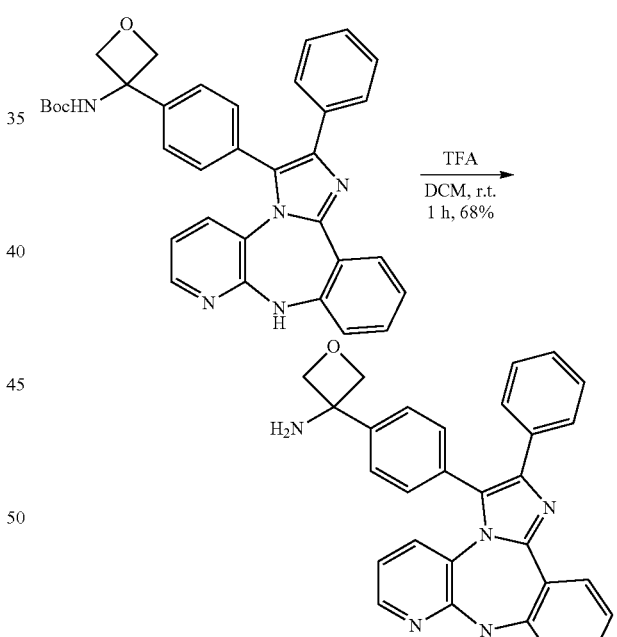

To a suspension of tert-butyl {3-[4-(2-phenyl-9H-imidazo[1,2-d]pyrido[2,3-b][1,4]benzodiazepin-3-yl)phenyl]oxetan-3-yl}carbamate (29 mg) in dichloromethane (4 mL) was added trifluoroacetic acid (2 mL) at 0° C. dropwise. After being stirred at room temperature for 1 h, the reaction mixture was concentrated under reduced pressure. Purification by column chromatography (NH-silica gel: 0-3% methanol in chloroform) gave the product (16 mg, 68%). $^1$HNMR (DMSO-d$_6$) 400 MHz δ: 8.57 (s, 1H), 8.08 (dd, J=4.8, 1.6 Hz, 1H), 7.96 (dd, J=7.8, 1.4 Hz, 1H), 7.61 (d, J=8.3 Hz, 2H), 7.53-7.49 (m, 2H), 7.38-7.21 (m, 7H), 7.12 (t, J=7.6 Hz, 1H), 6.90 (dd, J=8.0, 1.6 Hz, 1H), 6.74 (dd, J=8.0, 4.8 Hz, 1H), 4.71-4.65 (m, 4H). LCMS: 458 [M+H].

Example 70

Preparation of methyl 4-{3-[4-(1-aminocyclobutyl)phenyl]-9H-imidazo[1,2-d]pyrido[2,3-b][1,4]benzodiazepin-2-yl}-2-hydroxybenzoate Step 1: Preparation of methyl 4-[3-(4-{1-[(tert-butoxycarbonyl)amino]cyclobutyl}phenyl)-9H-imidazo[1,2-d]pyrido[2,3-b][1,4]benzodiazepin-2-yl]-2-hydroxybenzoate

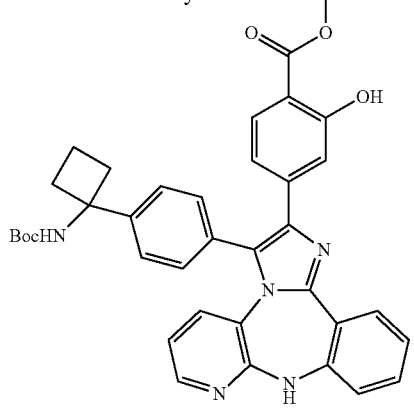

A mixture of tert-butyl {1-[4-(2-chloro-9H-imidazo[1,2-d]pyrido[2,3-b][1,4]benzodiazepin-3-yl)phenyl]cyclobutyl}carbamate (55 mg, 0.092 mmol), methyl 2-hydroxy-4-(4,4,5,5-tetramethyl-1,3,2-dioxaborolan-2-yl)benzoate (48 mg, 0.18 mmol), bis(di-tert-butyl(4-dimethylaminophenyl)phosphine)dichloropalladium(II) (7 mg, 0.009 mmol), and 2M Na₂CO₃ aq. (0.092 mL, 0.18 mmol) in DMF (2.5 mL) was treated with microwave (160° C. for 1 hour). The reaction mixture was added potassium carbonate (30 mg, 0.22 mmol) and iodomethane (0.050 mL, 0.80 mmol) and stirred at r.t for 8.5 hours. The mixture was diluted with AcOEt, washed with water(×3), brine, dried over Na₂SO₄, then filtrated through Celite pad. The filtrate was concentrated and the residue was purified by preparative thin-layer chromatography (n-hexane/AcOEt=1:2) to afford the desired product (33 mg, 57%) as a pale yellow solid. ¹HNMR (CDCl₃) 400 MHz δ: 8.16 (dd, J=8.0 Hz and 1.1 Hz, 1H), 8.01 (d, J=4.0 Hz, 1H), 7.70 (d, J=8.6 Hz, 1H), 7.39 (d, J=8.6 Hz, 2H), 7.31 (td, J=8.0 Hz and 1.1 Hz, 2H), 7.18-7.16 (m, 2H), 7.11-7.07 (m, 1H), 6.95 (d, J=8.0 Hz, 1H), 6.80-6.76 (m, 1H), 6.59 (dd, J=7.7 Hz and 4.9 Hz, 1H), 6.24 (s, 1H), 5.09 (br s, 1H), 3.92 (s, 3H), 2.59-2.40 (m, 4H), 2.19-2.12 (m, 1H), 1.93-1.88 (m, 1H), 1.40 (br s, 9H). LCMS: 630 [M+H].

Step 2: Preparation of methyl 4-{3-[4-(1-aminocyclobutyl)phenyl]-9H-imidazo[1,2-d]pyrido[2,3-b][1,4]benzodiazepin-2-yl}-2-hydroxybenzoate

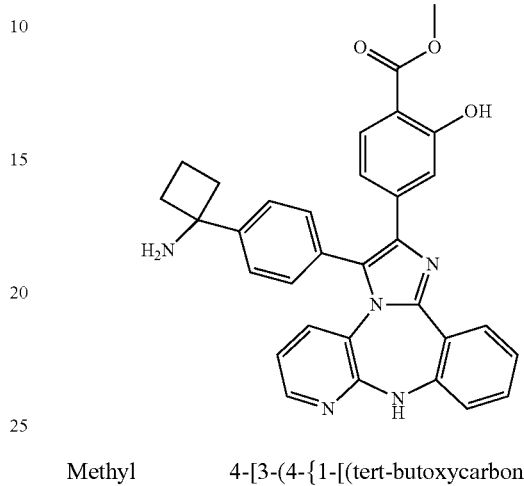

Methyl 4-[3-(4-{1-[(tert-butoxycarbonyl)amino]cyclobutyl}phenyl)-9H-imidazo[1,2-d]pyrido[2,3-b][1,4]benzodiazepin-2-yl]-2-hydroxybenzoate (33 mg, 0.052 mmol) in MeOH (0.5 mL) was added 4N HCl-dioxane (2 mL) and stirred at room temperature for 13 hours. The mixture was concentrated to afford the desired product (30 mg, 90%) as a yellow solid. ¹HNMR (DMSO-d₆) 400 MHz δ: 10.48 (s, 1H), 8.64-8.62 (m, 3H), 8.10 (dd, J=4.9 Hz and 1.4 Hz, 1H), 7.96 (dd, J=8.0 Hz and 1.4 Hz, 1H), 7.69 (d, J=8.0 Hz, 1H), 7.57 (d, J=8.0 Hz, 1H), 7.39-7.36 (m, 2H), 7.30 (dd, J=8.0 Hz and 1.1 Hz, 1H), 7.15-7.06 (m, 2H), 6.89 (dd, J=8.0 Hz and 1.1 Hz, 1H), 6.73 (dd, J=8.0 Hz and 4.6 Hz, 1H), 3.88 (s, 3H), 3.51-3.45 (m, 2H), 2.64-2.52 (m, 2H), 2.23-2.15 (m, 1H), 1.88-1.81 (m, 1H). LCMS: 530 [M+H].

Example 71

Preparation of 1-{4-[2-(3-Nitrophenyl)-9H-imidazo[1,2-d]pyrido[2,3-b][1,4]benzodiazepin-3-yl]phenyl}cyclobutanamine trihydrochloride Step 1: Preparation of tert-butyl (1-{4-[2-(3-nitrophenyl)-9H-imidazo[1,2-d]pyrido[2,3-b][1,4]benzodiazepin-3-yl]phenyl}cyclobutyl)carbamate

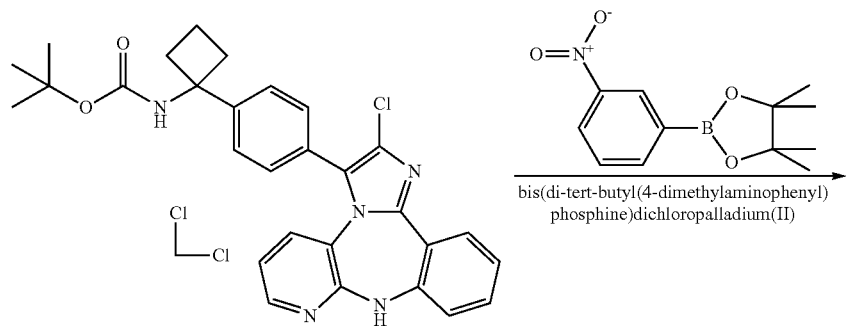

bis(di-tert-butyl(4-dimethylaminophenyl)phosphine)dichloropalladium(II)

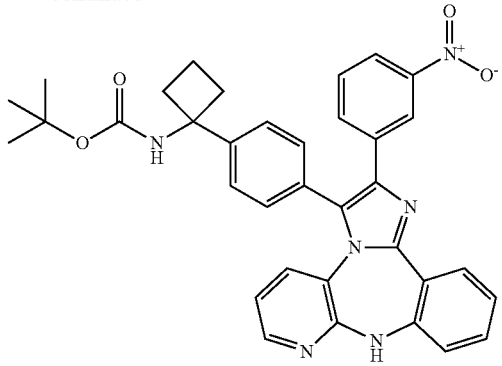

A mixture of tert-butyl {1-[4-(2-chloro-9H-imidazo[1,2-d]pyrido[2,3-b][1,4]benzodiazepin-3-yl)phenyl]cyclobutyl}carbamate (291 mg, 0.500 mmol), 3-nitrophenyl boronic acid pinacol ester (187 mg, 0.750 mmol), bis(di-tert-butyl(4-dimethylaminophenyl)phosphine)dichloropalladium(II) (35.4 mg, 0.0500 mmol) and 2M Na₂CO₃ (0.500 mL, 1.00 mmol) in DMF (4.00 mL) was heated at 160° C. under microwave irradiation for 1 hour under nitrogen. After cooling to room temperature, the mixture was diluted with EtOAc and washed with water (×3) and brine. The organic layer was dried over anhydrous Na₂SO₄ and concentrated. The residue was purified by silica gel column chromatography (EtOAc/hexane=1:4→1:2) to afford desired product (289 mg, 96.2%) as yellow solid. ¹HNMR (CDCl₃) 400 MHz δ: 8.45 (s, 1H), 8.18 (d, J=7.8 Hz, 1H), 8.07-8.00 (m, 2H), 7.91-7.86 (m, 1H), 7.47-7.36 (m, 3H), 7.34-7.26 (m, 1H), 7.22-7.12 (m, 3H), 6.98 (d, J=7.3 Hz, 1H), 6.90-6.69 (m, 2H), 6.62 (dd, J=7.8, 4.6 Hz, 1H), 5.77-5.09 (m, 1H), 2.65-2.31 (m, 4H), 2.28-2.07 (m, 1H), 1.99-1.82 (m, 1H), 1.39 (br s, 9H).

Step 2: Preparation of 1-{4-[2-(3-Nitrophenyl)-9H-imidazo[1,2-d]pyrido[2,3-b][1,4]benzodiazepin-3-yl]phenyl}cyclobutanamine trihydrochloride tert-Butyl (1-{4-[2-(3-nitrophenyl)-9H-imidazo[1,2-d]pyrido[2,3-b][1,4]benzodiazepin-3-yl]phenyl}cyclobutyl)carbamate (30.0 mg, 0.0499 mmol) was dissolved in DCM (1 mL). 4M HCl/dioxane (1 mL) was added to the mixture and stirred at room temperature for 18 hours. The mixture was concentrated and solidified with ether. The precipitated solids were collected by filtration and washed with ether to afford desired product (21.7 mg, 71.3%) as pale yellow solid. ¹HNMR (DMSO-d₆) 400 MHz δ: 8.69 (br s, 2H), 8.64 (s, 1H), 8.23 (t, J=1.8 Hz, 1H), 8.14-8.08 (m, 2H), 8.00 (dd, J=8.0, 1.8 Hz, 1H), 7.93-7.88 (m, 1H), 7.64-7.57 (m, 3H), 7.44-7.36 (m, 3H), 7.34-7.29 (m, 1H), 7.18-7.12 (m, 1H), 6.98 (dd, J=8.0, 1.8 Hz, 1H), 6.75 (dd, J=8.0, 4.8 Hz, 1H), 2.65-2.46 (m, 4H), 2.26-2.12 (m, 1H), 1.93-1.78 (m, 1H); LCMS: 501 [M+H].

Example 72

Preparation of 3-{3-[4-(1-Aminocyclobutyl)phenyl]-9H-imidazo[1,2-d]pyrido[2,3-b][1,4]benzodiazepin-2-yl}aniline tetrahydrochloride Step 1: Preparation of tert-butyl (1-{4-[2-(3-aminophenyl)-9H-imidazo[1,2-d]pyrido[2,3-b][1,4]benzodiazepin-3-yl]phenyl}cyclobutyl)carbamate

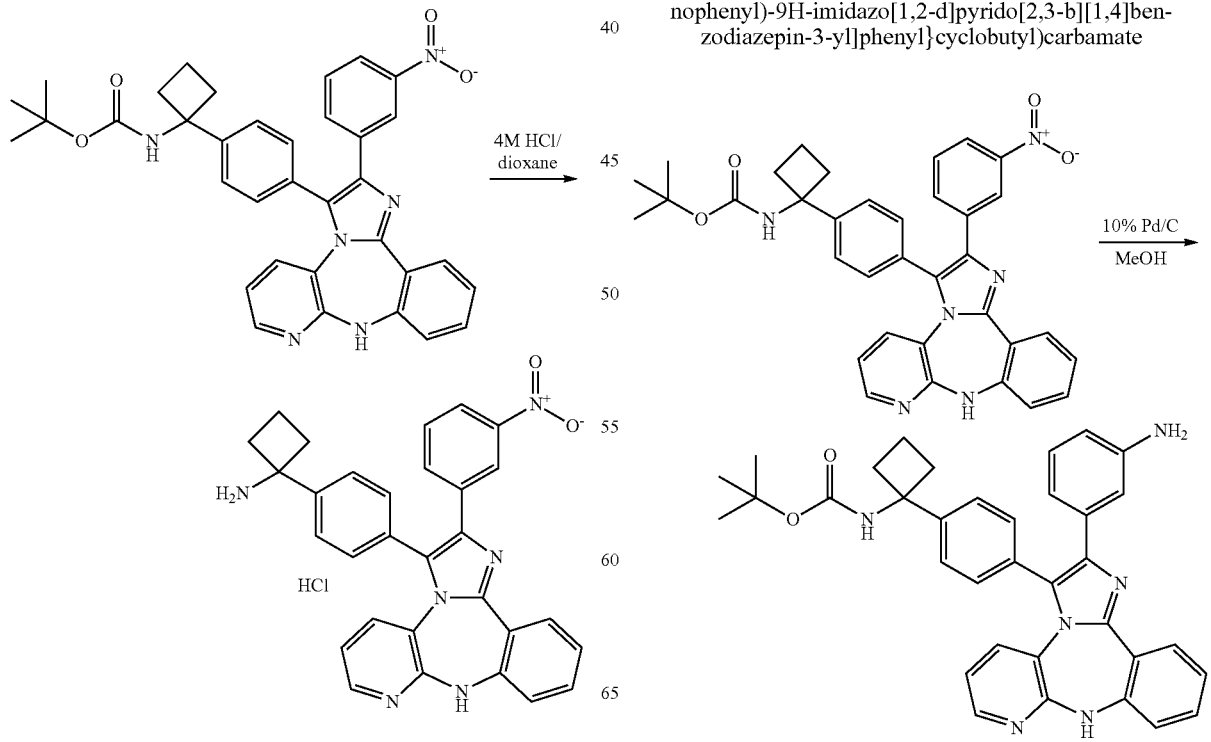

10% Pd/C (250 mg) was added to a solution of tert-butyl (1-{4-[2-(3-nitrophenyl)-9H-imidazo[1,2-d]pyrido[2,3-b][1,4]benzodiazepin-3-yl]phenyl}cyclobutyl) carbamate (259 mg, 0.431 mmol) in MeOH (25 mL), and the mixture was stirred for 3 hours under hydrogen atmosphere. The catalyst was filtered off and washed with MeOH. The combined filtrate and washings were concentrated to afford desired product (243 mg, 98.6%) as pale yellow solid. $^1$HNMR (CDCl$_3$) 400 MHz δ: 8.37-8.26 (m, 1H), 8.12-8.02 (m, 1H), 7.53-7.32 (m, 4H), 7.24-6.78 (m, 8H), 6.64 (dd, J=8.0, 4.8 Hz, 1H), 6.60 (br s, 1H), 5.25 (br s, 1H), 2.62-2.33 (m, 4H), 2.21-2.04 (m, 1H), 1.97-1.81 (m, 1H), 1.37 (br s, 9H).

Step 2: Preparation of 3-{3-[4-(1-aminocyclobutyl)phenyl]-9H-imidazo[1,2-d]pyrido[2,3-b][1,4]benzodiazepin-2-yl}aniline tetrahydrochloride

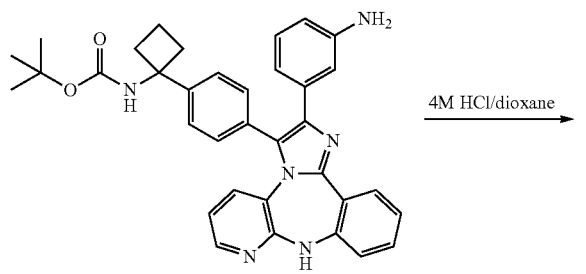

tert-Butyl (1-{4-[2-(3-aminophenyl)-9H-imidazo[1,2-d]pyrido[2,3-b][1,4]benzodiazepin-3-yl]phenyl}cyclobutyl) carbamate (40.0 mg, 0.0701 mmol) was dissolved in DCM (1 mL). 4M HCl/dioxane (1 mL) was added to the mixture and stirred at room temperature for 15.5 hours. The mixture was concentrated and solidified with ether. The precipitated solids were collected by filtration and washed with ether to afford desired product (36.2 mg, 83.8%) as pale red solid. $^1$H-NMR (DMSO-d$_6$) 400 MHz δ: 8.78 (br s, 2H), 8.63 (s, 1H), 8.11 (dd, J=4.8, 1.6 Hz, 1H), 7.96-7.92 (m, 1H), 7.60-7.48 (m, 3H), 7.42-7.09 (m, 8H), 6.93 (dd, J=8.2, 1.4 Hz, 1H), 6.75 (dd, J=7.8, 4.6 Hz, 1H), 2.65-2.48 (m, 4H), 2.27-2.13 (m, 1H), 1.90-1.76 (m, 1H); LCMS: 471 [M+H].

Example 73

Preparation of N-(3-{3-[4-(1-aminocyclobutyl)phenyl]-9H-imidazo[1,2-d]pyrido[2,3-b][1,4]benzodiazepin-2-yl}phenyl)methanesulfonamide trihydrochloride Step 1: Preparation of tert-Butyl {1-[4-(2-{3-[(methylsulfonyl)amino]phenyl}-9H-imidazo[1,2-d]pyrido[2,3-b][1,4]benzodiazepin-3-yl)phenyl]cyclobutyl}carbamate

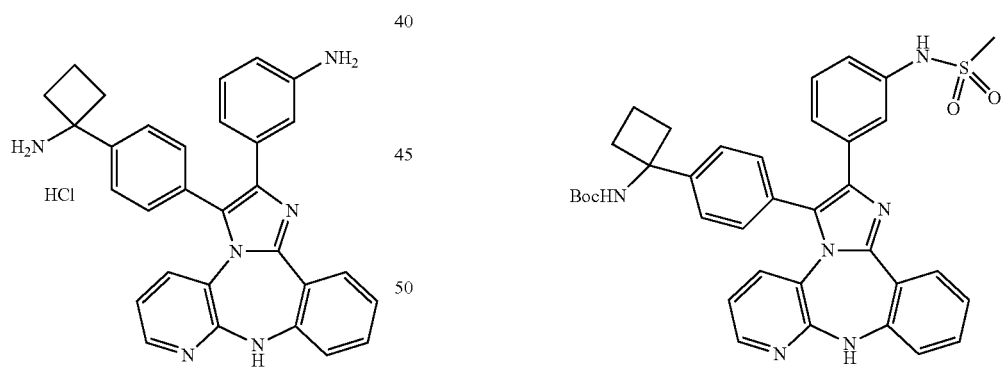

Et$_3$N (29.3 μL, 0.210 mmol) and methanesulfonyl chloride (5.70 μL, 0.0736 mmol) were added to a solution of tert-butyl (1-{4-[2-(3-aminophenyl)-9H-imidazo[1,2-d]pyrido[2,3-b][1,4]benzodiazepin-3-yl]phenyl}cyclobutyl)carbamate (40.0 mg, 0.0701 mmol) in DCM (1 mL) at 0° C. After stirring the mixture for 17 hours at room temperature, the mixture was diluted with sat. NaHCO$_3$ and extracted with CHCl$_3$ (3×). The combined organic layers were dried over anhydrous Na$_2$SO$_4$, and concentrated. The residue was purified by PTLC (CHCl$_3$/EtOAc=1:1) to afford desired product (13.7 mg, 30.1%) as white solid. $^1$HNMR (CDCl$_3$) 400 MHz δ: 8.14 (dd, J=7.8, 1.4 Hz, 1H), 8.02 (dd, J=4.6, 1.4 Hz, 1H), 7.54-7.10 (m, 10H), 6.99-6.87 (m, 2H), 6.82 (dd, J=7.8, 1.4 Hz, 1H), 6.61 (dd, J=7.8, 4.6 Hz, 1H), 6.45-6.38 (m, 1H), 5.25 (br s, 1H), 2.89 (s, 3H), 2.61-2.30 (m, 4H), 2.20-2.08 (m, 1H), 1.96-1.82 (m, 1H), 1.38 (br s, 9H).

Step 2: Preparation of N-(3-{3-[4-(1-aminocyclobutyl)phenyl]-9H-imidazo[1,2-d]pyrido[2,3-b][1,4]benzodiazepin-2-yl}phenyl)methanesulfonamide trihydrochloride

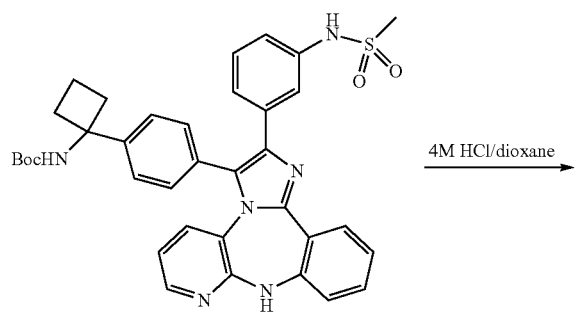

tert-Butyl {1-[4-(2-{3-[(methylsulfonyl)amino]phenyl}-9H-imidazo[1,2-d]pyrido[2,3-b][1,4]benzodiazepin-3-yl)phenyl]cyclobutyl}carbamate (13.7 mg, 0.0211 mmol) was dissolved in DCM (1 mL). 4M HCl/dioxane (1 mL) was added to the mixture and stirred at room temperature for 11.5 hours. The mixture was concentrated and solidified with ether. The precipitated solids were collected by filtration and washed with ether to afford desired product (12.5 mg, 89.7%) as pale yellow solid. $^1$HNMR (DMSO-$d_6$) 400 MHz δ: 9.76 (s, 1H), 8.67 (br s, 2H), 8.62 (s, 1H), 8.10 (dd, J=4.6, 1.4 Hz, 1H), 7.94 (dd, J=7.6, 1.6 Hz, 1H), 7.53 (d, J=8.7 Hz, 2H), 7.49-7.47 (m, 1H), 7.41-7.29 (m, 4H), 7.25 (t, J=7.8 Hz, 1H), 7.19-7.08 (m, 3H), 6.88 (dd, J=7.8, 1.4 Hz, 1H), 6.73 (dd, J=8.0, 4.6 Hz, 1H), 2.90 (s, 3H), 2.61-2.48 (m, 4H), 2.25-2.12 (m, 1H), 1.89-1.76 (m, 1H).

Example 74

Preparation of N-(3-{3-[4-(1-Aminocyclobutyl)phenyl]-9H-imidazo[1,2-d]pyrido[2,3-b][1,4]benzodiazepin-2-yl}phenyl)benzenesulfonamide trihydrochloride Step 1: Preparation of tert-butyl {1-[4-(2-{3-[(phenylsulfonyl)amino]phenyl}-9H-imidazo[1,2-d]pyrido[2,3-b][1,4]benzodiazepin-3-yl)phenyl]cyclobutyl}carbamate

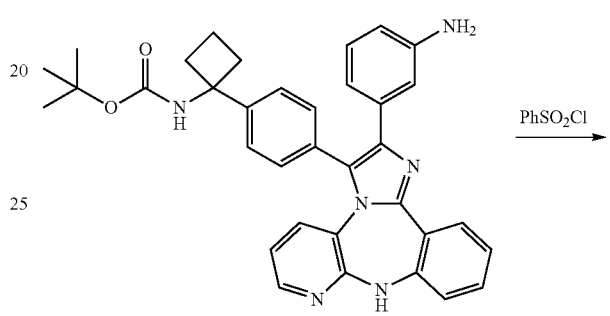

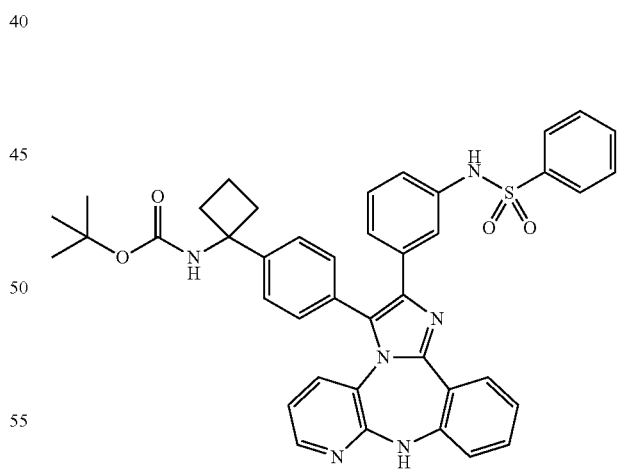

The title compound was synthesized according to the procedure described in step 1 of example 73 using benzenesulfonyl chloride instead of methanesulfonyl chloride. $^1$HNMR (DMSO-$d_6$) 400 MHz δ: 8.11 (dd, J=7.8, 1.6 Hz, 1H), 8.00 (dd, J=4.8, 1.6 Hz, 1H), 7.70 (d, J=7.8 Hz, 2H), 7.54-7.25 (m, 7H), 7.24-6.92 (m, 8H), 6.85-6.79 (m, 1H), 6.60 (dd, J=7.8, 4.8 Hz, 1H), 6.42-6.36 (m, 1H), 5.30-5.24 (m, 1H), 2.63-2.33 (m, 4H), 2.21-2.06 (m, 1H), 1.97-1.82 (m, 1H), 1.38 (br s, 9H).

Step 2: Preparation of N-(3-{3-[4-(1-aminocyclobutyl)phenyl]-9H-imidazo[1,2-d]pyrido[2,3-b][1,4]benzodiazepin-2-yl}phenyl)benzenesulfonamide trihydrochloride

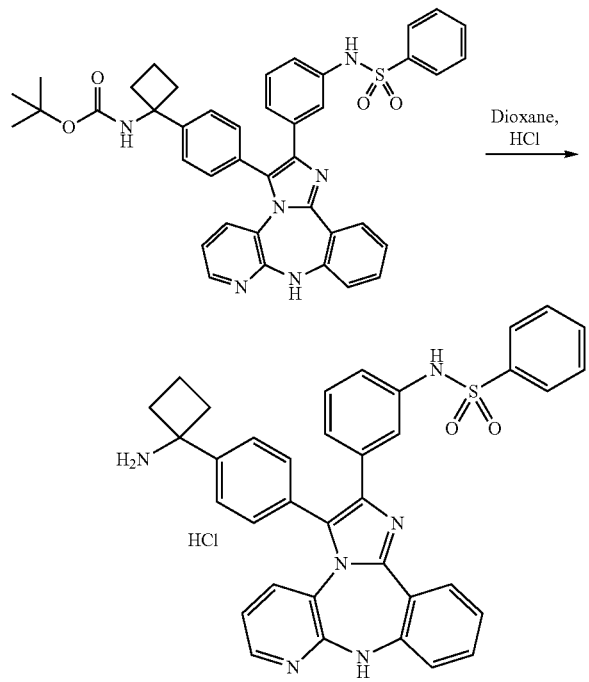

The title compound was synthesized according to the procedure described in step 2 of example 73. $^1$HNMR (DMSO-$d_6$) 400 MHz δ: 10.33 (s, 1H), 8.65 (br s, 2H), 8.60 (s, 1H), 8.09 (dd, J=4.8, 1.6 Hz, 1H), 7.93-7.89 (m, 1H), 7.74-7.45 (m, 8H), 7.41-7.34 (m, 1H), 7.33-7.25 (m, 3H), 7.18-7.02 (m, 3H), 6.98-6.92 (m, 1H), 6.88 (dd, J=7.8, 1.6 Hz, 1H), 6.72 (dd, J=7.8, 4.8 Hz, 1H), 2.64-2.44 (m, 4H), 2.24-2.09 (m, 1H), 1.88-1.73 (m, 1H); LCMS: 611 [M+H].

Example 75

Preparation of N-(3-{3-[4-(1-aminocyclobutyl)phenyl]-9H-imidazo[1,2-d]pyrido[2,3-b][1,4]benzodiazepin-2-yl}phenyl)-1,1,1-trifluoromethane sulfonamide trihydrochloride Step 1: Preparation of tert-butyl (1-{4-[2-(3-{[(trifluoromethyl)sulfonyl]amino}phenyl)-9H-imidazo[1,2-d]pyrido[2,3-b][1,4]benzodiazepin-3-yl]phenyl}cyclobutyl)carbamate

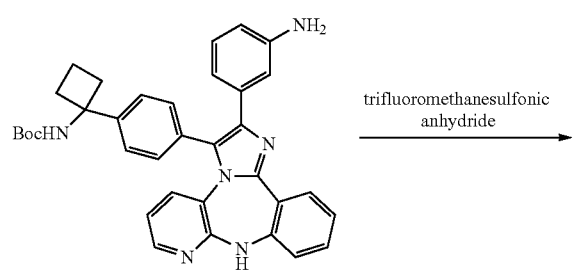

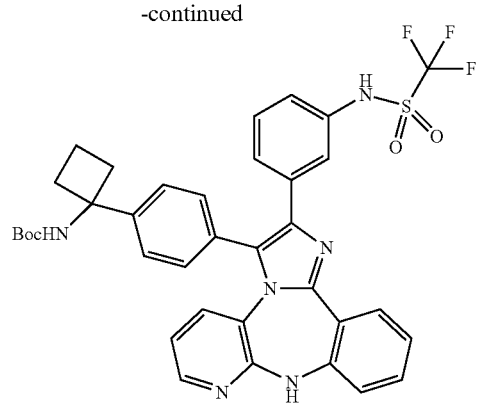

The title compound was synthesized according to the procedure described in step 1 of example 73 using trifluoromethanesulfonic anhydride instead of methanesulfonyl chloride. $^1$HNMR (DMSO-$d_6$) 400 MHz δ: 8.16-8.11 (m, 1H), 8.04-7.99 (m, 1H), 7.75-6.54 (m, 13H), 6.36, 6.30 (2s, total 1H), 5.21, 5.16 (2s, total 1H), 2.60-2.30 (m, 4H), 2.20-2.06 (m, 1H), 1.97-1.83 (m, 1H), 1.37 (br s, 9H).

Step 2: Preparation of N-(3-{3-[4-(1-aminocyclobutyl)phenyl]-9H-imidazo[1,2-d]pyrido[2,3-b][1,4]benzodiazepin-2-yl}phenyl)-1,1,1-trifluoromethanesulfonamide trihydrochloride

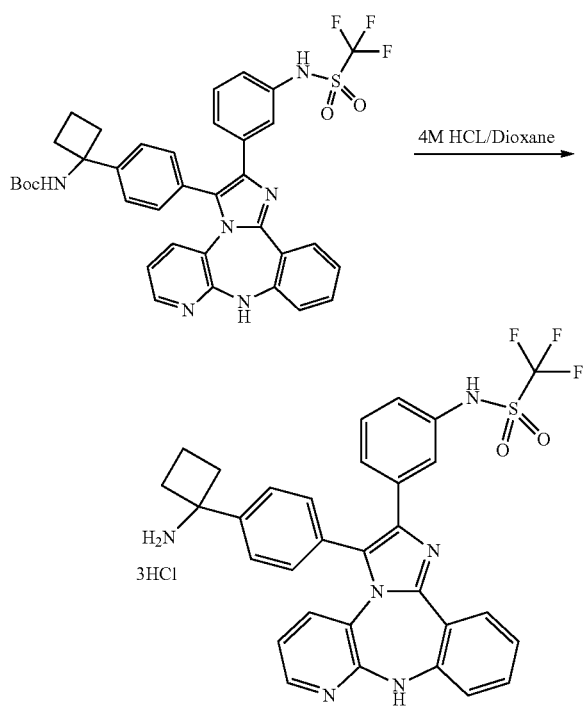

The title compound was synthesized according to the procedure described in step 2 of example 73. $^1$HNMR (DMSO-$d_6$) 400 MHz δ: 8.66 (br s, 2H), 8.61 (s, 1H), 8.10 (dd, J=4.8, 1.8 Hz, 1H), 7.94 (dd, J=7.8, 1.8 Hz, 1H), 7.57-7.47 (m, 3H), 7.41-7.28 (m, 6H), 7.18-7.11 (m, 2H), 6.91 (dd, J=7.8, 1.8 Hz, 1H), 6.72 (dd, J=7.8, 4.8 Hz, 1H), 2.63-2.45 (m, 4H), 2.26-2.11 (m, 1H), 1.89-1.75 (m, 1H); LCMS: 603 [M+H].

Example 76

Preparation of 4-{3-[4-(1-aminocyclobutyl)phenyl]-9H-imidazo[1,2-d]pyrido[2,3-b][1,4]benzodiazepin-2-yl}phenol

Step 1: Preparation of tert-butyl[1-(4-{2-[4-(benzyloxy)phenyl]-9H-imidazo[1,2-d]pyrido[2,3-b][1,4]benzodiazepin-3-yl}phenyl)cyclobutyl]carbamate

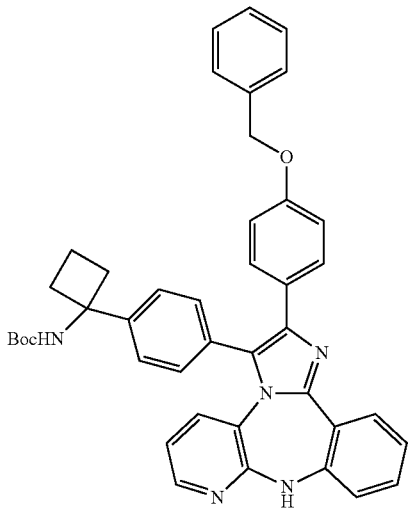 [SMILES: CC(C)(C)OC(=O)NC1(c2ccc(-c3c(-c4ccc(OCc5ccccc5)cc4)nc4n3-c3cccnc3Nc3ccccc3-4)cc2)CCC1]

A mixture of tert-butyl {1-[4-(2-chloro-9H-imidazo[1,2-d]pyrido[2,3-b][1,4]benzodiazepin-3-yl)phenyl]cyclobutyl}carbamate (400 mg, 0.778 mmol), [4-(benzyloxy)phenyl]boronic acid (355 mg, 1.56 mmol), bis(di-tert-butyl(4-dimethylaminophenyl)phosphine)dichloropalladium(II) (55 mg, 0.078 mmol), and 2M $Na_2CO_3$ aq. (0.780 mL, 1.56 mmol) in DMF (8 mL) was treated with microwave (160° C. for 1 hour). The mixture was diluted with AcOEt, washed with water(×3), brine, dried over $Na_2SO_4$, then filtrated through Celite pad. The filtrate was concentrated and the residue was purified by column chromatography (n-hexane/AcOEt=3:2) to afford the mixture of the desired product (430 mg, 84%) as a pale yellow solid. $^1$HNMR (CDCl$_3$) 400 MHz δ: 8.16 (dd, J=8.0, 1.1 Hz, 1H), 8.00 (d, J=4.0 Hz, 1H), 7.51 (d, J=8.0 Hz, 2H), 7.43 (d, J=8.0 Hz, 2H), 7.39-7.33 (m, 4H), 7.32-7.28 (m, 2H), 7.16-7.12 (m, 3H), 6.94 (d, J=8.0 Hz, 1H), 6.89 (d, J=8.6 Hz, 2H), 6.79 (d, J=7.4 Hz, 1H), 6.59 (dd, J=8.0, 4.6 Hz, 1H), 6.26 (s, 1H), 5.10 (br s, 1H), 5.05 (s, 2H), 2.56-2.46 (m, 4H), 2.18-2.09 (m, 1H), 1.93-1.84 (m, 1H), 1.39 (br s, 9H). LCMS: 662 [M+H].

Step 2: Preparation of tert-butyl (1-{4-[2-(4-hydroxyphenyl)-9H-imidazo[1,2-d]pyrido[2,3-b][1,4]benzodiazepin-3-yl]phenyl}cyclobutyl)carbamate

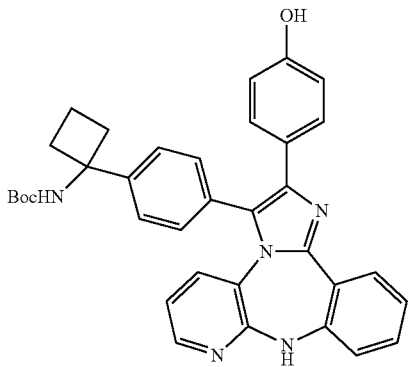 [SMILES: CC(C)(C)OC(=O)NC1(c2ccc(-c3c(-c4ccc(O)cc4)nc4n3-c3cccnc3Nc3ccccc3-4)cc2)CCC1]

Atmosphere of tert-butyl[1-(4-{2-[4-(benzyloxy)phenyl]-9H-imidazo[1,2-d]pyrido[2,3-b][1,4]benzodiazepin-3-yl}phenyl)cyclobutyl]carbamate (430 mg, 0.650 mmol) and 10% Pd—C(dry) (43 mg) in THF (7 mL) and MeOH (7 mL) was exchanged to H$_2$ and stirred at 50° C. for 24 hours. The mixture was diluted with CH$_2$Cl$_2$+MeOH and filtrated through Celite pad. The filtrate was concentrated and the reaction was repeated again. Atmosphere of the residue and 10% Pd—C(dry) (43 mg) in THF (21 mL) and MeOH (21 mL) was exchanged to H$_2$ and stirred at 50° C. for 25 hours. The mixture was diluted with CH$_2$Cl$_2$ and filtrated through Celite pad. The filtrate was concentrated and the residue was purified by column chromatography (CH$_2$Cl$_2$/MeOH=5:1) to afford the desired product (362 mg, 97%) as a pale brown solid. $^1$HNMR (DMSO-d$_6$) 400 MHz δ: 9.42 (s, 1H), 8.51 (s, 1H), 8.04 (d, J=3.4 Hz, 1H), 7.93 (dd, J=7.4, 1.4 Hz, 1H), 7.36-7.26 (m, 5H), 7.14-7.08 (m, 3H), 6.88-6.81 (m, 2H), 6.64 (d, J=8.6 Hz, 2H), 2.42-2.33 (m, 4H), 2.02-1.97 (m, 1H), 1.81-1.74 (m, 1H), 1.34 (br s, 5H), 1.17 (br s, 4H). LCMS: 572 [M+H].

Step 3: Preparation of 4-{3-[4-(1-aminocyclobutyl)phenyl]-9H-imidazo[1,2-d]pyrido[2,3-b][1,4]benzodiazepin-2-yl}phenol

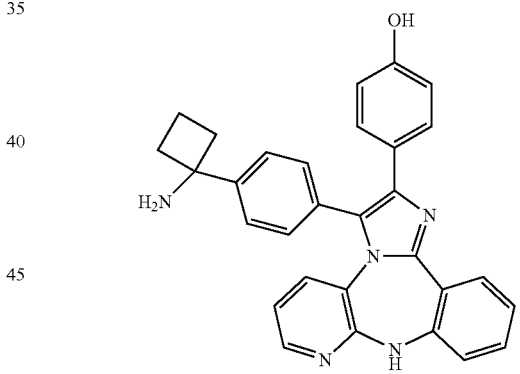

tert-Butyl (1-{4-[2-(4-hydroxyphenyl)-9H-imidazo[1,2-d]pyrido[2,3-b][1,4]benzodiazepin-3-yl]phenyl}cyclobutyl)carbamate (34 mg, 0.060 mmol) in MeOH (0.5 mL) was added 4N HCl-dioxane (2 mL) and stirred at room temperature for 34 hours. The mixture was concentrated to afford the desired product (33 mg, 96%) as a brown solid. $^1$HNMR (DMSO-d$_6$) 400 MHz δ: 8.71-8.67 (m, 3H), 8.13 (dd, J=4.6, 1.4 Hz, 1H), 7.94 (dd, J=8.0, 1.4 Hz, 1H), 7.53 (d, J=9.7 Hz, 2H), 7.41 (t, J=7.7 Hz, 1H), 7.32-7.28 (m, 4H), 7.15 (t, J=7.4 Hz, 1H), 6.89 (dd, J=8.6, 1.7 Hz, 1H), 6.76 (dd, J=8.6, 4.6 Hz, 1H), 6.72 (d, J=8.6 Hz, 1H), 3.73-3.65 (m, 1H), 3.51-3.45 (m, 1H), 2.60-2.53 (m, 2H), 2.23-2.14 (m, 1H), 1.86-1.78 (m, 1H). LCMS: 472 [M+H].

Example 77

Preparation of 1-[4-(2-quinolin-6-yl-9H-imidazo[1,2-d]pyrido[2,3-b][1,4]benzodiazepin-3-yl)phenyl]cyclobutanamine tetrahydrochloride Step 1: Preparation of tert-butyl {1-[4-(2-quinolin-6-yl-9H-imidazo[1,2-d]pyrido[2,3-b][1,4]benzodiazepin-3-yl)phenyl]cyclobutyl}carbamate

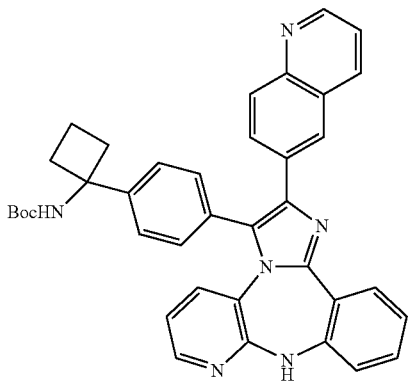 [SMILES: CC(C)(C)OC(=O)NC1(c2ccc(-c3c(-c4ccc5ncccc5c4)nc4n3-c3cccnc3Nc3ccccc3-4)cc2)CCC1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), 2-quinolin-6-ylboronic acid (31 mg, 0.18 mmol), bis(di-tert-butyl(4-dimethylaminophenyl)phosphine)dichloropalladium(II) (6 mg, 0.09 mmol), and 2M $Na_2CO_3$ aq. (0.090 mL, 0.18 mmol) in DMF (2.5 mL) was treated with microwave (160° C. for 1 hour). The mixture was diluted with AcOEt, washed with water(×3), brine, dried over $Na_2SO_4$, then filtrated through Celite pad. The filtrate was concentrated and the residue was purified by preparative thin-layer chromatography (n-hexane/AcOEt=1:4) to afford the desired product (53 mg, 98%) as a pale yellow solid. $^1$HNMR ($CDCl_3$) 400 MHz δ: 8.85 (dd, J=4.0 Hz and 1.7 Hz, 1H), 8.22 (dd, J=8.0 Hz and 1.7 Hz, 1H), 8.19-8.14 (m, 1H), 8.08 (d, J=7.4 Hz, 1H), 8.03 (d, J=3.4 Hz, 1H), 7.94-7.92 (m, 1H), 7.87-7.79 (m, 1H), 7.40 (d, J=8.0 Hz, 2H), 7.36-7.31 (m, 2H), 7.21-7.17 (m, 3H), 6.97 (d, J=7.4 Hz, 1H), 6.84 (d, J=7.4 Hz, 1H), 6.62 (dd, J=8.0 Hz and 4.6 Hz, 1H), 6.29 (s, 1H), 5.15 (br s, 1H), 2.58-2.53 (m, 2H), 2.50-2.40 (m, 2H), 2.20-2.12 (m, 1H), 1.95-1.87 (m, 1H), 1.40 (br s, 9H). LCMS: 607 [M+H].

Step 2: Preparation of 1-[4-(2-quinolin-6-yl-9H-imidazo[1,2-d]pyrido[2,3-b][1,4]benzodiazepin-3-yl)phenyl]cyclobutanamine tetrahydrochloride

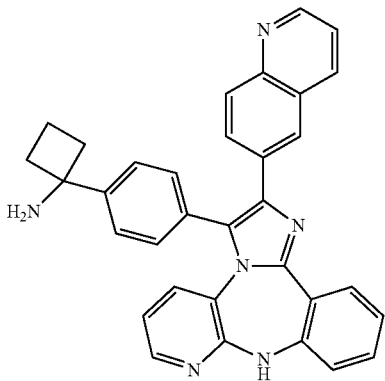 [SMILES: NC1(c2ccc(-c3c(-c4ccc5ncccc5c4)nc4n3-c3cccnc3Nc3ccccc3-4)cc2)CCC1]

Starting material (53 mg, 0.087 mmol) in MeOH (0.5 mL) was added 4N HCl-dioxane (2 mL) and stirred at r.t for 13 hours. The mixture was concentrated to afford the desired product (45 mg, 78%) as a yellow solid. $^1$HNMR (DMSO-$d_6$) 400 MHz δ: 9.06 (d, J=4.6 Hz, 1H), 8.74 (br s, 2H), 8.67 (s, 1H), 8.32 (s, 1H), 8.13 (dd, J=4.6 Hz and 1.7 Hz, 1H), 8.08 (d, J=8.6 Hz, 1H), 8.03 (dd, J=8.0 Hz and 1.7 Hz, 1H), 7.93 (d, J=8.6 Hz, 1H), 7.82-7.79 (m, 1H), 7.59 (d, J=8.6 Hz, 2H), 7.41-7.38 (m4, H), 7.33 (d, J=7.4 Hz, 1H), 7.17 (td, J=8.0 Hz and 1.1 Hz, 1H), 6.96 (dd, J=8.0 Hz and 1.7 Hz, 1H), 6.77 (dd, J=8.0 Hz and 4.6 Hz, 1H), 3.73-3.65 (m, 1H), 3.51-3.45 (m, 1H), 2.62-2.56 (m, 2H), 2.25-2.17 (m, 1H), 1.89-1.80 (m1H). LCMS: 507 [M+H].

Example 78

Preparation of methyl 5-{3-[4-(1-aminocyclobutyl)phenyl]-9H-imidazo[1,2-d]pyrido[2,3-b][1,4]benzodiazepin-2-yl}pyridine-2-carboxylate tetrahydrochloride Step 1: Preparation of methyl 5-[3-(4-{1-[(tert-butoxycarbonyl)amino]cyclobutyl}phenyl)-9H-imidazo[1,2-d]pyrido[2,3-b][1,4]benzodiazepin-2-yl]pyridine-2-carboxylate

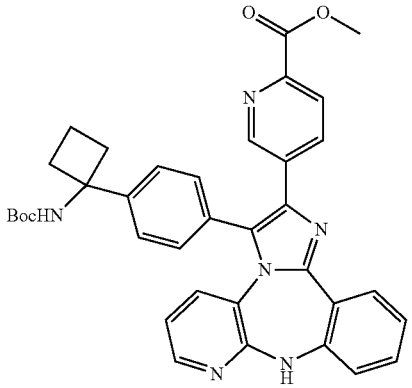 [SMILES: COC(=O)c1ccc(-c2nc3n(c2-c2ccc(C4(NC(=O)OC(C)(C)C)CCC4)cc2)-c2cccnc2Nc2ccccc2-3)cn1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), [6-(methoxycarbonyl)pyridin-3-yl]boronic acid (32 mg, 0.18 mmol), bis(di-tert-butyl(4-dimethylaminophenyl)phosphine)dichloropalladium(II) (6 mg, 0.09 mmol), and 2M $Na_2CO_3$ aq. (0.090 mL, 0.18 mmol) in DMF (2.5 mL) was treated with microwave (160° C. for 1 hour). The reaction mixture was added potassium carbonate (30 mg, 0.22 mmol) and iodomethane (0.050 mL, 0.80 mmol) and stirred at r.t for 17 hours. The mixture was diluted with AcOEt, washed with water(×3), brine, dried over $Na_2SO_4$, then filtrated through Celite pad. The filtrate was concentrated and the residue was purified by preparative thin-layer chromatography (n-hexane/AcOEt=1:3) to afford the desired product (52 mg, 95%) as a pale yellow solid. $^1$HNMR ($CDCl_3$) 400 MHz δ: 8.83 (d, J=2.3 Hz, 1H), 8.15 (dd, J=7.4 Hz and 1.7 Hz, 1H), 8.09 (d, J=8.0 Hz, 1H), 8.02 (d, J=4.0 Hz, 1H), 7.41 (d, J=8.0 Hz, 2H), 7.34 (td, J=7.4 Hz and 1.7 Hz, 1H), 7.19-7.17 (m, 3H), 6.96 (d, J=8.0 Hz, 1H), 6.80 (d, J=7.4 Hz, 1H), 6.60 (dd, J=8.0 Hz and 4.6 Hz, 1H), 6.26 (s, 1H), 5.14 (br s, 1H), 3.99 (s, 3H), 2.59-2.53 (m, 2H), 2.51-2.42 (m, 2H), 2.20-2.12 (m, 1H), 1.96-1.88 (m, 1H), 1.40 (br s, 9H). LCMS: 615 [M+H].

Step 2: Preparation of methyl 5-{3-[4-(1-aminocyclobutyl)phenyl]-9H-imidazo[1,2-d]pyrido[2,3-b][1,4]benzodiazepin-2-yl}pyridine-2-carboxylate tetrahydrochloride

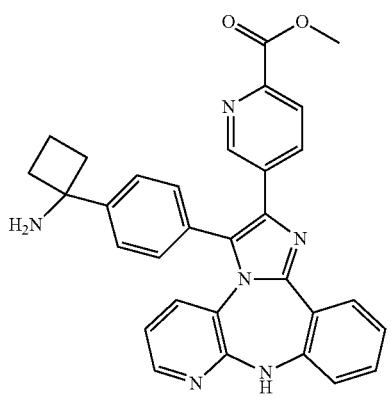 [SMILES: COC(=O)c1ccc(-c2nc3n(c2-c2ccc(C4(N)CCC4)cc2)-c2cccnc2Nc2ccccc2-3)cn1]

Methyl 5-[3-(4-{1-[(tert-butoxycarbonyl)amino]cyclobutyl}phenyl)-9H-imidazo[1,2-d]pyrido[2,3-b][1,4]benzodiazepin-2-yl]pyridine-2-carboxylate (52 mg, 0.085 mmol) in MeOH (0.5 mL) was added 4N HCl-dioxane (2 mL) and stirred at r.t for 23 hours. The mixture was concentrated to afford the desired product (49 mg, 88%) as an orange solid. ¹HNMR (DMSO-d₆) 400 MHz δ: 8.70-8.68 (m, 1H), 8.65 (br s, 1H), 8.63 (s, 1H), 8.56 (d, J=2.3 Hz, 1H), 8.16 (dd, J=8.0 Hz and 2.3 Hz, 1H), 8.10 (dd, J=4.6 Hz and 1.7 Hz, 1H), 8.04 (d, J=8.0 Hz, 1H), 7.97 (dd, J=8.0 Hz and 1.7 Hz, 1H), 7.57 (d, J=8.6 Hz, 2H), 7.39-7.35 (m, 3H), 7.29 (d, J=7.4 Hz, 1H), 7.12 (td, J=8.0 Hz and 1.1 Hz, 1H), 6.91 (dd, J=8.6 Hz and 1.1 Hz, 1H), 6.73 (dd, J=8.0 Hz and 4.6 Hz, 1H), 3.84 (s, 3H), 2.60-2.56 (m, 2H), 2.55-2.50 (m, 2H), 2.21-2.13 (m, 1H), 1.86-1.77 (m, 1H). LCMS: 515 [M+H].

Example 79

Preparation of 5-{3-[4-(1-aminocyclobutyl)phenyl]-9H-imidazo[1,2-d]pyrido[2,3-b][1,4]benzodiazepin-2-yl}-2-benzofuran-1(3H)-one Step 1: Preparation of 5-(4,4,5,5-tetramethyl-1,3,2-dioxaborolan-2-yl)-2-benzofuran-1(3H)-one

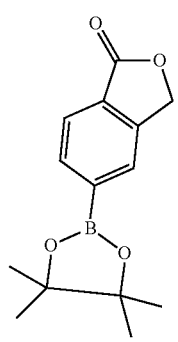 [SMILES: CC1(C)OB(c2ccc3c(c2)COC3=O)OC1(C)C]

A mixture of 5-bromo-2-benzofuran-1(3H)-one (500 mg, 2.34 mmol), 4,4,4',4',5,5,5',5'-octamethyl-2,2'-bi-1,3,2-dioxaborolane (653 mg, 2.57 mmol), [1,1'-bis(diphenylphosphino)ferrocene]dichloropalladium(II), complex with dichlorometahne(1:1) (96 mg, 0.12 mmol), and potassium acetate (689 mg, 7.02 mmol) in dioxane (12 mL) was heated at 80° C. for 48 hours under nitrogen. After cooling to room temperature, water was added and extracted with EtOAc. The organic layer was washed with brine, dried over Na₂SO₄ and filtered through a Celite pad. The filtrate was concentrated and used to the next reaction with no purification. (unstable on silica gel)

Step 2: Preparation of tert-butyl (1-{4-[2-(1-oxo-1,3-dihydro-2-benzofuran-5-yl)-9H-imidazo[1,2-d]pyrido[2,3-b][1,4]benzodiazepin-3-yl]phenyl}cyclobutyl)carbamate

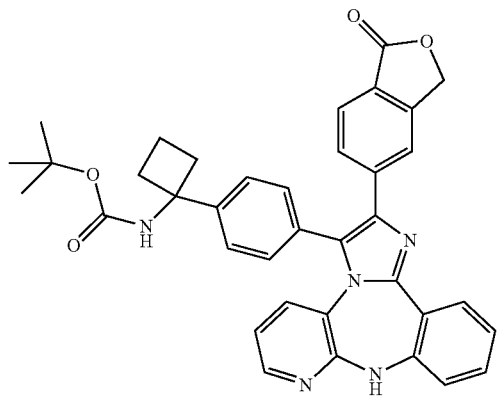 [SMILES: CC(C)(C)OC(=O)NC1(c2ccc(-c3c(-c4ccc5c(c4)COC5=O)nc4n3-c3cccnc3Nc3ccccc3-4)cc2)CCC1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), 5-(4,4,5,5-tetramethyl-1,3,2-dioxaborolan-2-yl)-2-benzofuran-1(3H)-one (80 mg, ca.0.267 mmol), bis(di-tert-butyl(4-dimethylaminophenyl)phosphine)dichloropalladium(II) (6 mg, 0.09 mmol), and 2M Na₂CO₃ aq. (0.090 mL, 0.18 mmol) in DMF (2.5 mL) was treated with microwave (160° C. for 1 hour). The mixture was diluted with AcOEt, washed with water(×3), brine, dried over Na₂SO₄, then filtrated through Celite pad. The filtrate was concentrated and the residue was purified by preparative thin-layer chromatography (n-hexane/AcOEt=1:2) to afford the desired product (39 mg, 71%) as a white solid. ¹HNMR (CDCl₃) 400 MHz δ: 8.15 (dd, J=8.0 Hz and 1.7 Hz, 1H), 8.03 (d, J=4.0 Hz, 1H), 7.87-7.83 (m, 2H), 7.74-7.72 (m, 1H), 7.65-7.59 (m, 2H), 7.41 (d, J=8.6 Hz, 1H), 7.34 (td, J=7.4 Hz and 1.7 Hz, 1H), 7.19-7.16 (m, 2H), 6.97 (d, J=7.4 Hz, 1H), 6.80 (d, J=7.4 Hz, 1H), 6.61 (dd, J=8.0 Hz and 4.6 Hz, 1H), 6.26 (s, 1H), 5.27 (s, 2H), 5.15 (br s, 1H), 2.59-2.52 (m, 2H), 2.50-2.40 (m, 2H), 2.21-2.12 (m, 1H), 1.96-1.87 (m, 1H), 1.39 (br s, 9H). LCMS: 612 [M+H].

Step 3: Preparation of 5-{3-[4-(1-aminocyclobutyl)phenyl]-9H-imidazo[1,2-d]pyrido[2,3-b][1,4]benzodiazepin-2-yl}-2-benzofuran-1(3H)-one

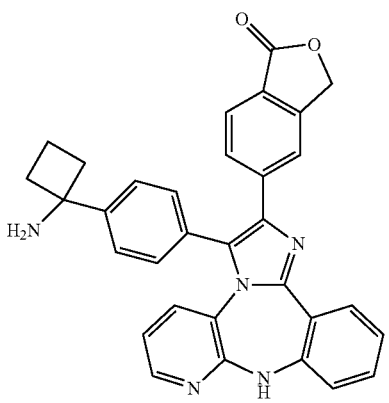 [SMILES: NC1(c2ccc(-c3c(-c4ccc5c(c4)COC5=O)nc4n3-c3cccnc3Nc3ccccc3-4)cc2)CCC1]

tert-Butyl (1-{4-[2-(1-oxo-1,3-dihydro-2-benzofuran-5-yl)-9H-imidazo[1,2-d]pyrido[2,3-b][1,4]benzodiazepin-3-yl]phenyl}cyclobutyl)carbamate (39 mg, 0.064 mmol) in MeOH (0.5 mL) was added 4N HCl-dioxane (2 mL) and stirred at r.t for 23 hours. The mixture was concentrated, then sat.NaHCO$_3$ aq. was added. The mixture was extracted with CH$_2$Cl$_2$+MeOH (×2), dried over Na$_2$SO$_4$, then filtrated through Celite pad. The filtrate was concentrated and the residue was purified by preparative thin-layer chromatography (CH$_2$Cl$_2$/MeOH=10:1) to afford the desired product (31 mg, 94%) as a pale yellow solid. $^1$HNMR (DMSO-d$_6$) 400 MHz δ: 8.62 (s, 1H), 8.10 (dd, J=5.2 Hz and 1.7 Hz, 1H), 7.98 (dd, J=8.0 Hz and 1.7 Hz, 1H), 7.85 (s, 1H), 7.72 (d, J=8.0 Hz, 1H), 7.55 (dd, J=8.6 Hz and 1.1 Hz, 1H), 7.51 (d, J=8.6 Hz, 2H), 7.37 (td, J=8.0 Hz and 1.7 Hz, 1H), 7.30 (d, J=7.4 Hz, 1H), 7.25 (d, J=8.0 Hz, 2H), 7.13 (td, J=8.0 Hz and 1.1 Hz, 1H), 6.91 (dd, J=8.0 Hz and 1.1 Hz, 1H), 6.75 (dd, J=8.0 Hz and 4.6 Hz, 1H), 5.39 (s, 2H), 2.45-2.41 (m, 2H), 2.23-2.18 (m, 2H), 2.10-2.02 (m, 1H), 1.77-1.70 (m, 1H). LCMS: 512 [M+H].

Example 80

Preparation of 1-{4-[2-(1,2,3,6-tetrahydropyridin-4-yl)-9H-imidazo[1,2-d]pyrido[2,3-b][1,4]benzodiazepin-3-yl]phenyl}cyclobutanamine tetrahydrochloride Step 1: Preparation of tert-butyl 4-[3-(4-{1-[(tert-butoxycarbonyl)amino]cyclobutyl}phenyl)-9H-imidazo[1,2-d]pyrido[2,3-b][1,4]benzodiazepin-2-yl]-3,6-dihydropyridine-1(2H)-carboxylate

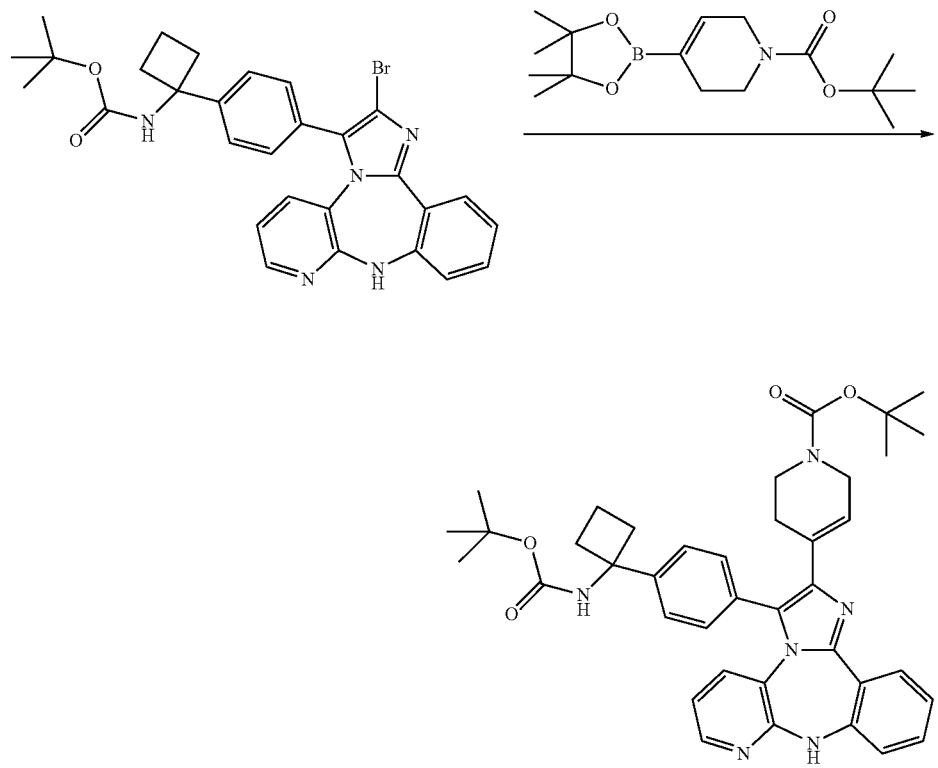

The title compound was synthesized according to the procedure described in example 19 using tert-butyl 4-(4,4,5,5-tetramethyl-1,3,2-dioxaborolan-2-yl)-5,6-dihydropyridine-1(2H)-carboxylate in step 1 instead of 6-(4,4,5,5-tetramethyl-1,3,2-dioxaborolan-2-yl)-1H-pyrrolo[3,2-b]pyridine.
$^1$HNMR (DMSO-d$_6$) 400 MHz δ: 8.03-7.96 (m, 1H), 7.95-7.87 (m, 1H), 7.34-7.26 (m, 2H), 7.24-7.15 (m, 1H), 7.13-

7.00 (m, 3H), 6.86 (d, J=7.8 Hz, 1H), 6.68 (d, J=7.8 Hz, 1H), 6.53-6.38 (m, 1H), 6.49 (dd, J=7.8, 4.6 Hz, 1H), 6.05 (br s, 1H), 5.15 (br s, 1H), 3.91 (d, J=2.7 Hz, 2H), 3.41 (t, J=5.5 Hz, 2H), 2.55-2.18 (m, 6H), 2.14-2.00 (m, 1H), 1.89-1.70 (m, 1H), 1.47 (s, 9H), 1.30 (br s, 9H).

Step 2: Preparation of 1-{4-[2-(1,2,3,6-tetrahydropyridin-4-yl)-9H-imidazo[1,2-d]pyrido[2,3-b][1,4]benzodiazepin-3-yl]phenyl}cyclobutanamine tetrahydrochloride

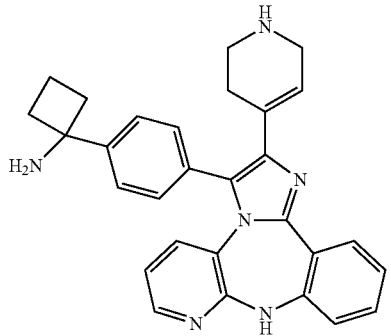 [SMILES: NC1(c2ccc(-c3c(C4=CCNCC4)nc4n3-c3cccnc3Nc3ccccc3-4)cc2)CCC1]

The title compound was synthesized according to the procedure described in step 2 of example 19. ¹HNMR (DMSO-$d_6$) 400 MHz δ: 9.14 (br s, 1H), 8.81 (br s, 2H), 8.58 (s, 1H), 8.08 (dd, J=4.6, 1.4 Hz, 1H), 7.85 (dd, J=7.8, 1.4 Hz, 1H), 7.57-7.51 (m, 2H), 7.38-7.32 (m, 3H), 7.30-7.26 (m, 1H), 7.13-7.07 (m, 1H), 6.85 (dd, J=7.8, 1.4 Hz, 1H), 6.71 (dd, J=7.8, 4.6 Hz, 1H), 5.94-5.89 (m, 1H), 3.66-3.56 (m, 2H), 3.24-3.15 (m, 2H), 2.62-2.30 (m, 6H), 2.28-2.14 (m, 1H), 1.88-1.75 (m, 1H); LCMS: 461 [M+H].

Example 81

Preparation of 1-[4-(2-cyclohex-1-en-1-yl-9H-imidazo[1,2-d]pyrido[2,3-b][1,4]benzodiazepin-3-yl)phenyl]cyclobutanamine trihydrochloride Step 1: Preparation of tert-butyl {1-[4-(2-cyclohex-1-en-1-yl-9H-imidazo[1,2-d]pyrido[2,3-b][1,4]benzodiazepin-3-yl)phenyl]cyclobutyl}carbamate

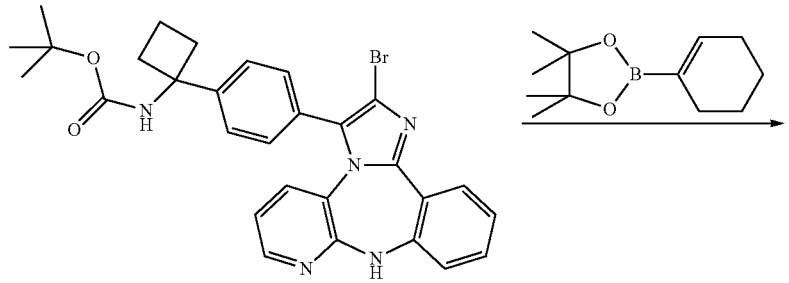

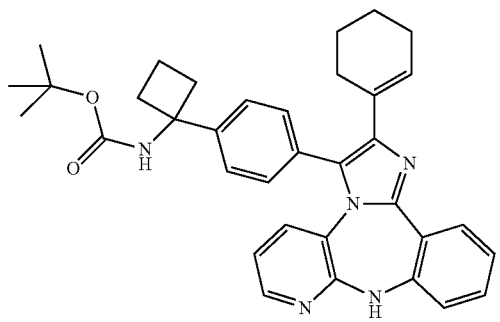

The title compound was synthesized according to the procedure described in example 19 using 2-(cyclohex-1-en-1-yl)-4,4,5,5-tetramethyl-1,3,2-dioxaborolane in step 1 instead of 6-(4,4,5,5-tetramethyl-1,3,2-dioxaborolan-2-yl)-1H-pyrrolo[3,2-b]pyridine. $^1$HNMR (DMSO-$d_6$) 400 MHz δ: 8.08 (dd, J=7.8, 1.4 Hz, 1H), 8.00-7.95 (m, 1H), 7.37-7.31 (m, 2H), 7.28-7.22 (m, 1H), 7.17-7.07 (m, 3H), 6.95-6.90 (m, 1H), 6.81-6.74 (m, 1H), 6.57 (dd, J=7.8, 4.8 Hz, 1H), 6.47 (br s, 1H), 6.13-6.08 (m, 1H), 5.20 (br s, 1H), 2.60-2.03 (m, 10H), 1.95-1.73 (m, 2H), 1.69-1.57 (m, 2H), 1.37 (br s, 9H).

Step 2: Preparation of 1-[4-(2-cyclohex-1-en-1-yl-9H-imidazo[1,2-d]pyrido[2,3-b][1,4]benzodiazepin-3-yl)phenyl]cyclobutanamine trihydrochloride

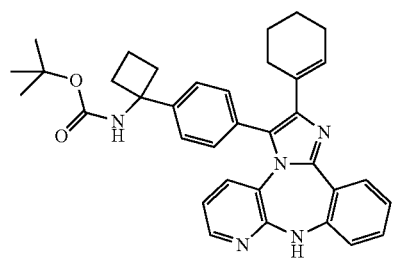

4M HCL/Dioxane

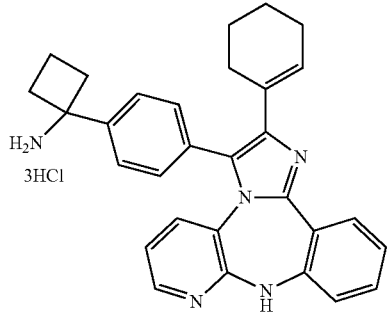

The title compound was synthesized according to the procedure described in step 2 of example 19. $^1$HNMR (DMSO-$d_6$) 400 MHz δ: 8.83-8.58 (m, 3H), 8.12 (d, J=4.6 Hz, 1H), 7.89-7.84 (m, 1H), 7.57-7.49 (m, 2H), 7.45-7.37 (m, 1H), 7.34-7.25 (m, 3H), 7.14 (t, J=7.8 Hz, 1H), 6.85 (d, J=8.2 Hz, 1H), 6.78-6.72 (m, 1H), 6.01 (br s, 1H), 2.61-2.35 (m, 4H), 2.25-2.13 (m, 3H), 2.11-2.03 (m, 2H), 1.88-1.74 (m, 1H), 1.65-1.50 (m, 4H); LCMS: 460 [M+H].

Example 82

Preparation of 5-{3-[4-(1-aminocyclobutyl)phenyl]-9H-imidazo[1,2-d]pyrido[2,3-b][1,4]benzodiazepin-2-yl}-2-methylaniline tetrahydrochloride Step 1: Preparation of tert-butyl (1-{4-[2-(4-methyl-3-nitrophenyl)-9H-imidazo[1,2-d]pyrido[2,3-b][1,4]benzodiazepin-3-yl]phenyl}cyclobutyl)carbamate

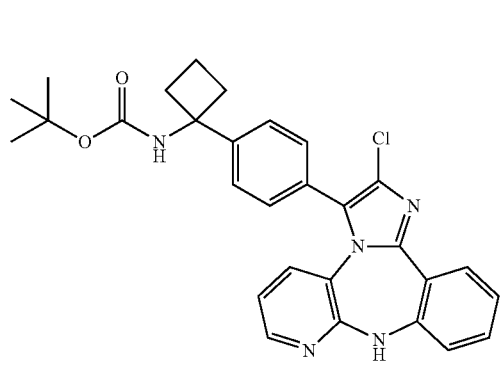

bis(di-tert-butyl(4-dimethylaminophenyl)phosphine)dichloropalladium(II)

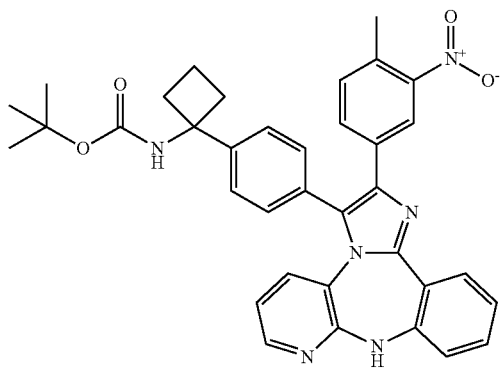

A mixture of tert-butyl {1-[4-(2-chloro-9H-imidazo[1,2-d]pyrido[2,3-b][1,4]benzodiazepin-3-yl)phenyl]cyclobutyl}carbamate (50.0 mg, 0.0835 mmol), 4-methyl-3-nitrophenylboronic acid pinacol ester (33.6 mg, 0.125 mmol), bis(di-tert-butyl(4-dimethylaminophenyl)phosphine)dichloropalladium(II) (5.91 mg, 0.00835 mmol) and 2M Na₂CO₃ aq. (0.0835 mL, 0.170 mmol) in DMF (1.00 mL) was heated at 160° C. under microwave irradiation for 1 hour. After cooling to room temperature, the mixture was diluted with EtOAc and washed with water(×3). The organic layer was dried over anhydrous Na₂SO₄ and concentrated. The residue was purified by silica gel column chromatography (EtOAc/hexane=1:4→1:3→1:2) to afford desired product (49.1 mg, 95.7%) as pale yellow solid. ¹HNMR (CDCl₃) 400 MHz δ: 8.21 (s, 1H), 8.16 (dd, J=7.8, 1.4 Hz, 1H), 8.02 (dd, J=4.6, 1.4 Hz, 1H), 7.67 (dd, J=8.2, 1.8 Hz, 1H), 7.42 (d, J=8.2 Hz, 2H), 7.31 (td, J=7.6, 1.5 Hz, 1H), 7.22-7.11 (m, 4H), 7.00-6.93 (m, 1H), 6.85 (d, J=7.8 Hz, 1H), 6.61 (dd, J=7.8, 5.0 Hz, 1H), 6.50 (s, 1H), 5.24 (br s, 1H), 2.67-2.27 (m, 4H), 2.56 (s, 3H), 2.23-2.07 (m, 1H), 1.97-1.85 (m, 1H), 1.39 (br s, 9H).

Step 2: Preparation of tert-butyl (1-{4-[2-(3-amino-4-methylphenyl)-9H-imidazo[1,2-d]pyrido[2,3-b][1,4]benzodiazepin-3-yl]phenyl}cyclobutyl)carbamate

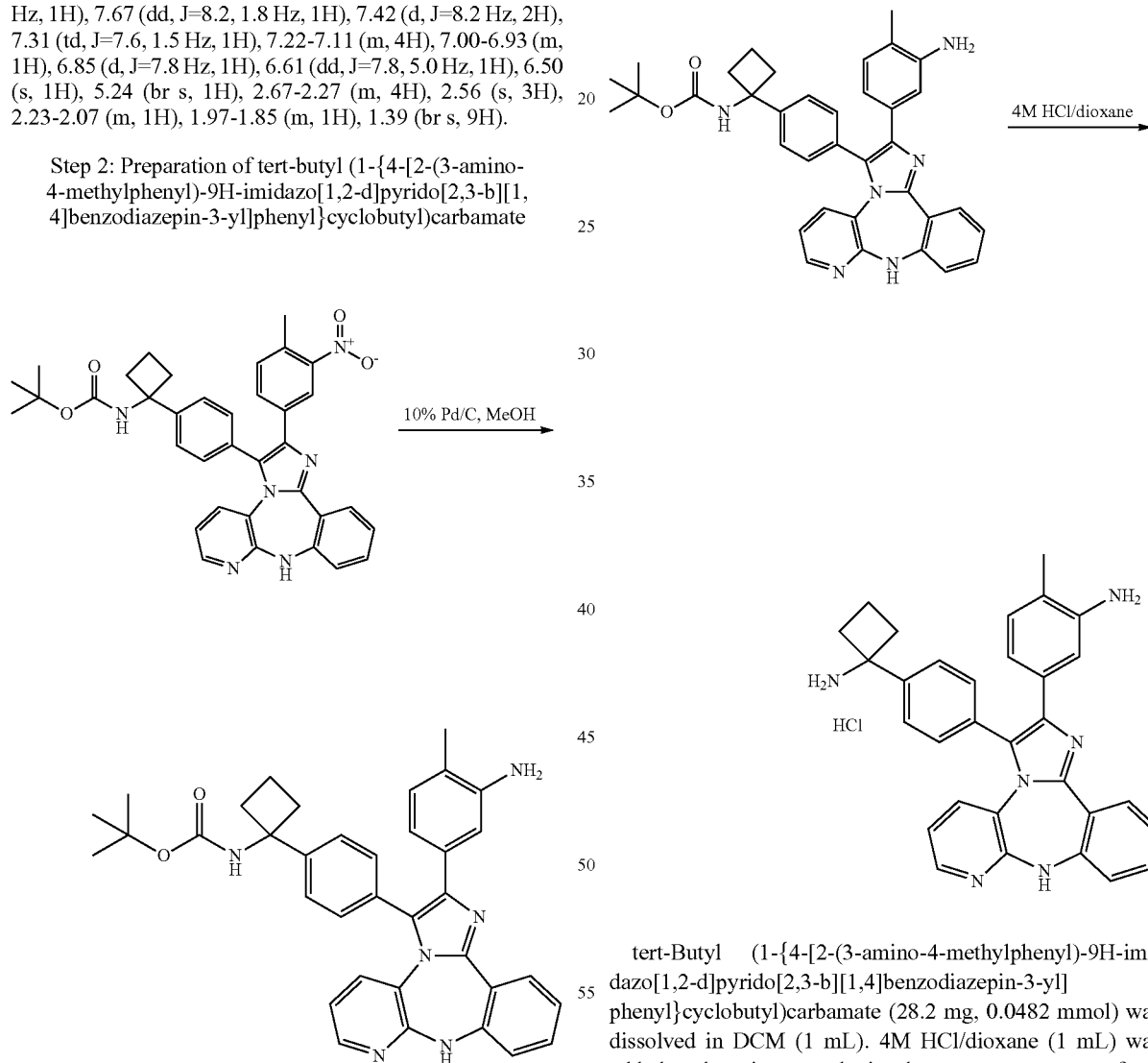

10% Pd/C (50.0 mg) was added to a solution of tert-butyl (1-{4-[2-(4-methyl-3-nitrophenyl)-9H-imidazo[1,2-d]pyrido[2,3-b][1,4]benzodiazepin-3-yl]phenyl}cyclobutyl)carbamate (49.1 mg, 0.0799 mmol) in MeOH (5 mL), and the mixture was stirred for 6.5 hours under hydrogen atmosphere. The catalyst was filtered off and washed with MeOH. The combined filtrate and washings were concentrated, and the residue was purified by silica gel column chromatography (EtOAc/hexane=1:2→1:1→2:1→EtOAc) to afford desired product (28.2 mg, 60.4%) as pale yellow solid. ¹HNMR (CDCl₃) 400 MHz δ: 8.17 (dd, J=7.8, 1.4 Hz, 1H), 8.00 (dd, J=5.0, 1.4 Hz, 1H), 7.39-7.31 (m, 2H), 7.27 (td, J=7.7, 1.5 Hz, 1H), 7.21-6.69 (m, 8H), 6.58 (dd, J=7.8, 4.6 Hz, 1H), 6.52-6.46 (m, 1H), 5.24 (br s, 1H), 3.56 (br s, 2H), 2.63-2.27 (m, 4H), 2.19-2.06 (m, 1H), 2.14 (s, 3H), 1.95-1.74 (m, 1H), 1.38 (br s, 9H).

Step 3: Preparation of 5-{3-[4-(1-aminocyclobutyl)phenyl]-9H-imidazo[1,2-d]pyrido[2,3-b][1,4]benzodiazepin-2-yl}-2-methylaniline tetrahydrochloride tert-Butyl (1-{4-[2-(3-amino-4-methylphenyl)-9H-imidazo[1,2-d]pyrido[2,3-b][1,4]benzodiazepin-3-yl]phenyl}cyclobutyl)carbamate (28.2 mg, 0.0482 mmol) was dissolved in DCM (1 mL). 4M HCl/dioxane (1 mL) was added to the mixture and stirred at room temperature for 2 hours. The mixture was concentrated and solidified with ether. The precipitated solids were collected by filtration and washed with ether to afford desired product (30.2 mg, 99.3%) as pale yellow solid. ¹HNMR (DMSO-d₆) 400 MHz δ: 8.86-8.70 (m, 2H), 8.63 (s, 1H), 8.11 (dd, J=4.8, 1.4 Hz, 1H), 7.92 (dd, J=8.0, 1.8 Hz, 1H), 7.70-7.64 (m, 1H), 7.57-7.52 (m, 2H), 7.41-7.35 (m, 1H), 7.35-7.28 (m, 3H), 7.19-7.10 (m, 3H), 6.91 (dd, J=8.0, 1.4 Hz, 1H), 6.75 (dd, J=8.0, 4.8 Hz, 1H), 2.64-2.37 (m, 4H), 2.30 (s, 3H), 2.26-2.13 (m, 1H), 1.89-1.75 (m, 1H); LCMS: 485 [M+H].

Example 83

Preparation of 1-{4-[2-(2-methoxypyrimidin-5-yl)-9H-imidazo[1,2-d]pyrido[2,3-b][1,4]benzodiazepin-3-yl]phenyl}cyclobutanamine Step 1: Preparation of tert-butyl (1-{4-[2-(2-methoxypyrimidin-5-yl)-9H-imidazo[1,2-d]pyrido[2,3-b][1,4]benzodiazepin-3-yl]phenyl}cyclobutyl)carbamate

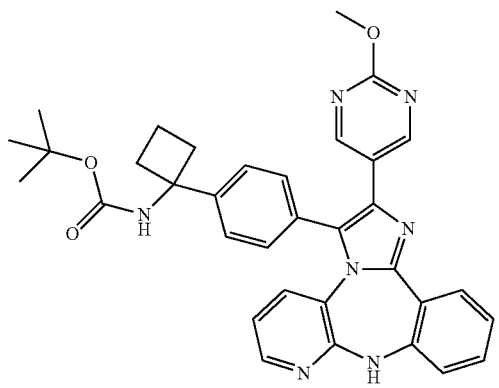 [SMILES: COc1ncc(-c2nc3n(c2-c2ccc(C4(NC(=O)OC(C)(C)C)CCC4)cc2)-c2cccnc2Nc2ccccc2-3)cn1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), (2-methoxypyrimidin-5-yl)boronic acid (28 mg, 0.18 mmol), bis(di-tert-butyl(4-dimethylaminophenyl)phosphine)dichloropalladium(II) (6 mg, 0.09 mmol), and 2M $Na_2CO_3$ aq. (0.090 mL, 0.18 mmol) in DMF (2.5 mL) was treated with microwave (160° C. for 1 hour). The mixture was diluted with AcOEt, washed with water(×3), brine, dried over $Na_2SO_4$, then filtrated through Celite pad. The filtrate was concentrated and the residue was purified by preparative thin-layer chromatography (n-hexane/AcOEt=1:2) to afford the desired product (45 mg, 86%) as a yellow solid. $^1$HNMR ($CDCl_3$) 400 MHz δ: 8.70 (s, 2H), 8.12 (dd, J=7.4 Hz and 1.7 Hz, 1H), 8.02 (d, J=3.4 Hz, 1H), 7.40 (d, J=8.0 Hz, 2H), 7.33 (td, J=8.0 Hz and 1.7 Hz, 1H), 7.18-7.14 (m, 2H), 6.97-6.94 (m, 1H), 6.82-6.79 (m, 1H), 6.61 (dd, J=8.0 Hz and 5.2 Hz, 1H), 6.25 (s, 1H), 5.07 (br s, 1H), 4.01 (s, 3H), 2.57-2.38 (m, 4H), 2.19-2.12 (m, 1H), 1.94-1.86 (m, 1H), 1.39 (br s, 9H). LCMS: 588 [M+H].

Step 2: Preparation of 1-{4-[2(2-methoxypyrimidin-5-yl)-9H-imidazo[1,2-d]pyrido[2,3-b][1,4]benzodiazepin-3-yl]phenyl}cyclobutanamine

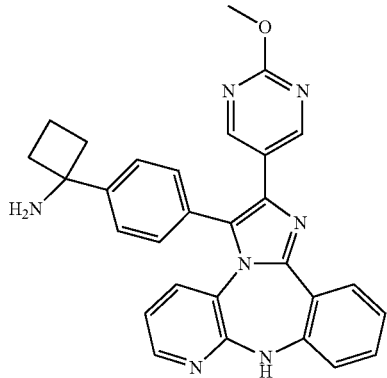 [SMILES: COc1ncc(-c2nc3n(c2-c2ccc(C4(N)CCC4)cc2)-c2cccnc2Nc2ccccc2-3)cn1]

Starting material (45 mg, 0.077 mmol) in MeOH (0.5 mL) was added 4N HCl-dioxane (2 mL) and stirred at r.t for 19 hours. The mixture was concentrated, then sat.$NaHCO_3$ aq. was added. The mixture was extracted with $CH_2Cl_2$+MeOH (×3), dried over $Na_2SO_4$, then filtrated through Celite pad. The filtrate was concentrated and the residue was purified by preparative thin-layer chromatography ($CH_2Cl_2$/MeOH=4:1) to afford the desired product (20 mg, 53%) as a yellow solid. $^1$HNMR (DMSO-$d_6$) 400 MHz δ: 8.63 (s, 2H), 8.61 (s, 1H), 8.11 (dd, J=4.6 Hz and 1.7 Hz, 1H), 7.95 (dd, J=7.4 Hz and 1.7 Hz, 1H), 7.53 (d, J=8.6 Hz, 2H), 7.37 (td, J=7.4 Hz and 1.7 Hz, 1H), 7.30 (dd, J=8.0 Hz and 2.9 Hz, 3H), 7.13 (td, J=7.4 Hz and 1.1 Hz, 1H), 6.91 (dd, J=8.0 Hz and 1.1 Hz, 1H), 6.76 (dd, J=8.0 Hz and 4.6 Hz, 1H), 3.92 (s, 3H), 3.17 (d, J=5.2 Hz, 1H), 2.32-2.26 (m, 2H), 2.13-2.05 (m, 2H), 1.79-1.71 (m, 2H). LCMS: 488 [M+H].

Example 84

Preparation of 5-{3-[4-(1-aminocyclobutyl)phenyl]-9H-imidazo[1,2-d]pyrido[2,3-b][1,4]benzodiazepin-2-yl}pyrimidin-2-ol

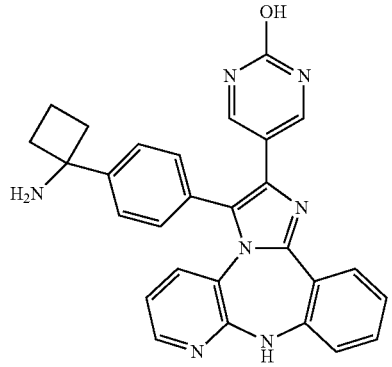 [SMILES: NC1(c2ccc(-c3c(-c4cnc(O)nc4)nc4n3-c3cccnc3Nc3ccccc3-4)cc2)CCC1]

tert-Butyl (1-{4-[2-(2-methoxypyrimidin-5-yl)-9H-imidazo[1,2-d]pyrido[2,3-b][1,4]benzodiazepin-3-yl]phenyl}cyclobutyl)carbamate (45 mg, 0.077 mmol) in MeOH (0.5 mL) was added 4N HCl-dioxane (2 mL) and stirred at r.t for 19 hours. The mixture was concentrated, then sat.$NaHCO_3$ aq. was added. The mixture was extracted with $CH_2Cl_2$+MeOH (×3), dried over $Na_2SO_4$, then filtrated through Celite pad. The filtrate was concentrated and the residue was purified by preparative thin-layer chromatography ($CH_2Cl_2$/MeOH=4:1) to afford the desired product (7 mg, 18%) as a yellow solid. $^1$HNMR (DMSO-$d_6$) 400 MHz δ: 8.58 (s, 1H), 8.23 (br s, 2H), 8.09 (dd, J=4.6 Hz and 1.7 Hz, 1H), 7.92 (dd, J=4.6 Hz and 1.1 Hz, 1H), 7.51 (d, J=8.6 Hz, 2H), 7.34 (td, J=8.6 Hz and 1.7 Hz, 1H), 7.28 (d, J=8.0 Hz, 1H), 7.23 (d, J=7.4 Hz, 2H), 7.10 (td, J=7.4 Hz and 1.1 Hz, 1H), 6.87 (dd, J=8.0 Hz and 1.7 Hz, 1H), 6.76 (dd, J=8.0 Hz and 4.6 Hz, 1H), 2.44-2.39 (m, 2H), 2.20-2.15 (m2H), 2.09-2.00 (m, 1H), 1.74-1.67 (m, 1H). LCMS: 474 [M+H].

Example 85

Preparation of 1-[4-(2-isoquinolin-6-yl-9H-imidazo[1,2-d]pyrido[2,3-b][1,4]benzodiazepin-3-yl)phenyl]cyclobutanamine tetrahydrochloride Step 1: Preparation of tert-butyl {1-[4-(2-isoquinolin-6-yl-9H-imidazo[1,2-d]pyrido[2,3-b][1,4]benzodiazepin-3-yl)phenyl]cyclobutyl}carbamate

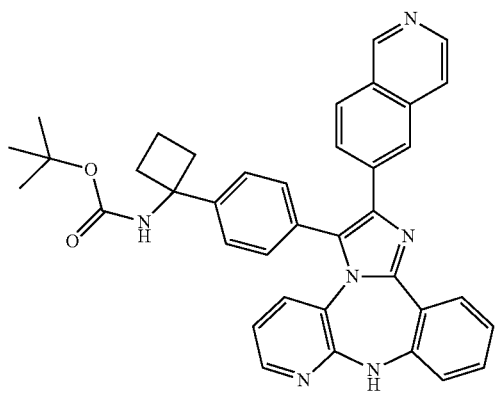 [SMILES: CC(C)(C)OC(=O)NC1(c2ccc(-c3c(-c4ccc5cnccc5c4)nc4n3-c3cccnc3Nc3ccccc3-4)cc2)CCC1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), isoquinolin-6-ylboronic acid (31 mg, 0.18 mmol), bis(di-tert-butyl(4-dimethylaminophenyl)phosphine)dichloropalladium(II) (6 mg, 0.09 mmol), and 2M $Na_2CO_3$ aq. (0.090 mL, 0.18 mmol) in DMF (2.5 mL) was treated with microwave (160° C. for 1 hour). The mixture was diluted with AcOEt, washed with water(×3), brine, dried over $Na_2SO_4$, then filtrated through Celite pad. The filtrate was concentrated and the residue was purified by preparative thin-layer chromatography (n-hexane/AcOEt=1:4) to afford the desired product (40 mg, 74%) as a white solid. $^1$HNMR (CDCl$_3$) 400 MHz δ: 9.17 (s, 1H), 8.45 (d, J=6.3 Hz, 1H), 8.22 (dd, J=8.0 Hz and 1.7 Hz, 1H), 8.13-8.11 (m, 1H), 8.04 (dd, J=4.0 Hz and 1.1 Hz, 1H), 7.82-7.73 (m, 2H), 7.54 (d, J=5.7 Hz, 1H), 7.41 (dd, J=8.6 Hz and 1.7 Hz, 2H), 7.33 (td, J=8.0 Hz and 1.7 Hz, 1H), 7.21-7.17 (m, 2H), 6.97 (d, J=6.9 Hz, 1H), 6.84 (d, J=7.4 Hz, 1H), 6.62 (dd, J=8.0 Hz and 5.2 Hz, 1H), 6.27 (s, 1H), 5.16 (br s, 1H), 2.60-2.52 (m, 2H), 2.52-2.30 (m, 2H), 2.23-2.13 (m, 1H), 1.96-1.88 (m, 1H), 1.39 (br s, 9H). LCMS: 607 [M+H].

Step 2: Preparation of 1-[4-(2-isoquinolin-6-yl-9H-imidazo[1,2-d]pyrido[2,3-b][1,4]benzodiazepin-3-yl)phenyl]cyclobutanamine tetrahydrochloride

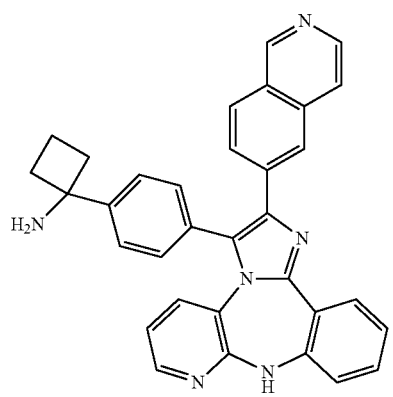 [SMILES: NC1(c2ccc(-c3c(-c4ccc5cnccc5c4)nc4n3-c3cccnc3Nc3ccccc3-4)cc2)CCC1]

tert-Butyl {1-[4-(2-isoquinolin-6-yl-9H-imidazo[1,2-d]pyrido[2,3-b][1,4]benzodiazepin-3-yl)phenyl]cyclobutyl}carbamate (40 mg, 0.066 mmol) in MeOH (0.5 mL) was added 4N HCl-dioxane (2 mL) and stirred at room temperature for 19 hours. The mixture was concentrated to afford the desired product (40 mg, 90%) as a yellow solid. $^1$HNMR (DMSO-d$_6$) 400 MHz δ: 8.76 (br s, 2H), 8.69 (s, 1H), 8.60 (d, J=6.3 Hz, 1H), 8.36 (s, 1H), 8.33-8.28 (m, 2H), 8.14 (dd, J=4.6 Hz and 1.7 Hz, 1H), 8.04 (dd, J=8.0 Hz and 1.7 Hz, 1H), 7.92 (d, J=7.4 Hz, 1H), 7.62 (d, J=8.6 Hz, 2H), 7.45-7.40 (m, 2H), 7.33 (d, J=8.6 Hz, 1H), 7.18 (td, J=7.4 Hz and 1.1 Hz, 1H), 6.98 (dd, J=8.0 Hz and 1.1 Hz, 1H), 6.77 (dd, J=8.0 Hz and 4.6 Hz, 1H), 2.65-2.58 (m, 3H), 2.26-2.19 (m, 2H), 1.90-1.81 (m, 2H). LCMS: 507 [M+H].

Example 86

Preparation of 1-[4-(2-isoquinolin-7-yl-9H-imidazo[1,2-d]pyrido[2,3-b][1,4]benzodiazepin-3-yl)phenyl]cyclobutanamine tetrahydrochloride

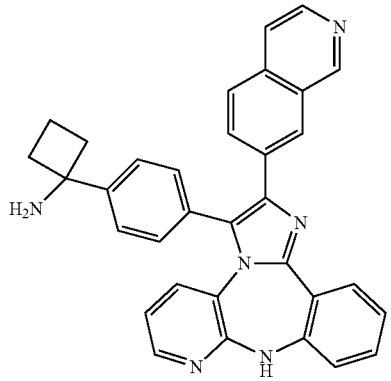 [SMILES: NC1(c2ccc(-c3c(-c4ccc5ccncc5c4)nc4n3-c3cccnc3Nc3ccccc3-4)cc2)CCC1]

The title compound was synthesized according to the procedure described in example 85 using isoquinolin-7-ylboronic acid in step 1 instead of isoquinolin-6-ylboronic acid. $^1$HNMR (DMSO-d$_6$) 400 MHz δ: 9.85 (s, 1H), 8.86 (br s, 2H), 8.69 (s, 1H), 8.62 (d, J=6.9 Hz, 1H), 8.58 (1H, s), 8.39 (d, J=5.7 Hz, 1H), 8.18 (d, J=8.6 Hz, 1H), 8.14-8.12 (m, 2H), 8.03 (dd, J=7.4 Hz and 1.7 Hz, 1H), 7.61 (d, J=8.6 Hz, 2H), 7.42 (d, J=8.6 Hz, 2H), 7.39 (d, J=1.7 Hz, 1H), 7.33 (d, J=7.4 Hz, 1H), 7.17 (td, J=7.4 Hz and 1.1 Hz, 1H), 6.98 (dd, J=7.4 Hz and 1.1 Hz, 1H), 6.78 (dd, J=8.0 Hz and 4.6 Hz, 1H), 2.65-2.57 (m, 2H), 2.27-2.19 (m, 2H), 1.87-1.82 (m, 2H). LCMS: 507 [M+H].

Example 87

Preparation of 1-[4-(2-quinolin-7-yl-9H-imidazo[1,2-d]pyrido[2,3-b][1,4]benzodiazepin-3-yl)phenyl]cyclobutanamine tetrahydrochloride

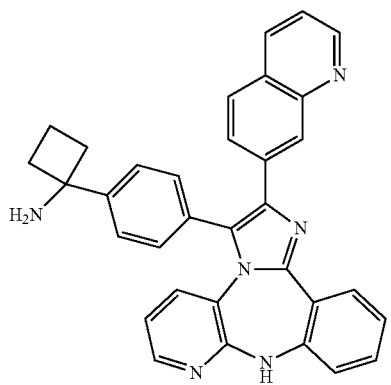 [SMILES: NC1(c2ccc(-c3c(-c4ccc5cccnc5c4)nc4n3-c3cccnc3Nc3ccccc3-4)cc2)CCC1]

The title compound was synthesized according to the procedure described in example 85 using quinolin-7-ylboronic acid in step 1 instead of isoquinolin-6-ylboronic acid. ¹HNMR (DMSO-d₆) 400 MHz δ: 9.10-9.05 (m, 1H), 8.88-8.81 (m, 1H), 8.75 (br s, 2H), 8.68 (br s, 1H), 8.31 (br s, 1H), 8.17-8.13 (m, 1H), 8.13 (dd, J=5.2 Hz and 1.7 Hz, 1H), 8.03 (dd, J=8.0 Hz and 1.7 Hz, 1H), 7.96 (d, J=8.6 Hz, 1H), 7.85-7.81 (m, 1H), 7.61 (d, J=8.6 Hz, 2H), 7.45-7.39 (m, 3H), 7.33 (d, J=8.6 Hz, 1H), 7.17 (td, J=7.4 Hz and 1.1 Hz, 1H), 6.96 (dd, J=8.6 Hz and 1.7 Hz, 1H), 6.77 (dd, J=8.0 Hz and 5.2 Hz, 1H), 3.73-3.65 (m, 1H), 3.55-3.42 (m, 1H), 2.63-2.56 (m, 2H), 2.26-2.18 (m, 1H), 1.90-1.81 (m, 1H). LCMS: 507 [M+H].

Example 88

Preparation of 1-{4-[2-(1,3-Benzothiazol-2-yl)-9H-imidazo[1,2-d]pyrido[2,3-b][1,4]benzodiazepin-3-yl]phenyl}cyclobutanamine trihydrochloride Step 1: Preparation of tert-Butyl (1-{4-[2-(1,3-benzothiazol-2-yl)-9H-imidazo[1,2-d]pyrido[2,3-b][1,4]benzodiazepin-3-yl]phenyl}cyclobutyl)carbamate

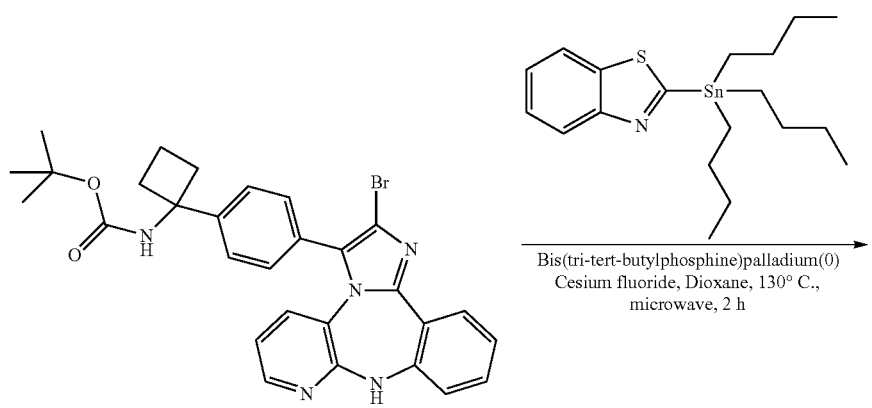

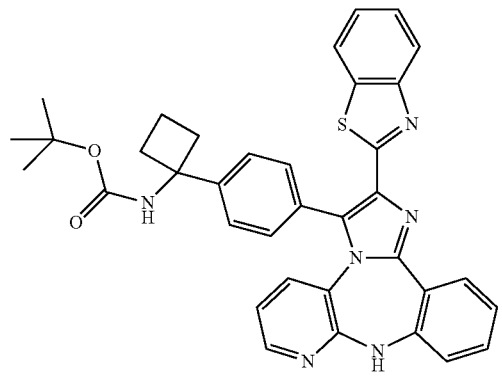

A mixture of tert-butyl {1-[4-(2-bromo-9H-imidazo[1,2-d]pyrido[2,3-b][1,4]benzodiazepin-3-yl)phenyl]cyclobutyl}carbamate (50.0 mg, 0.0895 mmol), 2-(tributylstannyl)-1,3-benzothiazole (76.0 mg, 0.179 mmol), bis (tri-tert-butylphosphine)palladium(0) (9.15 mg, 0.0179 mmol) and cesium fluoride (88.4 mg, 0.582 mmol) in dioxane (1.00 mL) was heated at 130° C. under microwave irradiation for 2 hours under nitrogen. After cooling to room temperature, the mixture was diluted with water and extracted with EtOAc (×3). The combined organic layer was dried over anhydrous Na$_2$SO$_4$ and concentrated. The residue was purified by silica gel column chromatography (EtOAc/hexane=4:1→2:1→1:1) and PTLC (DCM/EtOAc=95:5) to afford desired product (24.8 mg, 45.2%) as pale yellow solid. $^1$HNMR (CDCl$_3$) 500 MHz δ: 8.23 (dd, J=7.7, 1.4 Hz, 1H), 8.06-8.01 (m, 1H), 7.96 (d, J=8.0 Hz, 1H), 7.83 (d, J=8.0 Hz, 1H), 7.53-7.38 (m, 5H), 7.36-7.29 (m, 2H), 7.17 (td, J=7.4, 1.1 Hz, 1H), 6.99-6.96 (m, 1H), 6.93-6.85 (m, 1H), 6.62 (dd, J=8.0, 4.6 Hz, 1H), 6.49-6.45 (m, 1H), 5.20 (br s, 1H), 2.69-2.26 (m, 4H), 2.21-2.09 (m, 1H), 1.97-1.85 (m, 1H), 1.41 (br s, 9H).

Step 2: Preparation of 1-{4-[2-(1,3-Benzothiazol-2-yl)-9H-imidazo[1,2-d]pyrido[2,3-b][1,4]benzodiazepin-3-yl]phenyl}cyclobutanamine trihydrochloride

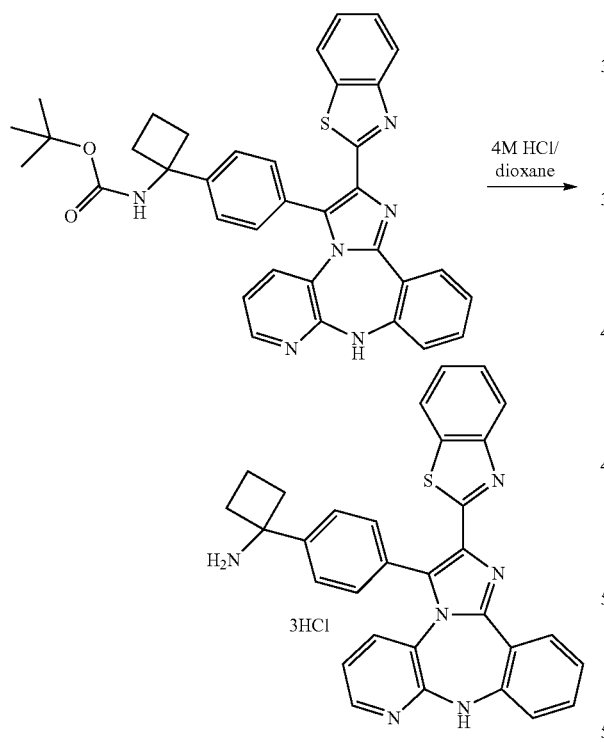

tert-Butyl (1-{4-[2-(1,3-benzothiazol-2-yl)-9H-imidazo[1,2-d]pyrido[2,3-b][1,4]benzodiazepin-3-yl]phenyl}cyclobutyl)carbamate (24.8 mg, 0.0405 mmol) was dissolved in DCM (1 mL). 4M HCl/dioxane (1 mL) was added to the mixture and stirred at room temperature for 18 hours. The mixture was concentrated and solidified with ether. The precipitated solids were collected by filtration and washed with ether to afford desired product (21.8 mg, 86.4%) as yellow solid. $^1$HNMR (DMSO-d$_6$) 400 MHz δ: 8.85-8.65 (m, 3H), 8.16 (dd, J=4.8, 1.6 Hz, 1H), 8.11-8.07 (m, 1H), 7.97 (dd, J=7.8, 1.8 Hz, 1H), 7.83-7.78 (m, 1H), 7.65-7.55 (m, 4H), 7.51-7.46 (m, 1H), 7.45-7.39 (m, 2H), 7.37-7.32 (m, 1H), 7.21-7.15 (m, 1H), 6.98 (dd, J=8.0, 1.6 Hz, 1H), 6.79 (dd, J=8.0, 4.8 Hz, 1H), 2.66-2.54 (m, 4H), 2.28-2.15 (m, 1H), 1.92-1.77 (m, 1H); LCMS: 513 [M+H].

Example 89

Preparation of 1-{4-[2-(1H-imidazo[4,5-b]pyridin-6-yl)-9H-imidazo[1,2-d]pyrido[2,3-b][1,4]benzodiazepin-3-yl]phenyl}cyclobutanamine tetrahydrochloride

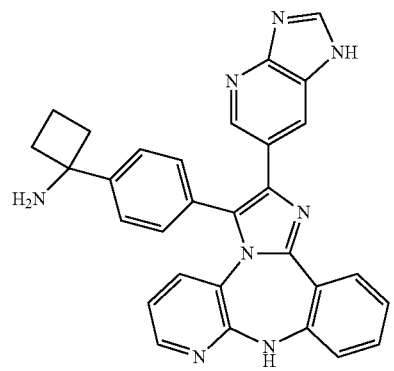 [SMILES: NC1(c2ccc(-c3c(-c4cnc5nc[nH]c5c4)nc4n3-c3cccnc3Nc3ccccc3-4)cc2)CCC1]

The title compound was synthesized according to the procedure described in example 19 using (1H-imidazo[4,5-b]pyridin-6-yl)boronic acid in step 1 instead of 6-(4,4,5,5-tetramethyl-1,3,2-dioxaborolan-2-yl)-1H-pyrrolo[3,2-b]pyridine. $^1$HNMR (DMSO-d$_6$) 400 MHz δ: 8.90-8.80 (m, 1H), 8.73-8.61 (m, 3H), 8.49-8.47 (m, 1H), 8.14-8.13 (m, 2H), 8.00 (d, J=7.4 Hz, 1H), 7.58-7.53 (m, 2H), 7.42-7.34 (m, 2H), 7.32 (dd, J=6.9, 1.1 Hz, 1H), 7.14 (td, J=8.0, 1.1 Hz, 1H), 6.91 (dd, J=8.0, 1.7 Hz, 1H), 6.76 (dd, J=8.6, 5.2 Hz, 1H), 2.61-2.55 (m, 2H), 2.26-2.15 (m, 2H), 1.88-1.79 (m, 2H). LCMS: 497 [M+H].

Example 90

Preparation of 1-(4-{2-[6-(4-methoxyphenyl)pyridin-3-yl]-9H-imidazo[1,2-d]pyrido[2,3-b][1,4]benzodiazepin-3-yl}phenyl)cyclobutanamine tetrahydrochloride Step 1: Preparation of 5-bromo-2-(4-methoxyphenyl)pyridine

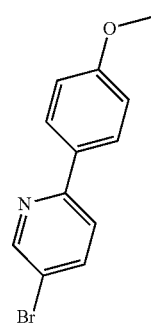

A mixture of 5-bromo-2-iodopyridine (600 mg, 2.11 mmol), (4-methoxyphenyl)boronic acid (353 mg, 2.32 mmol), tetrakis(triphenylphosphine)palladium(0) (122 mg, 0.106 mmol), and 2M $Na_2CO_3$ aq. (2.11 mL, 4.22 mmol) in toluene (10 mL) was heated at 80° C. for 40.5 hours under nitrogen. After cooling to room temperature, water was added and extracted with EtOAc. The organic layer was washed with brine, dried over $Na_2SO_4$ and filtered through a Celite pad. The filtrate was concentrated and the residue was purified by column chromatography ($CH_2Cl_2$ only) to afford the desired product (538 mg, 97%) as a yellow solid. $^1$HNMR ($CDCl_3$) 400 MHz δ: 8.69 (d, J=2.3 Hz, 1H), 7.92 (dt, J=8.6 Hz and 2.3 Hz, 2H), 7.82 (dd, J=8.6 Hz and 2.3 Hz, 1H), 7.56 (d, J=8.6 Hz, 1H), 6.99 (dt, J=8.6 Hz and 2.3 Hz, 2H), 3.87 (s, 3H). LCMS: 264 [M+H].

Step: 2: Preparation of 2-(4-methoxyphenyl)-5-(4,4,5,5-tetramethyl-1,3,2-dioxaborolan-2-yl)pyridine

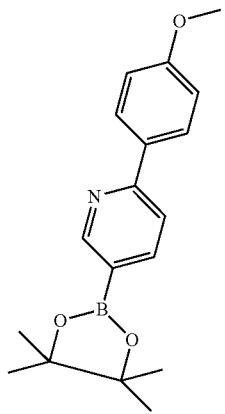

A mixture of 5-bromo-2-(4-methoxyphenyl)pyridine (538 mg, 2.04 mmol), 4,4,4',4',5,5,5',5'-octamethyl-2,2'-bi-1,3,2-dioxaborolane (621 mg, 2.44 mmol), [1,1'-Bis(diphenylphosphino)ferrocene]dichloropalladium(II), complex with dichlorometahne(1:1) (83 mg, 0.10 mmol), and potassium acetate (601 mg, 6.12 mmol) in dioxane (10 mL) was heated at 80° C. for 65.5 hours under nitrogen. The mixture was diluted with AcOEt, washed with water(×3), brine, dried over $Na_2SO_4$, then filtrated through Celite pad. The filtrate was concentrated and the residue was purified by column chromatography (n-hexane/AcOEt=100:0-0:100) to afford the mixture of the desired product and the starting material (198 mg) as a white solid. LCMS: 312 [M+H].

Step 3: Preparation of tert-butyl[1-(4-{2-[6-(4-methoxyphenyl)pyridin-3-yl]-9H-imidazo[1,2-d]pyrido[2,3-b][1,4]benzodiazepin-3-yl}phenyl)cyclobutyl]carbamate

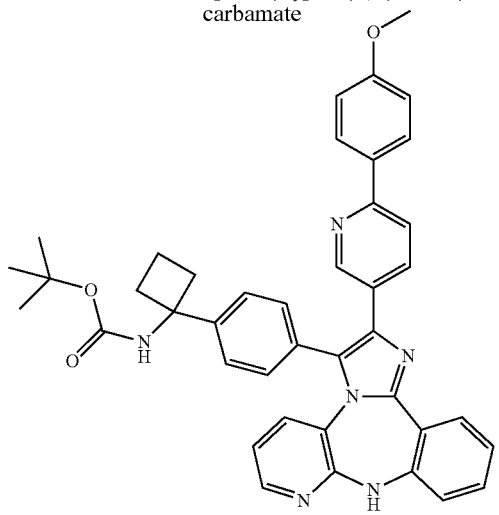

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), 2-(4-methoxyphenyl)-5-(4,4,5,5-tetramethyl-1,3,2-dioxaborolan-2-yl)pyridine (84 mg, 0.27 mmol), bis(di-tert-butyl(4-dimethylaminophenyl)phosphine)dichloropalladium(II) (6 mg, 0.09 mmol), and 2M $Na_2CO_3$ aq. (0.090 mL, 0.18 mmol) in DMF (2.5 mL) was treated with microwave (160° C. for 1 hour). The mixture was diluted with AcOEt, washed with water(×3), brine, dried over $Na_2SO_4$, then filtrated through Celite pad. The filtrate was concentrated and the residue was purified by preparative thin-layer chromatography (n-hexane/AcOEt=1:1) to afford the desired product (61 mg, quant) as a yellow solid. $^1$HNMR (CDCl3) 400 MHz δ: 8.79 (d, J=2.3 Hz, 1H), 8.17 (dd, J=7.4 Hz and 1.7 Hz, 1H), 8.06-8.00 (m, 2H), 7.95 (d, J=8.6 Hz, 2H), 7.63 (d, J=8.6 Hz, 1H), 7.39 (d, J=8.0 Hz, 2H), 7.32 (td, J=7.4 Hz and 1.7 Hz, 1H), 7.20 (d, J=8.0 Hz, 1H), 7.17 (td, J=8.0 Hz and 1.7 Hz, 1H), 7.00-6.95 (m, 3H), 6.83-6.78 (m, 1H), 6.61 (dd, J=8.0 Hz and 4.6 Hz, 1H), 6.26 (s, 1H), 5.12 (br s, 1H), 3.86 (s, 3H), 2.58-2.42 (m, 4H), 2.18-2.11 (m, 1H), 1.94-1.87 (m, 1H), 1.40 (br s, 9H). LCMS: 663 [M+H].

Step 4: Preparation of 1-(4-{2-[6-(4-methoxyphenyl)pyridin-3-yl]-9H-imidazo[1,2-d]pyrido[2,3-b][1,4]benzodiazepin-3-yl}phenyl)cyclobutanamine tetrahydrochloride

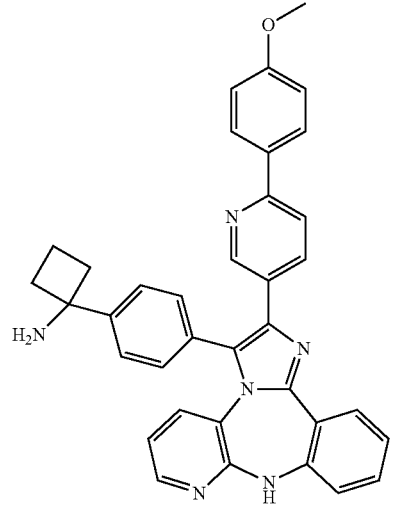 [SMILES: COc1ccc(-c2ccc(-c3nc4n(c3-c3ccc(C5(N)CCC5)cc3)-c3cccnc3Nc3ccccc3-4)cn2)cc1]

tert-Butyl {1-[4-(2-bromo-9H-imidazo[1,2-d]pyrido[2,3-b][1,4]benzodiazepin-3-yl)phenyl]cyclobutyl}carbamate (61 mg, 0.090 mmol) in MeOH (0.5 mL) was added 4N HCl-dioxane (2 mL) and stirred at r.t for 18 hours. The mixture was concentrated to afford the desired product (55 mg, 87%) as a yellow solid. $^1$HNMR (DMSO-$d_6$) 400 MHz δ: 8.67-8.60 (m, 4H), 8.12 (dd, J=4.6, Hz and 1.7 Hz, 1H), 8.03 (d, J=8.6 Hz, 2H), 7.99 (dd, J=8.0 Hz and 1.7 Hz, 1H), 7.94 (dd, J=8.6 Hz and 1.1 Hz, 1H), 7.58 (d, J=8.6 Hz, 2H), 7.42-7.37 (m, 2H), 7.32-7.30 (m, 1H), 7.15 (td, J=8.0 Hz and 1.7 Hz, 1H), 7.05 (d, J=9.2 Hz, 2H), 6.91 (dd, J=8.0 Hz and 1.1 Hz, 1H), 6.75 (dd, J=8.0 Hz and 5.2 Hz, 1H), 3.82 (s, 3H), 2.61-2.53 (m, 4H), 2.27-2.12 (m, 1H), 1.91-1.76 (m, 1H). LCMS: 563 [M+H].

Example 91

Preparation of 1-{4-[2-(1,3-benzoxazol-2-yl)-9H-imidazo[1,2-d]pyrido[2,3-b][1,4]benzodiazepin-3-yl]phenyl}cyclobutanamine trihydrochloride Step 1: Preparation of tert-Butyl (1-{4-[2-(1,3-benzoxazol-2-yl)-9H-imidazo[1,2-d]pyrido[2,3-b][1,4]benzodiazepin-3-yl]phenyl}cyclobutyl)carbamate

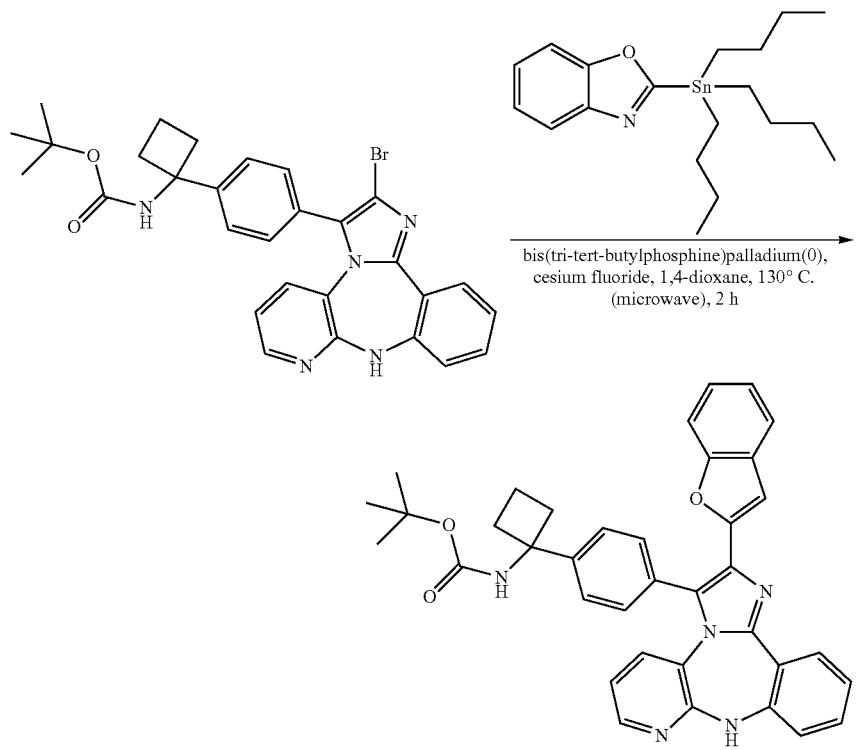

A mixture of tert-butyl {1-[4-(2-bromo-9H-imidazo[1,2-d]pyrido[2,3-b][1,4]benzodiazepin-3-yl)phenyl]cyclobutyl}carbamate (50.0 mg, 0.0895 mmol), 2-(tributylstannyl)-1,3-benzoxazole (81.2 mg, 0.179 mmol), bis (tri-tert-butylphosphine)palladium(0) (9.15 mg, 0.0179 mmol) and cesium fluoride (88.4 mg, 0.582 mmol) in 1,4-dioxane (1.00 mL) was heated at 130° C. under microwave irradiation for 2 hours under nitrogen. After cooling to room temperature, the mixture was diluted with water and extracted with EtOAc (×3). The combined organic layer was dried over anhydrous Na$_2$SO$_4$ and concentrated. The residue was purified by PTLC (EtOAc/hexane=1:1, DCM/EtOAc=1:1) to afford desired product (11.3 mg, 21.2%) as white solid. $^1$HNMR (CDCl$_3$) 500 MHz δ: 8.27 (dd, J=7.7, 1.7 Hz, 1H), 8.08-8.02 (m, 1H), 7.75-7.68 (m, 1H), 7.52-7.38 (m, 5H), 7.37-7.25 (m, 3H), 7.20-7.14 (m, 1H), 6.98 (d, J=8.0 Hz, 1H), 6.92-6.81 (m, 1H), 6.63 (dd, J=8.0, 4.6 Hz, 1H), 6.45 (s, 1H), 5.20 (s, 1H), 2.68-2.25 (m, 4H), 2.22-2.09 (m, 1H), 1.97-1.86 (m, 1H), 1.54-1.11 (m, 9H).

Step 2: Preparation of 1-{4-[2-(1,3-Benzoxazol-2-yl)-9H-imidazo[1,2-d]pyrido[2,3-b][1,4]benzodiazepin-3-yl]phenyl}cyclobutanamine trihydrochloride

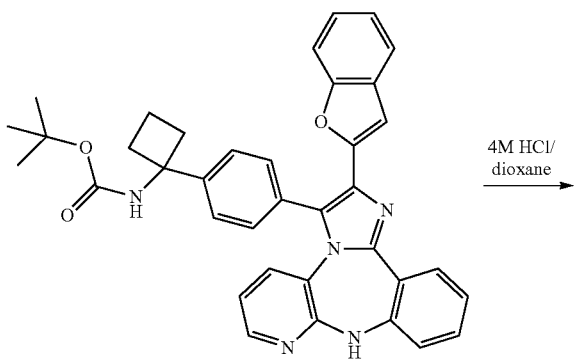

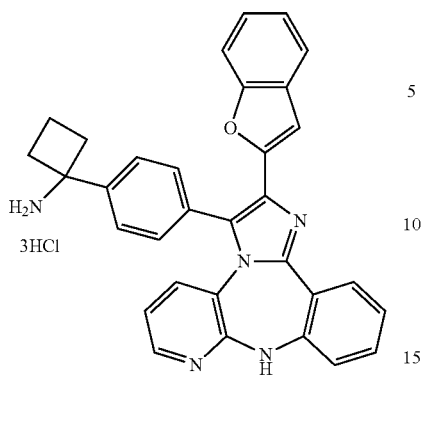

tert-Butyl (1-{4-[2-(1,3-benzoxazol-2-yl)-9H-imidazo[1,2-d]pyrido[2,3-b][1,4]benzodiazepin-3-yl]phenyl}cyclobutyl)carbamate (11.3 mg, 0.0189 mmol) was dissolved in DCM (1 mL). 4M HCl/dioxane (1 mL) was added to the mixture and stirred at room temperature for 17.5 hours. The mixture was concentrated and solidified with ether. The precipitated solids were collected by filtration and washed with ether to afford desired product (10.6 mg, 92.7%) as pale yellow solid. ¹HNMR (DMSO-$d_6$) 400 MHz δ: 8.73 (s, 1H), 8.67 (br s, 3H), 8.16 (dd, J=4.8, 1.6 Hz, 1H), 8.00 (dd, J=7.9, 1.6 Hz, 1H), 7.75-7.71 (m, 1H), 7.68-7.64 (m, 1H), 7.63-7.49 (m, 4H), 7.46-7.31 (m, 4H), 7.21-7.13 (m, 1H), 6.95 (dd, J=7.9, 1.6 Hz, 1H), 6.77 (dd, J=7.9, 4.8 Hz, 1H), 2.70-2.43 (m, 4H), 2.27-2.13 (m, 1H), 1.93-1.78 (m, 1H); LCMS: 497 [M+H].

Example 92

Preparation of N-(4-{3-[4-(1-aminocyclobutyl)phenyl]-9H-imidazo[1,2-d]pyrido[2,3-b][1,4]benzodiazepin-2-yl}phenyl)-N-methylacetamide trihydrochloride Step 1: Preparation of N-methyl-N-[4-(4,4,5,5-tetramethyl-1,3,2-dioxaborolan-2-yl)phenyl]acetamide

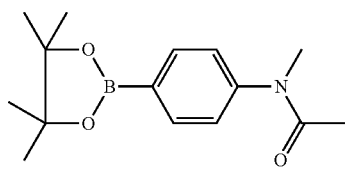 [SMILES: CC(=O)N(C)c1ccc(B2OC(C)(C)C(C)(C)O2)cc1]

A mixture of tert-butyl N-[4-(4,4,5,5-tetramethyl-1,3,2-dioxaborolan-2-yl)phenyl]acetamide (100 mg, 0.429 mmol) in pyridine (1 mL) was added acetic anhydrate (1 mL) and stirred at room temperature for 23 hours. The mixture was diluted with AcOEt, washed with 1N HCl, brine, dried over Na₂SO₄, then filtrated through Celite pad. The filtrate was concentrated to afford the desired product (91 mg, 77%) as a dark brown solid. ¹HNMR (CDCl₃) 400 MHz δ: 7.85 (d, J=8.0 Hz, 2H), 7.19 (d, J=8.0 Hz, 2H), 3.27 (s, 3H), 1.88 (s, 3H), 1.35 (s, 12H).

Step 2: Preparation of tert-butyl {1-[4-(2-{4-[acetyl(methyl)amino]phenyl}-9H-imidazo[1,2-d]pyrido[2,3-b][1,4]benzodiazepin-3-yl)phenyl]cyclobutyl}carbamate

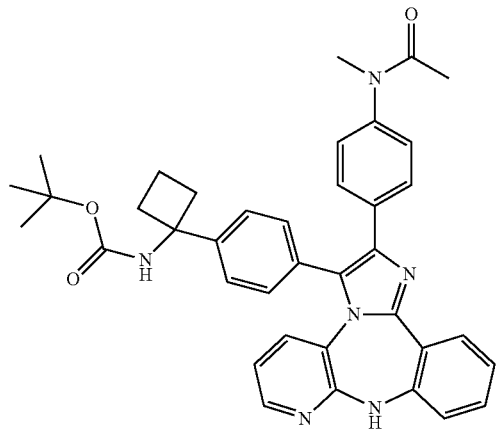 [SMILES: CC(=O)N(C)c1ccc(-c2nc3n(c2-c2ccc(C4(NC(=O)OC(C)(C)C)CCC4)cc2)-c2cccnc2Nc2ccccc2-3)cc1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), N-methyl-N-[4-(4,4,5,5-tetramethyl-1,3,2-dioxaborolan-2-yl)phenyl]acetamide (49 mg, 0.18 mmol), bis(di-tert-butyl(4-dimethylaminophenyl)phosphine)dichloropalladium(II) (6 mg, 0.009 mmol), and 2M Na₂CO₃ aq. (0.090 mL, 0.18 mmol) in DMF (3 mL) was treated with microwave (160° C. for 1 hour). The mixture was diluted with AcOEt, washed with water(×3), brine, dried over Na₂SO₄, then filtrated through Celite pad. The filtrate was concentrated and the residue was purified by preparative thin-layer chromatography (n-hexane/AcOEt=1:4) to afford the desired product (30 mg, 53%) as a pale pink solid. ¹HNMR (CDCl₃) 400 MHz δ: 8.16 (dd, J=8.0 Hz and 1.7 Hz, 1H), 8.02 (d, J=2.9 Hz, 1H), 7.63 (d, J=8.0 Hz, 2H), 7.39 (d, J=8.0 Hz, 2H), 7.32 (td, J=8.0 Hz and 1.7 Hz, 2H), 7.18 (d, J=8.0 Hz, 2H), 7.16 (t, J=8.0 Hz, 1H), 7.06 (d, J=8.0 Hz, 2H), 6.96 (d, J=8.0 Hz, 1H), 6.81 (d, J=8.0 Hz, 1H), 6.61 (dd, J=8.0 Hz and 4.6 Hz, 1H), 6.27 (s, 1H), 5.13 (br s, 1H), 3.26 (s, 3H), 2.58-2.52 (m, 2H), 2.51-2.39 (m, 2H), 2.19-2.13 (m, 1H), 1.95-1.85 (m, 4H), 1.39 (br s, 9H). LCMS: 627 [M+H].

Step 3: Preparation of N-(4-{3-[4-(1-aminocyclobutyl)phenyl]-9H-imidazo[1,2-d]pyrido[2,3-b][1,4]benzodiazepin-2-yl}phenyl)-N-methylacetamide trihydrochloride

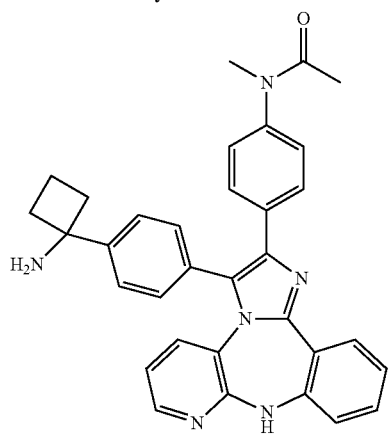

tert-Butyl {1-[4-(2-{4-[acetyl(methyl)amino]phenyl}-9H-imidazo[1,2-d]pyrido[2,3-b][1,4]benzodiazepin-3-yl)phenyl]cyclobutyl}carbamate (30 mg, 0.048 mmol) in MeOH (0.5 mL) was added 4N HCl-dioxane (2 mL) and stirred at room temperature for 20.5 hours. The mixture was concentrated to afford the desired product (28 mg, 93%) as a yellow solid. $^1$HNMR (DMSO-$d_6$) 400 MHz δ: 8.68 (br s, 2H), 8.62 (s, 1H), 8.10 (dd, J=4.9 Hz and 1.4 Hz, 1H), 7.96 (dd, J=7.7 Hz and 1.4 Hz, 1H), 7.56 (d, J=8.6 Hz, 3H), 7.37 (d, J=8.6 Hz, 2H), 7.31-7.26 (m, 2H), 7.13 (t, J=8.6 Hz, 1H), 6.88 (dd, J=8.0 Hz and 1.1 Hz, 1H), 6.73 (dd, J=8.0 Hz and 4.6 Hz, 1H), 3.73-3.65 (m, 1H), 3.51-3.45 (m, 1H), 3.17-3.13 (m, 2H), 2.59-2.47 (m, 3H), 2.23-2.15 (m, 2H), 1.88-1.75 (m, 3H). LCMS: 527 [M+H].

Example 93

Preparation of methyl (4-{3-[4-(1-aminocyclobutyl)phenyl]-9H-imidazo[1,2-d]pyrido[2,3-b][1,4]benzodiazepin-2-yl}phenyl)carbamate Step 1: Preparation of methyl[4-(4,4,5,5-tetramethyl-1,3,2-dioxaborolan-2-yl)phenyl]carbamate

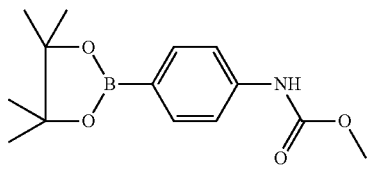

A mixture of 4-(4,4,5,5-tetramethyl-1,3,2-dioxaborolan-2-yl)aniline (150 mg, 0.685 mmol) and pyridine (0.277 mL, 3.43 mmol) in 1,2-dichloroethane (3.5 mL) was added methyl chloroformate (0.058 mL, 0.754 mmol) at 0° C. and stirred at 60° C. for 6 hours. The mixture was diluted with AcOEt, washed with 1N HCl, brine, dried over Na$_2$SO$_4$, then filtrated through Celite pad. The filtrate was concentrated to afford the desired product (198 mg, quant) as a pale yellow oil. $^1$HNMR (CDCl$_3$) 400 MHz δ: 7.75 (d, J=8.6 Hz, 2H), 7.39 (d, J=8.6 Hz, 2H), 6.64 (br s, 1H), 3.78 (s, 3H), 1.34 (s, 12H).

Step 2: Preparation of methyl {4-[3-(4-{1-[(tert-butoxycarbonyl)amino]cyclobutyl}phenyl)-9H-imidazo[1,2-d]pyrido[2,3-b][1,4]benzodiazepin-2-yl]phenyl}carbamate

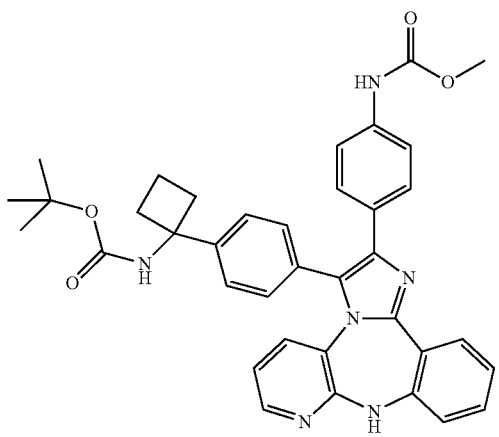 [SMILES: COC(=O)Nc1ccc(-c2nc3n(c2-c2ccc(C4(NC(=O)OC(C)(C)C)CCC4)cc2)-c2cccnc2Nc2ccccc2-3)cc1]

A mixture of tert-butyl {1-[4-(2-bromo-9H-imidazo[1,2-d]pyrido[2,3-b][1,4]benzodiazepin-3-yl)phenyl]cyclobutyl}carbamate (50 mg, 0.090 mmol), methyl[4-(4,4,5,5-tetramethyl-1,3,2-dioxaborolan-2-yl)phenyl]carbamate (49 mg, 0.18 mmol), Bis(di-tert-butyl(4-dimethylaminophenyl)phosphine)dichloropalladium(II) (6 mg, 0.009 mmol), and 2M Na$_2$CO$_3$ aq. (0.090 mL, 0.18 mmol) in DMF (3 mL) was treated with microwave (160° C. for 1 hour). The mixture was diluted with AcOEt, washed with water(×3), brine, dried over Na$_2$SO$_4$, then filtrated through Celite pad. The filtrate was concentrated and the residue was purified by preparative thin-layer chromatography (n-hexane/AcOEt=1:2) to afford the desired product (41 mg, 73%) as a yellow solid. $^1$HNMR (CDCl$_3$) 400 MHz δ: 8.16 (dd, J=8.0 Hz and 2.3 Hz, 1H), 8.00-7.99 (m, 1H), 7.53 (d, J=8.0 Hz, 2H), 7.36 (d, J=8.0 Hz, 2H), 7.30 (td, J=8.0 Hz and 2.9 Hz, 2H), 7.16-7.13 (m, 3H), 6.94 (d, J=8.0 Hz, 1H), 6.81-6.77 (m, 1H), 6.59 (dd, J=8.0, 4.6 Hz, 1H), 6.57-6.54 (m, 1H), 6.24-6.22 (m, 1H), 5.18-5.00 (m, 1H), 3.77 (s, 3H), 2.57-2.48 (m, 4H), 2.19-2.10 (m, 1H), 1.93-1.87 (m, 1H), 1.39 (br s, 9H). LCMS: 629 [M+H].

Step 3: Preparation of methyl (4-{3-[4-(1-aminocyclobutyl)phenyl]-9H-imidazo[1,2-d]pyrido[2,3-b][1,4]benzodiazepin-2-yl}phenyl)carbamate

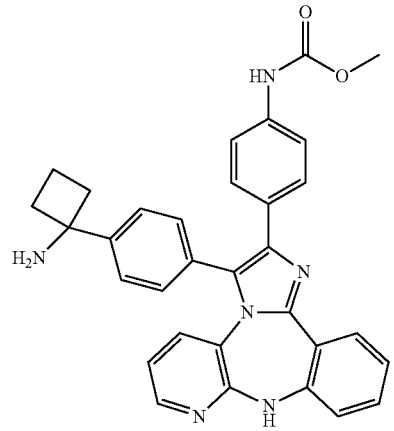 [SMILES: COC(=O)Nc1ccc(-c2nc3n(c2-c2ccc(C4(N)CCC4)cc2)-c2cccnc2Nc2ccccc2-3)cc1]

Methyl{4-[3-(4-{1-[(tert-butoxycarbonyl)amino]cyclobutyl}phenyl)-9H-imidazo[1,2-d]pyrido[2,3-b][1,4]benzodiazepin-2-yl]phenyl}carbamate (41 mg, 0.050 mmol) in MeOH (0.5 mL) was added 4N HCl-dioxane (2 mL) and stirred at room temperature for 24 hours. The mixture was concentrated to afford the desired product (35 mg, 83%) as a yellow solid. $^1$HNMR (DMSO-$d_6$) 400 MHz δ: 9.79 (s, 1H), 8.79-8.73 (m, 3H), 8.14 (dd, J=4.0 Hz and 1.7 Hz, 1H), 7.96 (dd, J=8.0 Hz and 1.1 Hz, 1H), 7.56 (d, J=8.0 Hz, 2H), 7.44-7.40 (m, 4H), 7.34-7.30 (m, 3H), 7.17 (t, J=7.2 Hz, 1H), 6.91 (dd, J=8.0 Hz and 1.1 Hz, 1H), 6.78 (dd, J=8.0 Hz and 4.6

Hz, 1H), 3.66 (s, 3H), 2.57 (t, J=7.7 Hz, 4H), 2.24-2.16 (m, 1H), 1.85-1.78 (m, 1H). LCMS: 529 [M+H].

Example 94

Preparation of N-(4-{3-[4-(1-Aminocyclobutyl)phenyl]-9H-imidazo[1,2-d]pyrido[2,3-b][1,4]benzodiazepin-2-yl}phenyl)-2-methylpropanamide trihydrochloride Step 1: Preparation of 2-methyl-N-[4-(4,4,5,5-tetramethyl-1,3,2-dioxaborolan-2-yl)phenyl]propanamide

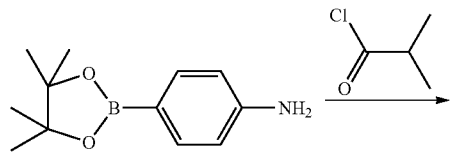

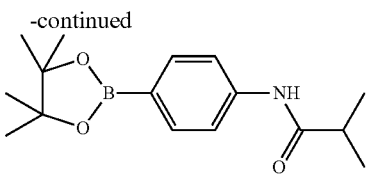

The title compound was synthesized according to step 1 of example 93 except isobutyryl chloride was used. $^1$HNMR (CDCl$_3$) 400 MHz δ: 7.76 (d, J=8.7 Hz, 2H), 7.55 (d, J=8.7 Hz, 2H), 7.29 (br s, 1H), 2.51 (septet, J=6.9 Hz, 1H), 1.33 (s, 12H), 1.25 (d, J=6.9 Hz, 6H).

Step 2: Preparation of tert-Butyl[1-(4-{2-[4-(isobutyrylamino)phenyl]-9H-imidazo[1,2-d]pyrido[2,3-b][1,4]benzodiazepin-3-yl}phenyl)cyclobutyl]carbamate

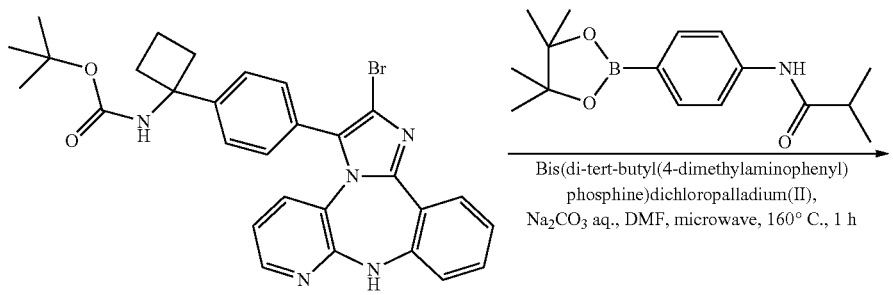

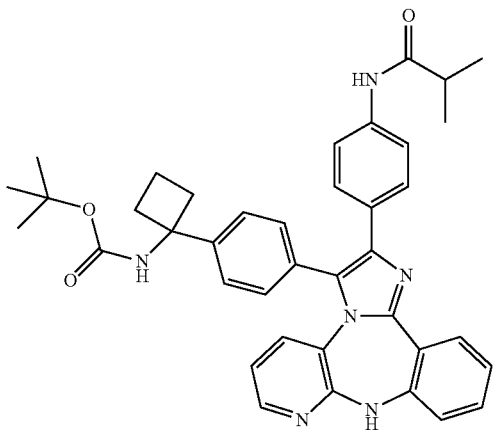

The title compound was synthesized according to the procedure described in step 2 of example 93. ¹HNMR (CDCl₃) 400 MHz δ: 8.16 (dd, J=7.7, 1.4 Hz, 1H), 8.03-7.98 (m, 1H), 7.58-7.49 (m, 2H), 7.48-7.41 (m, 2H), 7.38-7.24 (m, 4H), 7.20-7.06 (m, 3H), 6.95 (d, J=7.7 Hz, 1H), 6.85-6.73 (m, 1H), 6.59 (dd, J=8.2, 5.0 Hz, 1H), 6.45 (br s, 1H), 5.22 (s, 1H), 2.61-2.25 (m, 5H), 2.20-2.07 (m, 1H), 1.96-1.84 (m, 1H), 1.39 (br s, 9H), 1.24 (d, J=6.8 Hz, 6H).

Step 3: Preparation of N-(4-{3-[4-(1-Aminocyclobutyl)phenyl]-9H-imidazo[1,2-d]pyrido[2,3-b][1,4]benzodiazepin-2-yl}phenyl)-2-methylpropanamide trihydrochloride

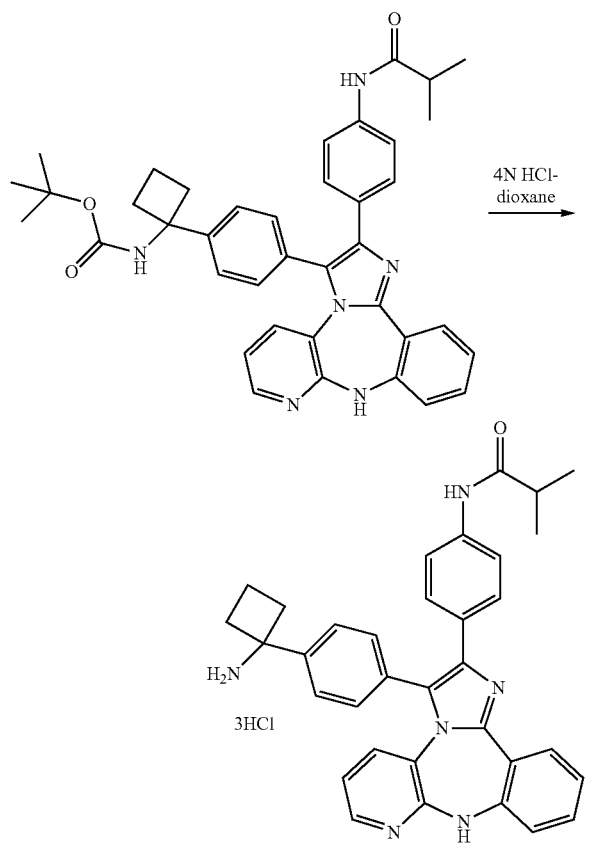

The title compound was synthesized according to the procedure described in step 3 of example 93. ¹HNMR (DMSO-d₆) 400 MHz δ: 9.99 (s, 1H), 8.82-8.57 (m, 3H), 8.12 (dd, J=4.5, 1.6 Hz, 1H), 7.95 (dd, J=7.7, 1.6 Hz, 1H), 7.61-7.51 (m, 4H), 7.44-7.25 (m, 6H), 7.18-7.11 (m, 1H), 6.90 (dd, J=7.7, 1.6 Hz, 1H), 6.76 (dd, J=7.7, 4.5 Hz, 1H), 2.65-2.35 (m, 5H), 2.26-2.12 (m, 1H), 1.89-1.74 (m, 1H), 1.09 (d, J=6.8 Hz, 6H); LCMS: 541 [M+H].

Example 95

Preparation of 1-(4-{3-[4-(1-Aminocyclobutyl)phenyl]-9H-imidazo[1,2-d]pyrido[2,3-b][1,4]benzodiazepin-2-yl}phenyl)piperidin-2-one trihydrochloride Step 1: Preparation of 1-[4-(4,4,5,5-tetramethyl-1,3,2-dioxaborolan-2-yl)phenyl]piperidin-2-one

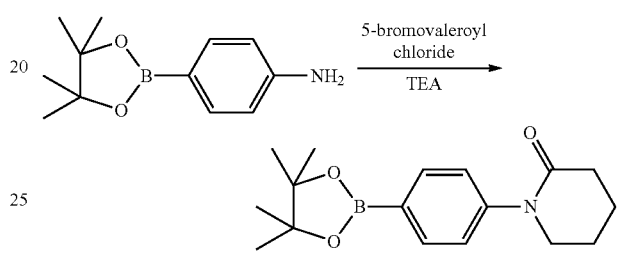

Et₃N (239 μL, 1.71 mmol) and 5-bromovaleroyl chloride (166 μL, 1.26 mmol) were added to a solution of 4-aminophenylboronic acid pinacol ester (250 mg, 1.14 mmol) in DCM (5 mL) at 0° C. After stirring the mixture for 18.5 hours at room temperature, the mixture was concentrated. The residue was diluted with EtOAc and washed with sat. NaHCO₃ and brine. The organic layer was dried over anhydrous Na₂SO₄, and concentrated. The residue was diluted with DMF (5 mL) and NaH (55% in liquid paraffin, 62.2 mg, 1.43 mmol) at 0° C. After stirring the mixture for 21 hours at room temperature, the mixture was concentrated. The residue was diluted with 10% aqueous citric acid and extracted with DCM (3×). The combined organic layers were dried over anhydrous Na₂SO₄, and concentrated. The residue was purified by PTLC (EtOAc/hexane=1:1) to afford desired product (124 mg, 36.1%) as white solid. ¹HNMR (CDCl₃) 400 MHz δ: 7.86-7.81 (m, 2H), 7.30-7.24 (m, 2H), 3.70-3.60 (m, 2H), 2.61-2.51 (m, 2H), 2.00-1.87 (m, 4H), 1.33 (s, 12H).

Step 2: Preparation of tert-Butyl[1-(4-{2-[4-(2-oxopiperidin-1-yl)phenyl]-9H-imidazo[1,2-d]pyrido[2,3-b][1,4]benzodiazepin-3-yl}phenyl)cyclobutyl]carbamate

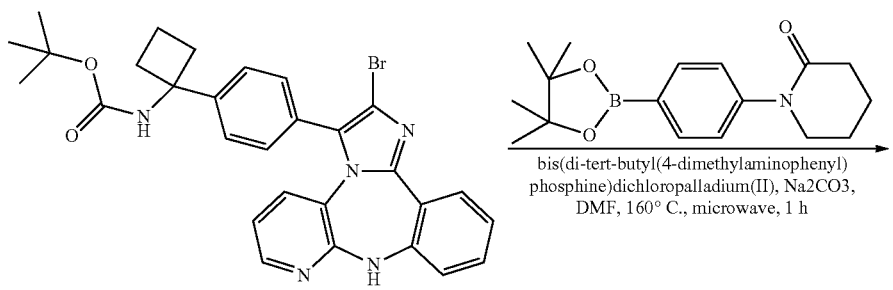

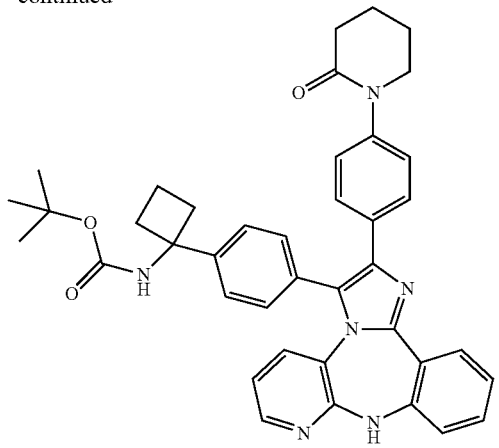

A mixture of tert-butyl {1-[4-(2-bromo-9H-imidazo[1,2-d]pyrido[2,3-b][1,4]benzodiazepin-3-yl)phenyl]cyclobutyl}carbamate (50.0 mg, 0.0895 mmol), 1-[4-(4,4,5,5-tetramethyl-1,3,2-dioxaborolan-2-yl)phenyl]piperidin-2-one (40.5 mg, 0.134 mmol), bis(di-tert-butyl(4-dimethylaminophenyl)phosphine)dichloropalladium(II) (6.34 mg, 0.00895 mmol) and 2 M Na₂CO₃ (0.0895 mL, 0.179 mmol) in DMF (1.00 mL) was heated at 160° C. under microwave irradiation for 1 hour. After cooling to room temperature, the mixture was diluted with water and extracted with CHCl₃ (×3). The combined organic layers were dried over anhydrous Na₂SO₄ and concentrated. The residue was purified by PTLC (CHCl₃/MeOH=9:1, EtOAc/CHCl₃=1:1) to afford desired product (31.9 mg, 54.6%) as a pale yellow solid. ¹HNMR (CDCl₃) 500 MHz δ: 8.16 (dd, J=7.7, 1.4 Hz, 1H), 8.03-7.97 (m, 1H), 7.61 (d, J=8.0 Hz, 2H), 7.35 (d, J=8.0 Hz, 2H), 7.31-7.25 (m, 1H), 7.21-7.10 (m, 5H), 6.95 (d, J=7.4 Hz, 1H), 6.84-6.69 (m, 1H), 6.59 (dd, J=8.0, 4.6 Hz, 1H), 6.51-6.45 (m, 1H), 5.21 (br s, 1H), 3.64-3.57 (m, 2H), 2.61-2.26 (m, 6H), 2.18-2.07 (m, 1H), 1.97-1.80 (m, 5H), 1.40 (br s, 9H).

Step 3: Preparation of 1-(4-{3-[4-(1-Aminocyclobutyl)phenyl]-9H-imidazo[1,2-d]pyrido[2,3-b][1,4]benzodiazepin-2-yl}phenyl) piperidin-2-one trihydrochloride

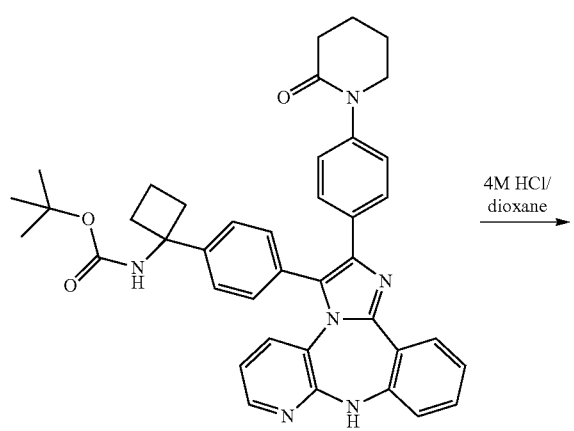

4M HCl/dioxane →

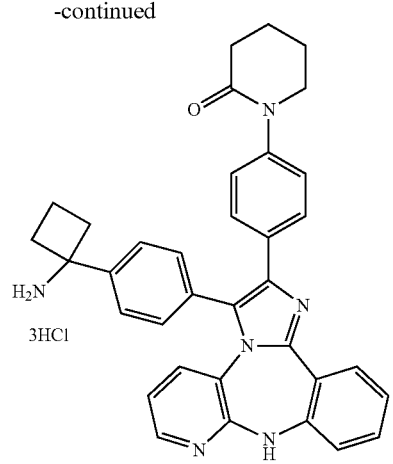

tert-Butyl[1-(4-{2-[4-(2-oxopiperidin-1-yl)phenyl]-9H-imidazo[1,2-d]pyrido[2,3-b][1,4]benzodiazepin-3-yl}phenyl)cyclobutyl]carbamate (31.9 mg, 0.0489 mmol) was dissolved in DCM (1 mL). 4M HCl/dioxane (1 mL) was added to the mixture and stirred at room temperature for 19 hours. The mixture was concentrated and solidified with ether. The precipitated solids were collected by filtration and washed with ether to afford desired product (27.2 mg, 84.1%) as yellow solid. ¹HNMR (DMSO-d₆) 500 MHz δ: 8.80-8.69 (m, 3H), 8.65 (br s, 1H), 8.13-8.09 (m, 1H), 7.98-7.93 (m, 1H), 7.59-7.54 (m, 2H), 7.51-7.47 (m, 2H), 7.41-7.29 (m, 4H), 7.25-7.21 (m, 2H), 7.16-7.11 (m, 1H), 6.93-6.88 (m, 1H), 6.75 (dd, J=7.7, 4.9 Hz, 1H), 3.62-3.57 (m, 2H), 2.62-

2.47 (m, 4H), 2.41-2.35 (m, 2H), 2.24-2.13 (m, 1H), 1.90-1.78 (m, 5H); LCMS: 553 [M+H].

Example 96

Preparation of N-(4-{3-[4-(1-Aminocyclobutyl)phenyl]-9H-imidazo[1,2-d]pyrido[2,3-b][1,4]benzodiazepin-2-yl}phenyl)cyclopropanecarboxamide trihydrochloride Step 1: Preparation of N-[4-(4,4,5,5-Tetramethyl-1,3,2-dioxaborolan-2-yl)phenyl]cyclopropanecarboxamide

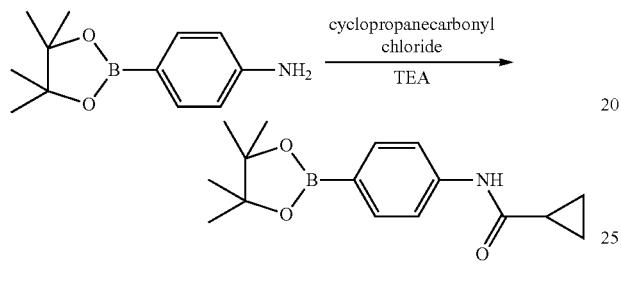

Et₃N (239 μL, 1.71 mmol) and cyclopropanecarbonyl chloride (114 μL, 1.26 mmol) were added to a solution of 4-aminophenylboronic acid pinacol ester (250 mg, 1.14 mmol) in DCM (5 mL) at 0° C. After stirring the mixture for 4 hours at room temperature, the mixture was concentrated. The residue was diluted with EtOAc and washed with 10% aqueous citric acid, sat. NaHCO₃ and brine. The organic layer was dried over anhydrous Na₂SO₄, and concentrated. The residue was purified by silica gel column chromatography (EtOAc/hexane=9:1→4:1) to afford desired product (291 mg, 88.9%) as white solid. $^1$HNMR (CDCl₃) 400 MHz δ: 7.82-7.70 (m, 2H), 7.59-7.47 (m, 2H), 7.43 (br s, 1H), 1.54-1.44 (m, 1H), 1.33 (s, 12H), 1.09 (dt, J=7.4, 4.2 Hz, 2H), 0.85 (td, J=7.4, 4.2 Hz, 2H).

Step 2: Preparation of tert-Butyl {1-[4-(2-{4-[(cyclopropylcarbonyl)amino]phenyl}-9H-imidazo[1,2-d]pyrido[2,3-b][1,4]benzodiazepin-3-yl)phenyl]cyclobutyl}carbamate

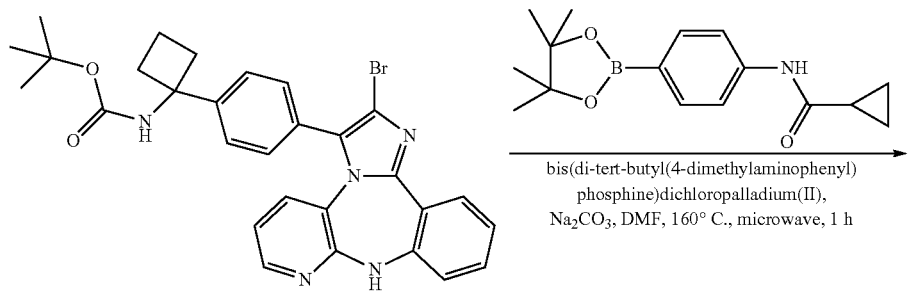

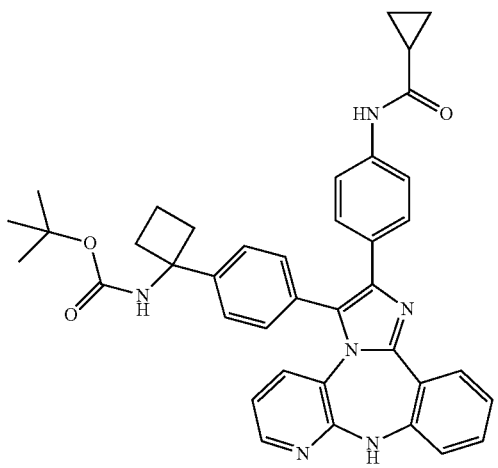

A mixture of tert-butyl {1-[4-(2-bromo-9H-imidazo[1,2-d]pyrido[2,3-b][1,4]benzodiazepin-3-yl)phenyl]cyclobutyl}carbamate (50.0 mg, 0.0895 mmol), N-[4-(4,4,5,5-tetramethyl-1,3,2-dioxaborolan-2-yl)phenyl]cyclopropanecarboxamide (38.6 mg, 0.134 mmol), bis(di-tert-butyl(4-dimethylaminophenyl)phosphine)dichloropalladium(II) (6.34 mg, 0.00895 mmol) and 2 M Na$_2$CO$_3$ (0.0895 mL, 0.179 mmol) in DMF (1.00 mL) was heated at 160° C. under microwave irradiation for 1 hour. After cooling to room temperature, the mixture was diluted with water and extracted with CHCl$_3$ (×3). The combined organic layers were dried over anhydrous Na$_2$SO$_4$ and concentrated. The residue was purified by PTLC (CHCl$_3$/MeOH=9:1) to afford desired product (53.9 mg, 94.3%) as pale yellow solid. $^1$HNMR (CDCl$_3$) 500 MHz δ: 8.15 (dd, J=7.7, 1.4 Hz, 1H), 8.02-7.97 (m, 1H), 7.70 (br s, 1H), 7.55-7.48 (m, 2H), 7.45-7.38 (m, 2H), 7.36-7.31 (m, 2H), 7.30-7.25 (m, 1H), 7.16-7.10 (m, 3H), 6.95 (d, J=8.0 Hz, 1H), 6.83-6.74 (m, 1H), 6.58 (dd, J=7.7, 4.9 Hz, 1H), 6.55-6.49 (m, 1H), 5.26 (br s, 1H), 2.59-2.24 (m, 4H), 2.19-2.06 (m, 1H), 1.95-1.79 (m, 1H), 1.57-1.19 (m, 10H), 1.09-1.02 (m, 2H), 0.84-0.75 (m, 2H).

Step 3: Preparation of N-(4-{3-[4-(1-Aminocyclobutyl)phenyl]-9H-imidazo[1,2-d]pyrido[2,3-b][1,4]benzodiazepin-2-yl}phenyl)cyclopropanecarboxamide trihydrochloride

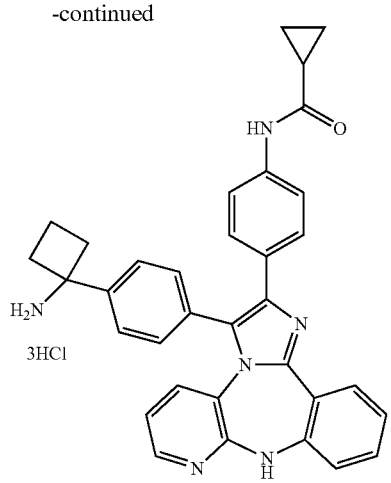

tert-Butyl {1-[4-(2-{4-[(cyclopropylcarbonyl)amino]phenyl}-9H-imidazo[1,2-d]pyrido[2,3-b][1,4]benzodiazepin-3-yl)phenyl]cyclobutyl}carbamate (53.9 mg, 0.0965 mmol) was dissolved in DCM (1 mL). 4M HCl/dioxane (1 mL) was added to the mixture and stirred at room temperature for 19 hours. The mixture was concentrated and solidified with ether. The precipitated solids were collected by filtration and washed with ether to afford desired product (48.8 mg, 78.1%) as yellow solid. $^1$HNMR (DMSO-d$_6$) 500 MHz δ: 10.36 (s, 1H), 8.71-8.63 (m, 3H), 8.13-8.10 (m, 1H), 7.97-7.93 (m, 1H), 7.58-7.52 (m, 4H), 7.43-7.37 (m, 3H), 7.34-7.29 (m, 3H), 7.17-7.12 (m, 1H), 6.92-6.88 (m, 1H), 6.75 (dd, J=8.3, 4.9 Hz, 1H), 2.63-2.40 (m, 4H), 2.25-2.12 (m, 1H), 1.86-1.76 (m, 2H), 0.81-0.75 (m, 4H); LCMS: 539 [M+H].

Example 97

Preparation of 1-{4-[2-(1,3-thiazol-2-yl)-9H-imidazo[1,2-d]pyrido[2,3-b][1,4]benzodiazepin-3-yl]phenyl}cyclobutanamine

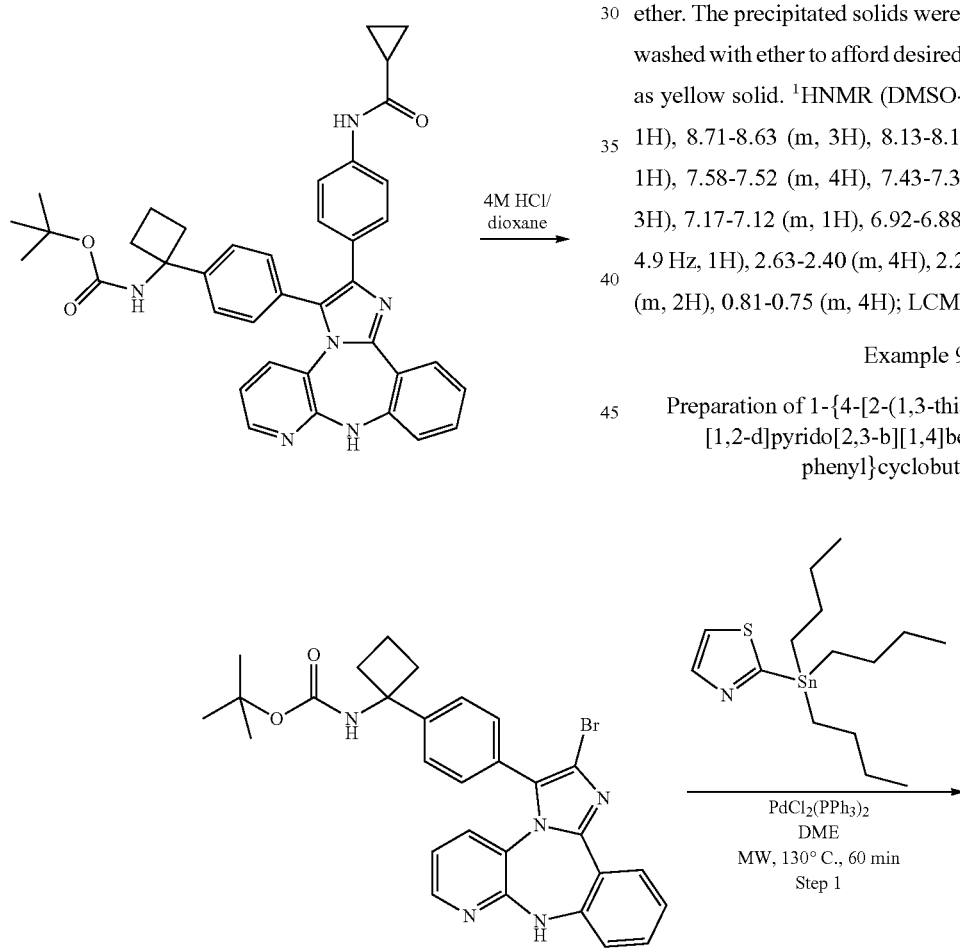

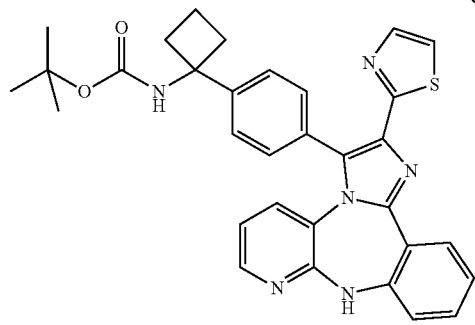 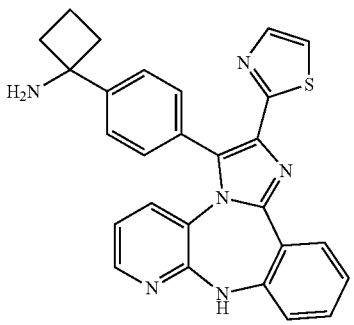

Step 1: Preparation of tert-butyl (1-{4-[2-(1,3-thiazol-2-yl)-9H-imidazo[1,2-d]pyrido[2,3-b][1,4]benzodiazepin-3-yl]phenyl}cyclobutyl)carbamate. A mixture of tert-butyl {1-[4-(2-bromo-9H-imidazo[1,2-d]pyrido[2,3-b][1,4]benzodiazepin-3-yl)phenyl]cyclobutyl}carbamate (300 mg, 0.54 mmol), 2-(tributylstannyl)thiazole (337 μA, 1.1 mmol), and PdCl$_2$(PPh$_3$)$_2$ (38 mg, 0.047 mmol) in 1,2-dimethoxyethane (10 ml) was added to a crimp top microwave vial, which was then sealed and heated under microwave irradiation conditions at 130° C. for 60 min. After cooling to room temperature the mixture was poured into water and extracted into ethyl acetate. The organic layers were washed with brine and dried over anhydrous Na$_2$SO$_4$. After filtration the solvent was evaporated in vacuo. The crude product was purified by silica gel chromatography (hexane/ethyl acetate; 0-100% ethyl acetate over 60 min) to give a yellow amorphous (quant.). $^1$HNMR (CDCl$_3$) 400 MHz δ: 8.18 (1H, dd, J=7.7, 1.4 Hz), 8.02 (1H, d, J=4.0 Hz), 7.75 (1H, d, J=2.9 Hz), 7.44-7.37 (3H, m), 7.32 (1H, td, J=7.5, 1.7 Hz), 7.24 (1H, d, J=2.9 Hz), 7.15 (1H, td, J=7.4, 1.2 Hz), 6.97 (1H, d, J=8.0 Hz) 6.89-6.81 (1H, m), 6.61 (1H, dd, J=7.7, 4.9 Hz), 6.48 (1H, s), 5.18 (1H, s), 2.60-2.32 (4H, m), 2.17-2.08 (1H, m), 1.93-1.84 (1H, m), 1.48-1.21 (9H, m); LC/MS [M+H]: 563.

Step 2: Preparation of 1-{4-[2-(1,3-thiazol-2-yl)-9H-imidazo[1,2-d]pyrido[2,3-b][1,4]benzodiazepin-3-yl]phenyl}cyclobutanamine. A mixture of tert-butyl (1-{4-[2-(1,3-thiazol-2-yl)-9H-imidazo[1,2-d]pyrido[2,3-b][1,4]benzodiazepin-3-yl]phenyl}cyclobutyl)carbamate (302 mg, 0.54 mmol) and 4N HCl/dioxane (1.5 ml) in dichloromethane (10 ml) was stirred at room temperature for 16 hours and diluted with diethyl ether. The precipitate was collected on a filter paper and dried to give a yellow solid (76%). $^1$HNMR (DMSO-d$_6$) 400 MHz δ: 8.79 (m, 2H), 8.69 (s, 1H), 8.13 (dd, J=4.9, 1.4 Hz, 1H), 7.93 (dd, J=7.7, 1.4 Hz, 1H), 7.76 (d, J=2.9 Hz, 1H), 7.72 (d, J=2.9 Hz, 1H), 7.56-7.50 (m, 4H), 7.40 (td, J=7.7, 1.7 Hz, 1H), 7.33 (d, J=7.5 Hz, 1H), 7.15 (td, J=7.5, 1.2 Hz, 1H) 6.91 (dd, J=8.0, 1.7 Hz, 1H), 6.76 (dd, J=8.0, 4.6 Hz, 1H), 2.60-2.55 (m, 4H), 2.25-2.15 (m, 1H), 1.86-1.76 (m, 1H); LC/MS [M+H]: 463.

Example 98

Preparation of 1-{4-[2-(1,3-oxazol-2-yl)-9H-imidazo[1,2-d]pyrido[2,3-b][1,4]benzodiazepin-3-yl]phenyl}cyclobutanamine

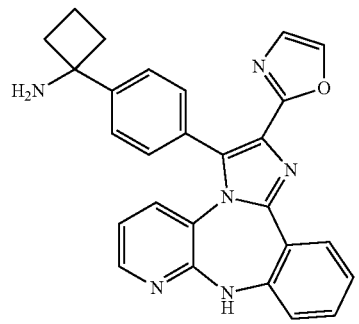 [SMILES: NC1(c2ccc(-c3c(-c4ncco4)nc4n3-c3cccnc3Nc3ccccc3-4)cc2)CCC1]

The title compound was synthesized according to the procedure described in example 97 using 2-(tributylstannyl)oxazole in step 1. $^1$HNMR (DMSO-d$_6$) 400 MHz δ: 8.79 (m, 2H), 8.69 (s, 1H), 8.15 (d, J=1.2 Hz, 1H), 8.14 (dd, J=5.2, 1.7 Hz, 1H), 7.93 (dd, J=7.7, 1.4 Hz, 1H), 7.55 (d, J=8.6 Hz, 2H), 7.46 (d, J=8.0 Hz, 2H), 7.40 (td, J=8.0, 1.2 Hz, 1H), 7.32 (d, J=7.5 Hz, 1H), 7.29 (s, 1H), 7.14 (td, J=7.5, 1.2 Hz, 1H) 6.91 (dd, J=8.0, 1.2 Hz, 1H), 6.76 (dd, J=7.7, 4.9 Hz, 1H), 2.59-2.54 (m, 4H), 2.23-2.15 (m, 1H), 1.85-1.77 (m, 1H); LC/MS [M+H]: 447.

Example 99

Preparation of 1-{4-[2-(2-methoxypyridin-4-yl)-9H-imidazo[1,2-d]pyrido[2,3-b][1,4]benzodiazepin-3-yl]phenyl}cyclobutanamine

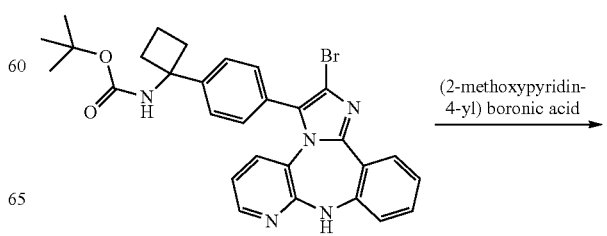

(2-methoxypyridin-4-yl) boronic acid

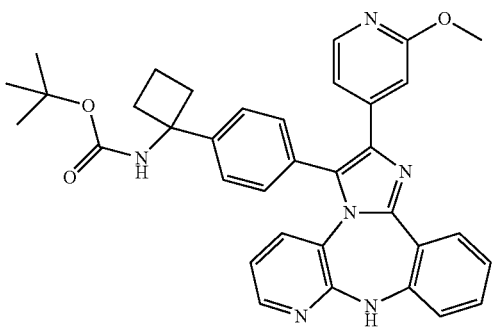
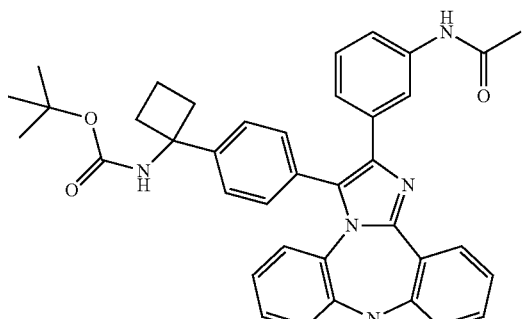

The title compound was synthesized according to the procedure described in example 19 using (2-methoxypyridin-4-yl)boronic acid in step 1 instead of 6-(4,4,5,5-tetramethyl-1,3,2-dioxaborolan-2-yl)-1H-pyrrolo[3,2-b]pyridine. ¹HNMR (CD₃OD) 400 MHz δ: 8.44 (s, 1H), 7.98 (dd, J=4.6, 1.7 Hz, 1H), 7.92-7.89 (m, 2H), 7.45 (d, J=8.6 Hz, 2H), 7.29 (t, J=8.0 Hz, 1H), 7.22 (d, J=8.0 Hz, 2H), 7.09 (d, J=8.0 Hz, 2H), 6.94 (dd, J=5.2, 1.1 Hz, 1H), 6.86 (dd, J=7.7, 1.4 Hz, 1H), 6.78 (s, 1H), 6.60 (dd, J=8.0, 5.2 Hz, 1H), 3.75 (s, 3H), 2.65-2.58 (m, 2H), 2.44-2.36 (m, 2H), 2.17-2.08 (m, 1H), 1.88-1.78 (m, 1H); LCMS: 487 [M+H].

The title compound was synthesized according to the procedure described in step 1 of example 73 using acetic anhydride instead of methanesulfonyl chloride. ¹HNMR (CDCl₃) 400 MHz δ: 8.18-8.13 (m, 1H), 8.04-8.00 (m, 1H), 7.74-7.64 (m, 1H), 7.49-7.11 (m, 10H), 6.95 (d, J=7.8 Hz, 1H), 6.86 (d, J=7.8 Hz, 1H), 6.62 (dd, J=7.8, 4.6 Hz, 1H), 6.32 (s, 1H), 5.26 (br s, 1H), 2.62-2.29 (m, 4H), 2.20-2.06 (m, 1H), 2.12 (s, 3H), 1.96-1.84 (m, 1H), 1.38 (br s, 9H).

Example 100

Preparation of N-(4-{3-[4-(1-Aminocyclobutyl)phenyl]-9H-imidazo[1,2-d]pyrido[2,3-b][1,4]benzodiazepin-2-yl}phenyl)acetamide trihydrochloride Step 1: Preparation of tert-butyl (1-{4-[2-(3-acetamidophenyl)-9H-imidazo[1,2-d]pyrido[2,3-b][1,4]benzodiazepin-3-yl]phenyl}cyclobutyl)carbamate

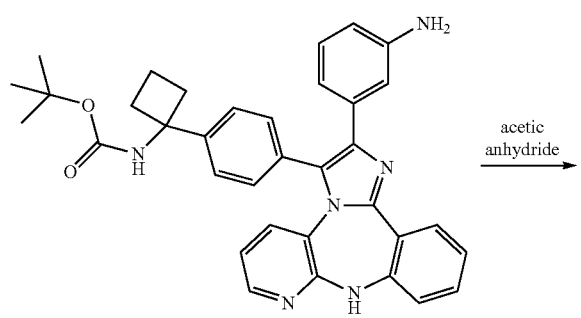

Step 2: Preparation of N-(4-{3-[4-(1-aminocyclobutyl)phenyl]-9H-imidazo[1,2-d]pyrido[2,3-b][1,4]benzodiazepin-2-yl}phenyl)acetamide trihydrochloride

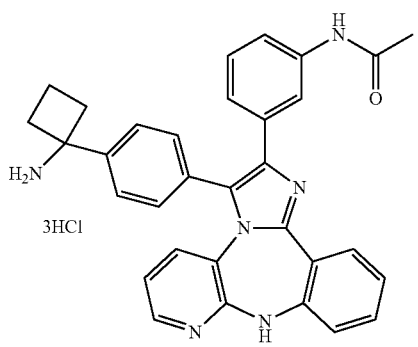 [SMILES: CC(=O)Nc1cccc(-c2nc3n(c2-c2ccc(C4(N)CCC4)cc2)-c2cccnc2Nc2ccccc2-3)c1]

The title compound was synthesized according to the procedure described in step 2 of example 73. ¹HNMR (DMSO-d₆) 400 MHz δ: 10.03 (s, 1H), 8.69 (br s, 2H), 8.63 (s, 1H), 8.11 (dd, J=4.8, 1.6 Hz, 1H), 7.93 (dd, J=7.8, 1.6 Hz, 1H), 7.90-7.86 (m, 1H), 7.57-7.49 (m, 3H), 7.42-7.27 (m, 4H), 7.19-7.10 (m, 2H), 6.99 (d, J=7.8 Hz, 1H), 6.93 (dd, J=7.8, 1.6 Hz, 1H), 6.75 (dd, J=7.8, 4.8 Hz, 1H), 2.64-2.44 (m, 4H), 2.25-2.12 (m, 1H), 2.03 (s, 3H), 1.89-1.76 (m, 1H); LCMS: 513 [M+H].

Example 101

Preparation of 4-{3-[4-(1-aminocyclobutyl)phenyl]-9H-imidazo[1,2-d]pyrido[2,3-b][1,4]benzodiazepin-2-yl}-N-(2-hydroxyethyl)benzamide trihydrochloride

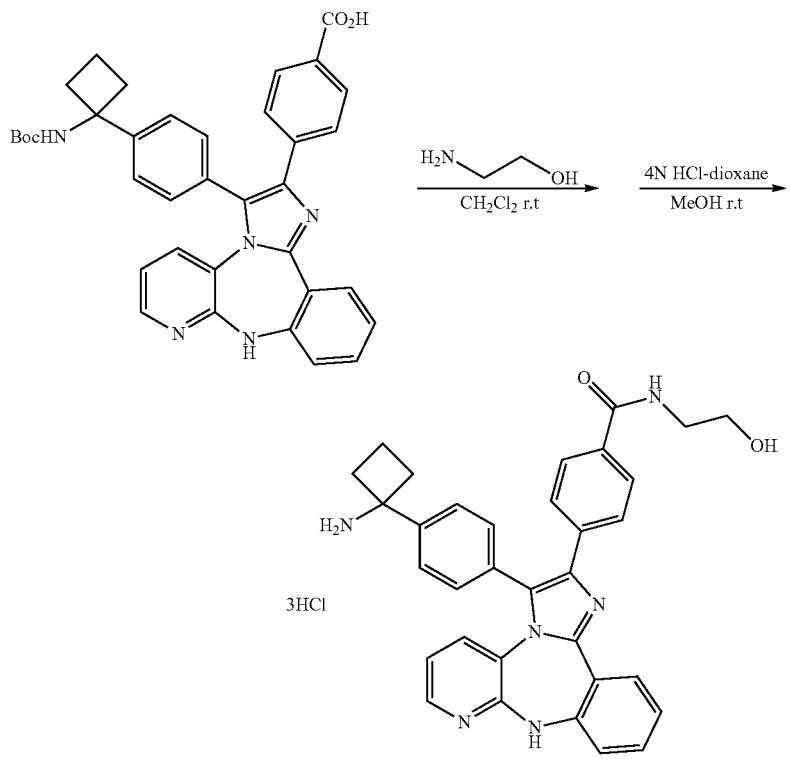

The title compound was synthesized according to the procedure described in step 1 and step 2 of example 35 using 2-aminoethanol instead of pyrrolidine. $^1$HNMR (DMSO-$d_6$) 400 MHz δ: 8.57 (s, 1H), 8.38 (t, J=5.7 Hz, 1H), 8.08 (dd, J=4.6, 1.7 Hz, 1H), 7.97 (dd, J=8.0, 1.7 Hz, 1H), 7.76 (d, J=8.6 Hz, 2H), 7.55 (d, J=8.6 Hz, 2H), 7.49 (d, J=8.6 Hz, 2H), 7.36 (td, J=8.0, 1.7 Hz, 1H), 7.29 (dd, J=8.6, 1.7 Hz, 1H), 7.19 (d, J=8.0 Hz, 2H), 7.12 (td, J=8.6, 1.7 Hz, 1H), 6.90 (dd, J=8.0, 1.7 Hz, 1H), 6.74 (dd, J=7.4, 4.9 Hz, 1H), 4.70 (t, J=5.7 Hz, 2H), 3.49 (q, J=6.3 Hz, 2H), 2.42-2.38 (m, 1H), 2.15-2.09 (m, 1H), 2.07-1.99 (m, 1H), 1.73-1.66 (m, 1H). LCMS: 543 [M+H].

Example 102

Preparation of 1-{4-[2-(1,3-benzothiazol-5-yl)-9H-imidazo[1,2-d]pyrido[2,3-b][1,4]benzodiazepin-3-yl]phenyl}cyclobutanamine

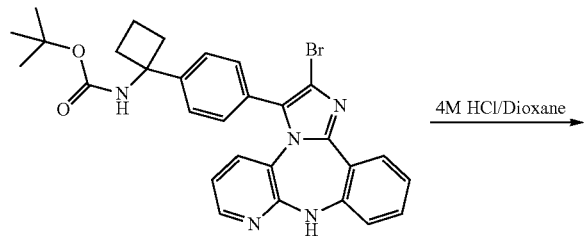

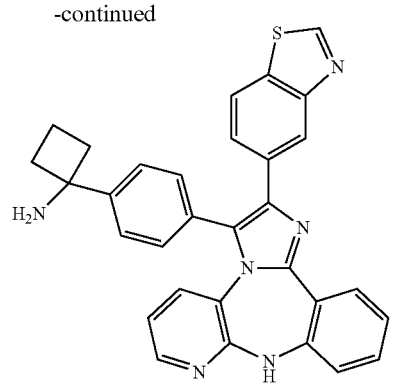

The title compound was synthesized according to the procedure described in example 19 using 5-(4,4,5,5-tetramethyl-1,3,2-dioxaborolan-2-yl)benzo[d]thiazole in step 1 instead of 6-(4,4,5,5-tetramethyl-1,3,2-dioxaborolan-2-yl)-1H-pyrrolo[3,2-b]pyridine. LCMS: 513 [M+H].

Example 103

Preparation of 3-(4-{3-[4-(1-aminocyclobutyl)phenyl]-9H-imidazo[1,2-d]pyrido[2,3-b][1,4]benzodiazepin-2-yl}phenyl)propanoic acid

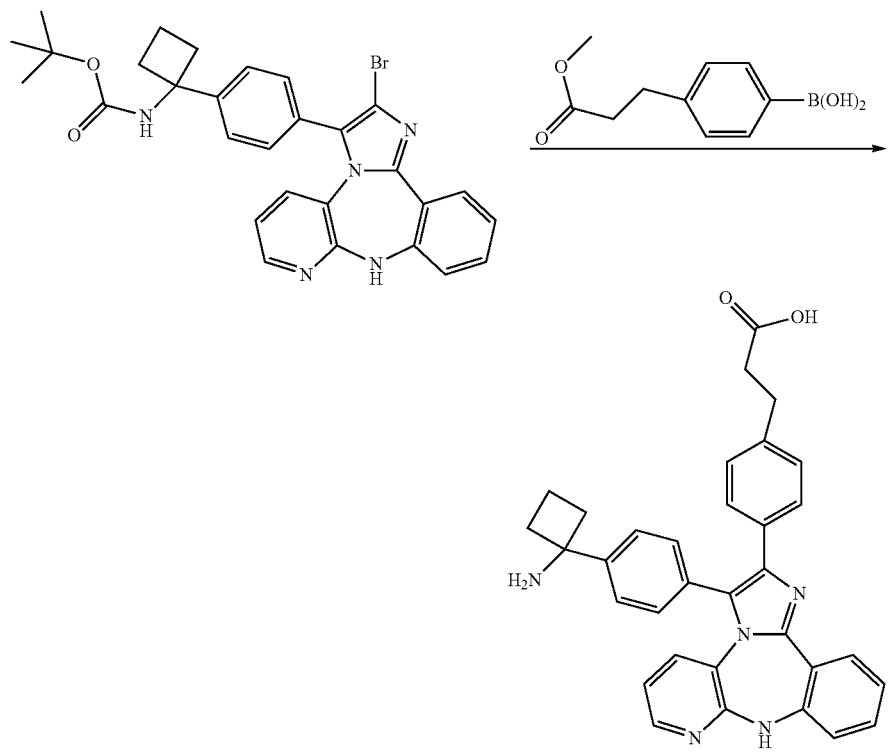

The title compound was synthesized according to the procedure described in example 46. In addition to the ester, the acid was also isolated by HPLC. LCMS: 528 [M+H].

Example 104

Preparation of 1-{3-[4-(1-aminocyclobutyl)phenyl]-9H-imidazo[1,2-d]pyrido[2,3-b][1,4]benzodiazepin-2-yl}ethanone Step 1: Preparation of tert-butyl {1-[4-(2-acetyl-9H-imidazo[1,2-d]pyrido[2,3-b][1,4]benzodiazepin-3-yl)phenyl]cyclobutyl}carbamate

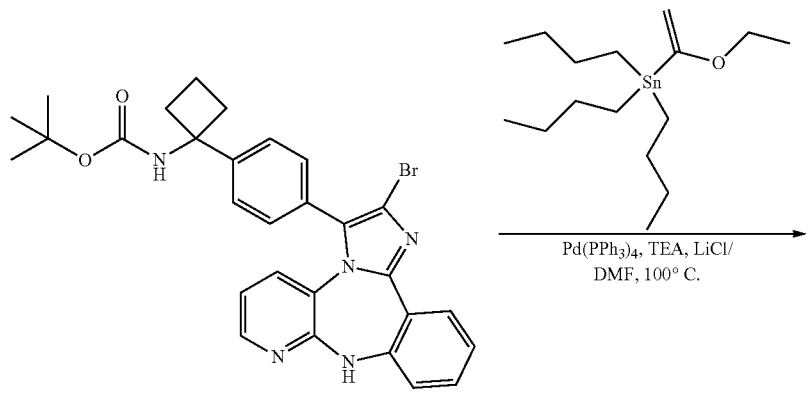

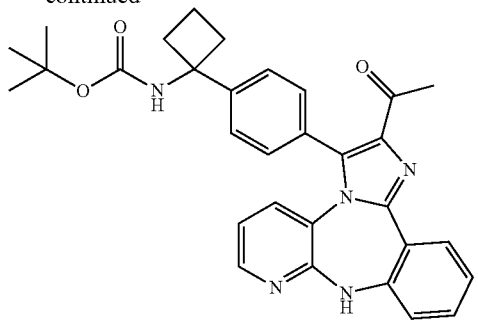

The title compound was synthesized according to the procedure described in step 1 of example 88 using tributyl(1-ethoxyvinyl)stannane instead of 2-(tributylstannyl)-1,3-benzothiazole. ¹HNMR (CDCl₃) 400 MHz δ: 8.10 (dd, J=8.0, 1.7 Hz, 1H), 8.02 (d, J=4.0 Hz, 1H), 7.39 (d, J=8.0 Hz, 2H), 7.34 (td, J=7.7, 1.5 Hz, 1H), 7.31-7.27 (m, 2H), 7.17 (td, J=7.5, 1.2 Hz, 1H), 6.96 (d, J=7.5 Hz, 1H), 6.82-6.75 (m, 1H), 6.59 (dd, J=8.0, 4.6 Hz, 1H), 6.25 (s, 1H), 5.11 (s, 1H), 2.65 (s, 3H), 2.60-2.35 (m, 4H), 2.16-2.05 (m, 1H), 1.93-1.81 (m, 1H), 1.49-1.17 (m, 9H); LC/MS [M+H]: 522.

Step 2: Preparation of 1-{3-[4-(1-aminocyclobutyl)phenyl]-9H-imidazo[1,2-d]pyrido[2,3-b][1,4]benzodiazepin-2-yl}ethanone

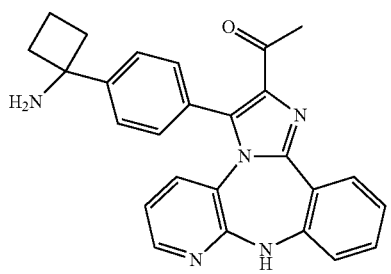 [SMILES: CC(=O)c1nc2n(c1-c1ccc(C3(N)CCC3)cc1)-c1cccnc1Nc1ccccc1-2]

The title compound was synthesized according to the procedure described in step 2 of example 88. ¹HNMR (DMSO-d₆) 400 MHz δ: 8.67 (s, 4H), 8.13 (dd, J=4.6, 1.7 Hz, 1H), 7.93 (dd, J=8.0, 1.7 Hz, 1H), 7.51 (d, J=8.6 Hz, 2H), 7.40 (td, J=8.0, 1.7 Hz, 1H), 7.38-7.33 (m, 1H), 7.32 (dd, J=8.0, 1.2 Hz, 1H), 7.14 (td, J=7.5, 1.2 Hz, 1H), 6.87 (dd, J=8.0, 1.7 Hz, 1H), 6.73 (dd, J=8.0, 5.2 Hz, 1H), 2.61-2.52 (m, 4H), 2.54 (s, 3H), 2.23-2.13 (m, 1H), 1.85-1.77 (m, 1H); LC/MS [M+H]: 422.

Example 105

Preparation of 1-(4-{2-[(E)-2-phenylethenyl]-9H-imidazo[1,2-d]pyrido[2,3-b][1,4]benzodiazepin-3-yl}phenyl)cyclobutanamine Step 1: Preparation of tert-butyl[1-(4-{2-[(E)-2-phenylethenyl]-9H-imidazo[1,2-d]pyrido[2,3-b][1,4]benzodiazepin-3-yl}phenyl)cyclobutyl]carbamate The title compound was synthesized according to the procedure described in step 1 of example 19 using (E)-styrylboronic acid instead of 6-(4,4,5,5-tetramethyl-1,3,2-dioxaborolan-2-yl)-1H-pyrrolo[3,2-b]pyridine. ¹HNMR (CDCl₃) 400 MHz δ: 8.21-8.17 (m, 1H), 8.05-8.00 (m, 1H), 7.62 (d, J=16.0 Hz, 1H), 7.53-7.41 (m, 4H), 7.35-7.29 (m, 3H), 7.25-7.06 (m, 5H), 6.98-6.94 (m, 1H), 6.89-6.82 (m, 1H), 6.63 (dd, J=7.7, 4.9 Hz, 1H), 6.38 (s, 1H), 5.16 (s, 1H), 2.65-2.28 (m, 4H), 2.22-2.09 (m, 1H), 1.98-1.85 (m, 1H), 1.40 (s, 9H). LC/MS [M+H]: 582

Step 2: Preparation of 1-(4-{2-[(E)-2-phenylethenyl]-9H-imidazo[1,2-d]pyrido[2,3-b][1,4]benzodiazepin-3-yl}phenyl)cyclobutanamine

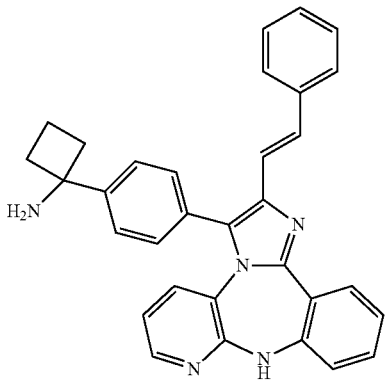 [SMILES: NC1(c2ccc(-c3c(/C=C/c4ccccc4)nc4n3-c3cccnc3Nc3ccccc3-4)cc2)CCC1]

The title compound was synthesized according to the procedure described in step 2 of example 19. $^1$HNMR (DMSO-$d_6$) 400 MHz δ: 8.84-8.76 (m, 2H), 8.73-8.69(m, 1H), 8.17-8.13 (m, 1H), 8.02 (d, J=8.0 Hz, 1H), 7.63 (d, J=7.5 Hz, 2H), 7.58-7.53 (m, 1H), 7.52 (d, J=7.5 Hz, 2H), 7.44-7.30 (m, 6H), 7.27 (t, J=6.9 Hz, 1H), 7.16 (t, J=7.5 Hz, 1H), 7.06 (d, J=16 Hz, 1H), 6.94 (d, J=8.0 Hz, 1H), 6.83-6.79 (m, 1H), 2.65-2.55 (m, 4H), 2.54 (s, 3H), 2.27-2.17 (m, 1H), 1.88-1.78 (m, 1H); LC/MS [M+H]: 482.

Example 106

Preparation of 1-{4-[2-(1-benzofuran-2-yl)-9H-imidazo[1,2-d]pyrido[2,3-b][1,4]benzodiazepin-3-yl]phenyl}cyclobutanamine Step 1: Preparation of tert-butyl (1-{4-[2-(1-benzofuran-2-yl)-9H-imidazo[1,2-d]pyrido[2,3-b][1,4]benzodiazepin-3-yl]phenyl}cyclobutyl)carbamate

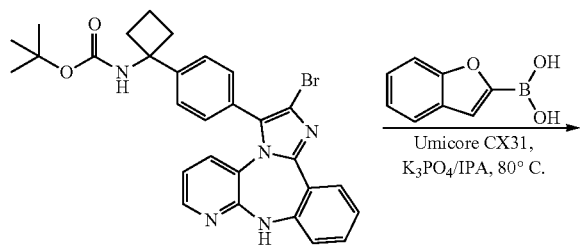

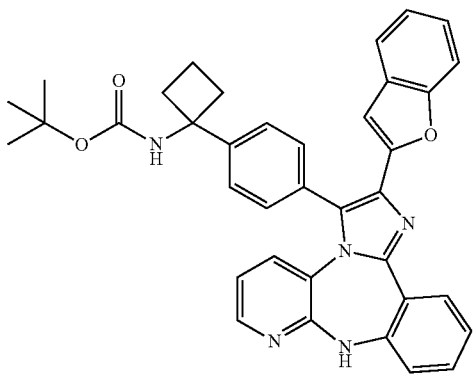

The title compound was synthesized according to the procedure described in step 1 of example 19 using benzofuran-2-ylboronic acid instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 8.20 (1H, dd, J=7.7, 1.4 Hz), 8.02 (1H, dd, J=4.6, 1.2 Hz), 7.50-7.40 (4H, m), 7.36-7.28 (3H, m), 7.22 (1H, td, J=6.9, 1.5 Hz), 7.19-7.12 (2H, m), 6.97 (1H, d, J=7.5 Hz), 6.87 (1H, d, J=7.5 Hz), 6.79 (1H, s), 6.62-6.60 (2H, m), 5.24 (1H, s), 2.62-2.32 (4H, m), 2.20-2.10 (1H, m), 1.96-1.87 (1H, m), 1.50-1.12 (9H, m); LC/MS [M+H]: 596.

Step 2: Preparation of 1-{4-[2-(1-benzofuran-2-yl)-9H-imidazo[1,2-d]pyrido[2,3-b][1,4]benzodiazepin-3-yl]phenyl}cyclobutanamine

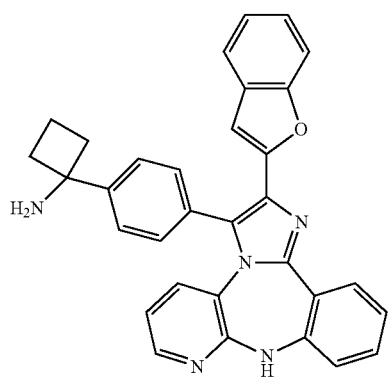 [SMILES: NC1(c2ccc(-c3c(-c4cc5ccccc5o4)nc4n3-c3cccnc3Nc3ccccc3-4)cc2)CCC1]

The title compound was synthesized according to the procedure described in step 2 of example 19. $^1$HNMR (DMSO-$d_6$) 400 MHz δ: 8.78 (s, 2H), 8.67 (s, 1H), 8.13 (dd, J=4.8, 1.4 Hz, 1H), 7.97 (dd, J=7.5, 1.7 Hz, 1H), 7.60 (d, J=8.0 Hz, 2H), 7.50-7.45 (m, 2H), 7.40 (td, J=8.0, 1.7 Hz, 1H), 7.33 (d, J=7.5 Hz, 2H), 77.30-7.21 (m, 2H), 7.15 (td, J=7.5, 1.2 Hz, 1H), 6.99-6.96 (m, 2H), 6.78 (dd, J=8.0, 5.2 Hz, 1H), 2.67-2.55 (m, 4H), 2.54 (s, 3H), 2.26-2.17 (m, 1H), 1.89-1.81 (m, 1H); LC/MS [M+H]: 496.

Example 107

Preparation of 1-[4-(2-cyclopropyl-9H-imidazo[1,2-d]pyrido[2,3-b][1,4]benzodiazepin-3-yl)phenyl]cyclobutanamine

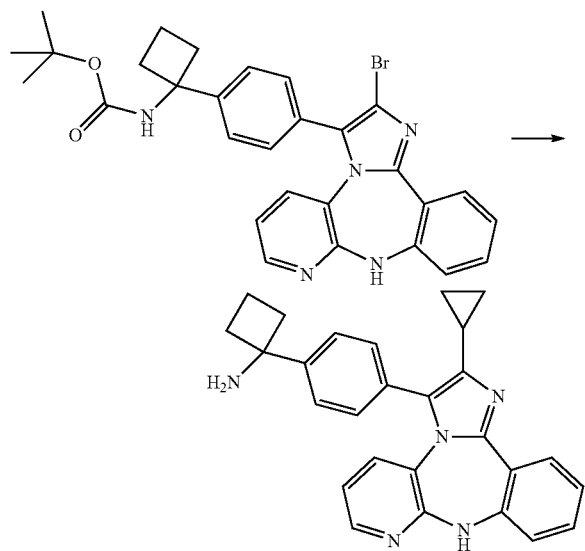

The title compound was synthesized according to the procedure described in example 19 using cyclopropylboronic acid in step 1 and concentrated HCl in step 2. $^1$HNMR (CD$_3$OD) 400 MHz δ: 8.54 (s, 1H), 8.05 (dd, J=4.9, 1.4 Hz, 1H), 7.85 (dd, J=7.7, 1.4 Hz, 1H), 7.51 (d, J=8.6 Hz, 2H), 7.36-7.30 (m, 3H), 7.14 (d, J=8.0 Hz, 1H), 7.11 (dt, J=1.1, 7.4 Hz, 1H), 6.95 (dd, J=8.0, 1.7 Hz, 1H), 6.71 (dd, J=7.7, 4.9 Hz, 1H), 2.75-2.68 (m, 2H), 2.53-2.46 (m, 2H), 2.24-2.15 (m, 1H), 2.01-1.95 (m, 1H), 1.94-1.88 (m, 1H), 0.94 (dd, J=4.6, 2.3 Hz, 2H), 0.86 (d, J=8.0 Hz, 2H); LCMS: 420 [M+H].

Example 108

Preparation of 1-(4-{3-[4-(1-aminocyclobutyl)phenyl]-9H-imidazo[1,2-d]pyrido[2,3-b][1,4]benzodiazepin-2-yl}phenyl)-3-phenylurea trihydrochloride Step 1: Preparation of tert-butyl {1-[4-(2-{4-[(anilinocarbonyl)amino]phenyl}-9H-imidazo[1,2-d]pyrido[2,3-b][1,4]benzodiazepin-3-yl)phenyl]cyclobutyl}carbamate

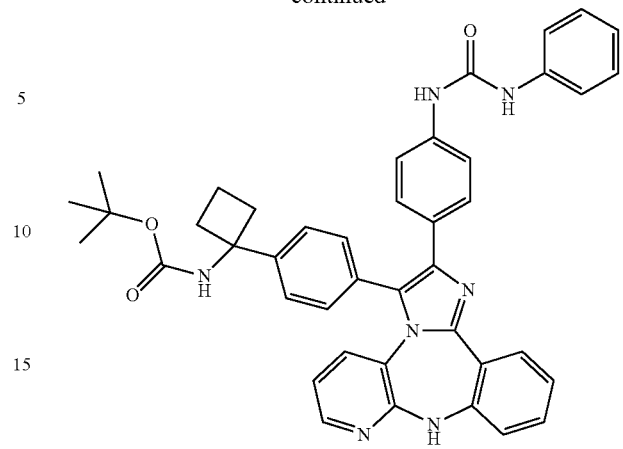

Et$_3$N (36.6 μL, 0.263 mmol) and phenyl isocyanate (10.4 μL, 0.0964 mmol) were added to a solution of tert-butyl (1-{4-[2-(4-aminophenyl)-9H-imidazo[1,2-d]pyrido[2,3-b][1,4]benzodiazepin-3-yl]phenyl}cyclobutyl)carbamate (50.0 mg, 0.0876 mmol) in DCM (1 mL) at 0° C., and stirred at room temperature. After reaction was completed, the mixture was diluted with sat. NaHCO$_3$ and extracted with CHCl$_3$ (3×). The combined organic layers were dried over anhydrous Na$_2$SO$_4$, and concentrated. The residue was purified by PTLC (CHCl$_3$/MeOH=9:1). The fractions were concentrated and solidified with CHCl$_3$. The precipitated solids were collected by filtration and washed with CHCl$_3$ to afford desired product (33.5 mg, 55.4%) as cream colored solid. $^1$HNMR (DMSO-d$_6$) 400 MHz δ: 8.16-8.11 (m, 1H), 8.03-7.99 (m, 1H), 7.54-7.48 (m, 2H), 7.38-7.21 (m, 9H), 7.16-7.05 (m, 4H), 6.95 (d, J=8.2 Hz, 1H), 6.89-6.73 (m, 3H), 6.59 (dd, J=8.0, 4.8 Hz, 1H), 6.29 (s, 1H), 5.19 (s, 1H), 2.61-2.23 (m, 4H), 2.20-2.06 (m, 1H), 1.95-1.80 (m, 1H), 1.49-1.16 (m, 9H).

Step 2: Preparation of 1-(4-{3-[4-(1-aminocyclobutyl)phenyl]-9H-imidazo[1,2-d]pyrido[2,3-b][1,4]benzodiazepin-2-yl}phenyl)-3-phenylurea trihydrochloride

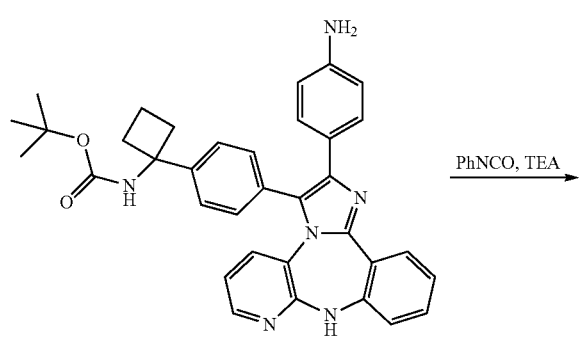

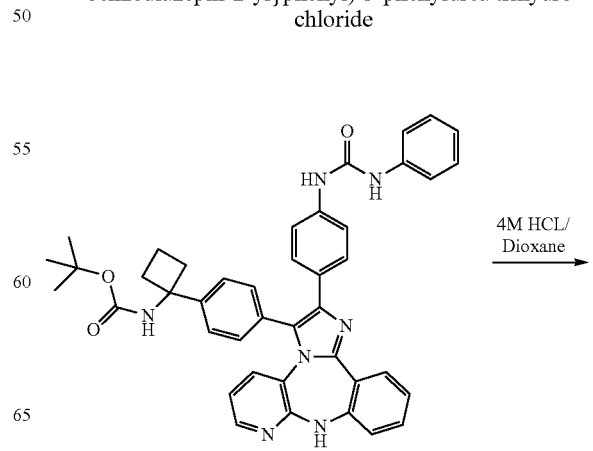

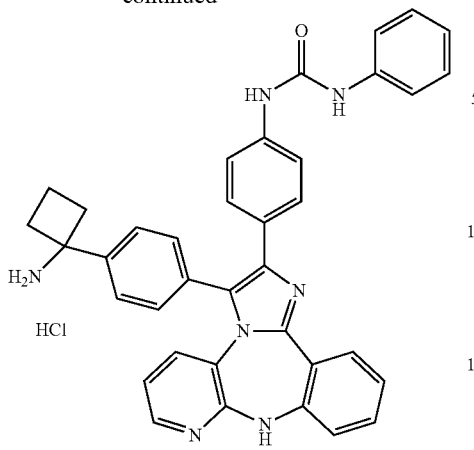
The title compound was synthesized according to the procedure described in step 2 of example 40. ¹HNMR (DMSO-d₆) 400 MHz δ: 9.23 (s, 1H), 9.10 (s, 1H), 8.66 (br s, 3H), 8.12 (dd, J=4.8, 1.4 Hz, 1H), 7.96 (dd, J=8.0, 1.4 Hz, 1H), 7.58-7.52 (m, 2H), 7.47-7.37 (m, 6H), 7.36-7.23 (m, 5H), 7.18-7.12 (m, 1H), 6.99-6.88 (m, 2H), 6.76 (dd, J=8.0, 4.8 Hz, 1H), 2.65-2.44 (m, 4H), 2.26-2.12 (m, 1H), 1.89-1.76 (m, 1H); LCMS: 590 [M+H].
Example 109
Preparation of 4'-{3-[4-(1-aminocyclobutyl)phenyl]-9H-imidazo[1,2-d]pyrido[2,3-b][1,4]benzodiazepin-2-yl}biphenyl-4-carboxamide
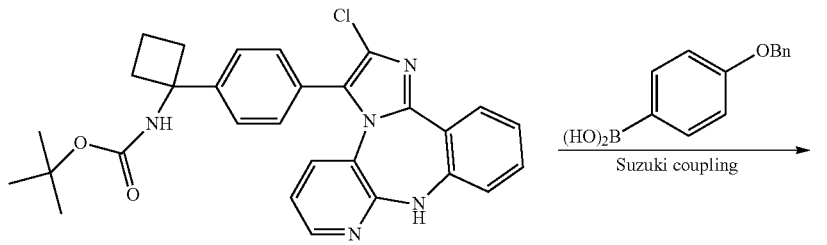
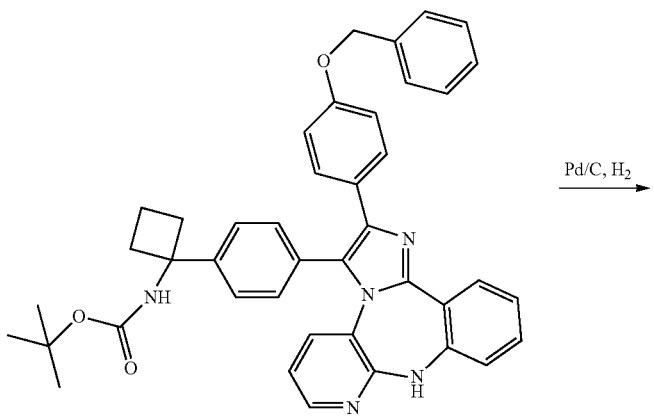
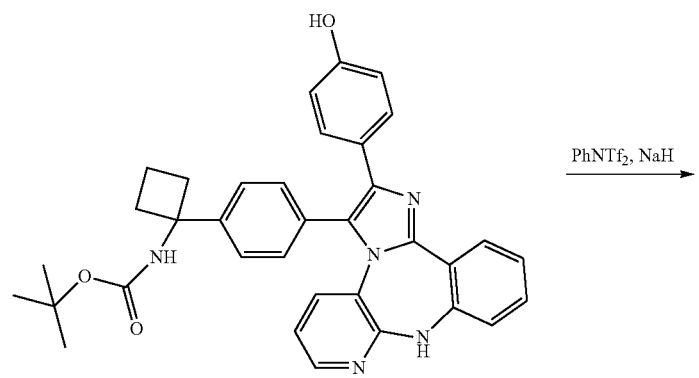

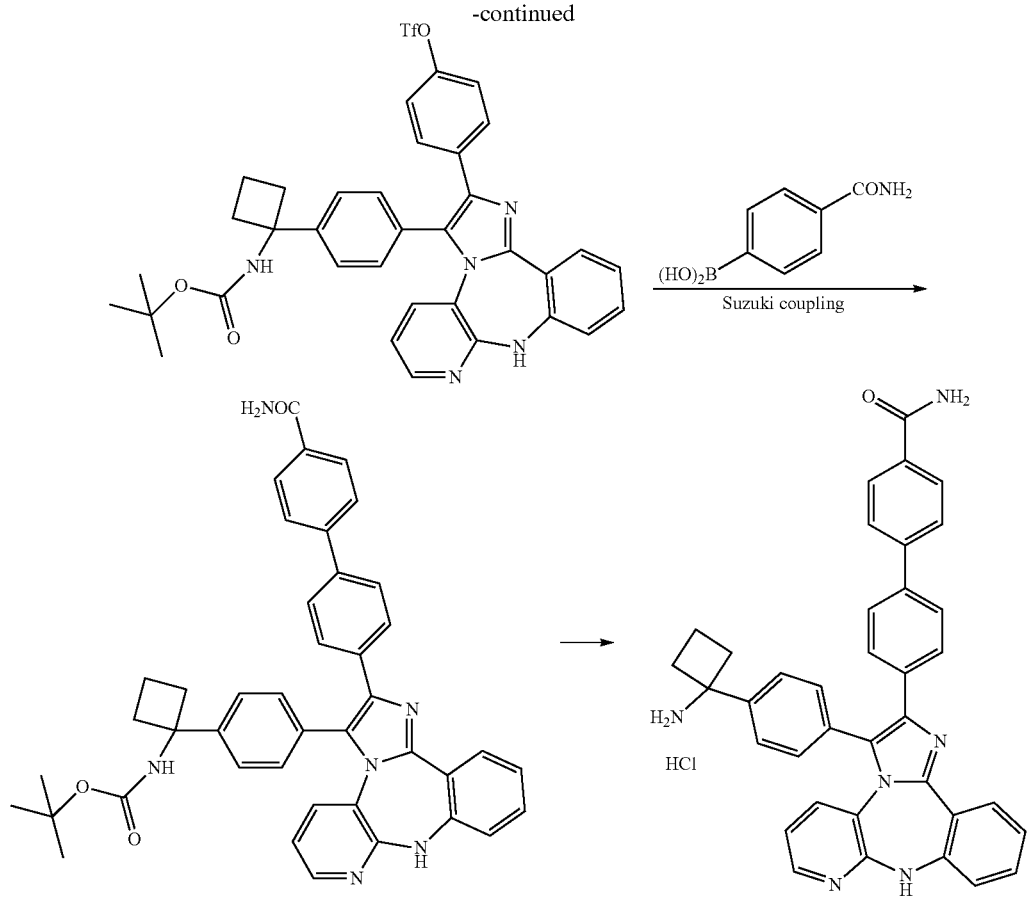

Step 1: Preparation of tert-butyl[1-(4-{2-[4-(benzyloxy) phenyl]-9H-imidazo[1,2-d]pyrido[2,3-b][1,4]benzodiazepin-3-yl}phenyl)cyclobutyl]carbamate: To a solution of tert-butyl {1-[4-(2-chloro-9H-imidazo[1,2-d]pyrido[2,3-b][1,4]benzodiazepin-3-yl)phenyl]cyclobutyl}carbamate (50 mg, 0.097 mmol) in DMF (1 mL) was added saturated NaHCO$_3$, 4-benzyloxyphenylboronic acid (45 mg, 0.20 mmol) and PdCl$_2$(Me$_2$NPhP(tBu)$_2$)$_2$ (7 mg, 0.0097 mmol). The reaction was degassed for 2 minutes and then heated at 160° C., 1 h (microwave reactor). The reaction mixture was cooled to room temperature, then was diluted with EtOAc (15 mL) and washed with brine. The organic phase was dried over sodium sulfate, filtered and concentrated. Purification by column chromatography (SiO2, 10% to 50% EtOAc in hexane) gave the title compound as a yellow solid (56 mg). $^1$HNMR (CDCl$_3$) 400 MHz δ: 8.17-8.15 (m, 1H), 8.00-7.99 (m, 1H), 7.51 (d, J=8.6 Hz, 2H), 7.48-7.23 (m, 8H), 7.15-7.13 (m, 3H), 6.94 (d, J=7.4 Hz, 1H), 6.89 (d, J=8.6 Hz, 2H), 6.79 (d, J=7.4 Hz, 1H), 6.59 (dd, J=7.7, 4.9 Hz, 1H), 6.30 (s, 1H), 5.12 (br s, 1H), 5.05 (s, 2H), 2.53-2.51 (m, 4H), 2.15-2.12 (m, 1H), 1.93-1.84 (m, 1H), 1.39 (br s, 9H).

Step 2: Preparation of tert-butyl (1-{4-[2-(4-hydroxyphenyl)-9H-imidazo[1,2-d]pyrido[2,3-b][1,4]benzodiazepin-3-yl]phenyl}cyclobutyl)carbamate: To a solution of tert-butyl [1-(4-{2-[4-(benzyloxy)phenyl]-9H-imidazo[1,2-d]pyrido[2,3-b][1,4]benzodiazepin-3-yl}phenyl)cyclobutyl] carbamate (236 mg, 0.36 mmol) in THF (10 mL) and MeOH (20 mL) was added 10%-Pd/C (100 mg). The reaction mixture was stirred under atomospheric hydrogen at room temperature for 19 hours. The reaction mixture was filtered through Celite and concentrated. The title compound was gave 125 mg as a white solid. LCMS: 572 [M+H].

Step 3: Preparation of 4-[3-(4-{1-[(tert-butoxycarbonyl) amino]cyclobutyl}phenyl)-9H-imidazo[1,2-d]pyrido[2,3-b][1,4]benzodiazepin-2-yl]phenyl trifluoromethane sulfonate: To a solution of tert-butyl (1-{4-[2-(4-hydroxyphenyl)-9H-imidazo[1,2-d]pyrido[2,3-b][1,4]benzodiazepin-3-yl]phenyl}cyclobutyl)carbamate (67 mg, 0.12 mmol) in THF (5 mL) cooled to 0° C. was added sodium hydride (0.21 mmol) and the mixture was stirred 30 min, then, added PhNTf$_2$ (54 mg, 0.15 mmol). The reaction was slowly allowed to warm to room temperature and stirred 2.5 h. The reaction was diluted with 5%-NaClaq (20 mL) and extracted with ethyl acetate (3×20 mL). The organic layers were combined, washed with brine. The organic phase was dried over sodium sulfate, filtered and concentrated. Purification by column chromatography (SiO$_2$, 20% to 50% EtOAc in hexane) gave the title compound as a white solid 61 mg, 75%); LCMS: 704 [M+H]

Step 4: Preparation of tert-butyl (1-{4-[2-(4'-carbamoylbiphenyl-4-yl)-9H-imidazo[1,2-d]pyrido[2,3-b][1,4]benzodiazepin-3-yl]phenyl}cyclobutyl)carbamate: To a solution of 4-[3-(4-{1-[(tert-butoxycarbonyl)amino] cyclobutyl}phenyl)-9H-imidazo[1,2-d]pyrido[2,3-b][1,4] benzodiazepin-2-yl]phenyl trifluoromethanesulfonate (30 mg, 0.043 mmol) in toluene (1 mL) and EtOH (1 mL) was added saturated 1M-K$_3$PO$_4$aq, 4-aminocarbonylphenylboronic acid (21 mg, 0.13 mmol) and Pd (PPh$_3$)$_4$ (5 mg, 0.0043 mmol). The reaction was degassed for 2 minutes and then heated at 100° C., 2.5 h. The reaction mixture was cooled to room temperature, then was diluted with EtOAc (15 mL) and washed with brine. The organic phase was dried over sodium sulfate, filtered and concentrated. Purification by column chromatography (SiO2, 20% to 50% to 100% EtOAc in hexane) gave the title compound as a white solid (22 mg, 76%); LCMS: 675 [M+H].

Step 5: Preparation of 4'-{3-[4-(1-aminocyclobutyl)phenyl]-9H-imidazo[1,2-d]pyrido[2,3-b][1,4]benzodiazepin-2-yl}biphenyl-4-carboxamide. The title compound was synthesized according to the procedure described in step 2 of example 19. ¹HNMR (DMSO-d₆) 400 MHz δ: 8.71 (br s, 2H), 8.63 (s, 1H), 8.11 (dd, J=4.58, 1.72 Hz, 1H), 8.03 (br s, 1H), 7.99 (dd, J=8.02, 1.72 Hz, 1H), 7.97 (d, J=8.59 Hz, 2H), 7.77 (d, J=6.87 Hz, 2H), 7.70 (d, J=8.59 Hz, 2H), 7.61 (d, J=8.59 Hz, 2H), 7.57 (d, J=8.59 Hz, 2H), 7.38 (d, J=8.02 Hz, 2H), 7.31 (d, J=7.45 Hz, 1H), 7.15 (t, J=7.73 Hz, 1H), 6.90 (dd, J=8.02, 1.15 Hz, 1H), 6.75 (dd, J=8.02, 4.58 Hz, 1H), 2.62-2.54 (m, 4H), 2.25-2.16 (m, 1H), 1.89-1.80 (m, 1H). LCMS: 575 [M+H].

Example 110

Preparation of tert-butyl 1-{4-[2-(4'-methylbiphenyl-4-yl)-9H-imidazo[1,2-d]pyrido[2,3-b][1,4]benzodiazepin-3-yl]phenyl}cyclobutanamine

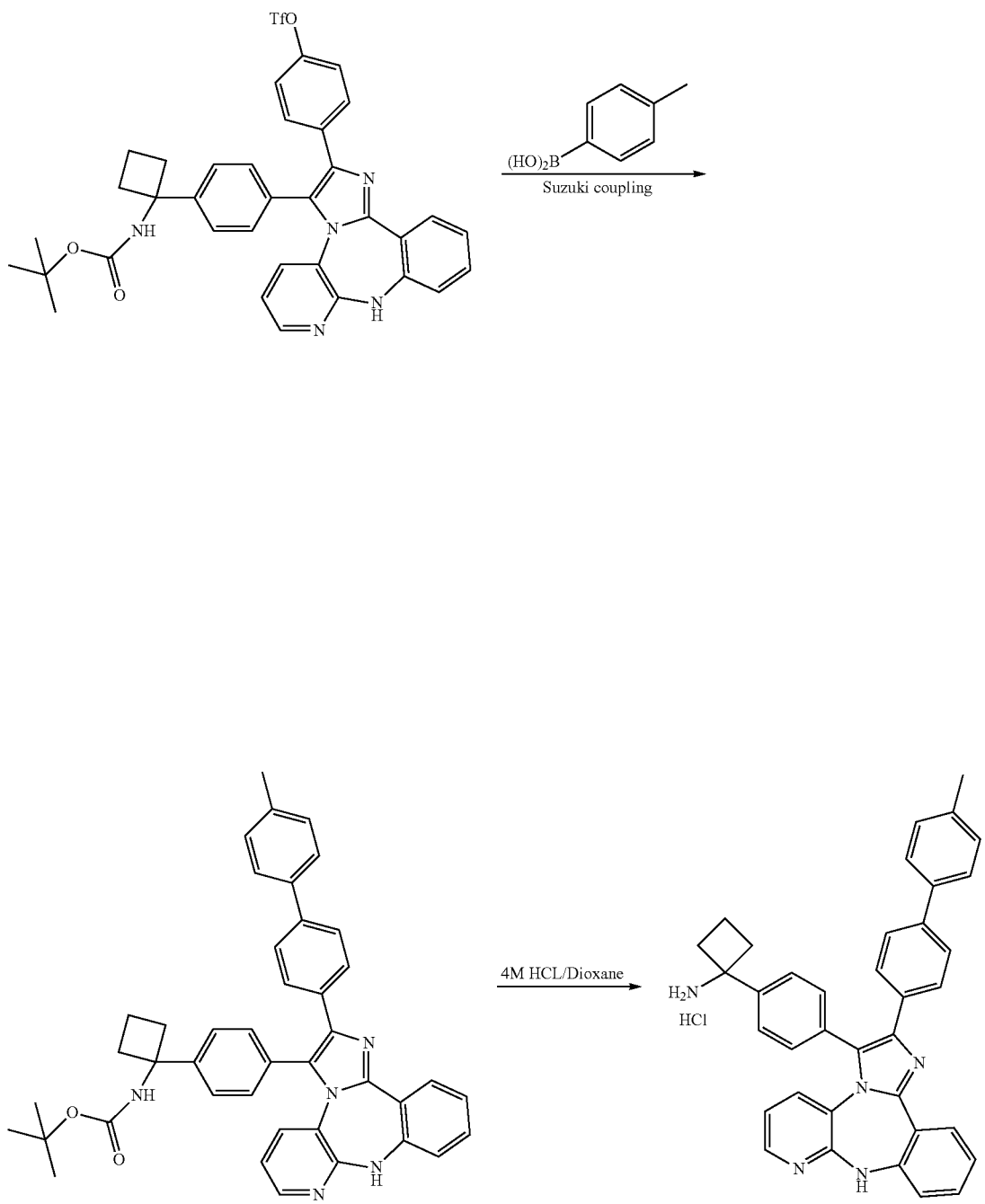

The title compound was synthesized according to the procedure described in step 4 and 5 of example 109 using p-tolylboronic acid in step 4 instead of aminocarbonylphenylboronic acid. LCMS:546 [M+H].
Example 111
Preparation of 4-{3-[4-(1-aminocyclobutyl)phenyl]-9H-imidazo[1,2-d]pyrido[2,3-b][1,4]benzodiazepin-2-yl}benzamide
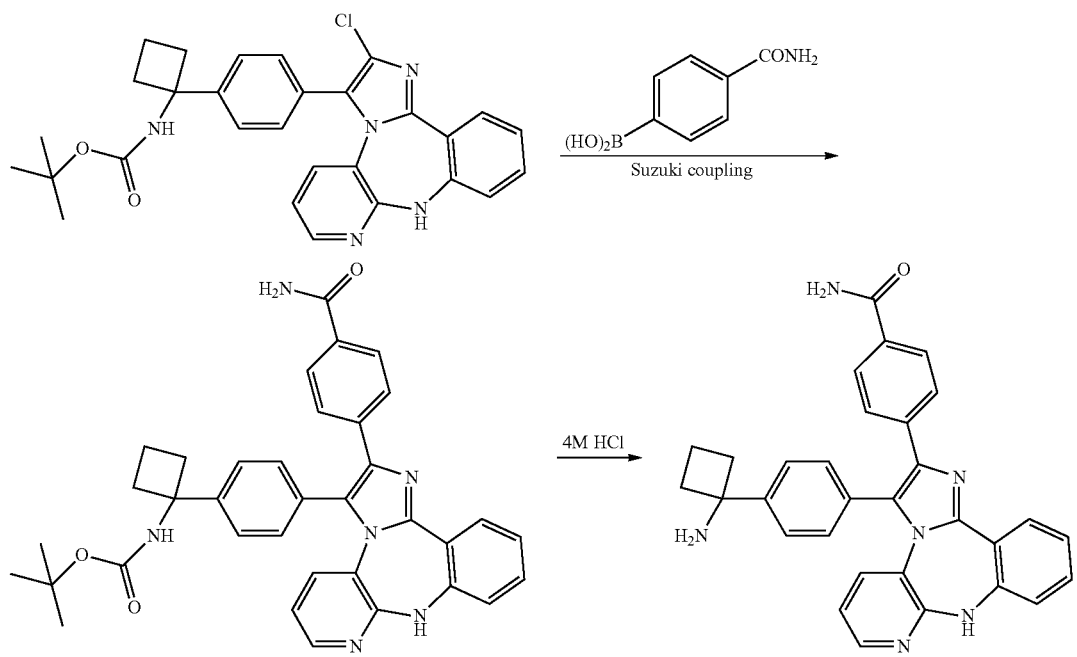

The title compound was synthesized according to the procedure described in example 18 using (4-carbamoylphenyl)boronic acid in step 1 instead of [4-(methoxycarbonyl)phenyl]boronic acid. ¹HNMR (DMSO-d$_6$) 400 MHz δ: 8.73-8.63 (m, 3H), 8.11 (dd, J=4.87, 1.43 Hz, 1H), 7.99-7.96 (m, 2H), 7.80 (d, J=8.59 Hz, 2H), 7.58-7.51 (m, 4H), 7.39-7.30 (m, 5H), 7.14 (t, J=7.45 Hz, 1H), 6.90 (dd, J=8.02, 1.72 Hz, 1H), 6.77-6.71 (m, 1H), 2.64-2.57 (m, 4H), 2.24-2.15 (m, 1H), 1.88-1.78 (m, 1H). LCMS: 499 [M+H].

Example 112

Preparation of 4-{3-[4-(1-aminocyclobutyl)phenyl]-9H-imidazo[1,2-d]pyrido[2,3-b][1,4]benzodiazepin-2-yl}benzonitrile

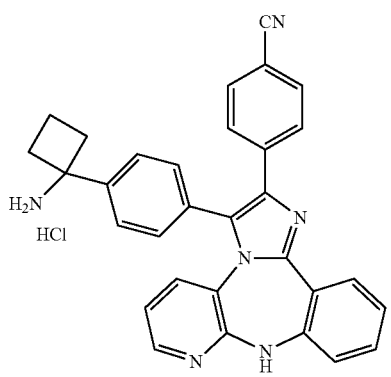 [SMILES: N#Cc1ccc(-c2nc3n(c2-c2ccc(C4(N)CCC4)cc2)-c2cccnc2Nc2ccccc2-3)cc1 ; Cl]

The title compound was synthesized according to the procedure described in example 18 using (4-cyanophenyl)boronic acid in step 1 instead of [4-(methoxycarbonyl)phenyl]boronic acid. ¹HNMR (DMSO-d$_6$) 400 MHz δ: 8.80 (br s, 2H), 8.65 (s, 1H), 8.11 (dd, J=4.58, 1.72 Hz, 1H), 7.97 (dd, J=8.02, 1.72 Hz, 1H), 7.77 (d, J=8.59 Hz, 2H), 7.65 (d, J=8.59 Hz, 2H), 7.59 (d, J=7.45 Hz, 2H), 7.38-7.34 (m, 2H), 7.16-7.12 (m, 1H), 6.89 (dd, J=8.02, 1.15 Hz, 1H), 6.75 (dd, J=8.02, 4.58 Hz, 1H), 2.61-2.54 (m, 4H), 2.24-2.19 (m, 1H), 1.86-1.75 (m, 1H). LCMS: 481 [M+H].

Example 113

Preparation of 1-[4-(2-ethyl-9H-imidazo[1,2-d]pyrido[2,3-b][1,4]benzodiazepin-3-yl)phenyl]cyclobutanamine

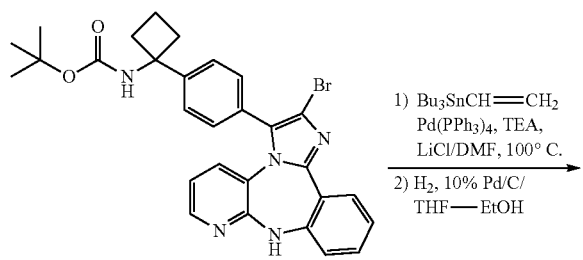

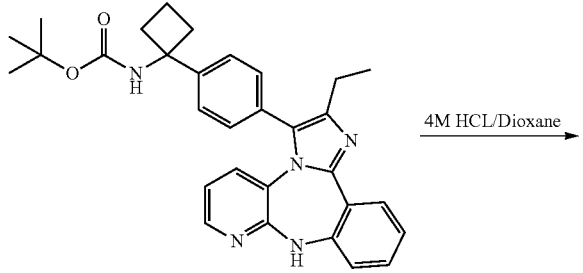

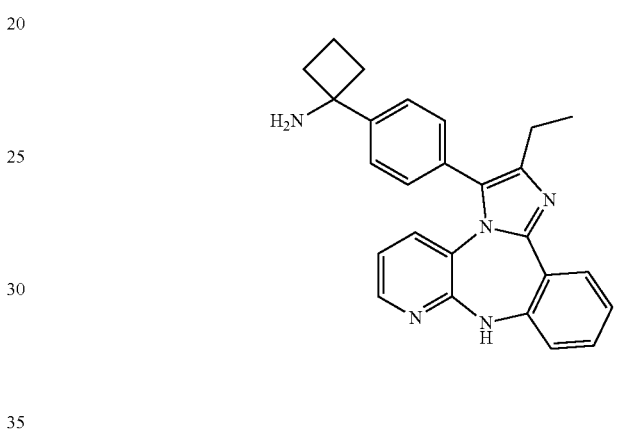

Step 1: Preparation of tert-butyl {1-[4-(2-ethyl-9H-imidazo[1,2-d]pyrido[2,3-b][1,4]benzodiazepin-3-yl)phenyl]cyclobutyl}carbamate The title compound was synthesized according to the procedure described in step 1 of example 88 using tributyl(vinyl)stannane, Pd(PPh$_3$)$_4$. Followed by hydrogenation with 10% Pd/C in THF-ethanol. LC/MS [M+H]: 508.

Step 2: Preparation of 1-[4-(2-ethyl-9H-imidazo[1,2-d]pyrido[2,3-b][1,4]benzodiazepin-3-yl)phenyl]cyclobutanamine

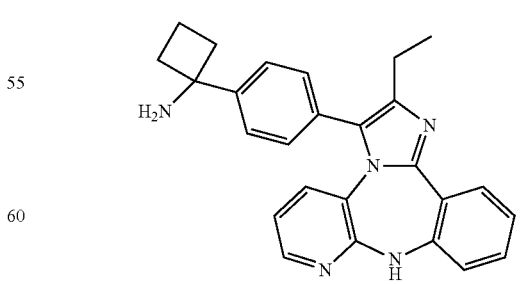

The title compound was synthesized according to the procedure described in step 2 of example 88. LC/MS [M+H]: 508.

Example 114

Preparation of 1-{4-[2-(2-methoxy-1,3-thiazol-5-yl)-9H-imidazo[1,2-d]pyrido[2,3-b][1,4]benzodiazepin-3-yl]phenyl}cyclobutanamine Step 1: Preparation of tert-butyl (1-{4-[2-(2-methoxy-1,3-thiazol-5-yl)-9H-imidazo[1,2-d]pyrido[2,3-b][1,4]benzodiazepin-3-yl]phenyl}cyclobutyl)carbamate

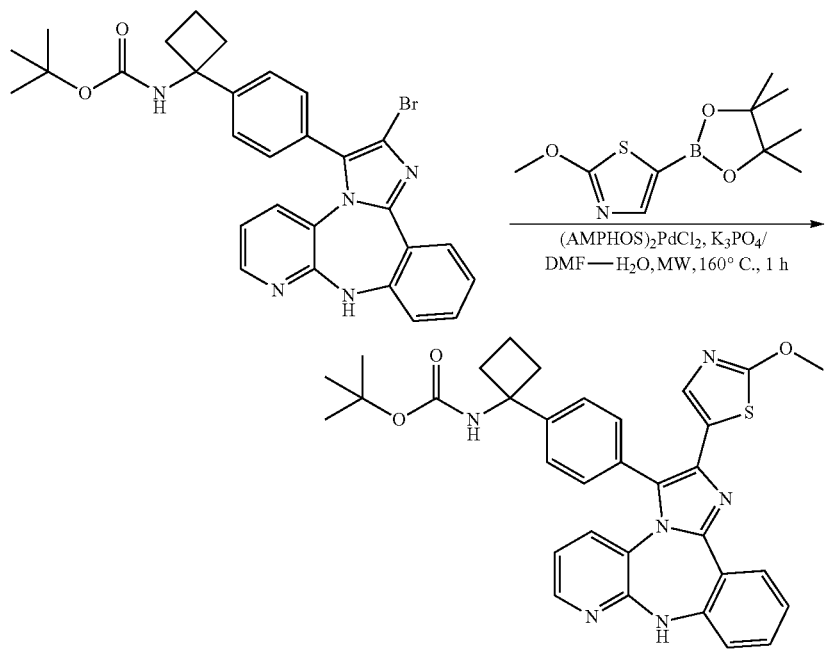

The title compound was synthesized according to the procedure described in step 1 of example 19 using 2-methoxy-5-(4,4,5,5-tetramethyl-1,3,2-dioxaborolan-2-yl)thiazole instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 8.03 (dd, J=7.4, 1.7 Hz, 1H), 7.99 (d, J=5.2 Hz, 1H), 7.43 (d, J=8.0 Hz, 2H), 7.30 (td, J=8.0, 1.7 Hz, 1H), 7.23 (d, J=7.5 Hz, 2H), 7.13 (td, J=7.5, 1.2 Hz, 1H), 6.97-6.91 (m, 2H), 6.84 (d, J=7.5 Hz, 1H), 6.59 (dd, J=8.0, 4.6 Hz, 1H), 6.53 (s, 1H), 5.23

(s, 1H), 3.30 (s, 3H), 2.60-2.33 (m, 4H), 2.20-2.09 (m, 1H), 1.96-1.85 (m, 1H), 1.47-1.18 (m, 9H); LC/MS [M+H]: 593.

Step 2: Preparation of 1-{4-[2-(2-methoxy-1,3-thiazol-5-yl)-9H-imidazo[1,2-d]pyrido[2,3-b][1,4]benzodiazepin-3-yl]phenyl}cyclobutanamine

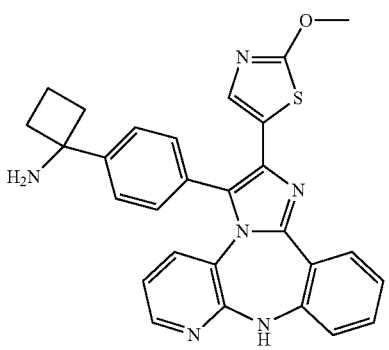 [SMILES: COc1ncc(-c2nc3n(c2-c2ccc(C4(N)CCC4)cc2)-c2cccnc2Nc2ccccc2-3)s1]

The title compound was synthesized according to the procedure described in step 2 of example 19. ¹HNMR (DMSO-d₆) 400 MHz δ: 8.76 (s, 2H), 8.61 (s, 1H), 8.09 (dd, J=4.9, 1.4 Hz, 1H), 7.85 (dd, J=7.7, 1.4 Hz, 1H), 7.58 (d, J=8.6 Hz, 2H), 7.43-7.34 (m, 3H), 7.29 (d, J=7.5 Hz, 1H), 7.20 (s, 1H), 7.11 (td, J=7.4, 1.2 Hz, 1H), 6.94 (dd, J=8.0, 1.2 Hz, 1H), 6.74 (dd, J=8.0, 4.6 Hz, 1H), 3.26 (s, 3H), 2.62-2.53 (m, 4H), 2.26-2.17 (m, 1H), 1.86-1.78 (m, 1H); LC/MS [M+H]: 493.

Example 115

Preparation of 1-{4-[2-(1-methyl-1H-pyrazol-4-yl)-9H-imidazo[1,2-d]pyrido[2,3-b][1,4]benzodiazepin-3-yl]phenyl}cyclobutanamine Step 1: Preparation of tert-butyl (1-{4-[2-(1-methyl-1H-pyrazol-4-yl)-9H-imidazo[1,2-d]pyrido[2,3-b][1,4]benzodiazepin-3-yl]phenyl}cyclobutyl)carbamate

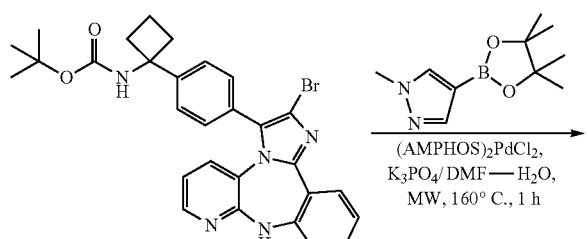

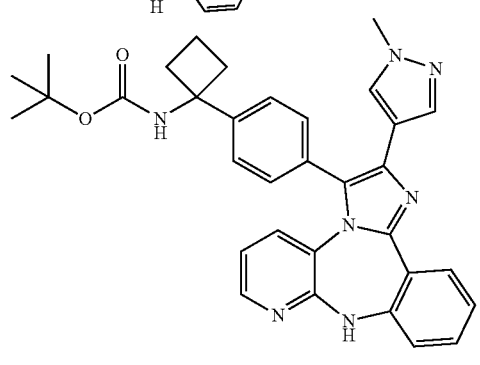

The title compound was synthesized according to the procedure described in step 1 of example 19 using 1-methyl-4-(4,4,5,5-tetramethyl-1,3,2-dioxaborolan-2-yl)-1H-pyrazole instead of 6-(4,4,5,5-tetramethyl-1,3,2-dioxaborolan-2-yl)-1H-pyrrolo[3,2-b]pyridine. ¹HNMR (CDCl₃) 400 MHz δ: 8.10 (dd, J=8.0, 1.7 Hz, 1H), 7.99 (dd, J=5.2, 1.7 Hz, 1H), 7.62 (s, 1H), 7.53 (s, 1H), 7.41 (d, J=8.6 Hz, 2H), 7.31-7.21 (m, 3H), 7.13 (td, J=7.5, 1.2 Hz, 1H), 6.94 (d, J=8.0 Hz, 1H), 6.84 (d, J=8.0 Hz, 1H), 6.59 (dd, J=7.7, 4.9 Hz, 1H), 6.39 (s, 1H), 5.19 (s, 1H), 3.89 (s, 3H), 2.58-2.33 (m, 4H), 2.18-2.11 (m, 1H), 1.94-1.85 (m, 1H), 1.46-1.13 (m, 9H); LC/MS [M+H]: 560.

Step 2: Preparation of 1-{4-[2-(1-methyl-1H-pyrazol-4-yl)-9H-imidazo[1,2-d]pyrido[2,3-b][1,4]benzodiazepin-3-yl]phenyl}cyclobutanamine

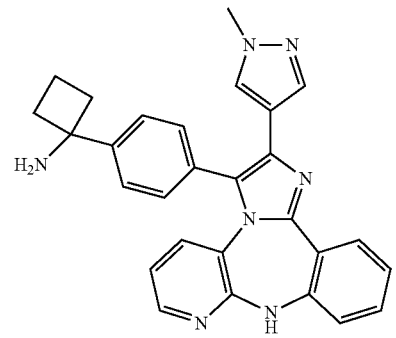 [SMILES: Cn1cc(-c2nc3n(c2-c2ccc(C4(N)CCC4)cc2)-c2cccnc2Nc2ccccc2-3)cn1]

The title compound was synthesized according to the procedure described in step 2 of example 19. ¹HNMR (DMSO-d₆) 400 MHz δ: 8.86 (s, 2H), 8.77 (s, 1H), 8.14 (dd, J=4.9, 1.4 Hz, 1H), 7.96-7.91 (m, 2H), 7.61 (d, J=8.6 Hz, 2H), 7.48-7.37 (m, 4H), 7.34 (d, J=8.0 Hz, 1H), 7.18 (t, J=7.2 Hz, 1H), 6.99 (dd, J=8.0, 1.2 Hz, 1H), 6.80 (dd, J=8.0, 5.2 Hz, 1H), 3.86 (s, 3H), 2.62-2.55 (m, 4H), 2.26-2.17 (m, 1H), 1.86-1.77 (m, 1H); LC/MS [M+H]: 460.

Example 116

Preparation of 1-{4-[2-(1-methyl-1H-pyrazol-5-yl)-9H-imidazo[1,2-d]pyrido[2,3-b][1,4]benzodiazepin-3-yl]phenyl}cyclobutanamine Step 1: Preparation of tert-butyl (1-{4-[2-(1-methyl-1H-pyrazol-5-yl)-9H-imidazo[1,2-d]pyrido[2,3-b][1,4]benzodiazepin-3-yl]phenyl}cyclobutyl)carbamate

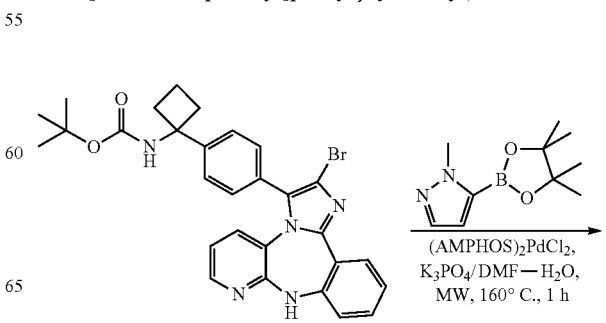

305
-continued

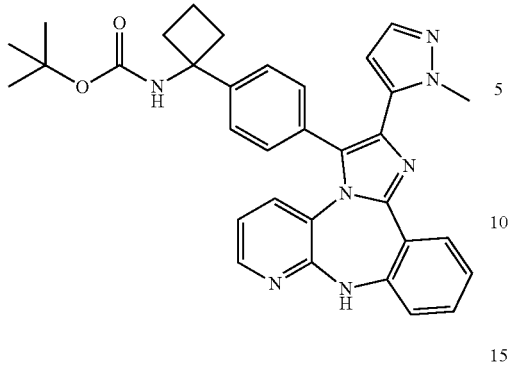

The title compound was synthesized according to the procedure described in step 1 of example 19 using 1-methyl-5-(4,4,5,5-tetramethyl-1,3,2-dioxaborolan-2-yl)-1H-pyrazole instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 8.10 (dd, J=8.0, 1.7 Hz, 1H), 8.06 (dd, J=4.6, 1.2 Hz, 1H), 7.38 (d, J=1.7 Hz, 1H), 7.35-7.30 (m, 3H), 7.14 (td, J=7.5, 1.2 Hz, 1H), 7.07 (d, J=8.0 Hz, 2H), 6.98 (d, J=8.0H, 1H, z), 6.89 (d, J=7.5 Hz, 1H), 6.65 (dd, J=8.0, 5.2 Hz, 1H), 6.53 (s, 1H), 6.06 (s, 1H), 5.19 (s, 1H), 3.98 (s, 3H), 2.55-2.31 (m, 4H), 2.18-2.08 (m, 1H), 1.92-1.83 (m, 1H), 1.48-1.15 (m, 9H); LC/MS [M+H]: 560.

306

Step 2: Preparation of 1-{4-[2-(1-methyl-1H-pyrazol-5-yl)-9H-imidazo[1,2-d]pyrido[2,3-b][1,4]benzodiazepin-3-yl]phenyl}cyclobutanamine

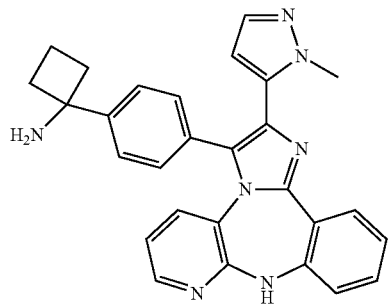 [SMILES: Cn1nccc1-c1nc2n(c1-c1ccc(C3(N)CCC3)cc1)-c1cccnc1Nc1ccccc1-2]

The title compound was synthesized according to the procedure described in step 2 of example 19. $^1$HNMR (DMSO-d$_6$) 400 MHz δ: 8.74 (s, 2H), 8.68 (s, 1H), 8.13 (dd, J=4.6, 1.7 Hz, 1H), 7.93 (dd, J=7.7, 1.4 Hz, 1H), 7.52 (d, J=8.6 Hz, 2H), 7.38 (td, J=7.7, 1.9 Hz, 2H), 7.32 (d, J=6.9 Hz, 1H), 7.25 (d, J=8.0 Hz, 2H), 7.12 (t, J=6.9 Hz, 1H), 6.94 (dd, J=8.0, 1.7 Hz, 1H), 6.78 (dd, J=8.0, 4.6 Hz, 1H), 6.06 (d, J=1.7 Hz, 1H), 3.90 (s, 3H), 2.58-2.52 (m, 4H), 2.23-2.14 (m, 1H), 1.83-1.75 (m, 1H); LC/MS [M+H]: 460.

Example 117

Preparation of 1-{4-[2-(7-methylimidazo[1,2-a]pyridin-6-yl)-9H-imidazo[1,2-d]pyrido[2,3-b][1,4]benzodiazepin-3-yl]phenyl}cyclobutanamine Step 1: Preparation of tert-butyl (1-{4-[2-(7-methylimidazo[1,2-a]pyridin-6-yl)-9H-imidazo[1,2-d]pyrido[2,3-b][1,4]benzodiazepin-3-yl]phenyl}cyclobutyl)carbamate

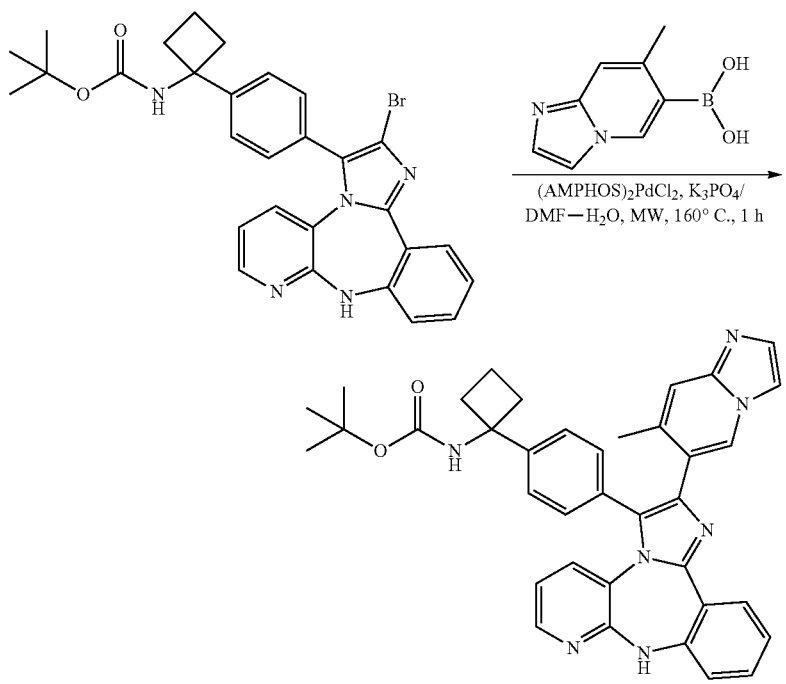

The title compound was synthesized according to the procedure described in step 1 of example 19 using (7-methylimidazo[1,2-a]pyridin-6-yl)boronic acid instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 8.12 (dd, J=7.7, 1.4 Hz, 1H), 8.09 (dd, J=4.6, 1.2 Hz, 1H), 8.05 (s, 1H), 7.55 (s, 1H), 7.43 (s, 2H), 7.31 (td, J=7.7, 1.5 Hz, 1H), 7.23 (d, J=8.0 Hz, 2H), 7.12 (t, J=8.0 Hz, 1H), 6.99 (d, J=8.0 Hz, 1H), 6.95 (d, J=8.6 Hz, 2H), 6.91 (d, J=7.5 Hz), 6.68 (dd, J=8.0, 5.2H, 1H, z), 6.61 (s, 1H), 5.20 (s, 1H), 2.52-2.29 (m, 4H), 2.20 (s, 3H), 2.14-2.05 (m, 1H), 1.89-1.80 (m, 1H), 1.47-1.17 (m, 9H); LC/MS [M+H]: 610.

Step 2: Preparation of 1-{4-[2-(7-methylimidazo[1,2-a]pyridin-6-yl)-9H-imidazo[1,2-d]pyrido[2,3-b][1,4]benzodiazepin-3-yl]phenyl}cyclobutanamine

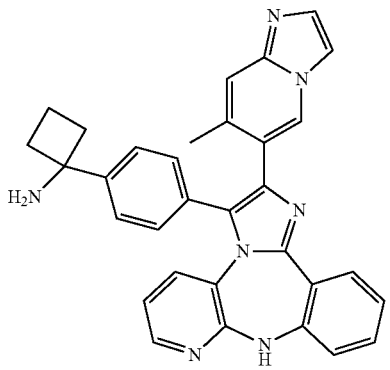 [SMILES: Cc1cc2nccn2cc1-c1nc2n(c1-c1ccc(C3(N)CCC3)cc1)-c1cccnc1Nc1ccccc1-2]

The title compound was synthesized according to the procedure described in step 2 of example 19. $^1$HNMR (DMSO-d$_6$) 400 MHz δ: 8.89 (s, 1H), 8.77 (s, 2H), 8.73 (s, 1H), 8.28 (d, J=1.7 Hz, 1H), 8.19-8.15 (m, 2H), 7.93 (dd, J=7.7, 1.4 Hz, 1H), 7.87 (s, 1H), 7.45 (d, J=8.6 Hz, 2H), 7.39 (td, J=7.6, 1.3 Hz, 2H), 7.33 (d, J=6.9 Hz, 1H), 7.14 (d, J=8.0 Hz, 2H), 7.13-7.09 (m, 1H), 6.95 (dd, J=8.0, 1.7 Hz, 1H), 6.82 (dd, J=7.7, 4.9 Hz, 1H), 2.56-2.52 (m, 4H), 2.28 (s, 3H), 2.21-2.13 (m, 1H), 1.79-1.72 (m, 1H); LC/MS [M+H]: 510.

Example 118

Preparation of 1-{4-[2-(cyclopent-1-en-1-yl)-9H-imidazo[1,2-d]pyrido[2,3-b][1,4]benzodiazepin-3-yl]phenyl}cyclobutanamine Step 1: Preparation of tert-butyl (1-{4-[2-(cyclopent-1-en-1-yl)-9H-imidazo[1,2-d]pyrido[2,3-b][1,4]benzodiazepin-3-yl]phenyl}cyclobutyl)carbamate

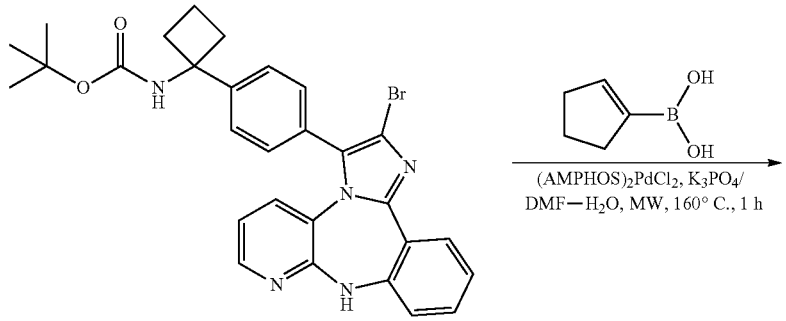

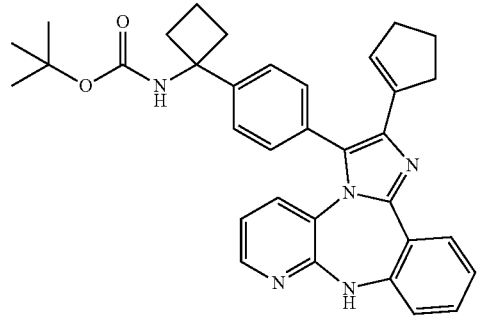

The title compound was synthesized according to the procedure described in step 1 of example 19 using cyclopent-1-en-1-ylboronic acid instead of 6-(4,4,5,5-tetramethyl-1,3,2-dioxaborolan-2-yl)-1H-pyrrolo[3,2-b]pyridine. ¹HNMR (CDCl₃) 400 MHz δ: 8.08 (dd, J=8.0, 1.4 Hz, 1H), 7.96 (d, J=4.0 Hz, 1H), 7.36 (d, J=8.0 Hz, 2H), 7.27 (td, J=8.0, 1.7 Hz, 1H), 7.20 (d, J=8.0 Hz, 2H), 7.11 (td, J=7.5, 1.2 Hz, 1H), 6.92 (d, J=8.0 Hz, 1H), 6.83-6.78 (m, 1H), 6.56 (dd, J=8.0, 4.6 Hz, 1H), 6.38 (s, 1H), 6.17 (s, 1H), 5.17 (s, 1H), 2.59-2.32 (m, 8H), 2.18-2.08 (m, 1H), 1.93-1.82 (m, 3H), 1.47-1.14 (m, 9H); LC/MS [M+H]: 546.

Step 2: Preparation of 1-{4-[2-(cyclopent-1-en-1-yl)-9H-imidazo[1,2-d]pyrido[2,3-b][1,4]benzodiazepin-3-yl]phenyl}cyclobutanamine

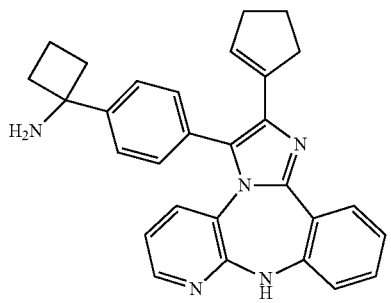 [SMILES: NC1(c2ccc(-c3c(C4=CCCC4)nc4n3-c3cccnc3Nc3ccccc3-4)cc2)CCC1]

The title compound was synthesized according to the procedure described in step 2 of example 19. ¹HNMR (DMSO-d₆) 400 MHz δ: 8.85 (s, 2H), 8.81 (s, 1H), 8.14 (dd, J=4.6, 1.7 Hz, 1H), 7.92 (d, J=7.5 Hz, 1H), 7.59 (d, J=8.0 Hz, 2H), 7.48 (t, J=7.7 Hz, 1H), 7.40 (d, J=7.5 Hz, 2H), 7.34 (d, J=8.0 Hz, 1H), 7.19 (t, J=7.7 Hz, 1H), 6.95 (d, J=8.0 Hz, 1H), 6.78 (dd, J=8.0, 4.6 Hz, 1H), 6.32 (s, 1H), 2.63-2.53 (m, 4H), 2.45-2.31 (m, 3H), 2.26-2.17 (m, 1H), 1.87-1.76 (m, 3H); LC/MS [M+H]: 446.

Example 119

Preparation of 1-(4-{2-[(1E)-3,3-dimethylbut-1-en-1-yl]-9H-imidazo[1,2-d]pyrido[2,3-b][1,4]benzodiazepin-3-yl}phenyl)cyclobutanamine Step 1: Preparation of tert-butyl[1-(4-{2-[(1E)-3,3-dimethylbut-1-en-1-yl]-9H-imidazo[1,2-d]pyrido[2,3-b][1,4]benzodiazepin-3-yl}phenyl)cyclobutyl]carbamate

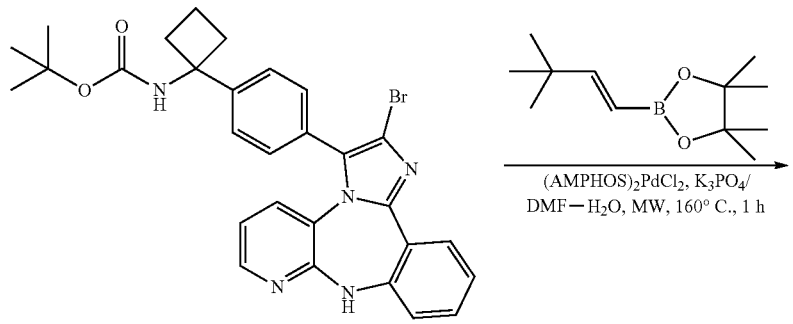

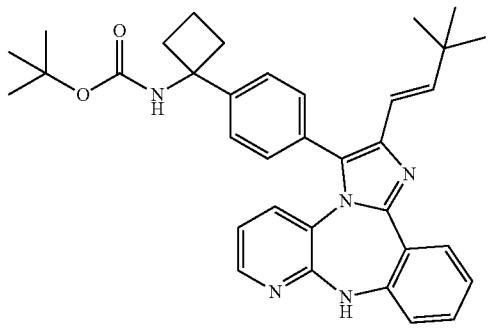

The title compound was synthesized according to the procedure described in step 1 of example 19 using (E)-2-(3,3-dimethylbut-1-en-1-yl)-4,4,5,5-tetramethyl-1,3,2-dioxaborolane instead of 6-(4,4,5,5-tetramethyl-1,3,2-dioxaborolan-2-yl)-1H-pyrrolo[3,2-b]pyridine. $^1$HNMR (CDCl$_3$) 400 MHz δ: 8.14 (dd, J=7.7, 1.4 Hz, 1H), 8.00 (dd, J=4.8, 1.4 Hz, 1H), 7.40 (d, J=8.0 Hz, 2H), 7.28 (td, J=8.0, 1.7 Hz, 1H), 7.17-7.09 (m, 3H), 6.93 (d, J=7.5 Hz, 1H), 6.84-6.77 (m, 2H), 6.60 (dd, J=8.0, 5.2 Hz, 1H), 6.41 (s, 1H), 6.35 (d, J=16 Hz, 1H), 5.18 (s, 1H), 2.59-2.31 (m, 4H), 2.18-2.08 (m, 1H), 1.94-1.84 (m, 1H), 1.47-1.19 (m, 9H), 1.12 (s, 9H); LC/MS [M+H]: 562.

Step 2: Preparation of 1-(4-{2-[(1E)-3,3-dimethyl-but-1-en-1-yl]-9H-imidazo[1,2-d]pyrido[2,3-b][1,4]benzodiazepin-3-yl}phenyl)cyclobutanamine

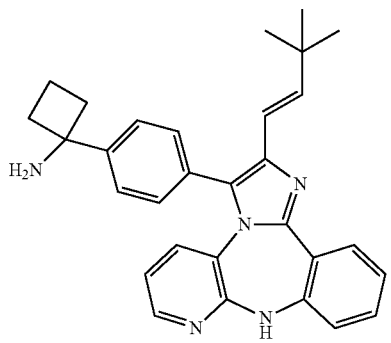 [SMILES: CC(C)(C)/C=C/c1nc2n(c1-c1ccc(C3(N)CCC3)cc1)-c1cccnc1Nc1ccccc1-2]

The title compound was synthesized according to the procedure described in step 2 of example 19. $^1$HNMR (DMSO-d$_6$) 400 MHz δ: 8.80 (s, 2H), 8.74 (s, 1H), 8.15 (dd, J=4.6, 1.7 Hz, 1H), 7.96 (dd, J=8.0, 1.2 Hz, 1H), 7.60 (d, J=8.6 Hz, 2H), 7.43 (t, J=8.0 Hz, 1H), 7.33 (d, J=7.5 Hz, 1H), 7.26 (d, J=7.5 Hz, 2H), 7.15 (t, J=8.0 Hz, 1H), 6.90 (dd, J=8.0, 1.7 Hz, 1H), 6.81 (dd, J=8.0, 4.6 Hz, 1H), 6.78 (d, J=16 Hz, 1H), 6.21 (d, J=16 Hz, 1H), 2.62-2.53 (m, 4H), 2.45-2.31 (m, 3H), 2.26-2.16 (m, 1H), 1.86-1.76 (m, 3H), 1.08 (s, 9H); LC/MS [M+H]: 462.

Example 120

Preparation of 1-{4-[2-(4-piperidin-4-ylphenyl)-9H-imidazo[1,2-d]pyrido[2,3-b][1,4]benzodiazepin-3-yl]phenyl}cyclobutanamine tetrahydrochloride

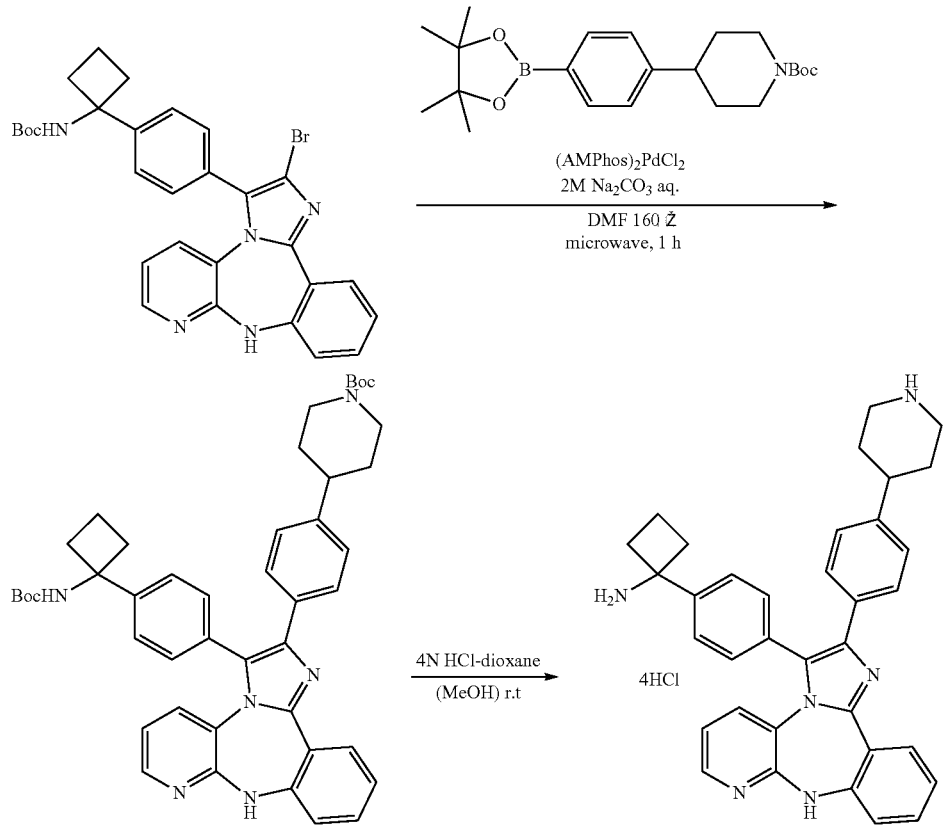

The title compound was synthesized according to the procedure described in example 19 using tert-butyl 4-(4-(4,4,5,5-tetramethyl-1,3,2-dioxaborolan-2-yl)phenyl)piperidine-1-carboxylate instead of 6-(4,4,5,5-tetramethyl-1,3,2-dioxaborolan-2-yl)-1H-pyrrolo[3,2-b]pyridine. $^1$HNMR (DMSO-d$_6$) 400 MHz δ: 8.76 (br s, 1H), 8.70 (br s, 2H), 8.61 (s, 1H), 8.10 (dd, J=4.6 Hz and 1.7 Hz, 1H), 7.95 (dd, J=8.0 Hz and 1.7 Hz, 1H), 7.55 (d, J=8.6 Hz, 2H), 7.48 (d, J=8.6 Hz, 2H), 7.39-7.29 (m, 4H), 7.17 (d, J=8.6 Hz, 2H), 7.13 (td, J=8.6 Hz and 1.1 Hz, 1H), 6.86 (dd, J=8.0 Hz and 1.7 Hz, 1H), 6.73 (dd, J=8.0 Hz and 4.6 Hz, 1H), 3.72-3.65 (m, 1H), 3.51-3.45 (m, 1H), 3.36-3.34 (m, 2H), 3.02-2.93 (m, 2H), 2.86-2.79 (m, 1H), 2.59-2.54 (m, 2H), 2.24-2.15 (m, 1H), 1.94-1.90 (m, 2H), 1.87-1.78 (m, 3H). LCMS: 539 [M+H].

Example 121

Preparation of 1,1'-(9H-imidazo[1,2-d]pyrido[2,3-b][1,4]benzodiazepine-2,3-diyldi-4,1-phenylene)dicyclobutanamine tetrahydrochloride

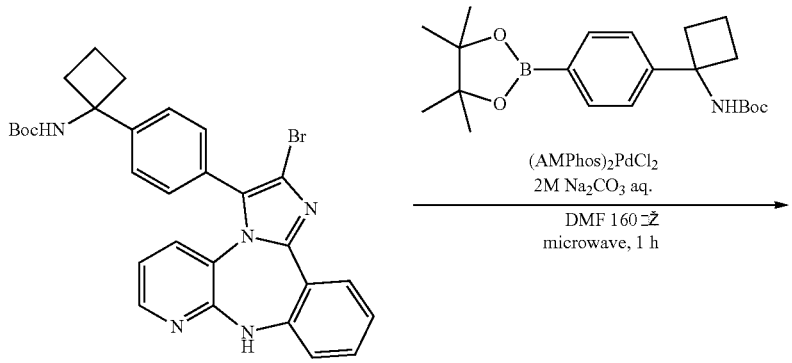

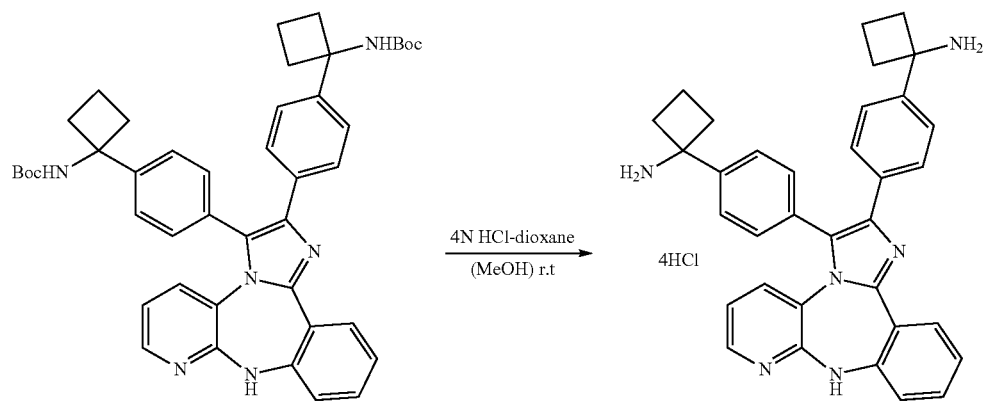

The title compound was synthesized according to the procedure described in step 1 of example 19 using tert-butyl (1-(4-(4,4,5,5-tetramethyl-1,3,2-dioxaborolan-2-yl)phenyl)cyclobutyl)carbamate instead of 6-(4,4,5,5-tetramethyl-1,3,2-dioxaborolan-2-yl)-1H-pyrrolo[3,2-b]pyridine. ¹HNMR (DMSO-d₆) 400 MHz δ: 8.78 (br s, 2H), 8.66-8.61 (m, 3H), 8.10 (dd, J=4.6, 1.7 Hz, 1H), 7.96 (dd, J=8.0, 1.7 Hz, 1H), 7.59 (t, J=8.6 Hz, 3H), 7.47 (d, J=8.6 Hz, 2H), 7.39-7.35 (m, 2H), 7.30 (d, J=8.6 Hz, 1H), 7.13 (td, J=7.4, 1.7 Hz, 1H), 6.88 (dd, J=8.0, 1.7 Hz, 1H), 6.73 (dd, J=8.0, 4.6 Hz, 1H), 2.58-2.55 (m, 4H), 2.25-2.12 (m, 1H), 1.87-1.75 (m, 1H). LCMS: 525 [M+H].

Example 122

Preparation of methyl N-(4-{3-[4-(1-aminocyclobutyl)phenyl]-9H-imidazo[1,2-d]pyrido[2,3-b][1,4]benzodiazepin-2-yl}benzoyl)-2-methylalaninate trihydrochloride

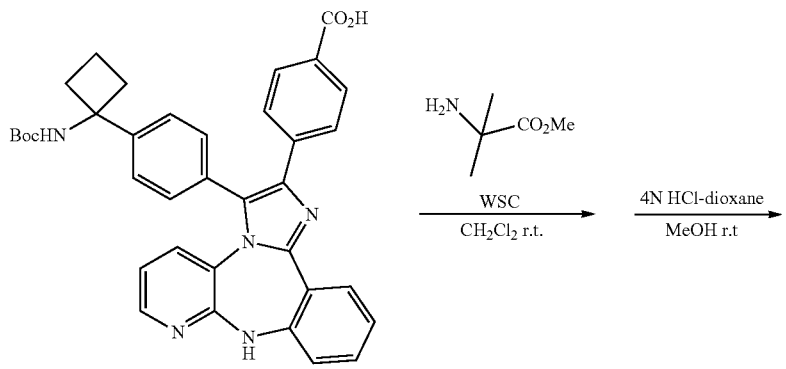

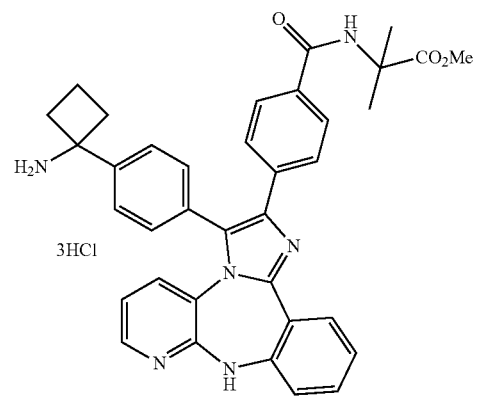

The title compound was synthesized according to the procedure described in step 1 and step 2 of example 35 using methyl 2-amino-2-methylpropanoate. $^1$HNMR (DMSO-$d_6$) 400 MHz δ: 8.62-8.61 (m, 3H), 8.11 (dd, J=4.6 Hz and 1.7 Hz, 1H), 7.98 (dd, J=8.0 Hz and 1.7 Hz, 1H), 7.79 (d, J=8.0 Hz, 2H), 7.54 (dd, J=8.6 Hz and 6.3 Hz, 4H), 7.39-7.30 (m, 4H), 7.14 (td, J=7.4 Hz and 1.1 Hz, 1H), 6.91 (dd, J=8.0 Hz and 1.7 Hz, 1H), 6.74 (dd, J=8.0 Hz and 4.6 Hz, 1H), 3.73-3.65 (m, 1H), 3.57 (s, 3H), 3.51-3.45 (m, 1H), 2.62-2.52 (m, 2H), 2.23-2.15 (m, 1H), 1.87-1.81 (m, 1H), 1.45 (s, 6H). LCMS: 599 [M+H].

Example 123

Preparation of 2-[(4-{3-[4-(1-aminocyclobutyl)phenyl]-9H-imidazo[1,2-d]pyrido[2,3-b][1,4]benzodiazepin-2-yl}phenyl)amino]-1,3-thiazol-4(5H)-one

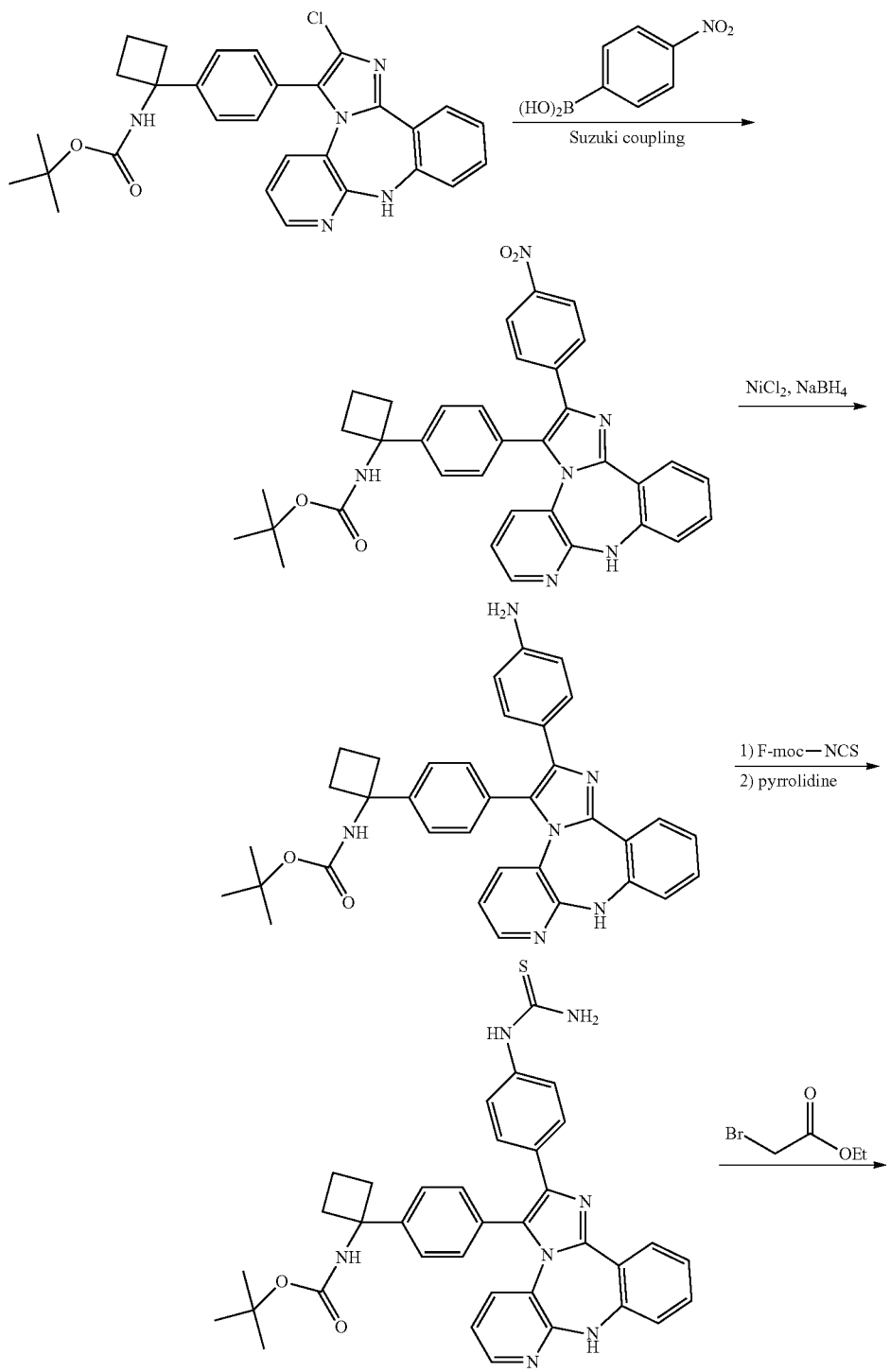

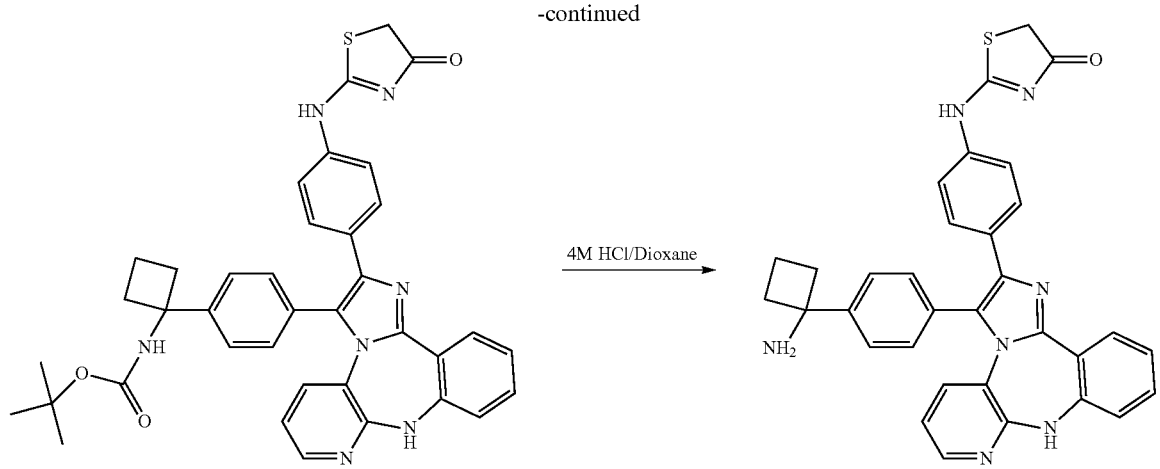

Step 1: Preparation of tert-butyl (1-{4-[2-(4-nitrophenyl)-9H-imidazo[1,2-d]pyrido[2,3-b][1,4]benzodiazepin-3-yl]phenyl}cyclobutyl)carbamate The title compound was synthesized according to the procedure described in step 1 of example 18 using (4-nitrophenyl)boronic acid instead of [4-(methoxycarbonyl)phenyl]boronic acid. LCMS: 601 [M+H].

Step 2: Preparation of tert-butyl (1-{4-[2-(4-aminophenyl)-9H-imidazo[1,2-d]pyrido[2,3-b][1,4]benzodiazepin-3-yl]phenyl}cyclobutyl)carbamate To a solution of tert-butyl (1-{4-[2-(4-nitrophenyl)-9H-imidazo[1,2-d]pyrido[2,3-b][1,4]benzodiazepin-3-yl]phenyl}cyclobutyl)carbamate (317 mg, 0.49 mmol) in THF (10 mL) and MeOH (5 mL) cooled to 0° C. was added $NiCl_2$ (245 mg, 1.03 mmol) and $NaBH_4$ (84 mg, 2.04 mmol). The reaction was slowly allowed to warm to room temperature and stirred 30 min. The reaction was diluted with sat.$NaHCO_3$aq and extracted with ethyl acetate (3×20 mL). The organic layers were combined, washed with brine. The organic phase was dried over sodium sulfate, filtered and concentrated gave the title compound as a yellow solid (214 mg, 76%).

Step 3: Preparation of tert-butyl {1-[4-(2-{4-[(aminocarbonothioyl)amino]phenyl}-9H-imidazo[1,2-d]pyrido[2,3-b][1,4]benzodiazepin-3-yl)phenyl]cyclobutyl}carbamate To a solution of tert-butyl (1-{4-[2-(4-aminophenyl)-9H-imidazo[1,2-d]pyrido[2,3-b][1,4]benzodiazepin-3-yl]phenyl}cyclobutyl)carbamate (52 mg, 0.091 mmol) in THF (2 mL) was added F-moc-N=C=S (35 mg, 0.12 mmol). The reaction was stirred 45 min then, added pyrrolidine (0.1 mL) and stirred 20 min. The reaction was concentrated. Purification by column chromatography ($SiO_2$, 20% to 50% to 100% EtOAc in hexane) gave the title compound as a yellow solid (61 mg). LCMS: 630 [M+H].

Step 4: Preparation of tert-butyl {1-[4-(2-{4-[(4-oxo-4,5-dihydro-1,3-thiazol-2-yl)amino]phenyl}-9H-imidazo[1,2-d]pyrido[2,3-b][1,4]benzodiazepin-3-yl)phenyl]cyclobutyl}carbamate To a solution of tert-butyl {1-[4-(2-{4-[(aminocarbonothioyl)amino]phenyl}-9H-imidazo[1,2-d]pyrido[2,3-b][1,4]benzodiazepin-3-yl)phenyl]cyclobutyl}carbamate (53 mg, 0.083 mmol) in EtOH (2 mL), THF (1 mL) and $CHCl_3$ (1 mL) was added ethyl bromoacetate (0.01 mL, 0.09 mmol). The reaction was heated at 70° C., 1.5 h. The reaction mixture was cooled to room temperature, then concentrated. Purification by column chromatography (SiO2, 50% to 100% EtOAc in hexane) gave the title compound as a yellow solid (51 mg, 91%). $^1$HNMR ($CDCl_3$) 400 MHz δ: 8.16 (d, J=8.0 Hz, 1H), 8.02-8.01 (m, 1H), 7.62-7.61 (m, 2H), 7.40-7.35 (m, 2H), 7.32-7.29 (m, 1H), 7.20-7.13 (m, 3H), 7.05-7.04 (m, 2H), 6.96 (d, J=8.0 Hz, 1H), 6.80-6.78 (m, 1H), 6.60 (dd, J=8.0, 4.6 Hz, 1H), 6.36 (br s, 1H), 5.18 (br s, 1H), 3.90-3.88 (m, 2H), 2.54-2.52 (m, 4H), 2.16-2.12 (m, 1H), 1.92-1.90 (m, 1H), 1.39 (br s, 9H).

Step 5: Preparation of 2-[(4-{3-[4-(1-aminocyclobutyl)phenyl]-9H-imidazo[1,2-d]pyrido[2,3-b][1,4]benzodiazepin-2-yl}phenyl)amino]-1,3-thiazol-4(5H)-one The title compound was synthesized according to the procedure described in step 2 of example 19. $^1$HNMR (DMSO-$d_6$) 400 MHz δ: 8.50 (s, 1H), 8.05 (dd, J=4.87, 1.43 Hz, 1H), 7.95 (d, J=6.30 Hz, 1H), 7.46 (d, J=8.59 Hz, 2H), 7.34-7.26 (m, 5H), 7.19-7.08 (m, 4H), 6.86 (d, J=7.45 Hz, 1H), 6.74-6.67 (m, 2H), 3.46-3.35 (m, 2H), 2.39-2.34 (m, 4H), 2.18-1.99 (m, 1H), 1.71-1.64 (m, 1H). LCMS: 570 [M+H].

Example 124
Preparation of 1-{4-[2-(pyrimidin-2-yl)-9H-imidazo[1,2-d]pyrido[2,3-b][1,4]benzodiazepin-3-yl]phenyl}cyclobutanamine
Step 1: Preparation of tert-butyl (1-{4-[2-(pyrimidin-2-yl)-9H-imidazo[1,2-d]pyrido[2,3-b][1,4]benzodiazepin-3-yl]phenyl}cyclobutyl)carbamate
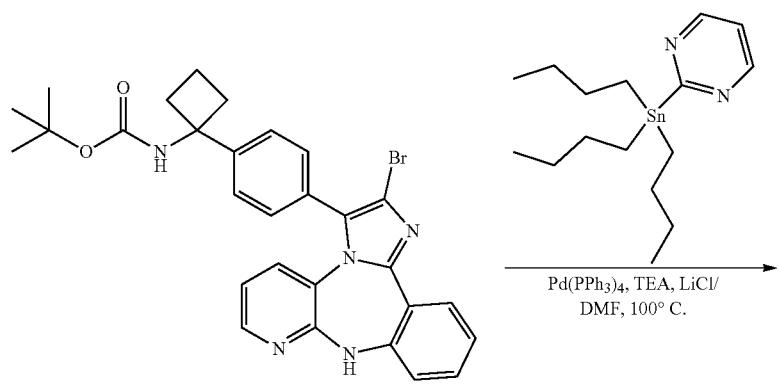
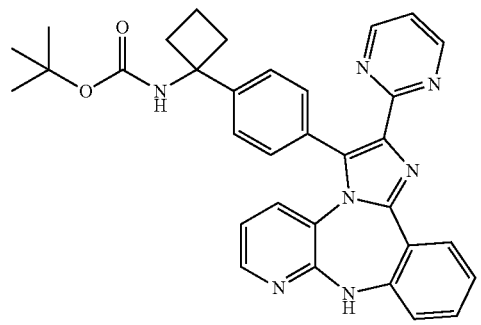

The title compound was synthesized according to the procedure described in step 1 of example 88 using 2-(tributylstannyl)pyrimidine instead of 2-(tributylstannyl)-1,3-benzothiazole. ¹HNMR (CDCl₃) 400 MHz δ: 8.70 (d, J=5.2 Hz, 2H), 8.30 (dd, J=8.0, 1.7 Hz, 1H), 7.57-7.52 (m, 2H), 7.35 (d, J=8.0 Hz, 2H), 7.29 (m, 2H), 7.15-7.09 (m, 2H), 6.96 (d, J=8.0 Hz, 1H), 6.85-6.78 (m, 1H), 6.59 (dd, J=8.0, 5.2 Hz, 1H), 6.56 (s, 1H), 5.23 (s, 1H), 2.60-2.34 (m, 4H), 2.17-2.08 (m, 1H), 1.92-1.82 (m, 1H), 1.48-1.20 (m, 9H); LC/MS [M+H]: 558.

Step 2: Preparation of 1-{4-[2-(pyrimidin-2-yl)-9H-imidazo[1,2-d]pyrido[2,3-b][1,4]benzodiazepin-3-yl]phenyl}cyclobutanamine

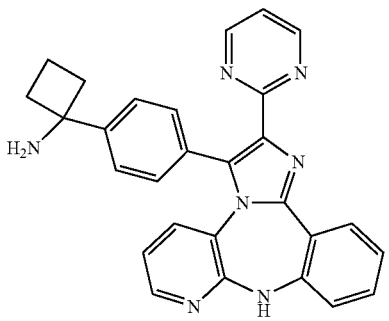 [SMILES: NC1(c2ccc(-c3c(-c4ncccn4)nc4n3-c3cccnc3Nc3ccccc3-4)cc2)CCC1]

The title compound was synthesized according to the procedure described in step 2 of example 88. ¹HNMR (DMSO-d₆) 400 MHz δ: 8.75-8.72 (m, 2H), 8.63 (brs, 3H), 8.10 (dd, J=4.6, 1.7 Hz, 1H), 7.94 (dd, J=7.7, 1.4 Hz, 1H), 7.45 (d, J=8.0 Hz, 2H), 7.39-7.34 (m, 2H), 7.31 (t, J=7.7 Hz, 2H), 7.12 (t, J=7.5 Hz, 1H), 6.85 (dd, J=8.0, 1.2 Hz, 1H), 6.72 (dd, J=8.0, 5.2 Hz, 1H), 6.78 (d, J=16 Hz, 1H), 2.60-2.39 (m, 4H), 2.20-2.10 (m, 1H), 1.85-1.73 (m, 1H); LC/MS [M+H]: 458.

Example 125

Preparation of 1-{4-[2-(pyridazin-4-yl)-9H-imidazo[1,2-d]pyrido[2,3-b][1,4]benzodiazepin-3-yl]phenyl}cyclobutanamine Step 1: Preparation of tert-butyl (1-{4-[2-(pyridazin-4-yl)-9H-imidazo[1,2-d]pyrido[2,3-b][1,4]benzodiazepin-3-yl]phenyl}cyclobutyl)carbamate

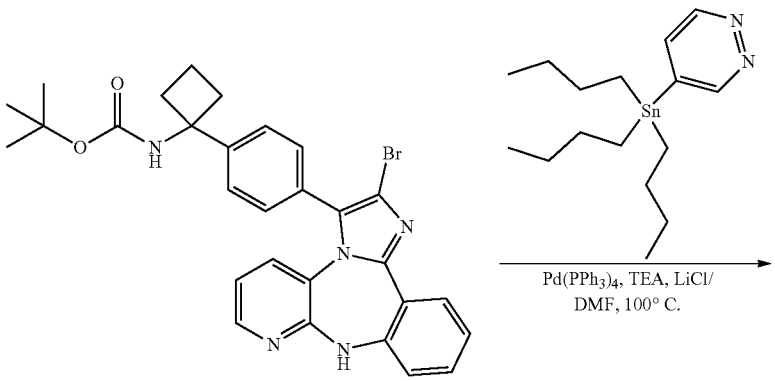

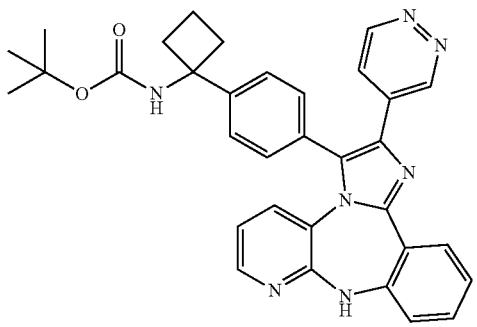

The title compound was synthesized according to the procedure described in step 1 of example 88 using 4-(tributylstannyl)pyridazine instead of 2-(tributylstannyl)-1,3-benzothiazole. ¹HNMR (CDCl₃) 400 MHz δ: 8.13 (dd, J=7.7, 1.4 Hz, 1H), 7.70-7.65 (m, 2H), 7.57-7.53 (m, 1H), 7.48 (d, J=8.6 Hz, 2H), 7.35 (td, J=7.5, 1.7 Hz, 1H), 7.32 (s, 1H), 7.22 (d, J=8.0 Hz, 2H), 7.18 (td, J=7.5, 1.2 Hz, 1H), 7.03 (d, J=8.0 Hz, 1H), 6.86-6.78 (m, 1H), 6.70 (s, 1H), 6.61 (dd, J=8.0, 4.6 Hz, 1H), 5.52 (s, 1H), 2.62-2.38 (m, 4H), 2.23-2.13 (m, 1H), 1.98-1.89 (m, 1H), 1.51-1.23 (m, 9H); LC/MS [M+H]: 558.

Step 2: Preparation of 1-{4-[2-(pyridazin-4-yl)-9H-imidazo[1,2-d]pyrido[2,3-b][1,4]benzodiazepin-3-yl]phenyl}cyclobutanamine

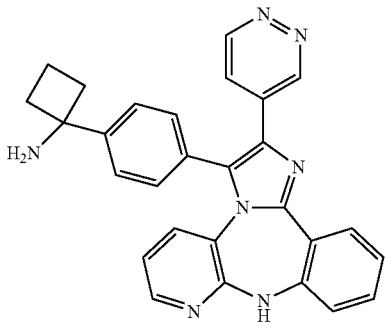 [SMILES: NC1(c2ccc(-c3c(-c4ccnnc4)nc4n3-c3cccnc3Nc3ccccc3-4)cc2)CCC1]

The title compound was synthesized according to the procedure described in step 2 of example 88. ¹HNMR (DMSO-d₆) 400 MHz δ: 9.20 (s, 2H), 8.77 (brs, 2H), 8.69 (s, 1H), 8.13 (dd, J=4.9, 1.4 Hz, 1H), 8.00 (dd, J=7.7, 1.4 Hz, 1H), 7.78-7.74 (m, 1H), 7.64 (d, J=7.5 Hz, 2H), 7.47 (d, J=8.0 Hz, 2H), 7.41 (td, J=8.0, 1.7 Hz, 1H), 7.32 (d, J=7.5 Hz, 1H), 7.16 (t, J=7.5 Hz, 1H), 6.94 (d, J=8.0 Hz, 1H), 6.76 (dd, J=7.7, 4.9 Hz, 1H), 2.66-2.53 (m, 4H), 2.27-2.17 (m, 1H), 1.88-1.80 (m, 1H); LC/MS [M+H]: 458.

Example 126

Preparation of 1-{4-[2-(thiophen-2-yl)-9H-imidazo[1,2-d]pyrido[2,3-b][1,4]benzodiazepin-3-yl]phenyl}cyclobutanamine Step 1: Preparation of tert-butyl (1-{4-[2-(thiophen-2-yl)-9H-imidazo[1,2-d]pyrido[2,3-b][1,4]benzodiazepin-3-yl]phenyl}cyclobutyl)carbamate

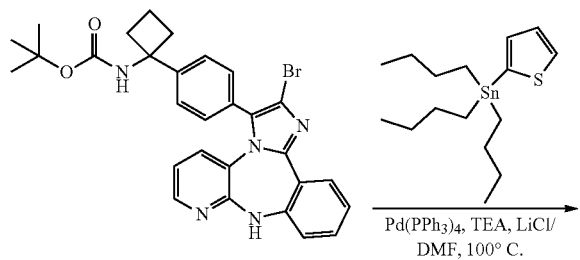

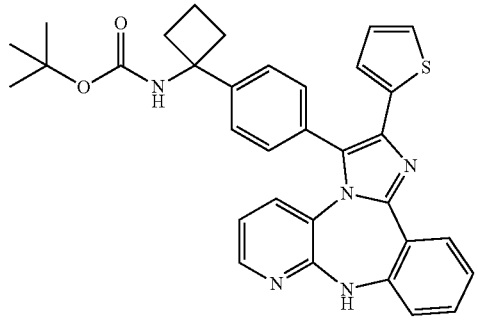

The title compound was synthesized according to the procedure described in step 1 of example 88 using tributyl(thiophen-2-yl)stannane instead of 2-(tributylstannyl)-1,3-benzothiazole. ¹HNMR (CDCl₃) 400 MHz δ: 8.13 (dd, J=7.7, 1.4 Hz, 1H), 7.99 (d, J=4.6 Hz, 1H), 7.42 (d, J=8.0 Hz, 2H), 7.32-7.25 (m, 4H), 7.29-7.09 (m, 3H), 6.94 (d, J=7.5 Hz, 1H), 6.93-6.89 (m, 1H), 6.87 (d, J=6.9 Hz, 1H), 6.59 (dd, J=8.0, 4.6 Hz, 1H), 6.52 (s, 1H), 5.22 (s, 1H), 2.60-2.38 (m, 4H), 2.20-2.09 (m, 1H), 1.95-1.85 (m, 1H), 1.50-1.16 (m, 9H); LC/MS [M+H]: 562.

Step 2: Preparation of 1-{4-[2-(thiophen-2-yl)-9H-imidazo[1,2-d]pyrido[2,3-b][1,4]benzodiazepin-3-yl]phenyl}cyclobutanamine

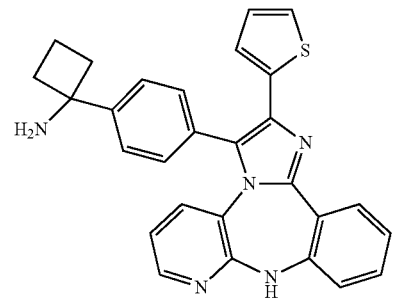 [SMILES: NC1(c2ccc(-c3c(-c4cccs4)nc4n3-c3cccnc3Nc3ccccc3-4)cc2)CCC1]

The title compound was synthesized according to the procedure described in step 2 of example 88. ¹HNMR (DMSO-d₆) 400 MHz δ: 8.77 (brs, 2H), 8.62 (s, 1H), 8.09 (dd, J=4.6, 1.7 Hz, 1H), 7.90 (d, J=7.5 Hz, 1H), 7.60 (d, J=8.6 Hz, 2H), 7.48-7.43 (m, 3H), 7.38 (td, J=8.0, 1.7 Hz, 1H), 7.30 (d, J=7.5 Hz, 1H), 7.13 (t, J=7.5 Hz, 1H), 7.05 (d, J=3.4 Hz, 1H), 7.00-6.94 (m, 2H), 6.74 (dd, J=8.0, 4.6 Hz, 1H), 2.63-2.53 (m, 4H), 2.26-2.16 (m, 1H), 1.87-1.77 (m, 1H); LC/MS [M+H]: 462.

Example 127

Preparation of {3-[4-(1-aminocyclobutyl)phenyl]-9H-imidazo[1,2-d]pyrido[2,3-b][1,4]benzodiazepin-2-yl}acetonitrile Step 1: Preparation of tert-butyl (1-{4-[2-(cyanomethyl)-9H-imidazo[1,2-d]pyrido[2,3-b][1,4]benzodiazepin-3-yl]phenyl}cyclobutyl)carbamate

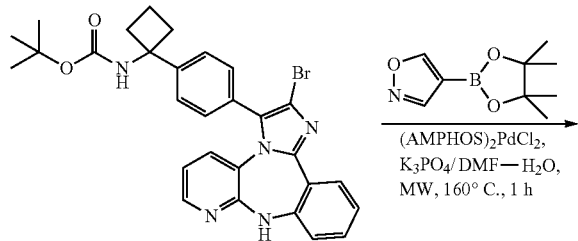

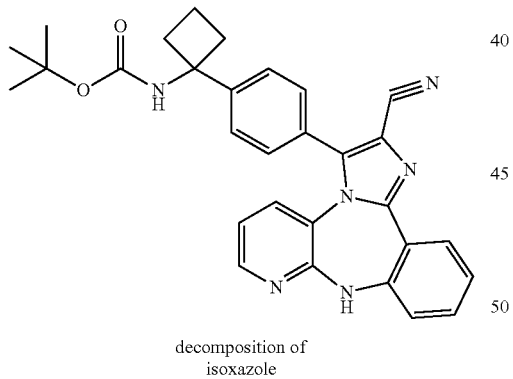

decomposition of isoxazole

The title compound was synthesized according to the procedure described in step 1 of example 19 using 4-(4,4,5,5-tetramethyl-1,3,2-dioxaborolan-2-yl)isoxazole instead of 6-(4,4,5,5-tetramethyl-1,3,2-dioxaborolan-2-yl)-1H-pyrrolo[3,2-b]pyridine. ¹HNMR (CDCl₃) 400 MHz δ: 8.06-8.02 (m, 2H), 7.44 (d, J=9.1 Hz, 2H), 7.32 (td, J=7.7, 1.5 Hz, 1H), 7.18-7.12 (m, 3H), 6.95 (d, J=8.0 Hz, 1H), 6.85 (d, J=8.0 Hz, 1H), 6.64 (dd, J=8.0, 4.6 Hz, 1H), 6.35 (s, 1H), 5.15 (s, 1H), 3.76 (s, 2H), 2.58-2.35 (m, 4H), 2.20-2.10 (m, 1H), 1.95-1.85 (m, 1H), 1.50-1.19 (m, 9H); LC/MS [M+H]: 519.

Step 2: Preparation of {3-[4-(1-aminocyclobutyl)phenyl]-9H-imidazo[1,2-d]pyrido[2,3-b][1,4]benzodiazepin-2-yl}acetonitrile

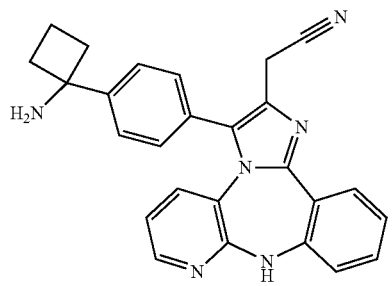 [SMILES: N#CCc1nc2n(c1-c1ccc(C3(N)CCC3)cc1)-c1cccnc1Nc1ccccc1-2]

The title compound was synthesized according to the procedure described in step 2 of example 19. ¹HNMR (DMSO-d₆) 400 MHz δ: 8.75 (brs, 2H), 8.64 (s, 1H), 8.13 (dd, J=4.6, 1.7 Hz, 1H), 7.87 (dd, J=7.7, 1.4 Hz, 1H), 7.58 (d, J=9.7 Hz, 2H), 7.37 (t, J=8.0 Hz, 1H), 7.32-7.25 (m, 3H), 7.10 (t, J=8.0 Hz, 1H), 6.89 (dd, J=8.0, 1.7 Hz, 1H), 6.78 (dd, J=8.0, 4.6 Hz, 1H), 2.61-2.53 (m, 4H), 2.23-2.15 (m, 1H), 1.85-1.77 (m, 1H); LC/MS [M+H]: 419.

Example 128

Preparation of 4-(hydroxymethyl)-4-[4-(2-phenyl-9H-imidazo[1,2-d]pyrido[2,3-b][1,4]benzodiazepin-3-yl)phenyl]-1,3-oxazolidin-2-one

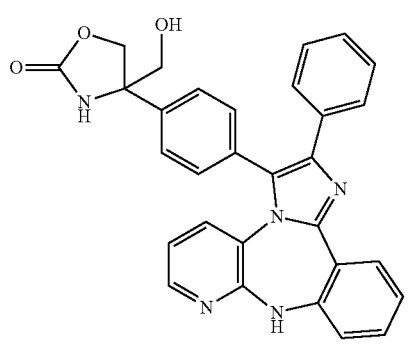 [SMILES: O=C1NC(CO)(c2ccc(-c3c(-c4ccccc4)nc4n3-c3cccnc3Nc3ccccc3-4)cc2)CO1]

The title compound was synthesized according to the procedure described in example 69 as a by-product. ¹HNMR (DMSO-d₆) 400 MHz δ: 8.58 (s, 1H), 8.34 (s, 1H), 8.07 (dd, 1H, J=4.8, 1.1 Hz), 7.99-7.92 (m, 1H), 7.49 (d, 2H, J=7.3 Hz), 7.40-7.19 (m, 9H), 7.12 (t, 1H, J=7.6 Hz), 6.84 (dd, 1H, J=7.8, 1.1 Hz), 6.73 (dd, 1H, J=7.8, 4.8 Hz), 5.76-5.04 (m, 1H), 4.63 (d, 1H, J=8.3 Hz), 4.18 (d, 1H, J=8.3 Hz), 3.59 (d, 1H, J=11.5 Hz), 3.46 (d, 1H, J=11.5 Hz).

Example 129

Preparation of ethyl 3-{3-[4-(1-aminocyclobutyl)phenyl]-9H-imidazo[1,2-d]pyrido[2,3-b][1,4]benzodiazepin-2-yl}benzoate trihydrochloride

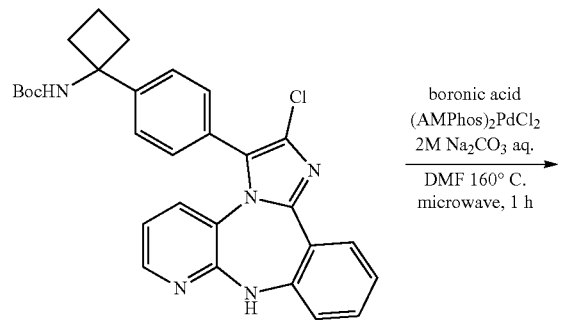

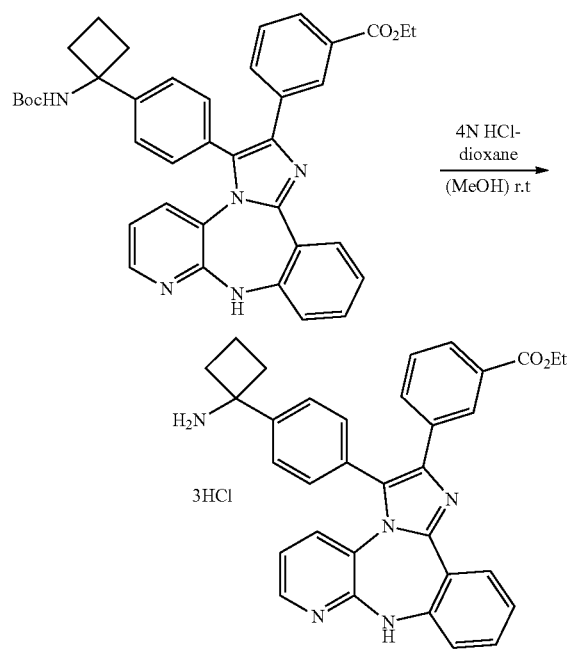

The title compound was synthesized according to the procedure described in example 18 using (3-(ethoxycarbonyl)phenyl)boronic acid in step 1 instead of [4-(methoxycarbonyl)phenyl]boronic acid. $^1$HNMR (DMSO-$d_6$) 400 MHz δ: 8.62 (br s, 3H), 8.18-8.16 (m, 1H), 8.11 (dd, J=4.6 Hz and 1.7 Hz, 1H), 7.98 (dd, J=7.4 Hz and 1.7 Hz, 1H), 7.85 (dt, J=7.4 Hz and 1.7 Hz, 1H), 7.69-7.67 (m, 1H), 7.55 (d, J=8.6 Hz, 2H), 7.43 (t, J=7.7 Hz, 1H), 7.40-7.35 (m, 3H), 7.31 (d, J=8.0 Hz, 1H), 7.14 (td, J=7.4 Hz and 1.1 Hz, 1H), 6.92 (dd, J=8.0 Hz and 1.7 Hz, 1H), 6.73 (dd, J=8.0 Hz and 5.2 Hz, 1H), 4.29 (q, J=6.9 Hz, 2H), 3.73-3.65 (m, 1H), 3.51-3.45 (m, 1H), 2.62-2.53 (m, 2H), 2.23-2.14 (m, 1H), 1.88-1.80 (m, 1H), 1.29 (t, J=6.9 Hz, 3H). LCMS: 528 [M+H].

Example 130

Preparation of 1-(3-{3-[4-(1-aminocyclobutyl)phenyl]-9H-imidazo[1,2-d]pyrido[2,3-b][1,4]benzodiazepin-2-yl}phenyl)-3-phenylurea trihydrochloride Step 1: Preparation of tert-butyl {1-[4-(2-{3-[(anilinocarbonyl)amino]phenyl}-9H-imidazo[1,2-d]pyrido[2,3-b][1,4]benzodiazepin-3-yl)phenyl]cyclobutyl}carbamate

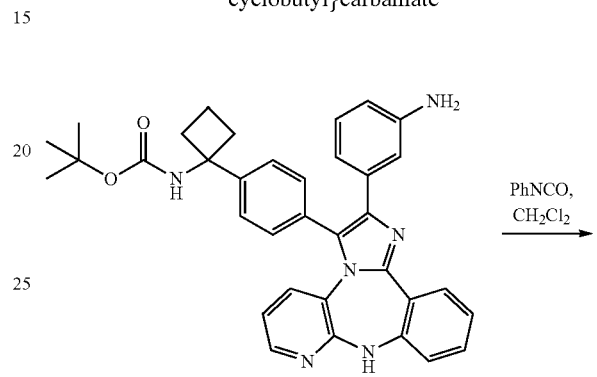

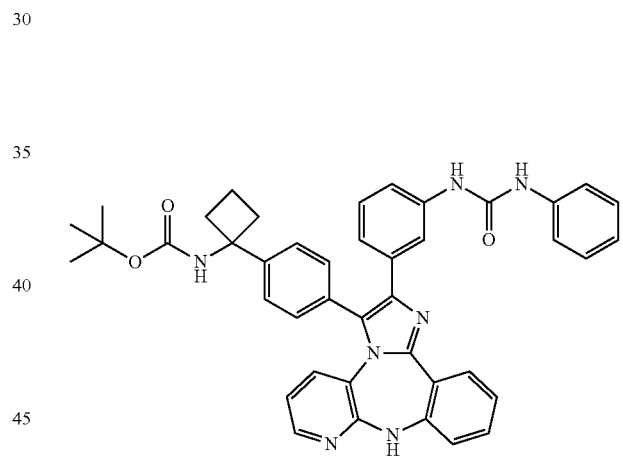

Et$_3$N (29.3 μL, 0.260 mmol) and phenyl isocyanate (8.0 μL, 0.0771 mmol) were added to a solution of tert-butyl (1-{4-[2-(3-aminophenyl)-9H-imidazo[1,2-d]pyrido[2,3-b][1,4]benzodiazepin-3-yl]phenyl}cyclobutyl)carbamate (40.0 mg, 0.0701 mmol) in DCM (1 mL) at 0° C., and stirred at room temperature. After reaction was completed, the mixture was diluted with sat. NaHCO$_3$ and extracted with CHCl$_3$ (3×). The combined organic layers were dried over anhydrous Na$_2$SO$_4$, and concentrated. The residue was purified by PTLC (CHCl$_3$/MeOH=9:1) to afford desired product (35.4 mg, 69.3%) as white solid. $^1$HNMR (DMSO-$d_6$) 400 MHz δ: 8.15 (dd, J=7.8, 1.4 Hz, 1H), 8.05 (dd, J=4.6, 1.8 Hz, 1H), 7.90-6.59 (m, 20H), 6.30 (s, 1H), 6.18-5.38 (m, 1H), 2.67-2.54 (m, 2H), 2.52-2.39 (m, 2H), 2.25-2.10 (m, 1H), 2.06-1.86 (m, 1H), 1.37 (s, 9H).

Step 2: Preparation of 1-(3-{3-[4-(1-aminocyclobutyl)phenyl]-9H-imidazo[1,2-d]pyrido[2,3-b][1,4]benzodiazepin-2-yl}phenyl)-3-phenylurea trihydrochloride

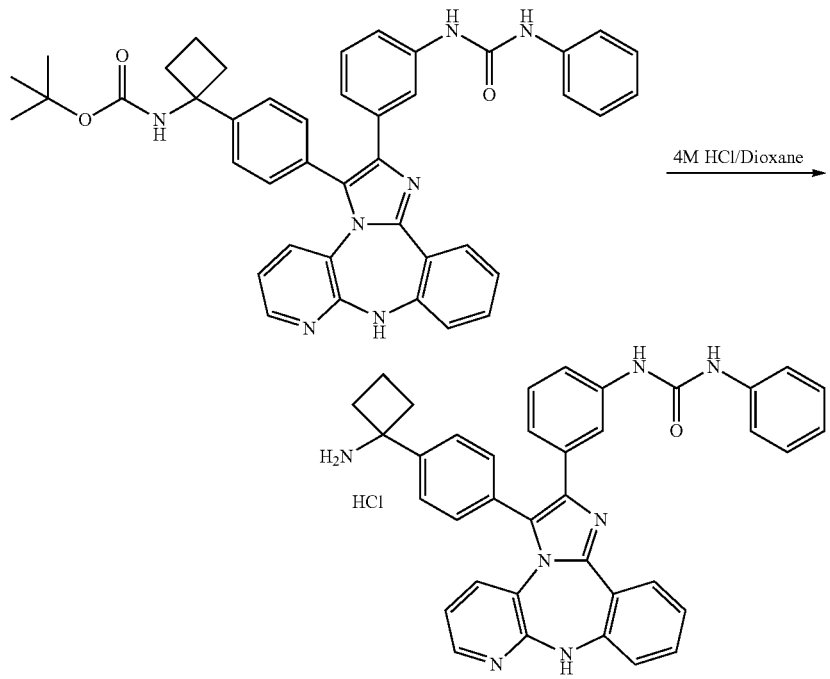

The title compound was synthesized according to the procedure described in step 2 of example 73. ¹HNMR (DMSO-d₆) 400 MHz δ: 9.04 (s, 1H), 8.95 (s, 1H), 8.67 (br s, 2H), 8.63 (s, 1H), 8.11 (dd, J=4.6, 1.4 Hz, 1H), 7.96 (dd, J=7.8, 1.4 Hz, 1H), 7.58-7.05 (m, 15H), 6.99-6.91 (m, 2H), 6.75 (dd, J=7.8, 4.6 Hz, 1H), 3.06-2.44 (m, 4H), 2.23-2.08 (m, 1H), 1.89-1.73 (m, 1H); LCMS: 590 [M+H].

Example 131

Preparation of 1-{4-[2-(2-phenylethyl)-9H-imidazo[1,2-d]pyrido[2,3-b][1,4]benzodiazepin-3-yl]phenyl}cyclobutanamine Step: 1: Preparation of tert-butyl (1-{4-[2-(2-phenylethyl)-9H-imidazo[1,2-d]pyrido[2,3-b][1,4]benzodiazepin-3-yl]phenyl}cyclobutyl)carbamate (E)-tert-butyl (1-(4-(2-styryl-9H-benzo[f]imidazo[1,2-d]pyrido[2,3-b][1,4]diazepin-3-yl)phenyl)cyclobutyl)carbamate was stirred in THF-MeOH under hydrogen in the presence of 5% Pd/C to give the title compound ¹HNMR (CDCl₃) 400 MHz δ: 8.10 (dd, J=7.7, 1.4 Hz, 1H), 7.99 (dd, J=4.6, 1.2 Hz, 1H), 7.34-7.27 (m, 3H), 7.24 (d, J=6.9 Hz, 1H), 7.18 (d, J=7.5 Hz, 2H), 7.14 (td, J=7.5, 1.2 Hz, 1H), 6.95 (d, J=7.5 Hz, 1H), 6.90 (d, J=7.5 Hz, 2H), 6.78 (d, J=7.5 Hz, 1H), 6.59 (dd, J=8.0, 4.6 Hz, 1H), 6.29 (s, 1H), 5.08 (s, 1H), 3.12-3.07 (m, 2H), 3.01-2.95 (m, 2H), 2.56-2.38 (m, 4H), 2.16-2.07 (m, 1H), 1.91-1.82 (m, 1H), 1.48-1.19 (m, 9H); LC/MS [M+H]: 584.

Step 2: Preparation of 1-{4-[2-(2-phenylethyl)-9H-imidazo[1,2-d]pyrido[2,3-b][1,4]benzodiazepin-3-yl]phenyl}cyclobutanamine

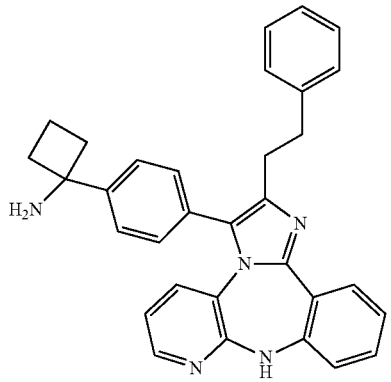 [SMILES: NC1(c2ccc(-c3c(CCc4ccccc4)nc4n3-c3cccnc3Nc3ccccc3-4)cc2)CCC1]

The title compound was synthesized according to the procedure described in step 2 of example 19. $^1$HNMR (DMSO-$d_6$) 400 MHz δ: 8.23 (d, J=4.6 Hz, 1H), 7.85 (d, J=8.0 Hz, 1H), 7.63 (t, J=7.7 Hz, 1H), 7.56 (d, J=7.5 Hz, 2H), 7.33 (d, J=6.9 Hz, 2H), 7.26-7.10 (m, 8H), 7.08 (d, J=7.5 Hz, 2H), 6.84-6.80 (m, 1H), 3.16-3.00 (m, 4H), 2.81-2.72 (m, 2H), 2.69-2.60 (m, 2H), 2.33-2.25 (m, 1H), 2.02-1.94 (m, 1H); LC/MS [M+H]: 484.

Example 132

Preparation of N-(4-{3-[4-(1-aminocyclobutyl)phenyl]-9H-imidazo[1,2-d]pyrido[2,3-b][1,4]benzodiazepin-2-yl}phenyl)-2-hydroxy-2-methylpropanamide

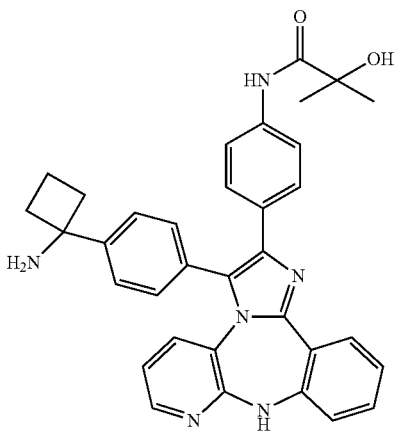 [SMILES: CC(C)(O)C(=O)Nc1ccc(-c2nc3n(c2-c2ccc(C4(N)CCC4)cc2)-c2cccnc2Nc2ccccc2-3)cc1]

The title compound was synthesized according to the similar procedure described for the synthesis of example 40. $^1$HNMR (CDCl$_3$) 400 MHz δ: 8.91 (s, 1H), 8.14 (d, J=8.0 Hz, 1H), 8.03 (d, J=5.2 Hz, 1H), 7.52 (d, J=1.1 Hz, 4H), 7.38 (d, J=8.0 Hz, 2H), 7.34-7.31 (m, 1H), 7.29 (d, J=8.0 Hz, 1H), 7.17-7.11 (m, 3H), 6.99 (d, J=8.0 Hz, 1H), 6.80 (d, J=8.0 Hz, 1H), 6.65-6.62 (m, 1H), 6.51 (s, 1H), 4.68 (br s, 1H), 2.59-2.53 (m, 8H), 2.19-2.12 (m, 2H), 1.85-1.77 (m, 2H). LCMS: 557 [M+H].

Example 133

Preparation of 3-phenyl 2-(pyridin-4-yl)-9H-imidazo[1,2-d]pyrido[2,3-b][1,4]benzodiazepine

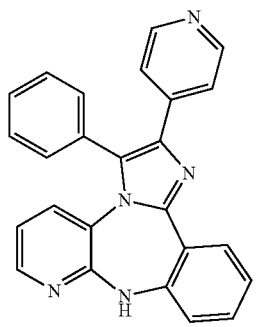 [SMILES: c1ccc(-c2c(-c3ccncc3)nc3n2-c2cccnc2Nc2ccccc2-3)cc1]

The title compound was synthesized according to the procedure described in step 1 of example 19 using 2-bromo-3-phenyl-9H-benzo[f]imidazo[1,2-d]pyrido[2,3-b][1,4]diazepine and pyridin-4-ylboronic acid. $^1$HNMR (CDCl$_3$) 400 MHz δ: 8.50-8.47 (m, 2H), 8.18-8.14 (m, 1H), 8.06-8.03 (m, 1H), 7.49-7.46 (m, 2H), 7.44-7.31 (m, 5H), 7.29-7.22 (m, 1H), 7.20-7.16 (m, 1H), 6.98-6.94 (m, 1H), 6.83-6.78 (m, 1H), 6.64 (dd, J=8.0, 4.6 Hz, 1H), 6.28 (br s, 1H); LC/MS: 388 [M+H].

Example 134

AKT1 Alpha Screen Assay

AKT1 activity is assayed using the GSK3-derived biotinylated peptide substrate, crosstide (biotin-GRPRTSSFAEG), and AlphaScreen™ (Amplified Luminescent Proximity Homogeneous Assay) technology. AKT1 activation is achieved by the addition of the activating kinases PDK1 and MAPKAPK2, lipid vesicles, and ATP. The extent of peptide phosphorylation is determined using a phospho-AKT substrate antibody and acceptor beads conjugated to Protein A and donor beads conjugated to streptavidin that will bind to the biotin on the peptide. Excitation of the donor beads converts ambient oxygen to excited singlet oxygen which, when in close proximity to acceptor beads, reacts with acceptor beads resulting in signal amplification.

Test inhibitors and controls are prepared in 10% DMSO at 10-fold the desired final concentration, and added to each well of a reaction plate (Corning 96-well half-area solid white nonbinding surface plate) in a volume of 2.5 μL. Full-length non-phosphorylated AKT1 is diluted in assay buffer (50 mM Tris, pH 8.0, 0.02 mg/mL BSA, 10 mM MgCl$_2$, 1 mM EGTA, 10% glycerol, 0.2 mM Na$_3$VO$_4$, 1 mM DTT, 0.1 mM β-glycerophosphate, and 0.2 mM NaF) and added to each well in a volume of 17.5 μL for a final concentration in the 25 μL reaction of 8 nM (Akt1). After a 20 minute pre-incubation at room temperature, the kinase reaction is initiated by the addition of 5 μL of an activation mixture diluted in assay buffer containing biotinylated crosstide, PDK1, MAPKAPK2, DOPS/DOPC, PtdIns(3,4,5)P3, and ATP for final concentrations of 60 nM biotinylated crosstide, 0.1 nM PDK1, 0.7 nM MK2, 5.5 μM DOPS, 5.5 μM DOPC, 0.5 μM PtdIns(3,4,5)P3, and 50 μM ATP. The plates are incubated for 30 minutes at room temperature, and then stopped in the dark by the addition of 10 μL stop/detection mixture prepared in assay buffer containing EDTA, AlphaScreen™ Streptavidin Donor and Protein A Acceptor beads, and phospho-AKT substrate antibody for final concentrations of 10 mM EDTA, 500 ng/well of both AlphaScreen™ Streptavidin Donor beads and Protein A Acceptor beads, and phospho-AKT substrate antibody at a final dilution of 1:350. Assay plates are incubated for 90 minutes at room temperature in the dark, and the plates are read on a Perkin Elmer Envision Multilabel plate reader (excitation wavelength: 640 nm, emission wavelength: 570 nm).

Reaction conditions: 2.5 μL 10× Akt inhibitor in 10% DMSO; 17.5 μL non-phosphorylated Akt or buffer for blank; 20 minute pre-incubation at room temperature; 5 μL Reaction Mix (5×ATP, 5×substrate, 5×PDK1, 5×MK2, and 5× lipid vesicle mixture); 30 minute incubation at room temperature; 10 μL Detection Buffer; 90 minute incubation at room temperature and Detection (excitation: 640 nm, emission: 570 nm).

Table 2 shows the AKT1 inhibition activity of the disclosed substituted benzo-imidazo-pyrido-diazepine compounds.

TABLE 2

| Cmpd. No. | Akt1 IC$_{50}$ (μM) |
|---|---|
| 3 | 0.496 |
| 4 | 0.019 |
| 5 | 0.027 |
| 7 | 0.038 |
| 8 | 0.009 |
| 9 | 0.028 |
| 10 | 0.004 |
| 12 | 0.010 |
| 13 | 0.061 |
| 14 | 0.016 |
| 15 | 0.014 |
| 16 | 0.013 |
| 17 | 0.004 |
| 18 | 0.011 |
| 19 | 0.010 |
| 20 | 0.021 |
| 21 | 0.016 |
| 22 | 0.007 |
| 23 | 0.005 |
| 24 | 0.029 |
| 25 | 0.028 |
| 26 | 0.008 |
| 27 | 0.083 |
| 28 | 0.016 |
| 29 | 0.005 |
| 30 | 0.020 |
| 31 | 0.003 |
| 32 | 0.006 |
| 33 | 0.023 |
| 34 | 0.020 |
| 35 | 0.004 |
| 36 | 0.002 |
| 37 | 0.022 |
| 38 | 0.030 |
| 39 | 0.017 |
| 40 | 0.016 |
| 41 | 0.007 |
| 42 | 0.003 |
| 43 | 0.006 |
| 44 | 0.009 |
| 45 | 0.007 |
| 46 | 0.010 |
| 47 | 0.041 |
| 48 | 0.002 |
| 51 | 0.014 |
| 52 | 0.654 |
| 53 | 0.013 |
| 54 | 0.041 |
| 56 | 0.035 |
| 57 | 0.010 |
| 58 | 0.021 |
| 59 | 0.007 |
| 60 | 0.006 |
| 61 | 0.013 |
| 62 | 0.006 |
| 63 | 0.030 |
| 64 | 0.004 |
| 65 | 0.016 |
| 66 | 0.016 |
| 68 | 0.027 |
| 69 | 0.018 |
| 70 | 0.343 |
| 71 | 0.971 |
| 72 | 0.060 |
| 73 | 0.005 |
| 74 | 0.943 |
| 75 | 0.042 |
| 77 | 0.050 |
| 78 | 0.033 |
| 79 | 0.055 |
| 80 | 0.015 |
| 81 | 0.004 |
| 82 | 0.006 |
| 83 | 0.073 |
| 85 | 0.009 |
| 86 | 0.080 |
| 87 | 0.021 |
| 88 | 0.017 |
| 89 | 0.045 |
| 90 | 0.015 |
| 91 | 0.019 |
| 92 | 0.067 |
| 93 | 0.066 |
| 94 | 0.013 |
| 95 | 0.006 |
| 96 | 0.004 |
| 97 | 0.010 |
| 98 | 0.021 |
| 99 | 0.488 |
| 100 | 0.237 |
| 101 | 0.063 |
| 102 | 0.057 |
| 103 | 0.003 |
| 104 | 0.058 |
| 105 | 0.002 |
| 106 | 0.007 |
| 107 | 0.033 |
| 108 | 0.003 |
| 109 | 0.013 |
| 110 | 0.006 |
| 111 | 0.002 |
| 112 | 0.004 |
| 113 | 0.003 |
| 114 | 0.008 |
| 115 | 0.034 |
| 116 | 0.024 |
| 117 | 0.034 |
| 118 | 0.029 |
| 119 | 0.007 |
| 120 | 0.191 |
| 121 | 0.021 |
| 122 | 0.159 |
| 123 | 0.060 |
| 124 | 0.023 |
| 125 | 0.045 |
| 126 | 0.012 |
| 127 | 0.083 |
| 128 | 3.210 |
| 129 | 0.040 |
| 130 | 0.327 |
| 131 | 0.035 |
| 132 | 0.046 |
| 133 | 0.295 |
| 134 | 0.053 |

TABLE 2-continued

| Cmpd. No. | Akt1 IC$_{50}$ (μM) |
| --- | --- |
| 135 | 0.119 |
| 136 | 0.084 |
| 137 | 0.168 |
| 138 | 0.053 |
| 139 | 0.074 |
| 140 | 0.295 |
| 141 | 0.451 |
| 142 | 0.485 |
| 143 | 0.122 |
| 144 | 0.184 |
| 145 | >1 |
| 146 | >1 |
| 147 | 0.046 |
| 148 | 0.066 |
| 149 | 0.018 |
| 150 | 0.003 |
| 151 | 0.004 |

The invention claimed is:

1. A compound of formula (I):

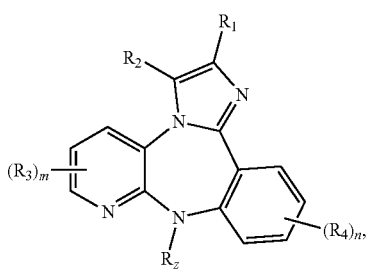

or a pharmaceutically acceptable salt or ester thereof, wherein:

$R_z$ is H or $C_1$-$C_6$ alkyl;

$R_1$ is H, halogen, cyano, unsubstituted or substituted $C_1$-$C_6$ alkyl, unsubstituted or substituted $C_2$-$C_6$ alkenyl, unsubstituted or substituted $C_2$-$C_6$ alkynyl, or $Q_1$-$T_1$, wherein said substituted $C_1$-$C_6$ alkyl, substituted $C_2$-$C_6$ alkenyl, or substituted $C_2$-$C_6$ alkynyl is substituted with one or more groups independently selected from hydroxy, halogen, cyano, amino, and phenyl;

$R_2$ is $C_1$-$C_6$ alkyl, $C_2$-$C_6$ alkenyl, $C_2$-$C_6$ alkynyl, or $Q_2$-$T_2$;

$Q_1$ and $Q_2$ are each independently a bond or $C_1$-$C_6$ alkyl linker;

$T_1$ is unsubstituted or substituted $C_6$-$C_{10}$ aryl, unsubstituted or substituted heteroaryl comprising one or two 5- or 6-membered rings and 1-4 heteroatoms selected from N, O and S, unsubstituted or substituted $C_3$-$C_{10}$ carbocycle, unsubstituted or substituted heterocycle comprising one or two 5- or 6-membered rings and 1-4 heteroatoms selected from N, O and S, OR$_t$, SR$_t$, C(O)NR$_t'$R$_t$, C(O)R$_t$, C(O)OR$_t$, NR$_t'$C(O)NR$_t''$R$_t$, NR$_t'$C(O)OR$_t$, NR$_t'$C(O)R$_t$, S(O)$_2$R$_t$, or NR$_t'$S(O)$_2$R$_t$, wherein said substituted $C_6$-$C_{10}$ aryl, substituted heteroaryl, substituted $C_3$-$C_{10}$ carbocycle, or substituted heterocycle is substituted with one or more R$_p$, wherein each R$_p$ is independently selected from:
a) hydroxy, halogen, cyano, nitro,
b) $C_1$-$C_6$ alkyl,
c) $C_1$-$C_6$ alkoxy,
d) amino, $C_1$-$C_6$ alkylamino, di-$C_1$-$C_6$ alkylamino,
e) $C_6$-$C_{10}$ aryl,
f) heteroaryl comprising one or two 5- or 6-membered rings and 1-4 heteroatoms selected from N, O and S,
g) $C_3$-$C_{10}$ carbocycle,
h) heterocycle comprising one or two 5- or 6-membered rings and 1-4 heteroatoms selected from N, O and S,
i) OR$_5$, NR$_s$,R$_5$, SR$_5$, C(O)R$_5$, C(O)OR$_5$, C(O)NR$_s$R$_5$, NR$_s'$C(O)R$_5$, NR$_s'$C(O)OR$_5$, NR$_s'$C(O)NR$_s$R$_5$, S(O)$_2$R$_5$, and NR$_s'$S(O)$_2$R$_5$, wherein R$_5$ is H, $C_1$-$C_6$ alkyl, $C_6$-$C_{10}$ aryl-$C_1$-$C_6$ alkyl, $C_6$-$C_{10}$ aryl, heteroaryl comprising one or two 5- or 6-membered rings and 1-4 heteroatoms selected from N, O and S, $C_3$-$C_{10}$ carbocycle, or heterocycle comprising one or two 5- or 6-membered rings and 1-4 heteroatoms selected from N, O and S; and R$_s$ and R$_s'$ are each independently H or $C_1$-$C_6$ alkyl;

$T_2$ is unsubstituted or substituted $C_6$-$C_{10}$ aryl, unsubstituted or substituted heteroaryl comprising one or two 5- or 6-membered rings and 1-4 heteroatoms selected from N,O and S, unsubstituted or substituted $C_3$-$C_{10}$ carbocycle, or unsubstituted or substituted heterocycle comprising one or two 5- or 6-membered rings and 1-4 heteroatoms selected from N, O and S, wherein said substituted $C_6$-$C_{10}$ aryl, substituted heteroaryl, substituted $C_3$-$C_{10}$ carbocycle, or substituted heterocycle is substituted with one or more groups independently selected from:
a) hydroxy, halogen, cyano, nitro,
b) $C_1$-$C_6$ alkyl,
c) $C_1$-$C_6$ alkoxy,
d) amino, $C_1$-$C_6$ alkylamino, di-$C_1$-$C_6$ alkylamino,
e) $C_6$-$C_{10}$ aryl,
f) heteroaryl comprising one or two 5- or 6-membered rings and 1-4 heteroatoms selected from N, O and S,
g) $C_3$-$C_{10}$ carbocycle, and
h) heterocycle comprising one or two 5- or 6-membered rings and 1-4 heteroatoms selected from N, O and S;

R$_t$ is H, $C_1$-$C_6$ alkyl, $C_6$-$C_{10}$ aryl, heteroaryl comprising one or two 5- or 6-membered rings and 1-4 heteroatoms selected from N, O and S, $C_3$-$C_{10}$ carbocycle, or heterocycle comprising one or two 5- or 6-membered rings and 1-4 heteroatoms selected from N, O and S;

R$_t'$ and R$_t''$ are each independently H or $C_1$-$C_6$ alkyl;

m is 0, 1, 2, or 3;

n is 0, 1, 2, 3, or 4;

each R$_3$ is independently halogen, cyano, nitro, hydroxy, $C_1$-$C_6$ alkyl, $C_2$-$C_6$ alkenyl, $C_2$-$C_6$ alkynyl, $C_1$-$C_6$ alkoxy, amino, $C_1$-$C_6$ alkylamino, or di-$C_1$-$C_6$ alkylamino; and each R$_4$ is independently halogen, cyano, nitro, hydroxy, $C_1$-$C_6$ alkyl, $C_2$-$C_6$ alkenyl, $C_2$-$C_6$ alkynyl, $C_1$-$C_6$ alkoxy, amino, $C_1$-$C_6$ alkylamino, or di-$C_1$-$C_6$ alkylamino.

2. The compound of claim 1, wherein R$_1$ is Q$_1$-T$_1$.

3. The compound of claim 2, wherein Q$_1$ is a bond, a methyl linker, or an ethyl linker.

4. The compound of claim 3, wherein T$_1$ is heterocycle comprising one or two 5- or 6-membered rings and 1-4 heteroatoms selected from N, O and S.

5. The compound of claim 3, wherein T$_1$ is OR$_t$, SR$_t$, C(O)R$_t$, C(O)OR$_t$, or C(O)NR$_t'$R$_t$.

6. The compound of claim 3, wherein T$_1$ is $C_3$-$C_{10}$ cycloalkyl or $C_3$-$C_{10}$ cycloalkenyl.

7. The compound of claim 3, wherein T$_1$ is phenyl or naphthyl.

8. The compound of claim 7, wherein T$_1$ is phenyl.

9. The compound of claim 3, wherein $T_1$ is heteroaryl comprising one or two 5- or 6-membered rings and 1-4 heteroatoms selected from N, O and S.

10. The compound of claim 9, wherein said heteroaryl is selected from the group consisting of pyrrolyl, furanyl, thienyl, thiazolyl, imidazolyl, pyrazolyl, oxazolyl, isoxazolyl, pyridinyl, pyrazinyl, pyridazinyl, pyrimidinyl, benzofuranyl, benzoxazolyl, benzothiazolyl, benzoimidazolyl, benzothienyl, quinolinyl, isoquinolinyl, indolyl, purinyl, pyrrolopyridinyl, imidazopyridinyl, and benzofuranonyl.

11. The compound of claim 1, wherein $R_z$ is H; m is 0; and n is 0.

12. The compound of claim 1, wherein each $R_3$ is independently halogen or $C_1$-$C_6$ alkyl.

13. The compound of claim 1, wherein each $R_4$ is independently halogen or $C_1$-$C_6$ alkyl.

14. The compound of claim 1, wherein $R_2$ is $Q_2$-$T_2$; $Q_2$ is a bond; and $T_2$ is phenyl.

15. The compound of claim 1, wherein $R_1$ is halogen or cyano.

16. The compound of claim 1, wherein $R_1$ is $C_1$-$C_6$ alkyl, $C_2$-$C_6$ alkenyl, or $C_2$-$C_6$ alkynyl.

17. The compound of claim 1, having formula (Ib):

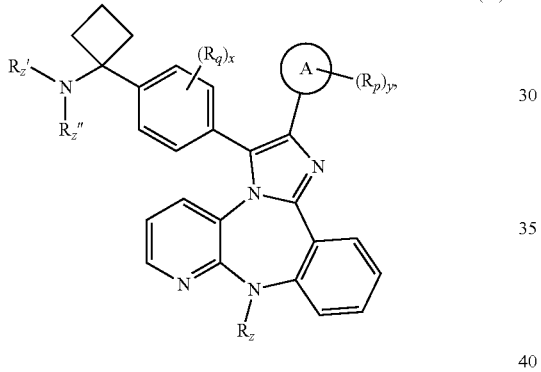

(Ib)

or a pharmaceutically acceptable salt or ester thereof, wherein:

$R_z$, $R_z'$ and $R_z''$ are each independently H or $C_1$-$C_6$ alkyl;
$R_s$ and $R_s'$ are each independently H or $C_1$-$C_6$ alkyl;

comprises one or two 5- or 6-membered rings and optionally 1-4 heteroatoms selected from N, O and S;
x and y are each independently 0, 1, 2, 3, or 4;
each $R_p$ is independently hydroxy, halogen, cyano, nitro, $C_1$-$C_6$ alkyl, $C_1$-$C_6$ alkoxy, amino, $C_1$-$C_6$ alkylamino, di-$C_1$-$C_6$ alkylamino, $C_6$-$C_{10}$ aryl, heteroaryl comprising one or two 5- or 6-membered rings and 1-4 heteroatoms selected from N, O and S, $C_3$-$C_{10}$ carbocycle, heterocycle comprising one or two 5- or 6-membered rings and 1-4 heteroatoms selected from N, O and S, $OR_5$, $NR_sR_5$, $SR_5$, $C(O)R_5$, $C(O)OR_5$, $C(O)NR_sR_5$, $NR_s'C(O)R_5$, $NR_s'C(O)O$ $R_5$, $NR_s'C(O)NR_sR_5$, $S(O)_2R_5$, or $NR_s'S(O)_2R_5$;
$R_5$ is H, $C_1$-$C_6$ alkyl, $C_6$-$C_{10}$ aryl-$C_1$-$C_6$ alkyl, $C_6$-$C_{10}$ aryl, heteroaryl comprising one or two 5- or 6-membered rings and 1-4 heteroatoms selected from N, O and S, $C_3$-$C_{10}$ carbocycle, or heterocycle comprising one or two 5- or 6-membered rings and 1-4 heteroatoms selected from N, O and S; and each $R_q$ is independently hydroxy, halogen, cyano, nitro, $C_1$-$C_6$ alkyl, $C_1$-$C_6$ alkoxy, amino, $C_1$-$C_6$ alkylamino, di-$C_1$-$C_6$ alkylamino $C_6$-$C_{10}$ aryl, heteroaryl comprising one or two 5- or 6-membered rings and 1-4 heteroatoms selected from N, O and S, $C_3$-$C_{10}$ carbocycle, or heterocycle comprising one or two 5- or 6-membered rings and 1-4 heteroatoms selected from N, O and S.

18. The compound of claim 1, selected from the group consisting of:

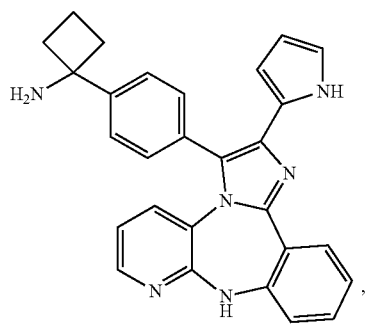

,

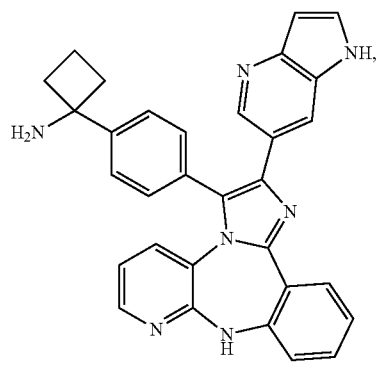

,

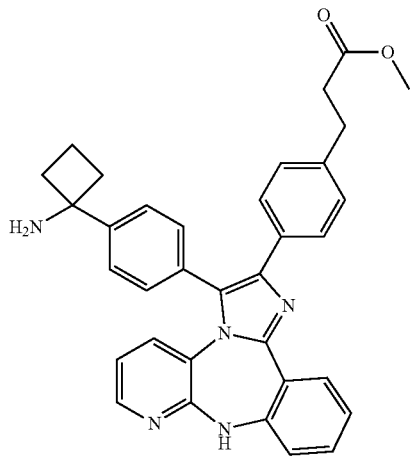

,

341
-continued
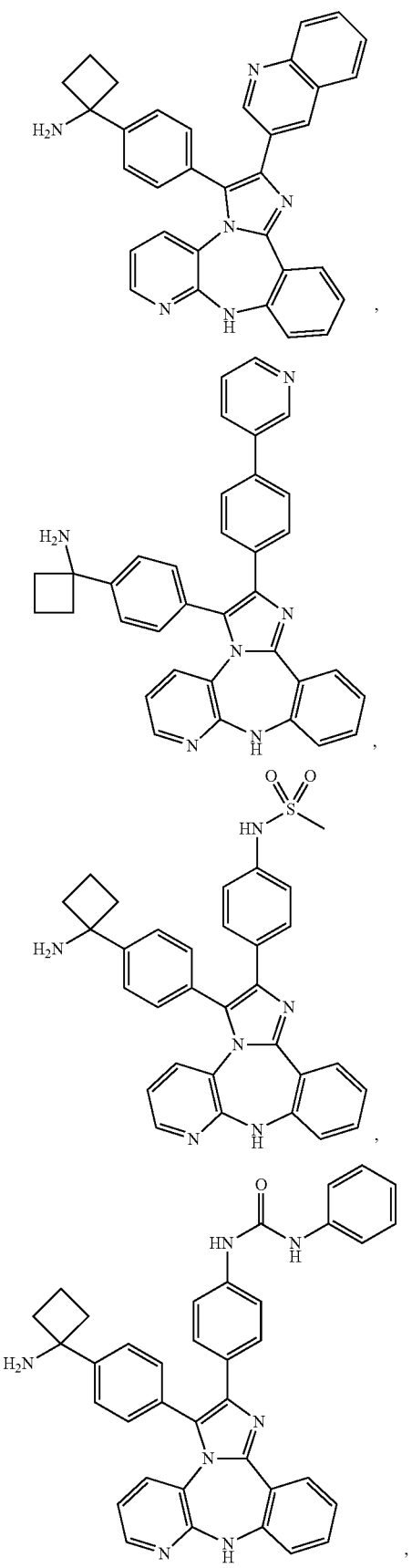
342
-continued
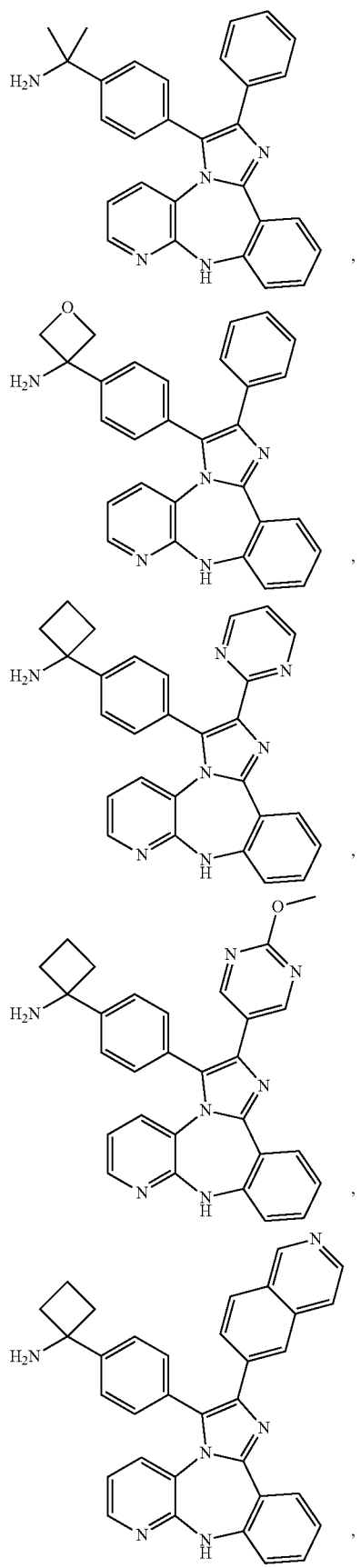

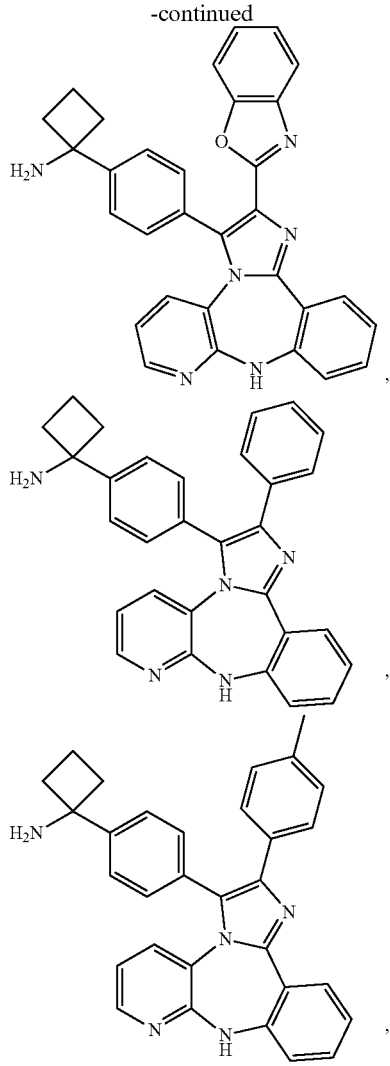
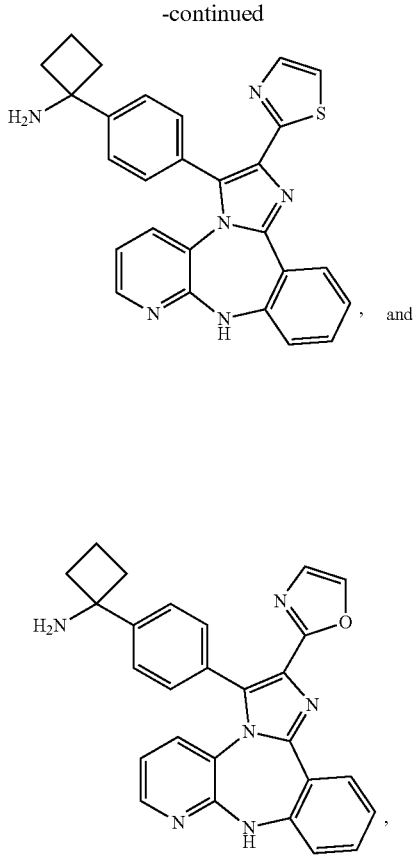
or a pharmaceutically acceptable salt or ester thereof.
19. A pharmaceutical composition comprising a therapeutically effective amount of a compound of claim 1, or a pharmaceutically acceptable salt or ester thereof, and a pharmaceutically acceptable carrier or excipient.
* * * * *